(12) United States Patent
Furet et al.

(10) Patent No.: US 8,969,341 B2
(45) Date of Patent: Mar. 3, 2015

(54) PYRAZOLOPYRROLIDINE COMPOUNDS

(71) Applicants: Pascal Furet, Thann (FR); Vito Guagnano, Basel (CH); Philipp Holzer, Sissach (CH); Robert Mah, Muttenz (CH); Keiichi Masuya, Basel (CH); Achim Schlapbach, Lorrach (DE); Stefan Stutz, Basel (CH); Andrea Vaupel, Riehen (CH)

(72) Inventors: Pascal Furet, Thann (FR); Vito Guagnano, Basel (CH); Philipp Holzer, Sissach (CH); Robert Mah, Muttenz (CH); Keiichi Masuya, Basel (CH); Achim Schlapbach, Lorrach (DE); Stefan Stutz, Basel (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/361,068

(22) PCT Filed: Nov. 28, 2012

(86) PCT No.: PCT/IB2012/056796
§ 371 (c)(1),
(2) Date: May 28, 2014

(87) PCT Pub. No.: WO2013/080141
PCT Pub. Date: Jun. 6, 2013

(65) Prior Publication Data
US 2014/0350010 A1 Nov. 27, 2014

Related U.S. Application Data

(60) Provisional application No. 61/564,591, filed on Nov. 29, 2011.

(51) Int. Cl.
| | | |
|---|---|---|
| A61K 31/5377 | (2006.01) | |
| A61K 31/497 | (2006.01) | |
| A61K 31/517 | (2006.01) | |
| A61K 31/519 | (2006.01) | |
| A61K 31/505 | (2006.01) | |
| A61K 31/4709 | (2006.01) | |
| A61K 31/4523 | (2006.01) | |
| A61K 31/4155 | (2006.01) | |
| C07D 413/14 | (2006.01) | |
| C07D 487/14 | (2006.01) | |
| C07D 239/02 | (2006.01) | |
| C07D 403/14 | (2006.01) | |
| C07D 215/00 | (2006.01) | |
| C07D 211/80 | (2006.01) | |
| C07D 401/14 | (2006.01) | |
| C07D 257/02 | (2006.01) | |
| C07D 487/04 | (2006.01) | |
| A61K 31/41 | (2006.01) | |
| A61K 31/4162 | (2006.01) | |
| A61K 31/4178 | (2006.01) | |
| A61K 31/4439 | (2006.01) | |

(Continued)

(52) U.S. Cl.
CPC .............. *C07D 487/04* (2013.01); *A61K 31/41* (2013.01); *A61K 31/4162* (2013.01); *A61K 31/4178* (2013.01); *A61K 31/4439* (2013.01); *A61K 31/454* (2013.01); *A61K 31/4709* (2013.01); *A61K 31/496* (2013.01); *A61K 31/506* (2013.01); *A61K 31/519* (2013.01); *A61K 31/5377* (2013.01)
USPC ................. 514/234.2; 514/254.06; 514/259.3; 514/272; 514/312; 514/322; 514/338; 514/381; 514/397; 514/406; 544/140; 544/281; 544/321; 544/371; 546/157; 546/199; 546/273.1; 548/253; 548/311.7; 548/360.5

(58) Field of Classification Search
USPC ............ 514/234.2, 254.06, 259.03, 272, 312, 514/322, 338, 381, 397, 406; 544/140, 281, 544/321, 371; 546/157, 199, 273.1; 548/253, 311.7, 360.5
See application file for complete search history.

(56) References Cited

U.S. PATENT DOCUMENTS 6,734,302 B2  5/2004  Kong et al.
7,541,354 B2  6/2009  Fancelli et al.
(Continued)

FOREIGN PATENT DOCUMENTS

EP  2 143 713 A1  1/2010
WO  95/19362 A1  7/1995
(Continued)

OTHER PUBLICATIONS

Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.
(Continued)

*Primary Examiner* — Samantha Shterengarts
(74) *Attorney, Agent, or Firm* — Scott W. Reid

(57) ABSTRACT

The invention relates to compounds of formula (I) as described herein, pharmaceutical preparations comprising such compounds, uses and methods of use for such compounds in the treatment of a disorder or a disease mediated by the activity of MDM2 and/or MDM4, and combinations comprising such compounds.

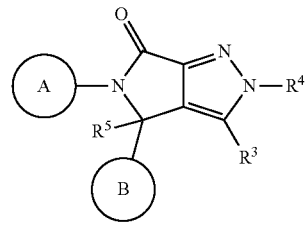

13 Claims, 4 Drawing Sheets

(51) Int. Cl.
*A61K 31/454* (2006.01)
*A61K 31/496* (2006.01)
*A61K 31/506* (2006.01)

(56) References Cited

U.S. PATENT DOCUMENTS

| | | | |
|---|---|---|---|
| 8,101,644 | B2 | 1/2012 | Kai et al. |
| 8,440,693 | B2 | 5/2013 | Berghausen et al. |
| 2006/0069085 | A1 | 3/2006 | Zhao et al. |
| 2009/0163545 | A1 | 6/2009 | Goldfarb |
| 2010/0210632 | A1 | 8/2010 | Kai et al. |
| 2011/0183939 | A1 | 7/2011 | Kai et al. |
| 2011/0230457 | A1 | 9/2011 | Berghausen et al. |
| 2012/0065210 | A1 | 3/2012 | Chu et al. |
| 2013/0281473 | A1 | 10/2013 | Berghausen et al. |
| 2013/0317024 | A1 | 11/2013 | Cotesta et al. |
| 2014/0011798 | A1 | 1/2014 | Furet et al. |
| 2014/0135306 | A1 | 5/2014 | Buschmann et al. |

FOREIGN PATENT DOCUMENTS

| | | |
|---|---|---|
| WO | 02/12242 A2 | 2/2002 |
| WO | 03/051359 A1 | 6/2003 |
| WO | 03/095625 A2 | 11/2003 |
| WO | 2005/110996 A1 | 11/2005 |
| WO | 2006/074262 A1 | 7/2006 |
| WO | 2007/068637 A1 | 6/2007 |
| WO | 2007/096334 A1 | 8/2007 |
| WO | 2008/034039 A2 | 3/2008 |
| WO | 2008/120725 A1 | 10/2008 |
| WO | 2010/007116 A2 | 1/2010 |
| WO | 2010/035727 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/046030 A2 | 4/2012 |
| WO | 2012/151512 A2 | 11/2012 |
| WO | 2012/174487 A2 | 12/2012 |
| WO | 2012/175487 A1 | 12/2012 |
| WO | 2012/175520 A1 | 12/2012 |
| WO | 2013/033268 A2 | 3/2013 |
| WO | 2013/111105 A1 | 8/2013 |

OTHER PUBLICATIONS

Dohrn et al., Berichte der Deutschen Chemischen Gesellschaft [Abteilung] B: Abhandlungen. 1931;64B:2863-5.

Gein et al., 5-Membered 2,3-Dioxoheterocyclic Compounds. Journal of General Chemistry. 1993;63(10):2324-8.

Gein et al., Reactions of 4-Acyl-1-alkoxyaryl-5-aryl-3-hydroxy-2,5-dihydro-1 H-pyrrol-2-ones with Nucleophilic Reagents. Russian Journal of Organic Chemistry. 2011;47(1):95-9.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Lee et al., Novel Pyrrolopyrimidine-Based alpha-Helix Mimetics: Cell Permeable Inhibitors of Protein-Protein Interactions. Journal of the American Chemical Society. 2010;133:676-9.

Miyazaki et al., Lead optimization of novel p53-MDM2 interaction inhibitors possessing dihydroimidazothiazole scaffold. Bioorganic and Medicinal Chemistry Letters. 2013;23:728-32.

Richter et al., An Optimised Small-Molecule Stabiliser of the 14-3-3-PMA2 Protein-Protein Interaction. Chem. Eur. J. 2012;18(21):6520-7.

Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.

Wang et al., Benzimidazole-2-one: A novel anchoring principle for antagonizing p53-Mdm2. Bioorganic & Medicinal Chemistry. 2013;21:3982-95.

Westphal The formation of pyrrolo[3,4-c]pyrazoles. Journal for Practical Chemistry. 1969;311:379-84.

Chung et al., Fragment-based discovery of bromodomain inhibitors part 1: inhibitor binding modes and implications for lead discovery. J Med Chem. Jan. 26, 2012;55(2):576-86.

Filippakopoulos et al., Benzodiazepines and benzotriazepines as protein interaction inhibitors targeting bromodomains of the BET family. Bioorg Med Chem. Mar. 15, 2012;20(6):1878-86.

Filippakopoulos et al., Selective inhibition of BET bromodomains. Nature. Dec. 23, 2010;468(7327):1067-73.

Wu et al., The double bromodomain-containing chromatin adaptor Brd4 and transcriptional regulation. J Biol Chem. May 4, 2007;282(18):13141-5.

PYRAZOLOPYRROLIDINE COMPOUNDS

This application is a U.S. National Phase filing of International Application No. PCT/IB2012/056796 filed 28 Nov. 2012, which claims priority to U.S. Application No. 61/564,591 filed 29 Nov. 2011, the contents of which are incorporated herein by reference in their entirety.

The present invention relates to novel pyrazolopyrrolidine compounds, capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor supressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

WO2011/076786 discloses isoquinolinone and quinazolinone compounds as inhibitors of the interaction between p53 and MDM2 and/or 4.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

It has now been found that a novel class of pyrazolopyrrolidine compounds shows inhibition of the MDM2/p53 and/or MDM4/p53 interaction (this term including in particular Hdm2/p53 and Hdm4/p53 interaction), and in particular potent inhibition of the MDM2/p53 interaction. The corresponding compounds thus represent a novel type of compound that are useful in the treatment of a number of disorders, such as proliferative diseases, especially cancer. The invention relates therefore to these compounds as drugs as well as to the other inventive embodiments indicated herein.

Particularly interesting compounds of the invention herein are highly potent in the p53-Hdm2 inhibition (TR-FRET) Assay described herein. Compounds of particular interest possess favourable pharmacokinetic properties. They should be non-toxic and demonstrate few side-effects. Furthermore, the ideal drug candidate will exist in a physical form that is stable, non-hygroscopic and easily formulated.

According to a first aspect of the invention there is provided a compound of formula (I) or a salt thereof,

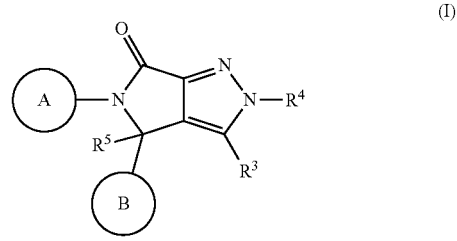

wherein
A is selected from

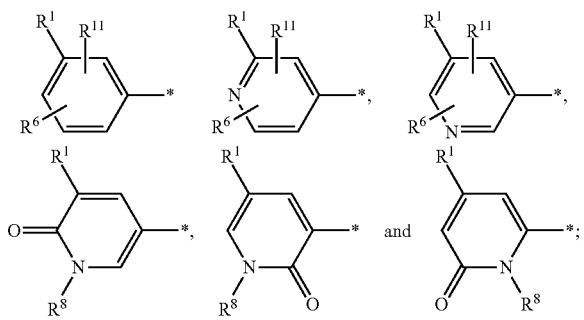

B is selected from

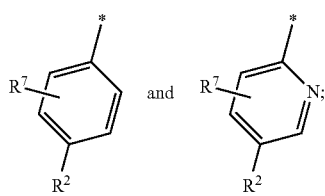

$R^1$ is selected from chloro, fluoro and methyl;
$R^2$ is selected from chloro, fluoro, trifluoromethyl, methyl, cyano;

$R^3$ is selected from isopropyl, cyclopropyl, isobutyl, tert-butyl, cyclobutyl, cyclopentyl, or $R^3$ is:

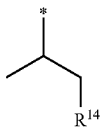

wherein $R^{14}$ is selected from OH, methoxy, $NH_2$, NHMe, $NMe_2$, NHCOMe and NHCOH;

$R^4$ is selected from
- H,
- —$(C_0$-$C_4)$alkyl-phenyl, said phenyl being optionally substituted with 1, 2 or 3 substituents independently selected from:
  - $(C_1$-$C_4)$alkyl, optionally substituted by $NR^9(R^{10})$ or —O—$(C_1$-$C_4)$alkyl or by 1, 2 or 3 halo substituents,
  - —O—$(C_1$-$C_4)$alkyl, optionally substituted by $NR^9(R^{10})$, phenyl or —O—$(C_1$-$C_4)$alkyl, or by 1, 2 or 3 halo substituents,
  - —$C(O)NR^9(R^{12})$,
  - cyano,
  - halo,
  - —$(CH_2)_m$—$S(O)_v NR^9(R^{10})$,
  - —$C(O)OH$,
  - —$C(O)O$—$(C_1$-$C_4)$alkyl,
  - —$(CH_2)_p$—$NR^9(R^{12})$,
  - heterocyclyl$^1$, and
  - phenyl and wherein —$(C_0$-$C_4)$alkyl of said —$(C_0$-$C_4)$alkyl-phenyl, when present, is optionally substituted by 1 or 2 OH,
- —$(C_0$-$C_4)$alkyl-C(O)-phenyl, said phenyl being optionally substituted with 1, 2 or 3 substituents independently selected from:
  - $(C_1$-$C_4)$alkyl, optionally substituted with from 1 to 3 halo,
  - —O—$(C_1$-$C_4)$alkyl,
  - cyano, and
  - halo,
- naphthyl,
- —$(C_0$-$C_4)$alkyl-$(C_3$-$C_6)$cycloalkyl, said $(C_3$-$C_6)$cycloalkyl being optionally substituted with 1, 2 or 3 substituents independently selected from OH, —$C(O)NR^9(R^{10})$, —O—$C(O)$—$(C_1$-$C_4)$alkyl, halo, —$(CH_2)_m$—$NR^9(R^{10})$, —$C(O)$—$O(C_1$-$C_4)$alkyl,
- —$(C_0$-$C_4)$alkyl-heteroaryl$^1$, the heteroaryl$^1$ of said —$(C_0$-$C_4)$alkyl-heteroaryl$^1$ being optionally substituted by 1, 2, 3 or 4 substituents independently selected from —O—$(C_1$-$C_4)$alkyl, =O, OH, cyano, $(C_1$-$C_4)$alkyl, halo, —$NR^9(R^{10})$,
- —$(C_0$-$C_4)$alkyl-$C(O)NR^9(R^{13})$,
- —$(C_0$-$C_4)$alkyl-$NR^9(R^{12})$, wherein —$(C_0$-$C_4)$alkyl of said —$(C_0$-$C_4)$alkyl-$NR^9(R^{12})$, when present, is optionally substituted with 1 or 2 OH,
- —$(C_0$-$C_4)$alkyl-heterocyclyl$^4$, said heterocyclyl$^4$ being optionally substituted by 1, 2, 3 or 4 substituents independently selected from
  - —$C(O)NR^9(R^{12})$,
  - OH,
  - —$C(O)(C_1$-$C_4)$alkyl, optionally substituted by $(C_1$-$C_4)$alkoxy,
  - —$C(O)$—$O(C_1$-$C_4)$alkyl, optionally substituted by $(C_1$-$C_4)$alkoxy,
  - =O,
  - halo,
  - —$C(O)$— heteroaryl$^2$, and
  - $(C_1$-$C_4)$alkyl, optionally substituted by phenyl, and wherein the —$(C_0$-$C_4)$alkyl of —$(C_0$-$C_4)$alkyl-heterocyclyl$^4$, when present, is optionally substituted with 1 or 2 OH,
- $(C_1$-$C_8)$alkyl, said $(C_1$-$C_8)$alkyl being optionally substituted by 1, 2 or 3 substituents independently selected from OH, halo, —O—$(C_1$-$C_4)$alkyl, —$C(O)(C_1$-$C_4)$alkyl, —$C(O)O$—$(C_1$-$C_4)$alkyl, —$C(O)OH$, cyano and $NR^9(R^{10})$, and
- $(C_1$-$C_8)$alkenyl, said $(C_1$-$C_8)$alkenyl being optionally substituted by 1, 2 or 3 substituents independently selected from OH, halo and —O—$(C_1$-$C_4)$alkyl;

$R^5$ is selected from:
- H,
- heterocyclyl$^1$-$C(O)$—$(CH_2)_n$—,
- $(C_1$-$C_4)$alkyl-, said $(C_1$-$C_4)$alkyl- being optionally substituted with 1 or 2 substituents independently selected from OH, =O,
- heterocyclyl$^1$-$(C_1$-$C_4)$alkyl-, wherein said alkyl of heterocyclyl$^1$-$(C_1$-$C_4)$alkyl- is optionally substituted by 1 or 2 OH, and said heterocyclyl$^1$ can be optionally substituted by methyl or ethyl,
- $(C_1$-$C_4)$alkyl-O—$C(O)$—$(CH_2)_m$—,
- cyano;

$R^6$ is selected from:
- H,
- $(C_1$-$C_4)$alkyl-, optionally substituted with $(C_1$-$C_4)$alkoxy,
- $(C_1$-$C_4)$alkoxy, optionally substituted with $(C_1$-$C_4)$alkoxy,
- $(C_1$-$C_4)$alkoxy$(C_1$-$C_4)$alkoxy$(C_1$-$C_4)$alkyl-,
- halo,
- $R^9(R^{10})N$—$C(O)$—$(CH_2)_m$—,
- cyano,
- $R^9(R^{10})N$—$(CH_2)_m$—
- $R^9(R^{10})N$—$(CH_2)_n$—O—$(CH_2)_m$—,
- $(C_1$-$C_4)$alkyl-$C(O)$—$(R^{10})N$—$(CH_2)_m$—,
- —O—$(CH_2)_p$-heteroaryl$^2$;

$R^7$ is selected from
- H,
- halo,
- $(C_1$-$C_4)$alkyl-, optionally substituted with $(C_1$-$C_4)$alkoxy,
- $(C_1$-$C_4)$alkoxy, optionally substituted with $(C_1$-$C_4)$alkoxy,
- $(C_1$-$C_4)$alkoxy$(C_1$-$C_4)$alkoxy$(C_1$-$C_4)$alkyl-,
- $R^9(R^{10})N$—$(CH_2)$, —O—$(CH_2)_m$—, and
- $(C_1$-$C_4)$alkyl-$C(O)O$—$(CH_2)_n$—$(R^{10})N$—;

$R^8$ is selected from
- H,
- $(C_1$-$C_4)$alkoxy$(C_1$-$C_4)$alkyl-,
- $(C_1$-$C_4)$alkyl-, said $(C_1$-$C_4)$alkyl- being optionally substituted by 1, 2 or 3 substituents independently selected from OH, halo, —O—$(C_1$-$C_4)$alkyl, $NR^9(R^{10})$, and $(C_1$-$C_4)$alkyl-$C(O)NR^9(R^{10})$;

$R^9$ is H, methyl or ethyl;

$R^{10}$ is H, methyl or ethyl, wherein said methyl and ethyl can each independently be substituted by 1 or 2 substituents independently selected from methoxy, ethoxy and halo;

$R^{11}$ is H, methyl, methoxy or halo;

$R^{12}$ is selected from
- H,
- $(C_1$-$C_4)$alkyl-, optionally substituted with heterocyclyl$^3$,
- —$C(O)(C_1$-$C_4)$alkyl,
- —$C(O)O(C_1$-$C_4)$alkyl,
- —$C(O)H$, and
- —$C(O)$-phenyl, optionally substituted with 1 or 2 substituents independently selected from $(C_1$-$C_4)$alkyl, —O—

(C$_1$-C$_4$)alkyl, cyano, halo, —C(O)OH, —C(O)O—(C$_1$-C$_4$)alkyl, —C(O)—(C$_1$-C$_4$)alkyl;

R$^{13}$ is selected from
- —(C$_0$-C$_3$)alkyl-phenyl, said phenyl being optionally substituted with 1 or 2 substituents independently selected from (C$_1$-C$_4$)alkyl, —O—(C$_1$-C$_4$)alkyl, cyano, halo, —C(O)OH, —C(O)O—(C$_1$-C$_4$)alkyl, —C(O)—(C$_1$-C$_4$)alkyl,
- —(C$_0$-C$_3$)alkyl-heterocyclyl$^4$, said heterocyclyl$^4$ being optionally substituted by 1, 2 or 3 substituents independently selected from —O—(C$_1$-C$_4$)alkyl, C(O)(C$_1$-C$_4$)alkyl, C(O)O—(C$_1$-C$_4$)alkyl,
- —(C$_1$-C$_4$)alkyl, said (C$_1$-C$_4$)alkyl being optionally substituted with a substituent independently selected from —O—(C$_1$-C$_4$)alkyl, C(O)(C$_1$-C$_4$)alkyl, C(O)O—(C$_1$-C$_4$)alkyl, and
- —(C$_0$-C$_3$)alkyl-(C$_3$-C$_6$)cycloalkyl;

or R$^9$ and R$^{13}$, together with the nitrogen to which they are attached form heterocyclyl$^3$, said heterocyclyl$^3$ being optionally substituted with 1, 2 or 3 substitutents selected independently from
=O,
(C$_1$-C$_4$)alkyl, said (C$_1$-C$_4$)alkyl being optionally substituted with 1, 2 or 3 substitutents selected independently from halo and OH,
OH,
C(O)(C$_1$-C$_4$)alkyl,
C(O)O—(C$_1$-C$_4$)alkyl, and
C(O)NR$^9$R$^{10}$;

m is 0, 1 or 2;
n is 1, 2 or 3;
p is 0, 1, 2 or 3;
v is 0, 1 or 2;
heterocyclyl$^1$ is a 3, 4, 5 or 6 membered fully saturated or partially unsaturated monocyclic group comprising ring carbon atoms and 1 or 2 ring heteroatoms independently selected from N, O and S;
heterocyclyl$^3$ is a 4, 5 or 6 membered fully saturated or partially unsaturated monocyclic group comprising ring carbon atoms and 1 or 2 ring heteroatoms independently selected from N, O and S;
heterocyclyl$^4$ is a 3, 4, 5, 6 or 7 membered fully saturated or partially unsaturated monocyclic group comprising carbon ring atoms and 1 or 2 ring atoms selected independently from N, O and S;
heteroaryl$^1$ is a 5, 6, 7, 8, 9 or 10 membered, mono or bicyclic, fully unsaturated or partially unsaturated group, comprising carbon ring atoms and 1, 2, 3 or 4 ring heteratoms independently selected from N, O and S, wherein the total number of S atoms does not exceed 1, and the total number of O atoms does not exceed 1;
heteroaryl$^2$ is 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;
and * indicates the point of attachment to the remainder of the molecule.

Unless specified otherwise, the term "compounds of the present invention" refers to compounds of formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

For example, a "compound of the present invention" or a "compound of formula (I)" can exist in tautomeric forms when R$^8$ is H. Where an embodiment is directed to one tautomer, the embodiment includes all possible tautomeric forms.

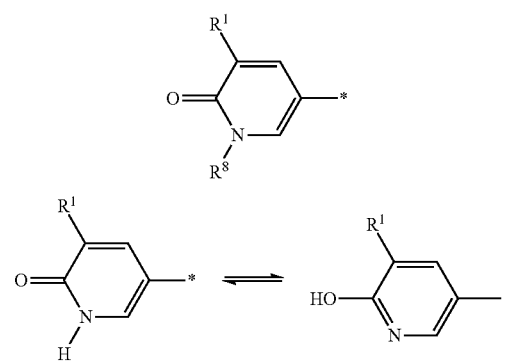

Various embodiments of the invention are described herein. It will be recognized that features specified in each embodiment may be combined with other specified features to provide further embodiments.

Described below are a number of embodiments (E) of the first aspect of the invention, where for convenience E1 is identical thereto.

E1 A compound of formula (I) as defined above or a salt thereof.

E2 A compound according to E1 wherein A is selected from

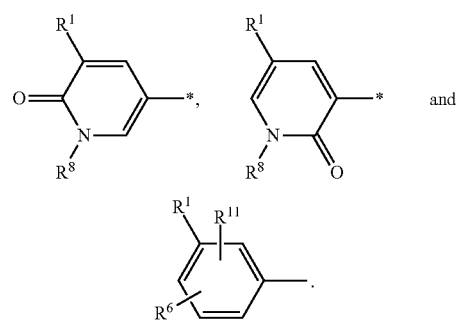

E3 A compound according to either of E1 or E2 wherein A is selected from

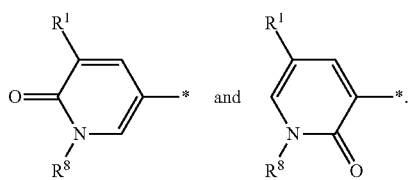

E4 A compound according to any of E1 to E3 wherein B is

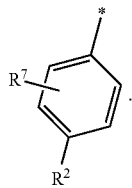

E5 A compound according to any of E1 to E4 wherein $R^1$ is chloro or methyl.
E6 A compound according to any of E1 to E5 wherein $R^1$ is chloro.
E7 A compound according to any of E1 to E6 wherein $R^2$ is selected from chloro and cyano.
E8 A compound according to any of E1 to E7 wherein $R^3$ is selected from isopropyl, cyclopropyl, isobutyl, tert-butyl, cyclobutyl and cyclopentyl.
E9 A compound according to any of E1 to E8 wherein $R^3$ is isopropyl.
E10 A compound according to any of E1 to E7 wherein $R^3$ is:

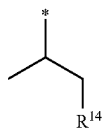

E11 A compound according to any of E1 to E7 and E10 wherein $R^3$ is:

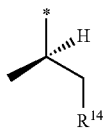

E12 A compound according to any of E1 to E11 wherein $R^4$ is selected from
H,
—$(C_0-C_2)$alkyl-phenyl, said phenyl being optionally substituted with 1, 2 or 3 substituents independently selected from:
  $(C_1-C_4)$alkyl, optionally substituted by $NR^9(R^{10})$ or —O—$(C_1-C_4)$alkyl or by 1, 2 or 3 halo substituents,
  —O—$(C_1-C_4)$alkyl, optionally substituted by $NR^9(R^{10})$, phenyl or —O—$(C_1-C_4)$alkyl, or by 1, 2 or 3 halo substituents,
  —C(O)$NR^9(R^{12})$,
  cyano,
  halo,
  —$(CH_2)_m$—S(O)$_v NR^9(R^{10})$,
  —C(O)OH,
  —C(O)O—$(C_1-C_4)$alkyl,
  —$(CH_2)_p$—$NR^9(R^{12})$,
  heterocyclyl$^1$, and
  phenyl,
and wherein —$(C_0-C_2)$alkyl of said —$(C_0-C_2)$alkyl-phenyl, when present, is optionally substituted by OH,
—$(C_0-C_2)$alkyl-C(O)-phenyl, said phenyl being optionally substituted with 1, 2 or 3 substituents independently selected from:
  $(C_1-C_4)$alkyl, optionally substituted with from 1 to 3 halo,
  —O—$(C_1-C_4)$alkyl,
  cyano, and
  halo,
naphthyl,
—$(C_0-C_2)$alkyl-$(C_3-C_6)$cycloalkyl, said $(C_3-C_6)$cycloalkyl being optionally substituted with 1, 2 or 3 substituents independently selected from OH, —C(O)$NR^9(R^{10})$, —O—C(O)—$(C_1-C_4)$alkyl, halo, —$(CH_2)_m$—$NR^9(R^{10})$ and —C(O)—O$(C_1-C_4)$alkyl,
—$(C_0-C_2)$alkyl-heteroaryl$^1$, the heteroaryl of said —$(C_0-C_2)$alkyl-heteroaryl$^1$ being optionally substituted by 1, 2, 3 or 4 substituents independently selected from —O—$(C_1-C_4)$alkyl, =O, OH, cyano, $(C_1-C_4)$alkyl, halo and —$NR^9(R^{10})$,
—$(C_0-C_2)$alkyl-C(O)$NR^9(R^{13})$,
—$(C_0-C_2)$alkyl-$NR^9(R^{12})$, wherein —$(C_0-C_2)$alkyl of said —$(C_0-C_2)$alkyl-$NR^9(R^{12})$, when present, is optionally substituted with 1 or 2 OH,
—$(C_0-C_2)$alkyl-heterocyclyl$^4$, said heterocyclyl$^4$ being optionally substituted by 1, 2, 3 or 4 substituents independently selected from
  —C(O)$NR^9(R^{12})$,
  OH,
  —C(O)$(C_1-C_4)$alkyl, optionally substituted by $(C_1-C_4)$alkoxy,
  —C(O)—O$(C_1-C_4)$alkyl, optionally substituted by $(C_1-C_4)$alkoxy,
  =O,
  halo,
  —C(O)— heteroaryl$^2$, and
  $(C_1-C_4)$alkyl, optionally substituted by phenyl,
and wherein the —$(C_0-C_2)$alkyl of —$(C_0-C_2)$alkyl-heterocyclyl$^4$, when present, is optionally substituted with OH,
—$(C_1-C_8)$alkyl, said $(C_1-C_8)$alkyl being optionally substituted by 1, 2 or 3 substituents independently selected from OH, halo, —O—$(C_1-C_4)$alkyl, —C(O)$(C_1-C_4)$alkyl, —C(O)O—$(C_1-C_4)$alkyl, —C(O)OH, cyano and $NR^9(R^{10})$,
and
—$(C_1-C_8)$alkenyl, said $(C_1-C_8)$alkenyl being optionally substituted by 1, 2 or 3 substituents independently selected from OH, halo, —O—$(C_1-C_4)$alkyl.
E13 A compound according to any of E1 to E12 wherein $R^4$ is selected from
phenyl, said phenyl being optionally substituted with 1, 2 or 3 substituents independently selected from:
  $(C_1-C_4)$alkyl, optionally substituted by $NR^9(R^{10})$ or —O—$(C_1-C_4)$alkyl or by 1, 2 or 3 halo substituents,
  —O—$(C_1-C_4)$alkyl, optionally substituted by $NR^9(R^{10})$, phenyl or —O—$(C_1-C_4)$alkyl, or by 1, 2 or 3 halo substituents,
  —C(O)$NR^9(R^{12})$,
  cyano,
  halo,
  —$(CH_2)_m$—S(O)$_v NR^9(R^{10})$,
  —C(O)OH,
  —C(O)O—$(C_1-C_4)$alkyl,
  —$(CH_2)_p$—$NR^9(R^{12})$,
  heterocyclyl$^1$,
  phenyl
and
heteroaryl$^1$, said heteroaryl$^1$ being optionally substituted by 1, 2, 3 or 4 substituents independently selected from —O—$(C_1-C_4)$alkyl, =O, OH, cyano, $(C_1-C_4)$alkyl, halo and —$NR^9(R^{10})$.
E14 A compound according to any of E1 to E12 wherein $R^4$ is selected from —(C₀-C₂)alkyl-phenyl, said phenyl being optionally substituted with 1 or 2 substituents independently selected from:
(C₁-C₄)alkyl,
—O—(C₁-C₄)alkyl,
—C(O)NR⁹(R¹²),
cyano,
halo,
—(CH₂)ₘ—S(O)ᵥNR⁹(R¹⁰), and
—(CH₂)ₚ—NR⁹(R¹²),
—(C₀-C₂)alkyl-(C₃-C₆)cycloalkyl, said (C₃-C₆)cycloalkyl being optionally substituted with OH,
—(C₀-C₂)alkyl-heteroaryl¹, the heteroaryl¹ of said —(C₀-C₂)alkyl-heteroaryl¹ being optionally substituted by 1, 2 or 3 substituents independently selected from —O—(C₁-C₄)alkyl, =O, cyano, (C₁-C₄)alkyl and —NR⁹(R¹⁰),
—(C₀-C₂)alkyl-C(O)NR⁹(R¹³),
—(C₀-C₂)alkyl-NR⁹(R¹²),
—(C₀-C₂)alkyl-heterocyclyl⁴, said heterocyclyl⁴ being optionally substituted by 1 or 2 substituents independently selected from
—C(O)NR⁹(R¹²),
OH,
—C(O)(C₁-C₄)alkyl, optionally substituted by (C₁-C₄)alkoxy,
—C(O)—O(C₁-C₄)alkyl, optionally substituted by (C₁-C₄)alkoxy,
=O, and
(C₁-C₄)alkyl,
(C₁-C₈)alkyl, said (C₁-C₈)alkyl being optionally substituted by 1 or 2 substituents independently selected from OH, —O—(C₁-C₄)alkyl, cyano and NR⁹(R¹⁰),
and
(C₁-C₈)alkenyl.

E15 A compound according to any of E1 to E14 wherein R⁴ is selected from

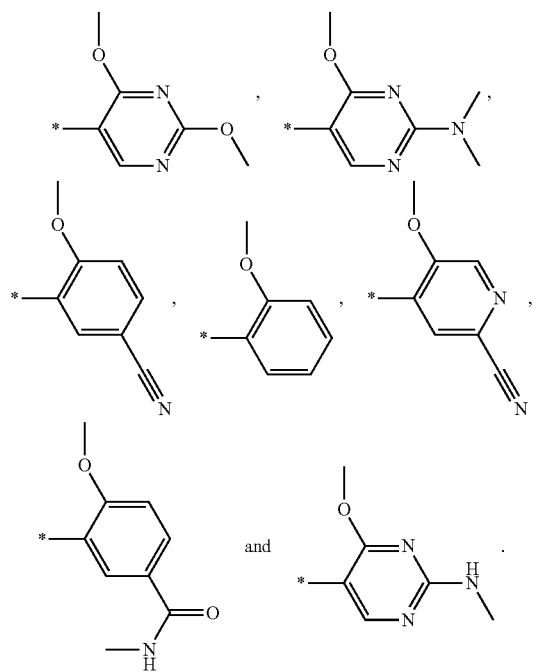

E16 A compound according to any of E1 to E15 wherein R⁴ is selected from

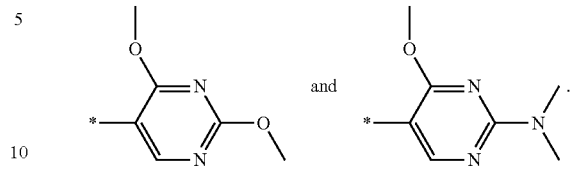

E17 A compound according to any of E1 to E16 wherein R⁵ is selected from H, 2-morpholin-4-yl-2-oxo-ethyl-, 2-methoxycarbonyl-ethyl-, ethoxycarbonyl-, methyl, 2-hydroxy-3-pyrrolidin-1-yl-propyl- and 2,3-dihydroxypropyl-.

E18 A compound according to any of E1 to E17 wherein R⁵ is H.

E19 A compound according to any of E1 and E2 and E4 to E18 wherein R⁶ is selected from fluoro, methyl, cyano, H₂N—C(O)—, H₃C—C(O)—HN—, tetrazolyl-methoxy-, dimethylaminoethoxy-, H and methoxy-.

E20 A compound according to any of E1 and E2 and E4 to E19 wherein, when ring A is phenyl, R⁶ is selected from fluoro, methyl, cyano, H₂N—C(O)—, H₃C—C(O)—HN—, tetrazolyl-methoxy and dimethylaminoethoxy.

E21 A compound according to any of E1 and E2 and E4 to E20 wherein, when ring A is phenyl, R⁶ is selected from fluoro and methyl.

E22 A compound according to E21 wherein the R⁶ methyl is para to R¹ or the R⁶ fluoro is ortho to R¹.

E23 A compound according to any of E1 and E4 to E18 wherein, when ring A is a heterocyclic ring, R⁶ is selected from H and methoxy.

E24 A compound according to E23 wherein said methoxy is para to R¹.

E25 A compound according to any of E1 to E24 wherein R⁷ is selected from methyl, fluoro, H and methoxyethoxymethyl.

E26 A compound according to any of E1 to E25 wherein, R⁷ is selected from methyl, fluoro and H.

E27 A compound according to any of E1 to E26 wherein R⁷ is selected from fluoro, wherein said fluoro is ortho to R².

E28 A compound according to any of E1 to E27 wherein R⁷ is selected from methyl and H.

E29 A compound according to any of E1 to E28 wherein R⁷ is selected from methyl.

E30 A compound according to any of E1 to E29 wherein R⁷ is selected from methyl, wherein said methyl is meta to R².

E31 A compound according to any of E1 to E19 and E25 to E30 wherein R⁸ is selected from
H,
(C₁-C₂)alkoxy(C₁-C₂)alkyl-,
(C₁-C₂)alkyl-, said (C₁-C₂)alkyl- being optionally substituted by 1, 2 or 3 substituents independently selected from OH, halo, —O—(C₁-C₂)alkyl and NR⁹(R¹⁰), and
(C₁-C₂)alkyl-C(O)NR⁹(R¹⁰).

E32 A compound according to any of E1 to E19 and E25 to E31 wherein R⁸ is selected from
H
(C₁-C₂)alkoxy(C₁-C₂)alkyl-,
and
(C₁-C₂)alkyl-, said (C₁-C₂)alkyl- being optionally substituted by 1, 2 or 3 substituents independently selected from OH, halo, —O—(C₁-C₂)alkyl and NR⁹(R¹⁰).

E33 A compound according to any of E1 to E19 and E25 to E32 wherein $R^8$ is selected from H, methyl, ethyl, methoxyethyl and dimethylaminoethyl.

E34 A compound according to any of E1 to E19 and E25 to E33 wherein $R^8$ is selected from H and methyl.

E35 A compound according to any of E1 to E19 and E25 to E34 wherein, when A is

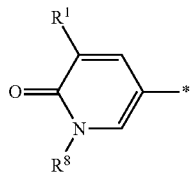

$R^8$ is methyl.

E36 A compound according to any of E1 to E19 and E25 to E34 wherein, when A is

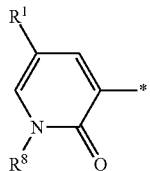

$R^8$ is H.

E37 A compound according to any of E1 to E36 wherein $R^9$ is H or methyl.

E38 A compound according to any of E1 to E37 wherein $R^{10}$ is H or methyl.

E39 A compound according to any of E1, E2, E4 to E34 and E37 to E38 wherein $R^{11}$ is selected from H and fluoro.

E40 A compound according to any of E1 to E14 and E17 to E39 wherein $R^{12}$ is selected from H and $(C_1-C_4)$alkyl.

E41 A compound according to any of E1 to E12 and E14 and E17 to E40 wherein $R^{13}$ is selected from
  phenyl, said phenyl being optionally substituted with 1 or 2 substituents independently selected from $(C_1-C_4)$alkyl, —O—$(C_1-C_4)$alkyl, cyano, halo, —C(O)OH, —C(O)O—$(C_1-C_4)$alkyl, —C(O)—$(C_1-C_4)$alkyl,
  heterocyclyl$^4$, said heterocyclyl$^4$ being optionally substituted by 1 or 2 substituents independently selected from —O—$(C_1-C_4)$alkyl, C(O)$(C_1-C_4)$alkyl, C(O)O—$(C_1-C_4)$alkyl,
  $(C_1-C_4)$alkyl, said $(C_1-C_4)$alkyl being optionally substituted with a substituent independently selected from —O—$(C_1-C_4)$alkyl, C(O)$(C_1-C_4)$alkyl, C(O)O—$(C_1-C_4)$alkyl,
  and
  $(C_3-C_6)$cycloalkyl.

E42 A compound according to any of E1 to E12, E14 and E17 to E41 wherein $R^{13}$ is selected from
  phenyl, said phenyl being optionally substituted with 1 or 2 substituents independently selected from $(C_1-C_4)$alkyl, —O—$(C_1-C_4)$alkyl, cyano, halo, —C(O)OH, —C(O)O—$(C_1-C_4)$alkyl, —C(O)—$(C_1-C_4)$alkyl, and
  heterocyclyl$^4$, said heterocyclyl$^4$ being optionally substituted by 1 or 2 substituents independently selected from —O—$(C_1-C_4)$alkyl, C(O)$(C_1-C_4)$alkyl, C(O)O—$(C_1-C_4)$alkyl.

E43 A compound according to any of E1 to E12, E14 and E17 to E42 wherein $R^{13}$ is selected from
  d piperidine, optionally substituted by —C(O)-methyl, and
  phenyl.

E44 A compound according to any of E1 to E12, E14, E17 to E36 and E38 to E40 wherein $R^9$ and $R^{13}$, together with the nitrogen to which they are attached form heterocyclyl$^3$, said heterocyclyl$^3$ being optionally substituted with 1 or 2 substitutents selected independently from
  =O,
  $(C_1-C_4)$alkyl, said $(C_1-C_4)$alkyl being optionally substituted with 1, 2 or 3 substitutents selected independently from halo and OH,
  OH, and
  C(O)$(C_1-C_4)$alkyl.

E45 A compound according to any of E1 to E12, E14, E17 to E36, E38 to E40 and E44 wherein $R^9$ and $R^{13}$, together with the nitrogen to which they are attached form heterocyclyl$^3$, said heterocyclyl$^3$ being selected from
  piperidinyl, said piperidinyl being optionally substituted by OH, or by $(C_1-C_3)$alkyl, said optionally substituted with 1 or 2 OH,
  piperazinyl, optionally substituted by 1 or 2 substituents selected from methyl, C(O)methyl and C=O, and
  pyrrolidinyl E46 A compound according to any of E1 to E45 wherein m is 0.

E47 A compound according to any of E1 to E46 wherein n is 1.

E48 A compound according to any of E1 to E47 wherein p is 0, 1 or 2.

E49 A compound according to any of E1 to E48 wherein v is 2.

E50 A compound according to any of E1 to E49 wherein heterocyclyl$^1$ is a 5 or 6 membered fully saturated monocyclic group comprising ring carbon atoms and 1 or 2 ring heteroatoms independently selected from N, O and S.

E51 A compound according to any of E1 to E50 wherein heterocyclyl$^1$ is pyrrolidinyl or morpholinyl.

E52 A compound according to any of E1 to E11 and E17 to E51 wherein heterocyclyl$^3$ is a 5 or 6 membered fully saturated monocyclic group comprising ring carbon atoms and 1 ring N atom, and optionally one further ring N atom.

E53 A compound according to any of E1 to E12, E14 and E17 to E52 wherein heterocyclyl$^4$ is a 3, 4, 5 or 6 membered fully saturated or partially unsaturated monocyclic group, which comprises carbon ring atoms and 1 or 2 ring atoms selected independently from N, O and S.

E54 A compound according to any of E1 to E12, E14 and E17 to E53 wherein heterocyclyl$^4$ is piperidinyl, pyrrolidinyl, tetrahydropyranyl, piperazinyl, imidazolidinyl, oxiranyl or tetrahydrofuranyl.

E55 A compound according to any of E1 to E14 and E17 to E54 wherein heteroaryl$^1$ is a 5, 6, 7, 8, 9 or 10 membered, mono or bicyclic, fully unsaturated or partially unsaturated group, comprising carbon ring atoms and
  1, 2, 3 or 4 ring N heteroatoms, or
  1 ring S atom and optionally 1 ring N atom.

E56 A compound according to any of E1 to E14 and E17 to E55 wherein heteroaryl$^1$ is a 5, 6, 9 or 10 membered, mono or bicyclic, fully unsaturated group, comprising carbon ring atoms and 1, 2, 3 or 4 ring heteratoms independently selected from N, O and S, wherein the total number of S atoms does not exceed 1, and the total number of O atoms does not exceed 1.

E57 A compound according to any of E1 to E14 and E17 to E56 wherein heteroaryl$^1$ is a 5, 6, 9 or 10 membered, mono or bicyclic, fully unsaturated group, comprising carbon ring atoms and
1, 2, 3 or 4 ring N heteroatoms, or
1 ring S atom and optionally 1 ring N atom.

E58 A compound according to any of E1 to E13 and E17 to E57 wherein R$^4$ is
—(C$_0$-C$_2$)alkyl-heteroaryl$^1$, the heteroaryl$^1$ of said —(C$_0$-C$_4$)alkyl-heteroaryl$^1$ being optionally substituted by 1, 2, 3 or 4 substituents independently selected from —O—(C$_1$-C$_4$)alkyl, OH, cyano, (C$_1$-C$_4$)alkyl, halo, —NR$^9$(R$^{10}$).

E59 A compound according to any of E1 to E14 and E17 to E57 wherein R$^4$ is —(C$_0$-C$_2$)alkyl-pyridinone, —(C$_0$-C$_2$)alkyl-pyridindione, —(C$_0$-C$_2$)alkyl-pyrimidinone or —(C$_0$-C$_2$)alkyl-pyrimidindione, optionally substituted on the ring carbon atoms by 1, 2 or 3 substituents independently selected from —O—(C$_1$-C$_4$)alkyl, OH, cyano, (C$_1$-C$_4$)alkyl, halo, —NR$^9$(R$^{10}$).

E60 A compound according to any of E1 to E14 and E17 to E58 wherein heteroaryl$^1$ is pyrimidinyl, pyridinyl, imidazolyl, quinolinyl, pyrazolopyrimidinyl, indolyl, isoindolyl, dioxoisoindolyl, pyrazolyl, tetrazolyl, thiazolyl or pyrazolyl.

E61 A compound according to any of E1 to E15, E17 to E58 and E60 wherein heteroaryl$^1$ is pyrimidinyl or pyridinyl.

E62 A compound according to any of E1 to E15, E17 to E58 and E60 to E61 wherein heteroaryl$^1$ is pyrimidinyl.

E63 A compound according to any of E1 to E12, E14 and E17 to E62 wherein heteroaryl$^2$ is 5 or 6 membered fully unsaturated monocyclic group comprising ring carbon atoms and 1, 2, 3 or 4 ring N heteroatoms.

E64 A compound according to any of E1 to E12 and E17 to E63 wherein heteroaryl$^2$ is tetrazole or imidazole.

E65 A compound according to any of E1 to E12, E14 and E17 to E64 wherein (C$_3$-C$_6$)cycloalkyl is cyclopropyl or cyclohexyl.

E66 A compound according to any of E1 to E65 wherein the compound of formula (I) has the stereochemistry shown in formula (Ia):

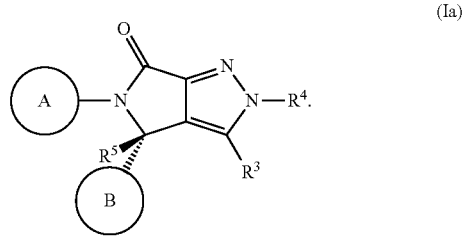

E67 A compound according to any of E1 to E65 wherein the compound of formula (I) has the stereochemistry shown in formula (Ib):

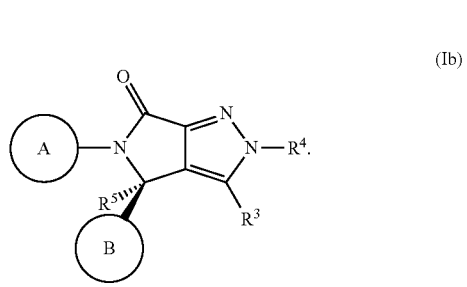

E68 A compound according to E1 selected from:

Example 1

5-(3-Chloro-2-fluoro-phenyl)-4-(4-chloro-2-methyl-phenyl)-3-isopropyl-2-pyridin-2-ylmethyl-4,5-dihydro-2H-pyrrolo[3,4-c]pyrazol-6-one;

Example 2

5-(3-Chloro-2-fluoro-phenyl)-4-(4-chloro-2-methyl-phenyl)-3-isopropyl-2-pyridin-3-ylmethyl-4,5-dihydro-2H-pyrrolo[3,4-c]pyrazol-6-one;

Example 3

5-(3-Chloro-2-fluoro-phenyl)-4-(4-chloro-2-methyl-phenyl)-2-[2-(1H-imidazol-4-yl)-ethyl]-3-isopropyl-4,5-dihydro-2H-pyrrolo[3,4-c]pyrazol-6-one;

Example 4

5-(3-Chloro-2-fluoro-phenyl)-4-(4-chloro-2-methyl-phenyl)-3-isopropyl-2-(3-methyl-butyl)-4,5-dihydro-2H-pyrrolo[3,4-c]pyrazol-6-one;

Example 5

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-1H-quinolin-2-one;

Example 6

7-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-5-oxo-4,5-dihydro-pyrazolo[1,5-a]pyrimidine-3-carbonitrile;

Example 7

5-(3-Chloro-2-fluoro-phenyl)-4-(4-chloro-2-methyl-phenyl)-3-isopropyl-2-(3-methyl-but-2-enyl)-4,5-dihydro-2H-pyrrolo[3,4-c]pyrazol-6-one;

Example 8

5-(3-Chloro-2-fluoro-phenyl)-4-(4-chloro-2-methyl-phenyl)-3-isopropyl-2-(2-pyridin-2-yl-ethyl)-4,5-dihydro-2H-pyrrolo[3,4-c]pyrazol-6-one;

Example 9

5-(3-Chloro-2-fluoro-phenyl)-4-(4-chloro-2-methyl-phenyl)-2-[2-(1H-indol-3-yl)-ethyl]-3-isopropyl-4,5-dihydro-2H-pyrrolo[3,4-c]pyrazol-6-one;

Example 10

2-{2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-ethyl}-isoindole-1,3-dione;

Example 11

5-(3-Chloro-2-fluoro-phenyl)-4-(4-fluoro-phenyl)-3-isopropyl-2-(3-methyl-butyl)-4,5-dihydro-2H-pyrrolo[3,4-c]pyrazol-6-one;

Example 12

5-(3-Chloro-2-fluoro-phenyl)-4-(3,4-difluoro-phenyl)-3-isopropyl-2-(3-methyl-butyl)-4,5-dihydro-2H-pyrrolo[3,4-c]pyrazol-6-one;

Example 13

5-(3-Chloro-2-fluoro-phenyl)-4-(4-chloro-phenyl)-2-[2-(3-ethyl-2-oxo-imidazolidin-1-yl)-ethyl]-3-isopropyl-4,5-dihydro-2H-pyrrolo[3,4-c]pyrazol-6-one;

Example 14

4-(4-Chloro-2-methyl-phenyl)-5-(5-chloro-2-methyl-phenyl)-3-isopropyl-2-oxiranylmethyl-4,5-dihydro-2H-pyrrolo[3,4-c]pyrazol-6-one;

Example 15

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-pyrrolidine-1-carboxylic acid tert-butyl ester;

Example 16

5-(3-Chloro-2-fluoro-phenyl)-4-(4-chloro-phenyl)-2-(2,5-dimethyl-2H-pyrazol-3-ylmethyl)-3-isopropyl-4,5-dihydro-2H-pyrrolo[3,4-c]pyrazol-6-one;

Example 17

5-(3-Chloro-2-fluoro-phenyl)-4-(4-chloro-phenyl)-2-(1H-imidazol-2-ylmethyl)-3-isopropyl-4,5-dihydro-2H-pyrrolo[3,4-c]pyrazol-6-one;

Example 18

5-(3-Chloro-2-fluoro-phenyl)-4-(4-chloro-phenyl)-3-isopropyl-2-(1H-tetrazol-5-ylmethyl)-4,5-dihydro-2H-pyrrolo[3,4-c]pyrazol-6-one;

Example 19

4-(4-Chloro-2-methyl-phenyl)-5-(5-chloro-2-methyl-phenyl)-2-[2-(4-hydroxy-piperidin-1-yl)-2-oxo-ethyl]-3-isopropyl-4,5-dihydro-2H-pyrrolo[3,4-c]pyrazol-6-one;

Example 20

4-(4-Chloro-2-methyl-phenyl)-5-(5-chloro-2-methyl-phenyl)-2-{2-[4-(2-hydroxy-ethyl)-piperidin-1-yl]-2-oxo-ethyl}-3-isopropyl-4,5-dihydro-2H-pyrrolo[3,4-c]pyrazol-6-one;

Example 21

N-(1-Acetyl-piperidin-4-yl)-2-[4-(4-chloro-2-methyl-phenyl)-5-(5-chloro-2-methyl-phenyl)-3-isopropyl-6-oxo-5,6,-dihydro-4H-pyrrolo[3,4-c]pyrazol-2-yl]acetamide;

Example 22

2-[2-(4-Acetyl-piperazin-1-yl)-2-oxo-ethyl]-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 23

4-(4-Chloro-2-methyl-phenyl)-5-(5-chloro-2-methyl-phenyl)-3-isopropyl-2-[2-oxo-2-(3-oxo-piperazin-1-yl)-ethyl]-4,5-dihydro-2H-pyrrolo[3,4-c]pyrazol-6-one;

Example 24

4-(4-Chloro-2-methyl-phenyl)-5-(5-chloro-2-methyl-phenyl)-3-isopropyl-2-[2-(4-methyl-3-oxo-piperazin-1-yl)-2-oxo-ethyl]-4,5-dihydro-2H-pyrrolo[3,4-c]pyrazol-6-one;

Example 25

2-(1-Acetyl-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 26

4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-piperidine-1-carboxylic acid isopropylamide;

Example 27

2-Allyl-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 28

4-(4-Chloro-2-methyl-phenyl)-5-(5-chloro-2-methyl-phenyl)-2-(2,3-dihydroxy-propyl)-3-isopropyl-4,5-dihydro-2H-pyrrolo[3,4-c]pyrazol-6-one;

Example 29

2-(1-Acetyl-4-hydroxy-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 30

4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-4-hydroxy-piperidine-1-carboxylic acid isopropylamide;

Example 31

5-(3-Chloro-2-fluoro-phenyl)-4-(4-chloro-2-methyl-phenyl)-3-isopropyl-2-phenethyl-4,5-dihydro-2H-pyrrolo[3,4-c]pyrazol-6-one;

Example 32

5-(3-Chloro-2-fluoro-phenyl)-4-(4-chloro-2-methyl-phenyl)-2-(2-dimethylamino-ethyl)-3-isopropyl-4,5-dihydro-2H-pyrrolo[3,4-c]pyrazol-6-one;

Example 33

2-[4-(4-Chloro-phenyl)-5-(3,4-difluoro-phenyl)-3-isopropyl-6-oxo-5,6-dihydro-4H-pyrrolo[3,4-c]pyrazol-2-ylmethyl]-benzonitrile;

Example 34

5-(3-Chloro-2-fluoro-phenyl)-4-(4-chloro-2-methyl-phenyl)-3-isopropyl-2-(2-methyl-thiazol-4-ylmethyl)-4,5-dihydro-2H-pyrrolo[3,4-c]pyrazol-6-one;

Example 35

5-(3-Chloro-2-fluoro-phenyl)-4-(4-chloro-2-methyl-phenyl)-3-isopropyl-2-(2-methoxy-ethyl)-4,5-dihydro-2H-pyrrolo[3,4-c]pyrazol-6-one;

Example 36

5-(3-Chloro-2-fluoro-phenyl)-4-(4-chloro-2-methyl-phenyl)-3-isopropyl-2-pyridin-4-ylmethyl-4,5-dihydro-2H-pyrrolo[3,4-c]pyrazol-6-one;

Example 37

5-(3-Chloro-2-fluoro-phenyl)-4-(4-chloro-2-methyl-phenyl)-3-isopropyl-2-thiazol-4-ylmethyl-4,5-dihydro-2H-pyrrolo[3,4-c]pyrazol-6-one;

Example 38

4-(4-Chloro-2-methyl-phenyl)-5-(5-chloro-2-methyl-phenyl)-3-isopropyl-2-(2-methoxy-ethyl)-4,5-dihydro-2H-pyrrolo[3,4-c]pyrazol-6-one;

Example 39

4-(4-Chloro-2-methyl-phenyl)-5-(5-chloro-2-methyl-phenyl)-3-isopropyl-2-pyridin-2-ylmethyl-4,5-dihydro-2H-pyrrolo[3,4-c]pyrazol-6-one;

Example 40

2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-N-methyl-acetamide;

Example 41

5-(3-Chloro-2-fluoro-phenyl)-4-(4-chloro-2-methyl-phenyl)-3-cyclopropyl-2-(3-methyl-butyl)-4,5-dihydro-2H-pyrrolo[3,4-c]pyrazol-6-one;

Example 42

5-(3-Chloro-2-fluoro-phenyl)-4-(4-chloro-2-methyl-phenyl)-2-(3-hydroxy-propyl)-3-isopropyl-4,5-dihydro-2H-pyrrolo[3,4-c]pyrazol-6-one;

Example 43

4-(4-Chloro-2-methyl-phenyl)-5-(5-chloro-2-methyl-phenyl)-3-isopropyl-2-(2-oxo-2-pyrrolidin-1-yl-ethyl)-4,5-dihydro-2H-pyrrolo[3,4-c]pyrazol-6-one;

Example 44

4-(4-Chloro-2-methyl-phenyl)-5-(5-chloro-2-methyl-phenyl)-3-isopropyl-2-(tetrahydro-furan-2-ylmethyl)-4,5-dihydro-2H-pyrrolo[3,4-c]pyrazol-6-one;

Example 45

4-(4-Chloro-2-methyl-phenyl)-5-(5-chloro-2-methyl-phenyl)-3-isopropyl-2-[2-(4-methyl-piperazin-1-yl)-ethyl]-4,5-dihydro-2H-pyrrolo[3,4-c]pyrazol-6-one;

Example 46

5-(3-Chloro-2-fluoro-phenyl)-4-(4-chloro-2-methyl-phenyl)-2-(2-hydroxy-2-methyl-propyl)-3-isopropyl-4,5-dihydro-2H-pyrrolo[3,4-c]pyrazol-6-one;

Example 47

5-[5-Chloro-2-(2-dimethylamino-ethoxy)-phenyl]-4-(4-chloro-2-methyl-phenyl)-2-ethyl-3-isopropyl-4,5-dihydro-2H-pyrrolo[3,4-c]pyrazol-6-one;

Example 48

4-(4-Chloro-2-methyl-phenyl)-5-(5-chloro-2-methyl-phenyl)-3-isopropyl-2-[2-(2-oxo-pyrrolidin-1-yl)-ethyl]-4,5-dihydro-2H-pyrrolo[3,4-c]pyrazol-6-one;

Example 49

2-Benzyl-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 50

4-(4-Chloro-2-methyl-phenyl)-5-(5-chloro-2-methyl-phenyl)-3-isopropyl-2-(4-methyl-piperazine-1-carbonyl)-4,5-dihydro-2H-pyrrolo[3,4-c]pyrazol-6-one;

Example 51

4-(4-Chloro-2-methyl-phenyl)-5-(5-chloro-2-methyl-phenyl)-3-isopropyl-6-oxo-5,6-dihydro-4H-pyrrolo[3,4-c]pyrazole-2-carboxylic acid methyl-phenyl-amide;

Example 52

(2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid methyl ester;

Example 53

(2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid dimethylamide;

Example 54

2-((2S)-1-Acetyl-pyrrolidin-2-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 55

2-Benzyl-5-(3-chloro-2-fluoro-phenyl)-4-(4-chloro-2-methyl-phenyl)-3-isopropyl-4,5-dihydro-2H-pyrrolo[3,4-c]pyrazol-6-one;

Example 56

5-(3-Chloro-2-fluoro-phenyl)-4-(4-chloro-2-methyl-phenyl)-2-cyclohexylmethyl-3-isopropyl-4,5-dihydro-2H-pyrrolo[3,4-c]pyrazol-6-one;

Example 57

5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 58

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile;

Example 59

5-(3-Chloro-2-fluoro-phenyl)-4-(4-chloro-2-methyl-phenyl)-2-(2-fluoro-phenyl)-3-isopropyl-4,5-dihydro-2H-pyrrolo[3,4-c]pyrazol-6-one;

Example 60

5-(3-Chloro-2-fluoro-phenyl)-4-(2,4-dichloro-phenyl)-2-(2-hydroxy-ethyl)-3-isopropyl-4,5-dihydro-2H-pyrrolo[3,4-c]pyrazol-6-one;

Example 61

C-{4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-phenyl}-N-methyl-methanesulfonamide;

Example 62

5-(3-Chloro-2-fluoro-phenyl)-4-(4-chloro-2-methyl-phenyl)-3-isopropyl-2-(1-methyl-piperidin-4-yl)-4,5-dihydro-2H-pyrrolo[3,4-c]pyrazol-6-one;

Example 63

5-(3-Chloro-2-fluoro-phenyl)-4-(4-chloro-2-methyl-phenyl)-2-(4-chloro-phenyl)-3-isopropyl-4,5-dihydro-2H-pyrrolo[3,4-c]pyrazol-6-one;

Example 64

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzamide;

Example 65

4-(4-Chloro-3-fluoro-phenyl)-5-(3-chloro-2-fluoro-phenyl)-2-(2-hydroxy-ethyl)-3-isopropyl-4,5-dihydro-2H-pyrrolo[3,4-c]pyrazol-6-one;

Example 66

5-(3-Chloro-2-fluoro-phenyl)-4-(4-fluoro-phenyl)-3-isopropyl-2-(2-methoxy-phenyl)-4,5-dihydro-2H-pyrrolo[3,4-c]pyrazol-6-one;

Example 67

5-(3-Chloro-2-fluoro-phenyl)-4-(3,4-difluoro-phenyl)-3-isopropyl-2-(2-methoxy-phenyl)-4,5-dihydro-2H-pyrrolo[3,4-c]pyrazol-6-one;

Example 68

5-(3-Chloro-2-fluoro-phenyl)-4-(4-chloro-phenyl)-3-isopropyl-2-pyridin-4-yl-4,5-dihydro-2H-pyrrolo[3,4-c]pyrazol-6-one;

Example 69

5-(3-Chloro-2-fluoro-phenyl)-3-isopropyl-2-(2-methoxy-phenyl)-4-p-tolyl-4,5-dihydro-2H-pyrrolo[3,4-c]pyrazol-6-one;

Example 70

5-(3-Chloro-2-fluoro-phenyl)-4-(4-chloro-phenyl)-3-isopropyl-2-(2-methoxy-phenyl)-4,5-dihydro-2H-pyrrolo[3,4-c]pyrazol-6-one;

Example 71

6-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-1,3-dimethyl-1H-pyrimidine-2,4-dione;

Example 72

4-(4-Chloro-2-methyl-phenyl)-5-(5-chloro-2-methyl-phenyl)-3-isopropyl-2-(1-methyl-piperidin-4-yl)-4,5-dihydro-2H-pyrrolo[3,4-c]pyrazol-6-one;

Example 73

5-(3-Chloro-2-fluoro-phenyl)-4-(4-chloro-2-methyl-phenyl)-3-isopropyl-2-(tetrahydro-pyran-4-yl)-4,5-dihydro-2H-pyrrolo[3,4-c]pyrazol-6-one;

Example 74

5-(3-Chloro-2-fluoro-phenyl)-4-(4-chloro-phenyl)-3-isopropyl-2-(2-methoxy-phenyl)-4-(2-morpholin-4-yl-2-oxo-ethyl)-4,5-dihydro-2H-pyrrolo[3,4-c]pyrazol-6-one;

Example 75

5-(3-Chloro-2-fluoro-phenyl)-4-(4-chloro-2-methyl-phenyl)-2-(2-chloro-phenyl)-3-isopropyl-4,5-dihydro-2H-pyrrolo[3,4-c]pyrazol-6-one;

Example 76

5-(3-Chloro-2-fluoro-phenyl)-4-(4-chloro-2-methyl-phenyl)-3-isopropyl-2-(2-methoxy-phenyl)-4,5-dihydro-2H-pyrrolo[3,4-c]pyrazol-6-one;

Example 77

5-(3-Chloro-2-fluoro-phenyl)-4-(4-chloro-2-methyl-phenyl)-2-(2,4-difluoro-phenyl)-3-isopropyl-4,5-dihydro-2H-pyrrolo[3,4-c]pyrazol-6-one;

Example 78

3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-propionitrile;

Example 79

5-(3-Chloro-4-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 80

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-3-methyl-benzonitrile;

Example 81

5-(3-Chloro-2-fluoro-phenyl)-4-(4-chloro-2-methyl-phenyl)-3-cyclobutyl-2-(2-hydroxy-ethyl)-4,5-dihydro-2H-pyrrolo[3,4-c]pyrazol-6-one;

Example 82

3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile;

Example 83

4-(4-Chloro-2-methyl-phenyl)-5-(5-chloro-2-methyl-phenyl)-2-(2-hydroxy-ethyl)-3-isopropyl-4,5-dihydro-2H-pyrrolo[3,4-c]pyrazol-6-one;

Example 84

4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 85

5-(3-Chloro-2-fluoro-phenyl)-4-(4-chloro-2-methyl-phenyl)-3-cyclopropyl-2-(2-hydroxy-ethyl)-4,5-dihydro-2H-pyrrolo[3,4-c]pyrazol-6-one;

Example 86

5-(3-Chloro-2-fluoro-phenyl)-4-(4-chloro-2-methyl-phenyl)-3-cyclopropyl-2-(2-methoxy-phenyl)-4,5-dihydro-2H-pyrrolo[3,4-c]pyrazol-6-one;

Example 87

5-(5-Chloro-2,4-difluoro-phenyl)-4-(4-chloro-2-methyl-phenyl)-3-isopropyl-2-(2-methoxy-phenyl)-4,5-dihydro-2H-pyrrolo[3,4-c]pyrazol-6-one;

Example 88

5-(3-Chloro-4-fluoro-phenyl)-4-(4-chloro-phenyl)-3-isopropyl-2-(2-methoxy-phenyl)-4,5-dihydro-2H-pyrrolo[3,4-c]pyrazol-6-one;

Example 89

3-[5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazol-4-yl]-propionic acid methyl ester;

Example 90

5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazole-4-carboxylic acid ethyl ester;

Example 91

4-(4-Chloro-2-methyl-phenyl)-5-(5-chloro-pyridin-3-yl)-3-isopropyl-2-(2-methoxy-phenyl)-4,5-dihydro-2H-pyrrolo[3,4-c]pyrazol-6-one;

Example 92

5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 93

5-(3-Chloro-4-fluoro-phenyl)-4-(4-chloro-phenyl)-3-isopropyl-2-(2-methoxy-phenyl)-4-methyl-4,5-dihydro-2H-pyrrolo[3,4-c]pyrazol-6-one;

Example 94

5-(3-Chloro-2-fluoro-phenyl)-4-[4-chloro-2-(2-methoxy-ethoxymethyl)-phenyl]-3-isopropyl-2-(2-methoxy-phenyl)-4,5-dihydro-2H-pyrrolo[3,4-c]pyrazol-6-one;

Example 95

5-(3-Chloro-4-fluoro-phenyl)-4-(4-chloro-phenyl)-4-(2-hydroxy-3-pyrrolidin-1-yl-propyl)-3-isopropyl-2-(2-methoxy-phenyl)-4,5-dihydro-2H-pyrrolo[3,4-c]pyrazol-6-one;

Example 96

3-[5-(5-Chloro-2-methyl-phenyl)-3-isopropyl-6-oxo-4-(4-trifluoromethyl-phenyl)-5,6-dihydro-4H-pyrrolo[3,4-c]pyrazol-2-yl]-4,N-dimethyl-benzamide;

Example 97

5-(3-Chloro-4-fluoro-phenyl)-4-(5-chloro-pyridin-2-yl)-3-isopropyl-2-(2-methoxy-phenyl)-4,5-dihydro-2H-pyrrolo[3,4-c]pyrazol-6-one;

Example 98

5-(5-Chloro-2-methyl-phenyl)-4-(5-chloro-pyridin-2-yl)-3-isopropyl-2-(2-methoxy-phenyl)-4,5-dihydro-2H-pyrrolo[3,4-c]pyrazol-6-one;

Example 99

5-(3-Chloro-4-fluoro-phenyl)-4-(4-chloro-phenyl)-4-(2,3-dihydroxy-propyl)-3-isopropyl-2-(2-methoxy-phenyl)-4,5-dihydro-2H-pyrrolo[3,4-c]pyrazol-6-one;

Example 100

5-(3-Chloro-4-fluoro-phenyl)-4-(4-chloro-phenyl)-4-(2-hydroxy-ethyl)-3-isopropyl-2-(2-methoxy-phenyl)-4,5-dihydro-2H-pyrrolo[3,4-c]pyrazol-6-one;

Example 101

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-methyl-benzamide;

Example 102

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-(2-pyrrolidin-1-yl-ethyl)-benzamide;

Example 103

3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzonitrile;

Example 104

3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzamide;

Example 105

N-{3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-phenyl}-acetamide;

Example 106

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N,N-dimethyl-benzamide;

Example 107

4-(4-Chloro-phenyl)-5-(3,4-difluoro-phenyl)-3-isopropyl-2-(2-methoxy-phenyl)-4,5-dihydro-2H-pyrrolo[3,4-c]pyrazol-6-one;

Example 108

5-(5-Chloro-1-methyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one;

Example 109

5-(5-Chloro-1-ethyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one;

Example 110

5-(5-Chloro-1-methyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one;

Example 111

5-[5-Chloro-1-(2-hydroxy-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one;

Example 112

5-[5-Chloro-1-(2-methoxy-ethyl)-6-oxo-1,6-dihydro-pyridin-3-yl]-4-(4-chloro-2-methyl-phenyl)-3-isopropyl-2-(2-methoxy-phenyl)-4,5-dihydro-2H-pyrrolo[3,4-c]pyrazol-6-one;

Example 113

5-(5-Chloro-1-ethyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one;

Example 114

3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-N-methyl-benzamide;

Example 115

5-[5-Chloro-1-(2-dimethylamino-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one;

Example 116

5-(3-Chloro-2-fluoro-phenyl)-4-(4-chloro-2-methyl-phenyl)-2-cyclopropyl-3-isopropyl-4,5-dihydro-2H-pyrrolo[3,4-c]pyrazol-6-one;

Example 117

5-(3-Chloro-2-fluoro-phenyl)-4-(4-chloro-2-methyl-phenyl)-2-(4-hydroxy-cyclohexyl)-3-isopropyl-4,5-dihydro-2H-pyrrolo[3,4-c]pyrazol-6-one;

Example 118

4-(4-Chloro-2-methyl-phenyl)-5-(2-chloro-pyridin-4-yl)-3-isopropyl-2-(2-methoxy-phenyl)-4,5-dihydro-2H-pyrrolo[3,4-c]pyrazol-6-one;

Example 119

5-(2-Chloro-5-methoxy-pyridin-4-yl)-4-(4-chloro-2-methyl-phenyl)-3-isopropyl-2-(2-methoxy-phenyl)-4,5-dihydro-2H-pyrrolo[3,4-c]pyrazol-6-one;

Example 120

5-(3-Chloro-2-fluoro-phenyl)-4-(4-chloro-phenyl)-3-isopropyl-2-(1H-pyrazol-4-yl)-4,5-dihydro-2H-pyrrolo[3,4-c]pyrazol-6-one;

Example 121

5-(3-Chloro-2-fluoro-phenyl)-4-(4-chloro-phenyl)-3-isopropyl-2-(4-methoxy-pyridin-3-yl)-4,5-dihydro-2H-pyrrolo[3,4-c]pyrazol-6-one;

Example 122

4-(4-Chloro-2-methyl-phenyl)-5-(5-chloro-2-methyl-phenyl)-3-isopropyl-2-(4-methoxy-pyridin-3-yl)-4,5-dihydro-2H-pyrrolo[3,4-c]pyrazol-6-one;

Example 123

3-tert-Butyl-5-(3-chloro-2-fluoro-phenyl)-4-(4-chloro-phenyl)-4,5-dihydro-2H-pyrrolo[3,4-c]pyrazol-6-one;

Example 124

4-(4-Chloro-phenyl)-5-[5-chloro-2-(2H-tetrazol-5-yl-methoxy)-phenyl]-3-isopropyl-2-(2-methoxy-phenyl)-4,5-dihydro-2H-pyrrolo[3,4-c]pyrazol-6-one;

Example 125

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzonitrile;

Example 126

2-(5-Aminomethyl-2-methoxy-phenyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 127

N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-acetamide;

Example 128

N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-formamide;

Example 129

3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzonitrile;

Example 130

2-(5-Aminomethyl-2-methoxy-phenyl)-5-(5-chloro-1-methyl-6-oxo-1,6-dihydro-pyridin-3-yl)-4-(4-chloro-2-methyl-phenyl)-3-isopropyl-4,5-dihydro-2H-pyrrolo[3,4-c]pyrazol-6-one;

Example 131

N-3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzyl}-acetamide;

Example 132

5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 133

4-(4-Chloro-2-methyl-phenyl)-5-(5-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 134

4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-5-methoxy-pyridine-2-carbonitrile;

Example 135

4-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-5-methoxy-pyridine-2-carbonitrile;

Example 136

3-[5-(5-Chloro-2-methyl-phenyl)-4-(4-cyano-phenyl)-3-isopropyl-6-oxo-5,6-dihydro-4H-pyrrolo[3,4-c]pyrazol-2-yl]-4-methoxy-benzonitrile;

Example 137

3-[5-(5-Chloro-1-methyl-6-oxo-1,6-dihydro-pyridin-3-yl)-4-(4-cyano-2-methyl-phenyl)-3-isopropyl-6-oxo-5,6-dihydro-4H-pyrrolo[3,4-c]pyrazol-2-yl]-4-methoxy-benzonitrile;

Example 138

3-[5-(5-Chloro-2-methyl-phenyl)-4-(4-cyano-2-methyl-phenyl)-3-isopropyl-6-oxo-5,6-dihydro-4H-pyrrolo[3,4-c]pyrazol-2-yl]-4-methoxy-benzonitrile;

Example 139

(S)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 140

(R)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 141

(S)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 142

(R)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 143

(S)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 144

(R)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 145

5-(5-Chloro-1-methyl-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 146

5-(5-Chloro-1-methyl-2-oxo-1,2-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 147

5-(5-Chloro-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 148

5-(5-Chloro-1-methyl-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 149

5-(5-Chloro-1-methyl-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 150

4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 151

4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 152

5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 153

(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 154

(R)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 155

5-(5-Chloro-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 156

5-(5-Chloro-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 157

4-[5-(5-Chloro-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 158

4-[5-(5-Chloro-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 159

4-[5-(5-Chloro-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 160

4-[5-(5-Chloro-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 161

4-[5-(5-Chloro-1-methyl-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 162

4-[5-(5-Chloro-1-methyl-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 163

5-(5-Chloro-1-methyl-2-oxo-1,2-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 164

5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 165

5-(5-Chloro-2-oxo-1,2-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 166

5-(5-Chloro-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 167

(R)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 168

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 169

4-[5-(5-Chloro-1-methyl-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile;

Example 170

4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 171

4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 172

5-(5-Chloro-1-methyl-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 173

4-[5-(5-Chloro-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile;

Example 174

4-[5-(5-Chloro-1-methyl-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile;

Example 175

4-[5-(5-Chloro-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile;

Example 176

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 177

(R)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 178

(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 179

(R)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 180

((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;

Example 181

((R)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;

Example 182

(R)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 183

(S)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 184

5-(5-Chloro-1-methyl-6-oxo-1,6-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one;

Example 185

5-(5-chloro-1-methyl-2-oxo-1,2-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one;

Example 186

5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one;

Example 187

5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one;

Example 188

4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile;

Example 189

4-(5-(5-chloro-1-methyl-2-oxo-1,2-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-2-fluorobenzonitrile;

Example 190

4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile;

Example 191

4-(5-(5-chloro-1-methyl-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 192

4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 193

4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 194

4-(5-(5-Chloro-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 195

5-(5-Chloro-1-methyl-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 196

5-(5-Chloro-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 197

5-(5-Chloro-1-methyl-6-oxo-1,6-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 198

4-(4-Chloro-3-fluorophenyl)-5-(5-chloro-6-oxo-1,6-dihydropyridin-3-yl)-2-(2-(dimethylamino)-4-methoxypyrimidin-5-yl)-3-isopropyl-4,5-dihydropyrrolo[3,4-c]pyrazol-6(2H)-one;

Example 199

4-(4-Chlorophenyl)-2-(2,4-dimethoxypyrimidin-5-yl)-5-(1,5-dimethyl-2-oxo-1,2-dihydropyridin-3-yl)-3-isopropyl-4,5-dihydropyrrolo[3,4-c]pyrazol-6(2H)-one; and Example 200

4-(4-chlorophenyl)-5-(1,5-dimethyl-2-oxo-1,2-dihydropyridin-3-yl)-2-(2-(dimethylamino)-4-methoxypyrimidin-5-yl)-3-isopropyl-4,5-dihydropyrrolo[3,4-c]pyrazol-6(2H)-one;

or a salt thereof.

E69 A compound according to either of E1 or E68 selected from:

Example 132

5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 147

5-(5-Chloro-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 150

4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 151

4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 152

5-(5-Chloro-2-oxo-1,2-dihydro-pyridin-3-yl)-4-(4-chlorophenyl)-2-(2,4-dimethoxy-pyrimidin-5-yl)-3-isopropyl-4,5-dihydro-2H-pyrrolo[3,4-c]pyrazol-6-one;

Example 153

(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 157

4-[5-(5-Chloro-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 161

4-[5-(5-Chloro-1-methyl-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 164

5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 168

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 171

4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 176

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 178

(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 180

((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;

Example 183

(S)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 187

5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one;

Example 195

5-(5-Chloro-1-methyl-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 197

5-(5-Chloro-1-methyl-6-oxo-1,6-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 198

4-(4-Chloro-3-fluorophenyl)-5-(5-chloro-6-oxo-1,6-dihydropyridin-3-yl)-2-(2-(dimethylamino)-4-methoxypyrimidin-5-yl)-3-isopropyl-4,5-dihydropyrrolo[3,4-c]pyrazol-6(2H)-one; and Example 200

4-(4-chlorophenyl)-5-(1,5-dimethyl-2-oxo-1,2-dihydropyridin-3-yl)-2-(2-(dimethylamino)-4-methoxypyrimidin-5-yl)-3-isopropyl-4,5-dihydropyrrolo[3,4-c]pyrazol-6(2H)-one;
or a salt thereof.
E70 A compound according to any of E1, E68 or E69 selected from:

Example 132

5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 147

5-(5-Chloro-2-oxo-1,2-dihydro-pyridin-3-yl)-4-(4-chlorophenyl)-2-(2-dimethylamino-4-methoxy-pyrimidin-5-yl)-3-isopropyl-4,5-dihydro-2H-pyrrolo[3,4-c]pyrazol-6-one;

Example 150

4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 152

5-(5-Chloro-2-oxo-1,2-dihydro-pyridin-3-yl)-4-(4-chlorophenyl)-2-(2,4-dimethoxy-pyrimidin-5-yl)-3-isopropyl-4,5-dihydro-2H-pyrrolo[3,4-c]pyrazol-6-one;

Example 153

(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 164

5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 168

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 176

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 178

(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile; and Example 180

((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;
or a salt thereof.
E71 A compound according to any of E1, E68, E69 or E70 selected from:

Example 153

(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 168

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 176

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 178

(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile; and Example 180

((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;
or a salt thereof.
E72 A compound according to any of E1 or E68 to E71 which is a crystalline form of (S)-5-(5-chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one; and (S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile.

E73 A compound according to any of E1 or E68 to E72 which is a crystalline form of (S)-5-(5-chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one having a powder X-ray diffraction pattern using Cu radiation at a wavelength of 1.5406 A which includes the peaks 7.4, 12.7, 22.5 and 27.3 angle 2-Theta®, with an error+/−0.2°.

E74 A compound according to any of E1 or E68 to E73 which is a crystalline form of (S)-5-(5-chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one having a powder X-ray diffraction pattern using Cu radiation at a wavelength of 1.5406 A which is substantially the same as the powder X-ray diffraction pattern shown in FIG. 1 herein.

E75 A compound according to any of E1 or E68 to E72 which is a crystalline form of (S)-5-(5-chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one having a powder X-ray diffraction pattern using Cu radiation at a wavelength of 1.5406 A which includes the peaks 8.8, 9.96, 11.6 and 21.9 angle 2-Theta®, with an error+/−0.2°.

E76 A compound according to any of E1, E68 to E72 or E75 which is a crystalline form of (S)-5-(5-chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one having a powder X-ray diffraction pattern using Cu radiation at a wavelength of 1.5406 A which is substantially the same as the powder X-ray diffraction pattern shown in FIG. 2 herein.

E77 A compound according to any of E1 or E68 to E72 which is a crystalline form of (S)-5-(5-chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one having a powder X-ray diffraction pattern using Cu radiation at a wavelength of 1.5406 A which includes the peaks 9.5, 11.1, 11.8 and 30.2 angle 2-Theta®, with an error+/−0.2°.

E78 A compound according to any of E1, E68 to E72 or E77 which is a crystalline form of (S)-5-(5-chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one having a powder X-ray diffraction pattern using Cu radiation at a wavelength of 1.5406 A which is substantially the same as the powder X-ray diffraction pattern shown in FIG. 3 herein.

E79 A compound according to any of E1 or E68 to E72 which is a crystalline form of (S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile having a powder X-ray diffraction pattern using Cu radiation at a wavelength of 1.5406 A which includes the peaks 9.96, 14.2, 16.2 and 24.6 angle 2-Theta®, with an error +/−0.2°.

E80 A compound according to any of E1, E68 to E72 or E79 which is a crystalline form of (S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile having a powder X-ray diffraction pattern using Cu radiation at a wavelength of 1.5406 A which is substantially the same as the powder X-ray diffraction pattern shown in FIG. 4 herein.

E81 A compound according to any of E73 to E80 in substantially pure form.

As used herein, the term "substantially pure" with reference to a particular polymorphic form means that the polymorphic form includes less than 10%, preferably less than 5%, more preferably less than 3%, most preferably less than 1% by weight of any other physical forms (polymorphs) of the compound.

As used herein "polymorph" refers to crystalline forms having the same chemical composition but different spatial arrangements of the molecules, atoms, and/or ions forming the crystal.

For purposes of interpreting this specification, terms used in the singular will also include the plural and vice versa.

In the above definitions, halo means fluoro, chloro or bromo, particularly fluoro or chloro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

"$(C_0-C_x)$alkyl" means that the alkyl has from 0 carbon atoms, in which case the alkyl group is not present and instead is a bond, or is an alkyl group containing up to and including 'x' carbon atoms.

For example "$(C_0-C_4)$alkyl" whenever present, denotes a bond ($C_0$ alkyl), $C_1$ alkyl, $C_2$ alkyl, $C_3$ alkyl or $C_4$ alkyl.

For example "$(C_0-C_2)$alkyl" whenever present, denotes a bond ($C_0$ alkyl), $C_1$ alkyl or $C_2$ alkyl.

As a further example, "—$(C_0-C_4)$alkyl-phenyl" includes the following alternatives:
- phenyl (alternatively written as —$(C_0)$alkyl-phenyl, where $(C_0)$alkyl is a bond),
- —CH$_2$-phenyl,
- —CH$_2$CH$_2$-phenyl,
- —CH$_2$CH$_2$CH$_2$-phenyl,
- —CH$_2$CH$_2$CH$_2$CH$_2$-phenyl, and also includes the branched alkyl variants of this list.

—$(C_0-C_x)$alkyl can therefore denote a bond or an alkyl group, said alkyl including straight chain and branched chain alternatives where the number of carbon atoms allows.

'=O' means an oxo substituent.

Specific preferred compounds according to the invention are those listed in the Examples section below As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, H DM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Research Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)—, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In another embodiment, the invention provides a pharmaceutical composition comprising a therapeutically effective amount of a compound of formula (I) or salt thereof as defined herein, and one or more pharmaceutically acceptable carriers.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

Compounds of the invention are believed to be useful in the treatment of a disease based on dysregulation of cell cycle, such as a proliferative disorder or disease, for example cancer or tumour diseases. In particular, such diseases or disorders include benign or malignant tumors, a soft tissue sarcoma or a sarcoma such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, meningioma, glioma, mesothelioma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma, such as of B- or T-cell origin, and metastases in other organs), viral infections (e.g. herpes, papilloma, HIV, Kaposi's, viral hepatitis).

Compounds of the invention are also believed to be useful in the treatment of or a disorder or disease involving the immune system, in particular autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin or hyperproliferative disorders, (e.g. Li-Fraumeni syndrome).

In another embodiment there is provided a compound of the formula (I) or salt thereof as defined herein, for use as a pharmaceutical.

A further embodiment provides a compound of the formula (I) or salt thereof as defined herein, for use in the treatment of a disorder or a disease mediated by the activity of MDM2 and/or MDM4.

A still further embodiment provides the use of a compound of formula (I) or salt thereof as defined herein, for the manufacture of a medicament for the treatment of a disorder or a disease in a subject mediated by the activity of MDM2 and/or MDM4.

As a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein.

In another embodiment, the invention provides a method of treating a disease or disorder which is treated by inhibition of the MDM2/p53 and/or MDM4/p53 interaction, comprising administration of a therapeutically acceptable amount of a compound of formula (I) or salt thereof, in particular a method of treating the diseases or disorders listed herein.

A further embodiment provides a method of modulating MDM2 and/or MDM4 activity in a subject, comprising the step of administering to a subject a therapeutically effective amount of a compound of formula (I) or salt thereof as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topo-tecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemeterxed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825);

i) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr <1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235 or BKM120;

n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α-γ- or δ-tocopherol or α-γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TK1258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™), rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2"-alphahydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Aced Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In another embodiment, the invention provides a compound of the formula (I) or salt thereof as defined herein, in combination with one or more therapeutically active agents.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I).

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

Typically, the compounds of formula (I) can be prepared according to the Schemes provided infra.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The following examples are intended to illustrate the invention and are not to be construed as being limitations thereon. Temperatures are given in degrees centrigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Abbreviations
API atmospheric pressure ionization
AD-mix commercially available mixture of reagents, available as α and β forms.
aq. aqueous
Boc tert-butoxycarbonyl
Brine saturated (at rt) sodium chloride solution
br. s broad singlet
$CH_2Cl_2$ dichloromethane
DIEA diisopropyl ethyl amine
DMAP 4-dimethylaminopyridine
DMF N,N-dimethylformamide
DMSO dimethylsulfoxide
EDCI 1-[3-(dimethylamino)propyl]-3-ethyl carbodiimide
ES-MS electrospray mass spectrometry
Et ethyl
EtOAc ethyl acetate
EtOH ethanol
h hour(s)
HATU 0-(7-azabenzotriazol-1-yl)-N,N,N',N'-tetramethyluronium-hexafluorophosphate
HCl hydrogen chloride
HOBt 1-hydroxybenzotriazole
HPLC high-performance liquid chromatography
KHMDS potassium hexamethyldisilazide
$K_3PO_4$ potassium phosphate
Me methyl
MeOH methanol
$MgSO_4$ magnesium sulfate
min minute(s)
mL milliliter(s)
MS Mass Spectrometry NaH sodium hydride
NaHCO$_3$ sodium bicarbonate
NaOH sodium hydroxide
Na$_2$SO$_4$ sodium sulfate
Na$_2$S$_2$O$_3$ sodium thiosulfate
NMR nuclear magnetic resonance
Pd(PPh$_3$)$_4$ tetrakis(triphenylphosphine)palladium(0)
Ph phenyl
R$_f$ ratio of fronts
rt (or RT) room temperature
t$_R$ time of retention
TBAF tetrabutylammonium fluoride
TFA trifluoroacetic acid
THF tetrahydrofuran In the following generic schemes only, R substituents are referred to as follows:

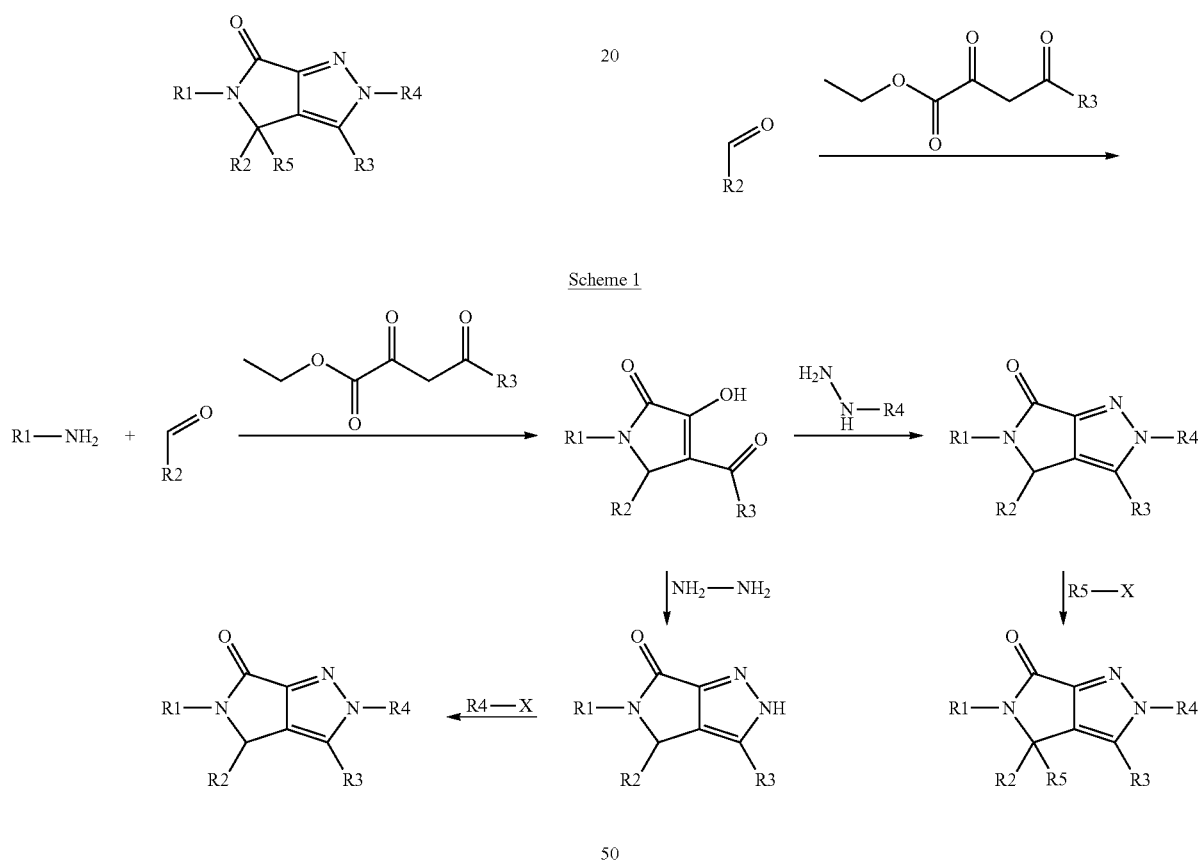

Scheme 1 illustrates one method of preparing compounds of the invention (e.g. example 1). The condensation of a representative aniline, a benzaldehyde, and a 2,4-dioxo-alkanoic acid ethyl ester is carried out in pure acetic acid or in a mixture of toluene, dioxane, and acetic acid at elevated temperatures (typically 110-130° C.). The cyclization with hydrazines requires heating and is performed in a 3:1 mixture of acetic acid and ethanol. When the simple hydrazine hydrochloride is used, the corresponding products may undergo alkylation on the pyrazole ring by reaction with suitable electrophiles (e.g. alkyl-, heteroaryl-halides, acid halides, epoxides, and carbamic chlorides). These alkylations are conducted in DMF in the presence of a base (typically sodium hydride or potassium carbonate). Alkylation of the sp3 C(4) of the pyrrolidinone ring is accomplished by using KHMDS at low temperature (−78° C.) in THF.

Scheme 2

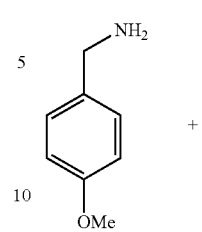

+

-continued

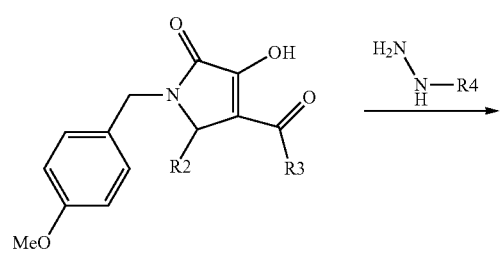

-continued

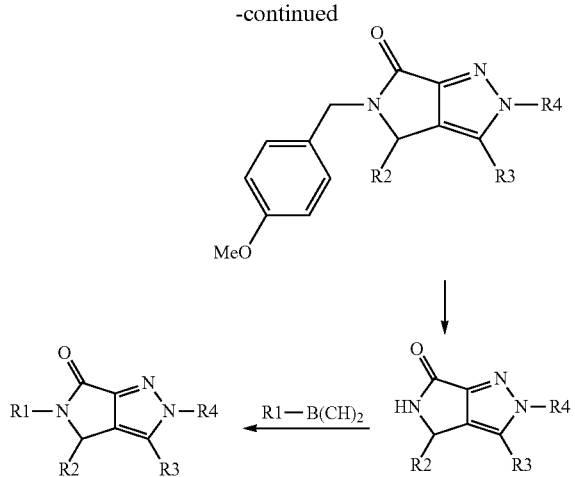

Scheme 2 illustrates a modification of the method shown in Scheme 1 of preparing compounds of the invention (e.g. examples 118, 119).

This method is similar to the one describe in Scheme 1 except that 4-methoxy-benzylamine is used instead of the anilines. The 4-methoxy-benzyl group is removed by treatment with ceric ammonium nitrate in acetonitrile and water at rt. The subsequent cross-coupling reaction of the resulting cyclic amide (pyrrolidinone) is carried out with a (hetero)aryl boronic acid or ester in the presence of copper(II) acetate and triethyl amine (Chan-Lam's or Lam-Chan's conditions). Alternatively, the cross-coupling reaction is conducted following Buchwald's condition for the C—N amidation reaction, typically following Buchwald literature procedure (A. Klapars, Xiaohua Huang, S. L. Buchwald; *J. Am. Chem. Soc.*, 2002, 124, 7421). Under an inert argon atmosphere and using degassed aprotic solvents encompassing toluene, dioxane, THF and DMF, but typically dioxane, the starting materials (pyrazolo-pyrrolidinone and (hetero)aryl halide) are mixed in the presence of a copper source, such as Cu powder, CuI, CuCN, $Cu_2O$, $CuCl_2$, but typically CuI and an diamine ligand, such as ethylenediamine, or other 1,2-diamine ligands, but typically trans-1,2-cyclohexanediamine in the presence of a base, such as $K_3PO_4$, $K_2CO_3$ or $CsCO_3$, but typically $K_3PO_4$. The reaction is heated to reflux and stirred for 4 to 48 hours depending the progress of the reaction.

Scheme 3

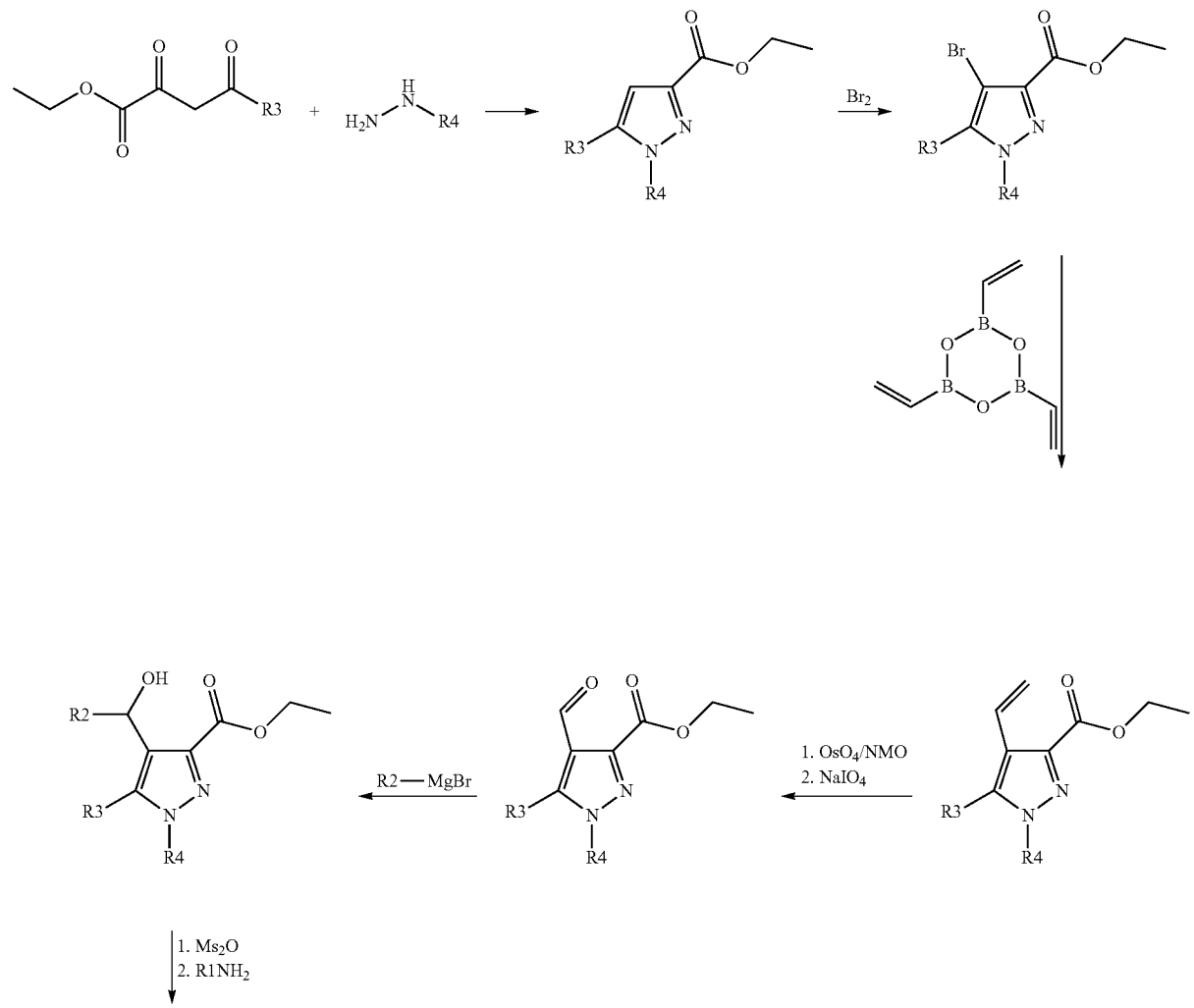

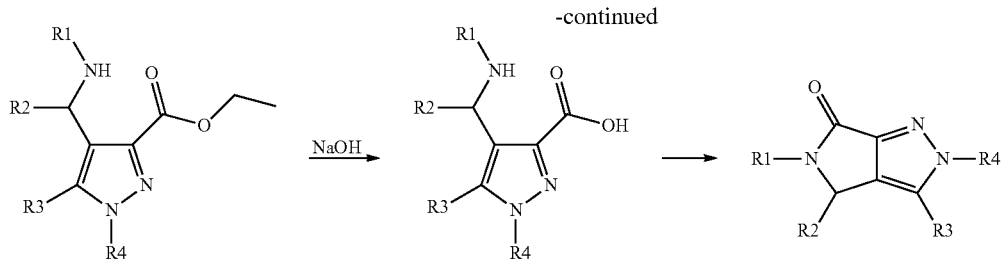

Scheme 3 illustrates an alternative method of preparing compounds of the invention (e.g. examples 124-138).

The condensation of a representative hydrazine and 5-methyl-2,4-dioxo-hexanoic acid ethyl ester is carried out in a mixture of ethanol and toluene at 100° C. and under inert atmosphere. The resulting pyrazole is treated with bromine in dichloromethane at 0° C. under argon for the appropriate time (typically 1-3 h). The bromo-pyrazole is then coupled with vinylboronic anhydride pyridine complex under typical Suzuki cross-coupling reaction conditions. This reaction is performed under inert atmosphere using a mixture of dioxane and water as the solvent and in the presence of a base (typically potassium carbonate) and a palladium catalyst (e.g. bis(tri-t-butylphosphine)palladium(0)). Heating is required (80° C.). According to a one-pot protocol, the vinyl group is converted in a formyl group by dihydroxylation using a catalytic and a stoichiometric amount of osmium tetroxide and N-methylmorpholine oxide, respectively, and oxidative cleavage of the resulting diol intermediate by treatment with sodium periodate. The subsequent addition of the aryl Grignard reagent to the aldehyde is carried out at −10° C. and provides the corresponding alcohol. Conversion of the alcohol into the secondary amine is achieved by reaction of the alcohol with methanesulfonic anhydride in dichloromethane and in the presence of triethylamine at rt, followed by addition of the aniline. Standard saponification of the pyrazole ethyl ester and intramolecular amide coupling give the compounds of the invention.

HPLC Methods:

HPLC 1:
Column: Chromolith RP18 3×100 mm. Flow: 1.3 mL/min. Gradient: 2% to 100% B in 6 min; A=0.1% TFA in water, B=0.1% TFA in acetonitrile HPLC 2:
Column: Zorbax XDB C18, 4.6×150 mm, 5μ. Flow: 1 mL/min. Column temperature: 40° C. Gradient: 30% B for 1 min, 30% to 100% B in 5 min, 100% to 30% B in 4 min, 30% B for 2 min; A=0.01% TFA in water, B=acetonitrile:methanol (1:1)

HPLC 3:
Column: Zorbax XDB C18, 4.6×150 mm, 5μ. Flow: 1 mL/min. Column temperature: 40° C. Gradient: 5% B for 1 min, 5% to 100% B in 5 min, 100% to 5% B in 4 min, 5% B for 2 min; A=0.01% TFA in water, B=acetonitrile:methanol (1:1)

HPLC 4:
Column: Zorbax XDB C18, 4.6×150 mm, 5μ. Flow: 0.8 mL/min. Column temperature: 25° C. Gradient: 5% B for 2 min, 5% to 100% B in 8 min, 100% B for 2 min, 100% to 5% B in 2 min, 5% B for 2 min; A=0.01% TFA in water, B=acetonitrile:methanol (1:1)

HPLC 5:
Column: Zorbax XDB C18, 4.6×150 mm, 5μ. Flow: 1 mL/min. Column temperature: 40° C. Gradient: 30% B for 1 min, 30% to 100% B in 1 min, 100% B for 6 min, 100% to 30% B in 2 min, 30% B for 2 min; A=0.01% TFA in water, B=acetonitrile:methanol (1:1)

HPLC 6:
Column: Nucleosil 100-3 C18 HD, 4.0×70 mm. Flow: 1 mL/min. Column temperature: 30° C. Gradient: 2% to 100% B in 5 min, 100% B for 1.5 min, 100% to 2% B in 0.5 min; A=0.01% TFA in water, B=0.01% TFA in acetonitrile HPLC 7:
Column: Chromolith RP18e 4.6×100 mm+Precolumn chromolith RP-18e 10×4.6 mm. Flow: 2 ml/min. Gradient: 2% to 100% B in 8 min and 100% B for 3 min; A=0.1% TFA in water, B=0.1% TFA in acetonitrile.

HPLC 8:
System: Waters. Column: Acquity UPLC BEH C18, 2.1*50 mm, 1.7 um. Solvent A: water+0.1% TFA. Solvent B: Acetonitril+0.1% TFA. Flow: 0.6 ml/min. Run time: 6.5 min. Gradient: 0.5 min 5% B, 5-100% B in 3.5 min, 1.5 min 100% B, 100-5% B in 1 min.

LC-MS Methods:

LC-MS 1:
Column: Ascentis Express C18 2.1×30 mm, 2.7 μm. Flow: 1.2 mL/min. Column temperature: 50° C. Gradient: 2% to 98% B in 1.4 min, 98% B for 0.75 min, 98% to 2% B in 0.04 min, 98% B for 0.01 min; A=water+0.05% formic acid+0.05% ammonium acetate, B=acetonitrile+0.04% formic acid LC-MS 2:
Column: Mercury MS Synergi 4×20 mm, 2 μm. Flow: 2 mL/min. Column temperature: 30° C. Gradient: 30% B for 0.5 min, 30% to 95% B in 1 min, 95% B for 1 min, 95% to 30% B in 0.5 min. A=0.1% formic acid in water, B=acetonitrile LC-MS 3:
Column: Acquity HSS T3 2.1×50 mm, 1.8 μm. Flow: 1.2 mL/min. Column temperature: 50° C. Gradient: 2% to 98% B in 1.7 min, 98% B for 0.45 min, 98% to 2% B in 0.05 min; A=water+0.05% formic acid+3.75 mM ammonium acetate, B=acetonitrile+0.04% formic acid LC-MS 4:
Column: Acquity HSS T3 2.1×50 mm, 1.8 μm. Flow: 1.2 mL/min. Column temperature: 50° C. Gradient: 2% to 98% B in 1.4 min, 98% B for 0.75 min, 98% to 2% B in 0.04 min, 2% B for 0.01 min; A=water+0.05% formic acid+3.75 mM ammonium acetate, B=acetonitrile+0.04% formic acid LC-MS 5:
Column: Acquity HSS T3 2.1×50 mm, 1.8 μm. Flow: 1.2 mL/min. Column temperature: 50° C. Gradient: 2% to 98% B in 1.4 min, 98% B for 0.75 min, 98% to 2% B in 0.04 min, 2% B for 0.01 min; A=water+0.05% formic acid+0.05% ammonium acetate, B=acetonitrile+0.04% formic acid.

LC-MS 6:
Column: Acquity HSS T3 2.1×50 mm, 1.8 μm. Flow: 1.0 ml/min. Column temperature: 60° C. Gradient: from 5 to 98%

B in 1.4 min; A=water+0.05% formic acid+3.75 mM ammonium acetate, B=acetonitrile+0.04% formic acid.

Intermediate A: 1-(3-Chloro-2-fluoro-phenyl)-5-(4-chloro-2-methyl-phenyl)-3-hydroxy-4-isobutyryl-1,5-dihydro-pyrrol-2-one

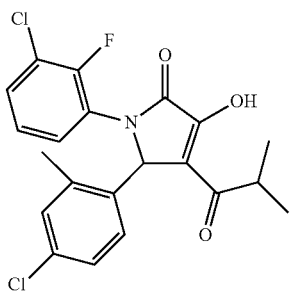 [SMILES: Cc1cc(Cl)ccc1C1C(C(=O)C(C)C)=C(O)C(=O)N1c1cccc(Cl)c1F]

A mixture of 3-chloro-2-fluoro-aniline (0.70 g, 4.8 mmol), 4-chloro-2-methyl-benzaldehyde (0.74 g, 4.8 mmol) and the sodium salt of 5-methyl-2,4-dioxo-hexanoic acid ethyl ester (1.0 g, 4.8 mmol) in acetic acid (6 mL) was refluxed for 3 h. The reaction mixture was diluted with water and extracted twice with ethyl acetate. The combined organic extracts were washed with brine, dried (Na$_2$SO$_4$), filtered, and concentrated. The residue was purified by silica gel column chromatography (CH$_2$Cl$_2$/MeOH, 1:0→9:1), followed by crystallization from EtOAc/hexane, to provide 426 mg of the title compound. $t_R$: 5.47 min (HPLC 1); ESI-MS: 422 [M+H]$^+$ (LC-MS 1).

Intermediate B: 1-(3-Chloro-2-fluoro-phenyl)-5-(4-chloro-phenyl)-3-hydroxy-4-isobutyryl-1,5-dihydro-pyrrol-2-one

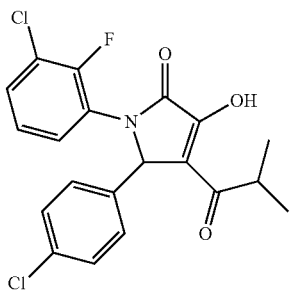

A mixture of 3-chloro-2-fluoro-aniline (10.9 g, 75 mmol) and 4-chloro-benzaldehyde (10.0 g, 71 mmol) was heated to 120° C., stirred for 18 h, allowed to cool to rt, and diluted with toluene (50 mL). A mixture of the sodium salt of 5-methyl-2,4-dioxo-hexanoic acid ethyl ester (14.8 g, 71 mmol) in dioxane (50 mL) and acetic acid (4.1 mL, 71 mmol) was added. The resulting mixture was refluxed for 18 h, allowed to cool to rt, diluted with EtOAc, and washed twice with an aqueous solution of NaHCO$_3$ and brine. The crude product, obtained after drying and concentration, was triturated with EtOAc/hexane to provide 14 g of the title compound. $t_R$: 5.23 min (HPLC 1); ESI-MS: 408 [M+H]$^+$ (LC-MS1).

Intermediate C: 1-(3-Chloro-2-fluoro-phenyl)-5-(2,4-dichloro-phenyl)-3-hydroxy-4-isobutyryl-1,5-dihydro-pyrrol-2-one

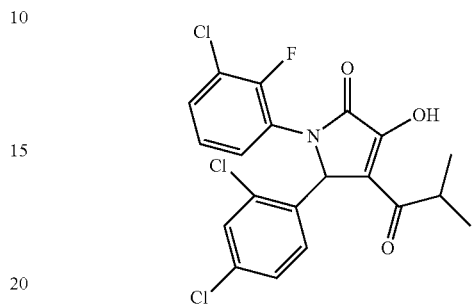

A mixture of 3-chloro-2-fluoro-aniline (428 mg, 2.94 mmol) and 2,4-dichloro-benzaldehyde (515 mg, 2.94 mmol) was heated to 110° C., stirred for 4 h, allowed to cool to rt, and diluted with toluene (5 mL). A solution of the sodium salt of 5-methyl-2,4-dioxo-hexanoic acid ethyl ester (615 mg, 2.94 mmol) in dioxane (5 mL) and acetic acid (0.17 mL) were added. The resulting mixture was refluxed for 15 h, allowed to cool to rt and diluted with EtOAc and water. The aqueous layer was separated and extracted with EtOAc. The combined organic extracts were washed with brine, dried (Na$_2$SO$_4$) filtered, and concentrated. The residue was purified by silica gel column chromatography (CH$_2$Cl$_2$/MeOH, 1:0→95:5) to provide 660 mg of the title compound. $t_R$: 1.40 min (LC-MS 1); ESI-MS: 443.8 [M+H]$^+$ (LC-MS 1).

Intermediate D: 5-(4-Chloro-phenyl)-1-(3,4-difluoro-phenyl)-3-hydroxy-4-isobutyryl-1,5-dihydro-pyrrol-2-one

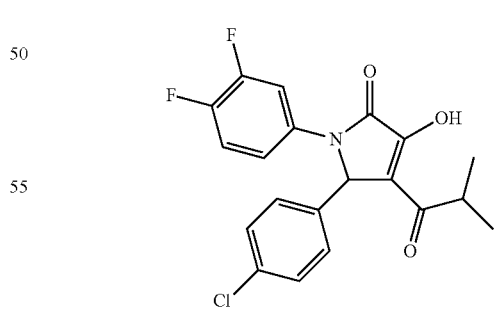

A mixture of 3,4-difluoro-aniline (1.8 g, 14.2 mmol), 4-chloro-benzaldehyde (2.0 g, 14.2 mmol) and 5-methyl-2,4-dioxo-hexanoic acid ethyl ester (2.6 g, 14.2 mmol) acetic acid (10 mL) was refluxed overnight. The reaction mixture was allowed to cool to rt and diluted with acetonitrile. The resulting precipitate was collected by vacuum filtration and dried to afford 3.1 g of the title compound. $t_R$: 5.89 min (HPLC 2); ESI-MS: 390 [M−H]⁻ (LC-MS 2).

Intermediate E: 1-(3-Chloro-2-fluoro-phenyl)-5-(4-fluoro-phenyl)-3-hydroxy-4-isobutyryl-1,5-dihydro-pyrrol-2-one

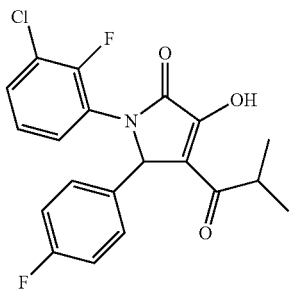 [SMILES: CC(C)C(=O)C1=C(O)C(=O)N(c2cccc(Cl)c2F)C1c1ccc(Cl)cc1]

The title compound was prepared in analogy to the procedure described for intermediate B but using 4-fluorobenzaldehyde and stirring the mixture of 4-fluoro-benzaldehyde and 3-chloro-2-fluoro-aniline at 130° C. for 4 h. The crude product was triturated in diethyl ether/hexane. $t_R$: 1.17 min (LC-MS 1); ESI-MS: 392 [M+H]⁺ (LC-MS 1).

Intermediate F: 1-(3-Chloro-2-fluoro-phenyl)-5-(4-chloro-3-fluoro-phenyl)-3-hydroxy-4-isobutyryl-1,5-dihydro-pyrrol-2-one

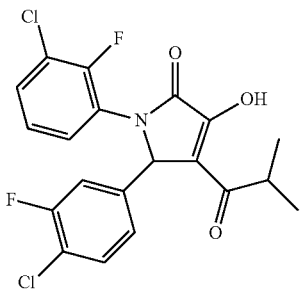 [SMILES: CC(C)C(=O)C1=C(O)C(=O)N(c2cccc(Cl)c2F)C1c1ccc(Cl)c(F)c1]

The title compound was prepared in analogy to the procedure described for intermediate B but using 4-chloro-3-fluoro-benzaldehyde, stirring the mixture of 4-chloro-3-fluoro-benzaldehyde and 3-chloro-2-fluoro-aniline at 130° C. for 5 h, and using 0.5 equivalents of acetic acid. The crude product was purified by silica gel column chromatography (CH₂Cl₂/MeOH, 1:0→9:1). $t_R$: 1.22 min (LC-MS 1); ESI-MS: 426 [M+H]⁺ (LC-MS 1).

Intermediate G: 1-(3-Chloro-2-fluoro-phenyl)-5-(3,4-difluoro-phenyl)-3-hydroxy-4-isobutyryl-1,5-dihydro-pyrrol-2-one

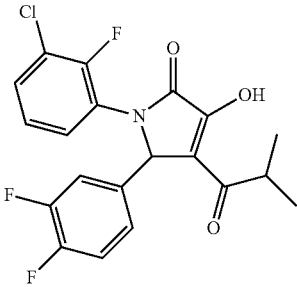

The title compound was prepared in analogy to the procedure described for intermediate B but using 3,4-difluoro-benzaldehyde, stirring the mixture of 3,4-difluoro-benzaldehyde and 3-chloro-2-fluoro-aniline at 130° C. overnight, and using 0.5 equivalents of acetic acid. The crude product was triturated in diethyl ether/hexane. $t_R$: 1.34 min (LC-MS 3); ESI-MS: 410 [M+H]⁺ (LC-MS 3).

Intermediate H: 1-(3-Chloro-2-fluoro-phenyl)-3-hydroxy-4-isobutyryl-5-p-tolyl-1,5-dihydro-pyrrol-2-one

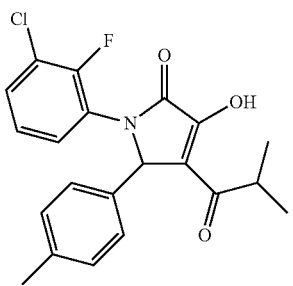 [SMILES: Cc1ccc(C2C(C(=O)C(C)C)=C(O)C(=O)N2c2cccc(Cl)c2F)cc1]

The title compound was prepared in analogy to the procedure described for intermediate B but using 4-methyl-benzaldehyde, stirring the mixture of 4-methyl-benzaldehyde and 3-chloro-2-fluoro-aniline for 18 h at 120° C., and for 20 h at 120° C. after addition of the acetic acid. The crude product was triturated in diethyl ether. $t_R$: 1.19 min (LC-MS 1); ESI-MS: 386 [M−H]⁻ (LC-MS 1).

Intermediate I: 1-(3-Chloro-4-fluoro-phenyl)-5-(4-chloro-2-methyl-phenyl)-3-hydroxy-4-isobutyryl-1,5-dihydro-pyrrol-2-one

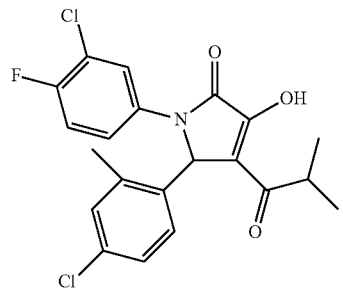 [SMILES: Cc1cc(Cl)ccc1C1C(C(=O)C(C)C)=C(O)C(=O)N1c1ccc(F)c(Cl)c1]

The title compound was prepared in analogy to the procedure described for intermediate D but using 3-chloro-4-fluoro-aniline and 4-chloro-2-methyl-benzaldehyde. $t_R$: 6.72 min (HPLC 2); ESI-MS: 422 [M+H]⁺ (LC-MS 2)

Intermediate J: 1-(3-Chloro-4-fluoro-phenyl)-5-(4-chloro-phenyl)-3-hydroxy-4-isobutyryl-1,5-dihydro-pyrrol-2-one

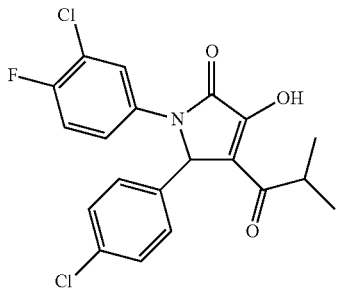 [SMILES: CC(C)C(=O)C1=C(O)C(=O)N(c2ccc(F)c(Cl)c2)C1c1ccc(Cl)cc1]

The title compound was prepared in analogy to the procedure described for intermediate D but using 3-chloro-4-fluoro-aniline. $t_R$: 5.91 min (HPLC 2); $R_f$=0.23 (hexane/EtOAc, 1:1).

Intermediate K: 1-(5-Chloro-2,4-difluoro-phenyl)-5-(4-chloro-2-methyl-phenyl)-3-hydroxy-4-isobutyryl-1,5-dihydro-pyrrol-2-one

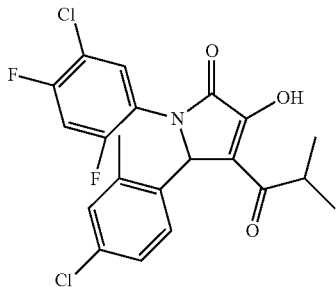 [SMILES: Cc1cc(Cl)ccc1C1C(C(=O)C(C)C)=C(O)C(=O)N1c1cc(Cl)c(F)cc1F]

The title compound was prepared in analogy to the procedure described for intermediate D but using 5-chloro-2,4-difluoro-aniline and 4-chloro-2-methyl-benzaldehyde. The reaction mixture was allowed to cool to rt, and concentrated. The residue was diluted with water and extracted with EtOAc. The organic phase was dried (Na$_2$SO$_4$), filtered and concentrated. The residue was purified by silica gel column chromatography (EtOAc/hexane, 9:1). $t_R$: 6.54 min (HPLC 2); ESI-MS: 438 [M−H]$^-$ (LC-MS 2).

Intermediate L: 1-(5-Chloro-2-methyl-phenyl)-5-(4-chloro-2-methyl-phenyl)-3-hydroxy-4-isobutyryl-1,5-dihydro-pyrrol-2-one

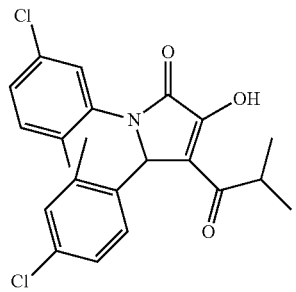 [SMILES: Cc1cc(Cl)ccc1C1C(C(=O)C(C)C)=C(O)C(=O)N1c1cc(Cl)ccc1C]

The title compound was prepared in analogy to the procedure described for intermediate D but using 5-chloro-2-methyl-aniline and 4-chloro-2-methyl-benzaldehyde. $t_R$: 6.55 min (HPLC 2); ESI-MS: 418 [M+H]$^+$ (LC-MS 2).

Intermediate M: 1-[5-Chloro-2-(2-dimethylamino-ethoxy)-phenyl]-5-(4-chloro-2-methyl-phenyl)-3-hydroxy-4-isobutyryl-1,5-dihydro-pyrrol-2-one

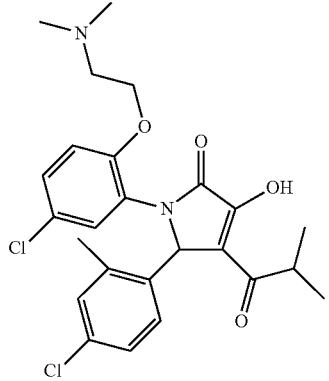 [SMILES: Cc1cc(Cl)ccc1C1C(C(=O)C(C)C)=C(O)C(=O)N1c1cc(Cl)ccc1OCCN(C)C]

The title compound was prepared in analogy to the procedure described for intermediate D but using the aniline prepared in step M1 and 4-chloro-2-methyl-benzaldehyde. The reaction mixture was allowed to cool to rt, and concentrated. The residue was purified by silica gel column chromatography (CHCl$_3$/MeOH, 9:1) followed by preparative HPLC (Column: Zorbax eclipse xdb C18, 21.2×150 mm, 5 μm. Flow: 20 mL/min. Gradient: 20% B for 2 min, 20% to 60% B in 10 min; A=0.1% TFA in water, B=acetonitrile). $t_R$: 3.57 min (HPLC 2); ESI-MS: 491.1 [M+H]$^+$ (LC-MS 2).

Step M1:
5-Chloro-2-(2-dimethylamino-ethoxy)-phenylamine

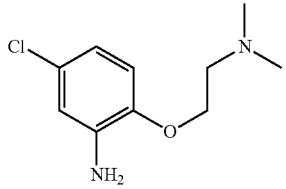

A saturated aqueous solution of ammonium chloride (30 mL) was added to a solution of the intermediate prepared in step M2 (3.0 g, 12.3 mmol) in ethanol (60 mL). After a 15 min stirring, iron powder (6.9 g, 123 mmol) was added and the resulting mixture was heated to reflux, stirred for 1 h, concentrated, diluted with ethanol, and filtered through a pad of celite. The filtrate was concentrated. The residue was purified by silica gel column chromatography (CHCl$_3$/MeOH, 98:2) to provide 2.2 g of the title compound. $t_R$: 1.10 min (LC-MS 2); ESI-MS: 215.1 [M+H]$^+$ (LC-MS 2); $R_f$=0.24 (CHCl$_3$/MeOH, 9:1).

Step M2: [2-(4-Chloro-2-nitro-phenoxy)-ethyl]-dimethyl-amine

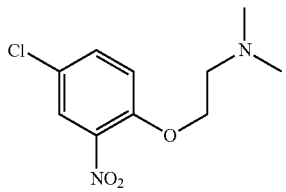 [SMILES: CN(C)CCOc1ccc(Cl)cc1[N+](=O)[O-]]

Potassium carbonate (3.2 g, 12.3 mmol) was added to a solution of 4-chloro-2-nitro-phenol (6.0 g, 34.6 mmol) in DMF (60 mL). The mixture was cooled to 0° C. 2-Chloro-N,N-dimethyl ethyl amine hydrochloride (9.96 g, 69.1 mmol) was added in portions. The reaction mixture was allowed to warm to rt, stirred for 4 h, heated to 95° C., stirred for 16 h, allowed to cool to rt, quenched by addition of a saturated aqueous solution of ammonium chloride and extracted with EtOAc. The organic phase was dried (Na$_2$SO$_4$), filtered, and concentrated. The residue was purified by silica gel column chromatography (CHCl$_3$/MeOH, 98:2) to provide 3.0 g of the title compound. t$_R$: 0.12 min (LC-MS 2); ESI-MS: 245 [M+H]$^+$ (LC-MS 2); R$_f$=0.29 (CHCl$_3$/MeOH, 9:1).

Intermediate N: 1-(3-Chloro-2-fluoro-phenyl)-5-(4-chloro-2-methyl-phenyl)-4-cyclobutanecarbonyl-3-hydroxy-1,5-dihydro-pyrrol-2-one

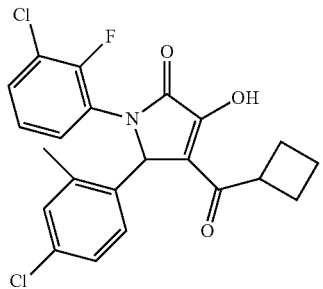 [SMILES: Cc1cc(Cl)ccc1C1C(C(=O)C2CCC2)=C(O)C(=O)N1c1cccc(Cl)c1F]

The title compound was prepared in analogy to the procedure described for intermediate D but using the compound prepared in step N1, 3-chloro-2-fluoro-aniline and 4-chloro-2-methyl-benzaldehyde. The crude product was purified by silica gel column chromatography (hexane/EtOAc, 3:1). R$_f$=0.13 (hexane/EtOAc, 1:1); $^1$H NMR (300 MHz, CDCl$_3$) δ ppm 1.70-2.35 (m 7H), 2.38 (s, 3H), [3.08 (quintet), 3.36 (quintet), 1H, rotamers], [5.82 (s), 6.04 (s), 1H, rotamers], 6.86-7.36 (m, 6H).

Step N1: 4-Cyclobutyl-2,4-dioxo-butyric acid methyl ester

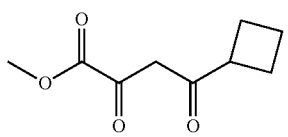

To a solution of cyclobutyl methyl ketone (4 g, 40.8 mmol) in MeOH (60 mL) was added sodium methoxide (3.3 g, 61.2 mmol) at rt. After a 5 min stirring, dimethyl oxalate (4.8 g, 40.8 mmol) was added. The reaction mixture was stirred for 3 h at rt and concentrated. The residue was taked up in diluted HCl and extracted with EtOAc. The organic layers were concentrated. The residue was purified by silica gel column chromatography (hexane/EtOAc, 9:1) to provide 4 g of the title compound. R$_f$=0.46 (hexane/EtOAc, 1:1); $^1$H NMR (300 MHz, CDCl$_3$) δ ppm 1.70-2.40 (m, 6H), 3.58 (quintet, 1H), 3.85 (s, 3H), 6.54 (s, 1H), 13.8-15.0 (br. s, 1H).

Intermediate O: 1-(3-Chloro-2-fluoro-phenyl)-5-(4-chloro-2-methyl-phenyl)-4-cyclopropanecarbonyl-3-hydroxy-1,5-dihydro-pyrrol-2-one

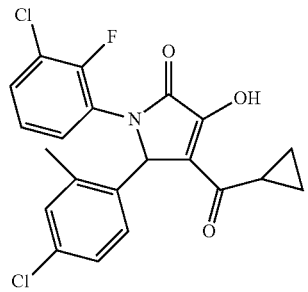 [SMILES: Cc1cc(Cl)ccc1C1C(C(=O)C2CC2)=C(O)C(=O)N1c1cccc(Cl)c1F]

The title compound was prepared in analogy to the procedure described for intermediate D but using the compound prepared in step O1, 3-chloro-2-fluoro-aniline and 4-chloro-2-methyl-benzaldehyde. t$_R$: 1.87 min (LC-MS 2); ESI-MS: 420 [M+H]$^+$ (LC-MS 2); R$_f$=0.19 (hexane/EtOAc, 1:1).

Step O1: 4-Cyclopropyl-2,4-dioxo-butyric acid methyl ester

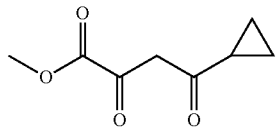

To a solution of cyclopropyl methyl ketone (5 g, 59.4 mmol) in MeOH (75 mL) was added sodium methoxide (4.8 g, 54.0 mmol) at rt. After a 15 min stirring, dimethyl oxalate (7 g, 59.4 mmol) was added. The reaction mixture was stirred for 16 h at rt and concentrated. The residue was taken up in a saturated aqueous solution of ammonium chloride and extracted with EtOAc. The organic layers were dried (Na$_2$SO$_4$), filtered, and concentrated. The residue was purified by silica gel column chromatography (hexane/EtOAc, 95:5) to provide 5 g of the title compound. R$_f$=0.59 (hexane/EtOAc, 4:1); $^1$H NMR (300 MHz, CDCl$_3$) δ ppm 1.00-1.30 (m, 4H), 1.80-1.95 (m, 1H), 3.85 (s, 3H), 6.48 (s, 1H), 14.2-15.0 (br. s, 1H).

Intermediate P: 1-(5-Chloro-2-methyl-phenyl)-3-hydroxy-4-isobutyryl-5-(4-trifluoromethyl-phenyl)-1,5-dihydro-pyrrol-2-one The title compound was prepared in analogy to the procedure described for intermediate B but using 2-methyl-5- chloro-aniline and 4-(trifluoromethyl)-benzaldehyde. $t_R$: 1.21 min (LC-MS 1); ESI-MS: 438 [M+H]$^+$ (LC-MS 1).

Intermediate Q: 1-(3-Chloro-2-fluoro-phenyl)-5-[4-chloro-2-(2-methoxy-ethoxymethyl)-phenyl]-3-hydroxy-4-isobutyryl-1,5-dihydro-pyrrol-2-one

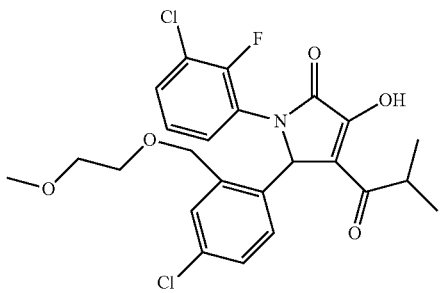 [SMILES: COCCOCc1cc(Cl)ccc1C1C(C(=O)C(C)C)=C(O)C(=O)N1c1cccc(Cl)c1F]

The title compound was prepared in analogy to the procedure described for intermediate D but using the aldehyde prepared in step Q1 and 3-chloro-2-fluoro-aniline. The residue was purified by silica gel column chromatography (CHCl$_3$/MeOH, 9:1). $t_R$: 5.99 min (HPLC 2); ESI-MS: 496 [M+H]$^+$ (LC-MS 2); $R_f$=0.14 (hexane/EtOAc, 1:1).

Step Q1:
4-Chloro-2-(2-methoxy-ethoxymethyl)-benzaldehyde

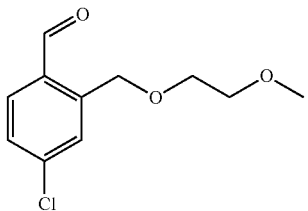

n-Buthyllithium (1.6 M in hexanes, 6.5 mL, 10.4 mmol) was added dropwise to a cold (−78° C.) solution of the compound prepared in step Q2 (3.4 g, 10.4 mmol) in THF (30 mL). To this mixture was added very slowly a solution of DMF (0.88 mL, 11.5 mmol) in THF (10 mL). the reaction mixture was allowed to warm to rt, stirred for 30 min, quenched by slow addition of water, and extracted with EtOAc. The organic layer was washed with brine, dried (Na$_2$SO$_4$), filtered, and concentrated. The residue was purified by silica gel column chromatography (hexane/EtOAc, 9:1) to provide 1.3 g of the title compound. $R_f$=0.41 (hexane/EtOAc, 4:1).

Step Q2:
4-Chloro-1-iodo-2-(2-methoxy-ethoxymethyl)-benzene

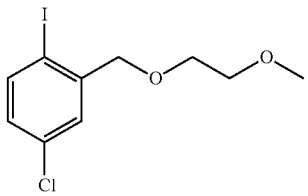

Bromoethylmethylether (3.7 mL, 16.9 mmol) was added slowly to a suspension of the compound prepared in step Q3 (3.5 g, 13.0 mmol) and NaH (60% suspension, 0.75 g, 15.6 mmol) in DMF (35 mL). The resulting mixture was stirred for 1 h at rt, quenched by addition of a saturated aqueous solution of ammonium chloride, and extracted with EtOAc. The organic layer was dried (Na$_2$SO$_4$), filtered, and concentrated. The residue was purified by silica gel column chromatography (hexane/EtOAc, 9:1) to provide 3.5 g of the title compound. $t_R$: 6.10 min (HPLC 2); $R_f$=0.34 (hexane/EtOAc, 9:1).

Step Q3: (5-Chloro-2-iodo-phenyl)-methanol

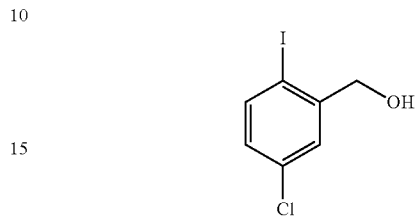

Borane-dimethylsulfide complex (3.7 mL, 38.9 mmol) was added slowly to a cold (0° C.) solution of 5-chloro-2-iodo-benzoic acid (10 g, 35.4 mmol) in THF (20 mL). The reaction mixture was allowed to warm to rt, stirred for 8 h, quenched by addition of a saturated aqueous solution of ammonium chloride, and extracted with EtOAc. The organic layer was dried (Na$_2$SO$_4$), filtered, and concentrated to provide 9.5 g of the title compound. $t_R$: 4.72 min (HPLC 2); $R_f$=0.66 (hexane/EtOAc, 7:3).

Intermediate R: 1-(5-Chloro-2-methyl-phenyl)-5-(5-chloro-pyridin-2-yl)-3-hydroxy-4-isobutyryl-1,5-dihydro-pyrrol-2-one

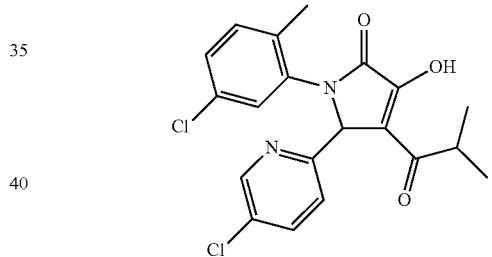

The title compound was prepared in analogy to the procedure described for intermediate D but using the aldehyde prepared in step R1 and 2-methyl-5-chloro-aniline. The reaction mixture was concentrated. The residue was purified by silica gel column chromatography (CHCl$_3$/MeOH, 98:2). $t_R$: 5.53 min (HPLC 2); ESI-MS: 405 [M+H]$^+$ (LC-MS 2); $R_f$=0.12 (CHCl$_3$/MeOH, 95:5).

Step R1: 5-Chloro-pyridine-2-carbaldehyde

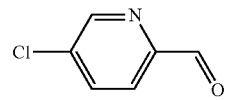

Isopropyl magnesium chloride (11.5 mL, 2 M in THF, 23 mmol) was added dropwise to a cold (−15° C.) solution of 5-chloro-2-iodo-pyridine (5 g, 20.9 mmol) in THF (35 mL). The mixture was stirred for 1 h at −15° C. DMF (2.3 g, 31.3 mmol) was added dropwise keeping the internal temperature below 0° C. The mixture was allowed to warm to rt, stirred for 1 h, cooled to 0° C., quenched by addition of a saturated aqueous solution of ammonium chloride, and extracted with EtOAc. The organic layer was washed with brine, dried (Na₂SO₄), filtered, and concentrated. The residue was purified by silica gel column chromatography (hexane/EtOAc, 95:5) to provide 1.1 g of the title compound. $t_R$: 0.39 min (LC-MS 2); ESI-MS: 142 [M+H]⁺ (LC-MS 2); $R_f$=0.22 (hexane/EtOAc, 4:1).

Intermediate S: 1-(3-Chloro-4-fluoro-phenyl)-5-(5-chloro-pyridin-2-yl)-3-hydroxy-4-isobutyryl-1,5-dihydro-pyrrol-2-one

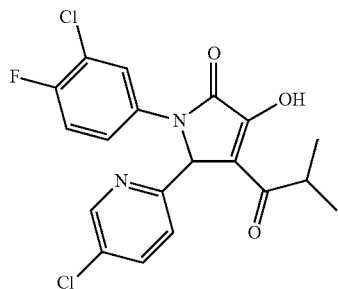

The title compound was prepared in analogy to the procedure described for intermediate D but using the aldehyde prepared in step R1 and 3-chloro-4-fluoro-aniline. The precipitate collected by vacuum filtration was purified by silica gel column chromatography (hexane/EtOAc, 1:4). $t_R$: 5.32 min (HPLC 2); ESI-MS: 408.9 [M+H]⁺ (LC-MS 2); $R_f$=0.11 (hexane/EtOAc, 1:9).

Intermediate T: 3-Chloro-5-[2-(4-chloro-2-methyl-phenyl)-4-hydroxy-3-isobutyryl-5-oxo-2,5-dihydro-pyrrol-1-yl]-benzonitrile

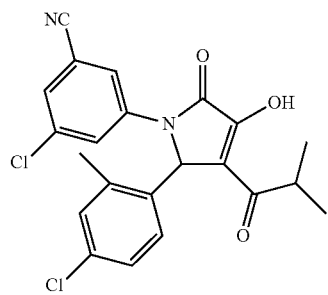 [SMILES: Cc1cc(Cl)ccc1C1C(C(=O)C(C)C)=C(O)C(=O)N1c1cc(Cl)cc(C#N)c1]

A mixture of 3-amino-5-chloro-benzonitrile (2.4 g, 15.7 mmol), 4-chloro-2-methyl-benzaldehyde (2.4 g, 15.7 mmol) and 5-methyl-2,4-dioxo-hexanoic acid ethyl ester (2.9 g, 15.7 mmol) in acetic acid (15 mL) was stirred at 120° C. for 16 h. The reaction mixture was allowed to cool to rt, concentrated, diluted with acetonitrile (15 mL), and stirred for 4 h at rt. The resulting precipitate was collected by vacuum filtration and dried to afford 1.8 g of the title compound. $t_R$: 6.50 min (HPLC 2); ESI-MS: 429 [M+H]⁺ (LC-MS 2); $R_f$=0.27 (hexane/EtOAc, 1:1).

Intermediate U: N-{3-Chloro-5-[2-(4-chloro-2-methyl-phenyl)-4-hydroxy-3-isobutyryl-5-oxo-2,5-dihydro-pyrrol-1-yl]-phenyl}-acetamide

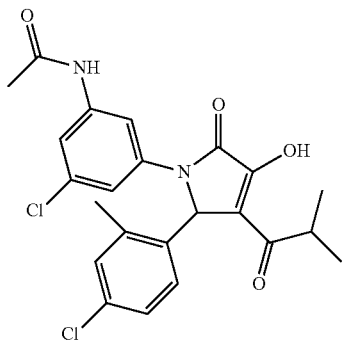 [SMILES: CC(=O)Nc1cc(Cl)cc(N2C(=O)C(O)=C(C(=O)C(C)C)C2c2ccc(Cl)cc2C)c1]

The title compound was prepared in analogy to the procedure described for intermediate T but using the aniline prepared in step U1. After concentration of the reaction mixture, the residue was purified by neutral alumina column chromatography (CH₂Cl₂/MeOH, 4:1). The resulting material was triturated with EtOAc/pentane to afford the title compound. $t_R$: 1.70 min (LC-MS 2); ESI-MS: 461 [M+H]⁺ (LC-MS 2); $R_f$=0.13 (hexane/EtOAc, 1:9).

Step U1: N-(3-Amino-5-chloro-phenyl)-acetamide

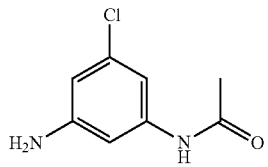

DMAP (50 mg) and acetic anhydride (3.9 g, 37.9 mmol) were added sequentially and dropwise to a cold solution of 5-chloro-benzene-1,3-diamine (4.5 g, 31.6 mmol) in pyridine (22 mL) keeping the internal temperature below 0° C. The reaction mixture was allowed to warm to rt, stirred for 2 h, cooled to 0° C., quenched by addition of ice cooled water, and extracted with EtOAc. The organic phase was washed with brine, dried (Na₂SO₄), filtered, and concentrated. The crude material was purified by silica gel column chromatography (CH₂Cl₂/MeOH, 99:1) to afford the title compound. $t_R$: 0.18 min (LC-MS 2); ESI-MS: 184.9 [M+H]⁺ (LC-MS 2); $R_f$=0.32 (hexane/EtOAc, 1:4).

Intermediate V: 5-(4-Chloro-2-methyl-phenyl)-1-(5-chloro-pyridin-3-yl)-3-hydroxy-4-isobutyryl-1,5-dihydro-pyrrol-2-one

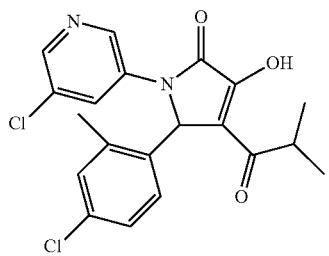 [SMILES: Cc1cc(Cl)ccc1C1C(C(=O)C(C)C)=C(O)C(=O)N1c1cncc(Cl)c1]

The title compound was prepared in analogy to the procedure described for intermediate D but using 3-amino-5- chloro pyridine and 4-chloro-2-methyl-benzaldehyde. $t_R$: 7.09 min (HPLC 2); ESI-MS: 405 [M+H]$^+$ (LC-MS 2); $R_f$=0.12 (CH$_2$Cl$_2$/MeOH, 9:1).

Intermediate W: 3-Chloro-5-[2-(4-chloro-phenyl)-4-hydroxy-3-isobutyryl-5-oxo-2,5-dihydro-pyrrol-1-yl]-1-methyl-1H-pyridin-2-one

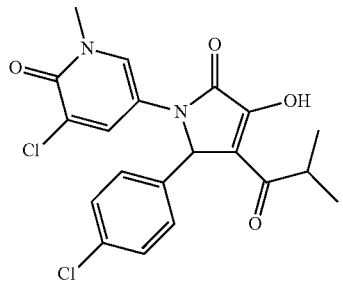 [SMILES: CC(C)C(=O)C1=C(O)C(=O)N(c2cc(Cl)c(=O)n(C)c2)C1c1ccc(Cl)cc1]

The title compound was prepared in analogy to the procedure described for intermediate D but using the amine prepared in step W1. The reaction mixture was allowed to cool to rt and diluted with diethyl ether. The resulting precipitate was collected by vacuum filtration, washed with diethyl ether, and dried to afford the title compound. $t_R$: 4.53 min (HPLC 2); ESI-MS: 421 [M+H]$^+$ (LC-MS 2); $R_f$=0.13 (CH$_2$Cl$_2$/MeOH, 9:1).

Step W1:
5-Amino-3-chloro-1-methyl-1H-pyridin-2-one

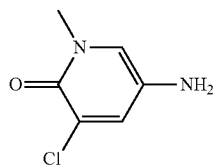

A mixture of the compound prepared in step W2 (3.4 g, 18.1 mmol), iron powder (3 g, 54.3 mmol), ethanol (68 mL), and a saturated aqueous solution of ammonium chloride (17 mL) was stirred for 1 h at reflux. The reaction mixture was allowed to cool to rt, filtered through a pad of celite, and concentrated. The residue was purified by silica gel column chromatography (CH$_2$Cl$_2$/MeOH, 97:3) to provide 2.7 g of the title compound. $t_R$: 2.39 min (HPLC 3); ESI-MS: 159 [M+H]$^+$ (LC-MS 2); $R_f$=0.06 (CH$_2$Cl$_2$/MeOH, 95:5).

Step W2:
3-Chloro-1-methyl-5-nitro-1H-pyridin-2-one

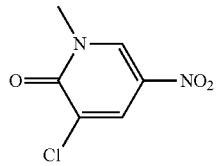

Methyl iodide (0.12 mL, 1.73 mmol) was added to a cold (0° C.) mixture of the compound prepared in step W3 (0.2 g, 1.15 mmol) and potassium carbonate (0.32 g, 2.23 mmol) in DMF (5 mL). The reaction mixture was allowed to warm to rt, stirred for 2 h, quenched by addition of water, and extracted with EtOAc. The organic layer was washed with brine, dried (Na$_2$SO$_4$), filtered, and concentrated. The crude material was purified by silica gel column chromatography (hexane/EtOAc, 9:1) to afford 0.136 g of the title compound. $t_R$: 0.25 min (LC-MS 2); ESI-MS: 189 [M+H]$^+$ (LC-MS 2); $R_f$=0.50 (hexane/EtOAc, 1:1).

Step W3: 3-Chloro-5-nitro-pyridin-2-ol

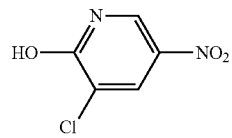

To a warm (50° C.) solution of 2-hydroxy-5-nitro-pyridine (17 g, 121 mmol) in concentrated HCl (80 mL) was added dropwise NaClO$_3$ (4.5 g, 42.5 mmol) in water (70 mL), keeping the internal temperature below 60° C. The reaction mixture was stirred for 15 min and then cooled to 0° C. The resulting precipitate was collected by vacuum filtration and dried to provide 19.7 g of the title compound. $t_R$: 5.45 min (HPLC 3); ESI-MS: 173 [M−H]$^-$ (LC-MS 2); $R_f$=0.55 (hexane/EtOAc, 1:1).

Intermediate X: 3-Chloro-5-[2-(4-chloro-phenyl)-4-hydroxy-3-isobutyryl-5-oxo-2,5-dihydro-pyrrol-1-yl]-1-ethyl-1H-pyridin-2-one

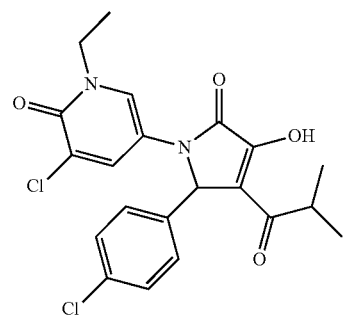 [SMILES: CCn1cc(N2C(=O)C(O)=C(C(=O)C(C)C)C2c2ccc(Cl)cc2)cc(Cl)c1=O]

The title compound was prepared in analogy to the procedure described for intermediate D but using the amine prepared in step X1. The reaction mixture was allowed to cool to rt and diluted with ethyl acetate. The resulting precipitate was collected by vacuum filtration, washed with diethyl ether, and dried to afford the title compound. $t_R$: 4.77 min (HPLC 2); ESI-MS: 435 [M+H]$^+$ (LC-MS 2); $R_f$=0.19 (CH$_2$Cl$_2$/MeOH, 9:1).

Step X1:
5-Amino-3-chloro-1-ethyl-1H-pyridin-2-one

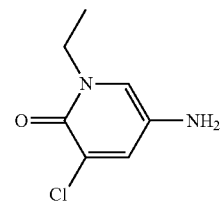

The title compound was prepared in analogy to the procedure described in step W1 but using the compound prepared in step X2. The crude material was purified by silica gel column chromatography (CH$_2$Cl$_2$/MeOH, 95:5) to provide the title compound. t$_R$: 2.39 min (HPLC 3); R$_f$=0.14 (CH$_2$Cl$_2$/MeOH, 9:1).

Step X2: 3-Chloro-1-ethyl-5-nitro-1H-pyridin-2-one

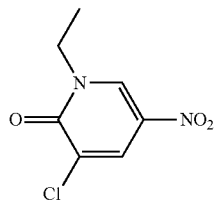

The title compound was prepared in analogy to the procedure described in step W2 but using ethyl iodide. The crude material was purified by silica gel column chromatography (hexane/EtOAc, 92:8) to afford the title compound. t$_R$: 3.49 min (HPLC 2); ESI-MS: 203 [M+H]$^+$ (LC-MS 2); R$_f$=0.49 (hexane/EtOAc, 1:1).

Intermediate Y: 3-Chloro-5-[2-(4-chloro-phenyl)-4-hydroxy-3-isobutyryl-5-oxo-2,5-dihydro-pyrrol-1-yl]-1-(2-hydroxy-ethyl)-1H-pyridin-2-one (Ya) and Acetic acid 2-{3-chloro-5-[2-(4-chloro-phenyl)-4-hydroxy-3-isobutyryl-5-oxo-2,5-dihydro-pyrrol-1-yl]-2-oxo-2H-pyridin-1-yl}-ethyl ester (Yb)

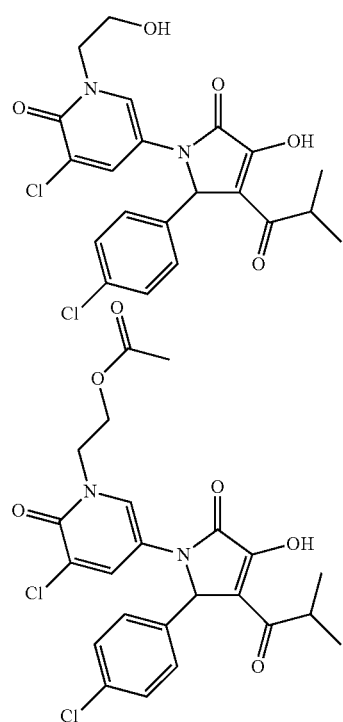

The title compounds were obtained in analogy to the procedure described for intermediate D but using the amine prepared in step Y1. The reaction mixture was allowed to 10° C. and stirred for 2 h at this temperature. The resulting precipitate was collected by vacuum filtration, washed with diethyl ether, and dried to afford a mixture of the two title compounds (Ya/Yb, 7:1). Ya: t$_R$: 3.96 min (HPLC 2); ESI-MS: 451 [M+H]$^+$ (LC-MS 2); R$_f$=0.12 (CHCl$_3$/MeOH, 9:1). Yb: t$_R$: 4.37 min (HPLC 2); R$_f$=0.34 (CHCl$_3$/MeOH, 9:1).

Step Y1: 5-Amino-3-chloro-1-(2-hydroxy-ethyl)-1H-pyridin-2-one

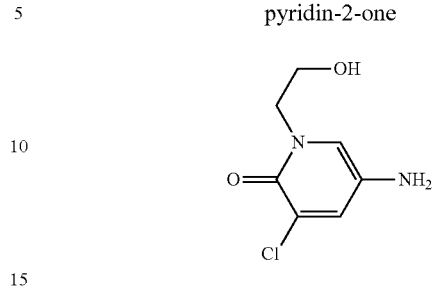

The title compound was prepared in analogy to the procedure described in step W1 but using the compound prepared in step Y2. The crude material was purified by silica gel column chromatography (CH$_2$Cl$_2$/MeOH, 99:1) to provide the title compound. t$_R$: 4.70 min (HPLC 4); ESI-MS: 189 [M+H]$^+$ (LC-MS 2); R$_f$=0.17 (CH$_2$Cl$_2$/MeOH, 99:1).

Step Y2: 3-Chloro-1-(2-hydroxy-ethyl)-5-nitro-1H-pyridin-2-one

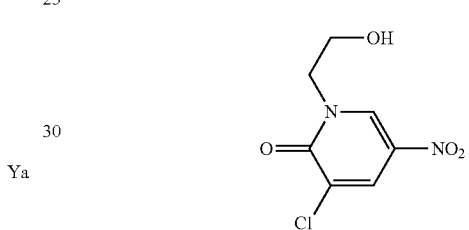

2-Bromo-ethanol (17.2 g, 138 mmol) was added dropwise to a cold (0° C.) mixture of the compound prepared in step W3 (12 g, 69 mmol) and potassium carbonate (19 g, 138 mmol) in DMF (60 mL). The reaction mixture was allowed to warm to rt, stirred for 48 h, cooled to 0° C., quenched by slow addition of ice cooled water, and stirred for 2 h. The resulting precipitate was collected by vacuum filtration to afford 11 g of the title compound. t$_R$: 5.42 min (HPLC 3); ESI-MS: 217 [M−H]$^−$ (LC-MS 2); R$_f$=0.27 (CH$_2$Cl$_2$/MeOH, 95:5).

Intermediate Z: 3-Chloro-5-[2-(4-chloro-2-methyl-phenyl)-4-hydroxy-3-isobutyryl-5-oxo-2,5-dihydro-pyrrol-1-yl]-1-(2-methoxy-ethyl)-1H-pyridin-2-one

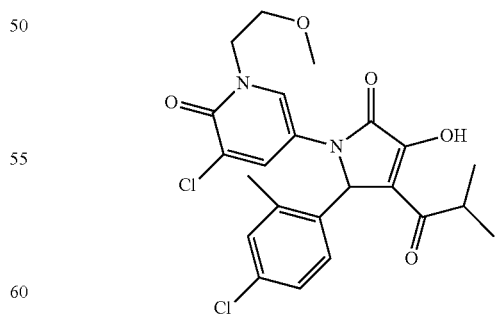

The title compound was prepared in analogy to the procedure described for intermediate D but using the amine prepared in step Z1 and 4-chloro-2-methyl-benzaldehyde. The reaction mixture was allowed to cool to rt and diluted with ethyl acetate. The resulting precipitate was collected by vacuum filtration, washed with diethyl ether, and dried to afford the title compound. $t_R$: 4.26 min (HPLC 2); ESI-MS: 479 [M+H]$^+$ (LC-MS 2); $R_f$=0.21 (CH$_2$Cl$_2$/MeOH, 9:1).

Step Z1: 5-Amino-3-chloro-1-(2-methoxy-ethyl)-1H-pyridin-2-one

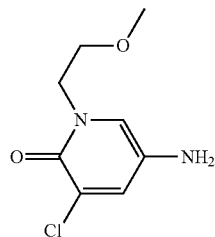

The title compound was prepared in analogy to the procedure described in step W1 but using the compound prepared in step Z2. The crude material was purified by silica gel column chromatography (CH$_2$Cl$_2$/MeOH, 95:5) to provide the title compound. $t_R$: 4.09 min (HPLC 3); ESI-MS: 203 [M+H]$^+$ (LC-MS 2); $R_f$=0.28 (CH$_2$Cl$_2$/MeOH, 99.75:0.25).

Step Z2: 3-Chloro-1-(2-methoxy-ethyl)-5-nitro-1H-pyridin-2-one

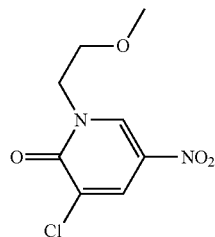

The title compound was prepared in analogy to the procedure described in step W2 but using 1-bromo-2-methoxy-ethane. The reaction mixture was allowed to warm to rt, stirred for 4 h, heated to 70° C., stirred for 4 h, and quenched by addition of ice cooled water. The resulting precipitate was collected by vacuum filtration to afford the title compound. $t_R$: 3.66 min (HPLC 2); ESI-MS: 233 [M–H]$^-$ (LC-MS 2); $R_f$=0.33 (CH$_2$Cl$_2$/MeOH, 95:5).

Intermediate AA: 3-Chloro-5-[2-(4-chloro-phenyl)-4-hydroxy-3-isobutyryl-5-oxo-2,5-dihydro-pyrrol-1-yl]-1-(2-dimethylamino-ethyl)-1H-pyridin-2-one

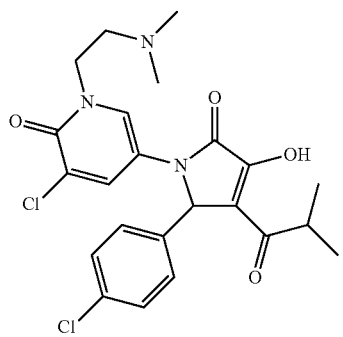 [SMILES: CC(C)C(=O)C1=C(O)C(=O)N(c2cc(Cl)c(=O)n(CCN(C)C)c2)C1c1ccc(Cl)cc1]

The title compound was prepared in analogy to the procedure described for intermediate D but using the amine prepared in step AA1. The reaction mixture was allowed to cool to rt, concentrated, diluted with ethyl acetate, and stirred for 2 h at rt. The resulting precipitate was collected by vacuum filtration, washed with diethyl ether, and dried to afford the title compound. $t_R$: 3.34 min (HPLC 2); ESI-MS: 478 [M+H]$^+$ (LC-MS 2); $R_f$=0.28 (CH$_2$Cl$_2$/MeOH, 85:15).

Step AA1: 5-Amino-3-chloro-1-(2-dimethylamino-ethyl)-1H-pyridin-2-one

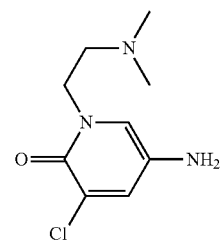

The title compound was prepared in analogy to the procedure described in step W1 but using the compound prepared in step AA2 and stirring the reaction mixture for 3 h at reflux. The crude material was purified by silica gel column chromatography (CH$_2$Cl$_2$/MeOH, 95:5) to provide the title compound. $t_R$: 4.79 min (HPLC 4); ESI-MS: 216.1 [M+H]$^+$ (LC-MS 2); $R_f$=0.09 (CHCl$_3$/MeOH, 85:15).

Step AA2: 3-Chloro-1-(2-dimethylamino-ethyl)-5-nitro-1H-pyridin-2-one

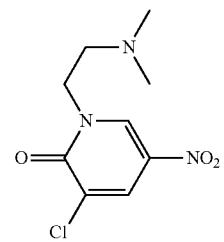 [SMILES: CN(C)CCn1cc([N+](=O)[O-])cc(Cl)c1=O]

The title compound was prepared in analogy to the procedure described in step W2 but using (2-chloro-ethyl)-dimethyl-amine hydrochloride. The reaction mixture was heated to 85° C., stirred for 16 h, quenched by slow addition of ice cooled water, and extracted with EtOAc. The organic layer was dried (Na$_2$SO$_4$), filtered, and concentrated to afford the title compound. $t_R$: 0.15 min (LC-MS 2); ESI-MS: 246.2 [M+H]$^+$ (LC-MS 2); $R_f$=0.31 (CHCl$_3$/MeOH, 9:1).

Intermediate AB: 3-Chloro-5-[2-(4-chloro-2-methyl-phenyl)-4-hydroxy-3-isobutyryl-5-oxo-2,5-dihydro-pyrrol-1-yl]-1-methyl-1H-pyridin-2-one

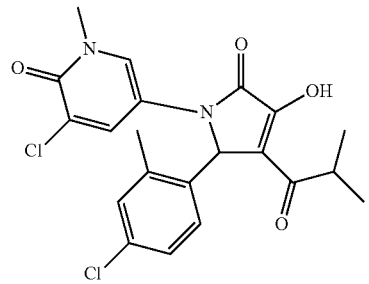 [SMILES: Cc1cc(Cl)ccc1C1C(C(=O)C(C)C)=C(O)C(=O)N1c1cc(Cl)c(=O)n(C)c1]

The title compound was prepared in analogy to the procedure described for intermediate D but using the amine prepared in step W1 and 4-chloro-2-methyl-benzaldehyde. The reaction mixture was allowed to cool to rt and diluted with diethyl ether. The resulting precipitate was collected by vacuum filtration, washed with diethyl ether, and dried to afford the title compound. $t_R$: 1.53 min (LC-MS 2); ESI-MS: 435 [M+H]$^+$ (LC-MS 2); $R_f$=0.16 (CH$_2$Cl$_2$/MeOH, 9:1).

Intermediate AC: 3-Chloro-5-[2-(4-chloro-2-methyl-phenyl)-4-hydroxy-3-isobutyryl-5-oxo-2,5-dihydro-pyrrol-1-yl]-1-ethyl-1H-pyridin-2-one

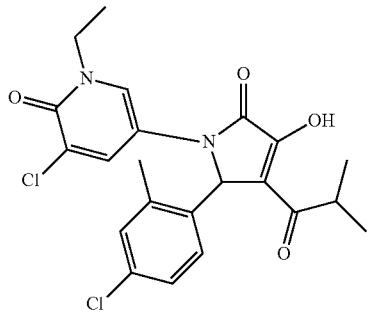 [SMILES: CCn1cc(N2C(=O)C(O)=C(C(=O)C(C)C)C2c2ccc(Cl)cc2C)cc(Cl)c1=O]

The title compound was prepared in analogy to the procedure described for intermediate D but using the amine prepared in step X1 and 4-chloro-2-methyl-benzaldehyde. The reaction mixture was allowed to cool to rt and diluted with ethyl acetate. The resulting precipitate was collected by vacuum filtration, washed with diethyl ether, and dried to afford the title compound. $t_R$: 5.16 min (HPLC 2); ESI-MS: 449 [M+H]$^+$ (LC-MS 2); $R_f$=0.14 (CH$_2$Cl$_2$/MeOH, 9:1).

Intermediate AD: 5-(3-Chloro-2-fluoro-phenyl)-4-(4-chloro-2-methyl-phenyl)-3-isopropyl-4,5-dihydro-2H-pyrrolo[3,4-c]pyrazol-6-one

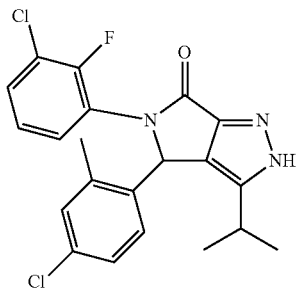 [SMILES: Cc1cc(Cl)ccc1C1c2c(n[nH]c2C(C)C)C(=O)N1c1cccc(Cl)c1F]

A mixture of intermediate A (4.0 g, 9.47 mmol) and hydrazine hydrate (1.83 mL, 37.9 mmol) in acetic acid (15 mL) and ethanol (5 mL) was heated to reflux for 1.5 h, allowed to cool to rt, concentrated, diluted with EtOAc, and neutralized by addition of a saturated aqueous solution of sodium bicarbonate. The organic layer was separated, dried (Na$_2$SO$_4$), filtered, and concentrated to provide 3.9 g of the title compound. $t_R$: 6.13 min (HPLC 2); ESI-MS: 418 [M+H]$^+$ (LC-MS 2); $R_f$=0.25 (hexane/EtOAc, 1:1).

Intermediate AE: 5-(3-Chloro-2-fluoro-phenyl)-4-(4-chloro-phenyl)-3-isopropyl-4,5-dihydro-2H-pyrrolo[3,4-c]pyrazol-6-one

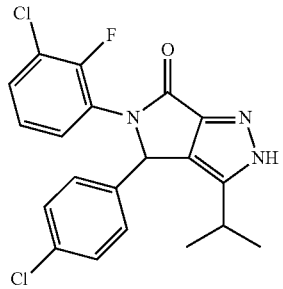 [SMILES: CC(C)c1[nH]nc2c1C(c1ccc(Cl)cc1)N(c1cccc(Cl)c1F)C2=O]

A mixture of intermediate B (8.0 g, 15.7 mmol) and hydrazine hydrate (1.83 mL, 37.9 mmol) in acetic acid (30 mL) and ethanol (15 mL) was heated to reflux for 1 h, allowed to cool to rt, diluted with EtOAc and water. The organic layer was separated and extracted with EtOAc. The combined organic extracts were washed with brine, dried (Na$_2$SO$_4$), filtered and concentrated to provide 5.3 g of the title compound. $t_R$: 1.17 min (LC-MS 1); ESI-MS: 404 [M+H]$^+$ (LC-MS 1).

Intermediate AF: 4-(4-Chloro-phenyl)-5-(3,4-difluoro-phenyl)-3-isopropyl-4,5-dihydro-2H-pyrrolo[3,4-c]pyrazol-6-one

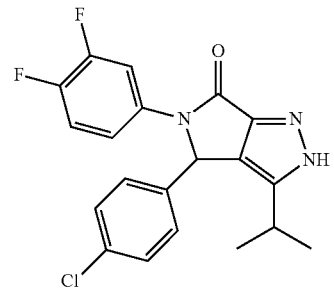 [SMILES: CC(C)c1[nH]nc2c1C(c1ccc(Cl)cc1)N(c1ccc(F)c(F)c1)C2=O]

The title compound was prepared in analogy to the procedure described for intermediate AD but using intermediate B. The crude material was purified by preparative HPLC (Column: AG/PP/C18-15/021. Flow: 20 mL/min. Gradient: 50% to 60% B in 3 min, 60% to 90% B in 3 min; A=10 mM ammonium acetate in water, B=acetonitrile) to provide 2.5 g of the title compound. $t_R$: 5.59 min (HPLC 2); ESI-MS: 388 [M+H]$^+$ (LC-MS 2); $R_f$=0.49 (hexane/EtOAc, 1:1).

Intermediate AG: 5-(3-Chloro-2-fluoro-phenyl)-4-(4-fluoro-phenyl)-3-isopropyl-4,5-dihydro-2H-pyrrolo[3,4-c]pyrazol-6-one

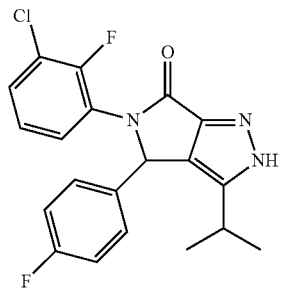

The title compound was prepared in analogy to the procedure described for intermediate AE but using intermediate E. $t_R$: 1.14 min (LC-MS 1); ESI-MS: 388 [M+H]$^+$ (LC-MS 1).

Intermediate AH: 5-(3-Chloro-2-fluoro-phenyl)-4-(3,4-difluoro-phenyl)-3-isopropyl-4,5-dihydro-2H-pyrrolo[3,4-c]pyrazol-6-one

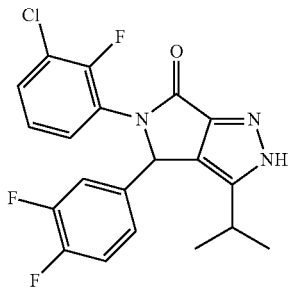 [SMILES: CC(C)c1[nH]nc2c1C(c1ccc(F)c(F)c1)N(c1cccc(Cl)c1F)C2=O]

The title compound was prepared in analogy to the procedure described for intermediate AE but using intermediate G. $t_R$: 1.15 min (LC-MS 1); ESI-MS: 406 [M+H]$^+$ (LC-MS 1).

Intermediate AI: 4-(4-Chloro-2-methyl-phenyl)-5-(5-chloro-2-methyl-phenyl)-3-isopropyl-4,5-dihydro-2H-pyrrolo[3,4-c]pyrazol-6-one

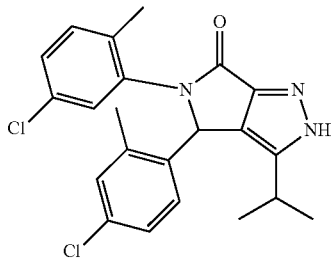 [SMILES: Cc1cc(Cl)ccc1C1c2c(n[nH]c2C(C)C)C(=O)N1c1cc(Cl)ccc1C]

The title compound was prepared in analogy to the procedure described for intermediate AD but using intermediate L. $t_R$: 6.30 min (HPLC 2); ESI-MS: 414 [M+H]$^+$ (LC-MS 2); $R_f$=0.24 (hexane/EtOAc, 1:1).

Intermediate AJ: 5-(3-Chloro-2-fluoro-phenyl)-4-(4-chloro-2-methyl-phenyl)-3-cyclopropyl-4,5-dihydro-2H-pyrrolo[3,4-c]pyrazol-6-one

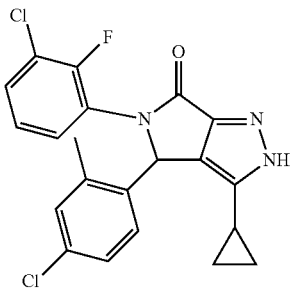 [SMILES: Cc1cc(Cl)ccc1C1c2c(n[nH]c2C2CC2)C(=O)N1c1cccc(Cl)c1F]

The title compound was prepared in analogy to the procedure described for intermediate AD but using intermediate O. The crude material was triturated with MeOH at rt, cooled to 0° C., collected by vacuum filtration, washed with pentane, and dried. $t_R$: 5.70 min (HPLC 2); ESI-MS: 415.8 [M+H]$^+$ (LC-MS 2); $R_f$=0.25 (hexane/EtOAc, 1:1).

Intermediate AK: 5-[5-Chloro-2-(2-dimethylamino-ethoxy)-phenyl]-4-(4-chloro-2-methyl-phenyl)-3-isopropyl-4,5-dihydro-2H-pyrrolo[3,4-c]pyrazol-6-one

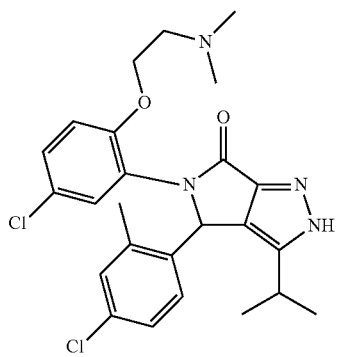 [SMILES: Cc1cc(Cl)ccc1C1c2c(n[nH]c2C(C)C)C(=O)N1c1cc(Cl)ccc1OCCN(C)C]

The title compound was prepared in analogy to the procedure described for intermediate AD but using intermediate M. The crude material was purified by silica gel column chromatography (CHCl$_3$/MeOH, 96:4). $t_R$: 3.54 min (HPLC 2); ESI-MS: 487.1 [M+H]$^+$ (LC-MS 2); $R_f$=0.44 (CHCl$_3$/MeOH, 85:15).

Intermediate AL: 5-(4-Chloro-2-methyl-phenyl)-3-hydroxy-4-isobutyryl-1-(4-methoxy-benzyl)-1,5-dihydro-pyrrol-2-one

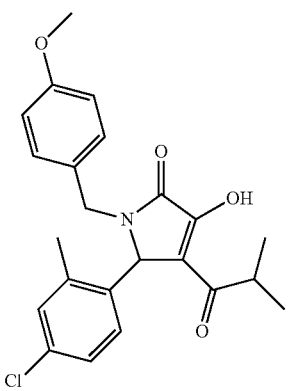 [SMILES: COc1ccc(CN2C(=O)C(O)=C(C(=O)C(C)C)C2c2ccc(Cl)cc2C)cc1]

5-Methyl-2,4-dioxo-hexanoic acid ethyl ester (5.6 g, 36.4 mmol) was added to a solution of 4-methoxybenzyl amine (5 g, 36.4 mmol) in acetic acid (40 mL). The mixture was stirred for 10 min at rt. 4-Chloro-2-methylbenzaldehyde (6.77 g, 36.4 mmol) was added. The reaction mixture was heated to 120° C., stirred at this temperature overnight, allowed to cool to rt and diluted with acetonitrile. The resulting precipitate was collected by vacuum filtration and dried to provide 11 g of the title compound. $t_R$: 1.80 min (LC-MS 2); ESI-MS: 414 [M+H]$^+$ (LC-MS 2).

Intermediate AM: 5-Isopropyl-1-(2-methoxy-phenyl)-1H-pyrazole-3-carboxylic acid ethyl ester

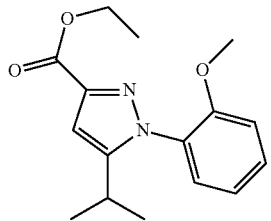 [SMILES: CCOC(=O)c1cc(C(C)C)n(-c2ccccc2OC)n1]

2-Methoxyphenylhydrazine (14.07 g, 81 mmol) in EtOH (100 mL) was added dropwise to a refluxing solution of 5-methyl-2,4-dioxo-hexanoic acid ethyl ester (10 g, 53.7 mmol) in toluene (100 mL), under an argon atmosphere. The reaction mixture was stirred for 18 h at 100° C., allowed to cool to rt, concentrated, diluted with a saturated aqueous solution of sodium bicarbonate (250 mL), and extracted with EtOAc. The organic extracts were washed with a saturated aqueous solution of sodium bicarbonate, dried (Na$_2$SO$_4$), filtered, and concentrated. The residue was purified by silica gel column chromatography (hexane/EtOAc, 95:5→7:3) to provide 10.1 g of the title compound. $t_R$: 1.11 min (LC-MS 4); ESI-MS: 289.2 [M+H]$^+$ (LC-MS 4); R$_f$=0.53 (hexane/EtOAc, 1:1).

Intermediate AN: 4-Bromo-5-isopropyl-1-(2-methoxy-phenyl)-1H-pyrazole-3-carboxylic acid ethyl ester

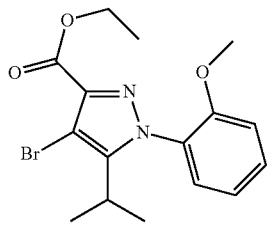 [SMILES: CCOC(=O)c1nn(-c2ccccc2OC)c(C(C)C)c1Br]

Bromine (5.4 mL, 105 mmol) was added dropwise to a cold (0° C.) solution of intermediate AM (10.1 g, 35.1 mmol) in CH$_2$Cl$_2$ (125 mL) under argon. The reaction mixture was stirred for 1 h at 0° C., concentrated, diluted with a saturated aqueous solution of sodium bicarbonate (250 mL), and extracted with EtOAc. The organic extracts were washed with a saturated aqueous solution of sodium bicarbonate, dried (Na$_2$SO$_4$), filtered, and concentrated. The residue was purified by silica gel column chromatography (hexane/EtOAc, 98:2→9:1) to provide 6.7 g of the title compound. $t_R$: 1.23 min (LC-MS 4); ESI-MS: 369.1 [M+H]$^+$ (LC-MS 4); R$_f$=0.63 (hexane/EtOAc, 1:1).

Intermediate AO: 5-Isopropyl-1-(2-methoxy-phenyl)-4-vinyl-1H-pyrazole-3-carboxylic acid ethyl ester

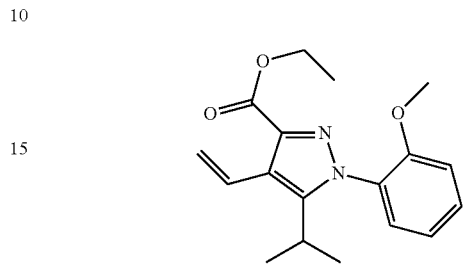

A mixture of intermediate AN (6.7 g, 18.3 mmol), vinylboronic anhydride pyridine complex (2.2 g, 9.16 mmol), potassium carbonate (3.8 g, 27.5 mmol) and bis(tri-t-butylphosphine)palladium(0) (0.468 g, 0.916 mmol) in dioxane (50 mL) and water (10 mL) was stirred for 1 hr at 80° C. under argon, quenched by addition of a saturated aqueous solution of ammonium chloride (150 mL), and extracted with EtOAc. The organic extracts were washed with a saturated aqueous solution of ammonium chloride, dried (Na$_2$SO$_4$), filtered, and concentrated. The residue was purified by silica gel column chromatography (hexane/EtOAc, 95:5→4:1) to provide 3.6 g of the title compound. $t_R$: 1.21 min (LC-MS 4); ESI-MS: 315.3 [M+H]$^+$ (LC-MS 4); R$_f$=0.68 (hexane/EtOAc, 1:1).

Intermediate AP: 4-Formyl-5-isopropyl-1-(2-methoxy-phenyl)-1H-pyrazole-3-carboxylic acid ethyl ester


A solution of intermediate AO (3.63 g, 11.6 mmol), 2.5% osmium tetroxide in tert-butanol (2.90 mL, 0.231 mmol) and N-methylmorpholine oxide (1.49 g, 12.7 mmol) in dioxane (50 mL) and water (15 mL) was stirred 2 h at rt. Sodium periodate (24.7 g, 115 mmol) was added. The reaction mixture was stirred for 1 h at rt, quenched by addition of a saturated aqueous solution of sodium bicarbonate (200 mL), and extracted with EtOAc. The organic extracts were washed with a saturated aqueous solution of sodium bicarbonate, dried (Na$_2$SO$_4$), filtered, and concentrated. The residue was purified by silica gel column chromatography (hexane/

EtOAc, 95:5→3:1) to provide 10.1 g of the title compound. $t_R$: 1.12 min (LC-MS 4); ESI-MS: 317.2 [M+H]$^+$ (LC-MS 4); $R_f$=0.67 (hexane/EtOAc, 1:1).

Intermediate AQ: 1-(5-Cyano-2-methoxy-phenyl)-1,2-hydrazinedicarboxylic acid 1,2-bis(1,1-dimethyl-ethyl) ester

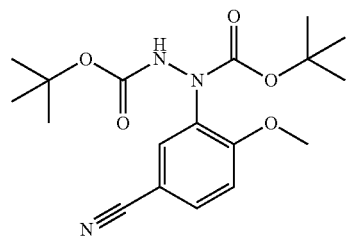 [SMILES: COc1ccc(C#N)cc1N(NC(=O)OC(C)(C)C)C(=O)OC(C)(C)C]

Isopropylmagnesium chloride-lithium chloride complex (1.3 M in THF, 21.8 mL, 28.3 mmol) was added dropwise to a cold (−78° C.) solution of 3-bromo-4-methoxybenzonitrile (5 g, 23.6 mmol) in THF (100 mL), under argon. The reaction mixture was allowed to warm to rt. Di-tertbutyl azodicarboxylate (5.43 g, 23.58 mmol) was added. The reaction mixture was stirred for 3 h at rt, diluted with a saturated aqueous solution of ammonium chloride (175 mL), and extracted with EtOAc. The organic layers were combined, washed with a saturated solution of sodium bicarbonate, dried (Na$_2$SO$_4$), and concentrated. The residue was purified by silica gel column chromatography (hexane/EtOAc, 95:5→7:3) to provide 5.5 g of the title compound. $t_R$: 1.16 min (LC-MS 4); ESI-MS: 362.2 [M−H]$^-$ (LC-MS 4); $R_f$=0.55 (hexane/EtOAc, 1:1).

Intermediate AR:
3-Hydrazino-4-methoxy-benzonitrile

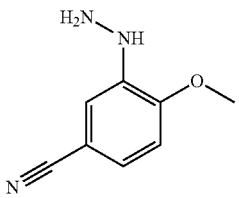

A mixture of intermediate AQ (5.5 g, 15.1 mmol) and HCl (4 N in dioxane, 75 mL) was stirred for 20 h at rt and concentrated. The residue was purified by silica gel column chromatography (CH$_2$Cl$_2$/MeOH/NH$_3$, 1:0:0→97:2:1) to provide 1.86 g of the title compound. $^1$H NMR (400 MHz, DMSO-d$_6$) δ ppm 3.81 (s, 3H), 4.06 (s, 2H), 6.46 (s, 1H), 6.91 (d, J=8.21 Hz, 1H), 7.03 (dd, J=8.21, 1.96 Hz, 1H), 7.21 (d, J=1.96 Hz, 1H); $R_f$=0.52 (CH$_2$Cl$_2$/MeOH, 9:1).

Intermediate AS: 1-(5-Cyano-2-methoxy-phenyl)-5-isopropyl-1H-pyrazole-3-carboxylic acid ethyl ester

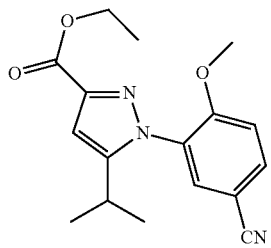 [SMILES: CCOC(=O)c1cc(C(C)C)n(-c2cc(C#N)ccc2OC)n1]

The title compound was prepared in analogy to the procedure described for intermediate AM but using intermediate AR dissolved in toluene, and stirring the reaction mixture for 1 h at 110° C. $t_R$: 1.08 min (LC-MS 4); ESI-MS: 314.2 [M+H]$^+$ (LC-MS 4); $R_f$=0.37 (hexane/EtOAc, 1:1).

Intermediate AT: 4-Bromo-1-(5-cyano-2-methoxy-phenyl)-5-isopropyl-1H-pyrazole-3-carboxylic acid ethyl ester

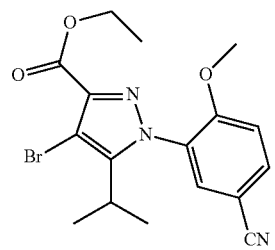 [SMILES: CCOC(=O)c1nn(-c2cc(C#N)ccc2OC)c(C(C)C)c1Br]

The title compound was prepared in analogy to the procedure described for intermediate AN but using intermediate AS, and stirring the reaction mixture for 3 h at rt. $t_R$: 1.20 min (LC-MS 4); ESI-MS: 394.1 [M+H]$^+$ (LC-MS 4); $R_f$=0.45 (hexane/EtOAc, 1:1).

Intermediate AU: 1-(5-Cyano-2-methoxy-phenyl)-5-isopropyl-4-vinyl-1H-pyrazole-3-carboxylic acid ethyl ester

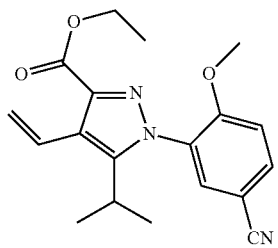 [SMILES: C=Cc1c(C(=O)OCC)nn(-c2cc(C#N)ccc2OC)c1C(C)C]

The title compound was prepared in analogy to the procedure described for intermediate AO but using intermediate AT. $t_R$: 1.14 min (LC-MS 5); ESI-MS: 340.3 [M+H]$^+$ (LC-MS 5); $R_f$=0.55 (hexane/EtOAc, 1:1).

Intermediate AV: 1-(5-Cyano-2-methoxy-phenyl)-4-formyl-5-isopropyl-1H-pyrazole-3-carboxylic acid ethyl ester

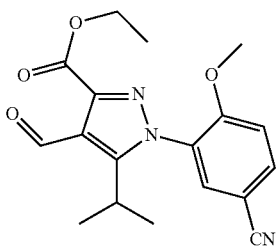 [SMILES: CCOC(=O)c1nn(-c2cc(C#N)ccc2OC)c(C(C)C)c1C=O]

The title compound was prepared in analogy to the procedure described for intermediate AP but using intermediate AU. $t_R$: 1.08 min (LC-MS 4); ESI-MS: 342.2 [M+H]$^+$ (LC-MS 4); $R_f$=0.50 (hexane/EtOAc, 1:1).

Intermediate AW: 1-(2,4-Dimethoxy-pyrimidin-5-yl)-1,2-hydrazinedicarboxylic acid 1,2-bis(1,1-dimethylethyl)ester

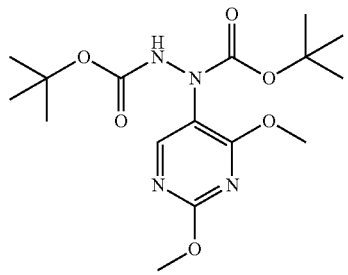 [SMILES: COc1ncc(N(NC(=O)OC(C)(C)C)C(=O)OC(C)(C)C)c(OC)n1]

Isopropylmagnesium chloride-lithium chloride complex (1.3 M in THF, 18.3 mL, 23.7 mmol) was added dropwise to a cold (0° C.) solution of 5-bromo-2,4-dimethoxypyrimidine (4 g, 18.3 mmol) in THF (50 mL), under argon. The reaction mixture was allowed to warm to rt and stirred for 1 h at this temperature. Di-tertbutyl azodicarboxylate (4.2 g, 18.3 mmol) was added portionwise. The reaction mixture was stirred for 1 h at rt, diluted with brine, and extracted with EtOAc. The organic layers were combined, washed with brine, dried (Na$_2$SO$_4$), and concentrated. The residue was purified by silica gel column chromatography (hexane/EtOAc, 9:1→7:3) to provide 6.78 g of the title compound. $t_R$: 1.08 min (LC-MS 4); ESI-MS: 371.3 [M+H]$^+$ (LC-MS 4); $R_f$=0.55 (hexane/EtOAc, 1:1).

Intermediate AX: (2,4-Dimethoxy-pyrimidin-5-yl)-hydrazine

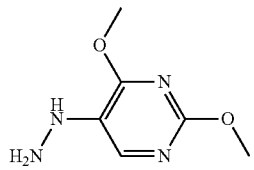

A mixture of intermediate AW (6.8 g, 18.3 mmol) and HCl (4 N in dioxane, 46 mL) was stirred for 1 h at rt and concentrated. The residue was purified by silica gel column chromatography (CH$_2$Cl$_2$/MeOH/NH$_3$, 94:5:1→89:10:1) to provide 2.88 g of the title compound. $^1$H NMR (400 MHz, DMSO-d$_6$) δ ppm 3.76 (s, 3H), 3.87 (s, 3H), 5.93 (b.s. 1H), 7.86 (s, 1H). $R_f$=0.50 (CH$_2$Cl$_2$/MeOH, 9:1).

Intermediate AY: 1(2,4-Dimethoxy-pyrimidin-5-yl)-5-isopropyl-1H-pyrazole-3-carboxylic acid ethyl ester

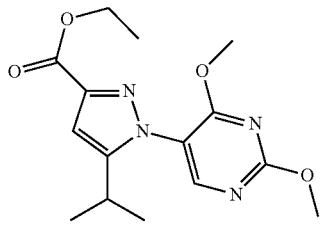 [SMILES: CCOC(=O)c1cc(C(C)C)n(-c2cnc(OC)nc2OC)n1]

The title compound was prepared in analogy to the procedure described for intermediate AM but using intermediate AX dissolved in toluene, and stirring the reaction mixture for 1 h at 110° C. $t_R$: 1.04 min (LC-MS 4); ESI-MS: 321.3 [M+H]$^+$ (LC-MS 4); $R_f$=0.43 (hexane/EtOAc, 1:1).

Intermediate AZ: 4-Bromo-1-(2,4-dimethoxy-pyrimidin-5-yl)-5-isopropyl-1H-pyrazole-3-carboxylic acid ethyl ester

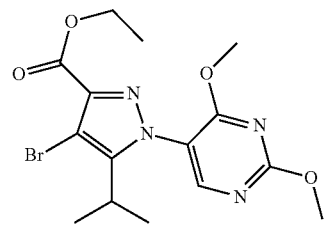 [SMILES: CCOC(=O)c1nn(-c2cnc(OC)nc2OC)c(C(C)C)c1Br]

The title compound was prepared in analogy to the procedure described for intermediate AN but using intermediate AY, stirring the reaction mixture for 1 h at rt, and quenching it by addition of 10% Na$_2$S$_2$O$_3$ in water. $t_R$: 1.18 min (LC-MS 4); ESI-MS: 401.2 [M+H]$^+$ (LC-MS 4); $R_f$=0.51 (hexane/EtOAc, 1:1).

Intermediate BA: 1-(2,4-Dimethoxy-pyrimidin-5-yl)-5-isopropyl-4-vinyl-1H-pyrazole-3-carboxylic acid ethyl ester

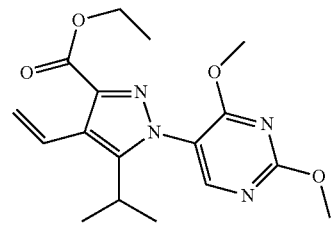 [SMILES: C=Cc1c(C(=O)OCC)nn(-c2cnc(OC)nc2OC)c1C(C)C]

The title compound was prepared in analogy to the procedure described for intermediate AO but using intermediate AZ and stirring the reaction mixture for 1 h at 90° C. $t_R$: 1.15 min (LC-MS 5); ESI-MS: 347.3 [M+H]$^+$ (LC-MS 5); $R_f$=0.40 (hexane/EtOAc, 1:1).

Intermediate BB: 1-(2,4-Dimethoxy-pyrimidin-5-yl)-4-formyl-5-isopropyl-1H-pyrazole-3-carboxylic acid ethyl ester

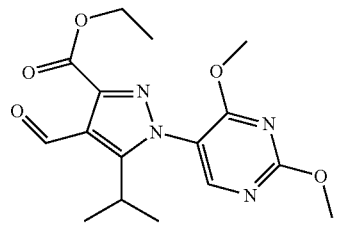 [SMILES: CCOC(=O)c1nn(-c2cnc(OC)nc2OC)c(C(C)C)c1C=O]

The title compound was prepared in analogy to the procedure described for intermediate AP but using intermediate BA. The reaction mixture was stirred for 5 h before and for 2 h after the addition of NaIO$_4$. t$_R$: 1.05 min (LC-MS 4); ESI-MS: 349.3 [M+H]$^+$ (LC-MS 4); R$_f$=0.44 (hexane/EtOAc, 1:1).

Intermediate BC: 1-(2-Bromo-5-methoxy-pyridin-4-yl)-1,2-hydrazinedicarboxylic acid 1,2-bis(1,1-dimethylethyl)ester

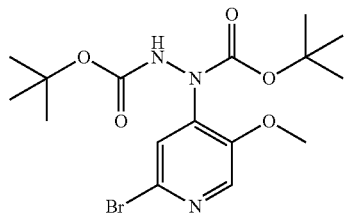 [SMILES: COc1cnc(Br)cc1N(NC(=O)OC(C)(C)C)C(=O)OC(C)(C)C]

A mixture of 2-bromo-5-methoxypyridine-4-boronic acid (10 g, 43.1 mmol), di-tert-butyl azodicarboxylate (9.93 g, 43.1 mmol), and copper(II) acetate (7.48 mg, 0.041 mmol) in MeOH (150 mL) was stirred 20 h at 50° C., filtered, concentrated, diluted with brine (100 mL), and extracted with EtOAc. The organic layers were combined, washed with brine, dried (Na$_2$SO$_4$), and concentrated. The residue was purified by silica gel column chromatography (hexane/EtOAc, 95:5→3:1) to provide 2.13 g of the title compound. t$_R$: 1.21 min (LC-MS 4); ESI-MS: 418.2 [M+H]$^+$ (LC-MS 4); R$_f$=0.67 (hexane/EtOAc, 1:1).

Intermediate BD: (2-Bromo-5-methoxy-pyridin-4-yl)-hydrazine

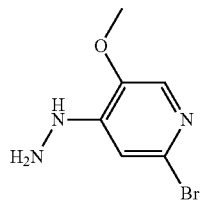

A mixture of intermediate BC (2.1 g, 5.09 mmol) and HCl (4 N in dioxane, 12.7 mL) was stirred for 1 h at rt, cooled to 0° C. and quenched by dropwise addition of a methanolic solution of ammonia (7 N, 10 mL). The resulting suspension was concentrated. The residue was purified by silica gel column chromatography (CH$_2$Cl$_2$/MeOH, 99:1→98:2) to provide 1.15 g of the title compound. t$_R$: 0.42 min (LC-MS 4); ESI-MS: 220.1 [M+H]$^+$ (LC-MS 4); R$_f$=0.53 (CH$_2$Cl$_2$/MeOH, 9:1).

Intermediate BE: 1(2-Bromo-5-methoxy-pyridin-4-yl)-5-isopropyl-1H-pyrazole-3-carboxylic acid ethyl ester

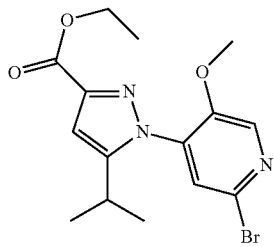 [SMILES: CCOC(=O)c1cc(C(C)C)n(-c2cc(Br)ncc2OC)n1]

The title compound was prepared in analogy to the procedure described for intermediate AM but using intermediate BD, and stirring the reaction mixture for 1 h at 110° C. t$_R$: 1.15 min (LC-MS 4); ESI-MS: 370.1 [M+H]$^+$ (LC-MS 4); R$_f$=0.60 (hexane/EtOAc, 1:1).

Intermediate BF: 1-(2-Cyano-5-methoxy-pyridin-4-yl)-5-isopropyl-1H-pyrazole-3-carboxylic acid ethyl ester

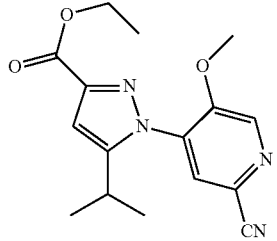 [SMILES: CCOC(=O)c1cc(C(C)C)n(-c2cc(C#N)ncc2OC)n1]

A mixture of intermediate BE (1.97 g, 5.35 mmol), zinc cyanide (2.63 g, 22.5 mmol) and Pd(PPh$_3$)$_4$ (1.236 g, 1.07 mmol) in DMF (10 mL) was stirred for 1 h at 100° C. under argon, allowed to cool to rt, diluted with a saturated aqueous solution of sodium bicarbonate (50 mL), and extracted with EtOAc. The organic layers were combined, washed with a saturated aqueous solution of sodium bicarbonate, dried (Na$_2$SO$_4$), filtered, and concentrated. The residue was purified by silica gel column chromatography (hexane/EtOAc, 9:1→65.45) to provide 1.22 g of the title compound. t$_R$: 1.06 min (LC-MS 4); ESI-MS: 315.3 [M+H]$^+$ (LC-MS 4); R$_f$=0.39 (hexane/EtOAc, 1:1).

Intermediate BG: 4-Bromo-1-(2-cyano-5-methoxy-pyridin-4-yl)-5-isopropyl-1H-pyrazole-3-carboxylic acid ethyl ester

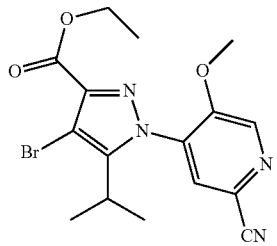 [SMILES: CCOC(=O)c1nn(-c2cc(C#N)ncc2OC)c(C(C)C)c1Br]

The title compound was prepared in analogy to the procedure described for intermediate AN but using intermediate BF, stirring the reaction mixture for 1 h at rt, and quenching it by addition of 10% Na$_2$S$_2$O$_3$ in water. t$_R$: 1.18 min (LC-MS 4); ESI-MS: 393.1/395.1 [M+H]$^+$ (LC-MS 4); R$_f$=0.44 (hexane/EtOAc, 1:1).

Intermediate BH: 1-(2-Cyano-5-methoxy-pyridin-4-yl)-5-isopropyl-4-vinyl-1H-pyrazole-3-carboxylic acid ethyl ester

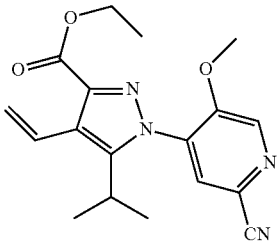 [SMILES: C=Cc1c(C(=O)OCC)nn(-c2cc(C#N)ncc2OC)c1C(C)C]

The title compound was prepared in analogy to the procedure described for intermediate AO but using intermediate BG and stirring the reaction mixture for 1 h at 100° C. $t_R$: 1.09 min (LC-MS 4); ESI-MS: 341.2 [M+H]$^+$ (LC-MS 4); $R_f$=0.54 (hexane/EtOAc, 1:1).

Intermediate BI: 1-(2-Cyano-5-methoxy-pyridin-4-yl)-4-formyl-5-isopropyl-1H-pyrazole-3-carboxylic acid ethyl ester

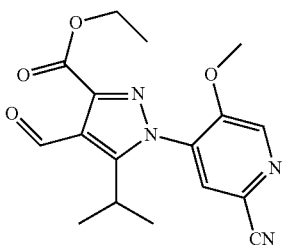 [SMILES: CCOC(=O)c1nn(-c2cc(C#N)ncc2OC)c(C(C)C)c1C=O]

The title compound was prepared in analogy to the procedure described for intermediate AP but using intermediate BH. The reaction mixture was stirred for 20 h before and for 2 h after the addition of NaIO$_4$. $t_R$: 1.06 min (LC-MS 4); ESI-MS: 343.2 [M+H]$^+$ (LC-MS 4); $R_f$=0.55 (hexane/EtOAc, 1:1).

Intermediate BJ:
3-Amino-5-chloro-1-methyl-1H-pyridin-2-one

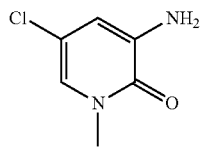

The title compound was prepared in analogy to the procedure described for Step 120.3 but using the compound prepared in step BJ1. The reaction was performed at rt for 16.5 hr and the product was purified by silica gel chromatography (hexane/EtOAc, 30:70). $t_R$: 0.52 min (LC-MS 5); ESI-MS: 159.1 [M+H]$^+$ (LC-MS 5), $R_f$=0.22 (hexane/EtOAc, 3:7).

Step BJ1:
5-Chloro-1-methyl-3-nitro-1H-pyridin-2-one

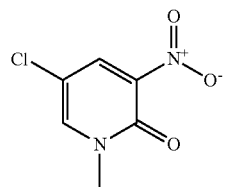

The title compound was prepared in analogy to the procedure described for Step 119.1 but using 5-chloro-2-hydroxy-3-nitropyridine [21427-61-2]. The reaction was performed at 5° C. and the product from extraction was used without purification. $t_R$: 0.60 min (LC-MS 4); ESI-MS: 189.1 [M+H]$^+$ (LC-MS 4).

Example 1

5-(3-Chloro-2-fluoro-phenyl)-4-(4-chloro-2-methyl-phenyl)-3-isopropyl-2-pyridin-2-ylmethyl-4,5-dihydro-2H-pyrrolo[3,4-c]pyrazol-6-one

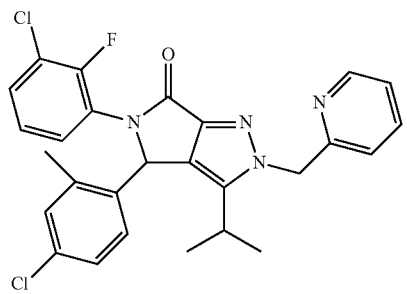 [SMILES: Cc1cc(Cl)ccc1C1c2c(nn(Cc3ccccn3)c2C(C)C)C(=O)N1c1cccc(Cl)c1F]

NaH (60% suspension, 21 mg, 0.526 mmol) was added to a mixture of intermediate AD (100 mg, 0.239 mmol) in DMF (1 mL) under an argon atmosphere. The reaction mixture was stirred for 5 min. Then, 2-(bromomethyl)pyridine hydrobromide (60.5 mg, 0.239 mmol) was added. The reaction mixture was stirred for 10 min at rt, diluted with water, and extracted with EtOAc. The organic extracts were washed with brine, dried, and concentrated. The residue was purified by silica gel column chromatography (heptane/ethyl acetate, 1:0→95:5→9:1→4:1→1:1) to provide 60 mg of the title compound. $t_R$: 5.10 min (HPLC 1); ESI-MS: 509 [M+H]$^+$ (LC-MS 4).

Example 2

5-(3-Chloro-2-fluoro-phenyl)-4-(4-chloro-2-methyl-phenyl)-3-isopropyl-2-pyridin-3-ylmethyl-4,5-dihydro-2H-pyrrolo[3,4-c]pyrazol-6-one

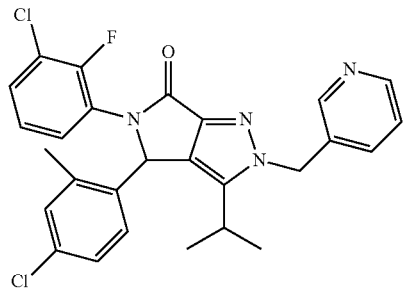 [SMILES: Cc1cc(Cl)ccc1C1c2c(nn(Cc3cccnc3)c2C(C)C)C(=O)N1c1cccc(Cl)c1F]

The title compound was prepared in analogy to the procedure described for example 1 but using 3-(bromomethyl)

Example 3

5-(3-Chloro-2-fluoro-phenyl)-4-(4-chloro-2-methyl-phenyl)-2-[2-(1H-imidazol-4-yl)-ethyl]3-isopropyl-4,5-dihydro-2H-pyrrolo[3,4-c]pyrazol-6-one

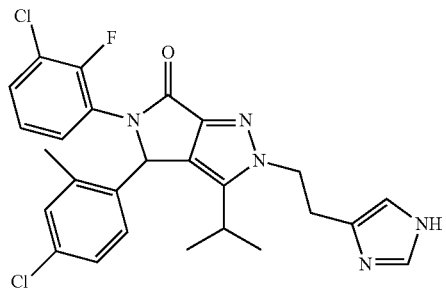 [SMILES: Cc1cc(Cl)ccc1C1c2c(nn(CCc3c[nH]cn3)c2C(C)C)C(=O)N1c1cccc(Cl)c1F]

HCl (4 M in dioxane, 1.0 mL, 4.17 mmol) was added to a solution of the compound prepared in step 3.1 (105 mg, 0.139 mmol) in dioxane (2 mL). The reaction mixture was heated to 100° C., stirred for 1 h, allowed to cool to rt, diluted with EtOAc, and neutralized by addition of a saturated aqueous solution of sodium bicarbonate. The organic phase was dried and concentrated. The residue was purified by preparative HPLC (Column: Sunfire 30×100 mm. Flow: 30 mL/min. Gradient: 30% to 70% B in 30 min; A=water+0.1% TFA, B=acetonitrile) to provide 46 mg of the title compound. $t_R$: 0.97 min (LC-MS 1); ESI-MS: 512 [M+H]$^+$ (LC-MS 1).

Step 3.1: 5-(3-Chloro-2-fluoro-phenyl)-4-(4-chloro-2-methyl-phenyl)-3-isopropyl-2-[2-(1-trityl-1H-imidazol-4-yl)-ethyl]-4,5-dihydro-2H-pyrrolo[3,4-c]pyrazol-6-one

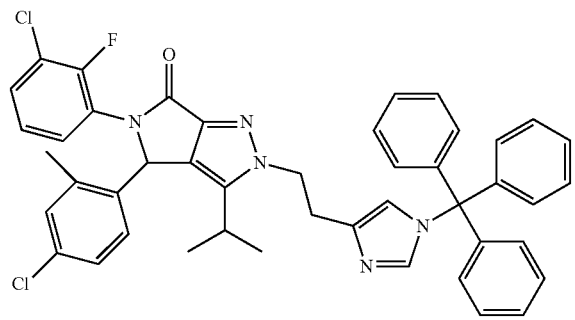 [SMILES: Cc1cc(Cl)ccc1C1c2c(nn(CCc3cn(C(c4ccccc4)(c4ccccc4)c4ccccc4)cn3)c2C(C)C)C(=O)N1c1cccc(Cl)c1F]

The title compound was prepared in analogy to the procedure described for example 1 but using 1.1 equivalents of 4-(2-bromo-ethyl)-1-trityl-1H-imidazole (Altman, J.; Wilchek, M. Journal of Heterocyclic Chemistry 1988, 25(3), 915-916), 1.25 equivalents of NaH, and stirring the reaction mixture for 26 h at rt. The crude material was purified by preparative HPLC (Column: Sunfire 30×100 mm. Flow 30 mL/min. Gradient: 40% to 80% B in 30 min; A=water+0.1% TFA, B=acetonitrile) to provide 105 mg of the title compound. $t_R$: 1.46 min (LC-MS 1); ESI-MS: 754 [M+H]$^+$ (LC-MS 1).

Example 4

5-(3-Chloro-2-fluoro-phenyl)-4-(4-chloro-2-methyl-phenyl)-3-isopropyl-2-(3-methyl-butyl)-4,5-dihydro-2H-pyrrolo[3,4-c]pyrazol-6-one

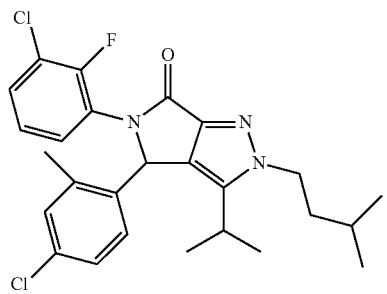 [SMILES: Cc1cc(Cl)ccc1C1c2c(nn(CCC(C)C)c2C(C)C)C(=O)N1c1cccc(Cl)c1F]

The title compound was prepared in analogy to the procedure described for example 1 but using 1-bromo-3-methyl-butane. $t_R$: 6.32 min (HPLC 1); ESI-MS: 488 [M+H]$^+$.

Example 5

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-1H-quinolin-2-one

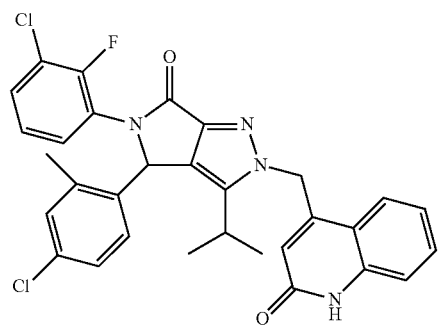 [SMILES: Cc1cc(Cl)ccc1C1c2c(nn(Cc3cc(=O)[nH]c4ccccc34)c2C(C)C)C(=O)N1c1cccc(Cl)c1F]

The title compound was prepared in analogy to the procedure described for example 1 but using 4-bromomethyl-1H-quinolin-2-one. $t_R$: 1.21 (LC-MS 1); ESI-MS: 575 [M+H]$^+$ (LC-MS 1).

Example 6

7-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-5-oxo-4,5-dihydro-pyrazolo[1,5-a]pyrimidine-3-carbonitrile

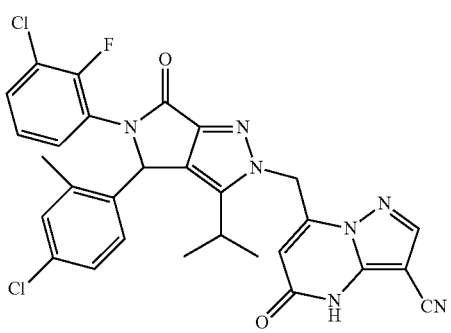 [SMILES: Cc1cc(Cl)ccc1C1c2c(nn(Cc3cc(=O)[nH]c4c(C#N)cnn34)c2C(C)C)C(=O)N1c1cccc(Cl)c1F]

The title compound was prepared in analogy to the procedure described for example 1 but using 7-chloromethyl-5-oxo-4,5-dihydro-pyrazolo[1,5-a]pyrimidine-3-carbonitrile. $t_R$: 1.24 (LC-MS 1); ESI-MS: 590 [M+H]$^+$ (LC-MS 1).

Example 7

5-(3-Chloro-2-fluoro-phenyl)-4-(4-chloro-2-methyl-phenyl)-3-isopropyl-2-(3-methyl-but-2-enyl)-4,5-dihydro-2H-pyrrolo[3,4-c]pyrazol-6-one

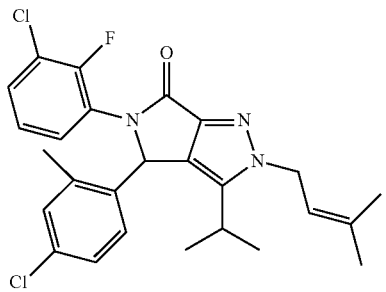 [SMILES: CC(C)=CCn1nc2c(c1C(C)C)C(c1ccc(Cl)cc1C)N(c1cccc(Cl)c1F)C2=O]

The title compound was prepared in analogy to the procedure described for example 1 but using 1-bromo-3-methyl-but-2-ene. $t_R$: 1.62 (LC-MS 1); ESI-MS: 486 [M+H]$^+$ (LC-MS 1).

Example 8

5-(3-Chloro-2-fluoro-phenyl)-4-(4-chloro-2-methyl-phenyl)-3-isopropyl-2-(2-pyridin-2-yl-ethyl)-4,5-dihydro-2H-pyrrolo[3,4-c]pyrazol-6-one

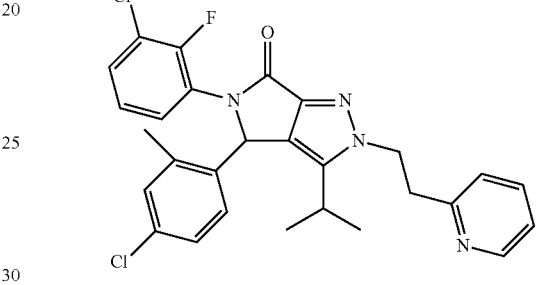

The title compound was prepared in analogy to the procedure described for example 1 but using 2-(2-bromoethyl)pyridine. $t_R$: 1.11 (LC-MS 1); ESI-MS: 523 [M+H]$^+$ (LC-MS 1).

Example 9

5-(3-Chloro-2-fluoro-phenyl)-4-(4-chloro-2-methyl-phenyl)-2-[2-(1H-indol-3-yl)-ethyl]-3-isopropyl-4,5-dihydro-2H-pyrrolo[3,4-c]pyrazol-6-one

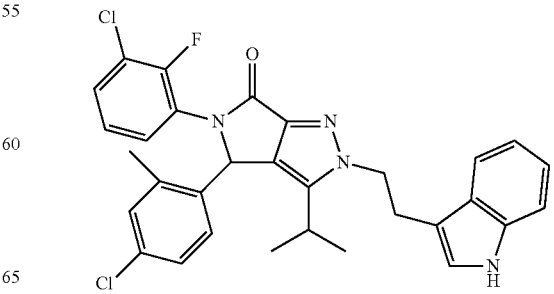

The title compound was prepared in analogy to the procedure described for example 1 but using 3-(2-bromo-ethyl)-1H-indole. $t_R$: 1.55 (LC-MS 1); ESI-MS: 561 [M+H]$^+$ (LC-MS 1).

Example 10

2-{2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-ethyl}-isoindole-1,3-dione

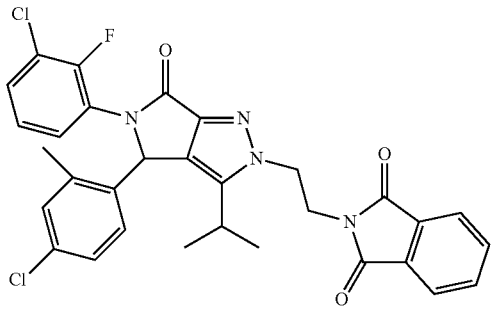 [SMILES: Cc1cc(Cl)ccc1C1c2c(nn(CCN3C(=O)c4ccccc4C3=O)c2C(C)C)C(=O)N1c1cccc(Cl)c1F]

The title compound was prepared in analogy to the procedure described for example 1 but using 2-(2-bromo-ethyl)-isoindole-1,3-dione. $t_R$: 1.49 (LC-MS 1); ESI-MS: 591 [M+H]$^+$ (LC-MS 1).

Example 11

5-(3-Chloro-2-fluoro-phenyl)-4-(4-fluoro-phenyl)-3-isopropyl-2-(3-methyl-butyl)-4,5-dihydro-2H-pyrrolo[3,4-c]pyrazol-6-one

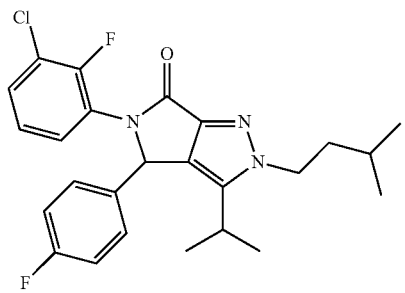 [SMILES: CC(C)CCn1nc2c(c1C(C)C)C(c1ccc(F)cc1)N(c1cccc(Cl)c1F)C2=O]

The title compound was prepared in analogy to the procedure described for example 1 but using intermediate AG, 1.1 equivalents of 1-bromo-3-methyl-butane, 1.1 equivalents of NaH, and stirring the reaction mixture for 2 h at rt. $t_R$: 1.38 (LC-MS 1); ESI-MS: 458.2 [M+H]$^+$ (LC-MS 1).

Example 12

5-(3-Chloro-2-fluoro-phenyl)-4-(3,4-difluoro-phenyl)-3-isopropyl-2-(3-methyl-butyl)-4,5-dihydro-2H-pyrrolo[3,4-c]pyrazol-6-one

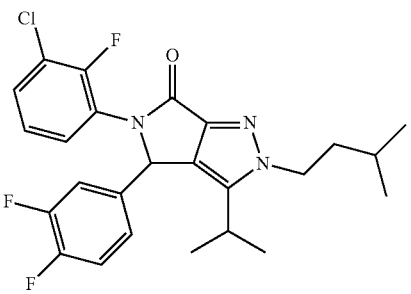 [SMILES: CC(C)CCn1nc2c(c1C(C)C)C(c1ccc(F)c(F)c1)N(c1cccc(Cl)c1F)C2=O]

The title compound was prepared in analogy to the procedure described for example 1 but using intermediate AH, 1.1 equivalents of 1-bromo-3-methyl-butane, 1.1 equivalents of NaH, and stirring the reaction mixture for 2 h at rt. $t_R$: 1.41 (LC-MS 1); ESI-MS: 476.1 [M+H]$^+$ (LC-MS 1).

Example 13

5-(3-Chloro-2-fluoro-phenyl)-4-(4-chloro-phenyl)-2-[2-(3-ethyl-2-oxo-imidazolidin-1-yl)-ethyl]-isopropyl-4,5-dihydro-2H-pyrrolo[3,4-c]pyrazol-6-one

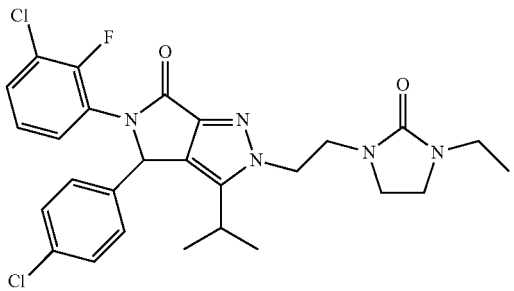 [SMILES: CCN1CCN(CCn2nc3c(c2C(C)C)C(c2ccc(Cl)cc2)N(c2cccc(Cl)c2F)C3=O)C1=O]

The title compound was prepared in analogy to the procedure described for example 1 but using intermediate AE, 2.2 equivalents of 1-(2-chloro-ethyl)-3-ethyl-imidazolidin-2-one (patent DE 1931193), and stirring the reaction mixture for 66 h at rt. The crude material was purified by preparative HPLC (Column: Sunfire 30×100 mm, 5 μm. Flow 30 mL/min. Gradient: 50% to 90% B in 30 min; A=water+0.1% TFA, B=acetonitrile), followed by silica gel column chromatography (hexane/EtOAc, 1:1→0:1). $t_R$: 1.18 (LC-MS 1); ESI-MS: 544 [M+H]$^+$ (LC-MS 1).

raphy (hexane/EtOAc, 1:0→7:3). $t_R$: 1.43 (LC-MS 4); ESI-MS: 600 [M+18]$^+$ (LC-MS 4).

Example 14

4-(4-Chloro-2-methyl-phenyl)-5-(5-chloro-2-methyl-phenyl)-3-isopropyl-2-oxiranylmethyl-4,5-dihydro-2H-pyrrolo[3,4-c]pyrazol-6-one

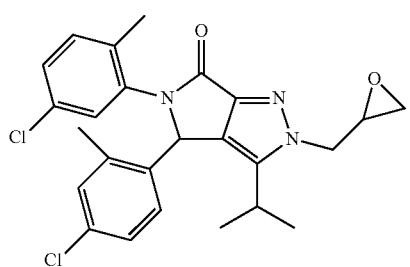 [SMILES: Cc1cc(Cl)ccc1C1c2c(nn(CC3CO3)c2C(C)C)C(=O)N1c1cc(Cl)ccc1C]

The title compound was prepared in analogy to the procedure described for example 1 but using intermediate AI, 1.6 equivalents of 1-bromo-2,3-epoxypropane, 1.6 equivalents of NaH, and stirring the reaction mixture at rt overnight. The crude material was purified by silica gel column chromatography (hexane/EtOAc, 1:0→1:1). $t_R$: 1.28 (LC-MS 1); ESI-MS: 470 [M+H]$^+$ (LC-MS 1).

Example 15

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-pyrrolidine-1-carboxylic acid tert-butyl ester

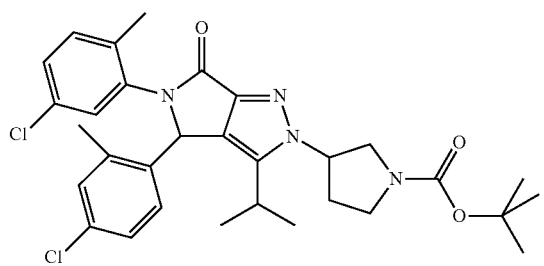 [SMILES: Cc1cc(Cl)ccc1C1c2c(nn(C3CCN(C(=O)OC(C)(C)C)C3)c2C(C)C)C(=O)N1c1cc(Cl)ccc1C]

The title compound was prepared in analogy to the procedure described for example 1 but using intermediate AI, 1.1 equivalents of 3-bromomethyl-pyrrolidine-1-carboxylic acid tert-butyl ester, 1.1 equivalents of NaH, and stirring the reaction mixture for 1 h at rt, for 1 h at 60° C. and for 16 h at rt. The crude material was purified by silica gel column chromatog-

Example 16

5-(3-Chloro-2-fluoro-phenyl)-4-(4-chloro-phenyl)-2-(2,5-dimethyl-2H-pyrazol-3-ylmethyl)-3-isopropyl-4,5-dihydro-2H-pyrrolo[3,4-c]pyrazol-6-one

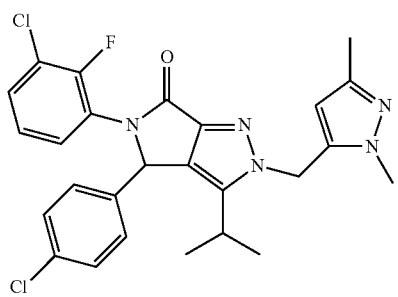 [SMILES: Cc1cc(Cn2nc3c(c2C(C)C)C(c2ccc(Cl)cc2)N(c2cccc(Cl)c2F)C3=O)n(C)n1]

The title compound was prepared in analogy to the procedure described for example 1 but using intermediate AE, 1.2 equivalents of 5-chloromethyl-1,3-dimethyl-1H-pyrazole, and stirring the reaction mixture for 16 h at rt. The crude material was purified by silica gel column chromatography (CH$_2$Cl$_2$/MeOH, 1:0→95:5→9:1). $t_R$: 1.31 (LC-MS 1); ESI-MS: 512 [M+H]$^+$ (LC-MS 1).

Example 17

5-(3-Chloro-2-fluoro-phenyl)-4-(4-chloro-phenyl)-2-(1H-imidazol-2-ylmethyl)-3-isopropyl-4,5-dihydro-2H-pyrrolo[3,4-c]pyrazol-6-one

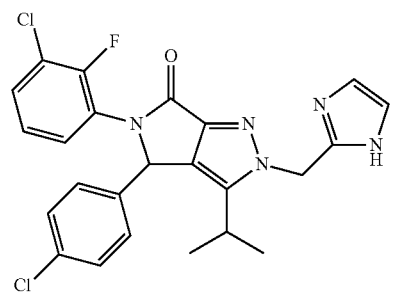 [SMILES: CC(C)c1c2c(nn1Cc1ncc[nH]1)C(=O)N(c1cccc(Cl)c1F)C2c1ccc(Cl)cc1]

The title compound was prepared in analogy to the procedure described for example 1 but using intermediate AE, 5 equivalents of 2-(chloromethyl)-1H-imidazole hydrochloride, 6.4 equivalents of NaH, and stirring the reaction mixture for 34 h at rt. The crude material was purified by silica gel column chromatography (CH$_2$Cl$_2$/MeOH, 99:1→98:2→95:5→9:1). t$_R$: 1.02 (LC-MS 1); ESI-MS: 484 [M+H]$^+$ (LC-MS 1).

Example 18

5-(3-Chloro-2-fluoro-phenyl)-4-(4-chloro-phenyl)-3-isopropyl-2-(1H-tetrazol-5-ylmethyl)-4,5-dihydro-2H-pyrrolo[3,4-c]pyrazol-6-one

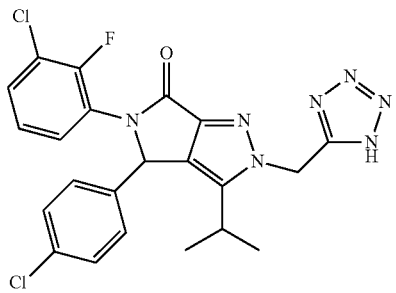 [SMILES: CC(C)c1c2c(nn1Cc1nnn[nH]1)C(=O)N(c1cccc(Cl)c1F)C2c1ccc(Cl)cc1]

HCl (4 M in dioxane, 2.0 mL, 8.18 mmol) was added to a solution of the mixture obtained in step 18.1 (80 mg, 0.136 mmol) in dioxane (1 mL). The reaction mixture was heated to 70° C. and stirred for 24 h. Further HCl (4 M in dioxane, 2.0 mL, 8.18 mmol) was added. The mixture was stirred at 100° C. for 24 h, allowed to cool to rt, neutralized by addition of a saturated aqueous solution of sodium bicarbonate, and concentrated. The residue was taken up in MeOH and filtered. The filtrate was concentrated and the residue was purified by MPLC (Column: XBridge 30×100 mm. Flow 30 mL/min. Gradient: 30% to 90% B in 28 min; A=water+0.1% TFA, B=acetonitrile) to provide 34 mg of the title compound. t$_R$: 1.10 min (LC-MS 1); ESI-MS: 486 [M+H]$^+$ (LC-MS 1).

Step 18.1: 5-[5-(3-Chloro-2-fluoro-phenyl)-4-(4-chloro-phenyl)-3-isopropyl-6-oxo-5,6-dihydro-4H-pyrrolo[3,4-c]pyrazol-2-ylmethyl]-tetrazole-1-carboxylic acid tert-butyl ester (Step 18.1a) and 5-[5-(3-Chloro-2-fluoro-phenyl)-4-(4-chloro-phenyl)-3-isopropyl-6-oxo-5,6-dihydro-4H-pyrrolo[3,4-c]pyrazol-2-ylmethyl]-tetrazole-2-carboxylic acid tert-butyl ester (Step 18.1b)

Step 18.1a

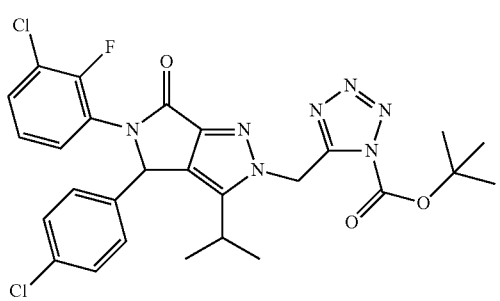

Step 18.1b

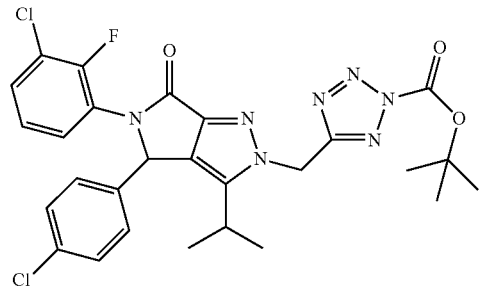

The title compound was prepared in analogy to the procedure described for example 1 but using intermediate AE, 2 equivalents of the mixture obtained in step 18.2, 2 equivalents of NaH, and stirring the reaction mixture for 40 min at rt. The crude material was purified by silica gel column chromatography (heptane/EtOAc, 1:0→95:5→9:1→4:1→1:1). t$_R$: 1.26 (LC-MS 1); ESI-MS: 586.3 [M+H]$^+$ (LC-MS 1).

Step 18.2: 5-Chloromethyl-tetrazole-1-carboxylic acid tert-butyl ester (Step 18.2a) and 5-Chloromethyl-tetrazole-2-carboxylic acid tert-butyl ester (Step 18.2b)

Steop 18.2a

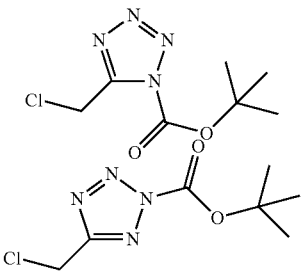

Step 18.2b

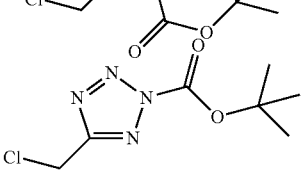

A mixture of di-tert-butyl dicarbonate (1.46 mL, 6.28 mmol), 5-(chloromethyl)-1H-tetrazole (620 mg, 5.23 mmol) and triethylamine (2.2 mL, 15.7 mmol) in CH$_2$Cl$_2$ (20 mL) was stirred for 2 h at rt, diluted with CH$_2$Cl$_2$, washed with 5% citric acid in water and water. The organic layer was concentrated to provide 220 mg of a mixture of the two regioisomeric products which was used without further purification.

Example 19

4-(4-Chloro-2-methyl-phenyl)-5-(5-chloro-2-methyl-phenyl)-2-[2-(4-hydroxy-piperidin-1-yl)-2-oxo-ethyl]-3-isopropyl-4,5-dihydro-2H-pyrrolo[3,4-c]pyrazol-6-one

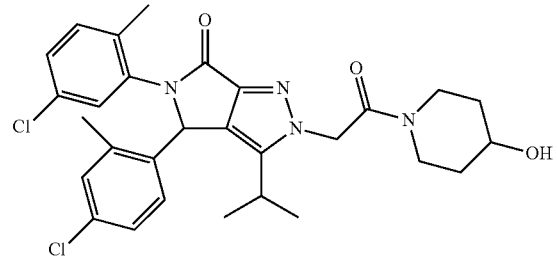 [SMILES: Cc1cc(Cl)ccc1C1c2c(nn(CC(=O)N3CCC(O)CC3)c2C(C)C)C(=O)N1c1cc(Cl)ccc1C]

A mixture of the compound prepared in step 19.1 (75 mg, 0.143 mmol), piperidin-4-ol (21.7 mg, 0.214 mmol), HATU (71 mg, 0.186 mmol) and N-methylmorpholine (0.079 mL, 0.714 mmol) in DMF (1.4 mL) was stirred for 17 h at rt, diluted with water, and extracted with EtOAc. The organic layer was washed with brine, dried ($Na_2SO_4$), filtered, and concentrated. The residue was purified by silica gel column chromatography (EtOAc) to provide 68 mg of the title compound. $t_R$: 1.15 min (LC-MS 3); ESI-MS: 555 [M+H]$^+$ (LC-MS 3).

Step 19.1: [4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-acetic acid

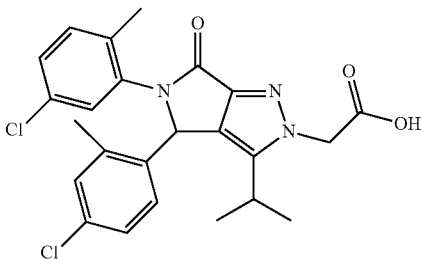 [SMILES: Cc1cc(Cl)ccc1C1c2c(nn(CC(=O)O)c2C(C)C)C(=O)N1c1cc(Cl)ccc1C]

A solution of lithium hydroxyde hydrate (8.9 mg, 0.211 mmol) in water (0.090 mL) was added to a cold (0° C.) solution of the compound prepared in step 19.2 (88 mg, 0.176 mmol) in THF (0.53 mL). The reaction mixture was stirred for 0.5 h at 0° C., allowed to warm to rt, quenched by addition of 5% citric acid in water, and extracted with EtOAc. The organic layer was washed with brine, dried ($Na_2SO_4$), filtered, and concentrated. The oily residue was triturated with diethyl ether and hexane to provide 78 mg of title compound. $t_R$: 1.12 (LC-MS 1); ESI-MS: 471.9 [M+H]$^+$ (LC-MS 1).

Step 19.2: [4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-acetic acid ethyl ester

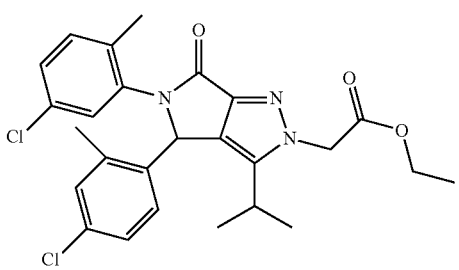 [SMILES: CCOC(=O)Cn1nc2c(c1C(C)C)C(c1ccc(Cl)cc1C)N(c1cc(Cl)ccc1C)C2=O]

The title compound was prepared in analogy to the procedure described for example 1 but using intermediate AI, 1.1 equivalents of ethylbromoacetate, 1.1 equivalents of NaH, and stirring the reaction mixture for 1 h at rt. The crude material was purified by silica gel column chromatography (hexane/EtOAc, 1:0→1:1). $t_R$: 1.34 (LC-MS 1); ESI-MS: 499.9 [M+H]$^+$ (LC-MS 1).

Example 20

4-(4-Chloro-2-methyl-phenyl)-5-(5-chloro-2-methyl-phenyl)-2-{2-[4-(2-hydroxy-ethyl)-piperidin-1-yl]-2-oxo-ethyl}-3-isopropyl-4,5-dihydro-2H-pyrrolo[3,4-c]pyrazol-6-one

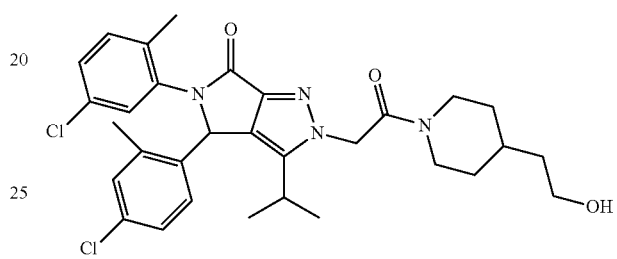

The title compound was prepared in analogy to the procedure described for example 19 from the product of step 19.1 and N-(2-hydroxyethyl)piperazine. $t_R$: 0.94 (LC-MS 1); ESI-MS: 488.1 [M+H]$^+$ (LC-MS 1).

Example 21

N-(1-Acetyl-piperidin-4-yl)-2-[4-(4-chloro-2-methyl-phenyl)-5-(5-chloro-2-methyl-phenyl)-3-isopropyl-6-oxo-5,6,-dihydro-4H-pyrrolo[3,4-c]pyrazol-2-yl]-acetamide

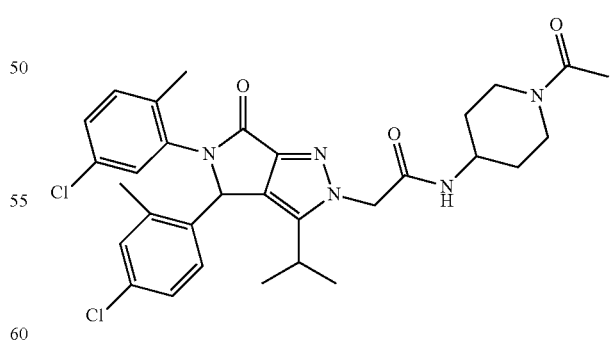

The product from step 21.1 (45 mg, 0.08 mmol) was dissolved in $CH_2Cl_2$ (1 mL) and TEA (13 μL, 0.09 mmol) and acetyl chloride (7 μL, 0.09 mmol) was added at rt. The reaction mixture was stirred for 1 h at rt, diluted with $CH_2Cl_2$, and was washed with brine. The organic layer was separated, dried ($Na_2SO_4$), filtered, and concentrated. Trituration of the residue with hexanes provided 25 mg of the title compound. $t_R$: 1.13 (LC-MS 1); ESI-MS: 596.1 [M+H]⁺ (LC-MS 1).

Step 21.1: 2-[4-(4-Chloro-2-methyl-phenyl)-5-(5-chloro-2-methyl-phenyl)-3-isopropyl-6-oxo-5,6,-dihydro-4H-pyrrolo[3,4-c]pyrazol-2-yl]-N-piperidin-4-yl-acetamide

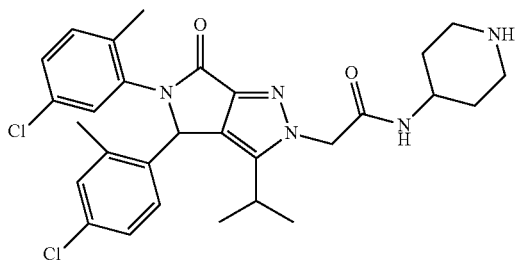 [SMILES: Cc1cc(Cl)ccc1C1c2c(nn(CC(=O)NC3CCNCC3)c2C(C)C)C(=O)N1c1cc(Cl)ccc1C]

The product from step 21.2 (90 mg, 0.14 mmol) was dissolved in dioxane (1 mL) and treated with a 4 M solution of HCl in dioxane (0.68 μL, 2.7 mmol) at rt. The reaction mixture was allowed to stir for 1.5 h at rt, diluted with EtOAc, and carefully neutralized by addition of a saturated aqueous solution of NaHCO₃. The organic layer separated, dried (Na₂SO₄), and concentrated. Trituration of the residue with hexanes provided 47 mg of title compound. $t_R$: 0.96 (LC-MS 1); ESI-MS: 554.0 [M+H]⁺ (LC-MS 1).

Step 21.2: 4-{2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-acetyl}-piperidine-1-carboxylic acid tert-butyl ester

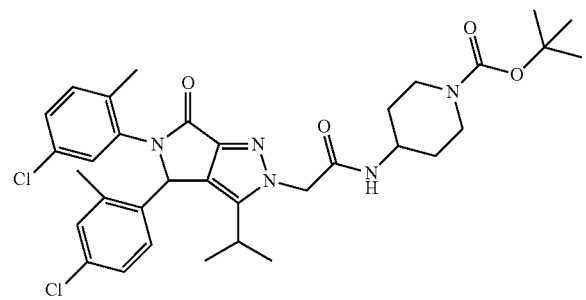 [SMILES: Cc1cc(Cl)ccc1C1c2c(nn(CC(=O)NC3CCN(C(=O)OC(C)(C)C)CC3)c2C(C)C)C(=O)N1c1cc(Cl)ccc1C]

The title compound was prepared in analogy to the procedure described for example 19 from the product of step 19.1 and 4-amino-1-tert-butoxycarbonylpiperidine. $t_R$: 1.35 (LC-MS 1); ESI-MS: 654.1 [M+H]⁺ (LC-MS 1).

Example 22

2-[2-(4-Acetyl-piperazin-1-yl)-2-oxo-ethyl]-4-(4-chloro-2-methyl-phenyl)-5-(5-chloro-2-methyl-phenyl)-3-isopropyl-4,5-dihydro-2H-pyrrolo[3,4-c]pyrazol-6-one

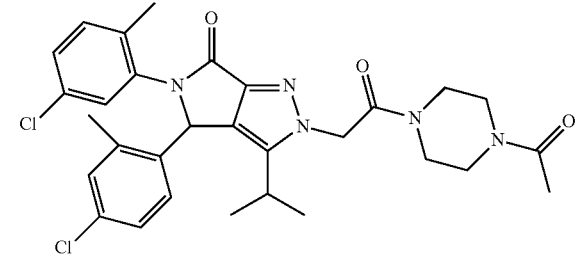 [SMILES: CC(=O)N1CCN(C(=O)Cn2nc3c(c2C(C)C)C(c2ccc(Cl)cc2C)N(c2cc(Cl)ccc2C)C3=O)CC1]

The title compound was prepared in analogy to the procedure described for example 21 from the product of step 22.1. $t_R$: 1.13 (LC-MS 1); ESI-MS: 582.1 [M+H]⁺ (LC-MS 1).

Step 22.1: 4-(4-Chloro-2-methyl-phenyl)-5-(5-chloro-2-methyl-phenyl)-3-isopropyl-2-(2-oxo-2-piperazin-1-yl-ethyl)-4,5-dihydro-2H-pyrrolo[3,4-c]pyrazol-6-one

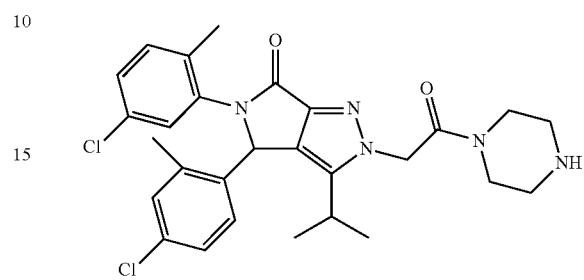

The title compound was obtained in analogy to the procedure described in step 21.1 from the product of step 22.2. $t_R$: 0.95 (LC-MS 1); ESI-MS: 540.0 [M+H]⁺ (LC-MS 1).

Step 22.2: 4-{2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-acetyl}-piperazine-1-carboxylic acid tert-butyl ester

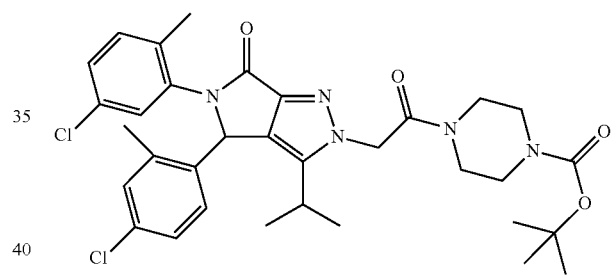

The title compound was prepared in analogy to the procedure described for example 19 from the product of step 19.1 and N-boc-piperazine. $t_R$: 1.37 (LC-MS 1); ESI-MS: 640.1 [M+H]⁺ (LC-MS 1).

Example 23

4-(4-Chloro-2-methyl-phenyl)-5-(5-chloro-2-methyl-phenyl)-3-isopropyl-2-[2-oxo-2-(3-oxo-piperazin-1-yl)-ethyl]-4,5-dihydro-2H-pyrrolo[3,4-c]pyrazol-6-one

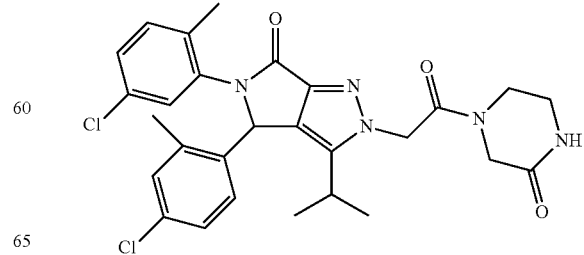

The title compound was prepared in analogy to the procedure described for example 19 from the product of step 19.1 and 2-oxopiperazine. $t_R$: 1.09 (LC-MS 1); ESI-MS: 554.0 [M+H]$^+$ (LC-MS 1).

Example 24

4-(4-Chloro-2-methyl-phenyl)-5-(5-chloro-2-methyl-phenyl)-3-isopropyl-2-[2-(4-methyl-3-oxo-piperazin-1-yl)-2-oxo-ethyl]-4,5-dihydro-2H-pyrrolo[3,4-c]pyrazol-6-one

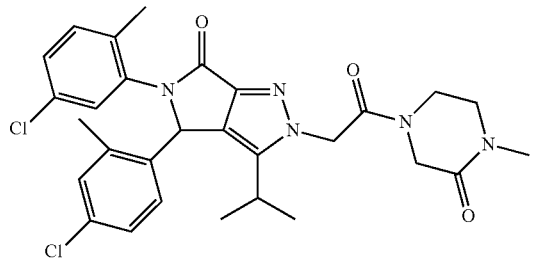 [SMILES: Cc1cc(Cl)ccc1C1c2c(nn(CC(=O)N3CCN(C)C(=O)C3)c2C(C)C)C(=O)N1c1cc(Cl)ccc1C]

The title compound was prepared in analogy to the procedure described for example 19 from the product of step 19.1 and 1-methyl-piperazin-2-one. $t_R$: 1.12 (LC-MS 1); ESI-MS: 568.1 [M+H]$^+$ (LC-MS 1).

Example 25

2-(1-Acetyl-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one

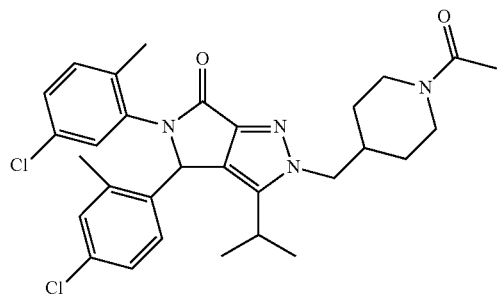 [SMILES: CC(=O)N1CCC(Cn2nc3c(c2C(C)C)C(c2ccc(Cl)cc2C)N(c2cc(Cl)ccc2C)C3=O)CC1]

The title compound was obtained in analogy to the procedure described for example 21 from the product of step 25.1. $t_R$: 1.25 (LC-MS 1); ESI-MS: 553.1 [M+H]$^+$ (LC-MS 1).

Step 25.1: 4-(4-Chloro-2-methyl-phenyl)-5-(5-chloro-2-methyl-phenyl)-3-isopropyl-2-piperidin-4-ylmethyl-4,5-dihydro-2H-pyrrolo[3,4-c]pyrazol-6-one

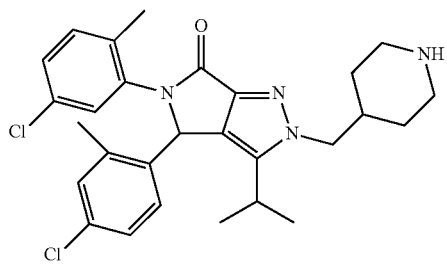 [SMILES: Cc1cc(Cl)ccc1C1c2c(nn(CC3CCNCC3)c2C(C)C)C(=O)N1c1cc(Cl)ccc1C]

The title compound was obtained in analogy to the procedure described in step 21.1 from the product of step 25.2. $t_R$: 0.98 (LC-MS 1); ESI-MS: 511.0 [M+H]$^+$ (LC-MS 1).

Step 25.2: 4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-piperidine-1-carboxylic acid tert-butyl ester

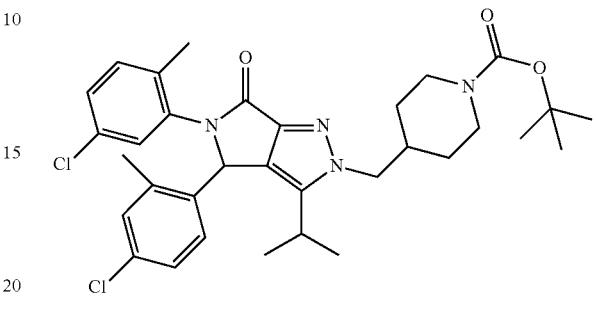

The title compound was prepared in analogy to the procedure described for example 1 but using the compound prepared in step 25.3. $t_R$: 1.55 (LC-MS 1); ESI-MS: 611.2 [M+H]$^+$ (LC-MS 1).

Step 25.3: 4-Bromomethyl-piperidine-1-carboxylic acid tert-butyl ester

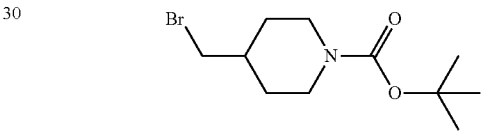

4-N-Boc-piperidine-methanol (200 mg, 0.93 mmol) was dissolved in diethyl ether (9 mL) and carbon tetrabromide (370 mg, 1.1 mmol) and PPh$_3$ (292 mg, 1.1 mmol) were added at rt. The reaction was allowed to stir for 18 h at rt and filtered over a pad of celite. The filtrate was concentrated and purified by flash chromatography (hexane/EtOAc, 1:0→4:1) to give 55 mg of the title compound. $^1$H-NMR (400 MHz, DMSO-d6) δ ppm 4.02-3.98 (m, 2H), 3.47 (d, 2H), 2.78-2.65 (m, 2H), 1.89-1.74 (m, 3H), 1.45 (s, 9H), 1.12-0.98 (m, 2H).

Example 26

4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-piperidine-1-carboxylic acid isopropylamide

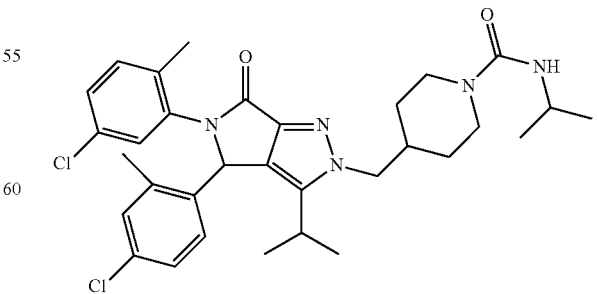

2-Isocyanato-propane (11 mL, 0.11 mmol) was added to a solution of the product of step 25.1 (50 mg, 0.10 mmol) in THF (2 mL) rt. The reaction mixture was stirred for 16 h at rt, diluted with EtOAc, washed with a saturated aqueous solution of sodium bicarbonate and brine, dried (Na$_2$SO$_4$), filtered, and concentrated. The residue was purified by preparative HPLC (Column: Waters SunFire C18, 30×100 mm, 5 µm. Flow: 50 mL/min. Gradient: 50% to 90% B in 16 min; A=0.1% TFA in water, B=acetonitrile) to give 24 mg of the title compound. $t_R$: 1.28 (LC-MS 1); ESI-MS: 596.1 [M+H]$^+$ (LC-MS 1).

Example 27

2-Allyl-4-(4-chloro-2-methyl-phenyl)-5-(5-chloro-2-methyl-phenyl)-3-isopropyl-4,5-dihydro-2H-pyrrolo[3,4-c]pyrazol-6-one

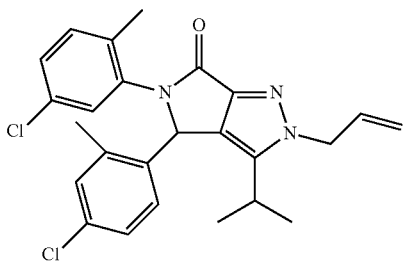 [SMILES: C=CCn1nc2c(c1C(C)C)C(c1ccc(Cl)cc1C)N(c1cc(Cl)ccc1C)C2=O]

The title compound was prepared in analogy to the procedure described for example 1 but using 1-bromo-propene. $t_R$: 1.36 (LC-MS 1); ESI-MS: 454.0 [M+H]$^+$ (LC-MS 1).

Example 28

4-(4-Chloro-2-methyl-phenyl)-5-(5-chloro-2-methyl-phenyl)-2-(2,3-dihydroxy-propyl)-3-isopropyl-4,5-dihydro-2H-pyrrolo[3,4-c]pyrazol-6-one

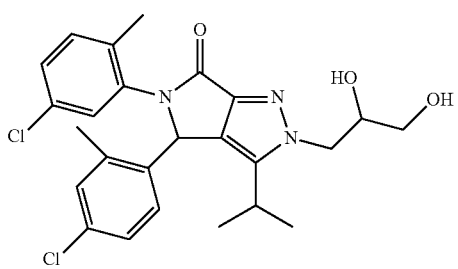 [SMILES: Cc1cc(Cl)ccc1C1c2c(nn(CC(O)CO)c2C(C)C)C(=O)N1c1cc(Cl)ccc1C]

AD-mix α (550 mg, 0.42 mmol) was added to a cold (0° C.) solution of the product from example 27 (190 mg, 0.42 mmol) in tert-butanol (5 mL) and water (5 mL). The reaction mixture was stirred for 1 h at 0° C., allowed to warm to rt, stirred for 2 days, diluted with EtOAc, washed with saturated aqueous solution of Na$_2$SO$_3$ and brine, dried (Na$_2$SO$_4$), filtered, and concentrated. The remaining crude material was purified by preparative HPLC (Column: XBridge, 30×100 mm. Flow: 30 mL/min. Gradient: 5% to 40% B in 1 min, 40% to 90% B in 22 min; A=0.1% TFA in water, B=0.1% TFA in acetonitrile) to give 125 mg of the title compound. $t_R$: 1.12 (LC-MS 1); ESI-MS: 488.0 [M+H]$^+$ (LC-MS 1).

Example 29

2-(1-Acetyl-4-hydroxy-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one

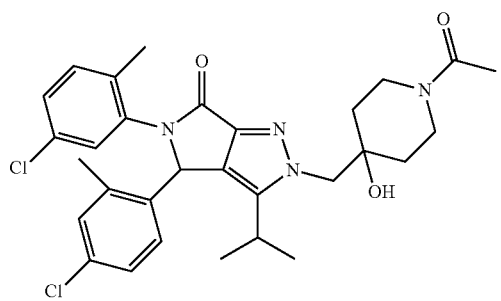 [SMILES: CC(=O)N1CCC(O)(Cn2nc3c(c2C(C)C)C(c2ccc(Cl)cc2C)N(c2cc(Cl)ccc2C)C3=O)CC1]

The title compound was obtained in analogy to the procedure described for example 21 from the product of step 29.1. $t_R$: 1.16 (LC-MS 1); ESI-MS: 569.0 [M+H]$^+$ (LC-MS 1).

Step 29.1: 4-(4-Chloro-2-methyl-phenyl)-5-(5-chloro-2-methyl-phenyl)-2-(4-hydroxy-piperidin-4-ylmethyl)-3-isopropyl-4,5-dihydro-2H-pyrrolo[3,4-c]pyrazol-6-one

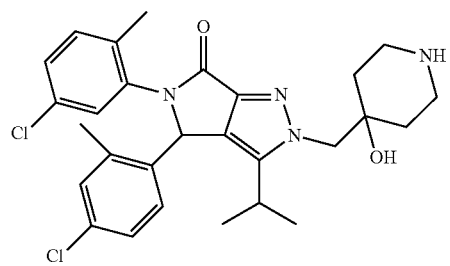 [SMILES: Cc1cc(Cl)ccc1C1c2c(nn(CC3(O)CCNCC3)c2C(C)C)C(=O)N1c1cc(Cl)ccc1C]

The title compound was obtained in analogy to the procedure described in step 21.1 from the product of step 29.2. $t_R$: 0.90 (LC-MS 1); ESI-MS: 527.0 [M+H]$^+$ (LC-MS 1).

Step 29.2: 4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-4-hydroxy-piperidine-1-carboxylic acid tert-butyl ester

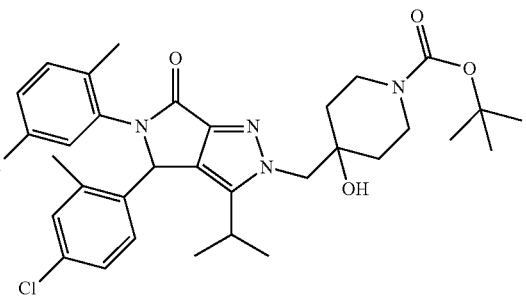

The title compound was prepared in analogy to the procedure described for example 1 but using the compound prepared in step 29.3. $t_R$: 1.53 (LC-MS 3); ESI-MS: 629.0 [M+H]$^+$ (LC-MS 3).

Step 29.3:
1-Oxa-6-aza-spiro[2,5]octane-6-carboxylic acid tert-butyl ester

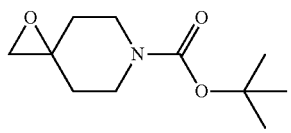

m-Chloroperbenzoic acid (1.14 g, 6.6 mmol) was added to a solution of tert-butyl 4-methylenepiperidine-1-carboxylate (1 g, 5.1 mmol) in CH$_2$Cl$_2$ (30 mL) at 0° C. The reaction mixture was stirred for 15 h at rt, diluted with CH$_2$Cl$_2$, washed with a saturated aqueous solution of NaHCO$_3$ and brine, dried (Na$_2$SO$_4$), and evaporated to afford 1.1 g of the title compound which was used without further purification. $^1$H-NMR (400 MHz, CDCl$_3$) δ ppm 3.74-3.65 (m, 2H), 3.45-3.38 (m, 2H), 2.68 (s, 2H), 1.82-1.75 (m, 2H), 1.48-1.41 (m, 2H), 1.46 (s, 9H).

Example 30

4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-4-hydroxy-piperidine-1-carboxylic acid isopropylamide

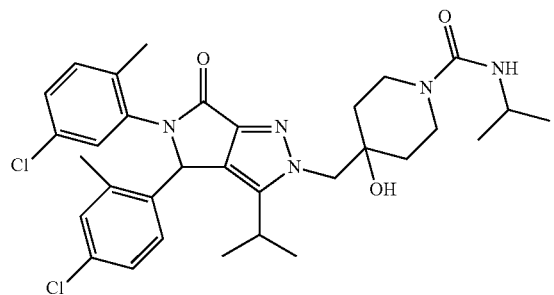 [SMILES: Cc1cc(Cl)ccc1C1c2c(nn(CC3(O)CCN(C(=O)NC(C)C)CC3)c2C(C)C)C(=O)N1c1cc(Cl)ccc1C]

The title compound was obtained in analogy to the procedure described for example 26 from the product of step 29.1. $t_R$: 1.21 (LC-MS 1); ESI-MS: 612.1 [M+H]$^+$ (LC-MS 1).

Example 31

5-(3-Chloro-2-fluoro-phenyl)-4-(4-chloro-2-methyl-phenyl)-3-isopropyl-2-phenethyl-4,5-dihydro-2H-pyrrolo[3,4-c]pyrazol-6-one

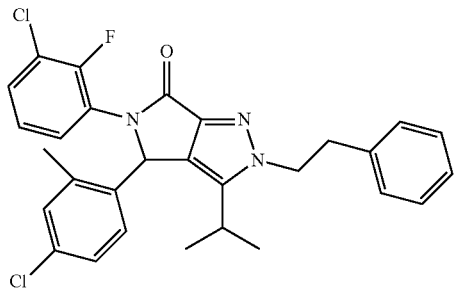 [SMILES: Cc1cc(Cl)ccc1C1c2c(nn(CCc3ccccc3)c2C(C)C)C(=O)N1c1cccc(Cl)c1F]

A mixture of intermediate AD (400 mg, 0.957 mmol), potassium carbonate (397 mg, 2.87 mmol) and (2-bromo-ethyl)-benzene (213 mg, 1.14 mmol) in DMF (8 mL) was stirred for 5 h at rt, quenched by slow addition of water and extracted with EtOAc. The organic phase was dried (Na$_2$SO$_4$), filtered and concentrated. The residue was purified by silica gel column chromatography (hexane/EtOAc, 95:5→4:1) to provide 100 mg of the title compound. $t_R$: 7.33 min (HPLC 2); ESI-MS: 522 [M+H]$^+$ (LC-MS 2); R$_f$=0.13 (hexane/EtOAc, 7:3).

Example 32

5-(3-Chloro-2-fluoro-phenyl)-4-(4-chloro-2-methyl-phenyl)-2-(2-dimethylamino-ethyl)-3-isopropyl-4,5-dihydro-2H-pyrrolo[3,4-c]pyrazol-6-one

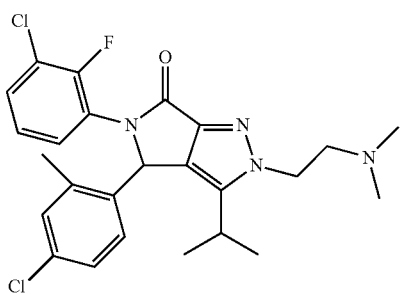 [SMILES: Cc1cc(Cl)ccc1C1c2c(nn(CCN(C)C)c2C(C)C)C(=O)N1c1cccc(Cl)c1F]

The title compound was prepared in analogy to the procedure described for example 31 but using (2-chloro-ethyl)-dimethyl amine, 4 equivalents of potassium carbonate and stirring the reaction mixture at rt overnight. The crude material was purified by silica gel column chromatography (hexane/EtOAc, 85:15→1:1) followed by preparative HPLC (Column: AG/PP/C18-15/024. Flow: 20 mL/min. Gradient: 50% to 60% B in 2 min, 60% to 90% B in 5 min; A=10 mM ammonium acetate in water, B=acetonitrile). $t_R$: 3.59 min (HPLC 2); ESI-MS: 489 [M+H]$^+$ (LC-MS 2); R$_f$=0.12 (hexane/EtOAc, 1:1).

Example 33

2-[4-(4-Chloro-phenyl)-5-(3,4-difluoro-phenyl)-3-isopropyl-6-oxo-5,6-dihydro-4H-pyrrolo[3,4-c]pyrazol-2-ylmethyl]-benzonitrile

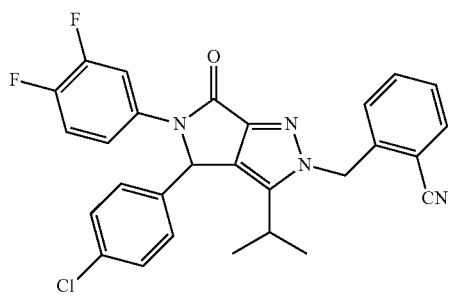 [SMILES: CC(C)c1c2c(nn1Cc1ccccc1C#N)C(=O)N(c1ccc(F)c(F)c1)C2c1ccc(Cl)cc1]

The title compound was prepared in analogy to the procedure described for example 31 but using intermediate AF, 2-bromethyl-benzonitrile, 4 equivalents of potassium carbonate and stirring the reaction mixture at rt overnight. The crude material was purified by silica gel column chromatography (hexane/EtOAc, 85:15→4:1). $t_R$: 6.27 min (HPLC 2); ESI-MS: 503 [M+H]$^+$ (LC-MS 2); $R_f$=0.38 (hexane/EtOAc, 7:3).

EtOAc, 8:1→7:3). $t_R$: 6.57 min HPLC 2); ESI-MS: 475.9 [M+H]$^+$ (LC-MS 2); $R_f$=0.38 (hexane/EtOAc, 1:1).

Example 34

5-(3-Chloro-2-fluoro-phenyl)-4-(4-chloro-2-methyl-phenyl)-3-isopropyl-2-(2-methyl-thiazol-4-ylm-ethyl)-4,5-dihydro-2H-pyrrolo[3,4-c]pyrazol-6-one

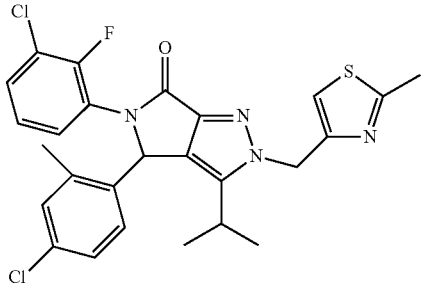 [SMILES: Cc1nc(Cn2nc3c(c2C(C)C)C(c2ccc(Cl)cc2C)N(c2cccc(Cl)c2F)C3=O)cs1]

The title compound was prepared in analogy to the procedure described for example 31 but using 4-chloromethyl-2-methyl-thiazole, 4 equivalents of potassium carbonate and stirring the reaction mixture at rt overnight. The crude material was purified by silica gel column chromatography (hexane/EtOAc, 8:1→7:3). $t_R$: 6.77 min (HPLC 2); ESI-MS: 529 [M+H]$^+$ (LC-MS 2); $R_f$=0.38 (hexane/EtOAc, 1:1).

Example 36

5-(3-Chloro-2-fluoro-phenyl)-4-(4-chloro-2-methyl-phenyl)-3-isopropyl-2-pyridin-4-ylmethyl-4,5-dihydro-2H-pyrrolo[3,4-c]pyrazol-6-one

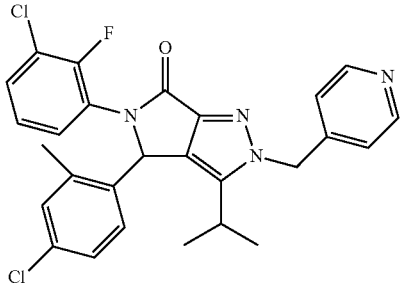

The title compound was prepared in analogy to the procedure described for example 31 but using 4-bromomethyl-pyridine hydrobromide, 4 equivalents of potassium carbonate and stirring the reaction mixture at rt overnight. The crude material was purified by silica gel column chromatography (hexane/EtOAc, 1:1→1:3). $t_R$: 5.59 min (HPLC 2); ESI-MS: 509 [M+H]$^+$ (LC-MS 2); $R_f$=0.14 (CH$_2$Cl$_2$/MeOH, 95:5).

Example 35

5-(3-Chloro-2-fluoro-phenyl)-4-(4-chloro-2-methyl-phenyl)-3-isopropyl-2-(2-methoxy-ethyl)-4,5-dihydro-2H-pyrrolo[3,4-c]pyrazol-6-one

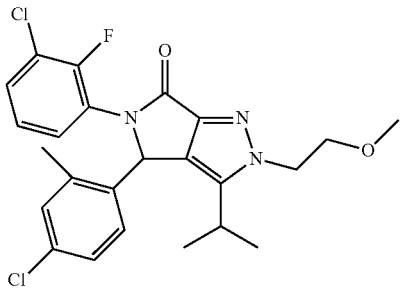 [SMILES: COCCn1nc2c(c1C(C)C)C(c1ccc(Cl)cc1C)N(c1cccc(Cl)c1F)C2=O]

The title compound was prepared in analogy to the procedure described for example 31 but using 1-bromo-2-methoxy-ethane, 4 equivalents of potassium carbonate and stirring the reaction mixture at rt overnight. The crude material was purified by silica gel column chromatography (hexane/

Example 37

5-(3-Chloro-2-fluoro-phenyl)-4-(4-chloro-2-methyl-phenyl)-3-isopropyl-2-thiazol-4-ylmethyl-4,5-dihydro-2H-pyrrolo[3,4-c]pyrazol-6-one

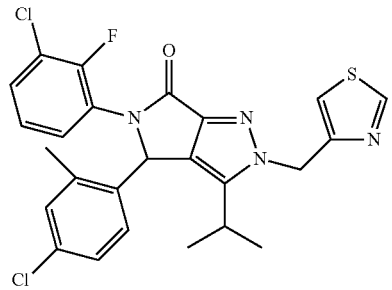 [SMILES: Cc1cc(Cl)ccc1C1c2c(nn(Cc3cscn3)c2C(C)C)C(=O)N1c1cccc(Cl)c1F]

The title compound was prepared in analogy to the procedure described for example 31 but using 4-chloromethyl-thiazole, 4 equivalents of potassium carbonate and stirring the reaction mixture at rt overnight. The crude material was purified by silica gel column chromatography (hexane/EtOAc, 7:3→1:1). $t_R$: 6.25 min (HPLC 2); ESI-MS: 514.9 [M+H]$^+$ (LC-MS 2); $R_f$=0.12 (hexane/EtOAc, 1:1).

Example 38

4-(4-Chloro-2-methyl-phenyl)-5-(5-chloro-2-methyl-phenyl)-3-isopropyl-2-(2-methoxy-ethyl)-4,5-dihydro-2H-pyrrolo[3,4-c]pyrazol-6-one

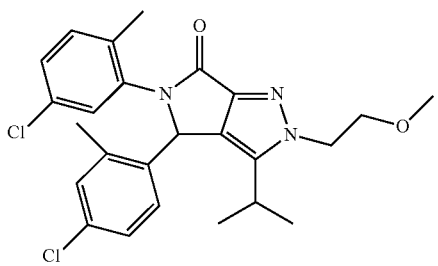 [SMILES: COCCn1nc2c(c1C(C)C)C(c1ccc(Cl)cc1C)N(c1cc(Cl)ccc1C)C2=O]

The title compound was prepared in analogy to the procedure described for example 31 but using intermediate AI, 1-bromo-2-methoxy-ethane, 4 equivalents of potassium carbonate and stirring the reaction mixture at rt overnight. The crude material was purified by silica gel column chromatography (hexane/EtOAc, 3:1→3:2) followed by preparative HPLC (Column: AG/PP/C18-15/022. Flow: 20 mL/min. Gradient: 50% to 90% B in 5 min; A=10 mM ammonium acetate in water, B=acetonitrile). $t_R$: 6.46 min (HPLC 2); ESI-MS: 471.7 [M+H]$^+$ (LC-MS 2); $R_f$=0.31 (hexane/EtOAc, 1:1).

Example 39

4-(4-Chloro-2-methyl-phenyl)-5-(5-chloro-2-methyl-phenyl)-3-isopropyl-2-pyridin-2-ylmethyl-4,5-dihydro-2H-pyrrolo[3,4-c]pyrazol-6-one

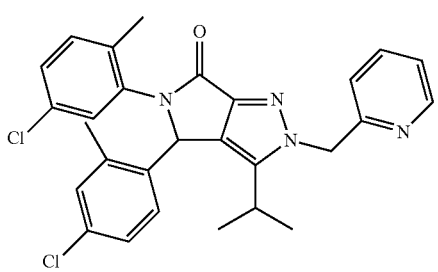 [SMILES: Cc1cc(Cl)ccc1C1c2c(nn(Cc3ccccn3)c2C(C)C)C(=O)N1c1cc(Cl)ccc1C]

The title compound was prepared in analogy to the procedure described for example 31 but using intermediate AI, 2-chloromethyl-pyridine, 4 equivalents of potassium carbonate and stirring the reaction mixture at rt overnight. The crude material was purified by silica gel column chromatography (hexane/EtOAc, 4:1→7:3). $t_R$: 6.35 min (HPLC 2); ESI-MS: 504.7 [M+H]$^+$ (LC-MS 2); $R_f$=0.21 (hexane/EtOAc, 1:1).

Example 40

2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-N-methyl-acetamide

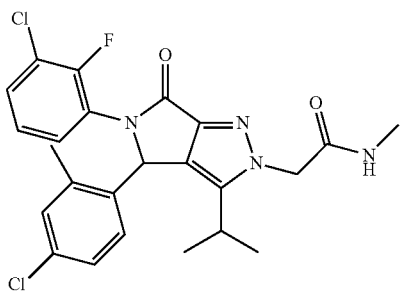 [SMILES: CNC(=O)Cn1nc2c(c1C(C)C)C(c1ccc(Cl)cc1C)N(c1cccc(Cl)c1F)C2=O]

A mixture of the compound prepared in step 40.1 (20 mg, 0.420 mmol), EDCI hydrochloride (145 mg, 0.756 mmol), HOBt (102 mg, 0.756 mmol), 4-(dimethylamino)-pyridine (5 mg) and DIEA (108 mg, 0.840 mmol) in $CH_2Cl_2$ (6 mL) was stirred for 90 min at rt. Methylamine hydrochloride (28 mg, 0.420 mmol) was added. The resulting mixture was stirred overnight at rt, quenched by slow addition of water and extracted with EtOAc. The organic phase was dried ($Na_2SO_4$), filtered, and concentrated. The residue was purified by silica gel column chromatography ($CH_2Cl_2$/MeOH, 99.5:0.05) to provide 40 mg of the title compound. $t_R$: 5.63 min (HPLC 2); ESI-MS: 488.9 [M+H]$^+$ (LC-MS 2); $R_f$=0.58 (hexane/EtOAc, 1:4).

Step 40.1: [5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-acetic acid

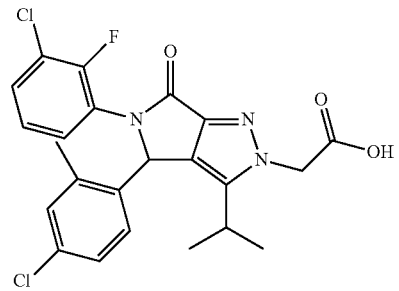 [SMILES: Cc1cc(Cl)ccc1C1c2c(nn(CC(=O)O)c2C(C)C)C(=O)N1c1cccc(Cl)c1F]

A solution of lithium hydroxyde hydrate (401 mg, 9.54 mmol) in water (6 mL) was added to a cold (0° C.) solution of the compound prepared in step 40.2 (4 g, 7.95 mmol) in THF (24 mL). The reaction mixture was stirred for 0.5 h at 0° C. and concentrated. The residue was diluted with water, washed with diethyl ether, acidified by addition of 35% HCl in water and extracted with EtOAc. The organic (EtOAc) layer was dried ($Na_2SO_4$), filtered, and concentrated to provide 3.6 g of the title compound. $t_R$: 5.69 min (HPLC 2); ESI-MS: 476 [M+H]$^+$ (LC-MS 2); $R_f$=0.12 (hexane/EtOAc, 1:1).

Step 40.2: [5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-acetic acid ethyl ester

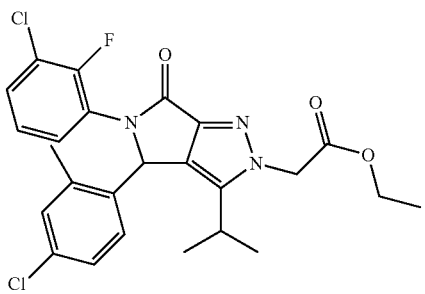 [SMILES: CCOC(=O)Cn1nc2c(c1C(C)C)C(c1ccc(Cl)cc1C)N(c1cccc(Cl)c1F)C2=O]

The title compound was prepared in analogy to the procedure described for example 31 but using 1.5 equivalents of ethylbromoacetate, 4 equivalents of potassium carbonate and stirring the reaction mixture at rt overnight. The crude material was triturated with n-pentane, collected by vacuum filtration and washed with hexane/EtOAc (95:5). $t_R$: 6.47 min (HPLC 2); ESI-MS: 504 [M+H]$^+$ (LC-MS 2); $R_f$=0.27 (hexane/EtOAc, 7:3).

Example 41

5-(3-Chloro-2-fluoro-phenyl)-4-(4-chloro-2-methyl-phenyl)-3-cyclopropyl-2-(3-methyl-butyl)-4,5-dihydro-2H-pyrrolo[3,4-c]pyrazol-6-one

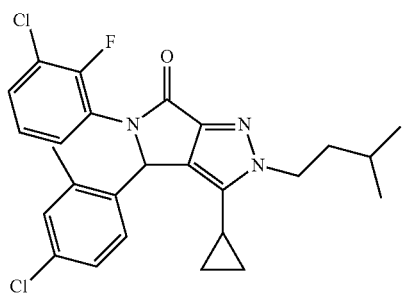 [SMILES: Cc1cc(Cl)ccc1C1c2c(nn(CCC(C)C)c2C2CC2)C(=O)N1c1cccc(Cl)c1F]

The title compound was prepared in analogy to the procedure described for example 31 but using intermediate AJ, 1.5 equivalents of 1-bromo-3-methyl-butane, 4 equivalents of potassium carbonate, stirring the reaction mixture for 8 h at rt, and quenching the reaction at 0° C. by slow addition of a saturated aqueous solution of ammonium chloride. The crude material was purified by silica gel column chromatography (hexane/EtOAc, 97:3→88:12). $t_R$: 7.32 min (HPLC 2); $t_R$: 2.14 min (LC-MS); ESI-MS: 486.0 [M+H]$^+$ (LC-MS 2); $R_f$=0.27 (hexane/EtOAc, 7:3).

Example 42

5-(3-Chloro-2-fluoro-phenyl)-4-(4-chloro-2-methyl-phenyl)-2-(3-hydroxy-propyl)-3-isopropyl-4,5-dihydro-2H-pyrrolo[3,4-c]pyrazol-6-one

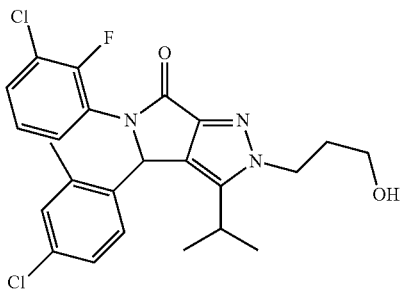 [SMILES: Cc1cc(Cl)ccc1C1c2c(nn(CCCO)c2C(C)C)C(=O)N1c1cccc(Cl)c1F]

TBAF (1 M in THF, 0.13 mL, 0.48 mmol) was added to a cold (0° C.) solution of the compound prepared in step 42.1 (0.19 g, 0.32 mmol) in THF (10 mL). The reaction mixture was allowed to warm to rt, stirred for 2 h, concentrated, diluted with a saturated solution of sodium bicarbonate, and extracted with EtOAc. The organic phase was dried (Na$_2$SO$_4$), filtered and concentrated to provide 110 mg of the title compound. $t_R$: 5.59 min (HPLC 2); ESI-MS: 476 [M+H]$^+$ (LC-MS 2); $R_f$=0.05 (hexane/EtOAc, 1:1).

Step 42.1: 2-[3-(tert-Butyl-dimethyl-silanyloxy)-propyl]-5-(3-chloro-2-fluoro-phenyl)-4-(4-chloro-2-methyl-phenyl)-3-isopropyl-4,5-dihydro-2H-pyrrolo[3,4-c]pyrazol-6-one

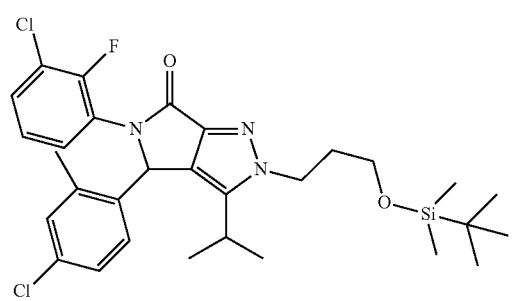 [SMILES: Cc1cc(Cl)ccc1C1c2c(nn(CCCO[Si](C)(C)C(C)(C)C)c2C(C)C)C(=O)N1c1cccc(Cl)c1F]

The title compound was prepared in analogy to the procedure described for example 31 but using (3-bromopropoxy)-tert-butyldimethylsilane, 4 equivalents of potassium carbonate, and stirring the reaction mixture at rt overnight. The crude material was purified by silica gel column chromatography (hexane/EtOAc, 4:1→7:3). $t_R$: 5.51 min (HPLC 2); ESI-MS: 590.0 [M+H]$^+$ (LC-MS 2); $R_f$=0.38 (hexane/EtOAc, 7:3).

Example 43

4-(4-Chloro-2-methyl-phenyl)-5-(5-chloro-2-methyl-phenyl)-3-isopropyl-2-(2-oxo-2-pyrrolidin-1-yl-ethyl)-4,5-dihydro-2H-pyrrolo[3,4-c]pyrazol-6-one

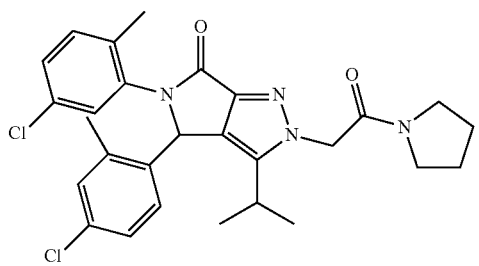 [SMILES: Cc1cc(Cl)ccc1C1c2c(nn(CC(=O)N3CCCC3)c2C(C)C)C(=O)N1c1cc(Cl)ccc1C]

The title compound was prepared in analogy to the procedure described for example 31 but using intermediate AI, 1.5 equivalents of 2-chloro-1-pyrrolidin-1-yl-ethanone, 4 equivalents of potassium carbonate, and stirring the reaction mixture at 80° C. overnight. The crude material was purified by silica gel column chromatography (CHCl$_3$/MeOH, 96:4). $t_R$: 6.44 min (HPLC 2); ESI-MS: 524.9 [M+H]$^+$ (LC-MS 2); $R_f$=0.19 (CHCl$_3$/MeOH, 9:1).

Example 44

4-(4-Chloro-2-methyl-phenyl)-5-(5-chloro-2-methyl-phenyl)-3-isopropyl-2-(tetrahydro-furan-2-ylm-ethyl)-4,5-dihydro-2H-pyrrolo[3,4-c]pyrazol-6-one

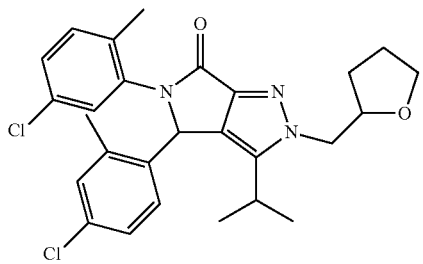 [SMILES: Cc1cc(Cl)ccc1C1c2c(nn(CC3CCCO3)c2C(C)C)C(=O)N1c1cc(Cl)ccc1C]

The title compound was prepared in analogy to the procedure described for example 31 but using intermediate AI, 1.5 equivalents of 2-(bromomethyl)tetrahydrofuran, 4 equivalents of potassium carbonate, and stirring the reaction mixture at rt overnight. The crude material was purified by silica gel column chromatography (hexane/EtOAc, 7:3→65:45). $t_R$: 7.09 min (HPLC 2); ESI-MS: 498.0 [M+H]$^+$ (LC-MS 2); $R_f$=0.32 (hexane/EtOAc, 2:1).

Example 45

4-(4-Chloro-2-methyl-phenyl)-5-(5-chloro-2-methyl-phenyl)-3-isopropyl-2-[2-(4-methyl-piperazin-1-A-ethyl]-4,5-dihydro-2H-pyrrolo[3,4-c]pyrazol-6-one

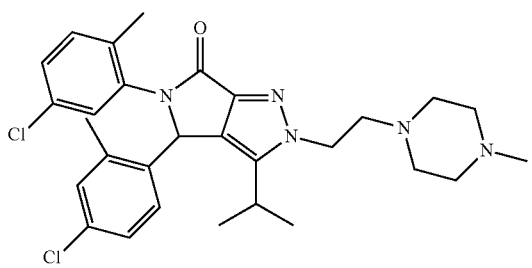 [SMILES: Cc1cc(Cl)ccc1C1c2c(nn(CCN3CCN(C)CC3)c2C(C)C)C(=O)N1c1cc(Cl)ccc1C]

The title compound was prepared in analogy to the procedure described for example 31 but using intermediate AI, 1-(2-chloro-ethyl)-4-methyl-piperazine, 4 equivalents of potassium carbonate, and stirring the reaction mixture at 100° C. overnight. The crude material was purified by silica gel column chromatography (hexane/EtOAc, 1:4) followed by preparative HPLC (Column: AG/PP/C18-15/021. Flow: 20 mL/min. Gradient: 30% to 40% B in 2 min, 40% to 90% B in 5 min; A=10 mM ammonium acetate in water, B=acetonitrile/MeOH, 1:1). $t_R$: 4.18 min (HPLC 2); ESI-MS: 540 [M+H]$^+$ (LC-MS 2); $R_f$=0.19 (hexane/EtOAc, 1:4).

Example 46

5-(3-Chloro-2-fluoro-phenyl)-4-(4-chloro-2-methyl-phenyl)-2-(2-hydroxy-2-methyl-propyl)-3-isopropyl-4,5-dihydro-2H-pyrrolo[3,4-c]pyrazol-6-one

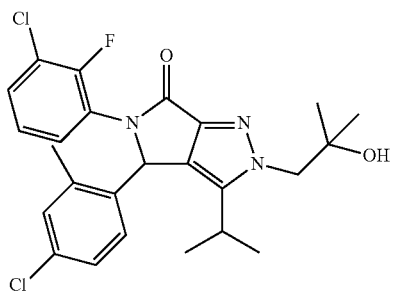 [SMILES: Cc1cc(Cl)ccc1C1c2c(nn(CC(C)(C)O)c2C(C)C)C(=O)N1c1cccc(Cl)c1F]

The title compound was prepared in analogy to the procedure described for example 31 but using 1.5 equivalents of 1-chloro-2-methyl-2-propanol, 4 equivalents of potassium carbonate, and stirring the reaction mixture for 4 h at rt and for 14 h at 85° C. overnight. The reaction mixture was cooled to 0° C. and quenched by addition of a saturated aqueous solution of ammonium chloride. The crude material was purified by silica gel column chromatography (CH$_2$Cl$_2$/MeOH, 99.5:

0.5→99.25:0.75). $t_R$: 6.22 min (HPLC 2); ESI-MS: 490 [M+H]$^+$ (LC-MS 2); $R_f$=0.22 (CH$_2$Cl$_2$/MeOH, 95:5).

Example 47

5-[5-Chloro-2-(2-dimethylamino-ethoxy)-phenyl]-4-(4-chloro-2-methyl-phenyl)-2-ethyl-3-isopropyl-4,5-dihydro-2H-pyrrolo[3,4-c]pyrazol-6-one

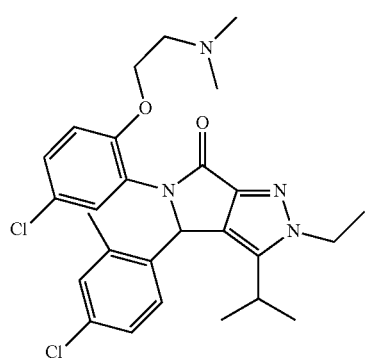 [SMILES: CCn1nc2c(c1C(C)C)C(c1ccc(Cl)cc1C)N(c1cc(Cl)ccc1OCCN(C)C)C2=O]

The title compound was prepared in analogy to the procedure described for example 31 but using intermediate AK, 1.5 equivalents of iodoethane, 4 equivalents of potassium carbonate, and stirring the reaction mixture for 16 h at rt. The reaction mixture was cooled to 0° C. and quenched by addition of a saturated aqueous solution of ammonium chloride. The crude material was purified by silica gel column chromatography (CH$_2$Cl$_2$/MeOH, 1:0→99:1) followed by preparative HPLC (Column: waters C18. Flow: 15 mL/min. Gradient: 40% to 50% B in 2 min, 50% to 90% B in 8 min; A=0.1% TFA in water, B=acetonitrile). $t_R$: 4.09 min (HPLC 2); ESI-MS: 515.2 [M+H]$^+$ (LC-MS 2); $R_f$=0.61 (CHCl$_3$/MeOH, 85:15).

Example 48

4-(4-Chloro-2-methyl-phenyl)-5-(5-chloro-2-methyl-phenyl)-3-isopropyl-2-[2-(2-oxo-pyrrolidin-1-yl)-ethyl]-4,5-dihydro-2H-pyrrolo[3,4-c]pyrazol-6-one

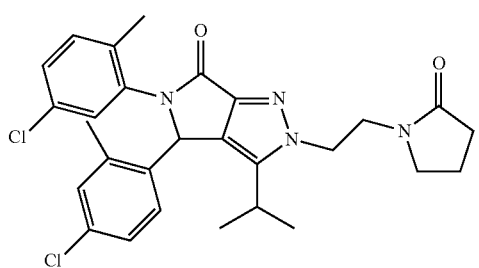 [SMILES: Cc1cc(Cl)ccc1C1c2c(nn(CCN3CCCC3=O)c2C(C)C)C(=O)N1c1cc(Cl)ccc1C]

Intermediate AI (350 mg, 0.845 mmol) was added to a cold (0° C.) suspension of NaH (60% suspension, 78 mg, 1.69 mmol) in DMF (2 mL). The mixture was stirred for 15 min at 0° C. and 1-(2-bromoethyl)-2-pyrrolidinone (242 mg, 1.27 mmol) in DMF (2 mL) was added dropwise. The resulting mixture was allowed to warm to rt, stirred for 16 h, quenched by slow addition of a saturated aqueous solution of ammonium chloride, and extracted with EtOAc. The combined organic extracts were dried (Na$_2$SO$_4$), filtered, and concentrated. The residue was purified by silica gel column chromatography (hexane/EtOAc, 1:1→1:4) to afford 25 mg of the title compound. $t_R$: 5.85 min (HPLC 2); ESI-MS: 525 [M+H]$^+$ (LC-MS 2); $R_f$=0.36 (hexane/EtOAc, 1:4).

Example 49

2-Benzyl-4-(4-chloro-2-methyl-phenyl)-5-(5-chloro-2-methyl-phenyl)-3-isopropyl-4,5-dihydro-2H-pyrrolo[3,4-c]pyrazol-6-one

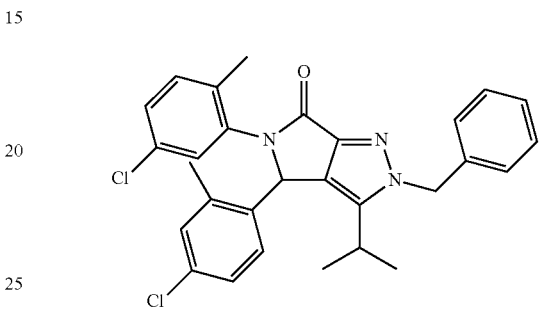

The title compound was prepared in analogy to the procedure described for example 31 but using intermediate AI, benzyl bromide, 4 equivalents of potassium carbonate, and stirring the reaction mixture first at rt overnight and then at 100° C. overnight. The crude material was purified by silica gel column chromatography (hexane/EtOAc, 95:5→9:1). $t_R$: 4.79 min (HPLC 5); ESI-MS: 504 [M+H]$^+$ (LC-MS 2); $R_f$=0.54 (hexane/EtOAc, 1:1).

Example 50

4-(4-Chloro-2-methyl-phenyl)-5-(5-chloro-2-methyl-phenyl)-3-isopropyl-2-(4-methyl-piperazine-1-carbonyl)-4,5-dihydro-2H-pyrrolo[3,4-c]pyrazol-6-one

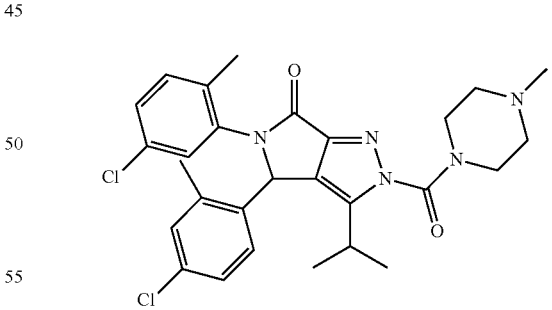

The title compound was prepared in analogy to the procedure described for example 31 but using intermediate AI, 4-methyl-piperazine-1-carbonyl chloride, 4 equivalents of potassium carbonate, and stirring the reaction mixture first at rt overnight and then at 80° C. for 2 h. The crude material was purified by silica gel column chromatography (hexane/EtOAc, 7:3→3:2) followed by preparative HPLC (Column: Zorbax, Eclipsewaters C18. Flow: 20 mL/min. Gradient: 70% to 80% B in 2 min, 80% to 90% B in 3 min; A=0.1% TFA

Example 51

4-(4-Chloro-2-methyl-phenyl)-5-(5-chloro-2-methyl-phenyl)-3-isopropyl-6-oxo-5,6-dihydro-4H-pyrrolo[3,4-c]pyrazole-2-carboxylic acid methyl-phenyl-amide

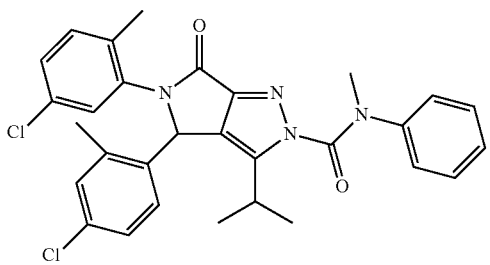 [SMILES: Cc1cc(Cl)ccc1C1c2c(nn(C(=O)N(C)c3ccccc3)c2C(C)C)C(=O)N1c1cc(Cl)ccc1C]

The title compound was prepared in analogy to the procedure described for example 31 but using intermediate AI, 2 equivalents of N-methyl-N-phenyl-carbamic chloride, 4 equivalents of potassium carbonate, and stirring the reaction mixture at rt overnight. The crude material was purified by silica gel column chromatography (hexane/EtOAc, 3:7) followed by preparative HPLC (Column: AG/PP/C-18-15. Flow: 20 mL/min. Gradient: 50% to 60% B in 2 min, 60% to 90% B in 3 min; A=0.1% TFA in water, B=acetonitrile). $t_R$: 6.90 min (HPLC 2); ESI-MS: 547.2 [M+H]$^+$ (LC-MS 2); $R_f$=0.24 (hexane/EtOAc, 7:3).

Example 52

(2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid methyl ester

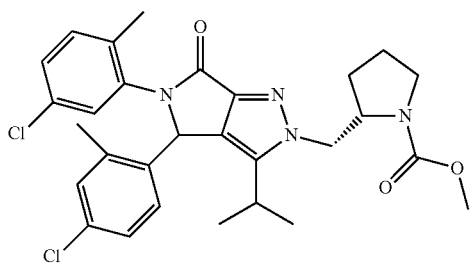

A mixture of the intermediate prepared in step 52.1 (50 mg, 0.0936 mmol) and triethylamine (24 mg, 0.234 mmol) in CH$_2$Cl$_2$ (3 mL) was stirred for 30 min at 0° C. Methyl chloroformate (11 mg, 0.112 mmol) in CH$_2$Cl$_2$ (2 mL) was added dropwise. The reaction mixture was stirred for 1 h at 0° C., quenched by slow addition of water and extracted with EtOAc. The organic phase was dried (Na$_2$SO$_4$), filtered and concentrated. The crude material was purified by preparative HPLC (Column: AG/PP/C-18-15. Flow: 20 mL/min. Gradient: 60% to 70% B in 2 min, 70% to 90% B in 2 min, 90% to 95% B in 3 min; A=water, B=acetonitrile) to provide 30 mg of the title compound. $t_R$: 6.82 min (HPLC 2); ESI-MS: 555 [M+H]$^+$ (LC-MS 2); $R_f$=0.46 (hexane/EtOAc, 1:1).

Step 52.1: 4-(4-Chloro-2-methyl-phenyl)-5-(5-chloro-2-methyl-phenyl)-3-isopropyl-2-((2S)-pyrrolidin-2-ylmethyl)-4,5-dihydro-2H-pyrrolo[3,4-c]pyrazol-6-one hydrochloride

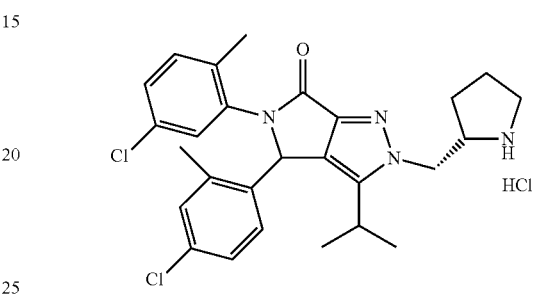

HCl in dioxane (4 mL) was added dropwise to a cold (0° C.) solution of the intermediate prepared in step 52.2 (400 mg, 0.0669 mmol) in dioxane (2 mL). The reaction mixture was allowed to warm to rt, stirred for 2 h and concentrated. The residue was triturated with diethyl ether to afford 240 mg of the title compound. $t_R$: 1.36 min (LC-MS 2); ESI-MS: 497 [M−HCl+H]$^+$ (LC-MS 2); $R_f$=0.09 (hexane/EtOAc, 3:7).

Step 52.2: (2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid tert-butyl ester

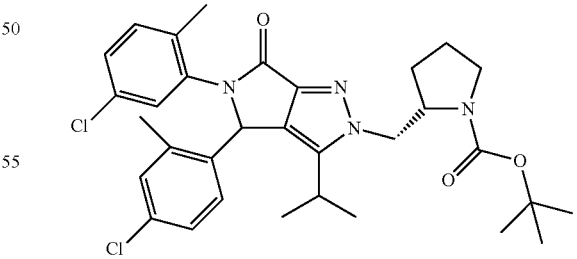

The title compound was prepared in analogy to the procedure described for example 31 but using intermediate AI, 3 equivalents of (2S)-2-(bromomethyl)-1-pyrrolidinecarboxylic acid 1,1-dimethylethyl ester, 4 equivalents of potassium carbonate, stirring the reaction mixture at rt for 16 h and at 80° C. for 12 h, and quenching the reaction mixture with a saturated aqueous solution of ammonium chloride. The crude material was purified by silica gel column chromatography (hexane/EtOAc, 85:15→3.2). $t_R$: 4.86 min (HPLC 5); $R_f$=0.52 (hexane/EtOAc, 3:7).

Example 53

(2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid dimethylamide

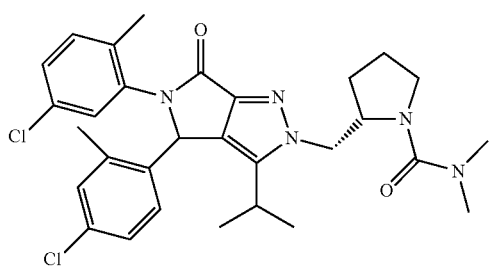

The title compound was prepared in analogy to the procedure described for example 52 but using N,N-dimethyl-carbamic chloride. The crude material was purified by preparative HPLC (Column: AG/PP/C-18-15. Flow: 20 mL/min. Gradient: 60% to 70% B in 2 min, 70% to 90% B in 2 min, 90% to 95% B in 3 min; A=water, B=acetonitrile). $t_R$: 6.81 min (HPLC 2); ESI-MS: 568.3 [M+H]$^+$ (LC-MS 2); $R_f$=0.46 (hexane/EtOAc, 1:1).

Example 54

2-((2S)-1-Acetyl-pyrrolidin-2-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one

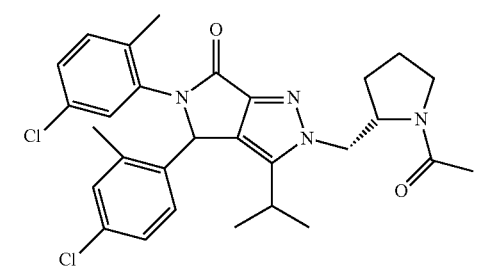

The title compound was prepared in analogy to the procedure described for example 52 but using acetyl chloride. The crude material was purified by preparative HPLC (Column: XBridge 21.2×150 mm, 5 µm. Flow: 20 mL/min. Gradient: 60% to 70% B in 2 min, 70% B for 2 min, 70% to 90% B in 6 min; A=water, B=acetonitrile). $t_R$: 6.36 min (HPLC 2); ESI-MS: 539.1 [M+H]$^+$ (LC-MS 2); $R_f$=0.46 (hexane/EtOAc, 1:1).

Example 55

2-Benzyl-5-(3-chloro-2-fluoro-phenyl)-4-(4-chloro-2-methyl-phenyl)-3-isopropyl-4,5-dihydro-2H-pyrrolo[3,4-c]pyrazol-6-one

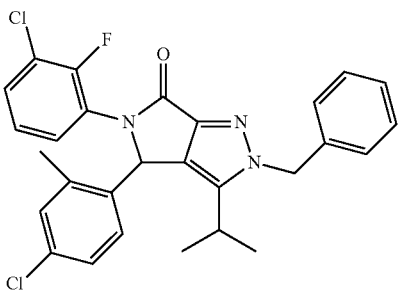

Intermediate A (100 mg, 0.237 mmol) and benzylhydrazine dihydrochloride (92 mg, 0.474 mmol) in a 3:1 mixture of acetic acid and ethanol (4 ml) was stirred at 100° C. for 18 hours. The reaction mixture was diluted with water and extracted twice with EtOAc. The combined organic extracts were dried and concentrated. The residue was purified by silica gel column chromatography (heptane/ethyl acetate, 1:0→95:5→9:1→4:1→3:1) to provide 68 mg of the title compound. $t_R$: 6.07 min (HPLC 1); API-MS: 508 [M+H]$^+$.

Example 56

5-(3-Chloro-2-fluoro-phenyl)-4-(4-chloro-2-methyl-phenyl)-2-cyclohexylmethyl-3-isopropyl-4,5-dihydro-2H-pyrrolo[3,4-c]pyrazol-6-one

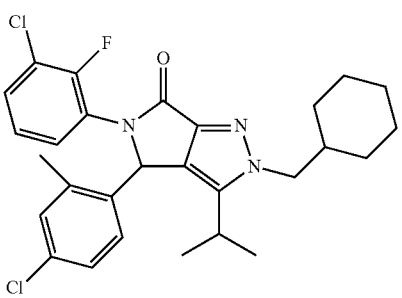 [SMILES: Cc1cc(Cl)ccc1C1c2c(nn(CC3CCCCC3)c2C(C)C)C(=O)N1c1cccc(Cl)c1F]

The title compound was prepared in analogy to the procedure described for example 55 but using 4 equivalents of (cyclohexylmethyl)hydrazine hydrochloride and stirring the mixture for 3 h at 120° C. The crude material was purified by silica gel column chromatography (hexane/ethyl acetate, 1:0→95:5→9:1→75:25→1:1). $t_R$: 6.62 min (HPLC 1); ESI-MS: 514.3 [M+H]$^+$ (LC-MS 1)

silica gel column chromatography (hexane/ethyl acetate, 1:0→95:5→9:1→75:25→1:1). $t_R$: 5.91 min (HPLC 1); ESI-MS: 519 [M+H]$^+$ (LC-MS 1).

Example 57

5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one

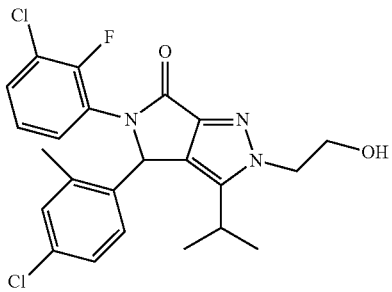 [SMILES: Cc1cc(Cl)ccc1C1c2c(nn(CCO)c2C(C)C)C(=O)N1c1cccc(Cl)c1F]

The title compound was prepared in analogy to the procedure described for example 55 but using 4 equivalents of 2-hydroxyethylhydrazine and stirring the mixture for 6 h at 120° C. The crude material was purified by silica gel column chromatography (heptane/ethyl acetate, 1:0→95:5→9:1→4:1→3:2). $t_R$: 5.11 min (HPLC 1); ESI-MS: 462.1 [M+H]$^+$ (LC-MS 1).

Example 58

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile

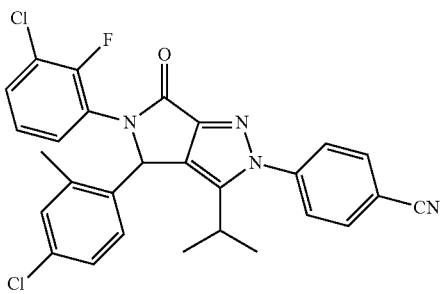 [SMILES: Cc1cc(Cl)ccc1C1c2c(nn(-c3ccc(C#N)cc3)c2C(C)C)C(=O)N1c1cccc(Cl)c1F]

The title compound was prepared in analogy to the procedure described for example 55 but using 4 equivalents of 4-hydrazinylbenzonitrile hydrochloride and stirring the mixture for 24 h at 120° C. The crude material was purified by

Example 59

5-(3-Chloro-2-fluoro-phenyl)-4-(4-chloro-2-methyl-phenyl)-2-(2-fluoro-phenyl)-3-isopropyl-4,5-dihydro-2H-pyrrolo[3,4-c]pyrazol-6-one

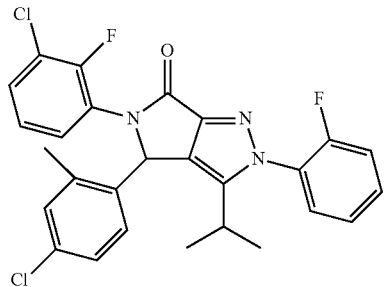 [SMILES: Cc1cc(Cl)ccc1C1c2c(nn(-c3ccccc3F)c2C(C)C)C(=O)N1c1cccc(Cl)c1F]

The title compound was prepared in analogy to the procedure described for example 55 but using 4 equivalents of 2-fluorophenylhydrazine hydrochloride and stirring the mixture at 120° C. overnight. The crude material was purified by silica gel column chromatography (heptane/ethyl acetate, 99:1→95:5→9:1→4:1→7:3→3:2). $t_R$: 6.04 min (HPLC 1); ESI-MS: 512 [M+H]$^+$ (LC-MS 1).

Example 60

5-(3-Chloro-2-fluoro-phenyl)-4-(2,4-dichloro-phenyl)-2-(2-hydroxy-ethyl)-3-isopropyl-4,5-dihydro-2H-pyrrolo[3,4-c]pyrazol-6-one

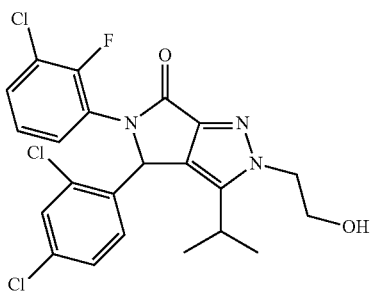 [SMILES: CC(C)c1c2c(nn1CCO)C(=O)N(c1cccc(Cl)c1F)C2c1ccc(Cl)cc1Cl]

The title compound was prepared in analogy to the procedure described for example 55 but using intermediate C, 4 equivalents of 2-hydroxyethylhydrazine and stirring the mixture for 16 h at 120° C. The crude material was purified by silica gel column chromatography (heptane/ethyl acetate, 1:0→95:5→9:1→4:1→1:1). $t_R$: 5.15 min (HPLC 1); ESI-MS: 483.9 [M+H]⁺ (LC-MS 1).

Example 61

C-{4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-phenyl}-N-methyl-methanesulfonamide

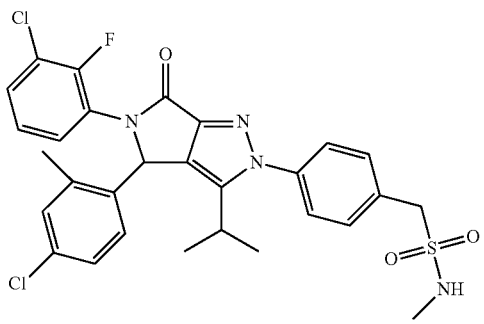 [SMILES: CNS(=O)(=O)Cc1ccc(-n2nc3c(c2C(C)C)C(c2ccc(Cl)cc2C)N(c2cccc(Cl)c2F)C3=O)cc1]

The title compound was prepared in analogy to the procedure described for example 55 but using 4 equivalents of 4-hydrazinyl-N-methylbenzenemethanesulfonamide hydrochloride, stirring the mixture for 21 h at 120° C. and diluting it with a saturated aqueous solution of sodium bicarbonate. The crude material was purified by silica gel column chromatography (CH₂Cl₂/ethyl acetate, 1:0→95:5→9:1→4:1→1:1). $t_R$: 1.44 min (LC-MS 1); ESI-MS: 600.9 [M+H]⁺ (LC-MS 1).

Example 62

5-(3-Chloro-2-fluoro-phenyl)-4-(4-chloro-2-methyl-phenyl)-3-isopropyl-2-(1-methyl-piperidin-4-yl)-4,5-dihydro-2H-pyrrolo[3,4-c]pyrazol-6-one

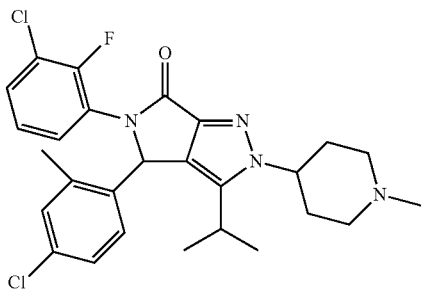 [SMILES: Cc1cc(Cl)ccc1C1c2c(nn(C3CCN(C)CC3)c2C(C)C)C(=O)N1c1cccc(Cl)c1F]

The title compound was prepared in analogy to the procedure described for example 55 but using 4 equivalents of 4-hydrazinyl-1-methylpiperidine hydrochloride, stirring the mixture for 4 h at 120° C. and diluting it with a saturated aqueous solution of sodium bicarbonate. The crude material was purified by silica gel column chromatography (CH₂Cl₂/

0.5 M NH₃ in MeOH, 1:0→99:1→98:2→95:5→9:1). $t_R$: 1.11 min (LC-MS 1); ESI-MS: 515.1 [M+H]⁺ (LC-MS 1).

Example 63

5-(3-Chloro-2-fluoro-phenyl)-4-(4-chloro-2-methyl-phenyl)-2-(4-chloro-phenyl)-3-isopropyl-4,5-dihydro-2H-pyrrolo[3,4-c]pyrazol-6-one

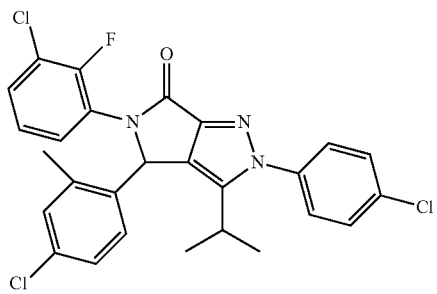 [SMILES: Cc1cc(Cl)ccc1C1c2c(nn(-c3ccc(Cl)cc3)c2C(C)C)C(=O)N1c1cccc(Cl)c1F]

The title compound was prepared in analogy to the procedure described for example 55 but using 4 equivalents of (4-chlorophenyl)hydrazine hydrochloride and stirring the mixture for 15 h at 120° C. The crude material was purified by silica gel column chromatography (hexane/ethyl acetate, 1:0→95:5→9:1→4:1→3:2). $t_R$: 6.39 min (HPLC 1); ESI-MS: 528 [M+H]⁺ (LC-MS 1).

Example 64

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzamide

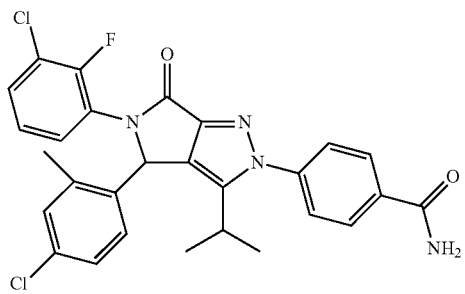 [SMILES: Cc1cc(Cl)ccc1C1c2c(nn(-c3ccc(C(N)=O)cc3)c2C(C)C)C(=O)N1c1cccc(Cl)c1F]

The compound prepared in example 58 (30 mg, 0.058 mmol) was stirred with concentrated sulfuric acid (3.1 µL, 0.058 mmol) for 24 h at rt. The reaction mixture was diluted with water/ice, basified by addition of a saturated aqueous solution of sodium bicarbonate and extracted with EtOAc. The organic phase was dried (Na₂SO₄), filtered and concentrated. The crude material was purified by MPLC (Column: Atlantis. Flow: 23 mL/min. Gradient: 5% to 100% B in 7 min;

A=0.1% TFA in water, B=acetonitrile) to provide 11 mg of the title compound. $t_R$: 1.18 min (LC-MS 1); ESI-MS: 537.3 [M+H]$^+$ (LC-MS 1).

Example 65

4-(4-Chloro-3-fluoro-phenyl)-5-(3-chloro-2-fluoro-phenyl)-2-(2-hydroxy-ethyl)-3-isopropyl-4,5-dihydro-2H-pyrrolo[3,4-c]pyrazol-6-one

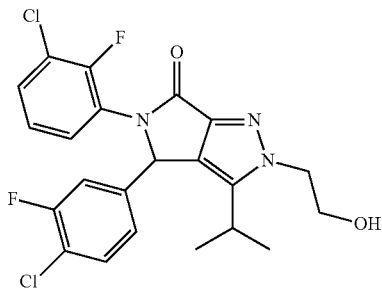 [SMILES: CC(C)c1c2c(nn1CCO)C(=O)N(c1cccc(Cl)c1F)C2c1ccc(Cl)c(F)c1]

The title compound was prepared in analogy to the procedure described for example 55 but using intermediate F, 4 equivalents of 2-hydroxyethylhydrazine and stirring the mixture for 2 h at 120° C. The crude material was purified by silica gel column chromatography (CH$_2$Cl$_2$/MeOH, 1:0→99:1→98:2→95:5→9:1). $t_R$: 4.96 min (HPLC 1); ESI-MS: 466 [M+H]$^+$ (LC-MS 3).

Example 66

5-(3-Chloro-2-fluoro-phenyl)-4-(4-fluoro-phenyl)-3-isopropyl-2-(2-methoxy-phenyl)-4,5-dihydro-2H-pyrrolo[3,4-c]pyrazol-6-one

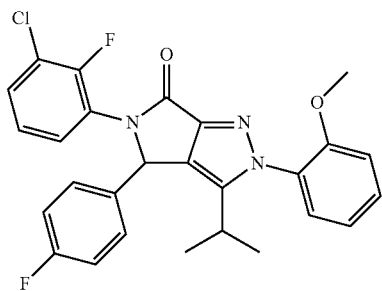

The title compound was prepared in analogy to the procedure described for example 55 but using intermediate E, 4 equivalents of 2-methoxyphenylhydrazine hydrochloride and stirring the mixture for 8 h at 120° C. and at rt over the weekend. The reaction mixture was concentrated. The residue was purified by preparative HPLC (Column: Waters SunFire C18, 30×100 mm, 5 µm. Flow: 50 mL/min. Gradient: 50% to 90% B in 16 min; A=0.1% TFA in water, B=0.1% TFA in acetonitrile). $t_R$: 1.32 min (LC-MS 1); ESI-MS: 494.2 [M+H]$^+$ (LC-MS 1).

Example 67

5-(3-Chloro-2-fluoro-phenyl)-4-(3,4-difluoro-phenyl)-3-isopropyl-2-(2-methoxy-phenyl)-4,5-dihydro-2H-pyrrolo[3,4-c]pyrazol-6-one

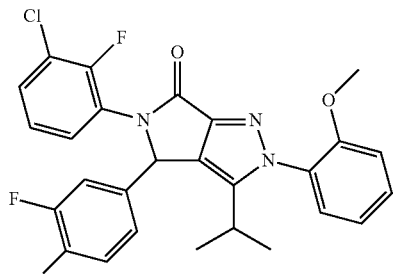

The title compound was prepared in analogy to the procedure described for example 55 but using intermediate G, 4 equivalents of 2-methoxyphenylhydrazine hydrochloride and stirring the mixture for 8 h at 120° C. and at rt over the weekend. The reaction mixture was concentrated. The residue was purified by preparative HPLC (Column: Waters SunFire C18, 30×100 mm, 5 µm. Flow: 50 mL/min. Gradient: 50% to 70% B in 16 min; A=0.1% TFA in water, B=0.1% TFA in acetonitrile). $t_R$: 1.35 min (LC-MS 1); ESI-MS: 512.1 [M+H]$^+$ (LC-MS 1).

Example 68

5-(3-Chloro-2-fluoro-phenyl)-4-(4-chloro-phenyl)-3-isopropyl-2-pyridin-4-yl-4,5-dihydro-2H-pyrrolo[3,4-c]pyrazol-6-one

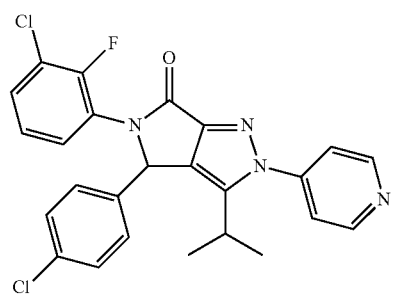 [SMILES: CC(C)c1c2c(nn1-c1ccncc1)C(=O)N(c1cccc(Cl)c1F)C2c1ccc(Cl)cc1]

A mixture of intermediate AE (50 mg, 0.124 mmol) and 4-chloro-pyridine hydrochloride (18.6 mg, 0.124 mmol) in acetic acid (0.6 mL) was stirred for 16 h at 80° C., for 24 h at 100° C., for 3 days at 110° C., and purified by preparative HPLC (Column: Waters SunFire C18, 30×100 mm, 5 µm. Flow: 50 mL/min. Gradient: 50% to 90% B in 16 min;

A=0.1% TFA in water, B=0.1% TFA in acetonitrile) to give 6 mg of the title compound. $t_R$: 1.34 min (LC-MS 1); ESI-MS: 481 [M+H]$^+$ (LC-MS 1).

Example 69

5-(3-Chloro-2-fluoro-phenyl)-3-isopropyl-2-(2-methoxy-phenyl)-4-p-tolyl-4,5-dihydro-2H-pyrrolo[3,4-c]pyrazol-6-one

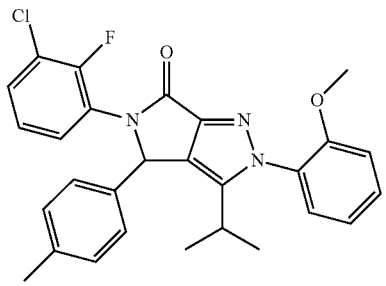 [SMILES: COc1ccccc1-n1nc2c(c1C(C)C)C(c1ccc(C)cc1)N(c1cccc(Cl)c1F)C2=O]

The title compound was prepared in analogy to the procedure described for example 55 but using intermediate H, 4 equivalents of 2-methoxyphenylhydrazine hydrochloride and stirring the mixture for 18 h at 120° C. The crude material was purified by silica gel column chromatography (heptane/EtOAc, 1:0→7:3→2:3). $t_R$: 1.33 min (LC-MS 1); ESI-MS: 490.2 [M+H]$^+$ (LC-MS 1).

Example 70

5-(3-Chloro-2-fluoro-phenyl)-4-(4-chloro-phenyl)-3-isopropyl-2-(2-methoxy-phenyl)-4,5-dihydro-2H-pyrrolo[3,4-c]pyrazol-6-one

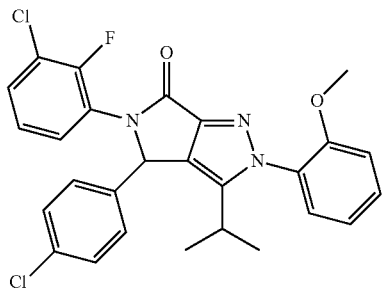 [SMILES: COc1ccccc1-n1nc2c(c1C(C)C)C(c1ccc(Cl)cc1)N(c1cccc(Cl)c1F)C2=O]

The title compound was prepared in analogy to the procedure described for example 55 but using intermediate B, 2.4 equivalents of 2-methoxyphenylhydrazine hydrochloride and stirring the mixture for 23 h at 120° C. The crude material was purified twice by silica gel column chromatography (heptane/EtOAc, 1:0→7:3→1:1). $t_R$: 1.45 min (LC-MS 3); ESI-MS: 510 [M+H]$^+$ (LC-MS 3).

Example 71

6-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-1,3-dimethyl-1H-pyrimidine-2,4-dione

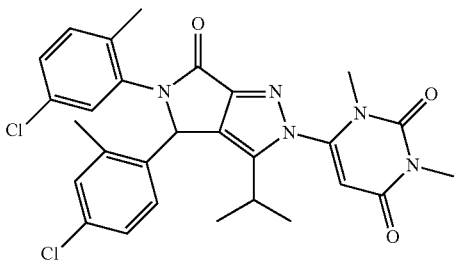 [SMILES: Cc1cc(Cl)ccc1C1c2c(nn(-c3cc(=O)n(C)c(=O)n3C)c2C(C)C)C(=O)N1c1cc(Cl)ccc1C]

The title compound was prepared in analogy to the procedure described for example 1 but using intermediate AI, 1.2 equivalents of, 6-chloro-1,3-dimethyl-2,4(1H,3H)-pyrimidinedione, 1.1 equivalents of NaH and stirring the reaction mixture for 2 h at rt. The crude material was purified by preparative HPLC (Column: Waters SunFire C18, 30×100 mm, 5 µm. Flow: 50 mL/min. Gradient: 50% to 90% B in 16 min; A=0.1% TFA in water, B=acetonitrile). $t_R$: 1.26 min (LC-MS 3); ESI-MS: 552.2 [M+H]$^+$ (LC-MS 3).

Example 72

4-(4-Chloro-2-methyl-phenyl)-5-(5-chloro-2-methyl-phenyl)-3-isopropyl-2-(1-methyl-piperidin-4-yl)-4,5-dihydro-2H-pyrrolo[3,4-c]pyrazol-6-one

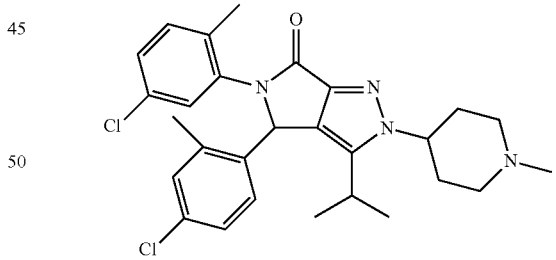

The title compound was prepared in analogy to the procedure described for example 55 but using intermediate L, 4 equivalents of 4-hydrazino-1-methyl-piperidine dihydrochloride, acetic acid as the solvent, and stirring the reaction mixture for 24 h at 120° C. The reaction mixture was diluted with EtOAc and washed with 5% citric acid in water, a saturated aqueous solution of sodium bicarbonate, and brine. The organic phase was dried (Na$_2$SO$_4$), filtered, and concentrated. The residue was purified by silica gel column chromatography (CH$_2$Cl$_2$/MeOH, 1:0→99:1→98:2→96:4→92:8) followed by MPLC (Column: XBridge 30×10 mm, 5 µm. Flow: 30 mL/min. Gradient: 40% to 90% B in 22 min; A=0.1% TFA

Example 73

5-(3-Chloro-2-fluoro-phenyl)-4-(4-chloro-2-methyl-phenyl)-3-isopropyl-2-(tetrahydro-pyran-4-yl)-4,5-dihydro-2H-pyrrolo[3,4-c]pyrazol-6-one

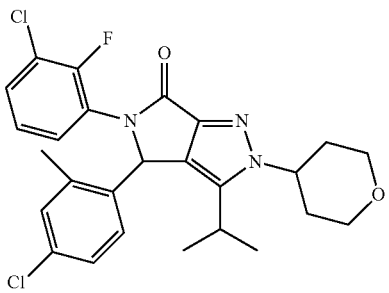 [SMILES: Cc1cc(Cl)ccc1C1c2c(nn(C3CCOCC3)c2C(C)C)C(=O)N1c1cccc(Cl)c1F]

The title compound was prepared in analogy to the procedure described for example 55 but using intermediate A, 4 equivalents of (tetrahydro-2H-pyran-4-yl)-hydrazine, and stirring the reaction mixture for 17 h at 120° C. The reaction mixture was concentrated and the residue purified by preparative HPLC (Column: Waters SunFire C18, 30×100 mm, 5 µm. Flow: 50 mL/min. Gradient: 40% to 80% B in 16 min; A=0.1% TFA in water, B=0.1% TFA in acetonitrile). $t_R$: 1.30 min (LC-MS 1); ESI-MS: 501.9 [M+H]$^+$ (LC-MS 1).

Example 74

5-(3-Chloro-2-fluoro-phenyl)-4-(4-chloro-phenyl)-3-isopropyl-2-(2-methoxy-phenyl)-4-(2-morpholin-4-yl-2-oxo-ethyl)-4,5-dihydro-2H-pyrrolo[3,4-c]pyrazol-6-one

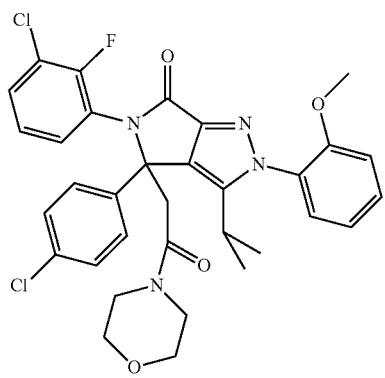 [SMILES: COc1ccccc1-n1nc2c(c1C(C)C)C(CC(=O)N1CCOCC1)(c1ccc(Cl)cc1)N(c1cccc(Cl)c1F)C2=O]

KHMDS (1 M in THF, 0.220 mL, 0.220 mmol) was added slowly to a solution of the compound prepared in Example 70 (102 mg, 0.200 mmol) in THF (3 mL) at −78° C. After stirring for 15 min at −78° C., 2-bromo-1-(4-morpholinyl)-ethanone (208 mg, 0.999 mmol) in THF (1 mL) was added. The reaction mixture was allowed to warm to rt, diluted with EtOAc, and washed with water and brine. Organic layer was dried (Na$_2$SO$_4$), filtered, and concentrated. The residue purified by preparative HPLC (Column: Waters SunFire C18, 30×100 mm, 5 µm. Flow: 50 mL/min. Gradient: 50% to 90% B in 16 min; A=0.1% TFA in water, B=0.1% TFA in acetonitrile) to give 2 mg of the title compound. $t_R$: 1.18 min (LC-MS 1); ESI-MS: 637.1 [M+H]$^+$ (LC-MS 1).

Example 75

5-(3-Chloro-2-fluoro-phenyl)-4-(4-chloro-2-methyl-phenyl)-2-(2-chloro-phenyl)-3-isopropyl-4,5-dihydro-2H-pyrrolo[3,4-c]pyrazol-6-one

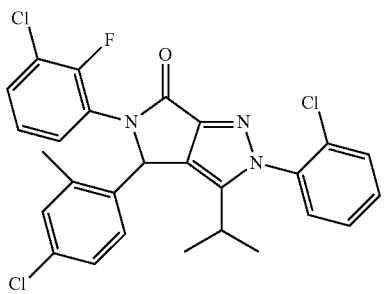 [SMILES: Cc1cc(Cl)ccc1C1c2c(nn(-c3ccccc3Cl)c2C(C)C)C(=O)N1c1cccc(Cl)c1F]

Intermediate A (500 mg, 1.18 mmol) and (2-chlorophenyl)-hydrazine hydrochloride (0.42 mg, 2.36 mmol) in a 3:1 mixture of acetic acid and ethanol (12 mL) was stirred at 120° C. for 1 h. The reaction mixture was allowed to cool to rt. (2-Chlorophenyl)-hydrazine hydrochloride (0.42 mg, 2.36 mmol) was added. The mixture was refluxed for 5 h at 120° C., allowed to cool to rt, and concentrated. The residue was neutralized to pH 7 and the product was extracted with EtOAc. The organic layer was dried (Na$_2$SO$_4$), filtered, and concentrated. The residue was purified by silica gel column chromatography (hexane/ethyl acetate, 92:8) to provide 120 mg of the title compound. $t_R$: 7.30 min (HPLC 2); ESI-MS: 528 [M+H]$^+$ (LC-MS 2); R$_f$=0.32 (hexane/EtOAc, 1:1).

Example 76

5-(3-Chloro-2-fluoro-phenyl)-4-(4-chloro-2-methyl-phenyl)-3-isopropyl-2-(2-methoxy-phenyl)-4,5-dihydro-2H-pyrrolo[3,4-c]pyrazol-6-one

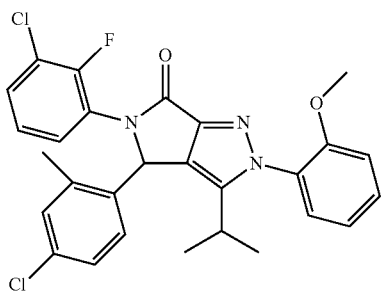 [SMILES: COc1ccccc1-n1nc2c(c1C(C)C)C(c1ccc(Cl)cc1C)N(c1cccc(Cl)c1F)C2=O]

The title compound was prepared in analogy to the procedure described for example 75 but using 2-methoxyphenyl-hydrazine hydrochloride. The crude material was purified by preparative HPLC (Column: Zorbax eclipse XDB C18, 21.2×150 mm. Flow: 20 mL/min. Gradient: 60% to 70% B in 2 min, 70% to 95% B in 8 min; A=water, B=acetonitrile). $t_R$: 7.08 min (HPLC 2); ESI-MS: 523.8 [M+H]$^+$ (LC-MS 2); $R_f$=0.31 (hexane/EtOAc, 1:1).

Example 77

5-(3-Chloro-2-fluoro-phenyl)-4-(4-chloro-2-methyl-phenyl)-2-(2,4-difluoro-phenyl)-3-isopropyl-4,5-dihydro-2H-pyrrolo[3,4-c]pyrazol-6-one

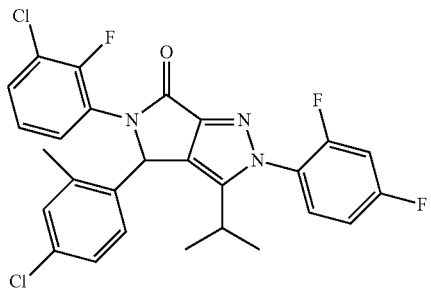 [SMILES: Cc1cc(Cl)ccc1C1c2c(nn(-c3ccc(F)cc3F)c2C(C)C)C(=O)N1c1cccc(Cl)c1F]

The title compound was prepared in analogy to the procedure described for example 75 but using (2,4-difluorophenyl)-hydrazine hydrochloride. The crude material was purified by silica gel column chromatography (hexane/ethyl acetate, 9:1) followed by preparative HPLC (Column: AG/PP/C18-15/012. Flow: 20 mL/min. Gradient: 60% to 70% B in 2 min, 70% to 90% B in 3 min; A=water, B=acetonitrile). $t_R$: 7.10 min (HPLC 2); ESI-MS: 530.1 [M+H]$^+$ (LC-MS 2); $R_f$=0.32 (hexane/EtOAc, 1:1).

Example 78

3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-propionitrile

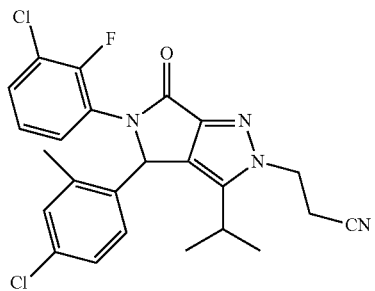 [SMILES: Cc1cc(Cl)ccc1C1c2c(nn(CCC#N)c2C(C)C)C(=O)N1c1cccc(Cl)c1F]

The title compound was prepared in analogy to the procedure described for example 75 but using (2-cyanoethyl)hydrazine. The crude material was purified by silica gel column chromatography (hexane/ethyl acetate, 75:25→65:35). $t_R$: 5.91 min (HPLC 2); ESI-MS: 471 [M+H]$^+$ (LC-MS 2); $R_f$=0.16 (hexane/EtOAc, 1:1).

Example 79

5-(3-Chloro-4-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one

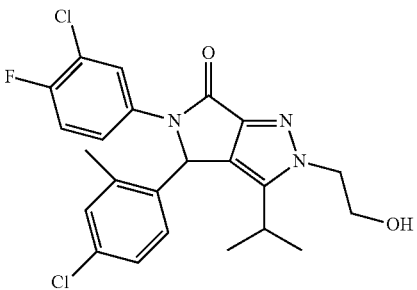 [SMILES: Cc1cc(Cl)ccc1C1c2c(nn(CCO)c2C(C)C)C(=O)N1c1ccc(F)c(Cl)c1]

The title compound was prepared in analogy to the procedure described for example 75 but using intermediate 1,2-hydroxyethylhydrazine. The crude material was purified by preparative HPLC (Column: Zorbax eclipse XDB C18, 21.2× 150 mm. Flow: 20 mL/min. Gradient: 50% B for 2 min, 50% to 90% B in 8 min; A=water, B=acetonitrile). $t_R$: 5.89 min (HPLC 2); ESI-MS: 462 [M+H]$^+$ (LC-MS 2); $R_f$=0.10 (hexane/EtOAc, 1:4).

Example 80

4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-3-methyl-benzonitrile

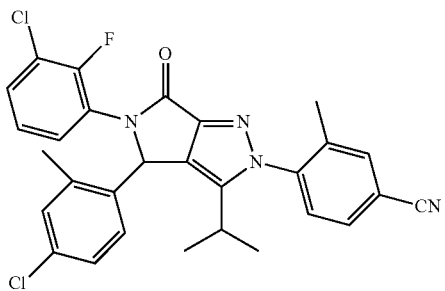 [SMILES: Cc1cc(Cl)ccc1C1c2c(nn(-c3ccc(C#N)cc3C)c2C(C)C)C(=O)N1c1cccc(Cl)c1F]

The title compound was prepared in analogy to the procedure described for example 75 but using the hydrazine prepared in step 80.1. The reaction mixture was stirred at reflux for 6 h after addition of the second portion of hydrazine, concentrated, diluted with a saturated aqueous solution of sodium bicarbonate, and extracted with EtOAc. The crude material was purified by silica gel column chromatography (hexane/ethyl acetate, 75:25→7:3). $t_R$: 6.50 min (HPLC 2); ESI-MS: 533 [M+H]$^+$ (LC-MS 2); $R_f$=0.36 (hexane/EtOAc, 1:1).

Step 80.1: 4-Hydrazino-3-methyl-benzonitrile hydrochloride

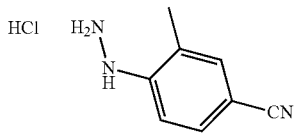

A solution of sodium nitrite (0.52 g, 7.57 mmol) in water (3 mL) was added dropwise to a cold (0° C.) mixture of 4-amino-3-methylbenzonitrile (1 g, 7.57 mmol) and concentrated HCl (12 mL) keeping the internal temperature below 0° C. After 5 min stirring, tin dichloride dihydrate (3.75 g, 16.6 mmol) in concentrated HCl (4 mL) was added at 0° C. The reaction mixture was allowed to warm to rt and stirred for 2 h. The resulting precipitate was collected by vacuum filtration and dried to provide 500 mg of the title compound. $t_R$: 0.24 min (LC-MS 2); ESI-MS: 148 [M+H]$^+$ (LC-MS 2).

Example 81

5-(3-Chloro-2-fluoro-phenyl)-4-(4-chloro-2-methyl-phenyl)-3-cyclobutyl-2-(2-hydroxy-ethyl)-4,5-dihydro-2H-pyrrolo[3,4-c]pyrazol-6-one

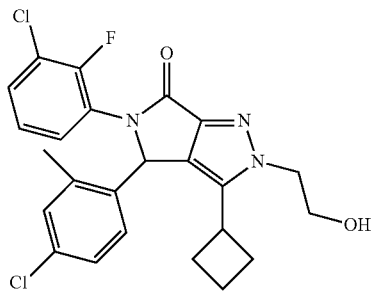 [SMILES: Cc1cc(Cl)ccc1C1c2c(nn(CCO)c2C2CCC2)C(=O)N1c1cccc(Cl)c1F]

The title compound was prepared in analogy to the procedure described for example 75 but using intermediate N and 2-hydroxyethylhydrazine. The reaction mixture was stirred at reflux for 6 h after addition of the second portion of hydrazine, concentrated, diluted with a saturated aqueous solution of sodium bicarbonate, and extracted with EtOAc. The crude material was purified by silica gel column chromatography (hexane/ethyl acetate, 65:35→45:55). $t_R$: 6.01 min (HPLC 2); ESI-MS: 473.9 [M+H]$^+$ (LC-MS 2); $R_f$=0.11 (hexane/EtOAc, 1:1).

Example 82

3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile

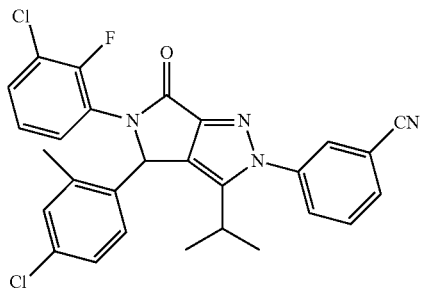 [SMILES: Cc1cc(Cl)ccc1C1c2c(nn(-c3cccc(C#N)c3)c2C(C)C)C(=O)N1c1cccc(Cl)c1F]

The title compound was prepared in analogy to the procedure described for example 75 but using 3-hydrazinylbenzonitrile. The reaction mixture was stirred at reflux for 12 h after addition of the second portion of hydrazine, concentrated, diluted with a saturated aqueous solution of sodium bicarbonate, and extracted with EtOAc. The crude material was purified by silica gel column chromatography (hexane/ethyl acetate, 65:35→1:1). $t_R$: 6.63 min (HPLC 2); ESI-MS: 518.8 [M+H]$^+$ (LC-MS 2); $R_f$=0.41 (hexane/EtOAc, 1:1).

Example 83

4-(4-Chloro-2-methyl-phenyl)-5-(5-chloro-2-methyl-phenyl)-2-(2-hydroxy-ethyl)-3-isopropyl-4,5-dihydro-2H-pyrrolo[3,4-c]pyrazol-6-one

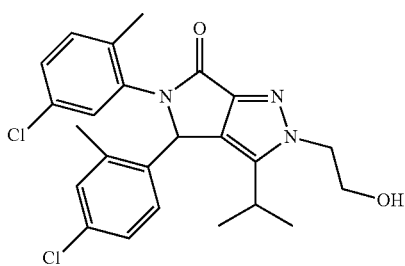 [SMILES: Cc1cc(Cl)ccc1C1c2c(nn(CCO)c2C(C)C)C(=O)N1c1cc(Cl)ccc1C]

The title compound was prepared in analogy to the procedure described for example 75 but using intermediate L and 2-hydroxyethylhydrazine. The reaction mixture was stirred at reflux for 12 h after addition of the second portion of hydrazine, concentrated, diluted with a saturated aqueous solution of sodium bicarbonate, and extracted with EtOAc. The crude material was purified by silica gel column chromatography (hexane/ethyl acetate, 4:1→3:2). $t_R$: 6.10 min (HPLC 2); ESI-MS: 457.9 [M+H]$^+$ (LC-MS 2); $R_f$=0.42 (hexane/EtOAc, 1:1).

Example 84

4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one

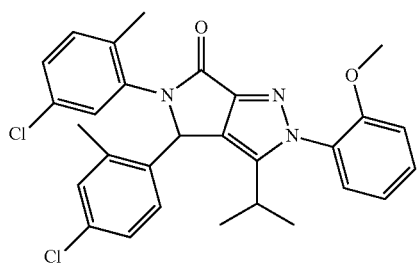 [SMILES: COc1ccccc1-n1nc2c(c1C(C)C)C(c1ccc(Cl)cc1C)N(c1cc(Cl)ccc1C)C2=O]

The title compound was prepared in analogy to the procedure described for example 75 but using intermediate L and 2-methoxyphenylhydrazine hydrochloride. The reaction mixture was stirred at reflux for 12 h after addition of the second portion of hydrazine, concentrated, diluted with a saturated aqueous solution of sodium bicarbonate, and extracted with EtOAc. The crude material was purified by silica gel column chromatography (hexane/ethyl acetate, 3:1→3:2). $t_R$: 6.90 min (HPLC 2); ESI-MS: 519.7 [M+H]$^+$ (LC-MS 2); $R_f$=0.40 (hexane/EtOAc, 1:1).

Example 85

5-(3-Chloro-2-fluoro-phenyl)-4-(4-chloro-2-methyl-phenyl)-3-cyclopropyl-2-(2-hydroxy-ethyl)-4,5-dihydro-2H-pyrrolo[3,4-c]pyrazol-6-one

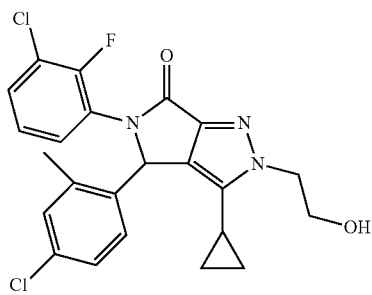 [SMILES: Cc1cc(Cl)ccc1C1c2c(nn(CCO)c2C2CC2)C(=O)N1c1cccc(Cl)c1F]

The title compound was prepared in analogy to the procedure described for example 75 but using intermediate O and 2-hydroxyethylhydrazine. The reaction mixture was stirred at reflux for 16 h after addition of the second portion of hydrazine. The crude material was purified by silica gel column chromatography (hexane/ethyl acetate, 4:1→65:35) followed by preparative HPLC (Column: Zorbax eclipse XDB C18, 21.2×150 mm, 5 μm. Flow: 20 mL/min. Gradient: 40% to 50% B in 2 min, 50% to 90% B in 8 min; A=0.1% TFA in water, B=acetonitrile). $t_R$: 5.24 min (HPLC 2); ESI-MS: 460 [M+H]$^+$ (LC-MS 2); $R_f$=0.22 (hexane/EtOAc, 1:4).

Example 86

5-(3-Chloro-2-fluoro-phenyl)-4-(4-chloro-2-methyl-phenyl)-3-cyclopropyl-2-(2-methoxy-phenyl)-4,5-dihydro-2H-pyrrolo[3,4-c]pyrazol-6-one

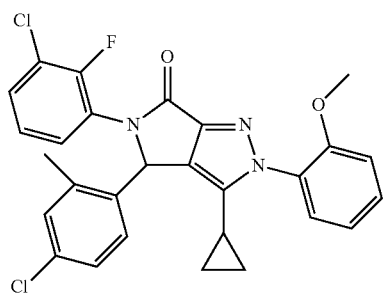 [SMILES: COc1ccccc1-n1nc2c(c1C1CC1)C(c1ccc(Cl)cc1C)N(c1cccc(Cl)c1F)C2=O]

The title compound was prepared in analogy to the procedure described for example 75 but using intermediate O and 2-methoxyphenylhydrazine hydrochloride. The reaction mixture was stirred at reflux for 16 h after addition of the second portion of hydrazine. The crude material was purified by silica gel column chromatography (hexane/ethyl acetate, 9:1) followed by preparative HPLC (Column: AG/PP/C-18-15/022. Flow: 20 mL/min. Gradient: 60% to 80% B in 2 min; A=0.1% TFA in water, B=acetonitrile). $t_R$: 6.73 min (HPLC 2); ESI-MS: 522 [M+H]$^+$ (LC-MS 2); $R_f$=0.29 (hexane/EtOAc, 1:1).

Example 87

5-(5-Chloro-2,4-difluoro-phenyl)-4-(4-chloro-2-methyl-phenyl)-3-isopropyl-2-(2-methoxy-phenyl)-4,5-dihydro-2H-pyrrolo[3,4-c]pyrazol-6-one

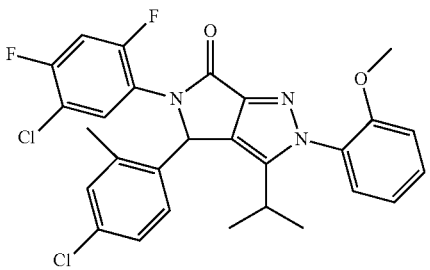 [SMILES: COc1ccccc1-n1nc2c(c1C(C)C)C(c1ccc(Cl)cc1C)N(c1cc(Cl)c(F)cc1F)C2=O]

The title compound was prepared in analogy to the procedure described for example 75 but using intermediate K and 2-methoxyphenylhydrazine hydrochloride. The reaction mixture was stirred at reflux for 16 h after addition of the second portion of hydrazine. The crude material was purified by silica gel column chromatography (hexane/ethyl acetate, 3:2). $t_R$: 7.30 min (HPLC 2); ESI-MS: 542 [M+H]$^+$ (LC-MS 2).

Example 88

5-(3-Chloro-4-fluoro-phenyl)-4-(4-chloro-phenyl)-3-isopropyl-2-(2-methoxy-phenyl)-4,5-dihydro-2H-pyrrolo[3,4-c]pyrazol-6-one

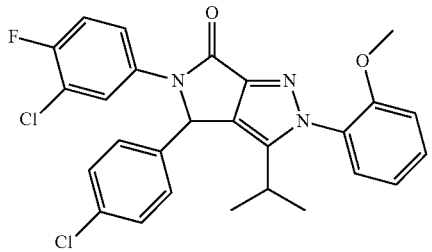

The title compound was prepared in analogy to the procedure described for example 75 but using intermediate J and 2-methoxyphenylhydrazine hydrochloride. The crude material was purified by silica gel column chromatography (hexane/ethyl acetate, 3:2). $t_R$: 6.76 min (HPLC 2); ESI-MS: 510.1 [M+H]$^+$ (LC-MS 2); $R_f$=0.43 (hexane/EtOAc, 1:1).

Example 89

3-[5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazol-4-yl]-propionic acid methyl ester

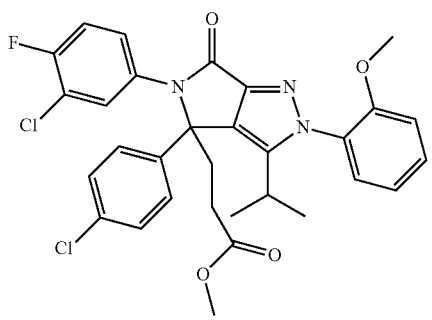 [SMILES: COC(=O)CCC1(c2ccc(Cl)cc2)c2c(nn(-c3ccccc3OC)c2C(C)C)C(=O)N1c1ccc(F)c(Cl)c1]

The title compound was prepared in analogy to the procedure described for example 74 but using the compound prepared in example 88 and 2 equivalents of 3-iodo-propionic acid methyl ester (Scapens, D.; Adams, H.; Johnson, T. R.; Mann, B. E.; Sawle, P.; Aqil, R.; Perrior, T.; Motterlini, R. Dalton Transactions 2007, 43, 4962-4973). The reaction mixture was stirred for 2 h at rt. The crude material was purified by silica gel column chromatography (heptane/ethyl acetate, 1:0→7:3→2:3) followed by preparative HPLC (Column: XBridge, 30×100 mm. Flow: 30 mL/min. Gradient: 30% to 60% B in 15 min, 60% B for 5 min, 60% to 90% B in 5 min; A=0.1% TFA in water, B=0.1% TFA in acetonitrile). $t_R$: 1.42 min (LC-MS 3); ESI-MS: 596.3 [M+H]$^+$ (LC-MS 3).

Example 90

5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazole-4-carboxylic acid ethyl ester

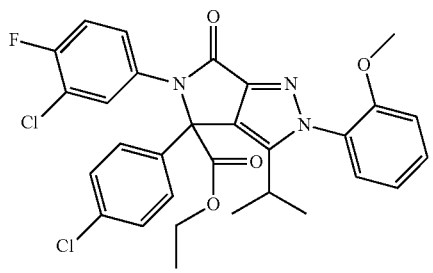 [SMILES: CCOC(=O)C1(c2ccc(Cl)cc2)c2c(nn(-c3ccccc3OC)c2C(C)C)C(=O)N1c1ccc(F)c(Cl)c1]

The title compound was prepared in analogy to the procedure described for example 74 but using the compound prepared in example 88, 1 equivalent of KHMDS and 5 equivalents of ethyl chloroformate. No purification was performed. $t_R$: 1.42 min (LC-MS 1); ESI-MS: 582.2 [M+H]$^+$ (LC-MS 1).

Example 91

4-(4-Chloro-2-methyl-phenyl)-5-(5-chloro-pyridin-3-yl)-3-isopropyl-2-(2-methoxy-phenyl)-4,5-dihydro-2H-pyrrolo[3,4-c]pyrazol-6-one

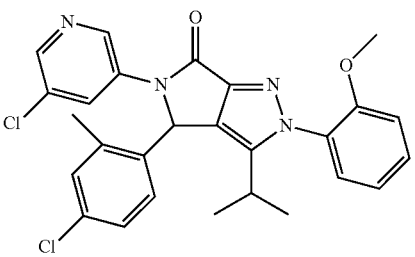 [SMILES: COc1ccccc1-n1nc2c(c1C(C)C)C(c1ccc(Cl)cc1C)N(c1cncc(Cl)c1)C2=O]

The title compound was prepared in analogy to the procedure described for example 75 but using intermediate V and 2-methoxyphenylhydrazine hydrochloride. The reaction mixture was stirred at reflux for 8 h after addition of the second portion of hydrazine. The crude material was purified by silica gel column chromatography (hexane/ethyl acetate, 3:2) followed by trituration in EtOAc/hexane. $t_R$: 5.10 min (HPLC 2); ESI-MS: 507.1 [M+H]$^+$ (LC-MS 2).

Example 92

5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one

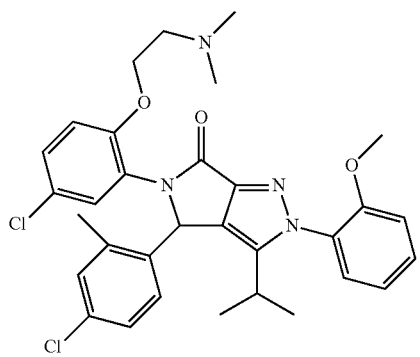 [SMILES: COc1ccccc1-n1nc2c(c1C(C)C)C(c1ccc(Cl)cc1C)N(c1cc(Cl)ccc1OCCN(C)C)C2=O]

The title compound was prepared in analogy to the procedure described for example 75 but using intermediate M and 2-methoxyphenylhydrazine hydrochloride. The reaction mixture was stirred at reflux for 16 h after addition of the second portion of hydrazine. The crude material was purified by silica gel column chromatography (CH$_2$Cl$_2$/MeOH, 99:1→98:2) followed by preparative HPLC (Column: AG/PP/C-18-15/021. Flow: 20 mL/min. Gradient: 30% to 40% B in 2 min, 40% to 90% B in 5 min; A=10 mM ammonium acetate, B=acetonitrile). $t_R$: 4.57 min (HPLC 2); ESI-MS: 593.2 [M+H]$^+$ (LC-MS 2); $R_f$=0.29 (hexane/EtOAc, 1:1).

Example 93

5-(3-Chloro-4-fluoro-phenyl)-4-(4-chloro-phenyl)-3-isopropyl-2-(2-methoxy-phenyl)-4-methyl-4,5-dihydro-2H-pyrrolo[3,4-c]pyrazol-6-one

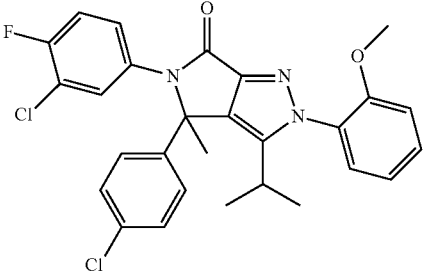 [SMILES: COc1ccccc1-n1nc2c(c1C(C)C)C(C)(c1ccc(Cl)cc1)N(c1ccc(F)c(Cl)c1)C2=O]

The title compound was prepared in analogy to the procedure described for example 74 but using the compound prepared in example 88, 3 equivalents of KHMDS and 2 equivalents of methyl iodide. The reaction mixture was stirred for 2 h at rt. The crude material was purified by silica gel column chromatography (hexane/EtOAc, 4:1) followed by preparative HPLC (Column: AG/PP/C-18-15/025. Flow: 20 mL/min.

Gradient: 25% B; A=0.1% TFA in water, B=acetonitrile/MeOH, 1:1). $t_R$: 6.92 min (HPLC 2); ESI-MS: 524.1 [M+H]$^+$ (LC-MS 2).

Example 94

5-(3-Chloro-2-fluoro-phenyl)-4-[4-chloro-2-(2-methoxy-ethoxymethyl)-phenyl]-3-isopropyl-2-(2-methoxy-phenyl)-4,5-dihydro-2H-pyrrolo[3,4-c]pyrazol-6-one

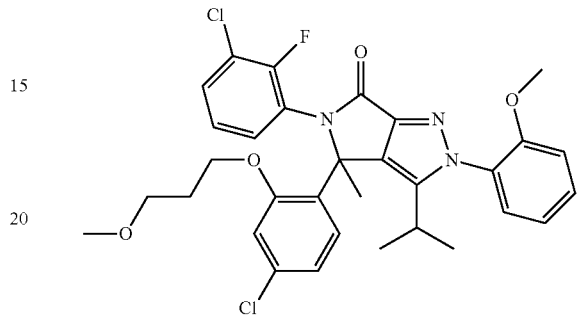

The title compound was prepared in analogy to the procedure described for example 75 but using intermediate Q and 2-methoxyphenylhydrazine hydrochloride. The reaction mixture was stirred at reflux overnight after addition of the second portion of hydrazine. The crude material was purified by silica gel column chromatography (hexane/ethyl acetate, 7:3) followed by preparative HPLC (Column: Zorbax eclipse XDB C18, 21.2×150 mm, 5 µm. Flow: 20 mL/min. Gradient: 70% B for 2 min, 70% to 90% B in 5 min; A=water, B=acetonitrile). $t_R$: 6.70 min (HPLC 2); ESI-MS: 598 [M+H]$^+$ (LC-MS 2).

Example 95

5-(3-Chloro-4-fluoro-phenyl)-4-(4-chloro-phenyl)-4-(2-hydroxy-3-pyrrolidin-1-yl-propyl)-3-isopropyl-2-(2-methoxy-phenyl)-4,5-dihydro-2H-pyrrolo[3,4-c]pyrazol-6-one

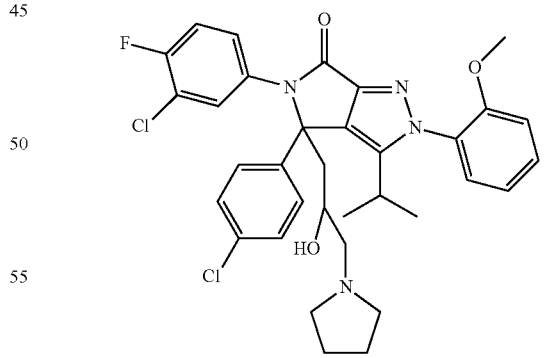

Pyrrolidine (15 mg, 0.212 mmol) was added to a cold (0° C.) solution of the compound prepared in step 95.1 (60 mg, 0.106 mmol) in DMF (3 mL). The reaction mixture was allowed to warm to rt, stirred for 1 h, heated to 60° C., stirred for 3 h, cooled to rt, and concentrated. The residue was purified by silica gel column chromatography (hexane/ethyl acetate, 1:9) to afford 25 mg of the title compound as a mixture of two diastereomers. Diastereomer 1. $t_R$: 4.10 min (HPLC 2); ESI-MS: 637.2 [M+H]+ (LC-MS 2). Diastereomer 2. t$_R$: 4.30 min (HPLC 2); ESI-MS: 637.2 [M+H]+ (LC-MS 2).

Step 95.1: 5-(3-Chloro-4-fluoro-phenyl)-4-(4-chloro-phenyl)-3-isopropyl-2-(2-methoxy-phenyl)-4-oxiranylmethyl-4,5-dihydro-2H-pyrrolo[3,4-c]pyrazol-6-one

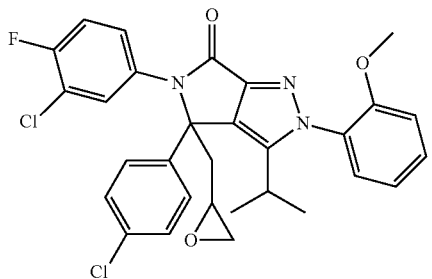 [SMILES: COc1ccccc1-n1nc2c(c1C(C)C)C(CC1CO1)(c1ccc(Cl)cc1)N(c1ccc(F)c(Cl)c1)C2=O]

m-Chloroperbenzoic acid (28 mg, 0.162 mmol) was added to a cold (0° C.) solution of the compound prepared in step 95.2 (60 mg, 0.108 mmol) in CH$_2$Cl$_2$ (3 mL). The reaction mixture was allowed to warm to rt, stirred overnight, diluted with CH$_2$Cl$_2$ and washed with water. The organic layer was dried (Na$_2$SO$_4$), filtered, and concentrated. The residue was purified by silica gel column chromatography (hexane/ethyl acetate, 1:9) to afford 60 mg of the title compound as a mixture of two diastereomers. Diastereomer 1. ESI-MS: 566.1 [M+H]+ (LC-MS 2); R$_f$=0.28 (hexane/EtOAc, 1:1). Diastereomer 2. ESI-MS: 566.1 [M+H]+ (LC-MS 2); R$_f$=0.22 (hexane/EtOAc, 1:1).

Step 95.2: 4-Allyl-5-(3-chloro-4-fluoro-phenyl)-4-(4-chloro-phenyl)-3-isopropyl-2-(2-methoxy-phenyl)-4,5-dihydro-2H-pyrrolo[3,4-c]pyrazol-6-one

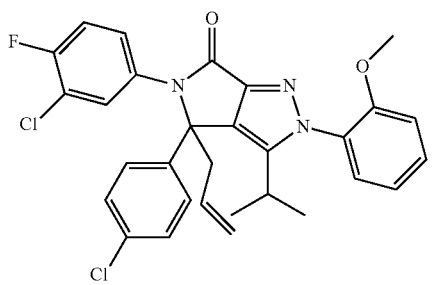 [SMILES: C=CCC1(c2ccc(Cl)cc2)c2c(nn(-c3ccccc3OC)c2C(C)C)C(=O)N1c1ccc(F)c(Cl)c1]

The title compound was prepared in analogy to the procedure described for example 74 but using the compound prepared in example 88, 2 equivalents of KHMDS and 2 equivalents of allyl bromide. The reaction mixture was stirred for 1 h at rt and quenched by addition of a saturated solution of ammonium chloride. The crude material was purified by silica gel column chromatography (hexane/EtOAc, 4:1). t$_R$: 6.90 min (HPLC 2); ESI-MS: 550.1 [M+H]+ (LC-MS 2); R$_f$=0.55 (hexane/EtOAc, 1:1).

Example 96

3-[5-(5-Chloro-2-methyl-phenyl)-3-isopropyl-6-oxo-4-(4-trifluoromethyl-phenyl)-5,6-dihydro-4H-pyrrolo[3,4-c]pyrazol-2-yl]-4,N-dimethyl-benzamide

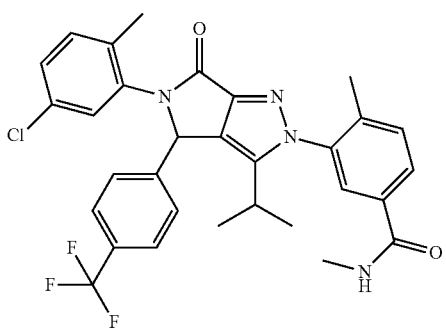 [SMILES: CNC(=O)c1ccc(C)c(-n2nc3c(c2C(C)C)C(c2ccc(C(F)(F)F)cc2)N(c2cc(Cl)ccc2C)C3=O)c1]

A mixture of the compound prepared in step 96.1 (70 mg, 0.123 mmol), HATU (51.5 mg, 0.136 mmol) and N-methylmorpholine (0.108 mL, 0.986 mmol) in DMF (1 mL) was stirred for 5 min at rt. Methylamine hydrochloride (41.6 mg, 0.616 mmol) was added. The mixture was stirred for 30 min at rt, diluted with EtOAc, and washed with water and brine. The organic layer was dried (Na$_2$SO$_4$), filtered, and concentrated. The residue was purified by silica gel column chromatography (CH$_2$Cl$_2$/MeOH, 1:0→99:1→98:2→96:4→92:8) to provide 45 mg of the title compound. t$_R$: 1.24 min (LC-MS 1); ESI-MS: 581.0 [M+H]+ (LC-MS 1).

Step 96.1: 3-[5-(5-Chloro-2-methyl-phenyl)-3-isopropyl-6-oxo-4-(4-trifluoromethyl-phenyl)-5,6-dihydro-4H-pyrrolo[3,4-c]pyrazol-2-yl]-4-methyl-benzoic acid

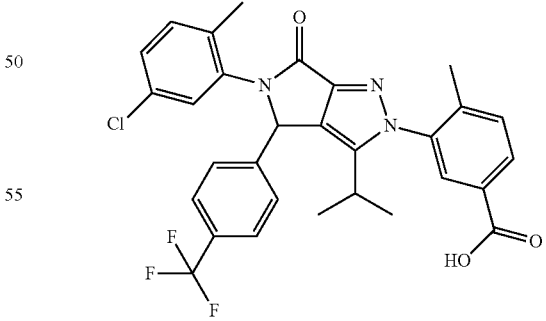

The title compound was prepared in analogy to the procedure described for example 55 but using intermediate P, 3 equivalents of 3-hydrazinyl-4-methylbenzoic acid, acetic acid as the solvet, and stirring the reaction mixture at 120° C. overnight. The crude material was purified by preparative HPLC (Column: XBridge, 30×100 mm. Flow: 30 mL/min.

Gradient: 40% to 90% B in 25 min, A=0.1% TFA in water, B=0.1% TFA in acetonitrile). $t_R$: 1.29 min (LC-MS 3); ESI-MS: 568 [M+H]$^+$ (LC-MS 3).

Example 97

5-(3-Chloro-4-fluoro-phenyl)-4-(5-chloro-pyridin-2-yl)-3-isopropyl-2-(2-methoxy-phenyl)-4,5-dihydro-2H-pyrrolo[3,4-c]pyrazol-6-one

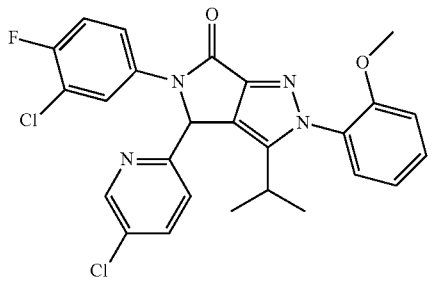 [SMILES: COc1ccccc1-n1nc2c(c1C(C)C)C(c1ccc(Cl)cn1)N(c1ccc(F)c(Cl)c1)C2=O]

The title compound was prepared in analogy to the procedure described for example 75 but using intermediate 5 and 2-methoxyphenylhydrazine hydrochloride. The reaction mixture was stirred at reflux for 16 h after addition of the second portion of hydrazine. The crude material was purified by silica gel column chromatography (hexane/ethyl acetate, 3:7) followed by preparative HPLC (Column: Zorbax eclipse XDB C18, 21.2×150 mm, 5 μm. Flow: 20 mL/min. Gradient: 70% B for 2 min, 70% to 90% B in 5 min; A=0.1% TFA in water, B=acetonitrile). $t_R$: 6.59 min (HPLC 2); ESI-MS: 511.1 [M+H]$^+$ (LC-MS 2).

Example 98

5-(5-Chloro-2-methyl-phenyl)-4-(5-chloro-pyridin-2-yl)-3-isopropyl-2-(2-methoxy-phenyl)-4,5-dihydro-2H-pyrrolo[3,4-c]pyrazol-6-one

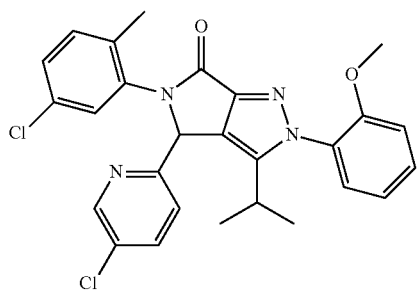 [SMILES: COc1ccccc1-n1nc2c(c1C(C)C)C(c1ccc(Cl)cn1)N(c1cc(Cl)ccc1C)C2=O]

The title compound was prepared in analogy to the procedure described for example 75 but using intermediate R and 2-methoxyphenylhydrazine hydrochloride. The reaction mixture was stirred at reflux for 16 h after addition of the second portion of hydrazine. The crude material was purified by silica gel column chromatography (hexane/ethyl acetate, 4:1) followed by preparative HPLC (Column: XBridge, 21.2×150 mm, 5 μm. Flow: 20 mL/min. Gradient: 70% B for 2 min, 70% to 80% B in 8 min; A=water, B=acetonitrile). $t_R$: 6.22 min (HPLC 2); ESI-MS: 507.1 [M+H]$^+$ (LC-MS 2); $R_f$=0.24 (hexane/EtOAc, 1:1).

Example 99

5-(3-Chloro-4-fluoro-phenyl)-4-(4-chloro-phenyl)-4-(2,3-dihydroxy-propyl)-3-isopropyl-2-(2-methoxy-phenyl)-4,5-dihydro-2H-pyrrolo[3,4-c]pyrazol-6-one

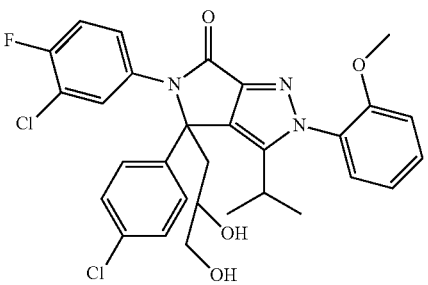 [SMILES: COc1ccccc1-n1nc2c(c1C(C)C)C(CC(O)CO)(c1ccc(Cl)cc1)N(c1ccc(F)c(Cl)c1)C2=O]

Osmium tetroxide (4% in water, 9 mg, 0.0361 mmol) was added to a solution of the compound prepared in step 95.2 (0.2 g, 0.364 mmol) in tert-butanol (2 mL), THF (2 mL) and water (0.2 mL). The reaction mixture was stirred for 12 h at rt, quenched by addition of a saturated aqueous solution of Na$_2$S$_2$O$_3$ and extracted with EtOAc. The organic layer was dried (Na$_2$SO$_4$), filtered and concentrated. The residue was purified by silica gel column chromatography (hexane/EtOAc, 1:4) to provide 180 mg of the title compound. ESI-MS: 583.9 [M+H]$^+$ (LC-MS 2); $R_f$=0.25 (hexane/EtOAc, 1:4).

Example 100

5-(3-Chloro-4-fluoro-phenyl)-4-(4-chloro-phenyl)-4-(2-hydroxy-ethyl)-3-isopropyl-2-(2-methoxy-phenyl)-4,5-dihydro-2H-pyrrolo[3,4-c]pyrazol-6-one

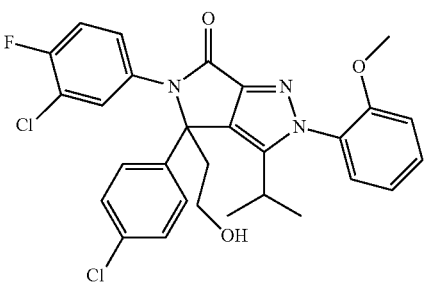 [SMILES: COc1ccccc1-n1nc2c(c1C(C)C)C(CCO)(c1ccc(Cl)cc1)N(c1ccc(F)c(Cl)c1)C2=O]

Sodium borohydride (10 mg, 0.272 mmol) was added to a cold (0° C.) solution of the compound prepared in step 100.1 (0.1 g, 0.181 mmol) in THF (4 mL). The reaction mixture was allowed to warm to rt, stirred for 5 h, quenched by addition of water and extracted with EtOAc. The organic layer was dried (Na$_2$SO$_4$), filtered, and concentrated. The residue was purified by silica gel column chromatography (hexane/EtOAc, 3:2) to provide 70 mg of the title compound. $t_R$: 6.59 min (HPLC 2); ESI-MS: 553.9 [M+H]$^+$ (LC-MS 2); $R_f$=0.24 (hexane/EtOAc, 1:1).

Step 100.1: [5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazol-4-yl]-acetaldehyde

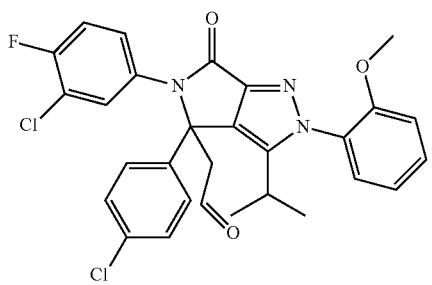 [SMILES: COc1ccccc1-n1nc2c(c1C(C)C)C(CC=O)(c1ccc(Cl)cc1)N(c1ccc(F)c(Cl)c1)C2=O]

Sodium periodate (93 mg, 0.435 mmol) was added to a cold (0° C.) solution of the compound prepared in example 99 (0.12 g, 0.217 mmol) in MeOH (3 mL) and water (0.6 mL). The reaction mixture was stirred for 1 h at 0° C., quenched by addition of a water, and extracted with EtOAc. The organic layer was dried (Na$_2$SO$_4$), filtered, and concentrated. The residue was purified by silica gel column chromatography (hexane/EtOAc, 4:1) to provide 100 mg of the title compound. $R_f$=0.53 (hexane/EtOAc, 7:3).

Example 101

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-methyl-benzamide

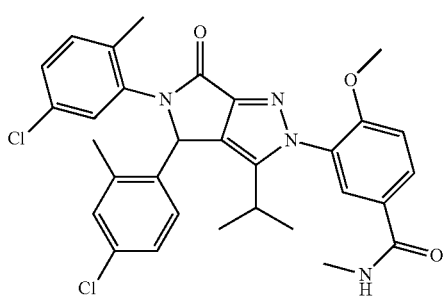 [SMILES: CNC(=O)c1ccc(OC)c(-n2nc3c(c2C(C)C)C(c2ccc(Cl)cc2C)N(c2cc(Cl)ccc2C)C3=O)c1]

A mixture of the compound prepared in step 101.1 (200 mg, 0.355 mmol), EDCI hydrochloride (122 mg, 0.638 mmol), HOBt (86 mg, 0.638 mmol), 4-(dimethylamino)-pyridine (10 mg) and DIEA (138 mg, 1.06 mmol) in CH$_2$Cl$_2$ (6 mL) was stirred for 90 min at rt. Methylamine hydrochloride (24 mg, 0.355 mmol) was added. The resulting mixture was stirred overnight at rt, quenched by slow addition of 2 N HCl, and extracted with EtOAc. The organic phase was dried (Na$_2$SO$_4$), filtered and concentrated. The residue was purified by silica gel column chromatography (CH$_2$Cl$_2$/MeOH, 98:2) to provide 100 mg of the title compound. $t_R$: 6.23 min (HPLC 2); ESI-MS: 577.1 [M+H]$^+$ (LC-MS 2); $R_f$=0.41 (CHCl$_3$/MeOH, 9:1).

Step 101.1: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzoic acid

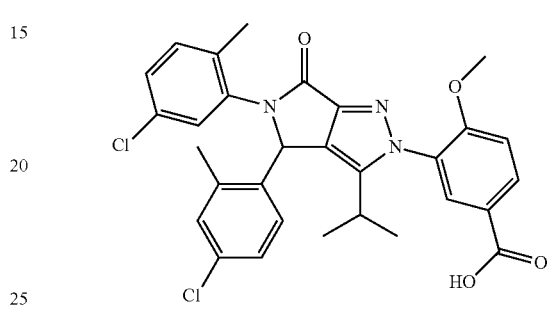

A solution of lithium hydroxide monohydrate (49 mg, 1.17 mmol) in water (1 mL) was added dropwise to a cold (0° C.) solution of the compound prepared in step 101.2 (450 mg, 0.778 mmol) in THF (4 mL). The reaction mixture was allowed to warm to rt, stirred overnight, concentrated, diluted with water, washed with diethyl ether, acidified to pH 2 by addition of 20% HCl in water, and extracted with EtOAc. The organic phase was dried (Na$_2$SO$_4$), filtered and concentrated to afford 420 mg of the compound. $t_R$: 6.23 min (HPLC 2); ESI-MS: 564 [M+H]$^+$ (LC-MS 2); $R_f$=0.12 (hexane/EtOAc, 1:1).

Step 101.2: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzoic acid methyl ester

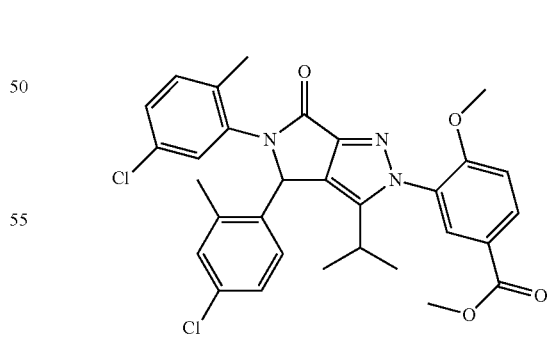

The title compound was prepared in analogy to the procedure described for example 75 but using intermediate L and the hydrazine prepared in step 101.3. The reaction mixture was stirred at reflux for 16 h after addition of the second portion of hydrazine. The crude material was purified by silica gel column chromatography (hexane/ethyl acetate, 85:15). $t_R$: 6.86 min (HPLC 2); ESI-MS: 578.1 [M+H]$^+$ (LC-MS 2); $R_f$=0.28 (hexane/EtOAc, 1:1).

Step 101.3: 3-Hydrazino-4-methoxy-benzoic acid methyl ester hydrochloride

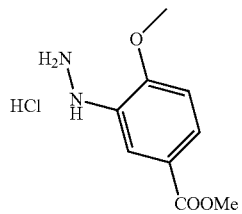

A solution of sodium nitrite (3.96 g, 57.4 mmol) in water (27 mL) was added to a cold (0° C.) mixture of 4-amino-3-methoxy-benzoic acid methyl ester (8 g, 44.2 mmol) in concentrated HCl (80 mL). After 30 min stirring at 0° C., tin dichloride dihydrate (20 g, 88.4 mmol) in concentrated HCl (40 mL) was added at 0° C. The reaction mixture was stirred for 1 h at 0° C., quenched by addition of 20% sodium hydroxyde (400 mL) maintaining the internal temperature a 0° C., and extracted with diethyl ether. The combined organic extracts were washed with water and brine, dried (Na$_2$SO$_4$), filtered and concentrated. To the residue was added pentane (80 mL). The resulting mixture was stirred for 30 min. Pentane was decanted. The residue was dissolved in dioxane. To this solution was added dropwise dioxane saturated with HCl keeping the internal temperature below 20° C. The resulting mixture was stirred for 12 h. The solid product was collected by vacuum filtration, washed with diethyl ether, and dried to provide 3.1 g of the title compound. $t_R$: 5.08 min (HPLC 3); $R_f$=0.20 (hexane/EtOAc, 1:1).

Example 102

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-(2-pyrrolidin-1-yl-ethyl)-benzamide

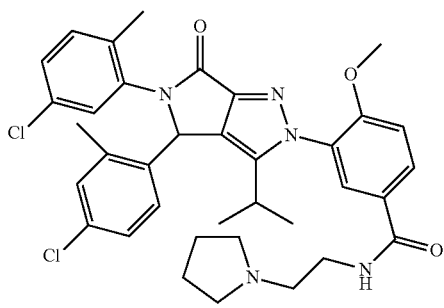 [SMILES: COc1ccc(C(=O)NCCN2CCCC2)cc1-n1nc2c(c1C(C)C)C(c1ccc(Cl)cc1C)N(c1cc(Cl)ccc1C)C2=O]

The title compound was prepared in analogy to the procedure described for example 101 but using 1-(2-aminoethyl)-pyrrolidine. The crude material was purified by silica gel column chromatography (CH$_2$Cl$_2$/MeOH, 95:5). The resulting material was dissolved in EtOAc, washed with a saturated aquous solution of sodium hydrogensulfate (to remove DMAP) and water, dried (Na$_2$SO$_4$), filtered, and concentrated to provide the title compound. $t_R$: 4.47 min (HPLC 2); ESI-MS: 660.2 [M+H]$^+$ (LC-MS 2); $R_f$=0.24 (CHCl$_3$/MeOH, 4:1).

Example 103

3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzonitrile

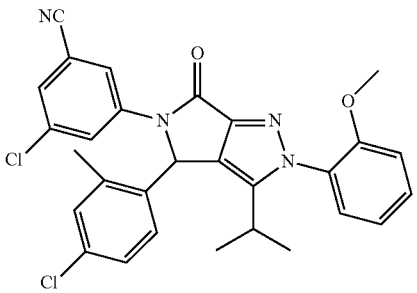 [SMILES: COc1ccccc1-n1nc2c(c1C(C)C)C(c1ccc(Cl)cc1C)N(c1cc(Cl)cc(C#N)c1)C2=O]

The title compound was prepared in analogy to the procedure described for example 75 but using intermediate T and 2-methoxyphenylhydrazine hydrochloride. The reaction mixture was stirred at reflux for 16 h after addition of the second portion of hydrazine. The crude material was purified by silica gel column chromatography (hexane/ethyl acetate, 4:1) followed by preparative HPLC (Column: XBridge C18 OBD. Flow: 15 mL/min. Gradient: 30% to 40% B in 2 min, 40% to 90% B in 3 min; A=water, B=acetonitrile). $t_R$: 6.96 min (HPLC 2); ESI-MS: 531.1 [M+H]$^+$ (LC-MS 2); $R_f$=0.24 (hexane/EtOAc, 1:1).

Example 104

3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzamide

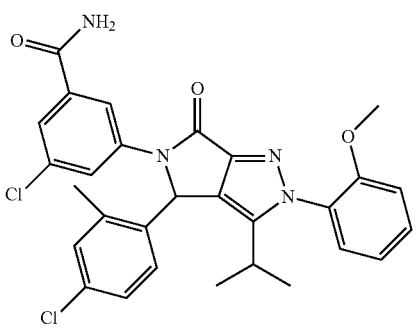 [SMILES: COc1ccccc1-n1nc2c(c1C(C)C)C(c1ccc(Cl)cc1C)N(c1cc(Cl)cc(C(N)=O)c1)C2=O]

A mixture of the compound prepared in example 103 (100 mg, 0.188 mmol) and concentrated HCl (10 mL) was heated to 70° C. and stirred at this temperature overnight. The reaction mixture was allowed to cool to rt, diluted with water and extracted with EtOAc. The organic layer was washed with a saturated aqueous solution of sodium bicarbonate and water, dried (Na$_2$SO$_4$), filtered, and concentrated. The residue was purified by silica gel column chromatography (CHCl$_3$/

Example 105

N-{3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-phenyl}-acetamide

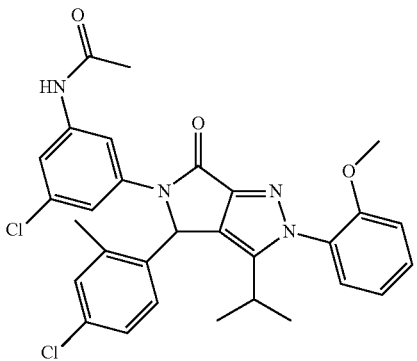 [SMILES: COc1ccccc1-n1nc2c(c1C(C)C)C(c1ccc(Cl)cc1C)N(c1cc(Cl)cc(NC(C)=O)c1)C2=O]

The title compound was prepared in analogy to the procedure described for example 75 but using intermediate U and 2-methoxyphenylhydrazine hydrochloride. The reaction mixture was stirred at reflux for 16 h after addition of the second portion of hydrazine. The crude material was purified by silica gel column chromatography (CH$_2$Cl$_2$/MeOH, 99:1) followed by preparative HPLC (Column: Zorbax C18, 21.2× 150 mm, 5 µm. Flow: 20 mL/min. Gradient: 60% B for 2 min, 60% to 90% B in 6 min; A=0.1% TFA in water, B=acetonitrile). t$_R$: 6.47 min (HPLC 2); ESI-MS: 563.2 [M+H]$^+$ (LC-MS 2); R$_f$=0.25 (hexane/EtOAc, 1:4); $^1$H NMR (600 MHz, DMSO-d$_6$) δ ppm [0.24-0.51 (m), 0.98-1.13 (m), 6H, rotamers], [1.79 (s), 2.57 (s), 3H, rotamers], 2.03 (s, 3H), 2.51-2.62 (m, 1H), 3.68-3.84 (m, 3H), 6.52-7.82 (m, 11H), 10.18 (s, 1H).

Example 106

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N,N-dimethyl-benzamide

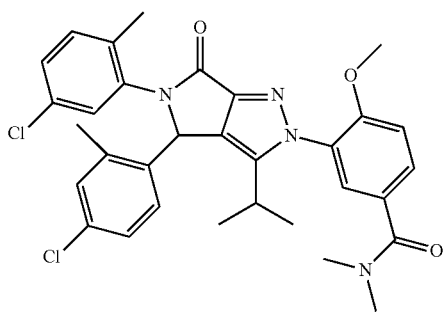 [SMILES: COc1ccc(C(=O)N(C)C)cc1-n1nc2c(c1C(C)C)C(c1ccc(Cl)cc1C)N(c1cc(Cl)ccc1C)C2=O]

The title compound was prepared in analogy to the procedure described for example 101 but using dimethlyamine hydrochloride. The crude material was purified by silica gel column chromatography (CH$_2$Cl$_2$/MeOH, 99:1). t$_R$: 6.51 min (HPLC 2); ESI-MS: 591.2 [M+H]$^+$ (LC-MS 2); R$_f$=0.49 (CH$_2$Cl$_2$/MeOH, 95:5); $^1$H NMR (400 MHz, DMSO-d$_6$) δ ppm [0.40-0.60 (m), 0.83-1.15 (m) 6H, rotamers], [1.83-1.96 (m), 2.21-2.37 (m), 6H, rotamers], 2.55-2.70 (m, 1H), 2.97 (s, 6H), 3.74-3.93 (m, 3H), 6.68-8.04 (m, 10H).

Example 107

4-(4-Chloro-phenyl)-5-(3,4-difluoro-phenyl)-3-isopropyl-2-(2-methoxy-phenyl)-4,5-dihydro-2H-pyrrolo[3,4-c]pyrazol-6-one

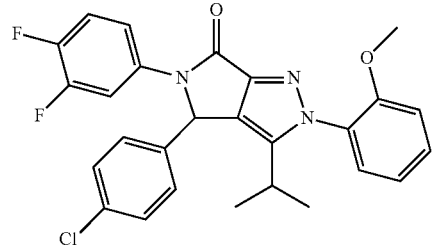 [SMILES: COc1ccccc1-n1nc2c(c1C(C)C)C(c1ccc(Cl)cc1)N(c1ccc(F)c(F)c1)C2=O]

The title compound was prepared in analogy to the procedure described for example 75 but using intermediate D and 2-methoxyphenylhydrazine hydrochloride. The crude material was purified by silica gel column chromatography (hexane/EtOAc, 95:5→4:1) followed by preparative HPLC (Column: AG/AD/PP C18-025. Flow: 18 mL/min. Gradient: 70% to 85% B in 6 min; A=0.01% TFA in water, B=acetonitrile). t$_R$: 6.04 min (HPLC 2); ESI-MS: 494.2 [M+H]$^+$ (LC-MS 2); R$_f$=0.42 (hexane/EtOAc, 1:1); $^1$H NMR (400 MHz, DMSO-d$_6$) δ ppm [0.29-0.53 (m), 1.03-1.21 (m), 6H], 2.48-2.63 (m, 1H), 3.68-3.87 (m, 3H), 6.64 (s, 1H), 7.07-7.19 (m, 1H), 7.29 (d, J=8.41 Hz, 1H), 7.35-7.51 (m, 7H), 7.52-7.63 (m, 1H), 7.69-7.83 (m, 1H).

Example 108

5-(5-Chloro-1-methyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one

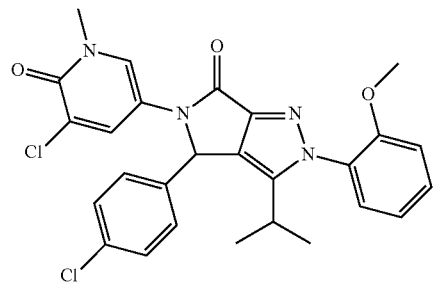 [SMILES: COc1ccccc1-n1nc2c(c1C(C)C)C(c1ccc(Cl)cc1)N(c1cc(Cl)c(=O)n(C)c1)C2=O]

The title compound was prepared in analogy to the procedure described for example 75 but using intermediate W and 2-methoxyphenylhydrazine hydrochloride. The reaction mixture was stirred at reflux overnight after addition of the second portion of hydrazine. The crude material was purified by silica gel column chromatography (CH$_2$Cl$_2$/MeOH, 95:5) followed by preparative HPLC (Column: LUNA-C18, 21.2× 250 mm. Flow: 20 mL/min. Gradient: 60% B for 2 min, 60% to 90% B in 6 min; A=0.1% TFA in water, B=acetonitrile). t$_R$: 5.24 min (HPLC 2); ESI-MS: 523.2 [M+H]$^+$ (LC-MS 2); R$_f$=0.34 (CH$_2$Cl$_2$/MeOH, 9:1); 1H NMR (600 MHz, DMSO-d$_6$) δ ppm 0.27-0.56 (m, 3H), 0.96-1.21 (m, 3H), 2.52-2.61 (m, 1H), 3.30-3.60 (m, 3H, obscured by water), 3.64-3.87 (m, 3H), 6.34 (s, 1H), 7.14 (t, J=7.53 Hz, 1H), 7.24-7.51 (m, 6H), 7.58 (t, J=7.91 Hz, 1H), 7.86-8.09 (m, 2H).

Example 109

5-(5-Chloro-1-ethyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one

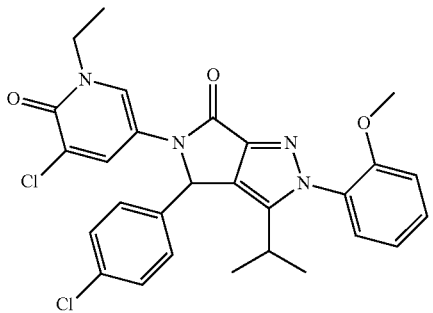 [SMILES: CCn1cc(N2C(=O)c3nn(-c4ccccc4OC)c(C(C)C)c3C2c2ccc(Cl)cc2)cc(Cl)c1=O]

The title compound was prepared in analogy to the procedure described for example 75 but using intermediate X and 2-methoxyphenylhydrazine hydrochloride. The reaction mixture was stirred at reflux overnight after addition of the second portion of hydrazine. The crude material was purified by silica gel column chromatography (CH$_2$Cl$_2$/MeOH, 95:5) followed by preparative HPLC (Column: LUNA-C18, 21.2×250 mm. Flow: 20 mL/min. Gradient: 60% B for 2 min, 60% to 90% B in 6 min; A=0.1% TFA in water, B=acetonitrile). t$_R$: 5.49 min (HPLC 2); ESI-MS: 537.2 [M+H]$^+$ (LC-MS 2); R$_f$=0.34 (CH$_2$Cl$_2$/MeOH, 9:1); $^1$H NMR (600 MHz, DMSO-d$_6$) δ ppm 0.33-0.58 (m, 3H), 1.00-1.25 (m, 6H), 2.53-2.64 (m, 1H), 3.70-3.85 (m, 3H), 3.87-4.02 (m, 2H), 6.33 (s, 1H), 7.14 (t, J=7.62 Hz, 1H), 7.25-7.51 (m, 6H), 7.58 (t, J=8.00 Hz, 1H), 7.94 (t, J=2.64 Hz, 2H).

Example 110

5-(5-Chloro-1-methyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one

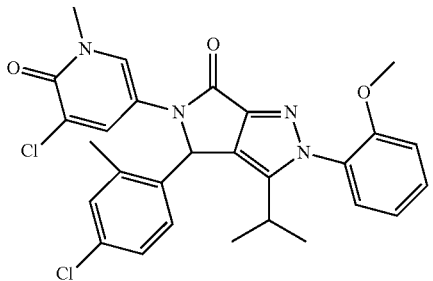 [SMILES: COc1ccccc1-n1nc2c(c1C(C)C)C(c1ccc(Cl)cc1C)N(c1cc(Cl)c(=O)n(C)c1)C2=O]

The title compound was prepared in analogy to the procedure described for example 75 but using intermediate AB and 2-methoxyphenylhydrazine hydrochloride. The reaction mixture was stirred at reflux overnight after addition of the second portion of hydrazine. The crude material was purified by silica gel column chromatography (CH$_2$Cl$_2$/MeOH, 95:5) followed by preparative HPLC (Column: LUNA-C18, 21.2×250 mm. Flow: 20 mL/min. Gradient: 70% B for 2 min, 70% to 90% B in 5 min; A=0.1% TFA in water, B=acetonitrile). t$_R$: 5.77 min (HPLC 2); ESI-MS: 537.1 [M+H]$^+$ (LC-MS 2); R$_f$=0.34 (CH$_2$Cl$_2$/MeOH, 9:1).

Example 111

5-[5-Chloro-1-(2-hydroxy-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one

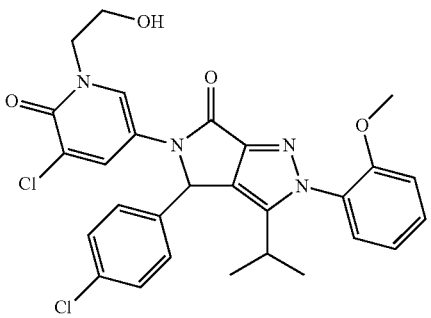

A mixture of the compounds obtained in step 111.1 (500 mg, 0.840 mml) and potassium carbonate in MeOH (12 mL) and water (3 mL) was stirred for 16 h at rt, quenched by addition of a saturated aqueous solution of ammonium chloride, concentrated (to remove MeOH), and extracted with EtOAc. The organic layer was dried (Na$_2$SO$_4$), filtered, and concentrated. The residue was purified by silica gel column chromatography (CH$_2$Cl$_2$/MeOH, 98.5:1.5→98:2) followed by preparative HPLC (Column: LUNA-C18, 21.2×250 mm. Flow: 20 mL/min. Gradient: 70% B for 2 min, 70% to 90% B in 5 min; A=0.1% TFA in water, B=acetonitrile). t$_R$: 5.04 min (HPLC 2); ESI-MS: 554.1 [M+H]$^+$ (LC-MS 2); R$_f$=0.26 (CH$_2$Cl$_2$/MeOH, 95:5).

Step 111.1: 5-[5-Chloro-1-(2-hydroxy-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one (111.1a) and Acetic acid 2-{3-chloro-5-[4-(4-chloro-phenyl)-3-isopropyl-2-(2-methoxy-phenyl)-6-oxo-2,6-dihydro-4H-pyrrolo[3,4-c]pyrazol-5-yl]-2-oxo-2H-pyridin-1-yl}-ethyl ester (111.1b)

111.1a

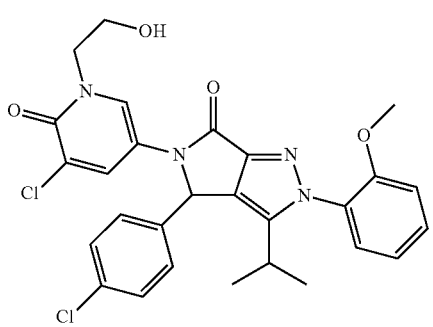 [SMILES: COc1ccccc1-n1nc2c(c1C(C)C)C(c1ccc(Cl)cc1)N(c1cc(Cl)c(=O)n(CCO)c1)C2=O]

-continued 111.1b

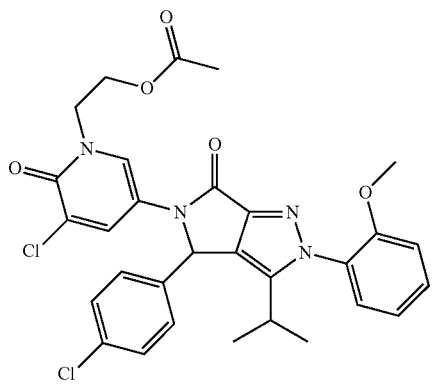

A mixture of the title compounds was obtained in analogy to the procedure described for example 75 but using intermediate Y and 2-methoxyphenylhydrazine hydrochloride. The reaction mixture was stirred at reflux for 16 h after addition of the second portion of hydrazine. The crude material was used without purification.

Example 112

5-[5-Chloro-1-(2-methoxy-ethyl)-6-oxo-1,6-dihydro-pyridin-3-yl]-4-(4-chloro-2-methyl-phenyl)-3-isopropyl-2-(2-methoxy-phenyl)-4,5-dihydro-2H-pyrrolo[3,4-c]pyrazol-6-one

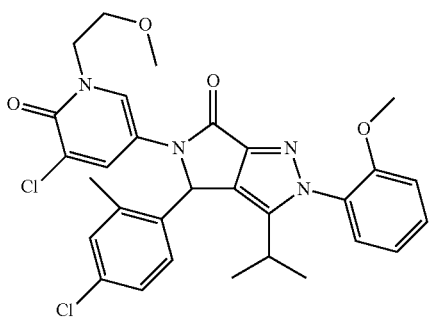 [SMILES: COCCn1cc(N2C(=O)c3nn(-c4ccccc4OC)c(C(C)C)c3C2c2ccc(Cl)cc2C)cc(Cl)c1=O]

The title compound was prepared in analogy to the procedure described for example 75 but using intermediate Z and 2-methoxyphenylhydrazine hydrochloride. The reaction mixture was stirred at reflux for 16 h after addition of the second portion of hydrazine. The crude material was purified by silica gel column chromatography (CH$_2$Cl$_2$/MeOH, 99.5:0.5→99:1) followed by preparative HPLC (Column: LUNA-C18, 21.2×250 mm. Flow: 20 mL/min. Gradient: 70% B for 2 min, 70% to 90% B in 5 min; A=0.1% TFA in water, B=acetonitrile). $t_R$: 5.63 min (HPLC 2); ESI-MS: 581.1 [M+H]$^+$ (LC-MS 2); $R_f$=0.29 (CH$_2$Cl$_2$/MeOH, 95:5).

Example 113

5-(5-Chloro-1-ethyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one

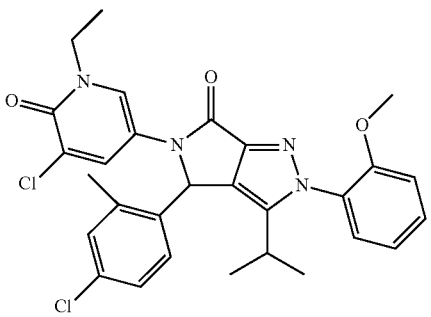 [SMILES: CCn1cc(N2C(=O)c3nn(-c4ccccc4OC)c(C(C)C)c3C2c2ccc(Cl)cc2C)cc(Cl)c1=O]

The title compound was prepared in analogy to the procedure described for example 75 but using intermediate AC and 2-methoxyphenylhydrazine hydrochloride. The reaction mixture was stirred at reflux overnight after addition of the second portion of hydrazine. The crude material was purified by silica gel column chromatography (CH$_2$Cl$_2$/MeOH, 99:1) followed by preparative HPLC (Column: Zorbax C18, 21.2×150 mm, 5 μm. Flow: 20 mL/min. Gradient: 50% to 60% B in 2 min, 60% to 80% in 5 min; A=0.1% TFA in water, B=acetonitrile). $t_R$: 5.78 min (HPLC 2); ESI-MS: 551.3 [M+H]$^+$ (LC-MS 2); $R_f$=0.34 (CH$_2$Cl$_2$/MeOH, 9:1).

Example 114

3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-N-methyl-benzamide

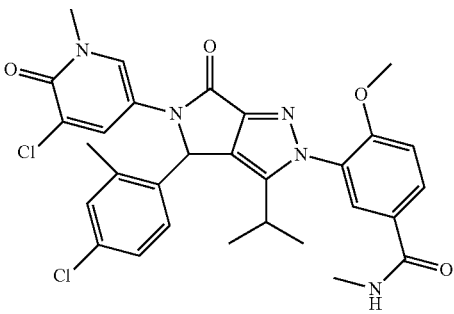 [SMILES: CNC(=O)c1ccc(OC)c(-n2nc3c(c2C(C)C)C(c2ccc(Cl)cc2C)N(c2cc(Cl)c(=O)n(C)c2)C3=O)c1]

A mixture of the compound prepared in step 114.1 (200 mg, 0.300 mmol), EDCI hydrochloride (117 mg, 0.620 mmol), HOBt (830 mg, 0.620 mmol), 4-(dimethylamino)-pyridine (5 mg) and DIEA (0.17 mL, 1.03 mmol) in CH$_2$Cl$_2$ (5 mL) was stirred for 30 min at 0° C. Methylamine hydrochloride (23 mg, 0.300 mmol) was added. The resulting mixture was allowed to warm to rt, stirred overnight, diluted with CH$_2$Cl$_2$, washed with water, dried (Na$_2$SO$_4$), filtered, and concentrated. The residue was purified by silica gel column chromatography (CH$_2$Cl$_2$/MeOH, 98.5:1.5) followed by trituration in diethyl ether first and then in EtOAc to afford 118 mg of the title compound. $t_R$: 4.70 min (HPLC 2); ESI-MS: 594.1 [M+H]$^+$ (LC-MS 2).

Step 114.1: 3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzoic acid

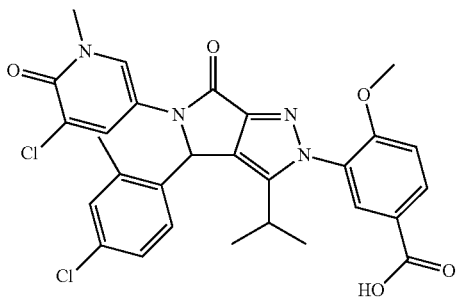 [SMILES: COc1ccc(C(=O)O)cc1-n1nc2c(c1C(C)C)C(c1ccc(Cl)cc1C)N(c1cc(Cl)c(=O)n(C)c1)C2=O]

A solution of lithium hydroxide monohydrate (98 mg, 1.38 mmol) in water (2 mL) was added dropwise to solution of the compound prepared in step 114.2 (750 mg, 1.18 mmol) in THF (8 mL). The reaction mixture was stirred for 24 h at rt, concentrated, diluted with water, washed with diethyl ether, acidified to pH 1 by addition of diluted HCl, and extracted with EtOAc. The organic layer was dried (Na$_2$SO$_4$), filtered, and concentrated to afford 480 mg of the compound. $t_R$: 4.78 min (HPLC 2); ESI-MS: 581 [M+H]$^+$ (LC-MS 2); R$_f$=0.19 (CH$_2$Cl$_2$/MeOH, 9:1).

Step 114.2: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzoic acid methyl ester

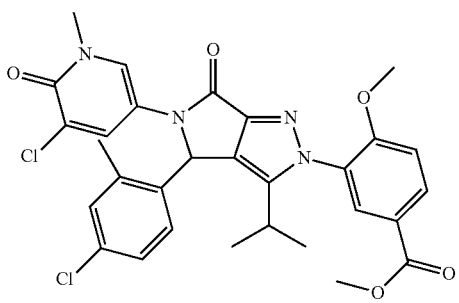 [SMILES: COC(=O)c1ccc(OC)c(-n2nc3c(c2C(C)C)C(c2ccc(Cl)cc2C)N(c2cc(Cl)c(=O)n(C)c2)C3=O)c1]

The title compound was prepared in analogy to the procedure described for example 75 but using intermediate AB and the hydrazine prepared in step 101.3. The reaction mixture was stirred at reflux overnight after addition of the second portion of hydrazine. The crude material was purified by silica gel column chromatography (hexane/ethyl acetate, 85:15). $t_R$: 5.71 min (HPLC 2); ESI-MS: 595 [M+H]$^+$ (LC-MS 2); R$_f$=0.34 (CH$_2$Cl$_2$/MeOH, 90:10).

Example 115

5-[5-Chloro-1-(2-dimethylamino-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one

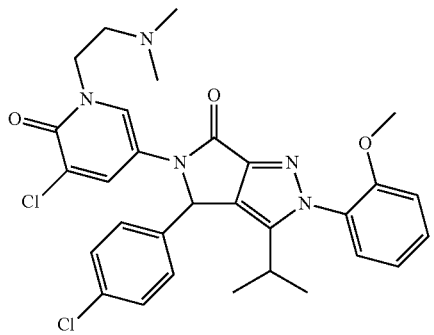 [SMILES: COc1ccccc1-n1nc2c(c1C(C)C)C(c1ccc(Cl)cc1)N(c1cc(Cl)c(=O)n(CCN(C)C)c1)C2=O]

The title compound was prepared in analogy to the procedure described for example 75 but using intermediate AA and 2-methoxyphenylhydrazine hydrochloride. The reaction mixture was stirred at reflux for 16 h after addition of the second portion of hydrazine, allowed to cool to rt, and concentrated. The residue was diluted with water and stirred for 30 min. The resulting precipitate was collected by vacuum filtration, washed with water, dried, and purified by silica gel column chromatography (CH$_2$Cl$_2$/MeOH, 98:2→97:3) followed by preparative HPLC (Column: Zorbax C18, 21.2×150 mm, 5 μm. Flow: 20 mL/min. Gradient: 50% to 60% B in 2 min, 60% to 70% in 8 min; A=10 mM ammonium acetate in water, B=acetonitrile). $t_R$: 3.89 min (HPLC 2); ESI-MS: 580.1 [M+H]$^+$ (LC-MS 2); R$_f$=0.26 (CH$_2$Cl$_2$/MeOH, 9:1).

Example 116

5-(3-Chloro-2-fluoro-phenyl)-4-(4-chloro-2-methyl-phenyl)-2-cyclopropyl-3-isopropyl-4,5-dihydro-2H-pyrrolo[3,4-c]pyrazol-6-one

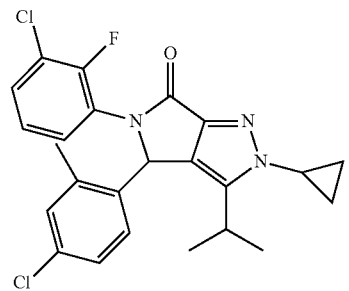 [SMILES: Cc1cc(Cl)ccc1C1c2c(nn(C3CC3)c2C(C)C)C(=O)N1c1cccc(Cl)c1F]

The title compound was prepared in analogy to the procedure described for example 75 but using 6 equivalents of cyclopropylhydrazine hydrochloride (WO2007107470). After addition of the 6 equivalents of hydrazine, the reaction mixture was stirred at 120° C. overnight, allowed to cool to rt, quenched by addition of water and extracted with EtOAc. The crude material was purified by silica gel column chromatography (hexane/ethyl acetate, 4:1). $t_R$: 6.61 min (HPLC 2); ESI-MS: 458.1 [M+H]$^+$ (LC-MS 2); $R_f$=0.42 (hexane/EtOAc, 1:1).

Example 117

5-(3-Chloro-2-fluoro-phenyl)-4-(4-chloro-2-methyl-phenyl)-2-(4-hydroxy-cyclohexyl)-3-isopropyl-4,5-dihydro-2H-pyrrolo[3,4-c]pyrazol-6-one

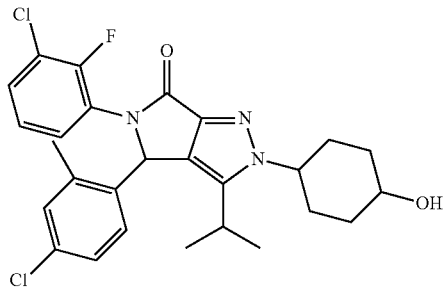 [SMILES: Cc1cc(Cl)ccc1C1c2c(nn(C3CCC(O)CC3)c2C(C)C)C(=O)N1c1cccc(Cl)c1F]

The title compound was prepared in analogy to the procedure described for example 75 but using 4-hydrazinylcyclohexanol hydrochloride. The reaction mixture was stirred at reflux overnight after addition of the second portion of hydrazine, allowed to cool to rt, quenched by addition of water, and extracted with EtOAc. The crude material, consisting of a mixture of cis/trans isomers, was purified by preparative HPLC (Column: LUNA-C18, 21.2×250 mm. Flow: 20 mL/min. Gradient: 70% B for 2 min, 70% to 90% B in 6 min; A=0.1% TFA in water, B=acetonitrile). $t_R$: 5.63 min (HPLC 2). The two isomers could be separated but the assignment could not be made according to the spectroscopic data. Isomer 117a. $t_R$: 6.00 min (HPLC 2); ESI-MS: 516.2 [M+H]$^+$ (LC-MS 2); $R_f$=0.36 (hexane/EtOAc, 1:1). Isomer 117b. $t_R$: 6.56 min (HPLC 2); ESI-MS: 516.1 [M+H]$^+$ (LC-MS 2); $R_f$=0.29 (hexane/EtOAc, 1:1).

Example 118

4-(4-Chloro-2-methyl-phenyl)-5-(2-chloro-pyridin-4-yl)-3-isopropyl-2-(2-methoxy-phenyl)-4,5-dihydro-2H-pyrrolo[3,4-c]pyrazol-6-one

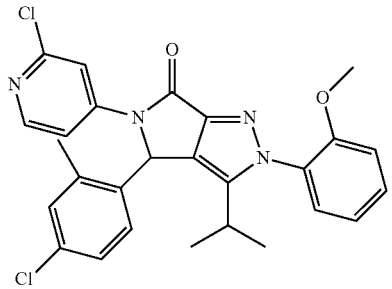 [SMILES: COc1ccccc1-n1nc2c(c1C(C)C)C(c1ccc(Cl)cc1C)N(c1ccnc(Cl)c1)C2=O]

A mixture of the compound prepared in step 118.1 (100 mg, 0.252 mmol), 2-chloro-pyridine-4-boronic acid (48 mg, 0.303 mmol), triethylamine (76 mg), and copper(II) acetate (23 mg, 0.5 mmol) in CH$_2$Cl$_2$ (5 mL) was stirred for 16 h at rt, under a nitrogen atmosphere. The reaction mixture was quenched by addition of water and extracted with EtOAc. The organic layer was dried (Na$_2$SO$_4$), filtered, and concentrated. The residue was purified by silica gel column chromatography (hexane/ethyl acetate, 3:1) to provide 18 mg of the title compound. $t_R$: 6.26 min (HPLC 2); ESI-MS: 507.1 [M+H]$^+$ (LC-MS 2); $R_f$=0.46 (hexane/EtOAc, 1:1).

Step 118.1: 4-(4-Chloro-2-methyl-phenyl)-3-isopropyl-2-(2-methoxy-phenyl)-4,5-dihydro-2H-pyrrolo[3,4-c]pyrazol-6-one

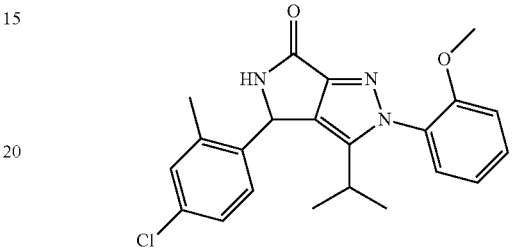

Ceric ammonium nitrate (11.6 g, 20.9 mmol) was added to a stirred solution of the compound prepared in step 118.2 (1.8 g, 3.49 mmol) in acetonitrile (45 mL) and water (5 mL). The reaction mixture was stirred for 48 h at rt, quenched by addition of water, and extracted with EtOAc. The organic layer was dried (Na$_2$SO$_4$), filtered, and concentrated. The residue was purified by silica gel column chromatography (CHCl$_3$/MeOH, 99:1) to provide 0.8 g of the title compound. $t_R$: 1.71 min (LC-MS 2); ESI-MS: 396 [M+H]$^+$ (LC-MS 2); $R_f$=0.16 (CHCl$_3$/MeOH, 95:5).

Step 118.2: 4-(4-Chloro-2-methyl-phenyl)-3-isopropyl-5-(4-methoxy-benzyl)-2-(2-methoxy-phenyl)-4,5-dihydro-2H-pyrrolo[3,4-c]pyrazol-6-one

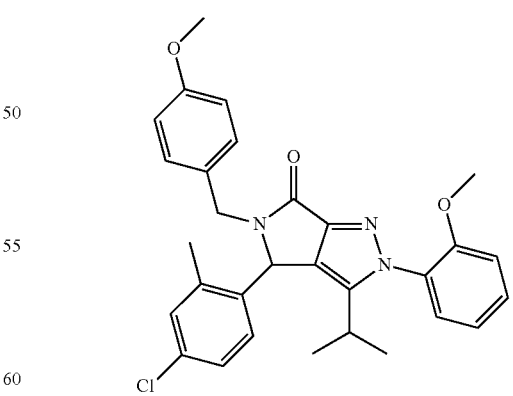

The title compound was prepared in analogy to the procedure described for example 55 but using intermediate AL and 4 equivalents of 2-methoxyphenylhydrazine hydrochloride. The reaction mixture was stirred at 120° C. overnight. The crude material was purified by silica gel column chromatography (hexane/ethyl acetate, 65:35). $t_R$: 1.98 min (LC-MS 2); ESI-MS: 516 [M+H]$^+$ (LC-MS 2).

Example 119

5-(2-Chloro-5-methoxy-pyridin-4-A-4-(4-chloro-2-methyl-phenyl)-3-isopropyl-2-(2-methoxy-phenyl-4,5-dihydro-2H-pyrrolo[3,4-c]pyrazol-6-one

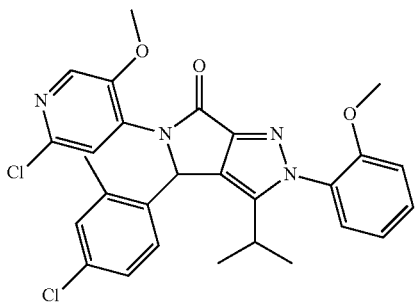 [SMILES: COc1cnc(Cl)cc1N1C(=O)c2nn(-c3ccccc3OC)c(C(C)C)c2C1c1ccc(Cl)cc1C]

A mixture of the compound prepared in step 118.1 (150 mg, 0.378 mmol), the compound prepared in step 119.1 (270 mg, 0.756 mmol), $K_3PO_4$ (320 mg, 1.50 mmol), 1,2-diaminocyclohexane (21 mg, 0.189 mmol), and copper(I) iodide (36 mg, 0.189 mmol) in dioxane (5 mL) was heated to reflux, stirred for 48 h, allowed to cool to rt, quenched by addition of water, and extracted with EtOAc. The organic layer was dried ($Na_2SO_4$), filtered, and concentrated. The residue was purified by silica gel column chromatography (hexane/ethyl acetate, 3:1). The resulting material underwent further purification by preparative HPLC (Column: LUNA-C18, 21.2× 250 mm. Flow: 20 mL/min. Gradient: 70% B for 2 min, 70% to 90% B in 6 min; A=0.1% TFA in water, B=acetonitrile). $t_R$: 6.27 min (HPLC 2); ESI-MS: 537.1 [M+H]$^+$ (LC-MS 2); $R_f$=0.34 ($CH_2Cl_2$/MeOH, 9:1).

Step 119.1: 2-Chloro-4-iodo-5-methoxy-pyridine

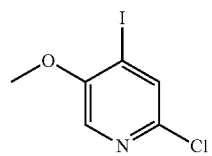

A mixture of NaH (125 mg, 3.14 mmol) and the compound prepared in step 119.2 (400 mg, 1.57 mmol) in DMF (5 mL) was stirred for 1 h at 0° C. Methyl iodide was added. The resulting mixture was allowed to warm to rt, stirred overnight, cooled to 0° C., quenched by addition of water, and extracted with EtOAc. The organic layer was dried ($Na_2SO_4$), filtered, and concentrated. The residue was purified by silica gel column chromatography (hexane/ethyl acetate, 98:2) to provide 300 mg of the title compound. $t_R$: 1.44 min (LC-MS 2); ESI-MS: 269.9 [M+H]$^+$ (LC-MS 2); $R_f$=0.65 (hexane/ethyl acetate, 4:1).

Step 119.2: 6-Chloro-4-iodo-pyridin-3-ol

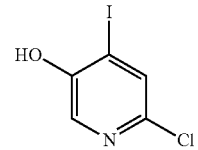

A mixture of the compound prepared in step 119.3 (2 g, 0.66 mmol), MeOH (21 mL) and concentrated HCl (0.6 mL) was heated to reflux, stirred for 4 h, allowed to cool to rt, and concentrated. The residue was used without purification. ESI-MS: 255.9 [M+H]$^+$ (LC-MS 2).

Step 119.3: 2-Chloro-4-iodo-5-methoxymethoxy-pyridine

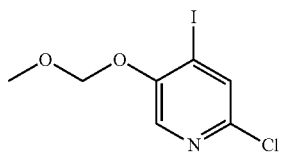

n-Buthyllithium (2 M in THF, 8 mL, 16 mmol) was added to a cold (−78° C.) solution of the compound prepared in step 119.4 (2.5 g, 14.5 mmol) in THF (20 mL). The reaction mixture was stirred for 1 h at −78° C. A solution of iodine (2.18 g, 17.3 mmol) in THF (10 mL) was added. The mixture was stirred for 1 h at −78° C., allowed to warm up to 0° C., quenched by addition of water, and extracted with EtOAc. The organic layer was dried ($Na_2SO_4$), filtered, and concentrated. The residue was purified by silica gel column chromatography (hexane/ethyl acetate, 98:2) to afford 2 g of the title compound. ESI-MS: 299.9 [M+H]$^+$ (LC-MS 2); $R_f$=0.59 (hexane/ethyl acetate, 4:1).

Step 119.4: 2-Chloro-5-methoxymethoxy-pyridine

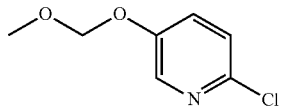

2-Chloro-5-hydroxy-pyridine (3 g, 30.9 mmol) in DMF (5 mL) was added to a cold (0° C.) solution of NaH (1.5 g, 37.1 mmol) in DMF (20 mL). The mixture was stirred at 0° C. for 1 h. Chloromethyl methyl ether (4.95 g, 60.8 mmol) was added. The reaction mixture was allowed to warm to rt, stirred overnight, cooled to 0° C., quenched by addition of water, and extracted with EtOAc. The organic layer was dried ($Na_2SO_4$), filtered, and concentrated. The residue was purified by silica gel column chromatography (hexane/ethyl acetate, 98:2) to afford 3 g of the title compound. $t_R$: 0.56 min (LC-MS 2); ESI-MS: 174.0 [M+H]$^+$ (LC-MS 2); $R_f$=0.67 (hexane/ethyl acetate, 1:1).

Example 120

5-(3-Chloro-2-fluoro-phenyl)-4-(4-chloro-phenyl)-3-isopropyl-2-(1H-pyrazol-4-yl)-4,5-dihydro-2H-pyrrolo[3,4-c]pyrazol-6-one

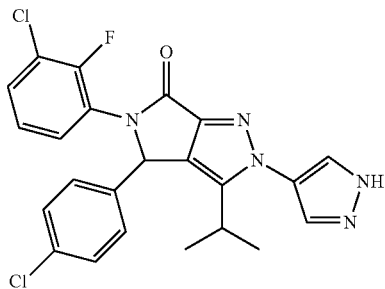 [SMILES: CC(C)c1c2c(nn1-c1cn[nH]c1)C(=O)N(c1cccc(Cl)c1F)C2c1ccc(Cl)cc1]

A mixture of the compound prepared in step 120.1 (127 mg, 0.215 mmol), anisole (93 mg, 0.860 mmol) and TFA (1 mL) was stirred under microwave irradiation for 10 min at 120° C. The reaction mixture was allowed to cool to rt, concentrated, diluted with a saturated aqueous solution of sodium bicarbonate, and extracted with CH$_2$Cl$_2$. The organic extracts were washed with water and brine, dried (Na$_2$SO$_4$), filtered, and concentrated. The residue was purified by silica gel column chromatography (CH$_2$Cl$_2$/MeOH, 95:5), followed by trituration of the resulting material in diethyl ether to afford 64 mg of the title compound. $t_R$: 1.14 min (LC-MS 4); ESI-MS: 470.2 [M+H]$^+$ (LC-MS 4); $R_f$=0.10 (CH$_2$Cl$_2$/MeOH, 95:5).

Step 120.1: 5-(3-Chloro-2-fluoro-phenyl)-4-(4-chloro-phenyl)-3-isopropyl-2-[1-(4-methoxy-benzyl)-1H-pyrazol-4-yl]-4,5-dihydro-2H-pyrrolo[3,4-c]pyrazol-6-one

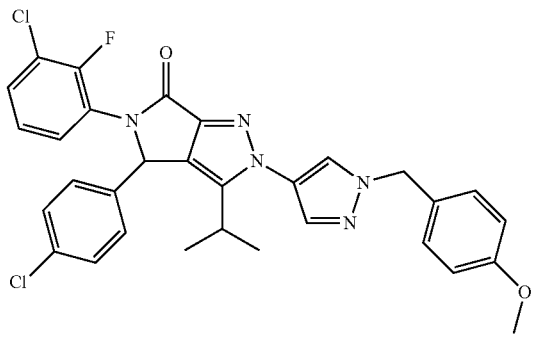 [SMILES: COc1ccc(Cn2cc(-n3nc4c(c3C(C)C)C(c3ccc(Cl)cc3)N(c3cccc(Cl)c3F)C4=O)cn2)cc1]

The title compound was prepared in analogy to the procedure described for example 55 but using intermediate B and 3.37 equivalents of the compound prepared in step 120.2. The reaction mixture was stirred for 1.5 h at 120° C. The crude material was purified by silica gel column chromatography (hexane/ethyl acetate, 2:3). $t_R$: 1.34 min (LC-MS 4); ESI-MS: 590.3 [M+H]$^+$ (LC-MS 4); $R_f$=0.18 (hexane/ethyl acetate, 2:3).

Step 120.2: [1-(4-Methoxy-benzyl)-1H-pyrazol-4-yl]-hydrazine

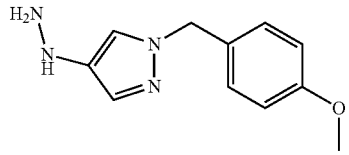 [SMILES: COc1ccc(Cn2cc(NN)cn2)cc1]

A solution of sodium nitrite (1.1 g, 15.9 mmol) in water (5 mL) was added slowly to a cold (0° C.) solution of the compound prepared in step 120.3 (2.16 g, 10.6 mmol) in concentrated HCl (24 mL), keeping the temperature below 0° C. A solution of tin(II) chloride dihydrate (5.27 g, 23.4 mmol) in concentrated HCl (6 mL) was added. The reaction mixture was allowed to warm to rt, basified by addition of 40% NaOH in water, and extracted with diethyl ether. The organic extracts were washed with water and brine, dried (Na$_2$SO$_4$), filtered, and concentrated. The residue was purified by silica gel column chromatography (CH$_2$Cl$_2$/MeOH, 95:5) to afford 362 mg of the title compound. $t_R$: 0.44 min (LC-MS 4); ESI-MS: 219.3 [M+H]$^+$ (LC-MS 4); $R_f$=0.13 (CH$_2$Cl$_2$/MeOH, 95:5).

Step 120.3: 1-(4-Methoxy-benzyl)-1H-pyrazol-4-ylamine

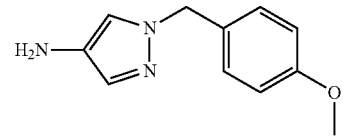

A mixture of the compound prepared in step 120.4 (5.6 g, 24 mmol) and Raney nickel (2.7 g) in MeOH (100 mL) and THF (30 mL) was stirred for 40 h at rt, under a hydrogen atmosphere. Further Raney nickel (2.2 g) was added. The reaction mixture was stirred for 47 h at 40° C. under hydrogen, filtered through a pad of celite, and concentrated. The residue was purified by silica gel column chromatography (CH$_2$Cl$_2$/MeOH, 95:5) to afford 4.55 g of the title compound. $t_R$: 0.47 min (LC-MS 4); ESI-MS: 204.2 [M+H]$^+$ (LC-MS 4); $R_f$=0.18 (CH$_2$Cl$_2$/MeOH, 95:5).

Step 120.4: 1-(4-Methoxy-benzyl)-4-nitro-1H-pyrazole

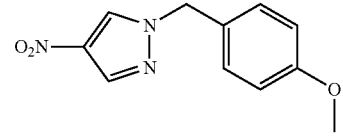 [SMILES: COc1ccc(Cn2cc([N+](=O)[O-])cn2)cc1]

A mixture of 4-nitro-imidazole (2.75 g, 24.3 mmol), benzyl chloride (4.3 g, 26.8 mmol), potassium carbonate (4 g, 29.2 mmol), and acetonitrile (50 mL) was stirred for 2 h at rt, warmed to 55° C., stirred for 16 h, allowed to cool to rt, concentrated, diluted with water, and extracted with EtOAc. The organic extracts were washed with brine, dried (Na$_2$SO$_4$), filtered, and concentrated. The residue was purified by silica gel column chromatography (hexane/EtOAc, 4:1) to afford 5.6 g of the title compound. $t_R$: 0.93 min (LC-MS 4); ESI-MS: 234.3 [M+H]$^+$ (LC-MS 4); $R_f$=0.25 (hexane/EtOAc, 4:1).

Example 121

5-(3-Chloro-2-fluoro-phenyl)-4-(4-chloro-phenyl)-3-isopropyl-2-(4-methoxy-pyridin-3-yl)-4,5-dihydro-2H-pyrrolo[3,4-c]pyrazol-6-one

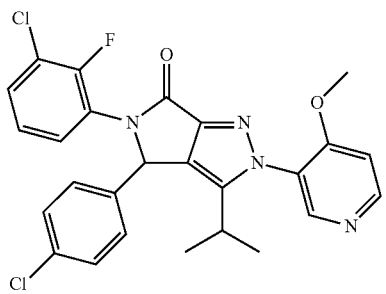 [SMILES: COc1ccncc1-n1nc2c(c1C(C)C)C(c1ccc(Cl)cc1)N(c1cccc(Cl)c1F)C2=O]

The title compound was prepared in analogy to the procedure described for example 55 but using intermediate B and 1.8 equivalents of the compound prepared in step 121.1. The reaction mixture was stirred for 6 h at reflux and diluted with EtOAc and a saturated aqueous solution of sodium bicarbonate. The organic extracts were washed with water and brine, dried (Na$_2$SO$_4$), filtered, and concentrated. The residue was purified twice by silica gel column chromatography (first: CH$_2$Cl$_2$/EtOAc, 7:3; second: CH$_2$Cl$_2$/EtOAc, 9:1), followed by trituration in diethyl ether/hexane (3:7). $t_R$: 1.35 min (LC-MS 4); ESI-MS: 511.2 [M+H]$^+$ (LC-MS 4); $R_f$=0.36 (hexane/EtOAc, 9:1).

Step 121.1: (4-Methoxy-pyridin-3-yl)-hydrazine

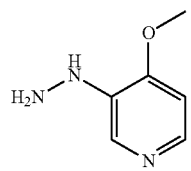

A mixture of the compound prepared in step 121.2 (500 mg) and HCl (4 N in dioxane, 10 mL) was stirred for 16 h at rt and concentrated to afford a yellow solid (325 mg). A portion of this material (225 mg) was dissolved in MeOH and loaded onto a Varian Bond Elut SCX column. Impurities were washed with MeOH, and product was eluted with 7 N ammonia in MeOH to afford after concentration 130 mg of the title compound. $t_R$: 0.31 min (LC-MS 4); ESI-MS: 140.2 [M+H]$^+$ (LC-MS 4).

Step 121.2: 1-(4-Methoxy-3-pyridinyl)-1,2-hydrazinedicarboxylic acid 1,2-bis(1,1-dimethylethyl)ester

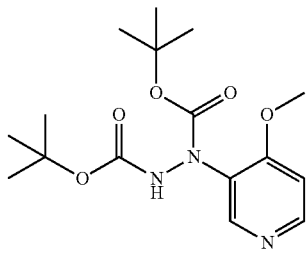 [SMILES: COc1ccncc1N(NC(=O)OC(C)(C)C)C(=O)OC(C)(C)C]

A mixture of 2-methoxy-5-pyridyl boronic acid (942 mg, 6.16 mmol), di-tert-butylazodicarboxylate (1.56 g, 6.78 mmol), and copper(II) acetate (112 mg, 0.616 mmol) was stirred for 3 h at 50° C., concentrated, diluted with CH$_2$Cl$_2$/water, and extracted with CH$_2$Cl$_2$. The residue was purified by silica gel column chromatography (hexane/EtOAc, 1:1) to give 1.56 g of the title compound. $t_R$: 1.10 min (LC-MS 4); ESI-MS: 340.32 [M+H]$^+$ (LC-MS 4); $R_f$=0.48 (hexane/EtOAc, 1:1).

Example 122

4-(4-Chloro-2-methyl-phenyl)-5-(5-chloro-2-methyl-phenyl)-3-isopropyl-2-(4-methoxy-pyridin-3-yl)-4,5-dihydro-2H-pyrrolo[3,4-c]pyrazol-6-one

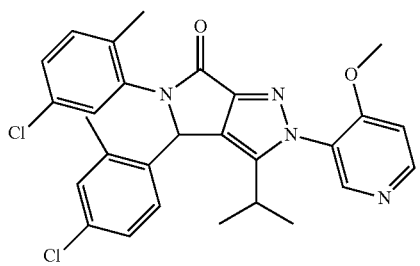 [SMILES: COc1ccncc1-n1nc2c(c1C(C)C)C(c1ccc(Cl)cc1C)N(c1cc(Cl)ccc1C)C2=O]

The title compound was prepared in analogy to the procedure described for example 55 but using intermediate L and 2 equivalents of the hydrazine prepared in step 121.1. The reaction mixture was stirred for 16 h at 50° C. and diluted with EtOAc and a saturated aqueous solution of sodium bicarbonate. The organic extracts were washed with water and brine, dried (Na$_2$SO$_4$), filtered, and concentrated. The residue was purified by silica gel column chromatography (hexane/EtOAc, 3:2), followed by trituration in diethyl ether/hexane (1:4). The resulting material underwent preparative HPLC purification (Column: Sunfire C18, 30×100 mm, 5 μm. Flow: 30 mL/min. Gradient: 30% to 60% B in 30 min; A=0.1% TFA in water, B=acetonitrile). $t_R$: 1.39 min (LC-MS 4); ESI-MS: 521.2 [M+H]$^+$ (LC-MS 4); $R_f$=0.19 (hexane/EtOAc, 3:2).

Example 123

3-tert-Butyl-5-(3-chloro-2-fluoro-phenyl)-4-(4-chloro-phenyl)-4,5-dihydro-2H-pyrrolo[3,4-c]pyrazol-6-one

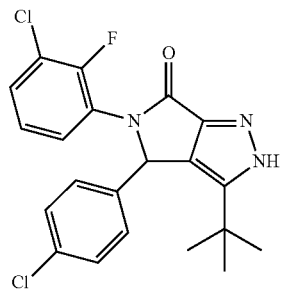 [SMILES: CC(C)(C)c1[nH]nc2c1C(c1ccc(Cl)cc1)N(c1cccc(Cl)c1F)C2=O]

The title compound was prepared in analogy to the procedure described for intermediate AD but using the compound prepared in step 123.1. The reaction mixture was concentrated. The residue was purified by silica gel column chromatography (CH$_2$Cl$_2$/MeOH, 95:5→3:1). $t_R$: 5.57 min (HPLC 6); ESI-MS: 418.0 [M+H]$^+$; $^1$H NMR (400 MHz, DMSO-d$_6$) δ ppm 1.05 (s, 9H), 6.25 (s, 1H), 7.10-7.50 (m, 7H), 13.50 (s, 1H).

Step 123.1: 3-tert-Butyl-5-(3-chloro-2-fluoro-phenyl)-4-(4-chloro-phenyl)-4,5-dihydro-2H-pyrrolo[3,4-c]pyrazol-6-one

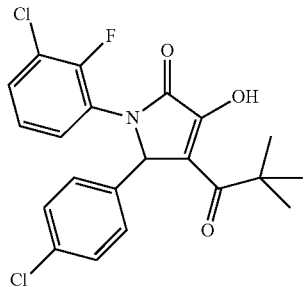 [SMILES: CC(C)(C)C(=O)C1=C(O)C(=O)N(c2cccc(Cl)c2F)C1c1ccc(Cl)cc1]

The title compound was prepared in analogy to the procedure described for intermediate A but using 5,5-dimethyl-2,4-dioxo-hexanoic acid ethyl ester. The reaction mixture was stirred for 3.5 h at reflux, concentrated, and purified. $t_R$: 5.73 min (HPLC 6); ESI-MS: 422.0 [M+H]$^+$; $^1$H NMR (400 MHz, DMSO-d$_6$) δ ppm 1.10 (s, 9H), 5.95 (s, 1H), 7.12-7.24 (m, 5H), 7.40-7.60 (m, 2H), 12.50 (s, 1H).

Example 124

4-(4-Chloro-phenyl)-5-[5-chloro-2-(2H-tetrazol-5-ylmethoxy)-phenyl]-3-isopropyl-2-(2-methoxy-phenyl)-4,5-dihydro-2H-pyrrolo[3,4-c]pyrazol-6-one

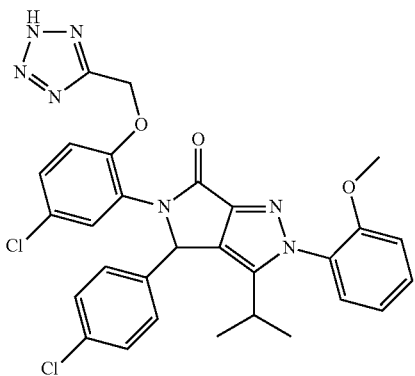 [SMILES: COc1ccccc1-n1nc2c(c1C(C)C)C(c1ccc(Cl)cc1)N(c1cc(Cl)ccc1OCc1nn[nH]n1)C2=O]

A mixture of the compound prepared in step 124.1 (30 mg, 0.055 mmol), sodium azide (10.7 mg, 0.164 mmol) and ammonium chloride (8.8 mg, 0.164 mmol) in DMF (1 mL) was stirred for 7 h at 100° C. under argon, allowed to cool to rt, quenched by addition of a saturated aqueous solution of sodium chloride, and extracted with EtOAc. The organic extracts were washed with brine, dried (Na$_2$SO$_4$), filtered, and concentrated. The residue was purified by preparative HPLC (Column: Sunfire C18, 30×100 mm, 5 μm. Flow: 30 mL/min. Gradient: 5% to 100% B in 20 min; A=0.1% TFA in water, B=0.1% TFA in acetonitrile) to provide 13 mg of the title compound. $t_R$: 1.22 min (LC-MS 4); ESI-MS: 590.2 [M+H]$^+$ (LC-MS 4); $^1$H NMR (400 MHz, DMSO-d$_6$) δ ppm 0.28-0.52 (m, 3H), 0.96-1.11 (m, 3H), 2.50-2.57 (m, 1H), 3.68-3.81 (m, 3H), 5.44-5.57 (m, 2H), 6.35-6.45 (m, 1H), 7.10 (t, J=7.6 Hz, 1H), 7.22-7.47 (m, 9H), 7.54 (t, J=8.0 Hz, 1H).

Step 124.1: {4-Chloro-2-[4-(4-chloro-phenyl)-3-isopropyl-2-(2-methoxy-phenyl)-6-oxo-2,6-dihydro-4H-pyrrolo[3,4-c]pyrazol-5-yl]-phenoxy}-acetonitrile

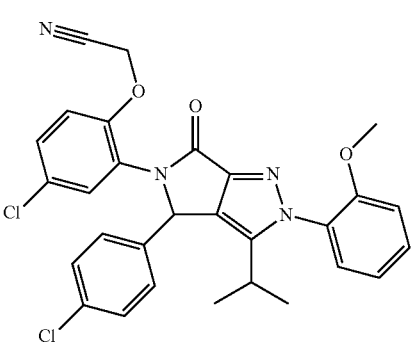 [SMILES: COc1ccccc1-n1nc2c(c1C(C)C)C(c1ccc(Cl)cc1)N(c1cc(Cl)ccc1OCC#N)C2=O]

A mixture of the compound prepared in step 124.2 (251 mg, 0.444 mmol), HATU (194 mg, 0.510 mmol), and N-methylmorpholine (0.146 mL, 1.33 mmol) in DMF (3 mL) was stirred for 1 h at 80° C. under argon, allowed to cool to rt, quenched by addition of a saturated aqueous solution of sodium bicarbonate, and extracted with EtOAc. The organic extracts were washed with a saturated aqueous solution of sodium bicarbonate, dried (Na$_2$SO$_4$), filtered, and concentrated. The residue was purified by preparative HPLC (Column: Sunfire C18, 30×100 mm, 5 μm. Flow: 30 mL/min. Gradient: 5% to 100% B in 20 min; A=0.1% TFA in water, B=0.1% TFA in acetonitrile) to provide 31 mg of the title compound. $t_R$: 1.31 min (LC-MS 4); ESI-MS: 547.2 [M+H]$^+$ (LC-MS 4).

Step 124.2: 4-[(5-Chloro-2-cyanomethoxy-phenylamino)-(4-chloro-phenyl)-methyl]-5-isopropyl-1-(2-methoxy-phenyl)-1H-pyrazole-3-carboxylic acid

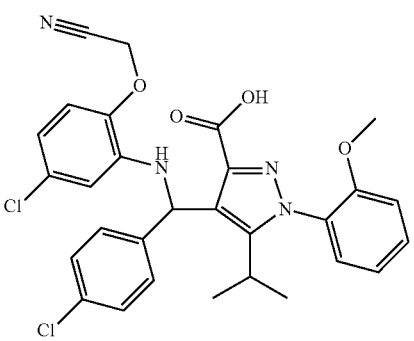 [SMILES: COc1ccccc1-n1nc(C(=O)O)c(C(Nc2cc(Cl)ccc2OCC#N)c2ccc(Cl)cc2)c1C(C)C]

A mixture of the compound prepared in step 124.3 (258 mg, 0.435 mmol), lithium hydroxyde monohydrate (27.4 mg, 0.652 mmol), dioxane (4 mL), and water (1 mL) was stirred for 20 h at rt, quenched by addition of 0.5 N HCl (50 mL), and extracted with EtOAc. The organic extracts were dried (Na$_2$SO$_4$), filtered, and concentrated. The residue (251 mg)

was used without purification. $t_R$: 1.35 min (LC-MS 4); ESI-MS: 565.0 [M+H]$^+$ (LC-MS 4).

Step 124.3: 4-[(5-Chloro-2-cyanomethoxy-phenylamino)-(4-chloro-phenyl)-methyl]-5-isopropyl-1-(2-methoxy-phenyl)-1H-pyrazole-3-carboxylic acid ethyl ester

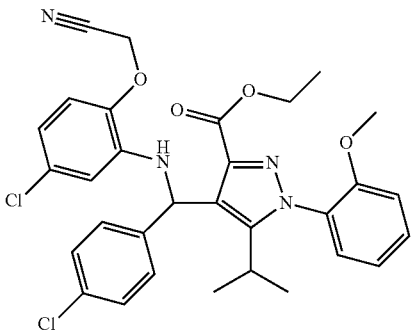 [SMILES: CCOC(=O)c1nn(-c2ccccc2OC)c(C(C)C)c1C(Nc1cc(Cl)ccc1OCC#N)c1ccc(Cl)cc1]

Methanesulfonic anhydride (244 mg, 1.40 mmol) and triethylamine (0.487 mL, 3.50 mmol) were added sequentially to a solution of the compound prepared in step 124.4 (300 mg, 0.699 mmol) in CH$_2$Cl$_2$ (5 mL) under argon. The mixture was stirred for 30 min at rt. Then, the compound prepared in step 124.5 (255 mg, 1.40 mmol) was added. The reaction mixture was stirred for 1 h at rt, quenched by addition of a saturated aqueous solution of sodium bicarbonate (75 mL), and extracted with EtOAc. The organic extracts were washed with a saturated aqueous solution of sodium bicarbonate, dried (Na$_2$SO$_4$), filtered, and concentrated. The residue was purified by silica gel column chromatography (hexane/EtOAc, 95:5→7:3) to provide 250 mg of the title compound. $t_R$: 1.46 min (LC-MS 4); ESI-MS: 593.2 [M+H]$^+$ (LC-MS 4); $R_f$=0.62 (hexane/EtOAc, 1:1).

Step 124.4: 4-[(4-Chloro-phenyl)-hydroxy-methyl]-5-isopropyl-1-(2-methoxy-phenyl)-1H-pyrazole-3-carboxylic acid ethyl ester

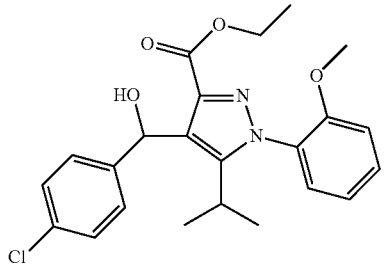 [SMILES: CCOC(=O)c1nn(-c2ccccc2OC)c(C(C)C)c1C(O)c1ccc(Cl)cc1]

4-Chlorophenylmagnesium bromide (1 M in diethyl ether, 6.32 mL, 6.32 mmol) was added to a cold (−10° C.) solution of intermediate AP (2 g, 6.32 mmol) in THF (40 mL) under argon. The reaction mixture was stirred for 10 min at −10° C., quenched by addition of a saturated aqueous solution of ammonium chloride, and extracted with EtOAc. The organic extracts were washed with a saturated aqueous solution of ammonium chloride, dried (Na$_2$SO$_4$), filtered, and concentrated. The residue was purified by silica gel column chromatography (hexane/EtOAc, 95:5→7:3) to provide 2.53 g of the title compound. $t_R$: 1.28 min (LC-MS 4); ESI-MS: 429.2 [M+H]$^+$ (LC-MS 4); $R_f$=0.56 (hexane/EtOAc, 1:1).

Step 124.5: (2-Amino-4-chloro-phenoxy)-acetonitrile

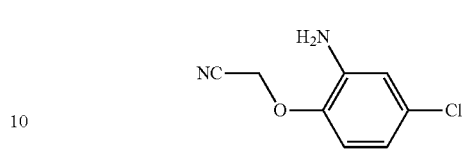

TFA (10.9 mL, 141 mmol) was added to a solution of the compound prepared in step 124.6 (8 g, 28.3 mmol) in CH$_2$Cl$_2$ (50 mL). The reaction mixture was stirred for 20 h at rt, quenched by addition of a saturated aqueous solution of sodium bicarbonate, and extracted with CH$_2$Cl$_2$. The organic extracts were washed with a saturated aqueous solution of sodium bicarbonate, dried (Na$_2$SO$_4$), filtered, and concentrated. The residue was purified by silica gel column chromatography (hexane/EtOAc, 95:5→3:1) and subsequent recrystallization of the resulting material in diethyl ether/hexane to provide 1.36 g of the title compound. $t_R$: 0.82 min (LC-MS 4); ESI-MS: 183.2 [M+H]$^+$ (LC-MS 4); $R_f$=0.71 (hexane/EtOAc, 1:1).

Step 124.6: (5-Chloro-2-cyanomethoxy-phenyl)-carbamic acid tert-butyl ester

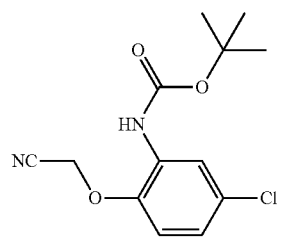 [SMILES: CC(C)(C)OC(=O)Nc1cc(Cl)ccc1OCC#N]

Chloroacetonitrile (4.26 mL, 67.5 mmol) was added to a suspension of the compound prepared in step 124.7 (13.7 g, 56.2 mmol), sodium iodide (10.1 g, 67.5 mmol), and potassium carbonate (9.32 g, 67.5 mmol) in 2-butanone (60 mL) under argon. The reaction mixture was stirred for 2 h at 80° C., allowed to cool to rt, quenched by addition of a saturated aqueous solution of sodium bicarbonate (175 mL), and extracted with EtOAc. The organic extracts were washed with a saturated aqueous solution of sodium bicarbonate, dried (Na$_2$SO$_4$), filtered, and concentrated to afford 16 g of the title compound. $t_R$: 1.16 min (LC-MS 4); ESI-MS: 281.0 [M−H]$^−$ (LC-MS 4).

Step 124.7: (5-Chloro-2-hydroxy-phenyl)-carbamic acid tert-butyl ester

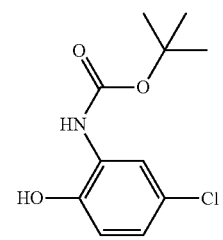 [SMILES: CC(C)(C)OC(=O)Nc1cc(Cl)ccc1O]

Di-tert-butyl dicarbonate (16.98 mL, 73.1 mmol) was added to a cold (0° C.) solution of 2-amino-4-chlorophenol (10 g, 69.7 mmol) in dioxane (50 mL), under argon. The reaction mixture was stirred for 3 days at rt, diluted with a saturated aqueous solution of sodium bicarbonate (175 mL), and extracted with $CH_2Cl_2$. The organic extracts were washed with a saturated aqueous solution of sodium bicarbonate, dried ($Na_2SO_4$), filtered, and concentrated. The residue was purified by silica gel column chromatography (hexane/EtOAc, 95:5) to provide 13.7 g of the title compound. $t_R$: 1.16 min (LC-MS 4); ESI-MS: 242.1 [M–H]⁻ (LC-MS 4); $R_f$=0.17 (hexane/EtOAc, 9:1).

Example 125

3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzonitrile

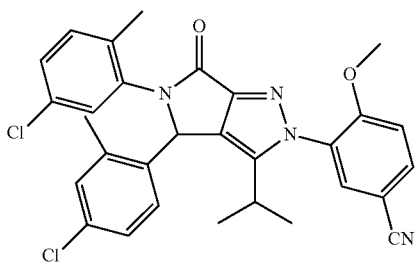 [SMILES: COc1ccc(C#N)cc1-n1nc2c(c1C(C)C)C(c1ccc(Cl)cc1C)N(c1cc(Cl)ccc1C)C2=O]

The title compound was prepared in analogy to the procedure described for step 124.1 but using the compound prepared in step 125.1. The crude product was purified by silica gel column chromatography (hexane/EtOAc, 4:1→1:1). $t_R$: 1.38 min (LC-MS 4); ESI-MS: 545.2 [M+H]⁺ (LC-MS 4); $R_f$=0.24 (hexane/EtOAc, 1:1).

Step 125.1: 4-[(4-Chloro-2-methyl-phenyl)-(5-chloro-2-methyl-phenylamino)-methyl]-1-(5-cyano-2-methoxy-phenyl)-5-isopropyl-1H-pyrazole-3-carboxylic acid

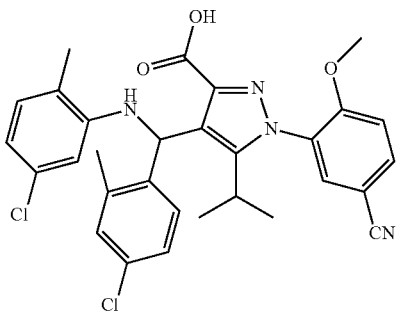 [SMILES: COc1ccc(C#N)cc1-n1nc(C(=O)O)c(C(Nc2cc(Cl)ccc2C)c2ccc(Cl)cc2C)c1C(C)C]

The title compound was prepared in analogy to the procedure described for step 124.2 but using the compound prepared in step 125.2. After stirring the mixture for 20 h at rt, further 1.5 equivalents of lithium hydroxide monohydrate were added, and the reaction mixture was stirred for 3 days at rt. $t_R$: 1.40 min (LC-MS 4); ESI-MS: 563.2 [M+H]⁺ (LC-MS 4).

Step 125.2: 4-[(4-Chloro-2-methyl-phenyl)-(5-chloro-2-methyl-phenylamino)-methyl]-1-(5-cyano-2-methoxy-phenyl)-5-isopropyl-1H-pyrazole-3-carboxylic acid ethyl ester

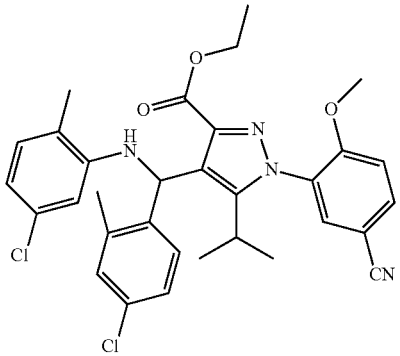 [SMILES: CCOC(=O)c1nn(-c2cc(C#N)ccc2OC)c(C(C)C)c1C(Nc1cc(Cl)ccc1C)c1ccc(Cl)cc1C]

The title compound was prepared in analogy to the procedure described for step 124.3 but using the compound prepared in step 125.3 and 5-chloro-2-methylaniline. $t_R$: 1.54 min (LC-MS 4); ESI-MS: 591.2 [M+H]⁺ (LC-MS 4); $R_f$=0.59 (hexane/EtOAc, 1:1).

Step 125.3: 4-[(4-Chloro-2-methyl-phenyl)-hydroxy-methyl]-1-(5-cyano-2-methoxy-phenyl)-5-isopropyl-1H-pyrazole-3-carboxylic acid ethyl ester

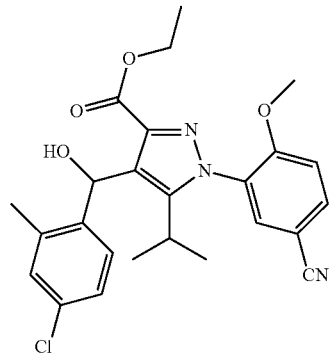 [SMILES: CCOC(=O)c1nn(-c2cc(C#N)ccc2OC)c(C(C)C)c1C(O)c1ccc(Cl)cc1C]

The title compound was prepared in analogy to the procedure described for step 124.4 but using the compound prepared in step 125.4 and 1.2 equivalents of 4-chloro-2-methylphenyl magnesium bromide (0.5 M in THF). $t_R$: 1.27 min (LC-MS 4); ESI-MS: 468.2 [M+H]⁺ (LC-MS 4); $R_f$=0.38 (hexane/EtOAc, 1:1).

Example 126

2-(5-Aminomethyl-2-methoxy-phenyl)-4-(4-chloro-2-methyl-phenyl)-5-(5-chloro-2-methyl-phenyl)-3-isopropyl-4,5-dihydro-2H-pyrrolo[3,4-c]pyrazol-6-one

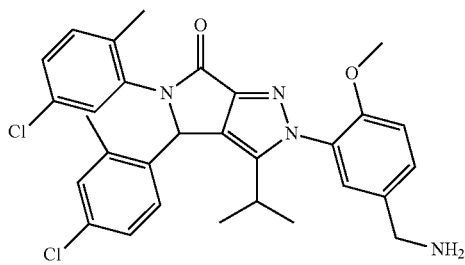 [SMILES: COc1ccc(CN)cc1-n1nc2c(c1C(C)C)C(c1ccc(Cl)cc1C)N(c1cc(Cl)ccc1C)C2=O]

A mixture of the compound prepared in step 125.1 (138 mg, 0.253 mmol), Raney nickel (30 mg) and 5% ammonia in MeOH (5 mL) was stirred for 16.5 h at rt under 0.1 bar of hydrogen. The reaction mixture was filtered through a pad of celite and concentrated to afford 140 mg of the title compound. $t_R$: 1.04 min (LC-MS 5); ESI-MS: 549.3 [M+H]$^+$ (LC-MS 5).

Example 127

N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-acetamide

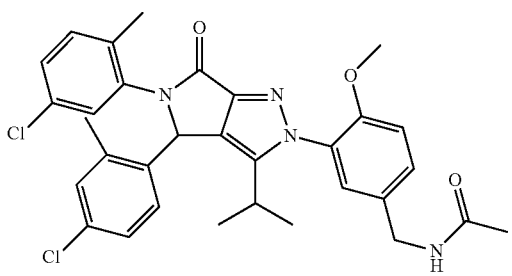 [SMILES: COc1ccc(CNC(C)=O)cc1-n1nc2c(c1C(C)C)C(c1ccc(Cl)cc1C)N(c1cc(Cl)ccc1C)C2=O]

A mixture of the compound prepared in example 126 (65 mg, 0.118 mmol), pyridine (1 mL), and acetic anhydride (0.022 mL, 0.237 mmol) was stirred for 3 h at rt under an argon atmosphere, diluted with of a saturated aqueous solution of sodium bicarbonate (75 mL), and extracted with EtOAc. The organic extracts were washed with a saturated aqueous solution of sodium bicarbonate, dried (Na$_2$SO$_4$), filtered, and concentrated. The residue was purified by preparative HPLC (Column: Sunfire C18, 30×100 mm, 5 μm. Flow: 30 mL/min. Gradient: 5% to 100% B in 20 min; A=0.1% TFA in water, B=0.1% TFA in acetonitrile) to give 31 mg of the title compound. $t_R$: 1.29 min (LC-MS 4); ESI-MS: 591.2 [M+H]$^+$ (LC-MS 4).

Example 128

N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-formamide

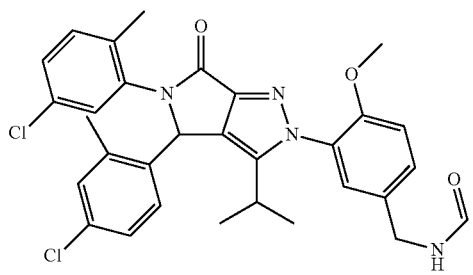 [SMILES: COc1ccc(CNC=O)cc1-n1nc2c(c1C(C)C)C(c1ccc(Cl)cc1C)N(c1cc(Cl)ccc1C)C2=O]

Formic acid (5.28 μL, 0.138 mmol) and N-methylmorpholine (0.014 mL, 0.126 mmol) were added sequentially to a mixture of the compound prepared in example 126 (63 mg, 0.115 mmol), 2-chloro-4,6-dimethoxy-1,3,5-triazine (22.1 mg, 0.126 mmol) and DMAP (0.700 mg, 5.73 μmol) in CH$_2$Cl$_2$ (2 mL) under argon. The reaction mixture was heated to 45° C., stirred for 2 h, allowed to cool to rt, diluted with of a saturated aqueous solution of sodium bicarbonate (75 mL), and extracted with EtOAc. The organic extracts were washed with a saturated aqueous solution of sodium bicarbonate, dried (Na$_2$SO$_4$), filtered, and concentrated. The residue was purified by preparative HPLC (Column: Sunfire C18, 30×100 mm, 5 μm. Flow: 30 mL/min. Gradient: 5% to 100% B in 20 min; A=0.1% TFA in water, B=0.1% TFA in acetonitrile) to give 29 mg of the title compound. $t_R$: 1.25 min (LC-MS 5); ESI-MS: 577.2 [M+H]$^+$ (LC-MS 5).

Example 129

3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzonitrile

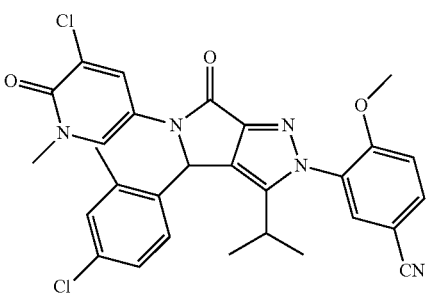 [SMILES: COc1ccc(C#N)cc1-n1nc2c(c1C(C)C)C(c1ccc(Cl)cc1C)N(c1cc(Cl)c(=O)n(C)c1)C2=O]

The title compound was prepared in analogy to the procedure described for step 124.1 but using the compound prepared in step 129.1. The crude product was purified by silica gel column chromatography CH$_2$Cl$_2$/MeOH, 99:1→97:3). $t_R$: 1.14 min (LC-MS 4); ESI-MS: 562.2 [M+H]$^+$ (LC-MS 4); $R_f$=0.51 (hexane/EtOAc, 1:1); $^1$H NMR (400 MHz, DMSO-d$_6$) ppm 0.26-0.50 (m, 3H), 0.97-1.05 (m, 3H), 1.73-1.88 (m, 2H), 2.35-2.44 (m, 1H), 2.50-2.59 (m, 1H), 3.40-3.47 (m, 3H), 3.78-3.93 (m, 3H), 6.35-6.54 (m, 1H), 6.80-8.27 (m, 8H).

Step 129.1: 4-[(1,5-Chloro-1-methyl-6-oxo-1,6-dihydro-pyridin-3-ylamino)-(4-chloro-2-methyl-phenyl)-methyl]-1-(5-cyano-2-methoxy-phenyl)-5-isopropyl-1H-pyrazole-3-carboxylic acid

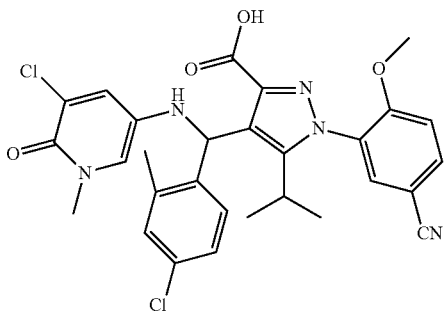 [SMILES: COc1ccc(C#N)cc1-n1nc(C(=O)O)c(C(Nc2cc(Cl)c(=O)n(C)c2)c2ccc(Cl)cc2C)c1C(C)C]

A mixture of the compound prepared in step 129.2 (1.10 g, 1.81 mmol), lithium hydroxyde monohydrate (228 mg, 5.42 mmol), dioxane (10 mL), and water (4 mL) was stirred for 2 h at rt, quenched by addition of 0.5 N HCl (50 mL), and extracted with EtOAc. The organic extracts were dried (Na$_2$SO$_4$), filtered, and concentrated. The residue was triturated in CH$_2$Cl$_2$ to afford 210 mg of the pure title compound. The mother liquor was concentrated. The residue was purified by silica gel column chromatography CH$_2$Cl$_2$/MeOH, 95:5→9:1) to afford additional 357 mg (70% purity) of the title compound. $t_R$: 1.08 min (LC-MS 4); ESI-MS: 580.2 [M+H]$^+$ (LC-MS 4); $R_f$=0.11 (CH$_2$Cl$_2$/MeOH, 9:1).

Step 129.2: 4-[(5-Chloro-1-methyl-6-oxo-1,6-dihydro-pyridin-3-ylamino)-(4-chloro-2-methyl-phenyl)-methyl]-1-(5-cyano-2-methoxy-phenyl)-5-isopropyl-1H-pyrazole-3-carboxylic acid ethyl ester

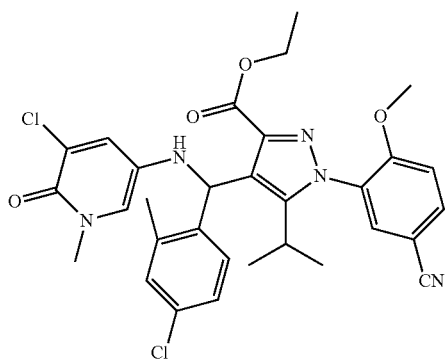 [SMILES: CCOC(=O)c1nn(-c2cc(C#N)ccc2OC)c(C(C)C)c1C(Nc1cc(Cl)c(=O)n(C)c1)c1ccc(Cl)cc1C]

The title compound was prepared in analogy to the procedure described for step 124.3 but using the compound prepared in step 125.3 and 1.2 equivalents of intermediate W1. The crude material was purified by silica gel column chromatography CH$_2$Cl$_2$/MeOH, 99:1→98:2). $t_R$: 1.20 min (LC-MS 4); ESI-MS: 608.2 [M+H]$^+$ (LC-MS 4); $R_f$=0.40 (CH$_2$Cl$_2$/MeOH, 9:1).

Example 130

2-(5-Aminomethyl-2-methoxy-phenyl)-5-(5-chloro-1-methyl-6-oxo-1,6-dihydro-pyridin-3-yl)-4-(4-chloro-2-methyl-phenyl)-3-isopropyl-4,5-dihydro-2H-pyrrolo[3,4-c]pyrazol-6-one

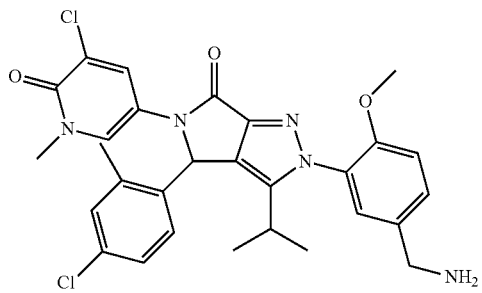 [SMILES: COc1ccc(CN)cc1-n1nc2c(c1C(C)C)C(c1ccc(Cl)cc1C)N(c1cc(Cl)c(=O)n(C)c1)C2=O]

The title compound was prepared in analogy to the procedure described for example 126 but using the compound prepared in example 129. The crude material was purified by preparative HPLC (Column: Sunfire C18, 30×100 mm, 5 µm. Flow: 30 mL/min. Gradient: 5% to 100% B in 20 min; A=0.1% TFA in water, B=0.1% TFA in acetonitrile). $t_R$: 0.83 min (LC-MS 4); ESI-MS: 566.4 [M+H]$^+$ (LC-MS 4).

Example 131

N-{3-[5-(5-Chloro-1-methyl-6-oxo-1,6-dihydro-pyridin-3-O-4-(4-chloro-2-methyl-phenyl)-3-isopropyl-6-oxo-5,6-dihydro-4H-pyrrolo[3,4-c]pyrazol-2-yl]-4-methoxy-benzyl}-acetamide

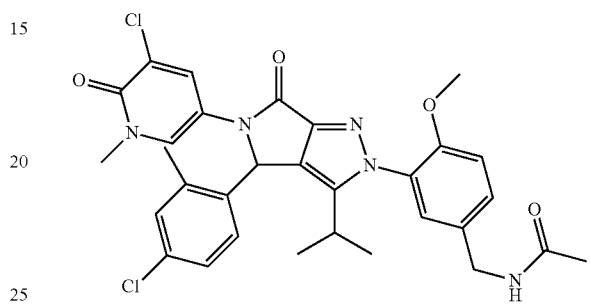

The title compound was prepared in analogy to the procedure described for example 127 but using the compound prepared in example 130 and stirring the reaction mixture for 1 h at rt. The crude material was purified by silica gel column chromatography (CH$_2$Cl$_2$/MeOH, 99:1→93:7). $t_R$: 1.00 min (LC-MS 4); ESI-MS: 608.3 [M+H]$^+$ (LC-MS 4); $R_f$=0.37 (CH$_2$Cl$_2$/MeOH, 9:1).

Example 132

5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one

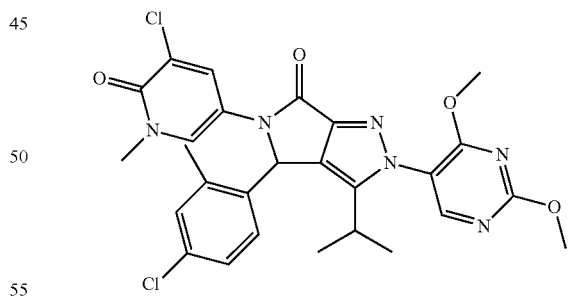

The title compound was prepared in analogy to the procedure described for step 124.1 but using the compound prepared in step 132.1. The crude product was purified by silica gel column chromatography (CH$_2$Cl$_2$/MeOH, 99:1→97:3). $t_R$: 1.14 min (LC-MS 4); ESI-MS: 569.3 [M+H]$^+$ (LC-MS 4); $R_f$=0.53 (CH$_2$Cl$_2$/MeOH, 9:1); $^1$H NMR (400 MHz, DMSO-d$_6$) δ ppm 0.35-0.53 (m, 3H), 0.98-1.06 (m, 3H), [1.80 (s), 2.40 (s), 3H, rotamers], 2.55-2.70 (m, 1H), 3.38-3.47 (m, 3H), 3.88-3.96 (m, 3H), 3.99 (s, 3H), [6.41 (s), 6.47 (s), 1H, rotamers], [6.91 (d, J=8.60 Hz), 7.65 (d, J=8.60 Hz), 1H, rotamers], [7.15-7.36 (m), 7.80 (d, J=2.74 Hz), 2H, rotamers], [7.85 (d, J=2.74 Hz), 8.00 (s), 1H, rotamers], 8.18 (br. s., 1H), 8.56-8.69 (m, 1H).

pared in step 132.3 and 1.2 equivalents of intermediate W1. $t_R$: 1.22 min (LC-MS 4); ESI-MS: 615.2 [M+H]$^+$ (LC-MS 4); $R_f$=0.44 (hexane/EtOAc, 1:1).

Step 132.1: 4-[(5-Chloro-1-methyl-6-oxo-1,6-dihydro-pyridin-3-ylamino)-(4-chloro-2-methyl-phenyl)-methyl]-1-(2,4-dimethoxy-pyrimidin-5-yl)-5-isopropyl-1H-pyrazole-3-carboxylic acid

Step 132.3: 4-[(4-Chloro-2-methyl-phenyl)-hydroxy-methyl]-1-(2,4-dimethoxy-pyrimidin-5-yl)-5-isopropyl-1H-pyrazole-3-carboxylic acid ethyl ester

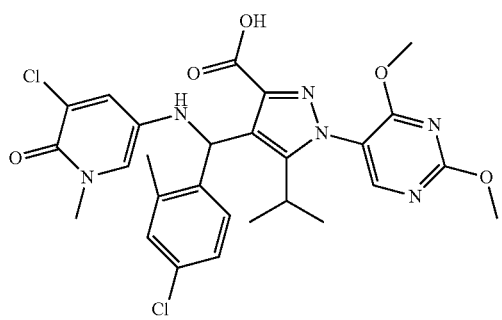 [SMILES: COc1ncc(-n2nc(C(=O)O)c(C(Nc3cc(Cl)c(=O)n(C)c3)c3ccc(Cl)cc3C)c2C(C)C)c(OC)n1]

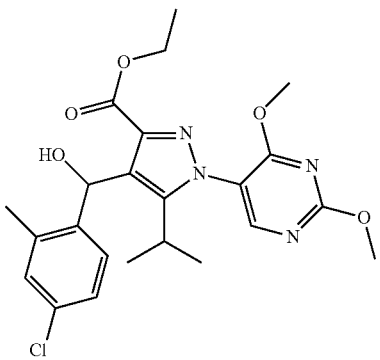

The title compound was prepared in analogy to the procedure described for step 129.1 but using the compound prepared in step 132.2 and stirring the reaction mixture for 1 h at rt. $t_R$: 1.08 min (LC-MS 4); ESI-MS: 587.2 [M+H]$^+$ (LC-MS 4); $R_f$=0.03 (CH$_2$Cl$_2$/MeOH, 9:1).

The title compound was prepared in analogy to the procedure described for step 124.4 but using intermediate BB and 1.3 equivalents of 4-chloro-2-methylphenyl magnesium bromide (0.5 M in THF). $t_R$: 1.27 min (LC-MS 4); ESI-MS: 475.3 [M+H]$^+$ (LC-MS 4); $R_f$=0.36 (hexane/EtOAc, 1:1).

Step 132.2: 4-[(5-Chloro-1-methyl-6-oxo-1,6-dihydro-pyridin-3-ylamino)-(4-chloro-2-methyl-phenyl)-methyl]-1-(2,4-dimethoxy-pyrimidin-5-yl)-5-isopropyl-1H-pyrazole-3-carboxylic acid ethyl ester

Example 133

4-(4-Chloro-2-methyl-phenyl)-5-(5-chloro-2-methyl-phenyl)-2-(2,4-dimethoxy-pyrimidin-5-yl)-3-isopropyl-4,5-dihydro-2H-pyrrolo[3,4-c]pyrazol-6-one

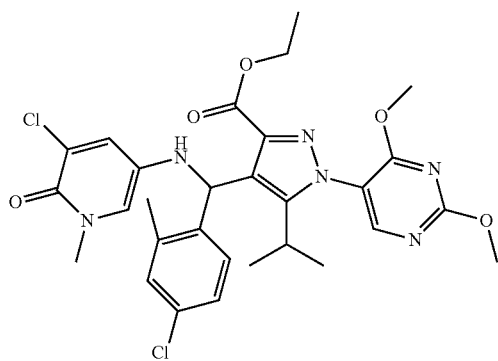 [SMILES: CCOC(=O)c1nn(-c2cnc(OC)nc2OC)c(C(C)C)c1C(Nc1cc(Cl)c(=O)n(C)c1)c1ccc(Cl)cc1C]

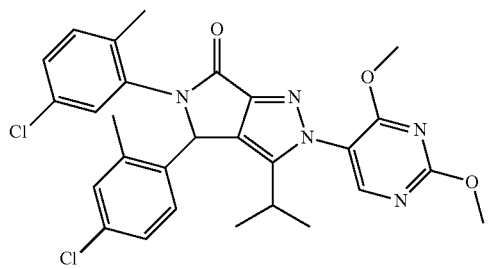 [SMILES: COc1ncc(-n2nc3c(c2C(C)C)C(c2ccc(Cl)cc2C)N(c2cc(Cl)ccc2C)C3=O)c(OC)n1]

The title compound was prepared in analogy to the procedure described for step 124.3 but using the compound pre- The title compound was prepared in analogy to the procedure described for step 124.1 but using the compound prepared in step 133.1. The crude product was purified by silica gel column chromatography (hexane/EtOAc, 1:1→3:7). $t_R$: 1.41 min (LC-MS 4); ESI-MS: 552.3 [M+H]$^+$ (LC-MS 4); $R_f$=0.24 (hexane/EtOAc, 1:1).

Step 133.1: 4-[(4-Chloro-2-methyl-phenyl)-(5-chloro-2-methyl-phenylamino)-methyl]-1-(2,4-dimethoxy-pyrimidin-5-yl)-5-isopropyl-1H-pyrazole-3-carboxylic acid

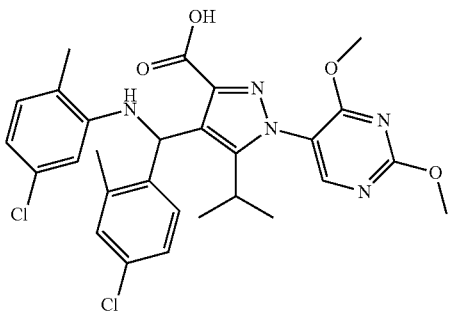 [SMILES: COc1ncc(-n2nc(C(=O)O)c(C(Nc3cc(Cl)ccc3C)c3ccc(Cl)cc3C)c2C(C)C)c(OC)n1]

The title compound was prepared in analogy to the procedure described for step 124.2 but using the compound prepared in step 133.2, 3 equivalents of lithium hydroxide monohydrate, and stirring the reaction mixture for 1 h at rt. The crude product was purified by silica gel column chromatography (CH$_2$Cl$_2$/MeOH, 99:1→91:9). $t_R$: 1.43 min (LC-MS 4); ESI-MS: 570.3 [M+H]$^+$ (LC-MS 4); $R_f$=0.38 (CH$_2$Cl$_2$/MeOH, 9:1).

Step 133.2: 4-[(4-Chloro-2-methyl-phenyl)-(5-chloro-2-methyl-phenylamino)-methyl]-1-(2,4-dimethoxy-pyrimidin-5-yl)-5-isopropyl-1H-pyrazole-3-carboxylic acid ethyl ester

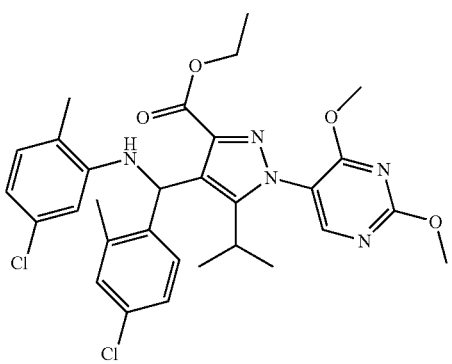 [SMILES: CCOC(=O)c1nn(-c2cnc(OC)nc2OC)c(C(C)C)c1C(Nc1cc(Cl)ccc1C)c1ccc(Cl)cc1C]

The title compound was prepared in analogy to the procedure described for step 124.3 but using the compound prepared in step 132.3 and 1.5 equivalents of 5-chloro-2-methyl-aniline. $t_R$: 1.56 min (LC-MS 4); ESI-MS: 598.2 [M+H]$^+$ (LC-MS 4); $R_f$=0.58 (hexane/EtOAc, 1:1).

Example 134

4-[(4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-5-methoxy-pyridine-2-carbonitrile

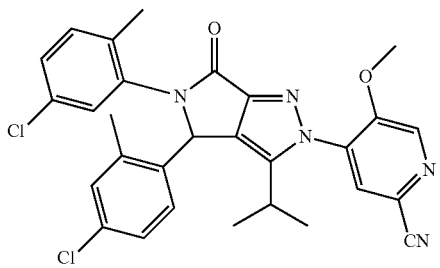 [SMILES: COc1cnc(C#N)cc1-n1nc2c(c1C(C)C)C(c1ccc(Cl)cc1C)N(c1cc(Cl)ccc1C)C2=O]

The title compound was prepared in analogy to the procedure described for step 124.1 but using the compound prepared in step 134.1. The crude product was purified by silica gel column chromatography (hexane/EtOAc, 7:3→1:1). $t_R$: 1.39 min (LC-MS 4); ESI-MS: 546.2 [M+H]$^+$ (LC-MS 4); $R_f$=0.38 (CH$_2$Cl$_2$/MeOH, 9:1).

Step 134.1: 4-[(4-Chloro-2-methyl-phenyl)-(5-chloro-2-methyl-phenylamino)-methyl]-1-(2-cyano-5-methoxy-pyridin-4-yl)-5-isopropyl-1H-pyrazole-3-carboxylic acid

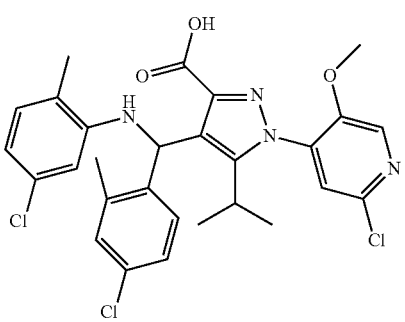 [SMILES: COc1cnc(Cl)cc1-n1nc(C(=O)O)c(C(Nc2cc(Cl)ccc2C)c2ccc(Cl)cc2C)c1C(C)C]

The title compound was prepared in analogy to the procedure described for step 124.2 but using the compound prepared in step 134.2, 3 equivalents of lithium hydroxide monohydrate, a 2.5:1 dioxane/water ratio, and stirring the reaction mixture for 5 h at rt. $t_R$: 1.39 min (LC-MS 4); ESI-MS: 564.3 [M+H]$^+$ (LC-MS 4); $R_f$=0.41 (CH$_2$Cl$_2$/MeOH, 9:1).

Step 134.2: 4-[(4-Chloro-2-methyl-phenyl)-(5-chloro-2-methyl-phenylamino)-methyl]-1-(2-cyano-5-methoxy-pyridin-4-yl)-5-isopropyl-1H-pyrazole-3-carboxylic acid ethyl ester

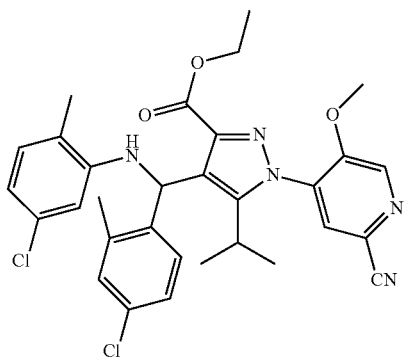 [SMILES: CCOC(=O)c1nn(-c2cc(C#N)ncc2OC)c(C(C)C)c1C(Nc1cc(Cl)ccc1C)c1ccc(Cl)cc1C]

The title compound was prepared in analogy to the procedure described for step 124.3 but using the compound prepared in step 134.3 and 1.3 equivalents of 5-chloro-2-methylaniline. $t_R$: 1.53 min (LC-MS 4); ESI-MS: 592.2 [M+H]$^+$ (LC-MS 4); $R_f$=0.66 (hexane/EtOAc, 1:1).

Step 134.3: 4-[(4-Chloro-2-methyl-phenyl)-hydroxy-methyl]-1-(2-cyano-5-methoxy-pyridin-4-yl)-5-isopropyl-1H-pyrazole-3-carboxylic acid ethyl ester

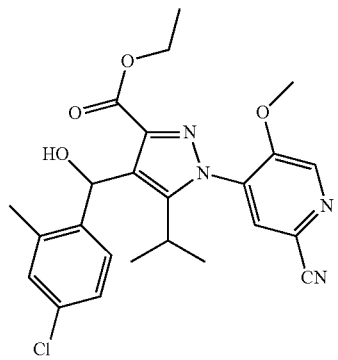 [SMILES: CCOC(=O)c1nn(-c2cc(C#N)ncc2OC)c(C(C)C)c1C(O)c1ccc(Cl)cc1C]

The title compound was prepared in analogy to the procedure described for step 124.4 but using intermediate B1 and 1.2 equivalents of 4-chloro-2-methylphenyl magnesium bromide (0.5 M in THF). $R_f$=0.38 (hexane/EtOAc, 1:1); $^1$H NMR (400 MHz, DMSO-d$_6$) δ ppm 0.6-1.05 (m, 6H), 1.11-1.33 (m, 3H), 2.23 (s, 3H), 2.90-3.10 (m, 1H), 4.00 (s, 3H), 4.19 (q, J=7.17 Hz, 2H), 5.86 (d, J=5.47 Hz, 1H), 6.39-6.59 (m, 1H), 7.05-7.37 (m, 3H), 8.39 (s, 1H), 8.84 (br s, 1H).

Example 135

4-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-5-methoxy-pyridine-2-carbonitrile

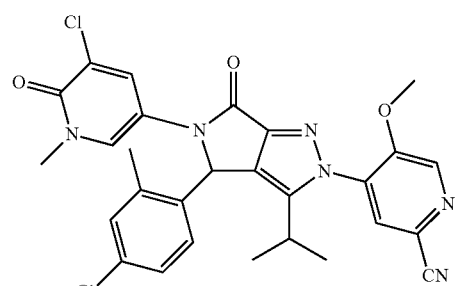

The title compound was prepared in analogy to the procedure described for step 124.1 but using the compound prepared in step 135.1 and diluting the reaction mixture with a saturated aqueous solution of sodium bicarbonate The crude product was purified by silica gel column chromatography (CH$_2$Cl$_2$/MeOH, 99:1→97:3). $t_R$: 1.13 min (LC-MS 4); ESI-MS: 563.3 [M+H]$^+$ (LC-MS 4); $R_f$=0.37 (CH$_2$Cl$_2$/MeOH, 9:1).

Step 135.1: 4-[(5-Chloro-1-methyl-6-oxo-1,6-dihydro-pyridin-3-ylamino)-(4-chloro-2-methyl-phenyl)-methyl]-1-(2-cyano-5-methoxy-pyridin-4-yl)-5-isopropyl-1H-pyrazole-3-carboxylic acid

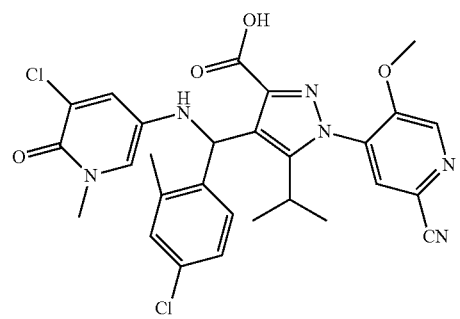 [SMILES: COc1cnc(C#N)cc1-n1nc(C(=O)O)c(C(Nc2cc(Cl)c(=O)n(C)c2)c2ccc(Cl)cc2C)c1C(C)C]

The title compound was prepared in analogy to the procedure described for step 124.2 but using the compound prepared in step 135.2, 3 equivalents of lithium hydroxide monohydrate, a 2:1 dioxane/water ratio, and stirring the reaction mixture for 1 h at rt. The crude product was purified by silica gel column chromatography (CH$_2$Cl$_2$/MeOH, 92.5:7.5→9:

1). $t_R$: 1.02 min (LC-MS 4); ESI-MS: 581.2 [M+H]$^+$ (LC-MS 4); $R_f$=0.04 (CH$_2$Cl$_2$/MeOH, 9:1).

Step 135.2: 4-[(5-Chloro-1-methyl-6-oxo-1,6-dihydro-pyridin-3-ylamino)-(4-chloro-2-methyl-phenyl)-methyl]-1-(2-cyano-5-methoxy-pyridin-4-yl)-5-isopropyl-1H-pyrazole-3-carboxylic acid ethyl ester

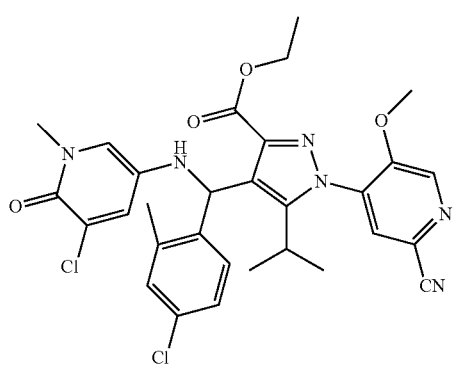 [SMILES: CCOC(=O)c1nn(-c2cc(C#N)ncc2OC)c(C(C)C)c1C(Nc1cc(Cl)c(=O)n(C)c1)c1ccc(Cl)cc1C]

The title compound was prepared in analogy to the procedure described for step 124.3 but using the compound prepared in step 134.3, 1.3 equivalents of intermediate W1, and stirring the reaction mixture for 30 min after the addition of intermediate W1. $t_R$: 1.22 min (LC-MS 4); ESI-MS: 609.3 [M+H]$^+$ (LC-MS 4); $R_f$=0.49 (CH$_2$Cl$_2$/MeOH, 9:1).

Example 136

3-[5-(5-Chloro-2-methyl-phenyl)-4-(4-cyano-phenyl)-3-isopropyl-6-oxo-5,6-dihydro-4H-pyrrolo[3,4-c]pyrazol-2-yl]-4-methoxy-benzonitrile

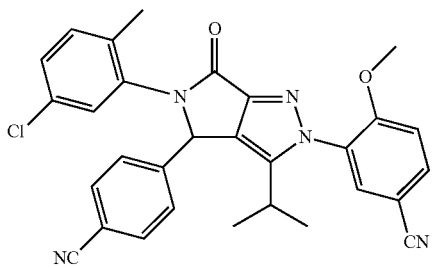 [SMILES: COc1ccc(C#N)cc1-n1nc2c(c1C(C)C)C(c1ccc(C#N)cc1)N(c1cc(Cl)ccc1C)C2=O]

The title compound was prepared in analogy to the procedure described for step 124.1 but using the compound prepared in step 136.1. $t_R$: 1.20 min (LC-MS 4); ESI-MS: 522.2 [M+H]$^+$ (LC-MS 4); $R_f$=0.17 (hexane/EtOAc, 1:1); $^1$H NMR (600 MHz, DMSO-d$_6$) δ ppm 0.25-0.52 (m, 3H), 0.97-1.08 (m, 3H), [1.75-1.95 (m), 2.22-2.34 (m), 3H, rotamers] 2.52-2.65 (m, 1H), 3.81-3.97 (m, 3H), [6.10-6.24 (m), 6.51-6.69 (m), 1H, rotamers], 7.00-7.29 (m, 2H), 7.37-7.55 (m, 3H), 7.69-7.88 (m, 3H) 8.00-8.22 (m, 2H).

Step 136.1: 4-[(5-Chloro-2-methyl-phenylamino)-(4-cyano-phenyl)-methyl]-1-(5-cyano-2-methoxy-phenyl)-5-isopropyl-1H-pyrazole-3-carboxylic acid

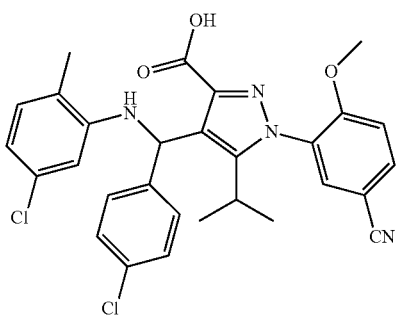 [SMILES: COc1ccc(C#N)cc1-n1nc(C(=O)O)c(C(Nc2cc(Cl)ccc2C)c2ccc(Cl)cc2)c1C(C)C]

The title compound was prepared in analogy to the procedure described for step 124.2 but using the compound prepared in step 136.2, 3 equivalents of lithium hydroxide monohydrate, and stirring the reaction for 4 h at rt. $t_R$: 1.27 min (LC-MS 4); ESI-MS: 540.3 [M+H]$^+$ (LC-MS 4).

Step 136.2: 4-[(5-Chloro-2-methyl-phenylamino)-(4-cyano-phenyl)-methyl]-1-(5-cyano-2-methoxy-phenyl)-5-isopropyl-1H-pyrazole-3-carboxylic acid ethyl ester

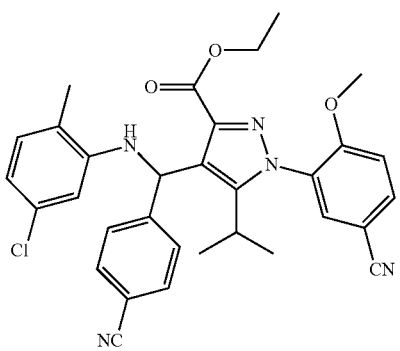 [SMILES: CCOC(=O)c1nn(-c2cc(C#N)ccc2OC)c(C(C)C)c1C(Nc1cc(Cl)ccc1C)c1ccc(C#N)cc1]

The title compound was prepared in analogy to the procedure described for step 124.3 but using the compound prepared in step 125.3, 1.5 equivalents of 5-chloro-2-methylaniline, and stirring the reaction mixture for 20 h at rt after addition of 5-chloro-2-methylaniline. $t_R$: 1.40 min (LC-MS 4); ESI-MS: 568.3 [M+H]⁺ (LC-MS 4); $R_f$=0.40 (hexane/EtOAc, 1:1).

Step 136.3: 1-(5-Cyano-2-methoxy-phenyl)-4-[(4-cyano-phenyl)-hydroxy-methyl]-5-isopropyl-1H-pyrazole-3-carboxylic acid ethyl ester

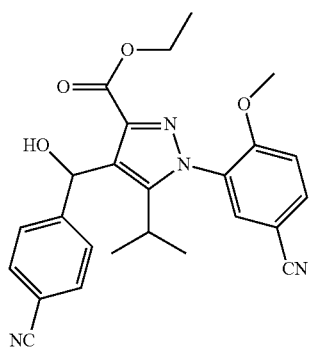 [SMILES: CCOC(=O)c1nn(-c2cc(C#N)ccc2OC)c(C(C)C)c1C(O)c1ccc(C#N)cc1]

Isopropylmagnesium chloride-lithium chloride complex (1.3 M in THF, 2.97 mL, 3.86 mmol) was added dropwise to a cold (−5° C.) solution of 4-bromobenzonitrile (635 mg, 3.49 mmol) in THF (10 mL), under argon. The reaction mixture was stirred for 3 h at −5° C. Intermediate AV (850 mg, 2.49 mmol) was added (exothermic reaction: temperature rised to 10° C.). The resulting mixture was allowed to warm to rt, stirred for 10 min, diluted with a saturated aqueous solution of ammonium chloride (75 mL), and extracted with EtOAc. The organic layers were combined, washed with a saturated solution of ammonium chloride, dried (Na₂SO₄), filtered, and concentrated. The residue was purified by silica gel column chromatography (hexane/EtOAc, 4:1→3:2) to provide 705 mg of the title compound. $t_R$: 1.10 min (LC-MS 4); ESI-MS: 445.3 [M−H]⁻ (LC-MS 4); $R_f$=0.33 (hexane/EtOAc, 1:1).

Example 137

3-[5-(5-Chloro-1-methyl-6-oxo-1,6-dihydro-pyridin-3-yl)-4-(4-cyano-2-methyl-phenyl)-3-isopropyl-6-oxo-5,6-dihydro-4H-pyrrolo[3,4-c]pyrazol-2-yl]-4-methoxy-benzonitrile

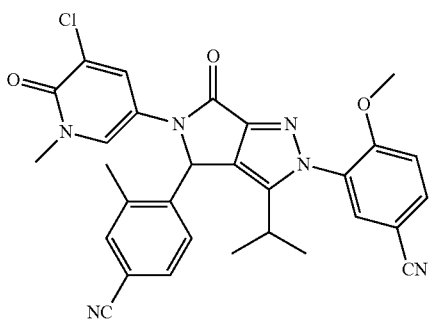 [SMILES: COc1ccc(C#N)cc1-n1nc2c(c1C(C)C)C(c1ccc(C#N)cc1C)N(c1cc(Cl)c(=O)n(C)c1)C2=O]

The title compound was prepared in analogy to the procedure described for step 124.1 but using the compound prepared in step 137.1 and stirring the reaction mixture for 2 h at 80° C. $t_R$: 1.01 min (LC-MS 4); ESI-MS: 553.3 [M+H]⁺ (LC-MS 4); $R_f$=0.63 (CH₂Cl₂/MeOH, 9:1); ¹H NMR (400 MHz, DMSO-d₆) δ ppm 0.27-0.49 (m), 0.93-1.07 (m), 6H, rotamers], [1.81-1.94 (m), 2.40-2.47 (m), 3H, rotamers], 2.51-2.63 (m, 1H), 3.38-3.47 (m, 3H), 3.75-3.97 (m, 3H), 6.33-6.67 (m, 1H), 7.00-8.24 (m, 8H).

Step 137.1: 4-[(5-Chloro-1-methyl-6-oxo-1,6-dihydro-pyridin-3-ylamino)-(4-cyano-2-methyl-phenyl)-methyl]-1-(5-cyano-2-methoxy-phenyl)-5-isopropyl-1H-pyrazole-3-carboxylic acid

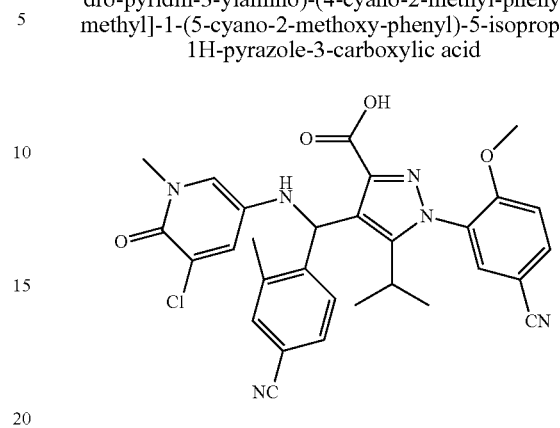

The title compound was prepared in analogy to the procedure described for step 124.2 but using the compound prepared in step 137.2, 3 equivalents of lithium hydroxide monohydrate, and stirring the reaction for 1 h at rt. $t_R$: 0.95 min (LC-MS 4); ESI-MS: 571.3 [M+H]⁺ (LC-MS 4).

Step 137.2: 4-[(5-Chloro-1-methyl-6-oxo-1,6-dihydro-pyridin-3-ylamino)-(4-cyano-2-methyl-phenyl)-methyl]-1-(5-cyano-2-methoxy-phenyl)-5-isopropyl-1H-pyrazole-3-carboxylic acid ethyl ester

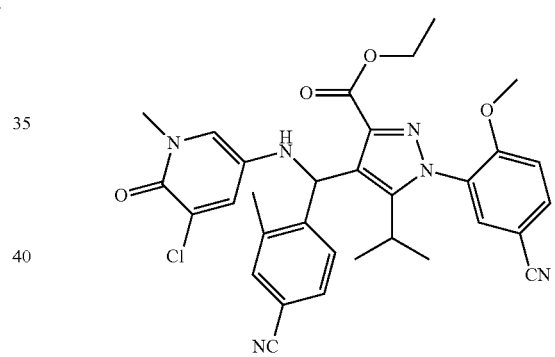

The title compound was prepared in analogy to the procedure described for step 124.3 but using the compound prepared in step 137.3 and 1.5 equivalents of intermediate W1. $t_R$: 1.07 min (LC-MS 4); ESI-MS: 599.3 [M+H]⁺ (LC-MS 4); $R_f$=0.49 (CH₂Cl₂/MeOH, 9:1).

Step 137.3: 145-Cyano-2-methoxy-phenyl)-4-[(4-cyano-2-methyl-phenyl)-hydroxy-methyl]-5-isopropyl-1H-pyrazole-3-carboxylic acid ethyl ester

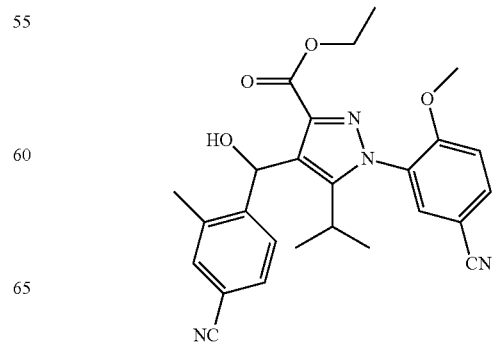

Isopropylmagnesium chloride-lithium chloride complex (1.3 M in THF, 2.93 mL, 3.81 mmol) was added dropwise to a solution of 4-iodo-3-methylbenzonitrile (712 mg, 2.93 mmol) in THF (10 mL) at rt and under argon. The reaction mixture was stirred for 1 h at rt and then cooled to 0° C. Intermediate AV (1 g, 2.93 mmol) was added. The resulting mixture was stirred for 30 min at 0° C., diluted with a saturated aqueous solution of ammonium chloride (75 mL), and extracted with EtOAc. The organic layers were combined, washed with a saturated solution of ammonium chloride, dried (Na$_2$SO$_4$), filtered, and concentrated. The residue was purified by silica gel column chromatography (hexane/EtOAc, 4:1→65:45) to provide 1.09 g of the title compound. $t_R$: 1.13 min (LC-MS 4); ESI-MS: 459.3 [M−H]$^-$ (LC-MS 4); R$_f$=0.31 (hexane/EtOAc, 1:1).

Example 138

3-[5-(5-Chloro-2-methyl-phenyl)-4-(4-cyano-2-methyl-phenyl)-3-isopropyl-6-oxo-5,6-dihydro-4H-pyrrolo[3,4-c]pyrazol-2-yl]-4-methoxy-benzonitrile

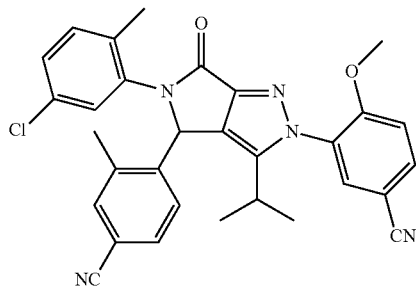 [SMILES: COc1ccc(C#N)cc1-n1nc2c(c1C(C)C)C(c1ccc(C#N)cc1C)N(c1cc(Cl)ccc1C)C2=O]

The title compound was prepared in analogy to the procedure described for step 124.1 but using the compound prepared in step 138.1, stirring the reaction mixture for 2 h at 80° C., and quenching the mixture by addition of a saturated aqueous solution of sodium bicarbonate. $t_R$: 1.24 min (LC-MS 4); ESI-MS: 536.3 [M+H]$^+$ (LC-MS 4); R$_f$=0.25 (hexane/EtOAc, 1:1); $^1$H NMR (400 MHz, DMSO-d$_6$) δ ppm 0.32-0.52 (m, 3H), 0.92-1.04 (m, 3H), 1.86 (s, 3H), 2.22-2.39 (m, 3H), 2.51-2.65 (m, 1H), 3.80-3.92 (m, 3H), 6.05-8.22 (m, 10H).

Step 138.1: 4-[(5-Chloro-2-methyl-phenylamino)-(4-cyano-2-methyl-phenyl)-methyl]-1-(5-cyano-2-methoxy-phenyl)-5-isopropyl-1H-pyrazole-3-carboxylic acid

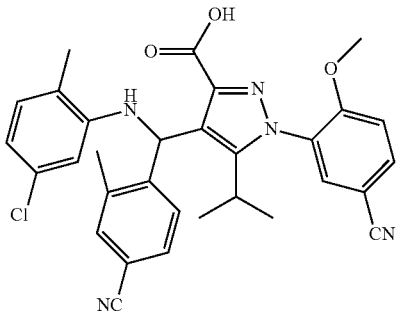 [SMILES: COc1ccc(C#N)cc1-n1nc(C(=O)O)c(C(Nc2cc(Cl)ccc2C)c2ccc(C#N)cc2C)c1C(C)C]

The title compound was prepared in analogy to the procedure described for step 124.2 but using the compound prepared in step 138.2, 3 equivalence of lithium hydroxide monohydrate, and stirring the reaction for 5 h at rt. $t_R$: 1.29 min (LC-MS 4); ESI-MS: 554.2 [M+H]$^+$ (LC-MS 4).

Step 138.2: 4-[(5-Chloro-2-methyl-phenylamino)-(4-cyano-2-methyl-phenyl)-methyl]-1-(5-cyano-2-methoxy-phenyl)-5-isopropyl-1H-pyrazole-3-carboxylic acid ethyl ester

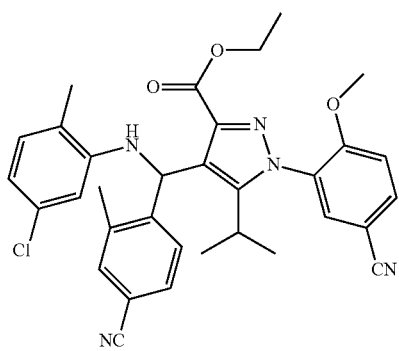 [SMILES: CCOC(=O)c1nn(-c2cc(C#N)ccc2OC)c(C(C)C)c1C(Nc1cc(Cl)ccc1C)c1ccc(C#N)cc1C]

The title compound was prepared in analogy to the procedure described for step 124.3 but using the compound prepared in step 137.3, 1.5 equivalents of 5-chloro-2-methylaniline, and quenching the mixture by addition of a saturated aqueous solution of sodium bicarbonate. $t_R$: 1.42 min (LC-MS 4); ESI-MS: 582.3 [M+H]$^+$ (LC-MS 4); R$_f$=0.71 (hexane/EtOAc, 1:1).

Example 139

(S)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one

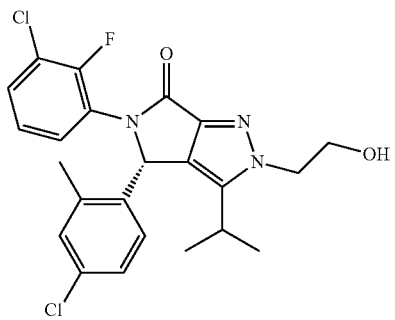 [SMILES: Cc1cc(Cl)ccc1[C@H]1c2c(nn(CCO)c2C(C)C)C(=O)N1c1cccc(Cl)c1F]

The title compound was obtained enantiomerically pure after preparative chiral chromatography (Column: cellulose-3,5-dichlorophenylcarbamate FA-2405/5 OCL, 185×48 mm, 20 μm. Flow: 50 mL/min. Mobile phase: heptane/EtOH, 1:1)

of example 57. $t_R$: 7.26 min (Column: FA-2405/5 OCL, 250× 4.6 mm, 20 μm. Flow: 1 mL/min. Mobile phase: heptane/ EtOH, 1:1).

Example 140

(R)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one

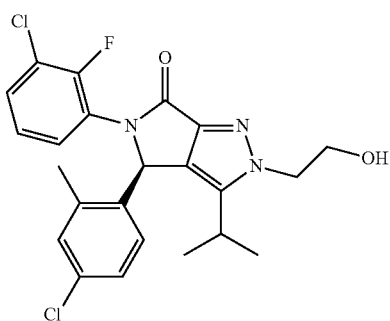 [SMILES: Cc1cc(Cl)ccc1[C@@H]1c2c(nn(CCO)c2C(C)C)C(=O)N1c1cccc(Cl)c1F]

The title compound was obtained enantiomerically pure after preparative chiral chromatography (Column: cellulose-3,5-dichlorophenylcarbamate FA-2405/5 OCL, 185×48 mm, 20 μm. Flow: 50 mL/min. Mobile phase: heptane/EtOH, 1:1) of example 57. $t_R$: 15.7 min (Column: FA-2405/5 OCL, 250× 4.6 mm, 20 μm. Flow: 1 mL/min. Mobile phase: heptane/ EtOH, 1:1).

Example 141

(S)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one

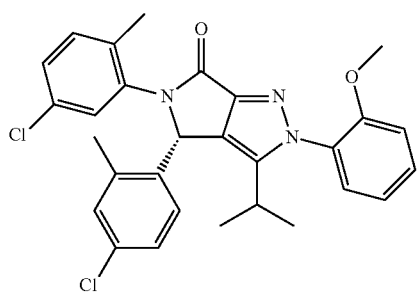 [SMILES: COc1ccccc1-n1nc2c(c1C(C)C)[C@H](c1ccc(Cl)cc1C)N(c1cc(Cl)ccc1C)C2=O]

The title compound was obtained enantiomerically pure after preparative chiral chromatography (Column: Chiralpak IC, 250×50 mm, 20 μm. Flow: 30 mL/min. Mobile phase: EtOH) of example 84. $t_R$: 9.87 min (Column: Chiralpak IC, 250×4.6 mm, 5 μm. Flow: 1 mL/min. Mobile phase: EtOH).

Example 142

(R)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one

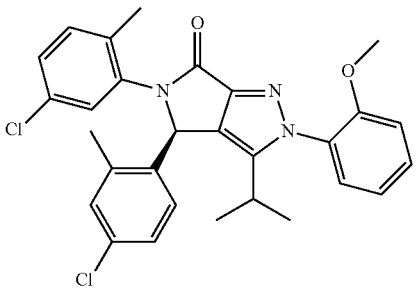 [SMILES: COc1ccccc1-n1nc2c(c1C(C)C)[C@@H](c1ccc(Cl)cc1C)N(c1cc(Cl)ccc1C)C2=O]

The title compound was obtained enantiomerically pure after preparative chiral chromatography (Column: Chiralpak IC, 250×50 mm, 20 μm. Flow: 30 mL/min. Mobile phase: EtOH) of example 84. $t_R$: 18.0 min (Column: Chiralpak IC, 250×4.6 mm, 5 μm. Flow: 1 mL/min. Mobile phase: EtOH).

Example 143

(S)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one

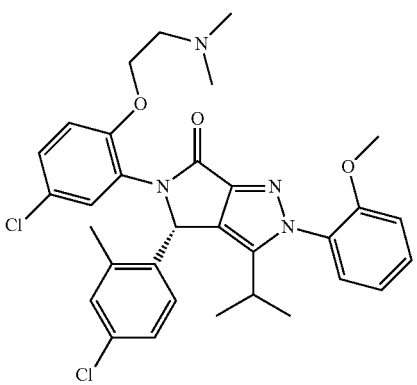 [SMILES: COc1ccccc1-n1nc2c(c1C(C)C)[C@H](c1ccc(Cl)cc1C)N(c1cc(Cl)ccc1OCCN(C)C)C2=O]

The title compound was obtained enantiomerically pure after preparative chiral chromatography (Column: FA2364/ 21 AD-1,230×50 mm, 20 μm. Flow: 50 mL/min. Mobile phase: heptane/$CH_2Cl_2$/isopropanol, 85:5:10+0.05% diethylamine) of example 92. $t_R$: 13.7 min (Column: FA2364/21

AD-I, 230×4.6 mm, 20 μm. Flow: 1 mL/min. Mobile phase: heptane/CH$_2$Cl$_2$/isopropanol, 85:5:10+0.05% diethylamine).

Example 144

(R)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one

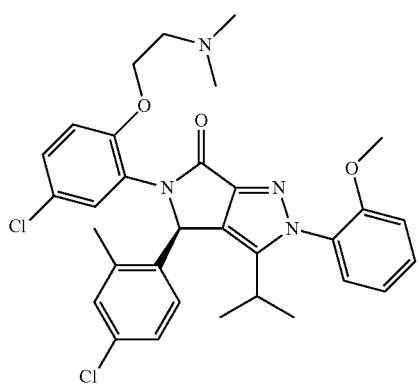 [SMILES: COc1ccccc1-n1nc2c(c1C(C)C)[C@@H](c1ccc(Cl)cc1C)N(c1cc(Cl)ccc1OCCN(C)C)C2=O]

The title compound was obtained enantiomerically pure after preparative chiral chromatography (Column: FA2364/21 AD-1,230×50 mm, 20 μm. Flow: 50 mL/min. Mobile phase: heptane/CH$_2$Cl$_2$/isopropanol, 85:5:10+0.05% diethylamine) of example 92. $t_R$: 18.6 min (Column: FA2364/21 AD-1, 250×4.6 mm, 20 μm. Flow: 1 mL/min. Mobile phase: heptane/CH$_2$Cl$_2$/isopropanol, 85:5:10+0.05% diethylamine).

Example 145

5-(5-Chloro-1-methyl-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

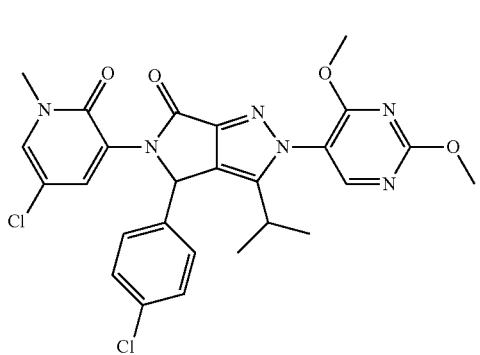 [SMILES: COc1ncc(-n2nc3c(c2C(C)C)C(c2ccc(Cl)cc2)N(c2cc(Cl)cn(C)c2=O)C3=O)c(OC)n1]

The title compound was prepared in analogy to the procedure described for step 124.1 but using the compound prepared in step 145.1. The crude product was purified by silica gel column chromatography (CH$_2$Cl$_2$/MeOH, 100:0→96.5: 3.5). $t_R$: 1.16 min (LC-MS 4); ESI-MS: 555.2 [M+H]$^+$ (LC-MS 4); R$_f$=0.49 (CH$_2$Cl$_2$/MeOH, 9:1).

Step 145.1: 4-[(5-Chloro-1-methyl-2-oxo-1,2-dihydro-pyridin-3-ylamino)-(4-chloro-phenyl)-methyl]-1-(2,4-dimethoxy-pyrimidin-5-yl)-5-isopropyl-1H-pyrazole-3-carboxylic acid

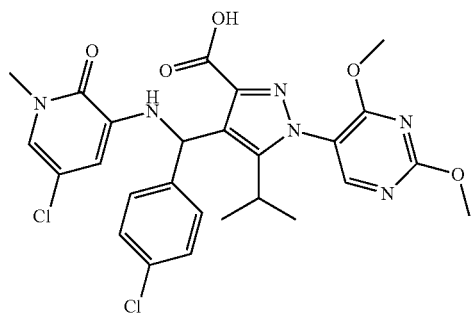

The title compound was prepared in analogy to the procedure described for step 124.2 but using the compound prepared in step 145.2, 3 equivalents of lithium hydroxide monohydrate, and stirring the reaction mixture for 1 h at rt. $t_R$: 1.13 min (LC-MS 4); ESI-MS: 573.2 [M+H]$^+$ (LC-MS 4).

Step 145.2: 4-[(5-Chloro-1-methyl-2-oxo-1,2-dihydro-pyridin-3-ylamino)-(4-chloro-phenyl)-methyl]-1-(2,4-dimethoxy-pyrimidin-5-yl)-5-isopropyl-1H-pyrazole-3-carboxylic acid ethyl ester

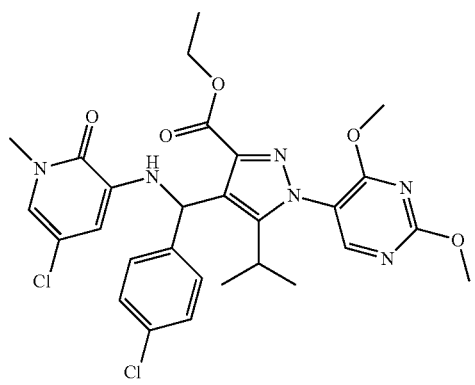

The title compound was prepared in analogy to the procedure described for step 124.3 but using the compound prepared in step 145.3 and intermediate BJ. The crude product was purified by silica gel column chromatography (CH$_2$Cl$_2$/

MeOH, 100:0→97:3). $t_R$: 1.32 min (LC-MS 4); ESI-MS: 601.3 [M+H]$^+$ (LC-MS 4); $R_f$=0.57 (CH$_2$Cl$_2$/MeOH, 9:1).

Step 145.3: 4-[(4-Chloro-phenyl)-hydroxy-methyl]-1-(2,4-dimethoxy-pyrimidin-5-yl)-5-isopropyl-1H-pyrazole-3-carboxylic acid ethyl ester

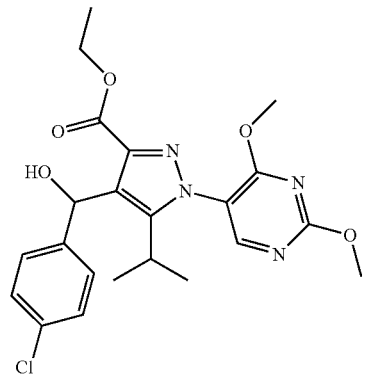 [SMILES: CCOC(=O)c1nn(-c2cnc(OC)nc2OC)c(C(C)C)c1C(O)c1ccc(Cl)cc1]

The title compound was prepared in analogy to the procedure described for step 124.4 but using the intermediate BB. The crude product was purified by silica gel column chromatography (hexane/EtOAc, 90:10→60:40). $t_R$: 1.22 min (LC-MS 4); ESI-MS: 461.2 [M+H]$^+$ (LC-MS 4); $R_f$=0.39 (hexane/EtOAc, 1:1).

Example 146

5-(5-Chloro-1-methyl-2-oxo-1,2-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one

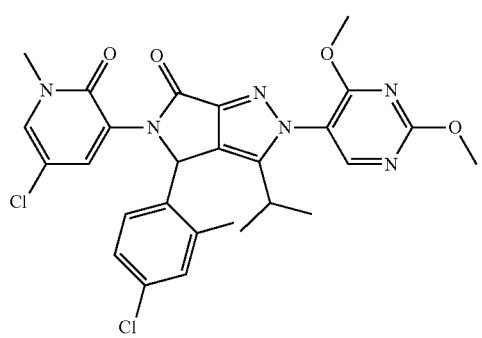 [SMILES: COc1ncc(-n2nc3c(c2C(C)C)C(c2ccc(Cl)cc2C)N(c2cc(Cl)cn(C)c2=O)C3=O)c(OC)n1]

The title compound was prepared in analogy to the procedure described for example 145 but using the compound prepared in step 146.1. $t_R$: 1.17 min (LC-MS 4); ESI-MS: 569.3 [M+H]$^+$ (LC-MS 4); $R_f$=0.54 (CH$_2$Cl$_2$/MeOH, 9:1).

Step 146.1: 4-[(5-Chloro-1-methyl-2-oxo-1,2-dihydro-pyridin-3-ylamino)-(4-chloro-2-methyl-phenyl)-methyl]-1-(2,4-dimethoxy-pyrimidin-5-yl)-5-isopropyl-1H-pyrazole-3-carboxylic acid

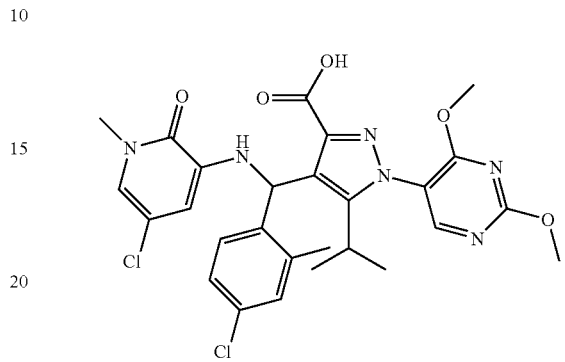

The title compound was prepared in analogy to the procedure described for step 124.2 but using the compound prepared in step 146.2, 3 equivalents of lithium hydroxide monohydrate, and stirring the reaction mixture for 2.5 h at rt. $t_R$: 1.16 min (LC-MS 4); ESI-MS: 587.4 [M+H]$^+$ (LC-MS 4).

Step 146.2: 4-[(5-Chloro-1-methyl-2-oxo-1,2-dihydro-pyridin-3-ylamino)-(4-chloro-2-methyl-phenyl)-methyl]-1-(2,4-dimethoxy-pyrimidin-5-yl)-5-isopropyl-1H-pyrazole-3-carboxylic acid ethyl ester

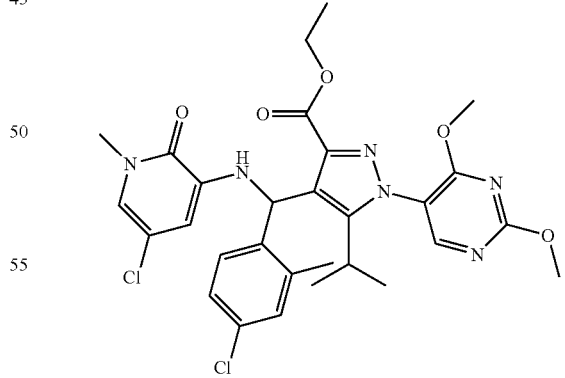

The title compound was prepared in analogy to the procedure described for step 145.2 but using the compound prepared in step 146.3. The residue was purified by preparative HPLC (Column: Sunfire C18, 30×100 mm, 5 um. Flow: 30 mL/min. Gradient: 5% to 100% B in 20 min; A=0.1% TFA in water, B=acetonitrile). $t_R$: 1.30 min (LC-MS 4); ESI-MS: 615.3 [M+H]⁺ (LC-MS 4); $R_f$=0.51 (CH₂Cl₂/MeOH, 9:1).

Step 146.3: 4-[(4-Chloro-2-methyl-phenyl)-hydroxy-methyl]-1-(2,4-dimethoxy-pyrimidin-5-yl)-5-isopropyl-1H-pyrazole-3-carboxylic acid ethyl ester

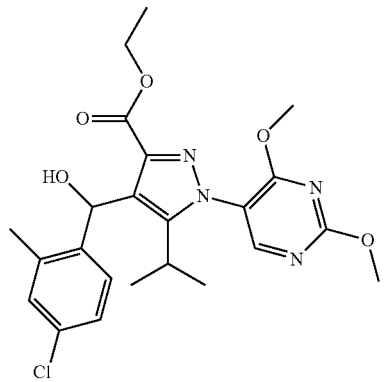

The title compound was prepared in analogy to the procedure described for step 145.3 but using 4-chloro-2-methylphenylmagnesium bromide. $t_R$: 1.21 min (LC-MS 4); ESI-MS: 475.3 [M+H]⁺ (LC-MS 4); $R_f$=0.33 (hexane/EtOAc, 1:1).

Example 147

5-(5-Chloro-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

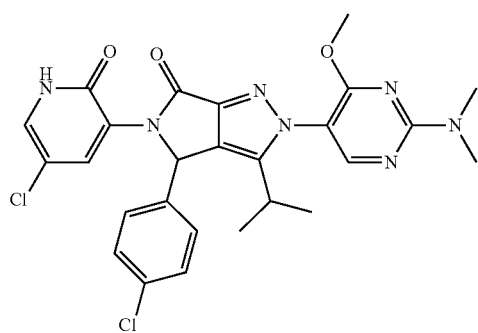 [SMILES: COc1nc(N(C)C)ncc1-n1nc2c(c1C(C)C)C(c1ccc(Cl)cc1)N(c1cc(Cl)c[nH]c1=O)C2=O]

The title compound was prepared in analogy to the procedure described for example 120 but using product from step 147.1. The reaction mixture was stirred under microwave irradiation 30 min at 100° C. $t_R$: 1.15 min (LC-MS 4); ESI-MS: 554.3 [M+H]⁺ (LC-MS 4); $R_f$=0.44 (CH₂Cl₂/MeOH, 9:1); ¹H NMR (400 MHz, DMSO-d₆) δ ppm 0.46 (d, J=7.0 Hz, 3H) 1.06 (d, J=7.0 Hz, 3H) 2.53-2.67 (m, 1H) 3.18 (s, 6H) 3.87 (s, 3H) 6.54 (s, 1H) 7.25 (d, J=8.6 Hz, 2H) 7.37 (d, J=8.6 Hz, 2H) 7.47-7.63 (m, 2H) 8.26 (s, 1H) 12.29 (br. s, 1H).

Step 147.1: 5-[5-Chloro-1-(4-methoxy-benzyl)-2-oxo-1,2-dihydro-pyridin-3-yl]-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

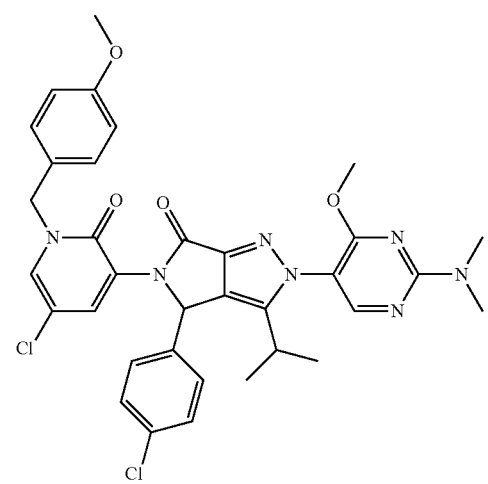 [SMILES: COc1ccc(Cn2cc(Cl)cc(N3C(=O)c4nn(-c5cnc(N(C)C)nc5OC)c(C(C)C)c4C3c3ccc(Cl)cc3)c2=O)cc1]

The title compound was prepared in analogy to the procedure described for step 124.1 but using product from step 147.2. The residue was purified by silica gel column chromatography (CH₂Cl₂/MeOH, 100:0→70:30). $t_R$: 1.37 min (LC-MS 4); ESI-MS: 674.4 [M+H]⁺ (LC-MS 4); $R_f$=0.43 (CH₂Cl₂/MeOH, 9:1).

Step 147.2: 4-[[5-Chloro-1-(4-methoxy-benzyl)-2-oxo-1,2-dihydro-pyridin-3-ylamino]-(4-chloro-phenyl)-methyl]-1-(2-dimethylamino-4-methoxy-pyrimidin-5-yl)-5-isopropyl-1H-pyrazole-3-carboxylic acid

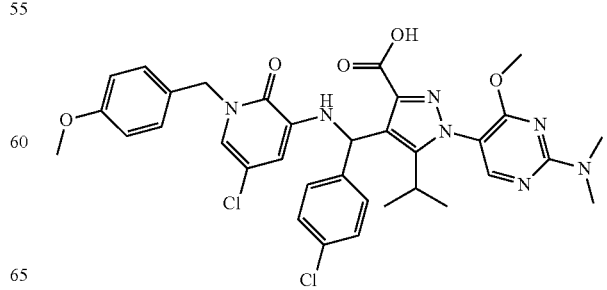

The title compound was prepared in analogy to the procedure described for step 124.2 but using product from step 147.3. $t_R$: 1.38 min (LC-MS 4); ESI-MS: 692.4 [M+H]$^+$ (LC-MS 4).

Step 147.3: 4-[[5-Chloro-1-(4-methoxy-benzyl)-2-oxo-1,2-dihydro-pyridin-3-ylamino]-(4-chloro-phenyl)-methyl]-1-(2-dimethylamino-4-methoxy-pyrimidin-5-yl)-5-isopropyl-1H-pyrazole-3-carboxylic acid ethyl ester

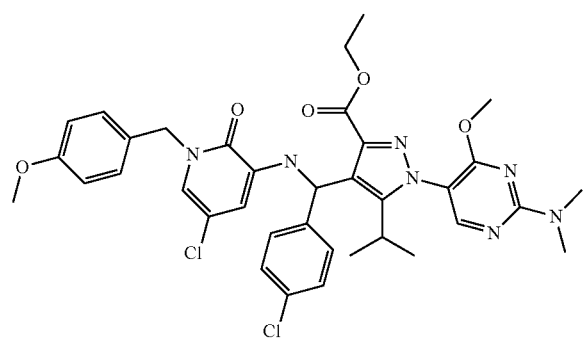

The title compound was prepared in analogy to the procedure described for step 124.3 but using product from step 147.4. The residue was purified by silica gel column chromatography (hexane/EtOAc, 8:2→45:55). $t_R$: 1.49 min (LC-MS 4); ESI-MS: 720.5 [M+H]$^+$ (LC-MS 4); $R_f$=0.30 (hexane/EtOAc, 1:1).

Step 147.4: 4-[(4-Chloro-phenyl)-hydroxy-methyl]-1-(2-dimethylamino-4-methoxy-pyrimidin-5-yl)-5-isopropyl-1H-pyrazole-3-carboxylic acid ethyl ester

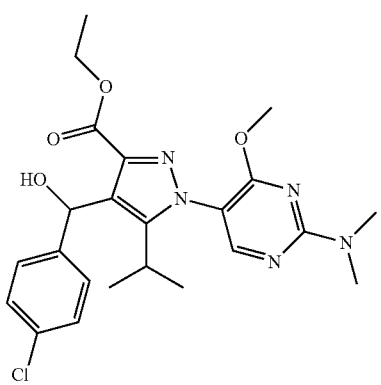 [SMILES: CCOC(=O)c1nn(-c2cnc(N(C)C)nc2OC)c(C(C)C)c1C(O)c1ccc(Cl)cc1]

The title compound was prepared in analogy to the procedure described for step 124.4 but using the product from step 147.5. $t_R$: 1.29 min (LC-MS 4); ESI-MS: 474.3 [M+H]$^+$ (LC-MS 4); $R_f$=0.50 (hexane/EtOAc, 1:1).

Step 147.5: 1-(2-Dimethylamino-4-methoxy-pyrimidin-5-yl)-4-formyl-5-isopropyl-1H-pyrazole-3-carboxylic acid ethyl ester

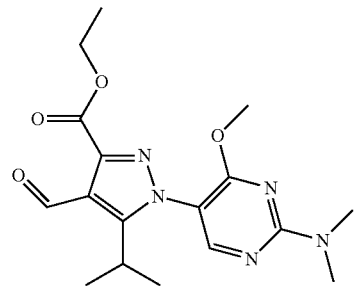 [SMILES: CCOC(=O)c1nn(-c2cnc(N(C)C)nc2OC)c(C(C)C)c1C=O]

The title compound was prepared in analogy to the procedure described for intermediate AP but using the product from step 147.6. The residue was purified by silica gel column chromatography (hexane/EtOAc, 9:1→7:3) to provide 3.1 g of the title compound. $t_R$: 1.16 min (LC-MS 4); ESI-MS: 362.3 [M+H]$^+$ (LC-MS 4); $R_f$=0.45 (hexane/EtOAc, 1:1).

Step 147.6: 1-(2-Dimethylamino-4-methoxy-pyrimidin-5-yl)-5-isopropyl-4-vinyl-1H-pyrazole-3-carboxylic acid ethyl ester

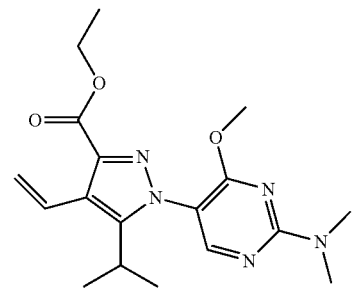 [SMILES: C=Cc1c(C(=O)OCC)nn(-c2cnc(N(C)C)nc2OC)c1C(C)C]

The title compound was prepared in analogy to the procedure described for intermediate BA but using the product from step 147.7. The residue was purified by silica gel column chromatography (hexane/EtOAc, 9:1→65:35) to provide 3.5 g of the title compound. $t_R$: 1.23 min (LC-MS 4); ESI-MS: 360.3 [M+H]$^+$ (LC-MS 4); $R_f$=0.48 (hexane/EtOAc, 1:1).

Step 147.7: 4-Bromo-1-(2-dimethylamino-4-methoxy-pyrimidin-5-yl)-5-isopropyl-1H-pyrazole-3-carboxylic acid ethyl ester

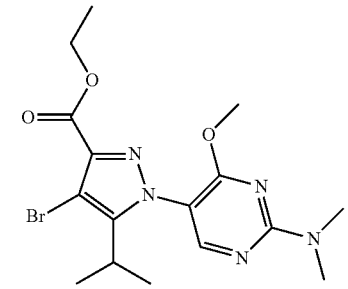 [SMILES: CCOC(=O)c1nn(-c2cnc(N(C)C)nc2OC)c(C(C)C)c1Br]

To a solution of the product from step 147.8 (4.5 g, 13.6 mmol) in CH₂Cl₂ (100 mL) under argon was added bromine (2.1 mL, 40.9 mmol) dropwise and the mixture was stirred for 1 h at rt. The reaction mixture was quenched with a 10% Na₂S₂O₃ solution (250 mL), then extracted with CH₂Cl₂. The combined organic layers were washed with brine, dried (Na₂SO₄), filtered and concentrated. The crude material was purified by silica gel column chromatography (hexane/EtOAc, 97.5:2.5→75:25) to afford 4.7 g of the title compound as a yellow solid. $t_R$: 1.26 min (LC-MS 4); ESI-MS: 412.2 [M+H]⁺ (LC-MS 4), $R_f$=0.54 (hexane/EtOAc, 1:1).

Step 147.8: 1-(2-Dimethylamino-4-methoxy-pyrimidin-5-yl)-5-isopropyl-1H-pyrazole-3-carboxylic acid ethyl ester

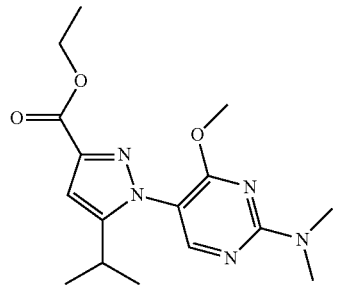 [SMILES: CCOC(=O)c1cc(C(C)C)n(-c2cnc(N(C)C)nc2OC)n1]

A solution of the product from step 147.9 (5.9 g, 16.0 mmol) and dimethylamine (2 M in THF, 16 mL, 31.9 mmol) in THF (100 mL) was stirred 18 h at 100° C., then concentrated. The crude material was purified by silica gel column chromatography (hexane/EtOAc, 95:5→75:25) to afford 4.5 g of the title compound as a yellow solid. $t_R$: 1.11 min (LC-MS 4); ESI-MS: 334.3 [M+H]⁺ (LC-MS 4), $R_f$=0.46 (hexane/EtOAc, 1:1).

Step 147.9: 5-Isopropyl-1-(2-methanesulfonyl-4-methoxy-pyrimidin-5-yl)-1H-pyrazole-3-carboxylic acid ethyl ester

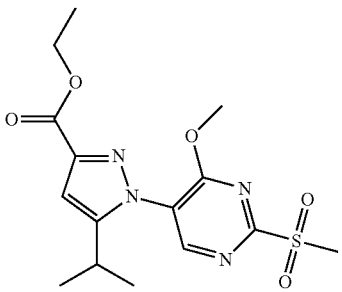 [SMILES: CCOC(=O)c1cc(C(C)C)n(-c2cnc(S(C)(=O)=O)nc2OC)n1]

To a solution of the product from step 147.10 (5 g, 14.9 mmol) in CH₂Cl₂ (100 mL) under argon was added mCPBA (7.7 g, 31.2 mmol) and the mixture was stirred for 1 h at rt. The reaction mixture was quenched with a saturated aqueous solution of sodium bicarbonate (100 mL), then extracted with CH₂Cl₂. The organic layers were washed with a saturated aqueous solution of sodium bicarbonate, dried (Na₂SO₄), filtered and concentrated. The crude material was purified by silica gel column chromatography (hexane/EtOAc, 1:1) to afford 5.9 g of the title compound as a white solid. $t_R$: 0.91 min (LC-MS 4); ESI-MS: 369.3 [M+H]⁺ (LC-MS 4), $R_f$=0.41 (hexane/EtOAc, 1:1).

Step 147.10: 5-Isopropyl-1-(4-methoxy-2-methylsulfanyl-pyrimidin-5-yl)-1H-pyrazole-3-carboxylic acid ethyl ester

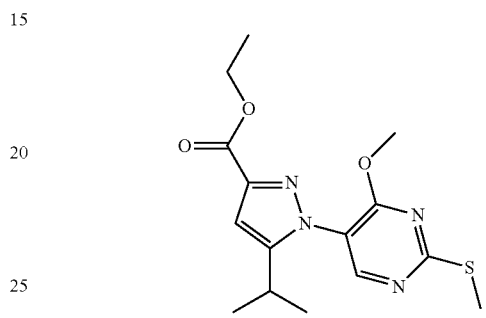

To a solution of the product from step 147.11 (12.8 g, 69 mmol) in toluene/EtOH (150 mL, 1:1) under argon was added dropwise ethyl 2,4-dioxo-5-methylhexanoate (15.4 g, 82 mmol) and the mixture was stirred 1 h at 110° C. The reaction mixture was concentrated, diluted with a saturated aqueous solution of sodium bicarbonate (100 mL), and extracted with EtOAc. The organic layers were combined, washed with a saturated aqueous solution of sodium bicarbonate, dried (Na₂SO₄), filtered and concentrated. The crude material was purified by silica gel column chromatography (hexane/EtOAc, 97.5:2.5→85:15) to afford 20.1 g of the title compound as a yellow solid. $t_R$: 1.12 min (LC-MS 4); ESI-MS: 337.3 [M+H]⁺ (LC-MS 4), $R_f$=0.77 (hexane/EtOAc, 1:1).

Step 147.11: (4-Methoxy-2-methylsulfanyl-pyrimidin-5-yl)-hydrazine

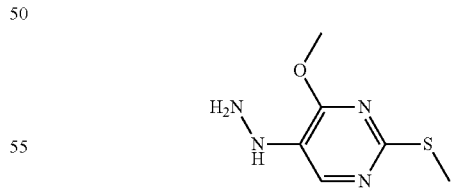

To a suspension of the product from step 147.12 (37.2 mg, 96 mmol) in dioxane (250 mL) at 0° C. was added dropwise a 4 M solution of HCl in dioxane (241 mL, 963 mmol) and the reaction mixture was allowed to stir for 20 h at rt. The mixture was cooled down to 0° C. and 7 N NH₃ in MeOH (150 mL) was added dropwise. The resulting suspension was diluted with CH₂Cl₂, stirred for 30 min, filtered and concentrated. The crude material was purified by silica gel column chromatography (CH₂Cl₂/MeOH, 100:0→97.5:2.5) to afford 12.8 g of the title compound as a brown solid. $t_R$: 0.49 min (LC-MS 4); ESI-MS: 187.2 [M+H]⁺ (LC-MS 4), $R_f$=0.45 (CH₂Cl₂/MeOH, 9:1).

Step 147.12: Di-tert-butyl 1-(4-methoxy-2-(methylthio)pyrimidin-5-yl)hydrazine-1,2-dicarboxylate

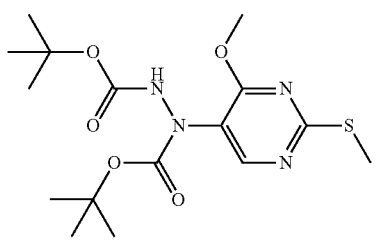 [SMILES: COc1nc(SC)ncc1N(NC(=O)OC(C)(C)C)C(=O)OC(C)(C)C]

To a solution of 5-bromo-4-methoxy-2-(methylthio)pyrimidine (25.3 g, 108 mmol) in THF (250 mL) was added under argon isopropylmagnesium chloride LiCl in THF (108 mL, 140 mmol) at 0° C. The mixture was allowed to warm up to rt and stirred for 1 h. di-tert-butylazodicarboxylate (24.8 g, 108 mmol) was added and the mixture was stirred 1 h at rt, quenched by addition of a saturated aqueous solution of ammonium chloride (250 mL) then extracted with EtOAc. The organic layer was washed with a saturated aqueous solution of ammonium chloride, dried (Na₂SO₄), filtered and concentrated. The crude material was purified by silica gel column chromatography (hexane/EtOAc, 100:0→75:25) to afford 37.2 g of the title compound as a white solid. $t_R$: 1.17 min (LC-MS 4); ESI-MS: 387.3 [M+H]⁺ (LC-MS 4), $R_f$=0.79 (hexane/EtOAc, 1:1).

Example 148

5-(5-Chloro-1-methyl-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

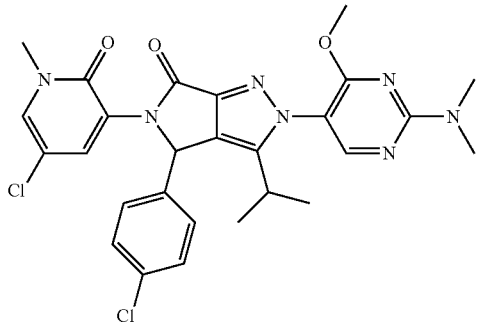 [SMILES: COc1nc(N(C)C)ncc1-n1nc2c(c1C(C)C)C(c1ccc(Cl)cc1)N(c1cc(Cl)cn(C)c1=O)C2=O]

The title compound was prepared in analogy to the procedure described for step 147.1 but using product from step 148.1. After silica gel column chromatography, the residue was triturated in diisopropylether. $t_R$: 1.23 min (LC-MS 4); ESI-MS: 568.3 [M+H]⁺ (LC-MS 4); $R_f$=0.53 (CH₂Cl₂/MeOH, 9:1).

Step 148.1: 4-[(5-Chloro-1-methyl-2-oxo-1,2-dihydro-pyridin-3-ylamino)-(4-chloro-phenyl)-methyl]-1-(2-dimethylamino-4-methoxy-pyrimidin-5-yl)-5-isopropyl-1H-pyrazole-3-carboxylic acid

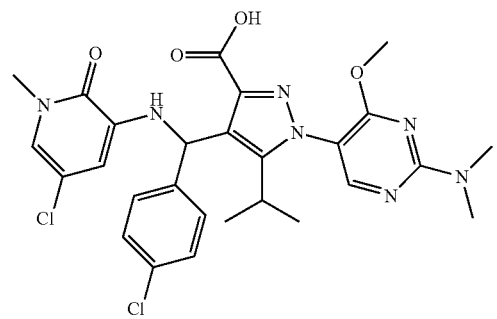

The title compound was prepared in analogy to the procedure described for step 124.2 but using the product from step 148.2. $t_R$: 1.35 min (LC-MS 4); ESI-MS: 586.4 [M+H]⁺ (LC-MS 4).

Step 148.2: 4-[(5-Chloro-1-methyl-2-oxo-1,2-dihydro-pyridin-3-ylamino)-(4-chloro-phenyl)-methyl]-1-(2-dimethylamino-4-methoxy-pyrimidin-5-yl)-5-isopropyl-1H-pyrazole-3-carboxylic acid ethyl ester

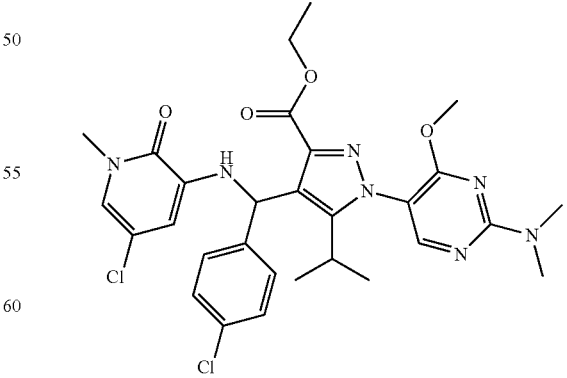

The title compound was prepared in analogy to the procedure described for step 147.3 but using intermediate BJ. The residue was purified by silica gel column chromatography (CH$_2$Cl$_2$/MeOH, 99.5:0.5→98.5:1.5). t$_R$: 1.38 min (LC-MS 4); ESI-MS: 614.4 [M+H]$^+$ (LC-MS 4); R$_f$=0.62 (CH$_2$Cl$_2$/MeOH, 9:1).

Example 149

5-(5-Chloro-1-methyl-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

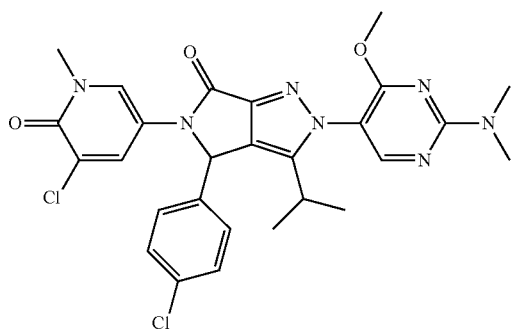 [SMILES: COc1nc(N(C)C)ncc1-n1nc2c(c1C(C)C)C(c1ccc(Cl)cc1)N(c1cc(Cl)c(=O)n(C)c1)C2=O]

The title compound was prepared in analogy to the procedure described for step 124.1 but using the product from step 149.1. The reaction was performed at 85° C. The residue was purified by silica gel column chromatography (CH$_2$Cl$_2$/MeOH, 100:0→97:3). t$_R$: 1.17 min (LC-MS 4); ESI-MS: 568.3 [M+H]$^+$ (LC-MS 4); R$_f$=0.53 (CH$_2$Cl$_2$/MeOH, 9:1).

Step 149.1: 4-[(5-Chloro-1-methyl-6-oxo-1,6-dihdro-pyridin-3-ylamino)-(4-chloro-phenyl)-methyl]-1-(2-dimethylamino-4-methoxy-pyrimidin-5-yl)-5-isopropyl-1H-pyrazole-3-carboxylic acid

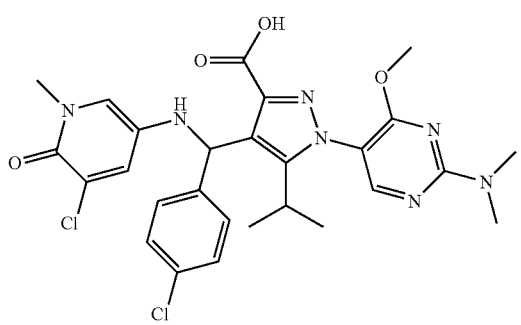 [SMILES: COc1nc(N(C)C)ncc1-n1nc(C(=O)O)c(C(Nc2cc(Cl)c(=O)n(C)c2)c2ccc(Cl)cc2)c1C(C)C]

The title compound was prepared in analogy to the procedure described for step 124.2 but using the product from step 149.2. t$_R$: 1.07 min (LC-MS 4); ESI-MS: 586.4 [M+H]$^+$ (LC-MS 4).

Step 149.2: 4-[(5-Chloro-1-methyl-6-oxo-1,6-dihydro-pyridin-3-ylamino)-(4-chloro-phenyl)-methyl]-1-(2-dimethylamino-4-methoxy-pyrimidin-5-yl)-5-isopropyl-1H-pyrazole-3-carboxylic acid ethyl ester

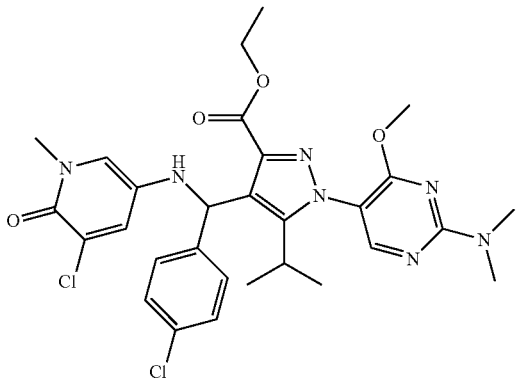 [SMILES: CCOC(=O)c1nn(-c2cnc(N(C)C)nc2OC)c(C(C)C)c1C(Nc1cc(Cl)c(=O)n(C)c1)c1ccc(Cl)cc1]

The title compound was prepared in analogy to the procedure described for step 124.3 but using the product from steps 147.4 and W1. The residue was purified by silica gel column chromatography (CH$_2$Cl$_2$/MeOH, 99.5:0.5→97:3). t$_R$: 1.23 min (LC-MS 4); ESI-MS: 614.4 [M+H]$^+$ (LC-MS 4); R$_f$=0.52 (CH$_2$Cl$_2$/MeOH, 9:1).

Example 150

4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

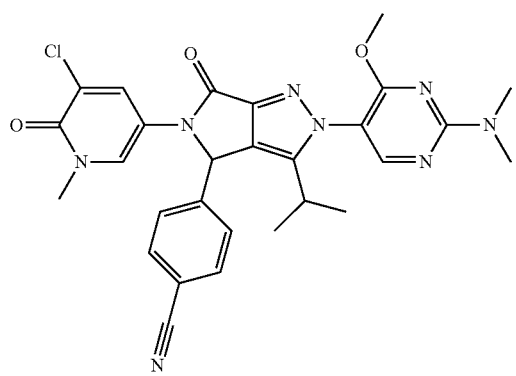 [SMILES: COc1nc(N(C)C)ncc1-n1nc2c(c1C(C)C)C(c1ccc(C#N)cc1)N(c1cc(Cl)c(=O)n(C)c1)C2=O]

The title compound was prepared in analogy to the procedure described for step 124.1 but using the product from step 150.1. The residue was purified by silica gel column chromatography (CH$_2$Cl$_2$/MeOH, 99:1→97:3). t$_R$: 1.03 min (LC-MS 4); ESI-MS: 559.4 [M+H]$^+$ (LC-MS 4); R$_f$=0.48 (CH$_2$Cl$_2$/MeOH, 9:1); $^1$H NMR (400 MHz, DMSO-d$_6$) δ ppm 0.41 (d, J=7.0 Hz, 3H) 1.07 (d, J=6.7 Hz, 3H) 2.55-2.69

(m, 1H) 3.17 (s, 6H) 3.43 (s, 3H) 3.86 (s, 3H) 6.38 (s, 1H) 7.52 (d, J=7.4 Hz, 2H) 7.82 (d, J=7.4 Hz, 2H) 7.93 (s, 2H) 8.25 (br. s, 1H).

Step 150.1: 4-[(5-Chloro-1-methyl-6-oxo-1,6-dihydro-pyridin-3-ylamino)-(4-cyano-phenyl)-methyl]-1-(2-dimethylamino-4-methoxy-pyrimidin-5-yl)-5-isopropyl-1H-pyrazole-3-carboxylic acid

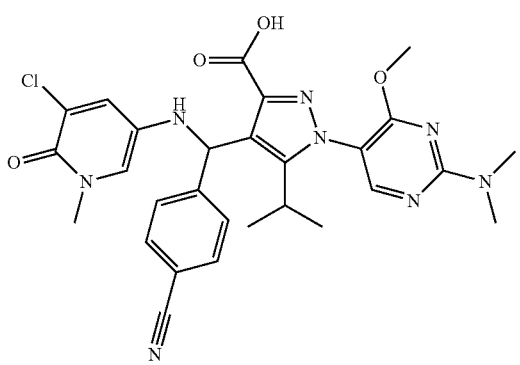 [SMILES: COc1nc(N(C)C)ncc1-n1nc(C(=O)O)c(C(Nc2cc(Cl)c(=O)n(C)c2)c2ccc(C#N)cc2)c1C(C)C]

The title compound was prepared in analogy to the procedure described for step 124.2 but using the product from step 150.2. $t_R$: 0.94 min (LC-MS 4); ESI-MS: 577.4 [M+H]$^+$ (LC-MS 4).

Step 150.2: 4-[(5-Chloro-1-methyl-6-oxo-1,6-dihydro-pyridin-3-ylamino)-(4-cyano-phenyl-methyl]-1-(2-dimethylamino-4-methoxy-pyrimidin-5-yl)-5-isopropyl-1H-pyrazole-3-carboxylic acid ethyl ester

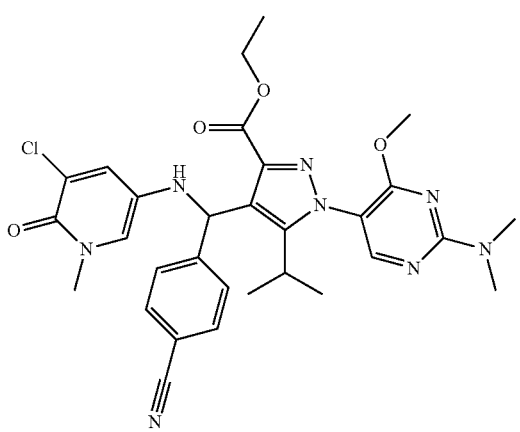 [SMILES: CCOC(=O)c1nn(-c2cnc(N(C)C)nc2OC)c(C(C)C)c1C(Nc1cc(Cl)c(=O)n(C)c1)c1ccc(C#N)cc1]

The title compound was prepared in analogy to the procedure described for step 149.2 but using the product from step 150.3. $t_R$: 1.09 min (LC-MS 4); ESI-MS: 605.4 [M+H]$^+$ (LC-MS 4); $R_f$=0.59 (CH$_2$Cl$_2$/MeOH, 9:1).

Step 150.3: 4-[(4-Cyano-phenyl)-hydroxy-methyl]-1-(2-dimethylamino-4-methoxy-pyrimidin-5-yl)-5-isopropyl-1H-pyrazole-3-carboxylic acid ethyl ester

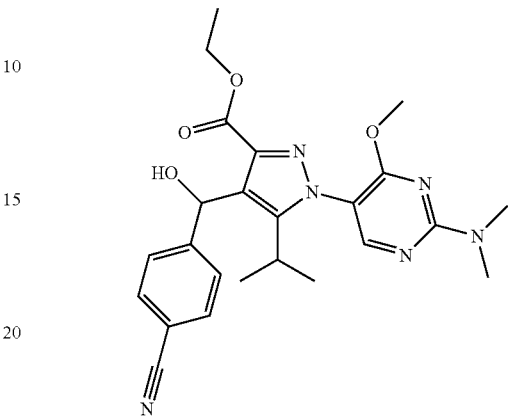

To a stirred solution of 4-iodobenzonitrile (3 g, 13.10 mmol) in THF (13.10 mL) under argon at 0° C. was added a 1.3 M solution of isopropylmagnesium chloride lithium chloride complex in THF (13.10 mL, 17.03 mmol). The reaction mixture was stirred at this temperature for 60 min. An aliquote of this Grignard reagent (18.79 mL, 9.40 mmol) was added to a cold (−78° C.) solution of the product from step 147.5 (2.83 g, 7.83 mmol) in THF (30 mL) under argon. The reaction mixture was stirred 5 min at −78° C., quenched by addition of a saturated aqueous solution of ammonium chloride (75 mL), and extracted with EtOAc (2×100 mL). The organic layers were combined, washed with a saturated aqueous solution of ammonium chloride (100 mL), dried (Na$_2$SO$_4$), and concentrated. The residue was purified by silica gel column chromatography (Hex/EtOAc, 85:15→55:45 to afford 2.64 g of the title compound as a white solid. $t_R$: 1.16 min (LC-MS 4); ESI-MS: 465.3 [M+H]$^+$ (LC-MS 4); $R_f$=0.38 (hexane/EtOAc, 1:1).

Example 151

4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

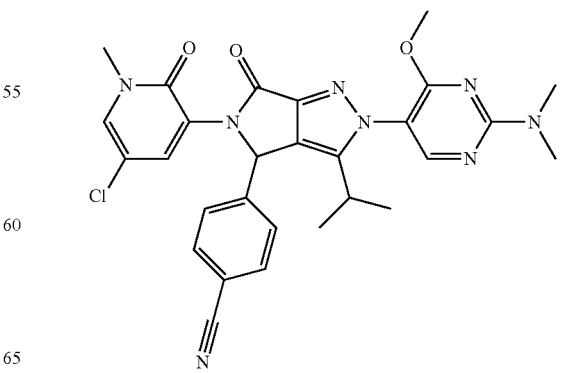

The title compound was prepared in analogy to the procedure described for example 148. $t_R$: 1.08 min (LC-MS 4); ESI-MS: 559.4 [M+H]$^+$ (LC-MS 4); $R_f$=0.65 (CH$_2$Cl$_2$/MeOH, 9:1); $^1$H NMR (400 MHz, DMSO-d$_6$) δ ppm 0.41 (d, J=6.7 Hz, 3H) 1.06 (d, J=7.0 Hz, 3H) 2.54-2.65 (m, 1H) 3.17 (s, 6H) 3.43 (s, 3H) 3.86 (s, 3H) 6.61 (s, 1H) 7.48 (d, J=8.2 Hz, 2H) 7.57 (br. s, 1H) 7.79 (d, J=8.2 Hz, 2H) 7.96 (d, J=2.7 Hz, 1H) 8.27 (s, 1H).

Step 151.1: 4-[(5-Chloro-1-methyl-2-oxo-1,2-dihydro-pyridin-3-ylamino)-(4-cyano-phenyl)-methyl]-1-(2-dimethylamino-4-methoxy-pyrimidin-5-yl)-5-isopropyl-1H-pyrazole-3-carboxylic acid

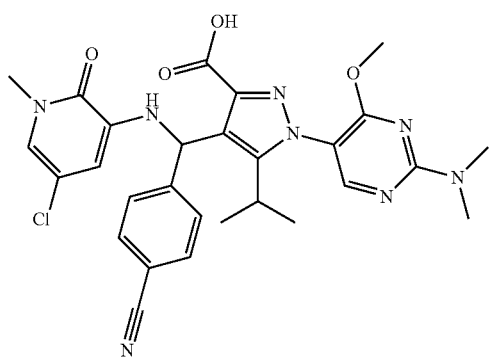

The title compound was prepared in analogy to the procedure described for step 124.2 but using the product from step 151.2. $t_R$: 1.13 min (LC-MS 4); ESI-MS: 577.4 [M+H]$^+$ (LC-MS 4).

Step 151.2: 4-[(5-Chloro-1-methyl-2-oxo-1,2-dihydro-pyridin-3-ylamino)-(4-cyano-phenyl)-methyl]-1-(2-dimethylamino-4-methoxy-pyrimidin-5-yl)-5-isopropyl-1H-pyrazole-3-carboxylic acid ethyl ester

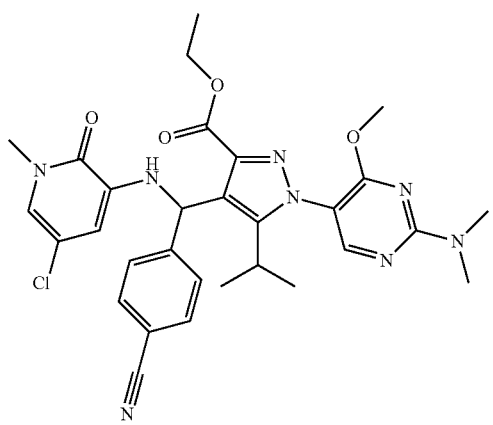

The title compound was prepared in analogy to the procedure described for step 150.2 but using intermediate BJ. $t_R$: 1.09 min (LC-MS 4); ESI-MS: 605.4 [M+H]$^+$ (LC-MS 4); $R_f$=0.59 (CH$_2$Cl$_2$/MeOH, 9:1).

Example 152

5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

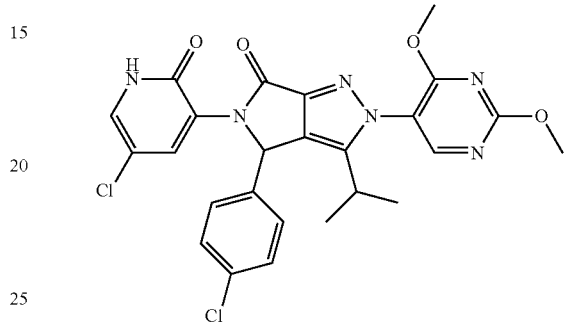

The title compound was prepared in analogy to the procedure described for example 120 but using the product from step 152.1. The reaction mixture was stirred under microwave irradiation for 20 min at 100° C. $t_R$: 1.03 min (LC-MS 4); ESI-MS: 541.3 [M+H]$^+$ (LC-MS 4); $R_f$=0.29 (CH$_2$Cl$_2$/MeOH, 9:1); $^1$H NMR (400 MHz, DMSO-d$_6$) δ ppm 0.46 (d, J=7.0 Hz, 3H) 1.07 (d, J=7.0 Hz, 3H) 2.61 (dt, J=13.7, 6.8 Hz, 1H) 3.87-4.02 (m, 6H) 6.56 (s, 1H) 7.27 (d, J=8.21 Hz, 2H) 7.38 (d, J=8.60 Hz, 2H) 7.50-7.64 (m, 2H) 8.61 (s, 1H) 12.31 (br. s, 1H).

Step 152.1: 5-[5-Chloro-1-(4-methoxy-benzyl)-2-oxo-1,2-dihydro-pyridin-3-yl]-4-(4-chloro-phenyl)-2-(2,4-dimethoxy-pyrimidin-5-yl)-3-isopropyl-4,5-dihydro-2H-pyrrolo[3,4-c]pyrazol-6-one

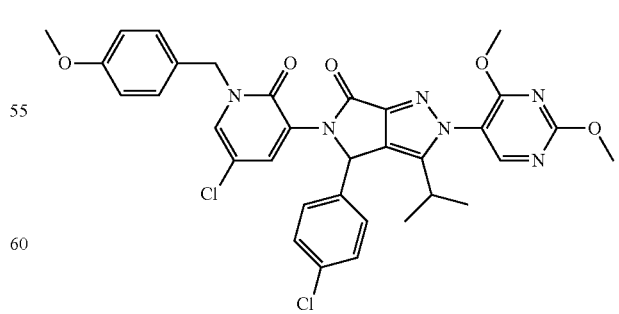

The title compound was prepared in analogy to the procedure described for step 124.1 but using the product from step 152.2. The residue was purified by silica gel column chromatography (CH$_2$Cl$_2$/MeOH, 99:1→96.5:3.5). t$_R$: 1.28 min (LC-MS 4); ESI-MS: 661.4 [M+H]$^+$ (LC-MS 4); R$_f$=0.50 (CH$_2$Cl$_2$/MeOH, 9:1).

Step 152.2: 4-[[5-Chloro-1-(4-methoxy-benzyl)-2-oxo-1,2-dihydro-pyridin-3-ylamino]-(4-chloro-phenyl)-methyl]-1-(2,4-dimethoxy-pyrimidin-5-yl)-5-isopropyl-1H-pyrazole-3-carboxylic acid

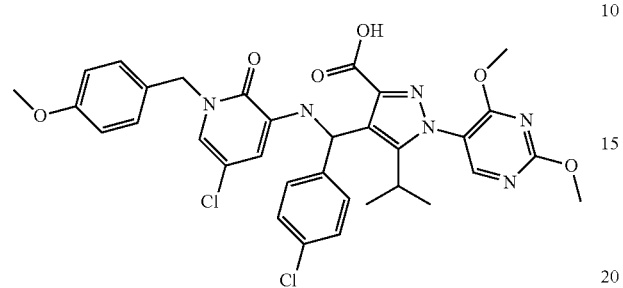

The title compound was prepared in analogy to the procedure described for step 124.2 but using the product from step 152.3. t$_R$: 1.27 min (LC-MS 4); ESI-MS: 679.4 [M+H]$^+$ (LC-MS 4).

Step 152.3: 4-[[5-Chloro-1-(4-methoxy-benzyl)-2-oxo-1,2-dihydro-pyridin-3-ylamino]-(4-chloro-phenyl)-methyl]-1-(2,4-dimethoxy-pyrimidin-5-yl)-5-isopropyl-1H-pyrazole-3-carboxylic acid ethyl ester

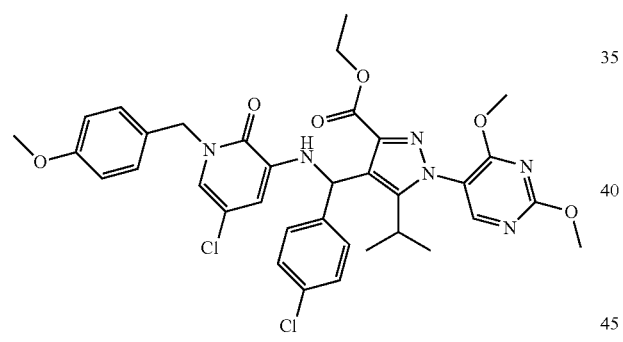

The title compound was prepared in analogy to the procedure described for step 124.3 but using the products from steps 152.4 and 145.3. The residue was purified by silica gel column chromatography (hexane/EtOAc, 8:2→4:6). t$_R$: 1.41 min (LC-MS 4); ESI-MS: 707.4 [M+H]$^+$ (LC-MS 4); R$_f$=0.28 (hexane/EtOAc, 1:1).

Step 152.4: 3-Amino-5-chloro-1-(4-methoxy-benzyl)-1H-pyridin-2-one

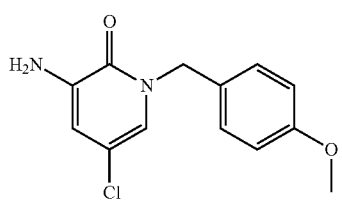

The title compound was prepared in analogy to the procedure described for step 120.3 but using the product from step 152.5. The residue was purified by silica gel column chromatography (hexane/EtOAc, 8:2→6:4). t$_R$: 0.87 min (LC-MS 4); ESI-MS: 265.3 [M+H]$^+$ (LC-MS 4); R$_f$=0.44 (hexane/EtOAc, 1:1).

Step 152.5: 5-Chloro-1-(4-methoxy-benzyl)-3-nitro-1H-pyridin-2-one

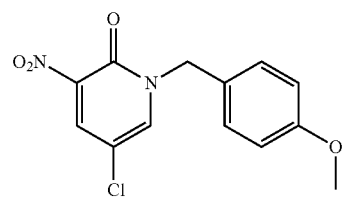 [SMILES: COc1ccc(Cn2cc(Cl)cc([N+](=O)[O-])c2=O)cc1]

The title compound was prepared in analogy to the procedure described for example 1 but using 5-chloro-3-nitropyridin-2-ol and 4-methoxybenzyl chloride. The reaction was stirred for 1 h at 80° C. The residue was purified by silica gel column chromatography (CH$_2$Cl$_2$/EtOAc, 8:2). t$_R$: 0.91 min (LC-MS 4); ESI-MS: 295.2 [M+H]$^+$ (LC-MS 4); R$_f$=0.59 (hexane/EtOAc, 1:1).

Example 153

(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one

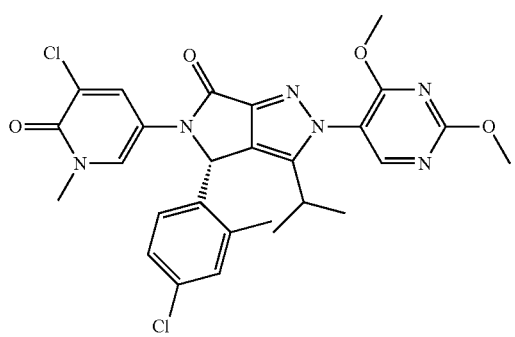 [SMILES: COc1ncc(-n2nc3c(c2C(C)C)[C@H](c2ccc(Cl)cc2C)N(c2cc(Cl)c(=O)n(C)c2)C3=O)c(OC)n1]

The title compound was obtained enantiomerically pure after preparative chiral chromatography (Column: chiralcel OD 20 μm 00SC-BD004, 500×50 mm, 20 μm. Flow: 60 mL/min. Mobile phase: heptane/ethanol/methanol, 70:15:15)

of example 132. $t_R$: 10.9 min (Column: Chiracel OD-H, 250× 4.6 mm, 5 μm. Flow: 1 mL/min. Mobile phase: heptane/ethanol/methanol, 70:15:15).

Example 154

(R)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one

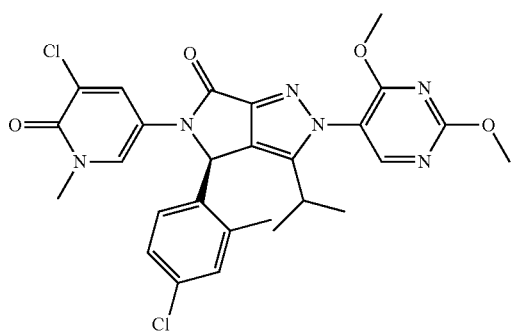 [SMILES: COc1ncc(-n2nc3c(c2C(C)C)[C@@H](c2ccc(Cl)cc2C)N(c2cc(Cl)c(=O)n(C)c2)C3=O)c(OC)n1]

The title compound was obtained enantiomerically pure after preparative chiral chromatography (Column: chiralcel OD 20 μm 00SC-BD004, 500×50 mm, 20 μm. Flow: 60 mL/min. Mobile phase: heptane/ethanol/methanol, 70:15:15) of example 132. $t_R$: 21.4 min (Column: Chiracel OD-H, 250× 4.6 mm, 5 μm. Flow: 1 mL/min. Mobile phase: heptane/ethanol/methanol, 70:15:15).

Example 155

5-(5-Chloro-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

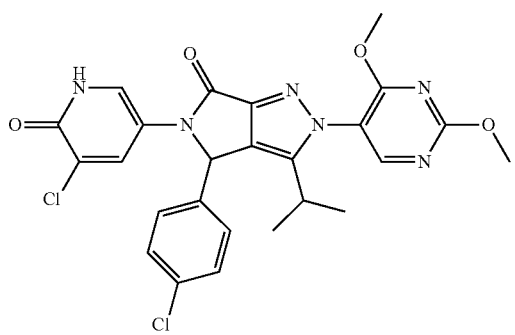 [SMILES: COc1ncc(-n2nc3c(c2C(C)C)C(c2ccc(Cl)cc2)N(c2c[nH]c(=O)c(Cl)c2)C3=O)c(OC)n1]

The title compound was prepared in analogy to the procedure described for example 120 but using the product from step 155.1. The reaction mixture was stirred under microwave irradiation for 30 min at 100° C. $t_R$: 0.99 min (LC-MS 4); ESI-MS: 541.3 [M+H]$^+$ (LC-MS 4); $R_f$=0.55 (CH$_2$Cl$_2$/MeOH, 9:1).

Step 155.1: 5-[5-Chloro-1-(4-methoxy-benzyl)-6-oxo-1,6-dihydro-pyridin-3-yl]-4-(4-chloro-phenyl)-2-(2,4-dimethoxy-pyrimidin-5-yl)-3-isopropyl-4,5-dihydro-2H-pyrrolo[3,4-c]pyrazol-6-one

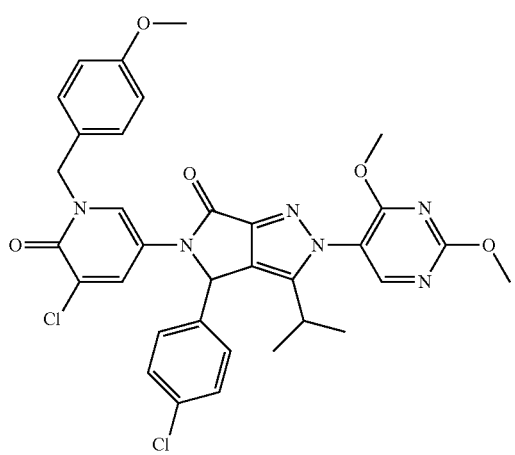 [SMILES: COc1ccc(Cn2cc(N3C(=O)c4nn(-c5cnc(OC)nc5OC)c(C(C)C)c4C3c3ccc(Cl)cc3)cc(Cl)c2=O)cc1]

The title compound was prepared in analogy to the procedure described for step 124.1 but using the product from step 155.2. The residue was purified by silica gel column chromatography (CH$_2$Cl$_2$/MeOH, 99:1→97:3). $t_R$: 1.18 min (LC-MS 4); ESI-MS: 661.4 [M+H]$^+$ (LC-MS 4); $R_f$=0.62 (CH$_2$Cl$_2$/MeOH, 9:1).

Step 155.2: 4-[[5-Chloro-1-(4-methoxy-benzyl-6-oxo-1,6-dihydro-pyridin-3-ylamino]-(4-chloro-phenyl)-methyl]-1-(2,4-dimethoxy-pyrimidin-5-yl)-5-isopropyl-1H-pyrazole-3-carboxylic acid

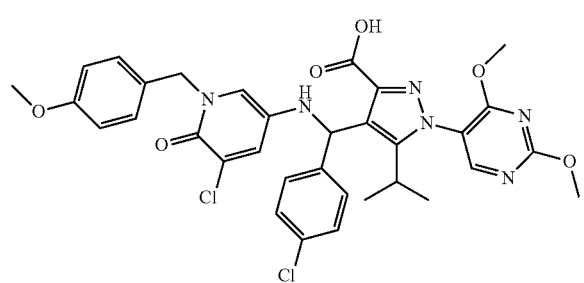

The title compound was prepared in analogy to the procedure described for step 124.2 but using the product from step 155.3. $t_R$: 1.09 min (LC-MS 4); ESI-MS: 679.5 [M+H]$^+$ (LC-MS 4).

Step 155.3: 4-[[5-Chloro-1-(4-methoxy-benzyl)-6-oxo-1,6-dihydro-pyridin-3-ylamino]-(4-chloro-phenyl)-methyl]-1-(2,4-dimethoxy-pyrimidin-5-yl)-5-isopropyl-1H-pyrazole-3-carboxylic acid ethyl ester

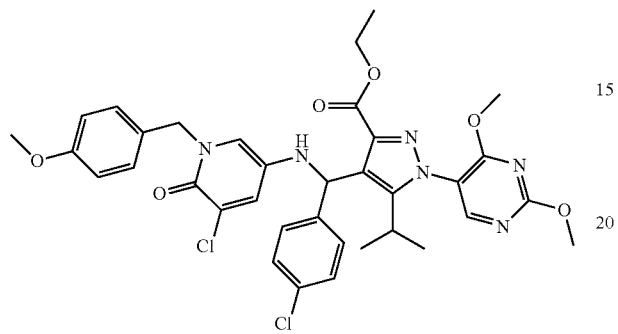

The title compound was prepared in analogy to the procedure described for step 124.3 but using the products from steps 145.3 and 155.4. The residue was purified by silica gel column chromatography (CH$_2$Cl$_2$/MeOH, 99:1). $t_R$: 1.27 min (LC-MS 4); ESI-MS: 707.5 [M+H]$^+$ (LC-MS 4); R$_f$=0.62 (CH$_2$Cl$_2$/MeOH, 9:1).

Step 155.4: 5-Amino-3-chloro-1-(4-methoxy-benzyl)-1H-pyridin-2-one

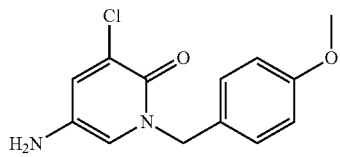

The title compound was prepared in analogy to the procedure described for step M1 but using the product from step 155.5. The residue was purified by silica gel column chromatography (CH$_2$Cl$_2$/MeOH, 100:0→96.5:3.5). $t_R$: 0.61 min (LC-MS 4); ESI-MS: 265.2 [M+H]$^+$ (LC-MS 4); R$_f$=0.53 (CH$_2$Cl$_2$/MeOH, 9:1).

Step 155.5: 3-Chloro-1-(4-methoxy-benzyl)-5-nitro-1H-pyridin-2-one

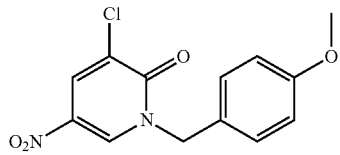 [SMILES: COc1ccc(Cn2cc([N+](=O)[O-])cc(Cl)c2=O)cc1]

The title compound was prepared in analogy to the procedure described for step W2 but using 3-chloro-2-hydroxy-5-nitropyridine and 4-methoxybenzyl bromide. The reaction was quenched with a saturated aqueous solution of sodium bicarbonate. The residue was purified by trituration in EtOAc. $t_R$: 0.98 min (LC-MS 4); ESI-MS: 295.2 [M+H]$^+$ (LC-MS 4).

Example 156

5-(5-Chloro-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

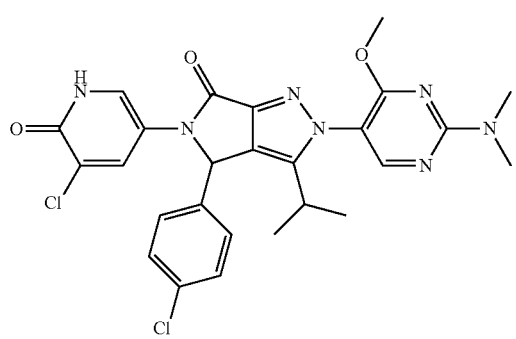 [SMILES: COc1nc(N(C)C)ncc1-n1nc2c(c1C(C)C)C(c1ccc(Cl)cc1)N(c1c[nH]c(=O)c(Cl)c1)C2=O]

The title compound was prepared in analogy to the procedure described for example 120 but the reaction was performed at 120° C. for 10 min. $t_R$: 1.10 min (LC-MS 4); ESI-MS: 554.3 [M+H]$^+$ (LC-MS 4); R$_f$=0.54 (CH$_2$Cl$_2$/MeOH, 9:1).

Step 156.1: 5-[5-Chloro-1-(4-methoxy-benzyl)-6-oxo-1,6-dihydro-pyridin-3-yl]-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one

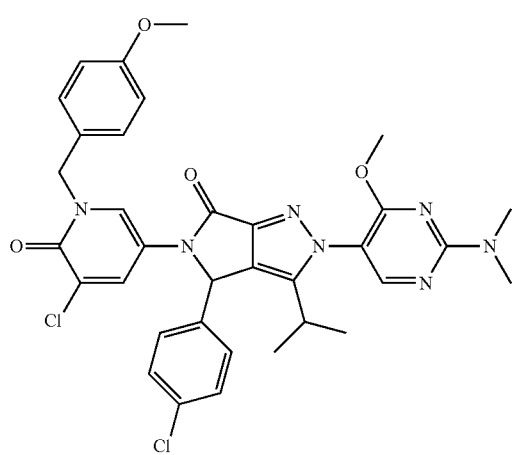 [SMILES: COc1ccc(Cn2cc(N3C(=O)c4nn(-c5cnc(N(C)C)nc5OC)c(C(C)C)c4C3c3ccc(Cl)cc3)cc(Cl)c2=O)cc1]

The title compound was prepared in analogy to the procedure described for step 124.1 but using the compound prepared in step 156.2. The crude product was purified by silica gel column chromatography (CH$_2$Cl$_2$/MeOH, 99:1→97.5:

2.5). $t_R$: 1.29 min (LC-MS 4); ESI-MS: 674.4 [M+H]$^+$ (LC-MS 4); $R_f$=0.57 (CH$_2$Cl$_2$/MeOH, 9:1).

Step 156.2: 4-[[5-(5-Chloro-1-(4-methoxy-benzyl)-6-oxo-1,6-dihydro-pyridin-3-ylamino]-(4-chloro-phenyl)-methyl]-1-(2-dimethylamino-4-methoxy-pyrimidin-5-yl)-5-isopropyl-1H-pyrazole-3-carboxylic acid

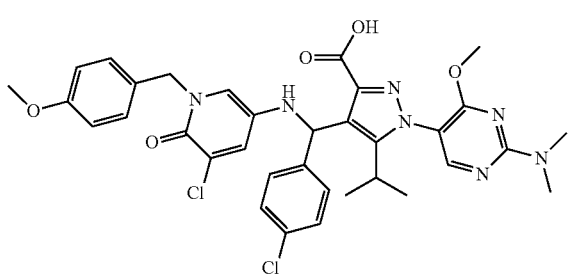

The title compound was prepared in analogy to the procedure described for step 124.2 but using the compound prepared in step 156.3, 3 equivalents of lithium hydroxide monohydrate, and stirring the reaction mixture for 1.5 h at rt. $t_R$: 1.19 min (LC-MS 4); ESI-MS: 692.5 [M+H]$^+$ (LC-MS 4).

tep 156.3: 4-[5-[5-Chloro-1-(4-methoxy-benzyl)-6-oxo-1,6-dihydro-pyridin-3-ylamino]-(4-chloro-phenyl)-methyl]-1-(2-dimethylamino-4-methoxy-pyrimidin-5-yl)-5-isopropyl-1H-pyrazole-3-carboxylic acid ethyl ester

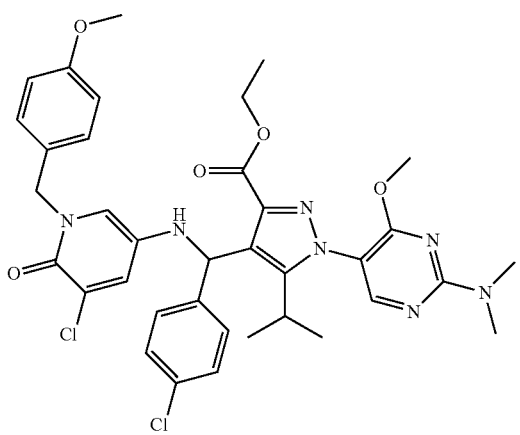 [SMILES: CCOC(=O)c1nn(-c2cnc(N(C)C)nc2OC)c(C(C)C)c1C(Nc1cc(Cl)c(=O)n(Cc2ccc(OC)cc2)c1)c1ccc(Cl)cc1]

The title compound was prepared in analogy to the procedure described for step 155.3 but using the product from step 147.4. $t_R$: 1.35 min (LC-MS 4); ESI-MS: 720.5 [M+H]$^+$ (LC-MS 4); $R_f$=0.58 (CH$_2$Cl$_2$/MeOH, 9:1).

Example 157

4-[5-(5-Chloro-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

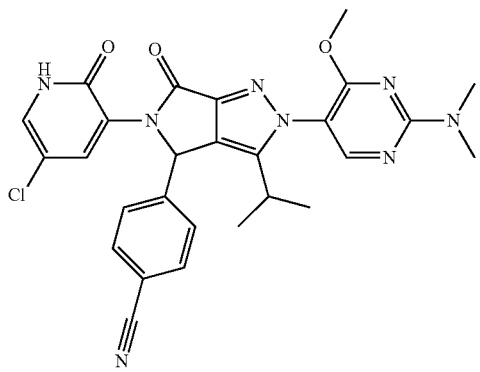 [SMILES: COc1nc(N(C)C)ncc1-n1nc2c(c1C(C)C)C(c1ccc(C#N)cc1)N(c1cc(Cl)c[nH]c1=O)C2=O]

The title compound was prepared in analogy to the procedure described for example 120 but using the product from step 157.1. The reaction was performed at 100° C. for 30 min. $t_R$: 1.01 min (LC-MS 4); ESI-MS: 545.4 [M+H]$^+$ (LC-MS 4); $R_f$=0.58 (CH$_2$Cl$_2$/MeOH, 9:1); $^1$H NMR (400 MHz, DMSO-$d_6$) δ ppm 0.41 (d, J=7.0 Hz, 3H) 1.06 (d, J=7.0 Hz, 3H) 2.54-2.64 (m, 1H) 3.17 (s, 6H) 3.86 (s, 3H) 6.63 (br. s., 1H) 7.47 (d, J=7.8 Hz, 2H) 7.55 (br s, 2H) 7.79 (d, J=8.2 Hz, 2H) 8.26 (s, 1H) 12.30 (br s, 1H).

Step 157.1: 4-[5-[5-Chloro-1-(4-methoxy-benzyl)-2-oxo-1,2-dihydro-pyridin-3-yl]-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

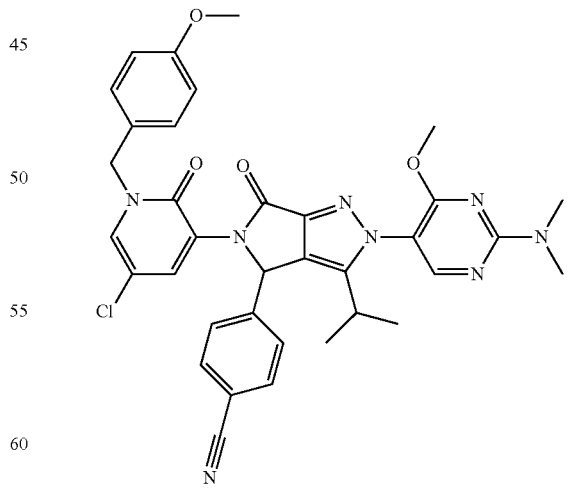

The title compound was prepared in analogy to the procedure described for step 124.1 but using the compound prepared in step 157.2. The crude product was purified by silica gel column chromatography (CH$_2$Cl$_2$/MeOH, 99.5:0.5→96.5:3.5). $t_R$: 1.25 min (LC-MS 4); ESI-MS: 665.5 [M+H]$^+$ (LC-MS 4); $R_f$=0.72 (CH$_2$Cl$_2$/MeOH, 9:1).

Step 157.2: 4-[[5-Chloro-1-(4-methoxy-benzyl)-2-oxo-1,2-dihydro-pyridin-3-ylamino]-(4-cyano-phenyl)-methyl]-1-(2-dimethylamino-4-methoxy-pyrimidin-5-yl)-5-isopropyl-1H-pyrazole-3-carboxylic acid

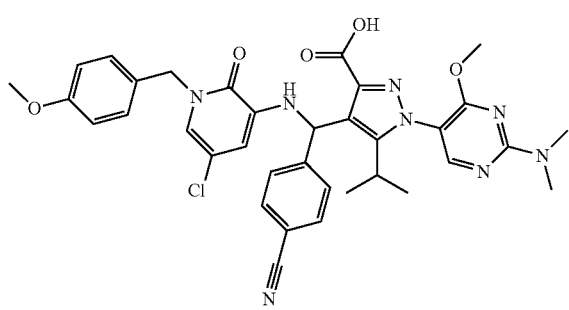

The title compound was prepared in analogy to the procedure described for step 124.2 but using the compound prepared in step 157.3, 3 equivalents of lithium hydroxide monohydrate, and stirring the reaction mixture for 3.5 h at rt. $t_R$: 1.26 min (LC-MS 4); ESI-MS: 683.4 [M+H]$^+$ (LC-MS 4).

Step 157.3: 4-[[5-Chloro-1-(4-methoxy-benzyl)-2-oxo-1,2-dihydro-pyridin-3-ylamino]-(4-cyano-phenyl)-methyl]-1-(2-dimethylamino-4-methoxy-pyrimidin-5-yl)-5-isopropyl-1H-pyrazole-3-carboxylic acid ethyl ester

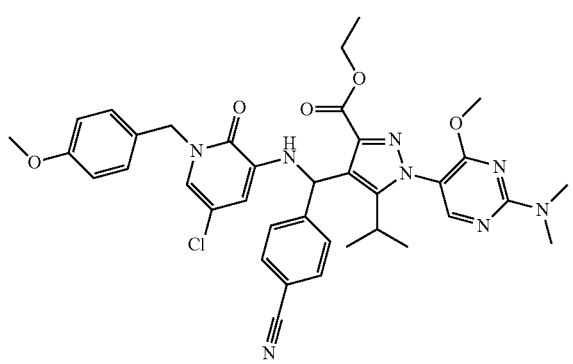

The title compound was prepared in analogy to the procedure described for step 124.3 but using the products from steps 150.3 and 152.4. $t_R$: 1.37 min (LC-MS 4); ESI-MS: 711.5 [M+H]$^+$ (LC-MS 4); $R_f$=0.30 (hexane/EtOAc, 1:1).

Example 158

4-[5-(5-Chloro-6-oxo-1,6-dihydro-pyridin-3-O-2-(2-dimethylamino-4-methoxy-pyrimidin-5-A-3-isopropyl-6-oxo-2,4,5,6-tetrahydro-pyrrolo[3,4-c]pyrazol-4-yl]-benzonitrile

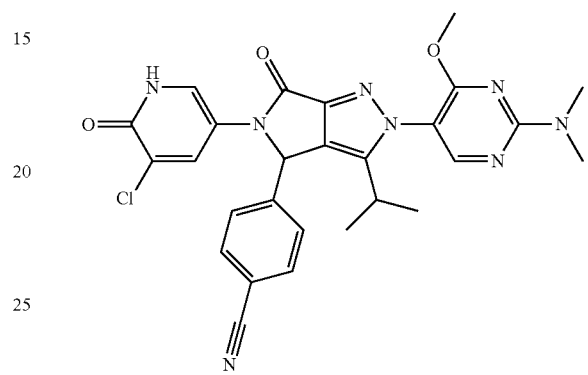

The title compound was prepared in analogy to the procedure described for example 120 but using product from step 158.1. The reaction was performed at 100° C. for 30 min. $t_R$: 0.98 min (LC-MS 4); ESI-MS: 545.4 [M+H]$^+$ (LC-MS 4); $R_f$=0.41 (CH$_2$Cl$_2$/MeOH, 9:1).

Step 158.1: 4-[5-[5-Chloro-1-(4-methoxy-benzyl)-6-oxo-1,6-dihydro-pyridin-3-yl]-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

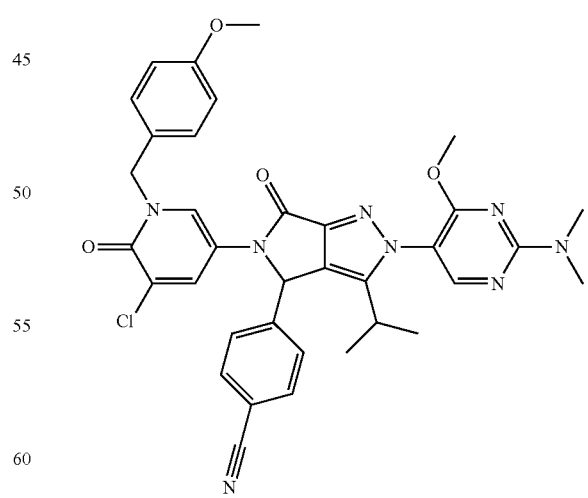

The title compound was prepared in analogy to the procedure described for step 124.1 but using the compound prepared in step 158.2. The crude product was purified by silica gel column chromatography (CH$_2$Cl$_2$/MeOH, 99.5:0.5→97.5:2.5). $t_R$: 1.16 min (LC-MS 4); ESI-MS: 665.5 [M+H]$^+$ (LC-MS 4); $R_f$=0.62 (CH$_2$Cl$_2$/MeOH, 9:1).

Step 158.2: 4-[[5-Chloro-1-(4-methoxy-benzyl)-6-oxo-1,6-dihydro-pyridin-3-ylamino]-(4-cyano-phenyl)-methyl]-1-(2-dimethylamino-4-methoxy-pyrimidin-5-yl)-5-isopropyl-1H-pyrazole-3-carboxylic acid

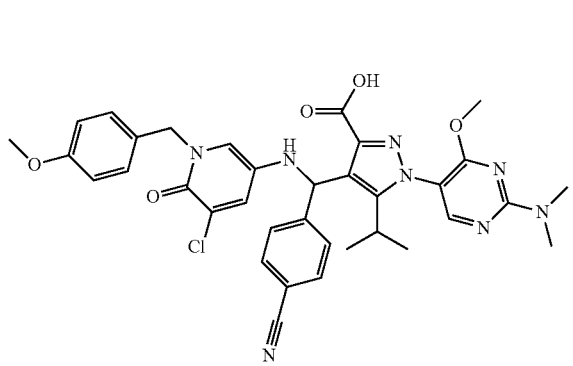

The title compound was prepared in analogy to the procedure described for step 124.2 but using the compound prepared in step 158.3, 3 equivalents of lithium hydroxide monohydrate, and stirring the reaction mixture for 1.5 h at rt. $t_R$: 1.09 min (LC-MS 4); ESI-MS: 683.5 [M+H]$^+$ (LC-MS 4).

Step 158.3: 4-[[5-Chloro-1-(4-methoxy-benzyl)-6-oxo-1,6-dihydro-pyridin-3-ylamino]-(4-cyano-phenyl)-methyl]-1-(2-dimethylamino-4-methoxy-pyrimidin-5-yl)-5-isopropyl-1H-pyrazole-3-carboxylic acid ethyl ester

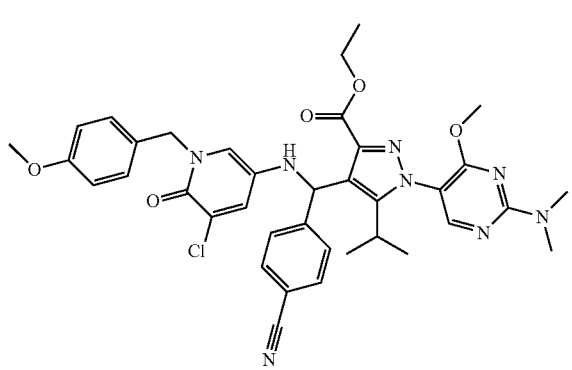

The title compound was prepared in analogy to the procedure described for step 124.3 but using the products from steps 150.3 and 155.4. The crude product was purified by silica gel column chromatography (hexane/EtOAc, 1:1→25:

75). $t_R$: 1.21 min (LC-MS 4); ESI-MS: 711.5 [M+H]$^+$ (LC-MS 4); $R_f$=0.71 (hexane/EtOAc, 1:1).

Example 159

4-[5-(5-Chloro-6-oxo-1,6-dihydro-pyridin-3-yl)-2-(2,4-dimethoxy-pyrimidin-5-yl-3-isopropyl-6-oxo-2,4,5,6-tetrahydro-pyrrolo[3,4-c]pyrazol-4-yl]-benzonitrile

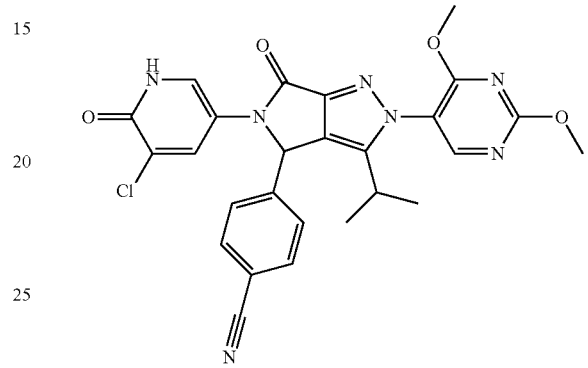

The title compound was prepared in analogy to the procedure described for example 120 but using the product from step 159.1. The reaction was performed at 100° C. for 30 min. $t_R$: 0.86 min (LC-MS 4); ESI-MS: 532.3 [M+H]$^+$ (LC-MS 4); $R_f$=0.37 (CH$_2$Cl$_2$/MeOH, 9:1).

Step 159.1: 4-[5-[5-Chloro-1-(4-methoxy-benzyl)-6-oxo-1,6-dihydro-pyridin-3-yl]-2-(2,4-dimethoxy-pyrimidin-5-yl)-3-isopropyl-6-oxo-2,4,5,6-tetrahydro-pyrrolo[3,4-c]pyrazol-4-yl]-benzonitrile

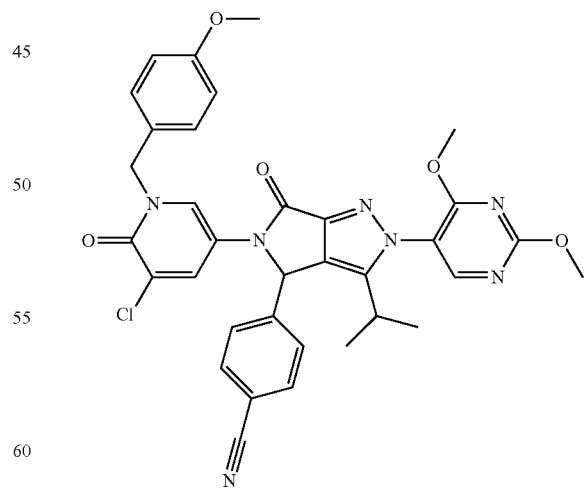

The title compound was prepared in analogy to the procedure described for step 124.1 but using the compound prepared in step 159.2. The crude product was purified by silica gel column chromatography (CH$_2$Cl$_2$/MeOH, 99.5:0.5→97.5:2.5). $t_R$: 1.06 min (LC-MS 4); ESI-MS: 652.4 [M+H]$^+$ (LC-MS 4); $R_f$=0.61 (CH$_2$Cl$_2$/MeOH, 9:1).

Step 159.2: 4-[[5-Chloro-1-(4-methoxy-benzyl)-6-oxo-1,6-dihydro-pyridin-3-ylamino]-(4-cyano-phenyl)-methyl]-1-(2,4-dimethoxy-pyrimidin-5-yl)-5-isopropyl-1H-pyrazole-3-carboxylic acid

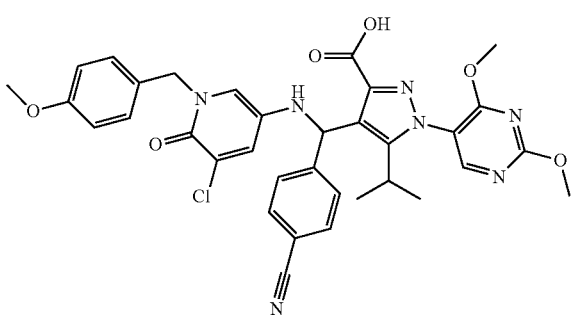

The title compound was prepared in analogy to the procedure described for step 124.2 but using the compound prepared in step 159.3, 3 equivalents of lithium hydroxide monohydrate, and stirring the reaction mixture for 1 h at rt. $t_R$: 0.98 min (LC-MS 4); ESI-MS: 670.4 [M+H]$^+$ (LC-MS 4).

Step 159.3: 4-[[5-Chloro-1-(4-methoxy-benzyl)-6-oxo-1,6-dihydro-pyridin-3-ylamino]-(4-cyano-phenyl)-methyl]-1-(2,4-dimethoxy-pyrimidin-5-yl)-5-isopropyl-1H-pyrazole-3-carboxylic acid ethyl ester

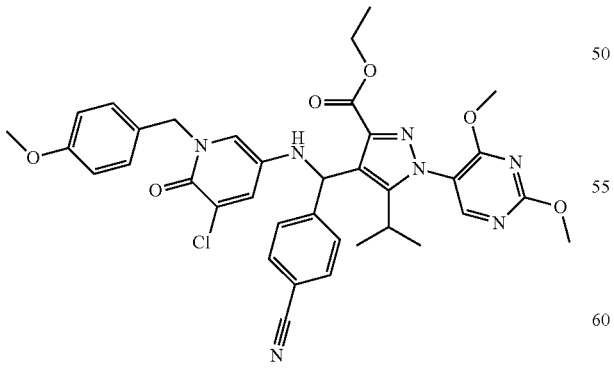

The title compound was prepared in analogy to the procedure described for step 124.3 but using the products from steps 159.4 and 155.4. The crude product was purified by silica gel column chromatography (CH$_2$Cl$_2$/MeOH, 100:0→98:2). $t_R$: 1.13 min (LC-MS 4); ESI-MS: 698.5 [M+H]$^+$ (LC-MS 4); $R_f$=0.64 (CH$_2$Cl$_2$/MeOH, 9:1).

Step 159.4: 4-[(4-Cyano-phenyl)-hydroxy-methyl]-1-(2,4-dimethoxy-pyrimidin-5-yl)-5-isopropyl-1H-pyrazole-3-carboxylic acid ethyl ester

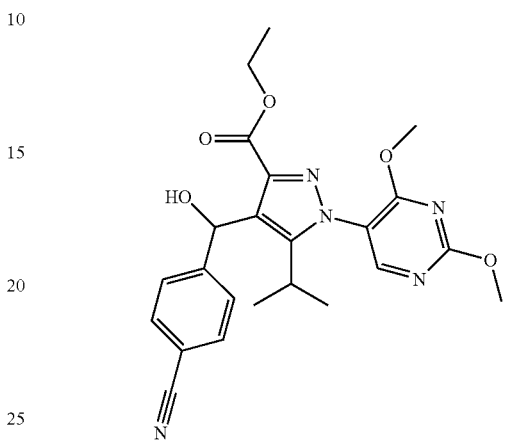

The title compound was prepared in analogy to the procedure described for step 150.3 but using intermediate BB and performing the reaction at 0° C. $t_R$: 1.04 min (LC-MS 4); ESI-MS: 452.4 [M+H]$^+$ (LC-MS 4); $R_f$=0.33 (hexane/EtOAc, 1:1).

Example 160

4-[5-(5-Chloro-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile

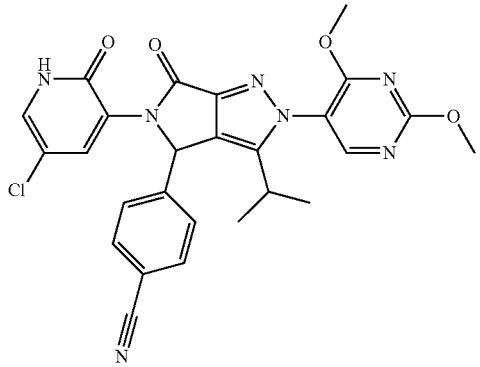

The title compound was prepared in analogy to the procedure described for example 120 but using the product from step 160.1. The reaction was performed at 100° C. for 30 min.

$t_R$: 0.90 min (LC-MS 4); ESI-MS: 532.3 [M+H]$^+$ (LC-MS 4); $R_f$=0.49 (CH$_2$Cl$_2$/MeOH, 9:1).

Step 160.1: 4-[5-[5-Chloro-1-(4-methoxy-benzyl)-2-oxo-1,2-dihydro-pyridin-3-yl]-2-(2,4-dimethoxy-pyrimidin-5-yl)-3-isopropyl-6-oxo-2,4,5,6-tetrahydro-pyrrolo[3,4-c]pyrazol-4-yl]-benzonitrile

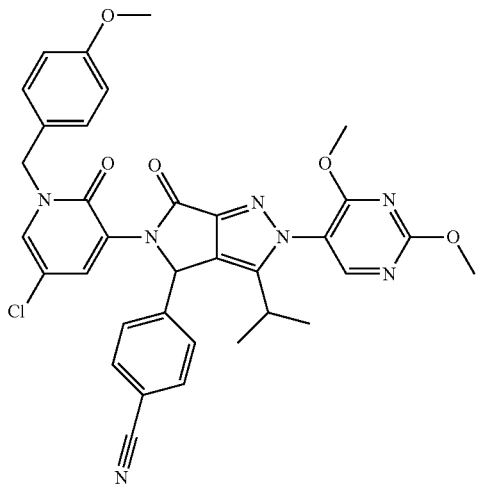 [SMILES: COc1ccc(Cn2cc(Cl)cc(N3C(=O)c4nn(-c5cnc(OC)nc5OC)c(C(C)C)c4C3c3ccc(C#N)cc3)c2=O)cc1]

To a solution of product from step 160.2 (130 mg, 0.194 mmol) was added 1-chloro-N,N,2-trimethyl-1-propenylamine (36 µl, 0.272 mmol) at 0° C. and the mixture was stirred for 1 h at 5° C. The reaction mixture was quenched with a saturated aqueous solution of sodium bicarbonate and extracted with EtOAc. The organic layers were washed with a saturated aqueous solution of sodium bicarbonate, dried (Na$_2$SO$_4$), filtered and concentrated. The residue was purified by silica gel column chromatography (CH$_2$Cl$_2$/MeOH, 99.5:0.5→97.5:2.5) to provide 88 mg of the title compound as a colorless solid. $t_R$: 1.14 min (LC-MS 4); ESI-MS: 652.5 [M+H]$^+$ (LC-MS 4); $R_f$=0.67 (CH$_2$Cl$_2$/MeOH, 9:1).

Step 160.2: 4-[[5-Chloro-1-(4-methoxy-benzyl)-2-oxo-1,2-dihydro-pyridin-3-ylamino]-(4-cyano-phenyl)-methyl]-1-(2,4-dimethoxy-pyrimidin-5-yl)-5-isopropyl-1H-pyrazole-3-carboxylic acid

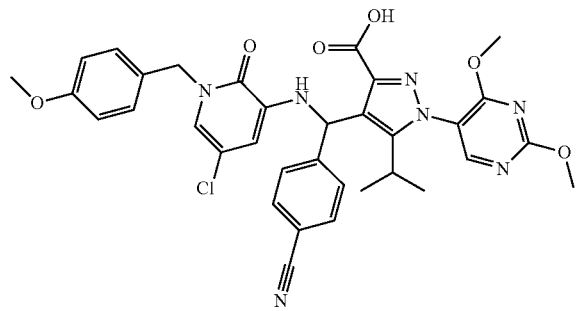

The title compound was prepared in analogy to the procedure described for step 124.2 but using the compound prepared in step 160.3, 3 equivalents of lithium hydroxide monohydrate, and stirring the reaction mixture for 2.5 h at rt. $t_R$: 1.17 min (LC-MS 4); ESI-MS: 670.4 [M+H]$^+$ (LC-MS 4).

Step 160.3: 4-[[5-Chloro-1-(4-methoxy-benzyl)-2-oxo-1,2-dihydro-pyridin-3-ylamino]-(4-cyano-phenyl)-methyl]-1-(2,4-dimethoxy-pyrimidin-5-yl)-5-isopropyl-1H-pyrazole-3-carboxylic acid ethyl ester

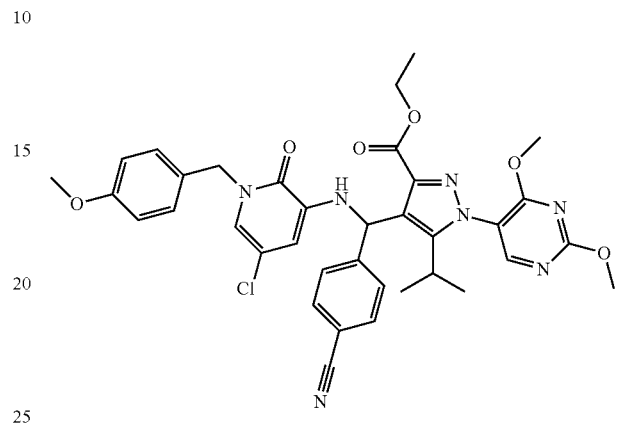

The title compound was prepared in analogy to the procedure described for step 124.3 but using the products from steps 159.4 and 152.4. The crude product was purified by silica gel column chromatography (hexane/EtOAc, 75:25→45:55). $t_R$: 1.28 min (LC-MS 4); ESI-MS: 698.5 [M+H]$^+$ (LC-MS 4); $R_f$=0.23 (hexane/EtOAc, 1:1).

Example 161

4-[5-(5-Chloro-1-methyl-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile

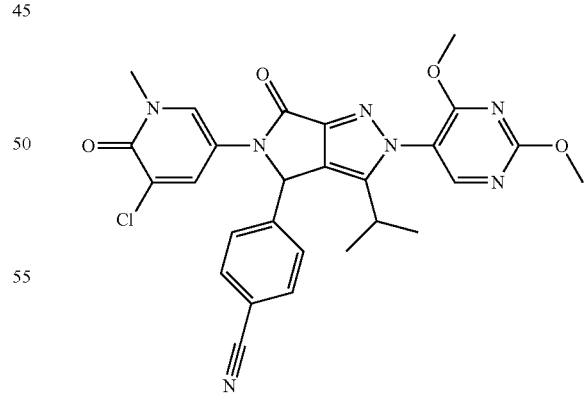

The title compound was prepared in analogy to the procedure described for step 160.1 but using the compound prepared in step 161.1. After the silica gel column chromatography, the residue was purified by preparative HPLC (Column: Sunfire C18, 30×100 mm, 5 µm. Flow: 30 mL/min. Gradient: 5% to 100% B in 20 min; A=0.1% TFA in water, B=acetonitrile). $t_R$: 0.91 min (LC-MS 4); ESI-MS: 546.3 [M+H]$^+$ (LC-MS 4); $R_f$=0.42 (CH$_2$Cl$_2$/MeOH, 9:1).

Step 161.1: 4-[(5-Chloro-1-methyl-6-oxo-1,6-dihydro-pyridin-3-ylamino)-(4-cyano-phenyl)-methyl]-1-(2,4-dimethoxy-pyrimidin-5-yl)-5-isopropyl-1H-pyrazole-3-carboxylic acid

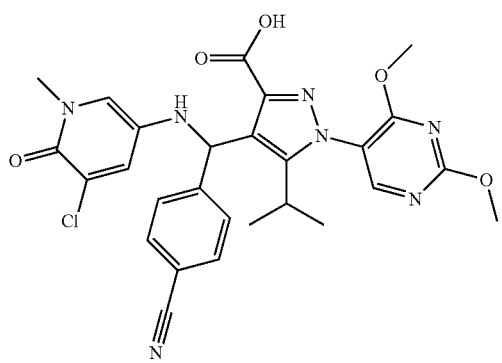 [SMILES: COc1ncc(-n2nc(C(=O)O)c(C(Nc3cc(Cl)c(=O)n(C)c3)c3ccc(C#N)cc3)c2C(C)C)c(OC)n1]

The title compound was prepared in analogy to the procedure described for step 124.2 but using the compound prepared in step 161.2, 3 equivalents of lithium hydroxide monohydrate, and stirring the reaction mixture for 1 h at rt. $t_R$: 0.84 min (LC-MS 4); ESI-MS: 564.4 [M+H]$^+$ (LC-MS 4).

Step 161.2: 4-[(5-Chloro-1-methyl-6-oxo-1,6-dihydro-pyridin-3-ylamino)-(4-cyano-phenyl)-methyl]-1-(2,4-dimethoxy-pyrimidin-5-yl)-5-isopropyl-1H-pyrazole-3-carboxylic acid ethyl ester

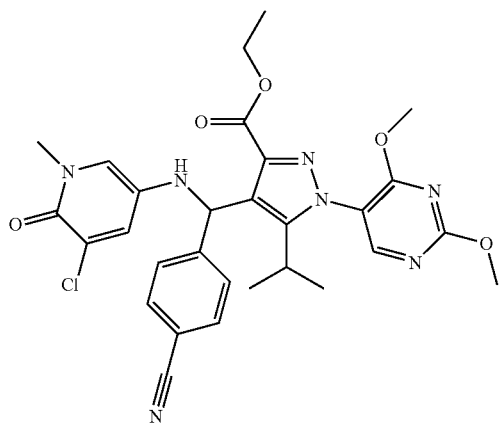 [SMILES: CCOC(=O)c1nn(-c2cnc(OC)nc2OC)c(C(C)C)c1C(Nc1cc(Cl)c(=O)n(C)c1)c1ccc(C#N)cc1]

The title compound was prepared in analogy to the procedure described for step 124.3 but using products from steps 159.4 and 149.3. The crude product was purified by silica gel column chromatography (CH$_2$Cl$_2$/MeOH, 100:0→98:2). $t_R$: 0.99 min (LC-MS 4); ESI-MS: 592.4 [M+H]$^+$ (LC-MS 4); $R_f$=0.61 (CH$_2$Cl$_2$/MeOH, 9:1).

Example 162

4-[5-(5-Chloro-1-methyl-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile

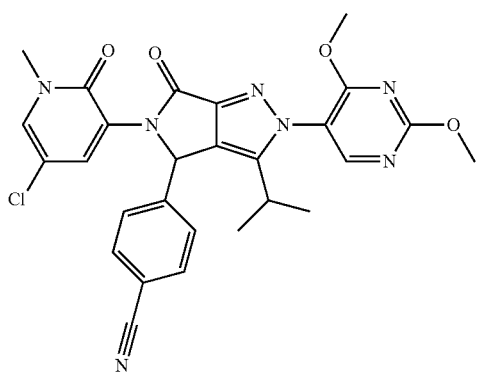

The title compound was prepared in analogy to the procedure described for step 160.1 but using the compound prepared in step 162.1. After the silica gel column chromatography, the residue was triturated in diisopropylether. $t_R$: 0.96 min (LC-MS 4); ESI-MS: 546.3 [M+H]$^+$ (LC-MS 4); $R_f$=0.51 (CH$_2$Cl$_2$/MeOH, 9:1).

Step 162.1: 4-[(5-Chloro-1-methyl-2-oxo-1,2-dihydro-pyridin-3-ylamino)-(4-cyano-phenyl)-methyl]-1-(2,4-dimethoxy-pyrimidin-5-yl)-5-isopropyl-1H-pyrazole-3-carboxylic acid

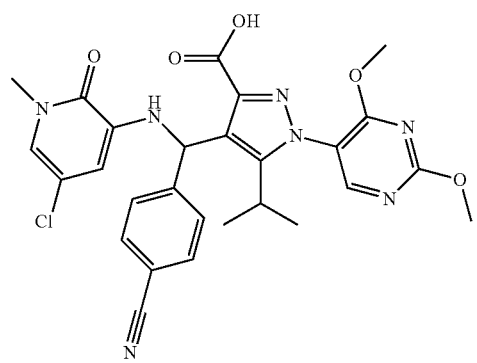

The title compound was prepared in analogy to the procedure described for step 124.2 but using the product from step 162.2. $t_R$: 1.01 min (LC-MS 4); ESI-MS: 564.4 [M+H]$^+$ (LC-MS 4).

Step 162.2: 4-[(5-Chloro-1-methyl-2-oxo-1,2-dihydro-pyridin-3-ylamino)-(4-cyano-phenyl)-methyl]-1-(2,4-dimethoxy-pyrimidin-5-yl)-5-isopropyl-1H-pyrazole-3-carboxylic acid ethyl ester

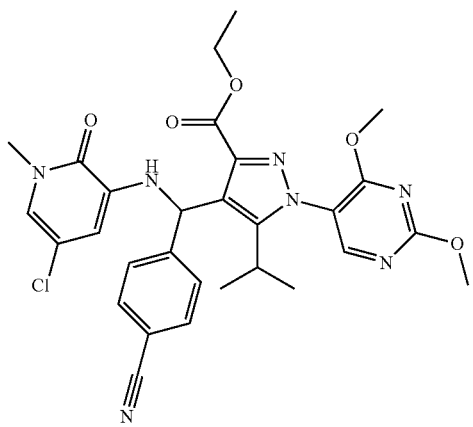

The title compound was prepared in analogy to the procedure described for step 124.3 but using the product from step 159.4 and intermediate BJ. The crude product was purified by silica gel column chromatography (hexane/EtOAc, 4:6→15:85). $t_R$: 1.13 min (LC-MS 4); ESI-MS: 592.4 [M+H]$^+$ (LC-MS 4); $R_f$=0.66 (EtOAc).

Example 163

5-(5-Chloro-1-methyl-2-oxo-1,2-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one

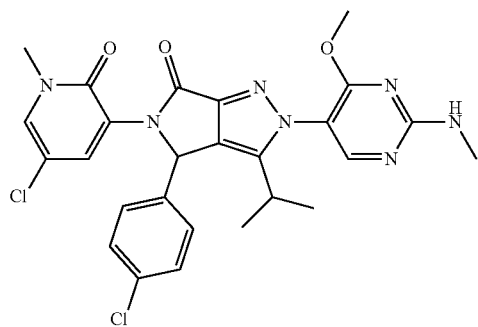 [SMILES: CNc1ncc(-n2nc3c(c2C(C)C)C(c2ccc(Cl)cc2)N(c2cc(Cl)cn(C)c2=O)C3=O)c(OC)n1]

To a solution of product from step 163.1 (92 mg, 0.14 mmol) in CH$_2$Cl$_2$ (2 mL) was added TFA (108 μL, 1.4 mmol) and the mixture was stirred for 1 h at rt. The reaction mixture was quenched with a saturated aqueous sodium bicarbonate solution then extracted with CH$_2$Cl$_2$. The organic layer was washed with a saturated aqueous sodium bicarbonate solution, dried (Na$_2$SO$_4$), filtered and concentrated. The residue was purified by silica gel column chromatography (CH$_2$Cl$_2$/MeOH, 98:2→97:3) to afford 64 mg of the title product as a white solid. $t_R$: 1.08 min (LC-MS 4); ESI-MS: 554.2 [M+H]$^+$ (LC-MS 4); $R_f$=0.57 (CH$_2$Cl$_2$/MeOH, 9:1).

Step 163.1: {5-[5-(5-Chloro-1-methyl-2-oxo-1,2-dihydro-pyridin-3-yl)-4-(4-chloro-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

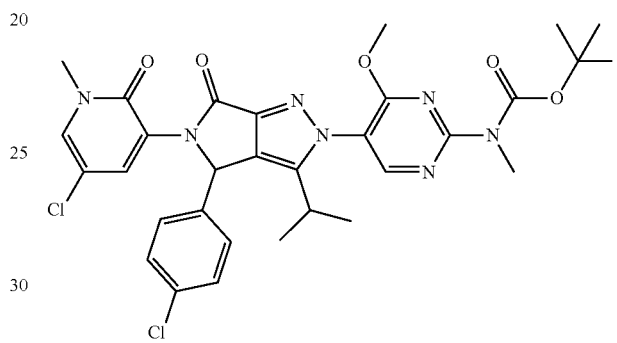

The title compound was prepared in analogy to the procedure described for step 160.1 but using the product from step 163.2. The reaction was performed at 5° C. $t_R$: 1.30 min (LC-MS 4); ESI-MS: 654.2 [M+H]$^+$ (LC-MS 4); $R_f$=0.70 (CH$_2$Cl$_2$/MeOH, 9:1).

Step 163.2: 1-[2-(tert-Butoxycarbonyl-methyl-amino)-4-methoxy-pyrimidin-5-yl]-4-[(5-chloro-1-methyl-2-oxo-1,2-dihydro-pyridin-3-ylamino)-(4-chloro-phenyl)-methyl]-5-isopropyl-1H-pyrazole-3-carboxylic acid

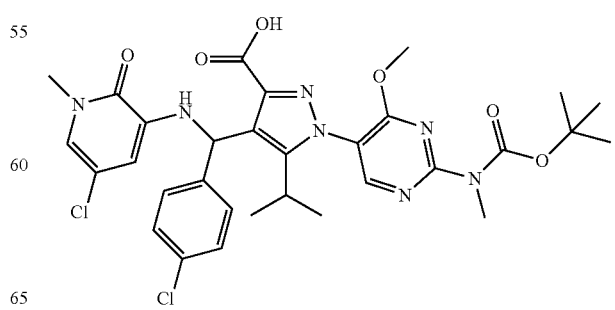

The title compound was prepared in analogy to the procedure described for step 124.2 but using the product from step 163.3. $t_R$: 1.29 min (LC-MS 4); ESI-MS: 672.5 [M+H]$^+$ (LC-MS 4).

Step 163.3: 1-[2-(tert-Butoxycarbonyl-methyl-amino)-4-methoxy-pyrimidin-5-yl]-4-[(5-chloro-1-methyl-2-oxo-1,2-dihydro-pyridin-3-ylamino)-(4-chloro-phenyl)-methyl]-5-isopropyl-1H-pyrazole-3-carboxylic acid ethyl ester

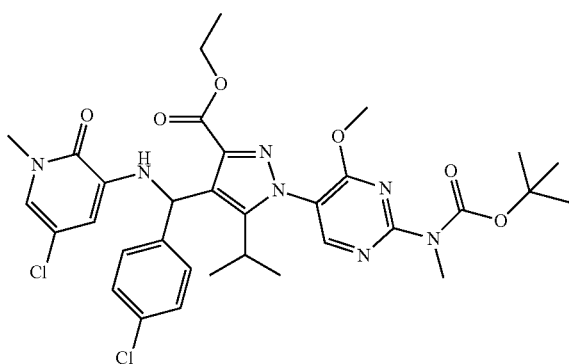 [SMILES: CCOC(=O)c1nn(-c2cnc(N(C)C(=O)OC(C)(C)C)nc2OC)c(C(C)C)c1C(Nc1cc(Cl)cn(C)c1=O)c1ccc(Cl)cc1]

The title compound was prepared in analogy to the procedure described for step 124.3 but using the product from step 163.4 and intermediate BJ. The residue was purified by silica gel column chromatography (hexane/EtOAc, 95:5→35:65). $t_R$: 1.43 min (LC-MS 4); ESI-MS: 700.5 [M+H]$^+$ (LC-MS 4); $R_f$=0.33 (hexane/EtOAc, 1:1).

Step 163.4: 1-[2-(tert-Butoxycarbonyl-methyl-amino)-4-methoxy-pyrimidin-5-yl]-4-[(4-chloro-phenyl)-hydroxy-methyl]-5-isopropyl-1H-pyrazole-3-carboxylic acid ethyl ester

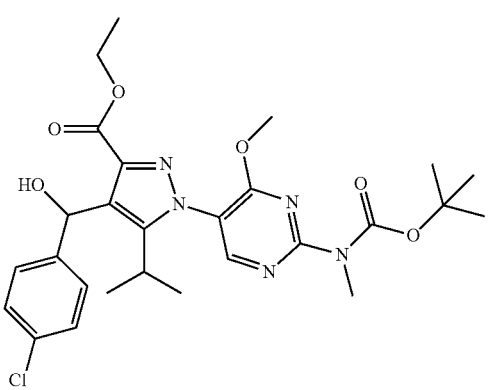 [SMILES: CCOC(=O)c1nn(-c2cnc(N(C)C(=O)OC(C)(C)C)nc2OC)c(C(C)C)c1C(O)c1ccc(Cl)cc1]

The title compound was prepared in analogy to the procedure described for step 124.4 but using the product from step 163.5. The reaction was performed at −78° C. $t_R$: 1.36 min (LC-MS 4); ESI-MS: 560.4 [M+H]$^+$ (LC-MS 4); $R_f$=0.80 (hexane/EtOAc, 1:1).

Step 163.5: 1-[2-(tert-Butoxycarbonyl-methyl-amino)-4-methoxy-pyrimidin-5-yl]-4-formyl-5-isopropyl-1H-pyrazole-3-carboxylic acid ethyl ester

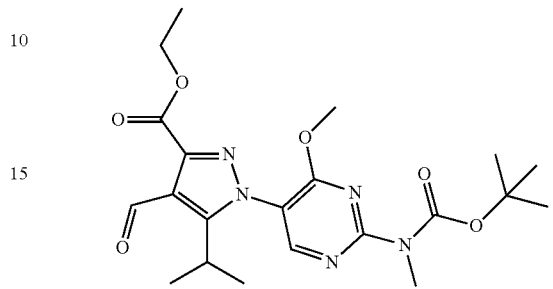

The title compound was prepared in analogy to the procedure described for intermediate AP but using the product from step 163.6. The residue was purified by silica gel column chromatography (hexane/EtOAc, 85:15→75:25). $t_R$: 1.24 min (LC-MS 4); ESI-MS: 448.4 [M+H]$^+$ (LC-MS 4); $R_f$=0.76 (hexane/EtOAc, 1:1).

Step 163.6: 1-[2-(tert-Butoxycarbonyl-methyl-amino)-4-methoxy-pyrimidin-5-yl]-5-isopropyl-4-vinyl-1H-pyrazole-3-carboxylic acid ethyl ester

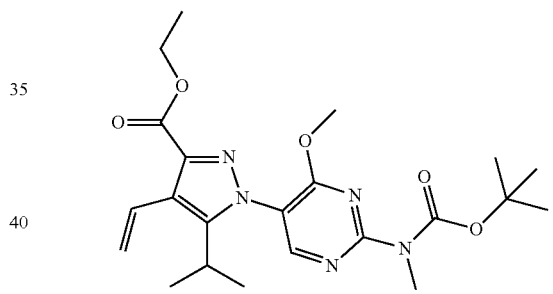

The title compound was prepared in analogy to the procedure described for intermediate BA but using the product from step 163.7. $t_R$: 1.31 min (LC-MS 4); ESI-MS: 446.4 [M+H]$^+$ (LC-MS 4); $R_f$=0.82 (hexane/EtOAc, 1:1).

Step 163.7: 4-Bromo-1-[2-(tert-butoxycarbonyl-methyl-amino)-4-methoxy-pyrimidin-5-yl]-5-isopropyl-1H-pyrazole-3-carboxylic acid ethyl ester

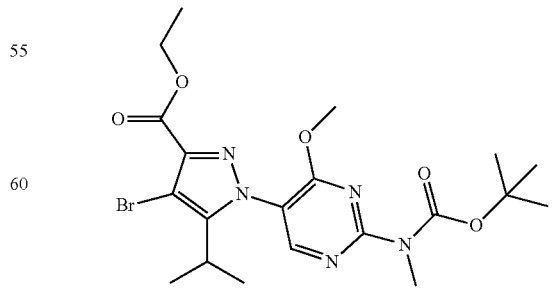

To a solution of product from step 163.8 (2.4 g, 5.9 mmol), triethylamine (2.5 mL, 17.8 mmol), and DMAP (362 mg, 3.0 mmol) in THF (50 mL) under argon was added di-tert-butyl dicarbonate (2.1 mL, 8.9 mmol) and the mixture was stirred for 3 h at rt. The reaction mixture was quenched with a saturated aqueous solution of sodium carbonate and extracted with EtOAc. The organic layers were washed with brine, dried ($Na_2SO_4$), filtered, and concentrated. The crude material was purified by silica gel column chromatography (hexane/EtOAc, 85:15→75:25) to afford 2.9 g of the title compound as a white solid. $t_R$: 1.33 min (LC-MS 4); ESI-MS: 498.3/500.3 $[M+H]^+$ (LC-MS 4), $R_f$=0.60 (hexane/EtOAc, 1:1).

Step 163.8: 4-Bromo-5-isopropyl-1-(4-methoxy-2-methylamino-pyrimidin-5-yl)-1H-pyrazole-3-carboxylic acid ethyl ester

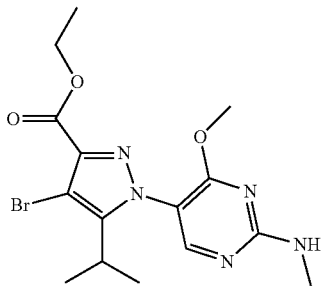 [SMILES: CCOC(=O)c1nn(-c2cnc(NC)nc2OC)c(C(C)C)c1Br]

The title compound was prepared in analogy to the procedure described for step 147.7 but using the product from step 163.9. The reaction was performed at rt for 10 min. The crude material was purified by silica gel column chromatography (hexane/EtOAc, 75:25→1:1). $t_R$: 1.10 min (LC-MS 4); ESI-MS: 398.3/400.3 $[M+H]^+$ (LC-MS 4), $R_f$=0.32 (hexane/EtOAc, 1:1).

Step 163.9: 5-Isopropyl-1-(4-methoxy-2-methylamino-pyrimidin-5-yl)-1H-pyrazole-3-carboxylic acid ethyl ester

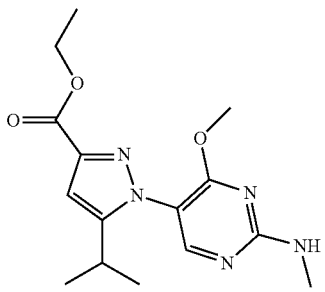 [SMILES: CCOC(=O)c1cc(C(C)C)n(-c2cnc(NC)nc2OC)n1]

The title compound was prepared in analogy to the procedure described for step 147.8 but using methylamine in THF. The crude material was purified by silica gel column chromatography ($CH_2Cl_2$/MeOH, 100:0→98:2). $t_R$: 0.99 min (LC-MS 4); ESI-MS: 320.3 $[M+H]^+$ (LC-MS 4), $R_f$=0.48 ($CH_2Cl_2$/MeOH, 9:1).

Example 164

5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

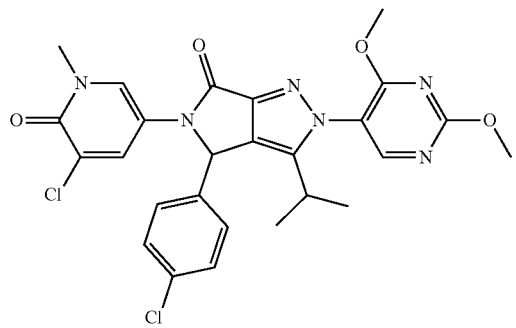 [SMILES: COc1ncc(-n2nc3c(c2C(C)C)C(c2ccc(Cl)cc2)N(c2cc(Cl)c(=O)n(C)c2)C3=O)c(OC)n1]

The title compound was prepared in analogy to the procedure described for step 119.1 but using the product from example 155. The reaction was performed at rt. The reaction mixture was quenched with a saturated aqueous solution of sodium bicarbonate and extracted with EtOAc. The organic layer was washed with a saturated aqueous solution of sodium bicarbonate, dried ($Na_2SO_4$), filtered, and concentrated. The residue was purified by silica gel column chromatography ($CH_2Cl_2$/MeOH, 99.5:0.5→97:3). $t_R$: 1.03 min (LC-MS 2); ESI-MS: 555.2 $[M+H]^+$ (LC-MS 4); $R_f$=0.51 ($CH_2Cl_2$/MeOH, 9:1); $^1$H NMR (400 MHz, DMSO-$d_6$) δ ppm 0.45 (d, J=7.0 Hz, 3H) 1.09 (d, J=7.0 Hz, 3H) 2.55-2.69 (m, 1H) 3.44 (s, 3H) 3.93 (s, 3H) 3.98 (s, 3H) 6.32 (s, 1H) 7.33 (d, J=8.2 Hz, 2H) 7.41 (d, J=8.2 Hz, 2H) 7.88-7.99 (m, 2H) 8.59 (s, 1H).

Example 165

5-(5-Chloro-2-oxo-1,2-dihydro-pyridin-3-O-4-(4-chloro-phenyl)-3-isopropyl-2-(4-methoxy-2-methylamino-pyrimidin-5-yl)-4,5-dihydro-2H-pyrrolo[3,4-c]pyrazol-6-one

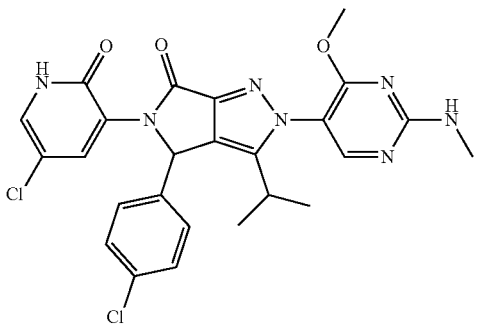

The title compound was prepared in analogy to the procedure described for example 120 but using the product from step 165.1. The reaction was performed at 100° C. for 30 min. The residue was purified by silica gel column chromatography (CH$_2$Cl$_2$/MeOH, 97.5:2.5→94:6). t$_R$: 1.00 min (LC-MS 4); ESI-MS: 540.1 [M+H]$^+$ (LC-MS 4); R$_f$=0.44 (CH$_2$Cl$_2$/MeOH, 9:1).

Step 165.1: {5-[5-[5-Chloro-1-(4-methoxy-benzyl)-2-oxo-1,2-dihydro-pyridin-3-yl]-4-(4-chloro-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

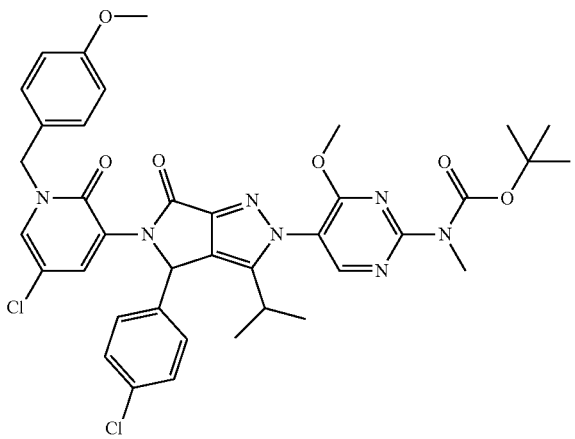 [SMILES: COc1ccc(Cn2cc(Cl)cc(N3C(=O)c4nn(-c5cnc(N(C)C(=O)OC(C)(C)C)nc5OC)c(C(C)C)c4C3c3ccc(Cl)cc3)c2=O)cc1]

The title compound was prepared in analogy to the procedure described for step 160.1 but using the product from step 165.2. The residue was purified by silica gel column chromatography (hexane/EtOAc, 75:25→1:1). t$_R$: 1.42 min (LC-MS 4); ESI-MS: 760.3 [M+H]$^+$ (LC-MS 4); R$_f$=0.40 (hexane/EtOAc, 1:1).

Step 165.2: 1-[2-(tert-Butoxycarbonyl-methyl-amino)-4-methoxy-pyrimidin-5-yl]-4-[[5-chloro-1-(4-methoxy-benzyl)-2-oxo-1,2-dihydro-pyridin-3-ylamino]-(4-chloro-phenyl)-methyl]-5-isopropyl-1H-pyrazole-3-carboxylic acid

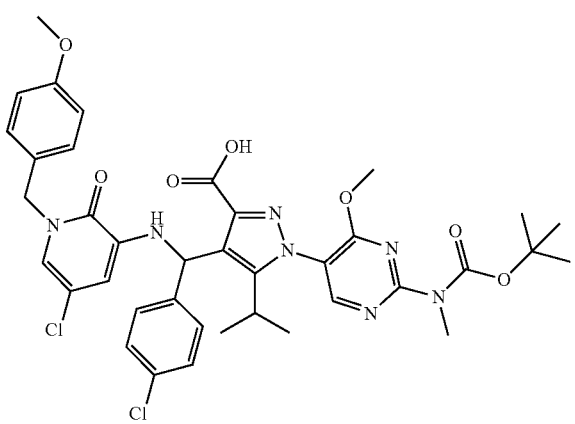 [SMILES: COc1ccc(Cn2cc(Cl)cc(NC(c3ccc(Cl)cc3)c3c(C(=O)O)nn(-c4cnc(N(C)C(=O)OC(C)(C)C)nc4OC)c3C(C)C)c2=O)cc1]

The title compound was prepared in analogy to the procedure described for step 124.2 but using the compound prepared in step 165.3, 3 equivalents of lithium hydroxide monohydrate, and stirring the reaction mixture for 3 h at rt. t$_R$: 1.41 min (LC-MS 4); ESI-MS: 778.5 [M+H]$^+$ (LC-MS 4).

Step 165.3: 1-[2-(tert-Butoxycarbonyl-methyl-amino)-4-methoxy-pyrimidin-5-yl]-4-[[5-chloro-1-(4-methoxy-benzyl)-2-oxo-1,2-dihydro-pyridin-3-ylamino]-(4-chloro-phenyl)-methyl]-5-isopropyl-1H-pyrazole-3-carboxylic acid ethyl ester

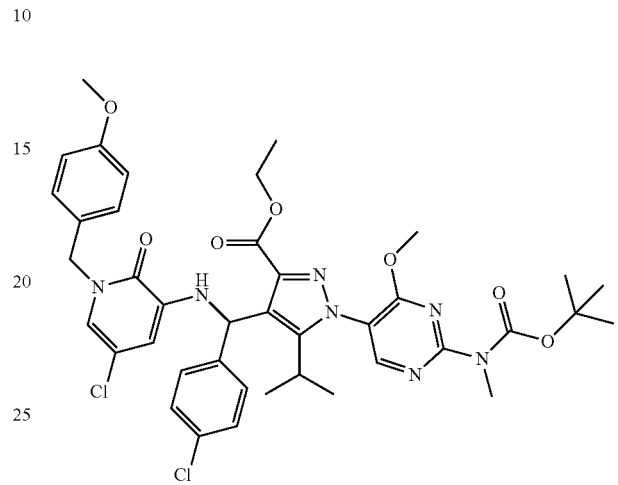

The title compound was prepared in analogy to the procedure described for step 124.3 but using the compounds prepared in steps 152.4 and 163.4. t$_R$: 1.51 min (LC-MS 4); ESI-MS: 806.5 [M+H]$^+$ (LC-MS 4); R$_f$=0.80 (hexane/EtOAc, 1:1).

Example 166

5-(5-Chloro-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one

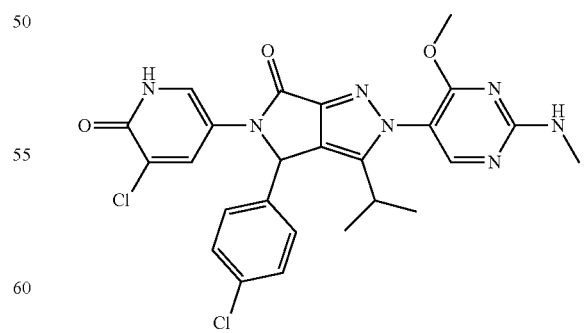

The title compound was prepared in analogy to the procedure described for example 120 but using the product from step 166.1. The reaction was performed at 100° C. for 30 min. The residue was purified by silica gel column chromatography (CH$_2$Cl$_2$/MeOH, 97.5:2.5→92.5:7.5). t$_R$: 0.95 min (LC-MS 4); ESI-MS: 540.2 [M+H]$^+$ (LC-MS 4); R$_f$=0.46 (CH$_2$Cl$_2$/MeOH, 9:1).

Step 166.1: {5-[5-[5-Chloro-1-(4-methoxy-benzyl-6-oxo-1,6-dihydro-pyridin-3-yl]-4-(4-chloro-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

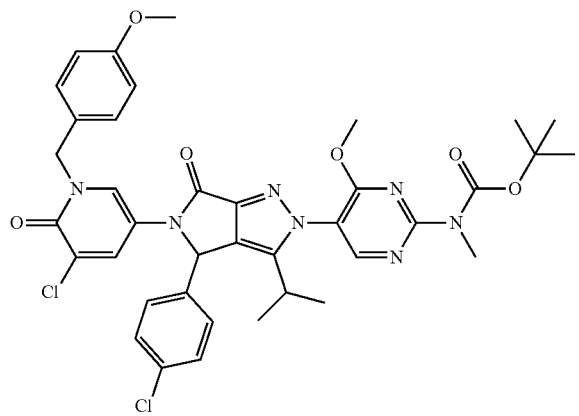 [SMILES: COc1ccc(Cn2cc(N3C(=O)c4nn(-c5cnc(N(C)C(=O)OC(C)(C)C)nc5OC)c(C(C)C)c4C3c3ccc(Cl)cc3)cc(Cl)c2=O)cc1]

The title compound was prepared in analogy to the procedure described for step 160.1 but using the product from step 166.2. t$_R$: 1.34 min (LC-MS 4); ESI-MS: 760.0/762.2 [M+H]$^+$ (LC-MS 4); R$_f$=0.54 (CH$_2$Cl$_2$/MeOH, 9:1).

Step 166.2: 1-[2-(tert-Butoxycarbonyl-methyl-amino)-4-methoxy-pyrimidin-5-yl]-4-[[5-chloro-1-(4-methoxy-benzyl)-6-oxo-1,6-dihydro-pyridin-3-ylamino]-(4-chloro-phenyl)-methyl]-5-isopropyl-1H-pyrazole-3-carboxylic acid

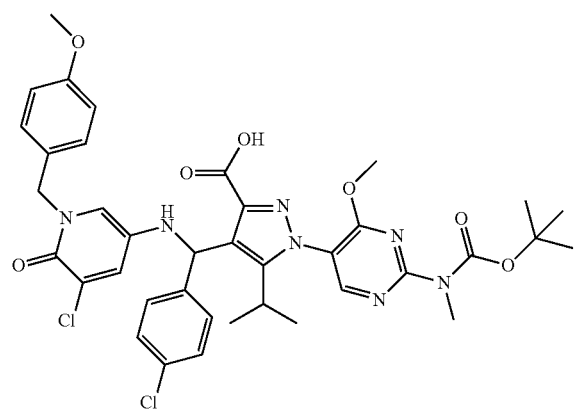 [SMILES: COc1ccc(Cn2cc(NC(c3ccc(Cl)cc3)c3c(C(=O)O)nn(-c4cnc(N(C)C(=O)OC(C)(C)C)nc4OC)c3C(C)C)cc(Cl)c2=O)cc1]

The title compound was prepared in analogy to the procedure described for step 124.2 but using the compound prepared in step 166.3, 3 equivalents of lithium hydroxide monohydrate, and stirring the reaction mixture 3 h at rt. t$_R$: 1.25 min (LC-MS 4); ESI-MS: 778.3 [M+H]$^+$ (LC-MS 4).

Step 166.3: 1-[2-(tert-Butoxycarbonyl-methyl-amino)-4-methoxy-pyrimidin-5-yl]-4-[[5-chloro-1-(4-methoxy-benzyl)-6-oxo-1,6-dihydro-pyridin-3-ylamino]-(4-chloro-phenyl)-methyl]-5-isopropyl-1H-pyrazole-3-carboxylic acid ethyl ester

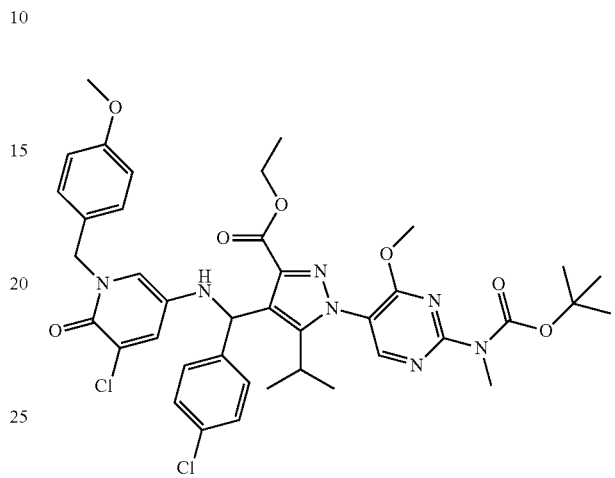

The title compound was prepared in analogy to the procedure described for step 124.3 but using the compounds prepared in steps 155.4 and 163.4. The residue was purified by silica gel column chromatography (hexane/EtOAc, 60:40→45:55). t$_R$: 1.40 min (LC-MS 4); ESI-MS: 806.5 [M+H]$^+$ (LC-MS 4); R$_f$=0.32 (hexane/EtOAc, 1:1).

Example 167

(R)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

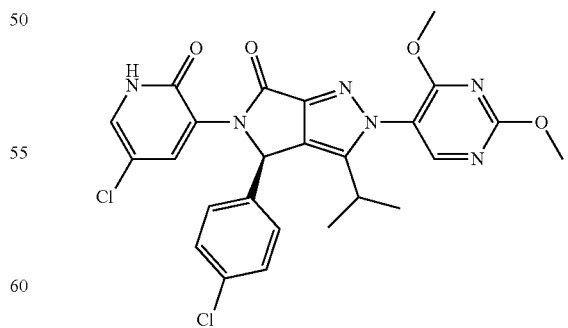

The title compound was obtained enantiomerically pure after preparative chiral chromatography (Column: Chiralpak IC, 250×50 mm, 5 μm. Flow: 11 mL/min. Mobile phase: heptane/iso-propanol 7:3) of example 152. t$_R$: 15.7 min (Column: Chiralpak AD-H5 μm, 250×4.6 mm, 5 μm. Flow: 1 mL/min. Mobile phase: heptane/iso-propanol 7:3).

Example 168

(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one

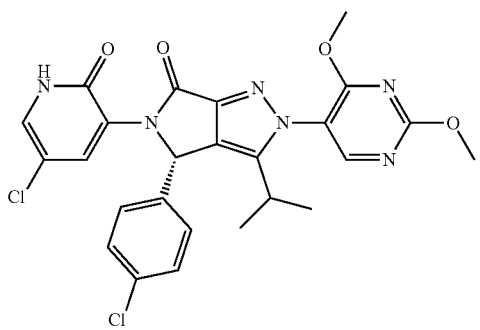 [SMILES: COc1ncc(-n2nc3c(c2C(C)C)[C@H](c2ccc(Cl)cc2)N(c2cc(Cl)c[nH]c2=O)C3=O)c(OC)n1]

The title compound was obtained enantiomerically pure after preparative chiral chromatography (Column: Chiralpak IC, 250×50 mm, 5 μm. Flow: 11 mL/min. Mobile phase: heptane/iso-propanol 7:3) of example 152. $t_R$: 21.2 min (Column: Chiralpak AD-H5 μm, 250×4.6 mm, 5 μm. Flow: 1 mL/min. Mobile phase: heptane/iso-propanol 7:3).

Example 169

4-[5-(5-Chloro-1-methyl-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile

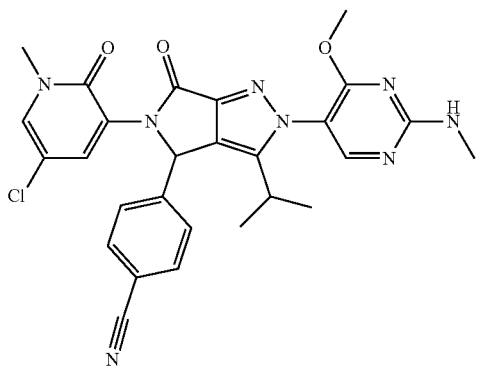 [SMILES: CNc1ncc(-n2nc3c(c2C(C)C)C(c2ccc(C#N)cc2)N(c2cc(Cl)cn(C)c2=O)C3=O)c(OC)n1]

The title compound was prepared in analogy to the procedure described for example 120 but using the product from step 169.1. The reaction was stirred (no microwave irradiation) for 3 h at rt. The residue was purified by silica gel column chromatography (CH$_2$Cl$_2$/MeOH, 99:1→97:3). $t_R$: 0.95 min (LC-MS 4); ESI-MS: 545.2 [M+H]$^+$ (LC-MS 4); $R_f$=0.46 (CH$_2$Cl$_2$/MeOH, 9:1).

Step 169.1: {5-[5-(5-Chloro-1-methyl-2-oxo-1,2-dihydro-pyridin-3-yl)-4-(4-cyano-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

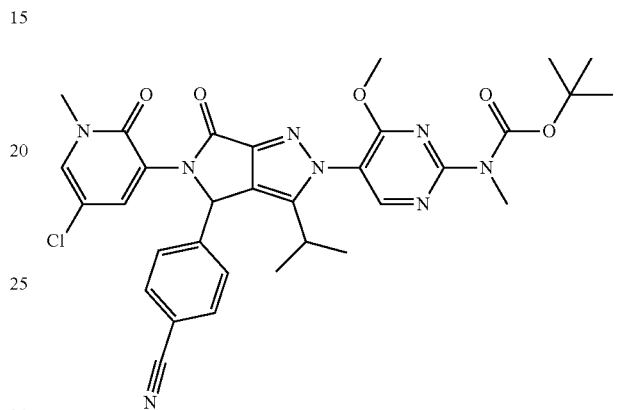

The title compound was prepared in analogy to the procedure described for step 160.1 but using the product from step 169.2. $t_R$: 1.17 min (LC-MS 4); ESI-MS: 645.3 [M+H]$^+$ (LC-MS 4); $R_f$=0.60 (CH$_2$Cl$_2$/MeOH, 9:1).

Step 169.2: 1-[2-(tert-Butoxycarbonyl-methyl-amino)-4-methoxy-pyrimidin-5-yl]-4-[(5-chloro-1-methyl-2-oxo-1,2-dihydro-pyridin-3-ylamino)-(4-cyano-phenyl)-methyl]-5-isopropyl-1H-pyrazole-3-carboxylic acid

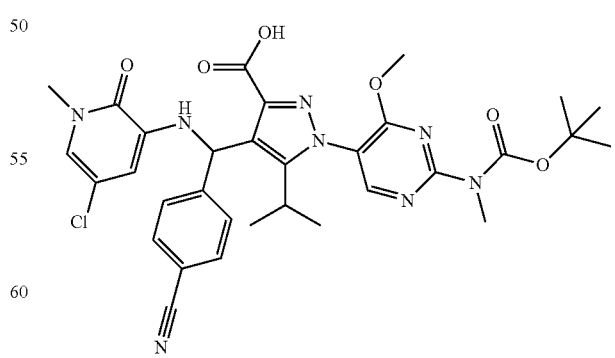

The title compound was prepared in analogy to the procedure described for step 124.2 but using the compound prepared in step 169.3, 3 equivalents of lithium hydroxide monohydrate, and stirring the reaction mixture for 1.5 h at rt. $t_R$: 1.18 min (LC-MS 4); ESI-MS: 663.3 [M+H]$^+$ (LC-MS 4).

Step 169.3: 1-[2-(tert-Butoxycarbonyl-methyl-amino)-4-methoxy-pyrimidin-5-yl]-4-[(5-chloro-1-methyl-2-oxo-1,2-dihydro-pyridin-3-ylamino)-(4-cyano-phenyl)-methyl]-5-isopropyl-1H-pyrazole-3-carboxylic acid ethyl ester

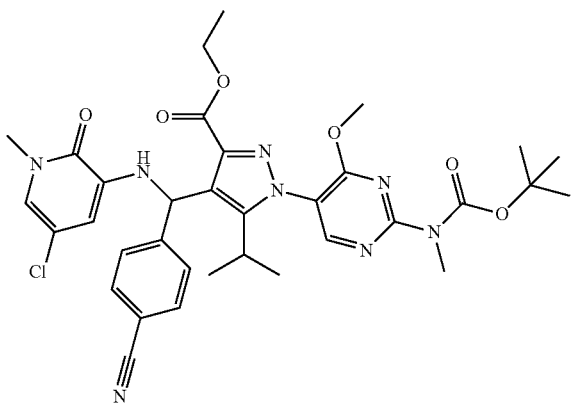 [SMILES: CCOC(=O)c1nn(-c2cnc(N(C)C(=O)OC(C)(C)C)nc2OC)c(C(C)C)c1C(Nc1cc(Cl)cn(C)c1=O)c1ccc(C#N)cc1]

The title compound was prepared in analogy to the procedure described for step 124.3 but using the product from step 169.4 and intermediate BJ. The residue was purified by silica gel column chromatography (CH$_2$Cl$_2$/MeOH, 100:0→98:2). $t_R$: 1.31 min (LC-MS 4); ESI-MS: 691.5 [M+H]$^+$ (LC-MS 4); R$_f$=0.48 (CH$_2$Cl$_2$/MeOH, 9:1).

Step 169.4: 1-[2-(tert-Butoxycarbonyl-methyl-amino)-4-methoxy-pyrimidin-5-yl]-4-[(4-cyano-phenyl)-hydroxy-methyl]-5-isopropyl-1H-pyrazole-3-carboxylic acid ethyl ester

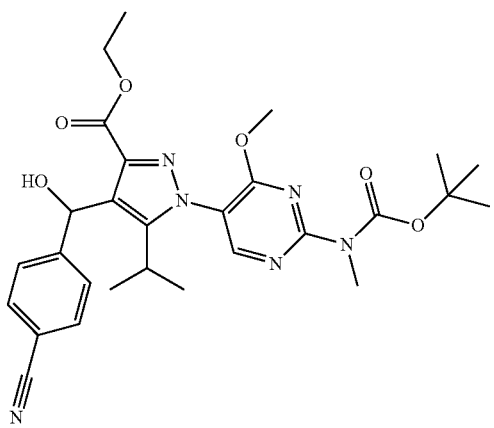 [SMILES: CCOC(=O)c1nn(-c2cnc(N(C)C(=O)OC(C)(C)C)nc2OC)c(C(C)C)c1C(O)c1ccc(C#N)cc1]

The title compound was prepared in analogy to the procedure described for step 150.3 but using the product from step 163.5. $t_R$: 1.22 min (LC-MS 4); ESI-MS: 551.3 [M+H]$^+$ (LC-MS 4); R$_f$=0.55 (hexane/EtOAc, 1:1).

Example 170

4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

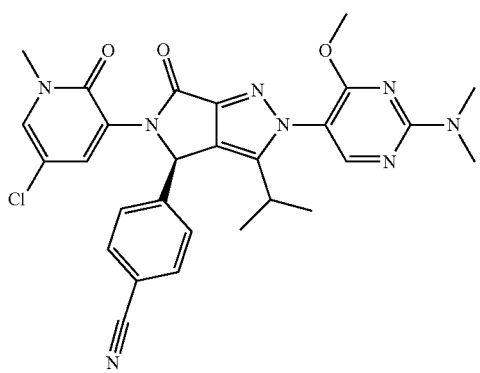 [SMILES: COc1nc(N(C)C)ncc1-n1nc2c(c1C(C)C)[C@@H](c1ccc(C#N)cc1)N(c1cc(Cl)cn(C)c1=O)C2=O]

The title compound was obtained enantiomerically pure after preparative chiral chromatography (Column: Chiralpak IC, 250×20 mm, 5 μm. Flow: 13 mL/min. Mobile phase: ethanol/methanol 1:1) of example 151. $t_R$: 27.9 min (Column: Chiralpak IC 5 μm, 250×4.6 mm, 5 μm. Flow: 1 mL/min. Mobile phase: ethanol/methanol 1:1).

Example 171

4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile

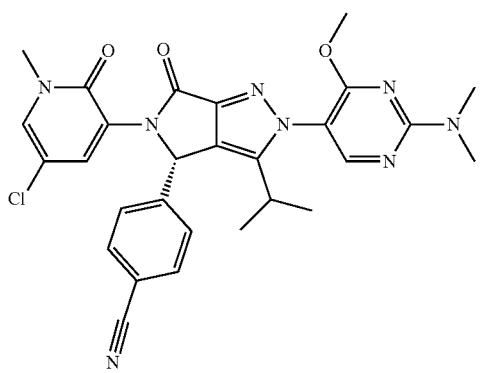 [SMILES: COc1nc(N(C)C)ncc1-n1nc2c(c1C(C)C)[C@H](c1ccc(C#N)cc1)N(c1cc(Cl)cn(C)c1=O)C2=O]

The title compound was obtained enantiomerically pure after preparative chiral chromatography (Column: Chiralpak IC, 250×20 mm, 5 μm. Flow: 13 mL/min. Mobile phase: ethanol/methanol 1:1) of example 151. $t_R$: 23.5 min (Column:

Chiralpak IC 5 μm, 250×4.6 mm, 5 μm. Flow: 1 mL/min. Mobile phase: ethanol/methanol 1:1).

Example 172

5-(5-Chloro-1-methyl-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one

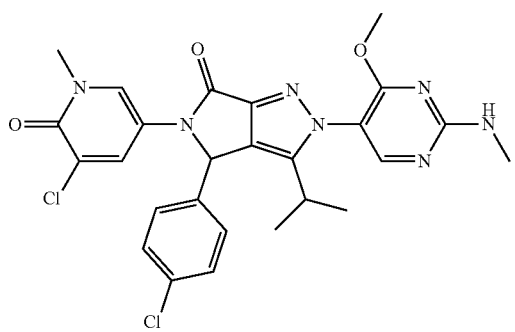 [SMILES: CNc1ncc(-n2nc3c(c2C(C)C)C(c2ccc(Cl)cc2)N(c2cc(Cl)c(=O)n(C)c2)C3=O)c(OC)n1]

The title compound was prepared in analogy to the procedure described for example 120 but using the product from step 172.1. The reaction was stirred (no microwave irradiation) for 2 h at rt. The residue was purified by silica gel column chromatography (CH$_2$Cl$_2$/MeOH, 99:1→96:4). $t_R$: 1.02 min (LC-MS 4); ESI-MS: 554.1 [M+H]$^+$ (LC-MS 4); R$_f$=0.48 (CH$_2$Cl$_2$/MeOH, 9:1).

Step 172.1: {5-[5-(5-Chloro-1-methyl-6-oxo-1,6-dihydro-pyridin-3-yl)-4-(4-chloro-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

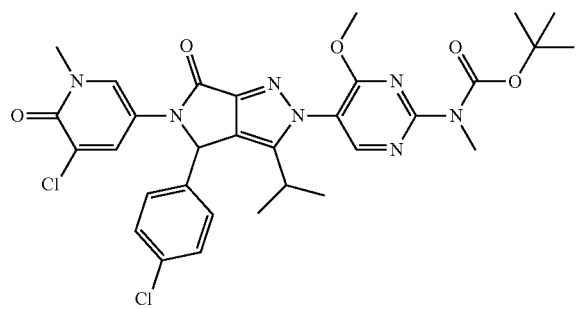 [SMILES: COc1nc(N(C)C(=O)OC(C)(C)C)ncc1-n1nc2c(c1C(C)C)C(c1ccc(Cl)cc1)N(c1cc(Cl)c(=O)n(C)c1)C2=O]

The title compound was prepared in analogy to the procedure described for step 160.1 but using the product from step 172.2. $t_R$: 1.24 min (LC-MS 4); ESI-MS: 654.2 [M+H]$^+$ (LC-MS 4); R$_f$=0.45 (CH$_2$Cl$_2$/MeOH, 9:1).

Step 172.2: 1-[2-(tert-Butoxycarbonyl-methyl-amino)-4-methoxy-pyrimidin-5-yl]-4-[(5-chloro-1-methyl-6-oxo-1,6-dihydro-pyridin-3-ylamino)-(4-chloro-phenyl)-methyl]-5-isopropyl-1H-pyrazole-3-carboxylic acid

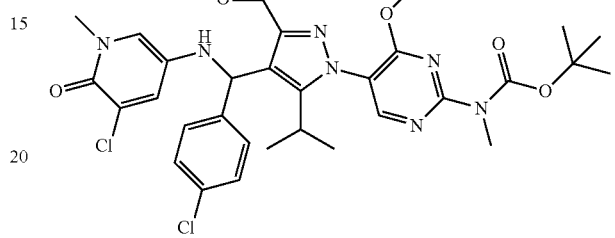

The title compound was prepared in analogy to the procedure described for step 124.2 but using the compound prepared in step 172.3, 3 equivalents of lithium hydroxide monohydrate, and stirring the reaction mixture for 1.5 h at rt. $t_R$: 1.15 min (LC-MS 4); ESI-MS: 672.3 [M+H]$^+$ (LC-MS 4).

Step 172.3: 1-[2-(tert-Butoxycarbonyl-methyl-amino)-4-methoxy-pyrimidin-5-yl]-4-[(5-chloro-1-methyl-6-oxo-1,6-dihydro-pyridin-3-ylamino)-(4-chloro-phenyl)-methyl]-5-isopropyl-1H-pyrazole-3-carboxylic acid ethyl ester

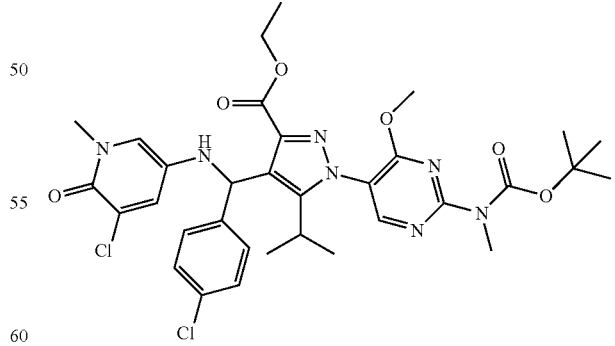

The title compound was prepared in analogy to the procedure described for step 124.3 but using the products from steps 149.3 and 163.4. The residue was purified by silica gel column chromatography (CH$_2$Cl$_2$/MeOH, 100:0→97:3). $t_R$:

1.30 min (LC-MS 4); ESI-MS: 700.3 [M+H]⁺ (LC-MS 4); R$_f$=0.41 (CH$_2$Cl$_2$/MeOH, 9:1).

Example 173

4-[5-(5-Chloro-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile

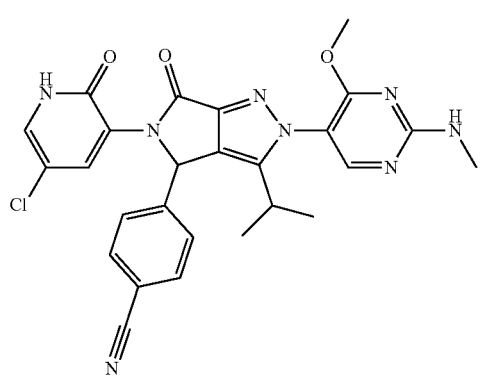

The title compound was prepared in analogy to the procedure described for example 120 but using the product from step 166.1. The reaction was performed at 100° C. for 30 min. The residue was purified by silica gel column chromatography (CH$_2$Cl$_2$/MeOH, 98:2→94:6). t$_R$: 0.88 min (LC-MS 4); ESI-MS: 531.2 [M+H]⁺ (LC-MS 4); R$_f$=0.47 (CH$_2$Cl$_2$/MeOH, 9:1).

Step 173.1: {5-[5-[5-Chloro-1-(4-methoxy-benzyl)-2-oxo-1,2-dihydro-pyridin-3-yl]-4-(4-cyano-phenyl)-3-isopropyl-6-oxo-5,6-dihydro-4H-pyrrolo[3,4-c]pyrazl-2-yl]-4-methoxy-pyrimidin-2-yl}-methyl-carbamic acid tert-butyl ester

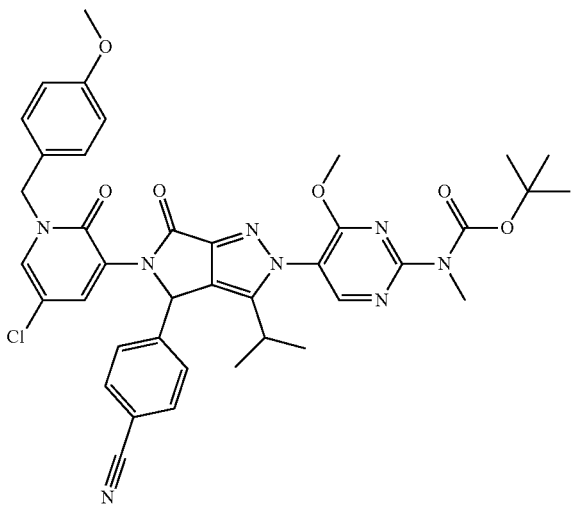 [SMILES: COc1ccc(Cn2cc(Cl)cc(N3C(=O)c4nn(-c5cnc(N(C)C(=O)OC(C)(C)C)nc5OC)c(C(C)C)c4C3c3ccc(C#N)cc3)c2=O)cc1]

The title compound was prepared in analogy to the procedure described for step 160.1 but using the product from step 173.2. t$_R$: 1.31 min (LC-MS 4); ESI-MS: 751.3 [M+H]⁺ (LC-MS 4); R$_f$=0.76 (CH$_2$Cl$_2$/MeOH, 9:1).

Step 173.2: 1-[2-(tert-Butoxycarbonyl-methyl-amino)-4-methoxy-pyrimidin-5-yl]-4-[[5-chloro-1-(4-methoxy-benzyl)-2-oxo-1,2-dihydro-pyridin-3-ylamino]-(4-cyano-phenyl)-methyl]-5-isopropyl-1H-pyrazole-3-carboxylic acid

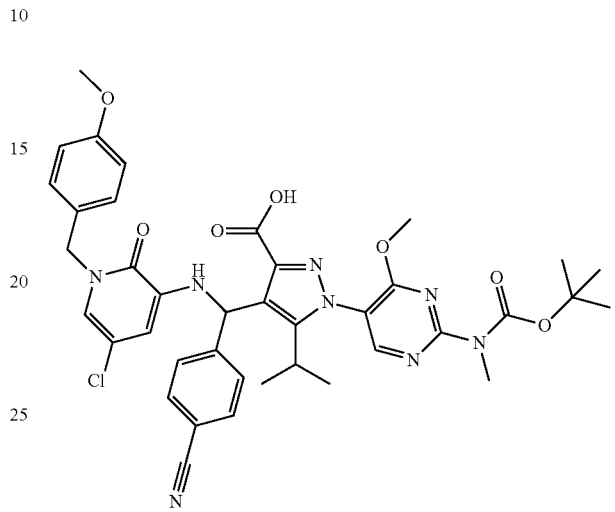

The title compound was prepared in analogy to the procedure described for step 173.3 but using the compound prepared in step 166.3, 3 equivalents of lithium hydroxide monohydrate, and stirring the reaction mixture for 2 h at rt. t$_R$: 1.30 min (LC-MS 4); ESI-MS: 769.4 [M+H]⁺ (LC-MS 4).

Step 173.3: 1-[2-(tert-Butoxycarbonyl-methyl-amino)-4-methoxy-pyrimidin-5-yl]-4-[[5-chloro-1-(4-methoxy-benzyl)-2-oxo-1,2-dihydro-pyridin-3-ylamino]-(4-cyano-phenyl)-methyl]-5-isopropyl-1H-pyrazole-3-carboxylic acid ethyl ester

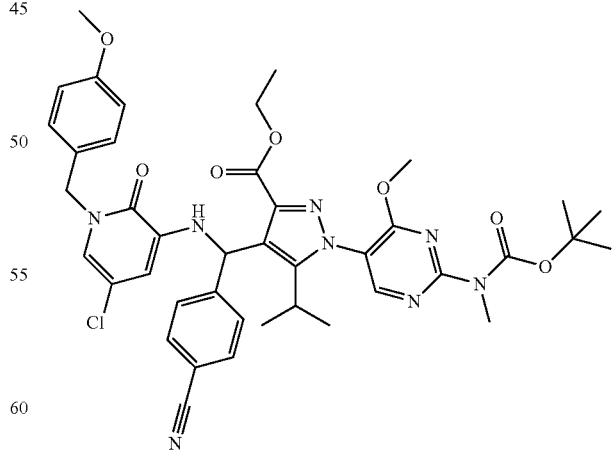

The title compound was prepared in analogy to the procedure described for step 124.3 but using the compounds prepared in steps 152.4 and 169.4. The residue was purified by silica gel column chromatography (hexane/EtOAc, 85:15→55:45). $t_R$: 1.40 min (LC-MS 4); ESI-MS: 797.3 [M+H]$^+$ (LC-MS 4); $R_f$=0.57 (hexane/EtOAc, 1:1).

Example 174

4-[5-(5-Chloro-1-methyl-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile

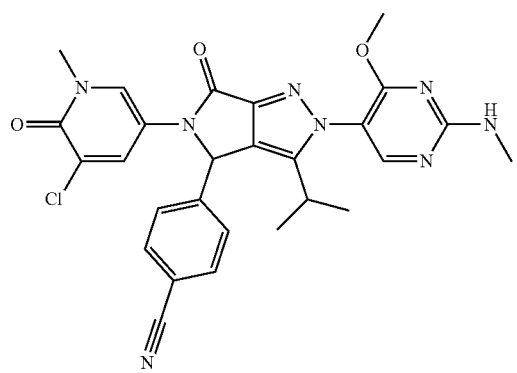 [SMILES: CNc1ncc(-n2nc3c(c2C(C)C)C(c2ccc(C#N)cc2)N(c2cc(Cl)c(=O)n(C)c2)C3=O)c(OC)n1]

The title compound was prepared in analogy to the procedure described for example 120 but using the product from step 174.1. The reaction was stirred (no microwave irradiation) for 2 h at rt. The residue was purified by silica gel column chromatography (CH$_2$Cl$_2$/MeOH, 99:1→97:3). $t_R$: 0.90 min (LC-MS 4); ESI-MS: 545.2 [M+H]$^+$ (LC-MS 4); $R_f$=0.47 (CH$_2$Cl$_2$/MeOH, 9:1).

Step 174.1: 5-[5-(5-Chloro-1-methyl-6-oxo-1,6-dihydro-pyridin-3-yl)-4-(4-cyano-phenyl)-3-isopropyl-6-oxo-5,6-dihydro-4H-pyrrolo[3,4-c]pyrazol-2-yl]-4-methoxy-pyrimidin-2-yl]-methyl-carbamic acid tert-butyl ester

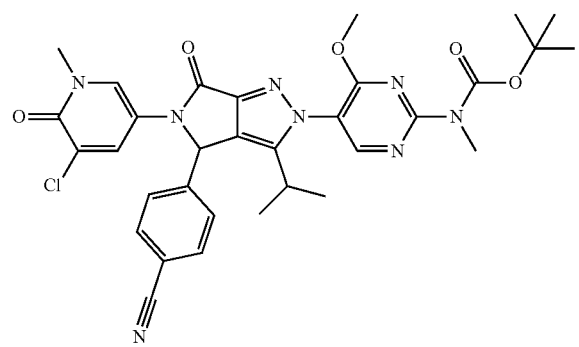 [SMILES: COc1nc(N(C)C(=O)OC(C)(C)C)ncc1-n1nc2c(c1C(C)C)C(c1ccc(C#N)cc1)N(c1cc(Cl)c(=O)n(C)c1)C2=O]

The title compound was prepared in analogy to the procedure described for step 160.1 but using the product from step 174.2. $t_R$: 1.12 min (LC-MS 4); ESI-MS: 645.2 [M+H]$^+$ (LC-MS 4); $R_f$=0.55 (CH$_2$Cl$_2$/MeOH, 9:1).

Step 174.2: 1-[2-(tert-Butoxycarbonyl-methyl-amino)-4-methoxy-pyrimidin-5-yl]-4-[(5-chloro-1-methyl-6-oxo-1,6-dihydro-pyridin-3-ylamino)-(4-cyano-phenyl)-methyl]-5-isopropyl-1H-pyrazole-3-carboxylic acid

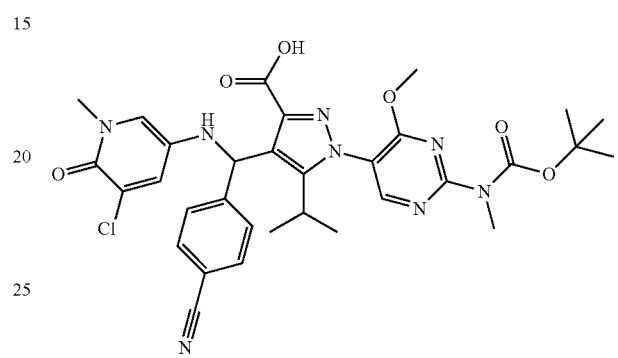

The title compound was prepared in analogy to the procedure described for step 124.2 but using the compound prepared in step 174.3, 3 equivalents of lithium hydroxide monohydrate, and stirring the reaction mixture for 1 h at rt. $t_R$: 1.04 min (LC-MS 4); ESI-MS: 663.2 [M+H]$^+$ (LC-MS 4).

Step 174.3: 1-[2-(tert-Butoxycarbonyl-methyl-amino)-4-methoxy-pyrimidin-5-yl]-4-[(5-chloro-1-methyl-6-oxo-1,6-dihydro-pyridin-3-ylamino)-(4-cyano-phenyl)-methyl]-5-isopropyl-1H-pyrazole-3-carboxylic acid ethyl ester

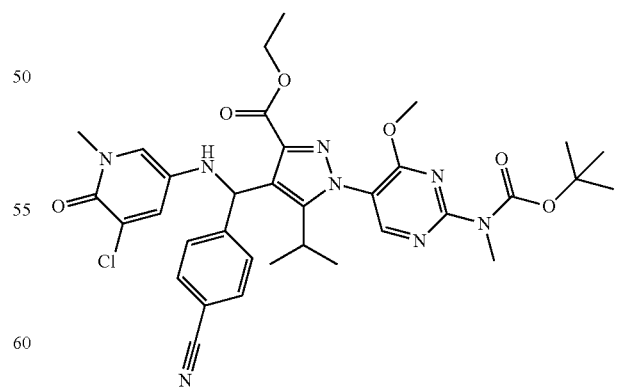

The title compound was prepared in analogy to the procedure described for step 124.3 but using the compounds prepared in steps 149.3 and 169.4. The residue was purified by silica gel column chromatography (CH$_2$Cl$_2$/MeOH, 100:0→97:3). t$_R$: 1.16 min (LC-MS 4); ESI-MS: 691.3 [M+H]$^+$ (LC-MS 4); R$_f$=0.62 (CH$_2$Cl$_2$/MeOH, 9:1).

Example 175

4-[5-(5-Chloro-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile

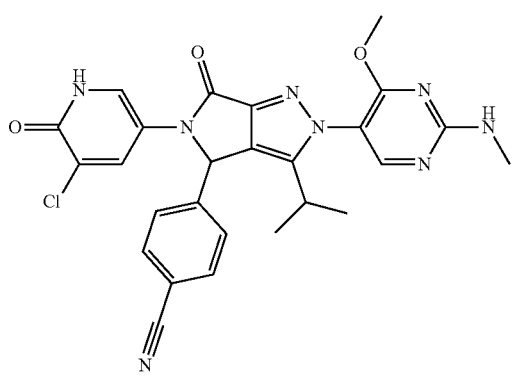 [SMILES: CNc1ncc(-n2nc3c(c2C(C)C)C(c2ccc(C#N)cc2)N(c2c[nH]c(=O)c(Cl)c2)C3=O)c(OC)n1]

The title compound was prepared in analogy to the procedure described for example 120 but using the product from step 175.1. The reaction was performed at 100° C. for 30 min. The residue was purified by silica gel column chromatography (CH$_2$Cl$_2$/MeOH, 98:2→94:6). t$_R$: 0.85 min (LC-MS 4); ESI-MS: 531.2 [M+H]$^+$ (LC-MS 4); R$_f$=0.18 (CH$_2$Cl$_2$/MeOH, 9:1).

Step 175.1: {5-[5-[5-Chloro-1-(4-methoxy-benzyl-6-oxo-1,6-dihydro-pyridin-3-yl]-4-(4-cyano-phenyl)-3-isopropyl-6-oxo-5,6-dihydro-4H-pyrrolo[3,4-c]pyrazol-2-yl]-4-methoxy-pyrimidin-2-yl}-methyl-carbamic acid tert-butyl ester

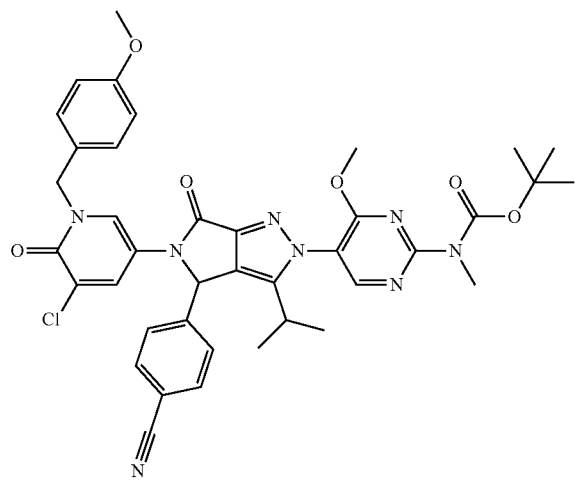 [SMILES: COc1ccc(Cn2cc(N3C(=O)c4nn(-c5cnc(N(C)C(=O)OC(C)(C)C)nc5OC)c(C(C)C)c4C3c3ccc(C#N)cc3)cc(Cl)c2=O)cc1]

The title compound was prepared in analogy to the procedure described for step 160.1 but using the product from step 175.2. The residue was purified by silica gel column chromatography (CH$_2$Cl$_2$/MeOH, 99.5:0.5→97.5:2.5). t$_R$: 1.24 min (LC-MS 4); ESI-MS: 751.3 [M+H]$^+$ (LC-MS 4); R$_f$=0.55 (CH$_2$Cl$_2$/MeOH, 1:1).

Step 175.2: 1-[2-(tert-Butoxycarbonyl-methyl-amino)-4-methoxy-pyrimidin-5-yl]-4-[[5-chloro-1-(4-methoxy-benzyl-6-oxo-1,6-dihydro-pyridin-3-ylamino]-(4-cyano-phenyl)-methyl]-5-isopropyl-1H-pyrazole-3-carboxylic acid

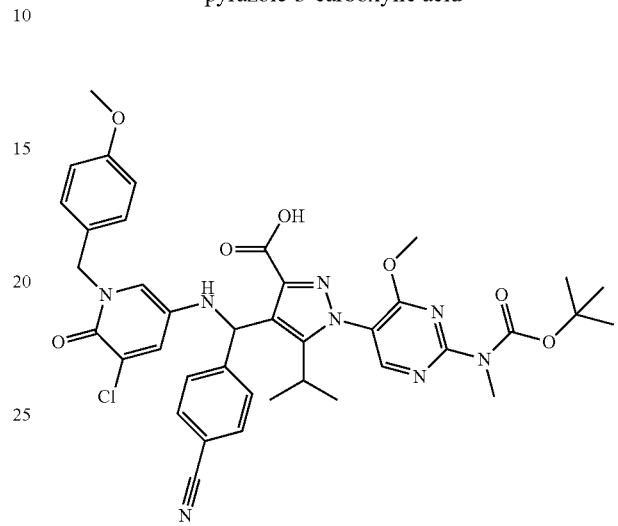

The title compound was prepared in analogy to the procedure described for step 124.2 but using the compound prepared in step 175.3, 3 equivalents of lithium hydroxide monohydrate, and stirring the reaction mixture for 1 h at rt. t$_R$: 1.16 min (LC-MS 4); ESI-MS: 769.5 [M+H]$^+$ (LC-MS 4).

Step 175.3: 1-[2-(tert-Butoxycarbonyl-methyl-amino)-4-methoxy-pyrimidin-5-yl]-4-[[5-chloro-1-(4-methoxy-benzyl)-6-oxo-1,6-dihydro-pyridin-3-ylamino]-(4-cyano-phenyl)-methyl]-5-isopropyl-1H-pyrazole-3-carboxylic acid ethyl ester

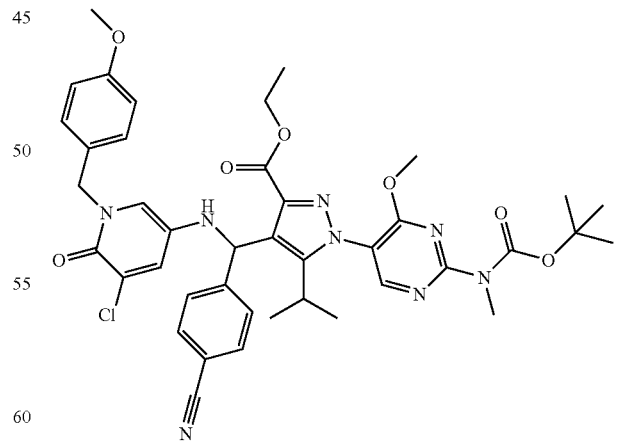

The title compound was prepared in analogy to the procedure described for step 124.3 but using the compounds prepared in steps 155.4 and 169.4. t$_R$: 1.27 min (LC-MS 4); ESI-MS: 797.3 [M+H]$^+$ (LC-MS 4); R$_f$=0.23 (hexane/EtOAc, 1:1).

Example 176

(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one

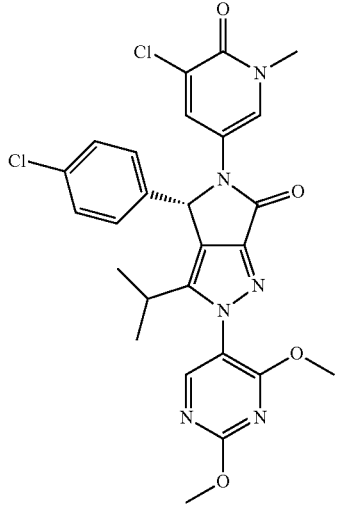 [SMILES: COc1ncc(-n2nc3c(c2C(C)C)[C@H](c2ccc(Cl)cc2)N(c2cc(Cl)c(=O)n(C)c2)C3=O)c(OC)n1]

The title compound was obtained enantiomerically pure after preparative chiral chromatography of example 164 (System: PLC 2020; Column: Chiralpak iA 5 μm, 2×25 cm; Mobile phase: heptane/ethanol/methanol 70:15:15; Flow: 15 ml/min; Injection volume: 4 ml; Detection UV: 210 and 254 nm; Concentration: 0.2 g/4 ml methanol+ethanol). LCMS: (M+H)=555/557; $t_R$=1.04 min (LC-MS 4). HPLC: $t_R$=10.12 min (System: Agilent 1200 Chemstation; Column: Chiralpak iA 5 μm, 250×4.6 mm; Flow: 1.0 ml/min; Mobile Phase: heptane/ethanol/MeOH 70:15:15; Detection: 254 nm). 1H-NMR (DMSO-$d_6$, 400 MHz) δ ppm 8.59 (s, 1H) 7.94 (d, 2H) 7.40 (d, 2H) 7.34 (d, 2H) 6.31 (s, 1H) 3.98 (s, 3H) 3.92 (s, 3H) 3.44 (s, 3H) 2.61 (m, 1H) 1.09 (d, 3H) 0.46 (d, 3H).

Example 177

(R)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one

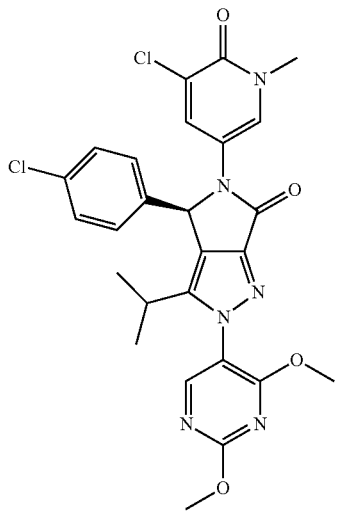 [SMILES: COc1ncc(-n2nc3c(c2C(C)C)[C@@H](c2ccc(Cl)cc2)N(c2cc(Cl)c(=O)n(C)c2)C3=O)c(OC)n1]

The title compound was obtained enantiomerically pure after preparative chiral chromatography of example 164 (System: PLC 2020; Column: Chiralpak iA 5 μm, 2×25 cm; mobile phase: heptane/ethanol/methanol 70:15:15; flow: 15 ml/min; Injection volume: 4 ml; detection UV: 210 and 254 nm; concentration: 0.2 g/4 ml methanol+ethanol). LCMS: (M+H)=555/557; $t_R$=1.04 min (LC-MS 4). HPLC: $t_R$=17.13 min (System: Agilent 1200 Chemstation; Column: Chiralpak iA 5 μm, 250×4.6 mm; Flow: 1.0 ml/min; Mobile Phase: heptane/ethanol/MeOH 70:15:15; Detection: 254 nm). 1H-NMR (DMSO-d6, 400 MHz) δ ppm 8.59 (s, 1H) 7.94 (d, 2H) 7.40 (d, 2H) 7.34 (d, 2H) 6.31 (s, 1H) 3.98 (s, 3H) 3.92 (s, 3H) 3.44 (s, 3H) 2.61 (m, 1H) 1.09 (d, 3H) 0.46 (d, 3H).

Example 178

(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile

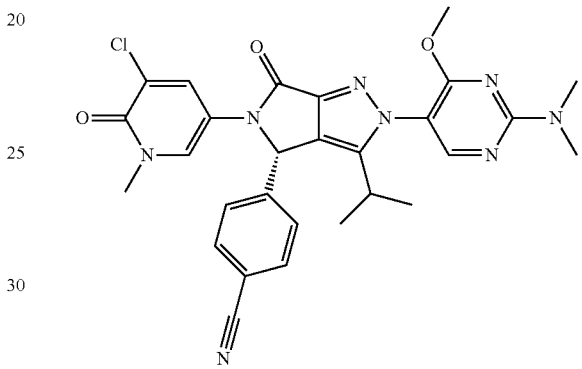

The title compound was obtained enantiomerically pure after preparative chiral chromatography of example 150 (System: PLC 2020; Column: Chiralpak OD-H 5 μm, 2×25 cm; Mobile phase: heptane/ethanol/methanol 80:10:10; Flow: 15 ml/min; injection volume: 4 ml; detection UV: 210 and 240 nm; concentration: 0.1 g/4 ml methanol+ethanol). HPLC: $t_R$=16.88 min (System: Agilent 1200 Chemstation; Column: Chiralcel OD-H 5 μm, 250×4.6 mm; Flow: 1.0 ml/min; Mobile Phase: heptane/ethanol/MeOH 80:10:10; Detection: 240 nm). 1H-NMR (DMSO-d6, 400 MHz) δ ppm 8.25 (s, 1H) 7.93 (s, 2H) 7.83 (d, 2H) 7.53 (d, 2H) 6.38 (s, 1H) 3.86 (s, 3H) 3.42 (s, 3H) 3.17 (s, 6H) 2.61 (m, 1H) 1.08 (d, 3H) 0.42 (d, 3H).

Example 179

(R)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile

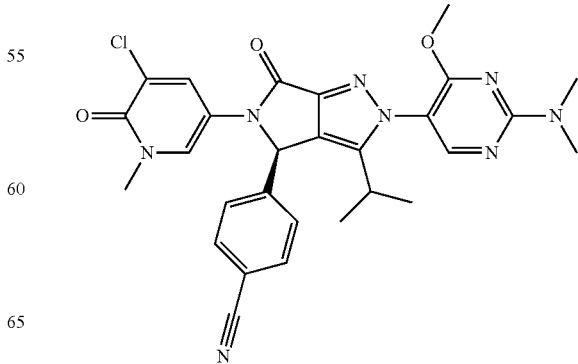

The title compound was obtained enantiomerically pure after preparative chiral chromatography of example 150 (System: Gilson PLC 2020; column: Chiralpak OD-H 5 µm, 2×25 cm; mobile phase: heptane/ethanol/methanol 80:10:10; flow: 15 ml/min; injection volume: 4 ml; detection UV: 210 and 240 nm; concentration: 0.1 g/4 ml methanol+ethanol). HPLC: $t_R$=24.42 min (System: Agilent 1200 Chemstation; Column: Chiralcel OD-H 5 µm, 250×4.6 mm; Flow: 1.0 ml/min; Mobile Phase: Heptane/Ethanol/MeOH 80:10:10; Detection: 240 nm). 1H-NMR (DMSO-d6, 400 MHz) δ ppm 8.24 (s, 1H) 7.93 (s, 2H) 7.83 (d, 2H) 7.53 (d, 2H) 6.38 (s, 1H) 3.86 (s, 3H) 3.43 (s, 3H) 3.17 (s, 6H) 2.61 (m, 1H) 1.08 (d, 3H) 0.42 (d, 3H).

Example 180

((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one

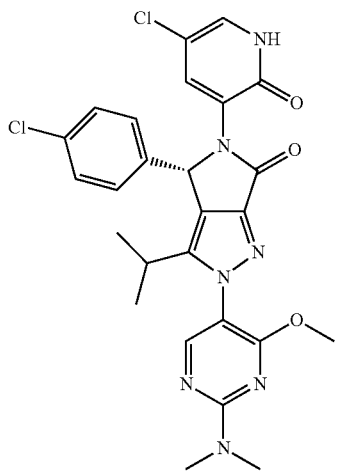 [SMILES: COc1nc(N(C)C)ncc1-n1nc2c(c1C(C)C)[C@H](c1ccc(Cl)cc1)N(c1cc(Cl)c[nH]c1=O)C2=O]

The title compound was obtained enantiomerically pure after preparative chiral chromatography of example 147 (System: Gilson PLC 2020; column: Chiralpak IC 5 µm, 2×25 cm; mobile phase: heptane/ethanol 55:45; flow: 15 ml/min; injection volume: 4 ml; detection UV: 210 and 250 nm; concentration: 15 mg/2 ml methanol+ethanol). LCMS: (M+H)=554/556; $t_R$=1.44 min (LC-MS 4). HPLC: $t_R$=12.62 min (System: Agilent 1200 Chemstation; Column: Chiralpak IC 5 µm, 250×4.6 mm; Flow: 1.1 ml/min; Mobile Phase: Heptane/Ethanol 1:1; Detection: 250 nm). 1H-NMR (DMSO-d6, 400 MHz) δ ppm 12.29 (bs, 1H) 8.26 (s, 1H) 7.55 (d, 2H) 7.38 (d, 2H) 7.26 (d, 2H) 6.54 (s, 1H) 3.86 (s, 3H) 3.17 (s, 6H) 2.58 (m, 1H) 1.06 (d, 3H) 0.46 (d, 3H).

Example 181

((R)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one

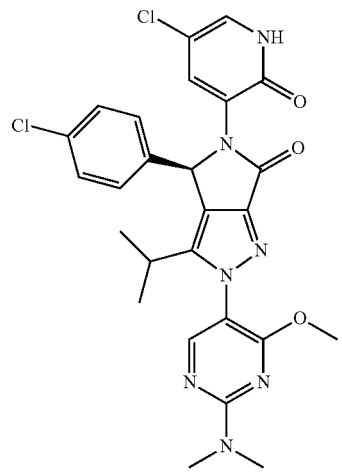 [SMILES: COc1nc(N(C)C)ncc1-n1nc2c(c1C(C)C)[C@@H](c1ccc(Cl)cc1)N(c1cc(Cl)c[nH]c1=O)C2=O]

The title compound was obtained enantiomerically pure after preparative chiral chromatography of example 147 (System: PLC 2020; column: Chiralpak IC 5 µm, 2×25 cm; mobile phase: heptane/ethanol 55:45; flow: 15 ml/min; injection volume: 4 ml; detection UV: 210 and 250 nm; concentration: 15 mg/2 ml methanol+ethanol). LCMS: (M+H)=554/556; $t_R$=1.44 min (LC-MS 4). HPLC: $t_R$=13.86 min (System: Agilent 1200 Chemstation; Column: Chiralpak IC 5 µm, 250×4.6 mm; Flow: 1.1 ml/min; Mobile Phase: Heptane/Ethanol 1:1; Detection: 250 nm). 1H-NMR (DMSO-d6, 400 MHz) δ ppm 12.28 (s, 1H) 8.26 (s, 1H) 7.55 (d, 2H) 7.38 (d, 2H) 7.26 (d, 2H) 6.54 (s, 1H) 3.86 (s, 3H) 3.17 (s, 6H) 2.58 (m, 1H) 1.07 (d, 3H) 0.46 (d, 3H).

Example 182

(R)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile

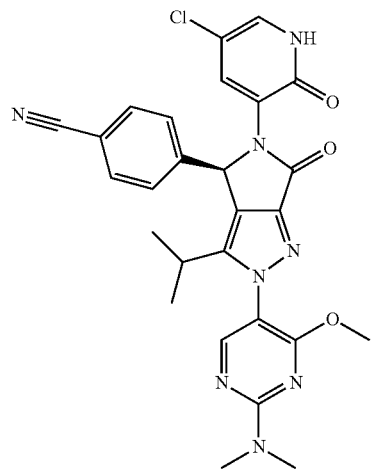 [SMILES: COc1nc(N(C)C)ncc1-n1nc2c(c1C(C)C)[C@@H](c1ccc(C#N)cc1)N(c1cc(Cl)c[nH]c1=O)C2=O]

The title compound was obtained enantiomerically pure after preparative chiral chromatography of example 157 (System: LaPrep+Injector; column: AD 20 μm, 5×50 cm; mobile phase: heptane/isopropyl alcohol/MeOH 50:40:10; flow: 100 ml/min; injection volume: 50 ml; detection UV: 210 nm; concentration: 2050 mg/50 ml methanol+ethanol at 60° C.). LCMS: (M+H)=545; $t_R$=1.01 min (LC-MS 4). HPLC: $t_R$=9.72 min (System: Shimadzu SCL 10A; Column: AD 20 μm, 250×4.6 mm; Flow: 1.0 ml/min; Mobile Phase: Heptane/IPA/MeOH 50:40:10; Detection: 220 nm). 1H-NMR (DMSO-d6, 400 MHz) δ ppm 12.31 (bs, 1H) 8.26 (s, 1H) 7.80 (d, 2H) 7.56 (s, 2H) 7.48 (d, 2H) 6.63 (s, 1H) 3.86 (s, 3H) 3.17 (s, 6H) 2.59 (m, 1H) 1.06 (d, 3H) 0.42 (d, 3H).

Example 183

(S)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile

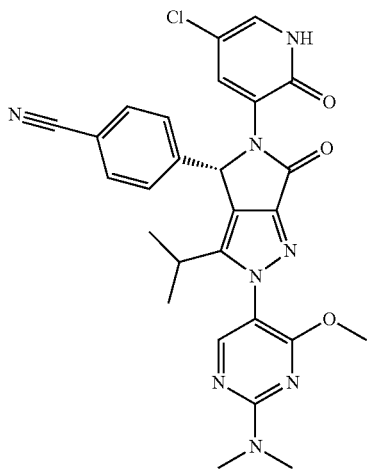 [SMILES: COc1nc(N(C)C)ncc1-n1nc2c(c1C(C)C)[C@H](c1ccc(C#N)cc1)N(c1cc(Cl)c[nH]c1=O)C2=O]

The title compound was obtained enantiomerically pure after preparative chiral chromatography of example 157 (System: LaPrep+Injector; column: AD 20 μm, 5×50 cm; mobile phase: heptane/isopropyl alcohol/MeOH 50:40:10; flow: 100 ml/min; injection volume: 50 ml; detection UV: 210 nm; concentration: 2050 mg/50 ml methanol+ethanol at 60° C.). LCMS: (M+H)=545; $t_R$=1.01 min (LC-MS 4). HPLC: $t_R$=25.82 min (System: Shimadzu SCL 10A; Column: AD 20 μm, 250×4.6 mm; Flow: 1.0 ml/min; Mobile Phase: Heptane/IPA/MeOH 50:40:10; Detection: 220 nm). 1H-NMR (DMSO-d6, 400 MHz) δ ppm 12.31 (bs, 1H) 8.26 (s, 1H) 7.80 (d, 2H) 7.56 (s, 2H) 7.48 (d, 2H) 6.63 (s, 1H) 3.86 (s, 3H) 3.17 (s, 6H) 2.59 (m, 1H) 1.06 (d, 3H) 0.42 (d, 3H).

Example 184

5-(5-Chloro-1-methyl-6-oxo-1,6-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one

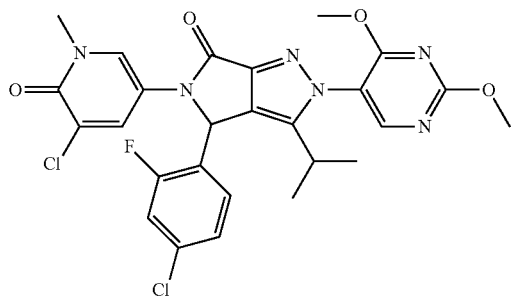 [SMILES: COc1ncc(-n2nc3c(c2C(C)C)C(c2ccc(Cl)cc2F)N(c2cc(Cl)c(=O)n(C)c2)C3=O)c(OC)n1]

A solution of 460 mg (0.739 mmol) 4-((5-chloro-1-methyl-6-oxo-1,6-dihydropyridin-3-ylamino)(4-chloro-2-fluorophenyl)methyl)-1-(2,4-dimethoxypyrimidin-5-yl)-5-isopropyl-1H-pyrazole-3-carboxylic acid (product from step 184.1) in 14.8 ml $CH_2Cl_2$ under argon was cooled down to 0° C. and 0.137 ml (1.034 mmol) of 1-chloro-N,N,2-trimethyl-prop-1-en-1-amine was added drop wise and the solution was stirred at 0° C. for 25 min. The reaction mixture was given to 30 ml of a 1M $NaHCO_3$ solution and extracted twice with 60 ml EtOAc. The combined organic phases were dried ($Na_2SO_4$), filtered and evaporated. The crude product was purified by column chromatography (Silicagel, heptane/EtOAc 1:1, EtOAc), then by prep-HPLC (Column: Sunfire C18, 30×100 mm, 5 μm. Flow: 30 ml/min. Gradient: 5% to 100% B in 20 min; A=0.1% TFA in water, B=0.1% TFA in acetonitrile) to give 252 mg (0.435 mmol, 58.9% yield) of the title compound as a beige foam. LCMS: (M+H)=573/575; $t_R$=1.06 min (LC-MS 4). HPLC: $t_R$=5.24 min (HPLC 7). TLC: R=0.41 ($CH_2Cl_2$/MeOH 10:1). 1H-NMR (DMSO-d6, 600 MHz) δ ppm 8.61 (s, 1H) 7.95 (m, 2H) 7.48-7.31 (m, 3H) 6.53 (bs, 1H) 3.99 (s, 3H) 3.94 (s, 3H) 3.46 (s, 3H) 2.66 (m, 1H) 1.09 (d, 3H) 0.54 (d, 3H).

Step 184.1: 4-((5-Chloro-1-methyl-6-oxo-1,6-dihydropyridin-3-ylamino)(4-chloro-2-fluorophenyl)methyl)-1-(2,4-dimethoxypyrimidin-5-yl)-5-isopropyl-1H-pyrazole-3-carboxylic acid

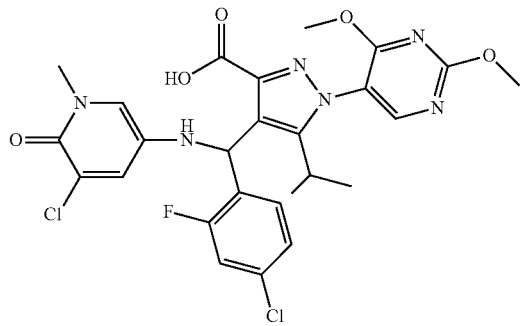 [SMILES: COc1ncc(-n2nc(C(=O)O)c(C(Nc3cc(Cl)c(=O)n(C)c3)c3ccc(Cl)cc3F)c2C(C)C)c(OC)n1]

A solution of 465 mg (0.743 mmol) ethyl 4-((5-chloro-1-methyl-6-oxo-1,6-dihydropyridin-3-ylamino)(4-chloro-2- fluorophenyl)methyl)-1-(2,4-dimethoxypyrimidin-5-yl)-5-isopropyl-1H-pyrazole-3-carboxylate (product from step 184.2) in 7.42 ml THF/MeOH (1:1) under N₂ atmosphere was cooled down to 0° C. After that 2.60 ml (5.20 mmol) of a 2M NaOH solution was added drop wise and the solution was stirred at 0° C. for 10 min and at RT for 1.5 hour. The solvent was evaporated, diluted in 50 ml CH₂Cl₂ and washed with 1M citric acid aqueous solution (30 ml). The water phase was extracted twice with CH₂Cl₂. The combined organic phases were dried (Na₂SO₄), filtered and evaporated to give 461 mg (0.741 mmol, 100% yield) of the title compound as a foam, which was used in the next step without purification. LCMS: (M+H)=591/593; $t_R$=0.97 min (LC-MS 4). HPLC: $t_R$=4.69 min (HPLC 7). TLC: R=0.14 (CH₂Cl₂/MeOH 20:1).

Step 184.2: Ethyl 4-((5-chloro-1-methyl-6-oxo-1,6-dihydropyridin-3-ylamino)(4-chloro-2-fluorophenyl)methyl)-1-(2,4-dimethoxypyrimidin-5-yl)-5-isopropyl-1H-pyrazole-3-carboxylate

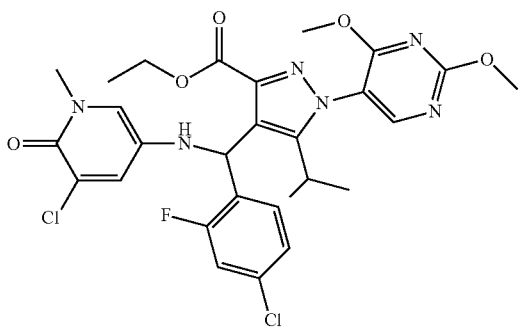 [SMILES: CCOC(=O)c1nn(-c2cnc(OC)nc2OC)c(C(C)C)c1C(Nc1cc(Cl)c(=O)n(C)c1)c1ccc(Cl)cc1F]

A solution of 485 mg (0.944 mmol) ethyl 4-((4-chloro-2-fluorophenyl)(hydroxy)methyl)-1-(2,4-dimethoxypyrimidin-5-yl)-5-isopropyl-1H-pyrazole-3-carboxylate (product from step 184.3), 0.658 ml (4.72 mmol) TEA in 19 ml CH₂Cl₂ was cooled down to 0° C. 411 mg (1.41 mmol) methanesulfonic anhydride was added and the solution was allowed to warm to RT. 229 mg (1.416 mmol) 5-amino-3-chloro-1-methylpyridin-2(1H)-one (intermediate W1) was added and the solution was stirred for 1.5 hour. The mixture was diluted with CH₂Cl₂ and washed with 1M NaHCO₃ solution. The water phase was extracted with CH₂Cl₂. The combined organic phases were dried (Na₂SO₄), filtered and evaporated. The crude product was purified by column chromatography (Silicagel, heptane, EtOAc) to give 474 mg (0.758 mmol, 80% yield) of the title compound as a brown oil. LCMS: (M+H)=619/621; $t_R$=1.13 min (LC-MS 4). HPLC: $t_R$=5.52 min (HPLC 7). TLC: Rf=0.09 (Heptane/EtOAc 1:2).

Step 184.3: Ethyl 4-((4-chloro-2-fluorophenyl)(hydroxy)methyl)-1-(2,4-dimethoxypyrimidin-5-yl)-5-isopropyl-1H-pyrazole-3-carboxylate

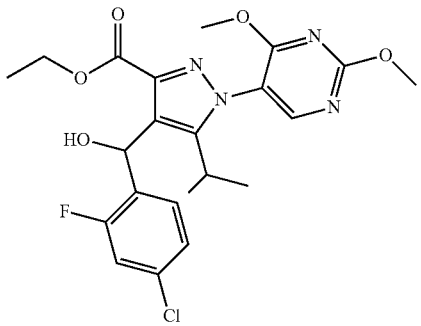 [SMILES: CCOC(=O)c1nn(-c2cnc(OC)nc2OC)c(C(C)C)c1C(O)c1ccc(Cl)cc1F]

To a solution of ethyl 1-(2,4-dimethoxypyrimidin-5-yl)-4-iodo-5-isopropyl-1H-pyrazole-3-carboxylate (product from step 184.4, 1.15 g, 2.55 mmol) in 14 ml THF, a solution of 1M isopropylmagnesium chloride lithium chloride complex (2.68 ml, 2.68 mmol) was added at 0° C. and the mixture was stirred for 15 min. Then the solution was cooled down to −78° C. and a solution of 4-chloro-2-fluorobenzaldehyde (405 mg, 2.55 mmol) in 3 ml THF was added. The reaction mixture was stirred for 30 min at temperatures between −78° C. to −20° C. The solution was quenched with 10 ml of 1M NH₄Cl solution, washed with brine and extracted 3 times with EtOAc. The combined organic phases were dried (Na₂SO₄), filtered and evaporated. The crude product was purified by chromatography (Silicagel, heptane, heptane/EtOAc 1:4) to give 977 mg (1.901 mmol, 74.5% yield) of the title compound as a white foam. LCMS: (M+H)=479; $t_R$=1.18 min (LC-MS 4). HPLC: $t_R$=5.48 min (HPLC 7). TLC: Rf=0.35 (Heptane/EtOAc 1:2).

Step 184.4: Ethyl 1-(2,4-dimethoxypyrimidin-5-yl)-4-iodo-5-isopropyl-1H-pyrazole-3-carboxylate

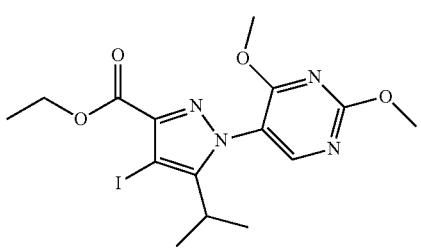 [SMILES: CCOC(=O)c1nn(-c2cnc(OC)nc2OC)c(C(C)C)c1I]

To a stirred solution of 1-(2,4-dimethoxy-pyrimidin-5-yl)-5-isopropyl-1H-pyrazole-3-carboxylic acid ethyl ester (intermediate AY, 3.24 g, 10 mmol) in 100 ml acetonitrile, I₂ (1.53 g, 6.0 mmol) and ceric ammonium nitrate (3.29 g, 6.0 mmol) were added and the solution was stirred at 80° for 6 hours. The mixture was added to a stirred 1M sodium thiosulfate solution (200 ml) and extracted twice with EtOAc. The solution was washed with a 1M NaHCO₃ solution, brine, dried (Na₂SO₄), filtered and evaporated. The crude product was purified by chromatography (Silicagel, Heptane/EtOAc 80:20 to 70:30) to give 3.20 g (7.17 mmol, 71.6% yield) of the title compound as a white foam. LCMS: (M+H)=447; $t_R$=1.14 min (LC-MS 4). HPLC: $t_R$=5.28 min (HPLC 7). TLC: Rf=0.31 (Heptane/EtOAc 1:1).

Example 185

5-(5-chloro-1-methyl-2-oxo-1,2-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one

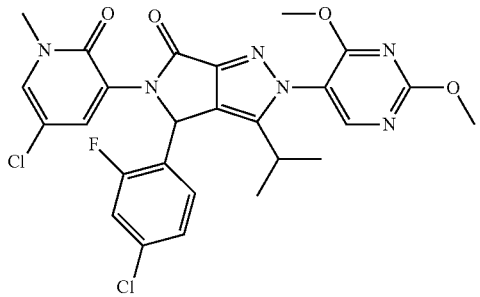 [SMILES: COc1ncc(-n2nc3c(c2C(C)C)C(c2ccc(Cl)cc2F)N(c2cc(Cl)cn(C)c2=O)C3=O)c(OC)n1]

The title compound was prepared in analogy to the procedure described in example 184 but using the product of step 185.1. LCMS: (M+H)=573/575; $t_R$=1.13 min (LC-MS 4). HPLC: $t_R$=5.48 min (HPLC 7). TLC: Rf=0.52 (CH$_2$Cl$_2$/MeOH 10:1). 1H-NMR (DMSO-d6, 600 MHz) δ ppm 8.62 (s, 1H) 8.01 (s, 1H) 7.58-7.27 (m, 4H) 6.80 (bs, 1H) 3.99 (s, 3H) 3.94 (s, 3H) 3.44 (s, 3H) 2.65 (m, 1H) 1.10 (d, 3H) 0.53 (d, 3H).

Step 185.1: 4-((5-chloro-1-methyl-2-oxo-1,2-dihydropyridin-3-ylamino)(4-chloro-2-fluorophenyl)methyl)-1-(2,4-dimethoxypyrimidin-5-yl)-5-isopropyl-1H-pyrazole-3-carboxylic acid

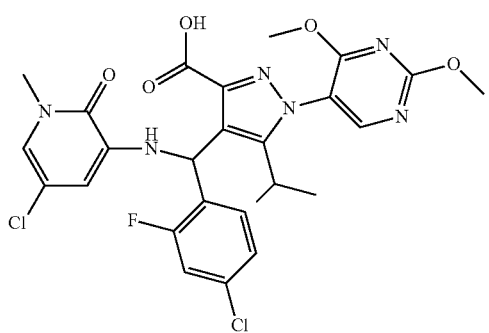 [SMILES: COc1ncc(-n2nc(C(=O)O)c(C(Nc3cc(Cl)cn(C)c3=O)c3ccc(Cl)cc3F)c2C(C)C)c(OC)n1]

The title compound was prepared in analogy to the procedure described in step 184.1 but using the product of step 185.2. LCMS: (M+H)=591/593; $t_R$=1.15 min (LC-MS 4). HPLC: $t_R$=5.62 min (HPLC 7). TLC: Rf=0.19 (CH$_2$Cl$_2$/MeOH 20:1).

Step 185.2: Ethyl 4-((5-chloro-1-methyl-2-oxo-1,2-dihydropyridin-3-ylamino)(4-chloro-2-fluorophenyl)methyl)-1-(2,4-dimethoxypyrimidin-5-yl)-5-isopropyl-1H-pyrazole-3-carboxylate

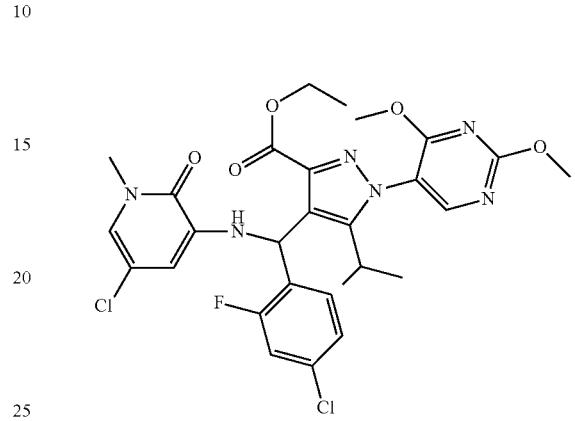

The title compound was prepared in analogy to the procedure described in step 184.2 but using 3-amino-5-chloro-1-methyl-1H-pyridin-2-one (intermediate BJ). LCMS: (M+H)= 619/621; $t_R$=1.29 min (LC-MS 4). HPLC: $t_R$=6.06 min (HPLC 7). TLC: Rf=0.15 (Heptane/EtOAc 1:2). 1H-NMR (DMSO-d6, 400 MHz) δ ppm 8.60 (d, 1H) 7.39 (d, 1H) 7.25-7.19 (m, 3H) 6.54-6.43 (m, 2H) 6.15 (m, 1H) 4.11 (m, 2H) 3.98 (s, 3H) 3.92 (m, 3H) 3.44 (s, 3H) 3.23 (m, 1H) 1.17-0.97 (m, 9H).

Example 186

5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one

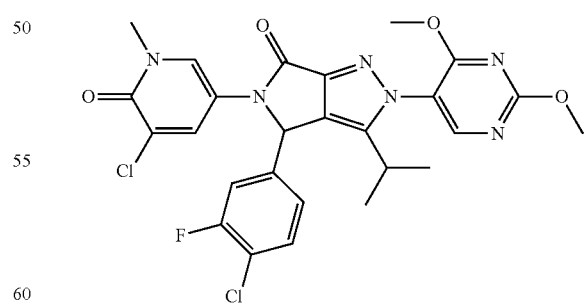

The title compound was prepared in analogy to the procedure described in example 184 but using the product of step 186.1. LCMS: (M+H)=573/575; $t_R$=1.05 min (LC-MS 4). HPLC: $t_R$=5.24 min (HPLC 7). TLC: Rf=0.56 (CH$_2$Cl$_2$/MeOH 20:1). 1H-NMR (DMSO-d6, 600 MHz) δ ppm 8.61

(s, 1H) 7.96 (s, 2H) 7.59 (t, 1H) 7.42 (d, 1H) 7.27 (d, 1H) 6.34 (s, 1H) 4.00 (s, 3H) 3.95 (s, 3H) 3.47 (s, 3H) 2.65 (m, 1H) 1.11 (d, 3H) 0.51 (d, 3H).

Step 186.1: 4-((5-chloro-1-methyl-6-oxo-1,6-dihydropyridin-3-ylamino)(4-chloro-3-fluorophenylmethyl)-1-(2,4-dimethoxypyrimidin-5-yl)-5-isopropyl-1H-pyrazole-3-carboxylic acid

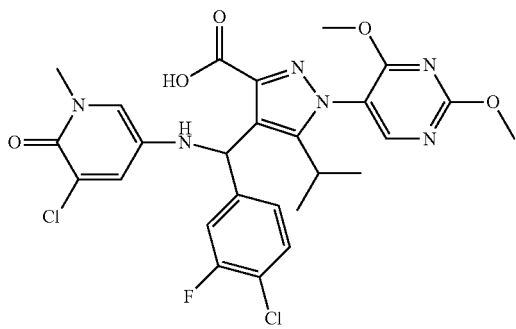 [SMILES: COc1ncc(-n2nc(C(=O)O)c(C(Nc3cc(Cl)c(=O)n(C)c3)c3ccc(Cl)c(F)c3)c2C(C)C)c(OC)n1]

To a solution of 393 mg (0.628 mmol) ethyl 4-((5-chloro-1-methyl-6-oxo-1,6-dihydropyridin-3-ylamino)(4-chloro-3-fluorophenyl)methyl)-1-(2,4-dimethoxypyrimidin-5-yl)-5-isopropyl-1H-pyrazole-3-carboxylate (product of step 186.2) in 6.3 ml dioxan under $N_2$ atmosphere at 10° C., a solution of 1.88 ml (1.88 mmol) 1M LiOH solution was added drop wise and the solution was stirred at RT for 3 hours. The solvent was evaporated, the residue was diluted in ice-water and 1M citric acid solution. The water phase was extracted twice with EtOAc. The combined organic phases were washed with water, brine, dried ($Na_2SO_4$), filtered and evaporated to give 401 mg (0.529 mmol, 84% yield) of the title compound as a foam, which was used in the next step without purification. LCMS: (M+H)=591/593; $t_R$=0.98 min (LC-MS 4).

Step 186.2: ethyl 4-((5-chloro-1-methyl-6-oxo-1,6-dihydropyridin-3-ylamino)(4-chloro-3-fluorophenyl) methyl)-1-(2,4-dimethoxypyrimidin-5-yl)-5-isopropyl-1H-pyrazole-3-carboxylate

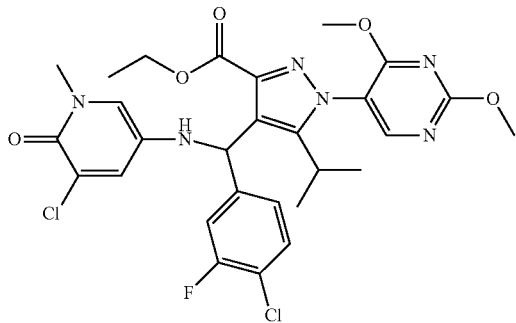 [SMILES: CCOC(=O)c1nn(-c2cnc(OC)nc2OC)c(C(C)C)c1C(Nc1cc(Cl)c(=O)n(C)c1)c1ccc(Cl)c(F)c1]

The title compound was prepared in analogy to the procedure described in step 184.2 but using the product of step 186.3. LCMS: (M+H)=619/621; $t_R$=1.15 min (LC-MS 4). HPLC: $t_R$=5.60 min (HPLC 7). TLC: Rf=0.07 (EtOAc/Heptane 4:1). 1H-NMR (DMSO-d6, 400 MHz) δ ppm 8.61-8.52 (m, 1H) 7.70 (m, 1H) 7.52 (m, 1H) 7.30 (d, 1H) 7.09 (t, 1H) 6.95-6.84 (m, 1H) 5.89-5.76 (m, 1H) 5.57-5.47 (m, 1H) 4.16 (m, 2H) 3.98 (s, 3H) 3.92-3.87 (m, 3H) 3.36 (s, 3H) 3.05 (m, 1H) 1.17-0.89 (m, 9H).

Step 186.3: Ethyl 4-((4-chloro-3-fluorophenyl)(hydroxy)methyl)-1-(2,4-dimethoxypyrimidin-5-yl)-5-isopropyl-1H-pyrazole-3-carboxylate

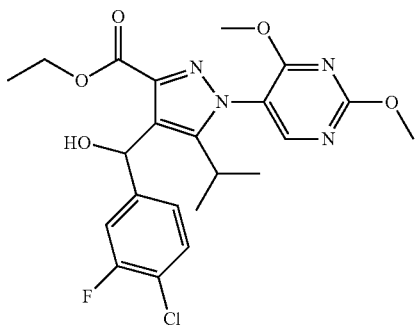 [SMILES: CCOC(=O)c1nn(-c2cnc(OC)nc2OC)c(C(C)C)c1C(O)c1ccc(Cl)c(F)c1]

The title compound was prepared in analogy to the procedure described in step 184.3 but using 4-chloro-3-fluorobenzaldehyde. After the workup, the crude product was purified by chromatography (Silicagel, Heptane/EtOAc 70:30 to 15:85) to give 766 mg of a white foam. LCMS: (M+H)=479; $t_R$=1.21 min (LC-MS 4). HPLC: $t_R$=5.99 min (HPLC 7). TLC: Rf=0.35 (EtOAc/Heptane 2:1). 1H-NMR (DMSO-d6, 400 MHz) δ ppm 8.53 (d, 1H) 7.51 (t, 1H) 7.30 (d, 1H) 7.10 (t, 1H) 6.45-6.35 (m, 1H) 6.17-6.07 (m, 1H) 4.22 (m, 2H) 3.97 (s, 3H) 3.91 (m, 3H) 3.19-3.04 (m, 1H) 1.23-078 (m, 9H).

Example 187

5-(5-chloro-1-methyl-6-oxo-1,6-dihydropyridin-3-A-4-(4-chloro-3-fluorophenyl)-2-(2,4-dimethoxypyrimidin-5-yl)-3-isopropyl-4,5-dihydropyrrolo[3,4-c]pyrazol-6(2H)-one

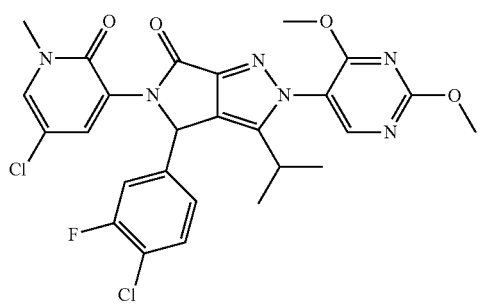 [SMILES: COc1ncc(-n2nc3c(c2C(C)C)C(c2ccc(Cl)c(F)c2)N(c2cc(Cl)cn(C)c2=O)C3=O)c(OC)n1]

The title compound was prepared in analogy to the procedure described in example 184 but using the product of step 187.1. LCMS: (M+H)=573/575; $t_R$=1.13 min (LC-MS 4). HPLC: $t_R$=5.49 min (HPLC 7). TLC: Rf=0.59 ($CH_2Cl_2$/MeOH 20:1). 1H-NMR (DMSO-d6, 600 MHz) δ ppm 8.63 (s, 1H) 7.99 (s, 1H) 7.63 (s, 1H) 7.56 (t, 1H) 7.38 (d, 1H) 7.21

(d, 1H) 6.57 (s, 1H) 4.00 (s, 3H) 3.95 (s, 3H) 3.46 (s, 3H) 2.64 (m, 1H) 1.09 (d, 3H) 0.49 (d, 3H).

Step 187.1: 4-((5-chloro-1-methyl-2-oxo-1,2-dihydropyridin-3-ylamino)(4-chloro-3-fluorophenylmethyl)-1-(2,4-dimethoxypyrimidin-5-O-5-isopropyl-1H-pyrazole-3-carboxylic acid

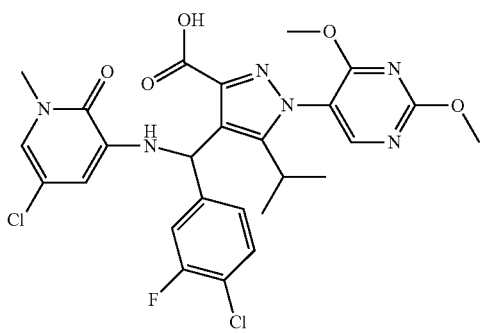 [SMILES: COc1ncc(-n2nc(C(=O)O)c(C(Nc3cc(Cl)cn(C)c3=O)c3ccc(Cl)c(F)c3)c2C(C)C)c(OC)n1]

The title compound was prepared in analogy to the procedure described in step 186.1 but using the product of step 187.2. LCMS: (M+H)=591/593; $t_R$=1.14 min (LC-MS 4).

Step 187.2: Ethyl 4-((5-chloro-1-methyl-2-oxo-1,2-dihydropyridin-3-ylamino)(4-chloro-3-fluorophenylmethyl)-1-(2,4-dimethoxypyrimidin-5-yl)-5-isopropyl-1H-pyrazole-3-carboxylate

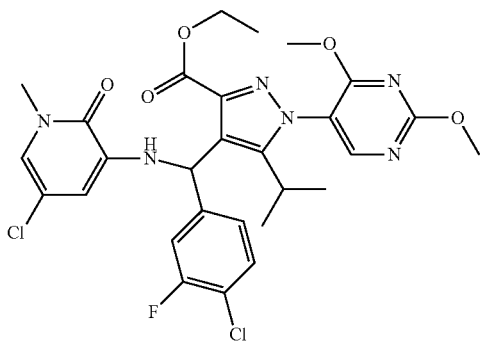 [SMILES: CCOC(=O)c1nn(-c2cnc(OC)nc2OC)c(C(C)C)c1C(Nc1cc(Cl)cn(C)c1=O)c1ccc(Cl)c(F)c1]

The title compound was prepared in analogy to the procedure described in step 184.2 but using the product of step 186.3 and 3-amino-5-chloro-1-methyl-1H-pyridin-2-one (intermediate BJ). LCMS: (M+H)=619/621; $t_R$=1.28 min (LC-MS 4). HPLC: $t_R$=6.05 min (HPLC 7). TLC: Rf=0.24 (EtOAc/Heptane 4:1). 1H-NMR (DMSO-d6, 400 MHz) δ ppm 8.69-8.60 (m, 1H) 7.55 (m, 1H) 7.19 (m, 1H) 7.11-7.02 (m, 2H) 6.94-6.66 (m, 1H) 6.58 (s, 1H) 6.07 (t, 1H) 4.16-4.10 (m, 2H) 3.98 (s, 3H) 3.95-3.89 (m, 3H) 3.44 (s, 3H) 3.20 (m, 1H) 1.18-1.02 (m, 9H).

Example 188

4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile

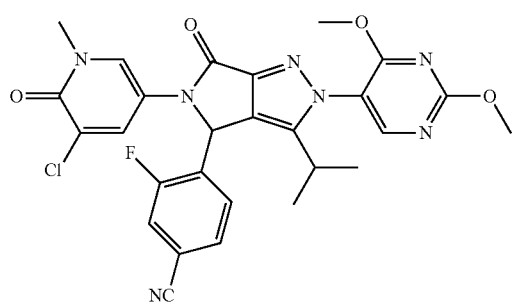 [SMILES: COc1ncc(-n2nc3c(c2C(C)C)C(c2ccc(C#N)cc2F)N(c2cc(Cl)c(=O)n(C)c2)C3=O)c(OC)n1]

The title compound was prepared in analogy to the procedure described in example 184 but using the product of step 188.1. LCMS: (M+H)=564.1/565.9; $t_R$=0.93 min (LC-MS 4). HPLC: $t_R$=4.71 min (HPLC 7). TLC: Rf=0.43 (CH$_2$Cl$_2$/MeOH 10:1). 1H-NMR (DMSO-d6, 600 MHz) δ ppm 8.61 (s, 1H) 7.97-7.73 (m, 5H) 6.62 (s, 1H) 4.00 (s, 3H) 3.95 (s, 3H) 3.46 (5, 3H) 2.68 (m, 1H) 1.08 (d, 3H) 0.51 (d, 3H).

Step 188.1: 4-((5-chloro-1-methyl-6-oxo-1,6-dihydropyridin-3-ylamino)(4-cyano-2-fluorophenyl)methyl)-1-(2,4-dimethoxypyrimidin-5-yl)-5-isopropyl-1H-pyrazole-3-carboxylic acid

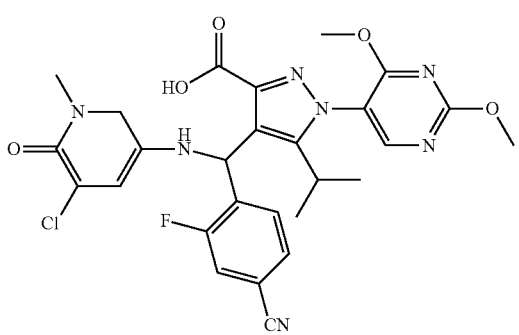

The title compound was prepared in analogy to the procedure described in step 186.1 but using the product of step 188.2. LCMS: (M+H)=582; $t_R$=0.85 min (LC-MS 4). HPLC: $t_R$=4.53 min (HPLC 7).

Step 188.2: Ethyl 4-((5-chloro-1-methyl-6-oxo-1,6-dihydropyridin-3-ylamino)(4-cyano-2-fluorophenyl)methyl)-1-(2,4-dimethoxypyrimidin-5-yl)-5-isopropyl-1H-pyrazole-3-carboxylate

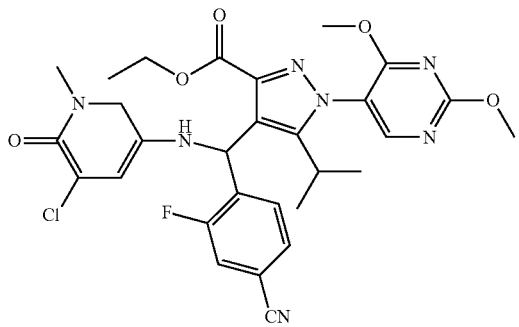

The title compound was prepared in analogy to the procedure described in step 184.2 but using the product of 188.3 and 5-amino-3-chloro-1-methyl-1H-pyridin-2-one (intermediate W1). LCMS: (M+H)=610/612; $t_R$=1.00 min (LC-MS 4). HPLC: $t_R$=4.97 min (HPLC 7). TLC: Rf=0.07 (EtOAc/Heptane 4:1). 1H-NMR (DMSO-d6, 400 MHz) δ ppm 8.52-8.48 (m, 1H) 7.80 (d, 1H) 7.68-7.61 (m, 3H) 6.83-6.75 (m, 1H) 6.07-5.98 (m, 1H) 4.12 (m, 2H) 3.97 (s, 3H) 3.91-3.88 (m, 3H) 3.34 (s, 3H) 3.12 (m, 1H) 1.15 (t, 3H) 1.04-0.77 (m, 6H).

Step 188.3: Ethyl 44(4-cyano-2-fluorophenyl)(hydroxy)methyl)-1-(2,4-dimethoxypyrimidin-5-yl)-5-isopropyl-1H-pyrazole-3-carboxylate

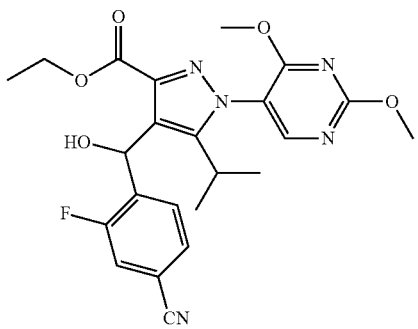 [SMILES: CCOC(=O)c1nn(-c2cnc(OC)nc2OC)c(C(C)C)c1C(O)c1ccc(C#N)cc1F]

The title compound was prepared in analogy to the procedure described in step 184.3 but using the product of step 184.4 4-cyano-2-fluorobenzaldehyde.

LCMS: (M+H)=470; $t_R$=1.04 min (LC-MS 4). HPLC: $t_R$=4.89 min (HPLC 7). TLC: Rf=0.34 (Heptane/EtOAc 1:2). 1H–NMR (DMSO–d6, 400 MHz) δ ppm 8.53 (m, 1H) 7.78– 7.68 (m, 3H) 6.70–6.60 (m, 1H) 4.19 (m, 2H) 3.97 (s, 3H) 3.90 (m, 3H) 3.26 (m, 1H) 1.23–0.71 (m, 9H).

Example 189

4-(5-(5-chloro-1-methyl-2-oxo-1,2-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-2-fluorobenzonitrile

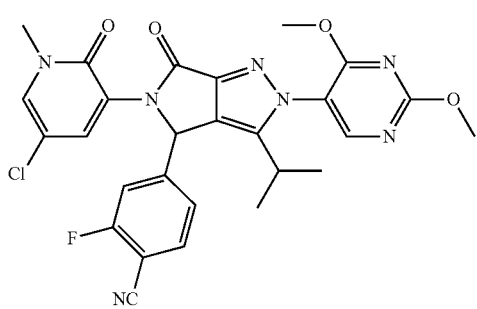

The title compound was prepared in analogy to the procedure described in example 184 but using the product of step 189.1. LCMS: (M+H)=564/566; $t_R$=1.01 min (LC-MS 4). HPLC: $t_R$=4.94 min (HPLC 7). TLC: Rf=0.31 (CH$_2$Cl$_2$/MeOH 10:1). 1H-NMR (DMSO-d6, 600 MHz) δ ppm 8.63 (s, 1H) 8.00 (bs, 1H) 7.92 (t, 1H) 7.68 (s, 1H) 7.56 (d, 1H) 7.43 (d, 1H) 6.66 (s, 1H) 4.00 (s, 3H) 3.95 (s, 3H) 3.46 (s, 3H) 2.65 (m, 1H) 1.11 (d, 3H) 0.47 (d, 3H).

Step 189.1: 4-((5-chloro-1-methyl-2-oxo-1,2-dihydropyridin-3-ylamino)(4-cyano-3-fluorophenyl)methyl)-1-(2,4-dimethoxypyrimidin-5-yl)-5-isopropyl-1H-pyrazole-3-carboxylic acid

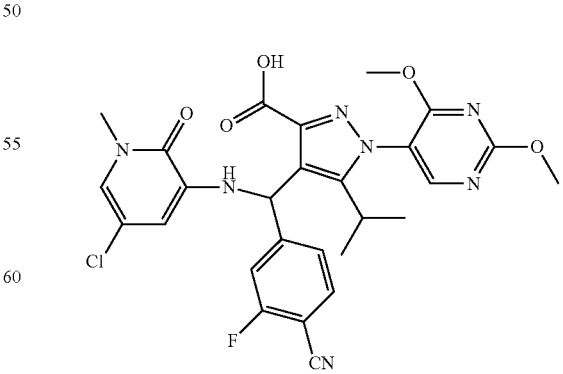

The title compound was prepared in analogy to the procedure described in step 186.1 but using the product of step 189.2. LCMS: (M+H)=582; $t_R$=1.04 min (LC-MS 4). HPLC: $t_R$=5.21 min (HPLC 7). TLC: Rf=0.21 (CH$_2$Cl$_2$/Methanol 20:1)

Step 189.2: Ethyl 4-((5-chloro-1-methyl-6-oxo-1,6-dihydropyridin-3-ylamino)(4-cyano-2-fluorophenyl)methyl)-1-(2,4-dimethoxypyrimidin-5-yl)-5-isopropyl-1H-pyrazole-3-carboxylate

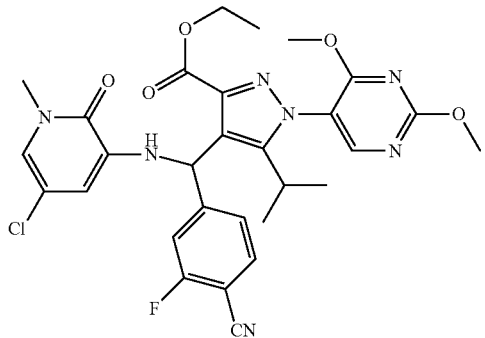 [SMILES: CCOC(=O)c1nn(-c2cnc(OC)nc2OC)c(C(C)C)c1C(Nc1cc(Cl)cn(C)c1=O)c1ccc(C#N)c(F)c1]

The title compound was prepared in analogy to the procedure described in step 184.2 but using the product of step 189.3 and 3-amino-5-chloro-1-methyl-1H-pyridin-2-one (intermediate BJ). LCMS: (M+H)=610/612; $t_R$=1.16 min (LC-MS 4). HPLC: $t_R$=5.58 min (HPLC 7). TLC: Rf=0.13 (EtOAc/Heptane 2:1). 1H-NMR (DMSO-d6, 400 MHz) δ ppm 8.69–8.60 (m, 1H) 7.88 (m, 1H) 7.21–7.12 (m, 3H) 6.74–6.66 (m, 2H) 6.15 (t, 1H) 4.10 (m, 2H) 3.99 (s, 3H) 3.95–3.89 (m, 3H) 3.44 (s, 3H) 3.18 (m, 1H) 1.15 (t, 3H) 1.19–1.03 (m, 6H).

Step 189.3: Ethyl 44(4-cyano-3-fluorophenyl)(hydroxy)methyl)-1-(2,4-dimethoxypyrimidin-5-yl)-5-isopropyl-1H-pyrazole-3-carboxylate

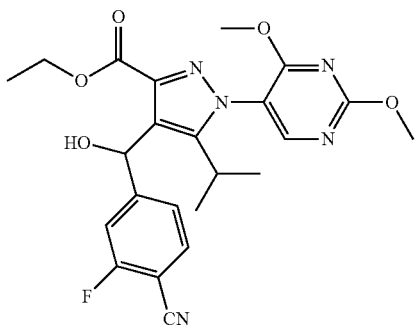 [SMILES: CCOC(=O)c1nn(-c2cnc(OC)nc2OC)c(C(C)C)c1C(O)c1ccc(C#N)c(F)c1]

The title compound was prepared in analogy to the procedure described in step 184.3 but using the product of step 184.4 and 4-cyano-3-fluorobenzaldehyde. LCMS: (M+H)=470; $t_R$=1.08 min (LC-MS 4). HPLC: $t_R$=5.09 min (HPLC 7). TLC: Rf=0.34 (Heptane/EtOAc 1:2). 1H-NMR (DMSO-d6, 400 MHz) δ ppm 8.56 (m, 1H) 7.86 (t, 1H) 7.42 (d, 1H) 7.27 (t, 1H) 6.53–6.24 (m, 2H) 4.26–4.15 (m, 2H) 3.98 (s, 3H) 3.92–3.88 (m, 3H) 3.16–2.98 (m, 1H) 1.23–0.77 (m, 9H).

Example 190

4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile

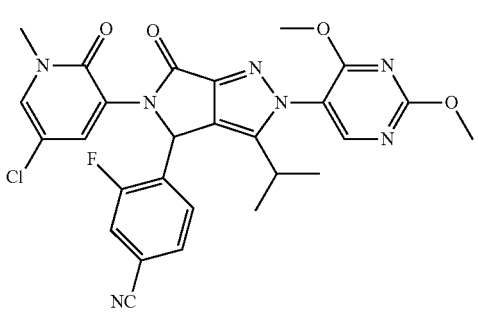 [SMILES: COc1ncc(-n2nc3c(c2C(C)C)C(c2ccc(C#N)cc2F)N(c2cc(Cl)cn(C)c2=O)C3=O)c(OC)n1]

The title compound was prepared in analogy to the procedure described in example 184 but using the product of step 190.1. After the extraction, the product was purified by column chromatography (Silicagel, heptane, EtOAc), then by preparative HPLC (Column: Sunfire 30×100 mm. Flow: 30 ml/min. Gradient: 5% to 100% B in 40 min; A=water+0.1% TFA, B=acetonitrile) to afford 159 mg of a beige foam. LCMS: (M+H)=564/566; $t_R$=0.99 min (LC-MS 4). HPLC: $t_R$=4.86 min (HPLC 7). TLC: Rf=0.28 (CH$_2$Cl$_2$/MeOH 10:1). 1H-NMR (DMSO-d6, 600 MHz) δ ppm 8.63 (s, 1H) 8.00 (s, 1H) 7.88 (d, 1H) 7.69 (d, 1H) 7.63 (bs, 2H) 6.90 (bs, 1H) 4.00 (s, 3H) 3.95 (s, 3H) 3.44 (s, 3H) 2.67 (m, 1H) 1.10 (d, 3H) 0.51 (d, 3H).

Step 190.1: 4-((5-chloro-1-methyl-6-oxo-1,6-dihydropyridin-3-ylamino)(4-cyano-2-fluorophenylmethyl)-1-(2,4-dimethoxypyrimidin-5-yl)-5-isopropyl-1H-pyrazole-3-carboxylic acid

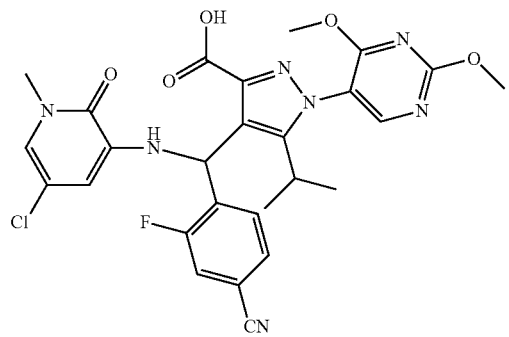 [SMILES: COc1ncc(-n2nc(C(=O)O)c(C(Nc3cc(Cl)cn(C)c3=O)c3ccc(C#N)cc3F)c2C(C)C)c(OC)n1]

The title compound was prepared in analogy to the procedure described in step 186.1 but using the product of step 190.2. LCMS: (M+H)=582; $t_R$=1.03 min (LC-MS 4). HPLC: $t_R$=5.15 min (HPLC 7). TLC: Rf=0.18 (CH$_2$Cl$_2$/MeOH 20:1).

Step 190.2: Ethyl 4-((5-chloro-1-methyl-2-oxo-1,2-dihydropyridin-3-ylamino)(4-cyano-2-fluorophenyl)methyl)-1-(2,4-dimethoxypyrimidin-5-yl)-5-isopropyl-1H-pyrazole-3-carboxylate

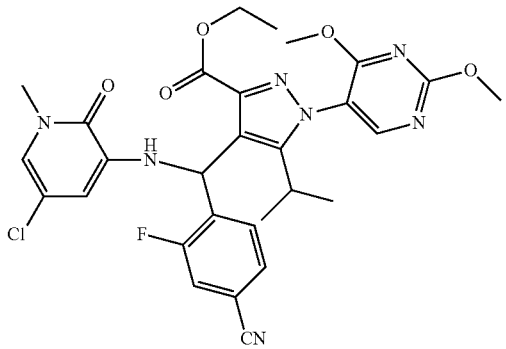 [SMILES: CCOC(=O)c1nn(-c2cnc(OC)nc2OC)c(C(C)C)c1C(Nc1cc(Cl)cn(C)c1=O)c1ccc(C#N)cc1F]

The title compound was prepared in analogy to the procedure described in step 184.2 but using intermediate 188.3 and 3-amino-5-chloro-1-methylpyridin-2(1H)-one (intermediate BJ). LCMS: (M+H)=610/612; $t_R$=1.15 min (LC-MS 4). HPLC: $t_R$=5.53 min (HPLC 7). TLC: Rf=0.23 (EtOAc/Heptane 4:1). 1H-NMR (DMSO-d6, 400 MHz) δ ppm 8.51 (d, 1H) 7.81 (d, 1H) 7.67 (d, 1H) 7.40 (m, 1H) 7.20 (s, 1H) 6.55–6.49 (m, 2H) 6.25 (d, 1H) 4.12 (m, 2H) 3.98 (s, 3H) 3.93–3.90 (m, 3H) 3.45 (s, 3H) 3.22 (m, 1H) 1.17–0.98 (m, 9H).

Example 191

4-(5-(5-chloro-1-methyl-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile

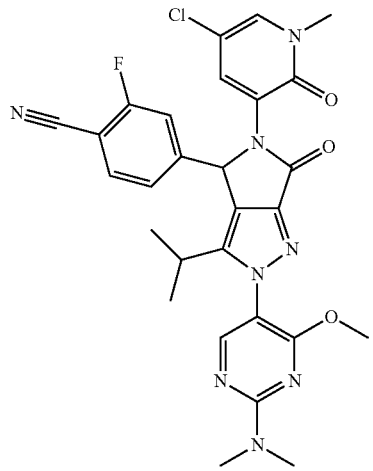 [SMILES: COc1nc(N(C)C)ncc1-n1nc2c(c1C(C)C)C(c1ccc(C#N)c(F)c1)N(c1cc(Cl)cn(C)c1=O)C2=O]

The title compound was prepared in analogy to the procedure described in example 184 but using the product of step 191.1. LCMS: (M+H)=577/579; $t_R$=1.11 min (LC-MS 4). TLC: Rf=0.41 (EtOAc). 1H-NMR (DMSO-d6, 600 MHz) δ ppm 8.28 (s, 1H) 8.00 (s, 1H) 7.91 (t, 1H) 7.66 (bs, 1H) 7.55 (bs, 1H) 7.41 (bs, 1H) 6.62 (bs, 1H) 3.87 (s, 3H) 3.44 (s, 3H) 3.18 (s, 6H) 2.61 (m, 1H) 1.09–0.95 (m, 3H) 0.46 (d, 3H).

Step 191.1: 4-((5-chloro-1-methyl-2-oxo-1,2-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylic acid

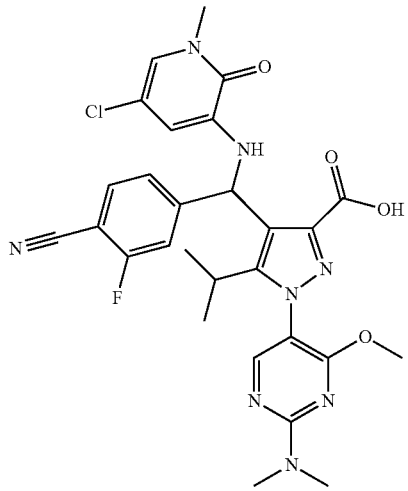 [SMILES: COc1nc(N(C)C)ncc1-n1nc(C(=O)O)c(C(Nc2cc(Cl)cn(C)c2=O)c2ccc(C#N)c(F)c2)c1C(C)C]

The title compound was prepared in analogy to the procedure described in step 186.1 but using the product of step 191.2. The reaction mixture was quenched with 0.5N HCl, then extracted twice with EtOAc. The organic layers were combined and washed with 0.5N HCl, dried on Na$_2$SO$_4$ and evaporated to dryness to afford a brown solid, which was used in the next step without purification. LCMS: (M+H)=595/597; $t_R$=1.15 min (LC-MS 4). 1H-NMR (DMSO-d6, 400 MHz) δ ppm 13.00 (bs, 1H) 8.33, 8.22 (m, 1H) 7.88 (m, 1H) 7.21–6.92 (m, 4H) 6.64 (m, 1H) 6.09 (t, 1H) 3.88–3.83 (m, 3H) 3.43 (s, 3H) 3.21 (m, 1H) 3.17 (s, 6H) 1.21–1.04 (m, 6H).

Step 191.2: Ethyl 4-((5-chloro-1-methyl-2-oxo-1,2-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylate

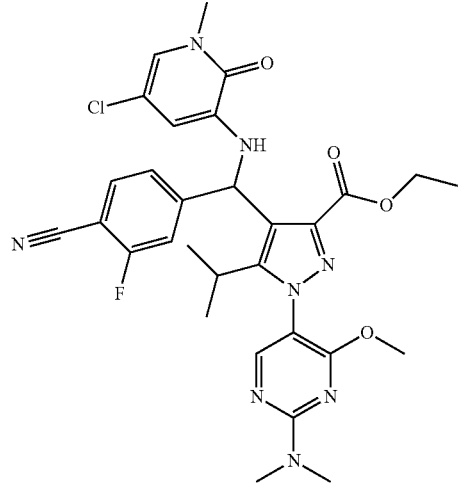 [SMILES: CCOC(=O)c1nn(-c2cnc(N(C)C)nc2OC)c(C(C)C)c1C(Nc1cc(Cl)cn(C)c1=O)c1ccc(C#N)c(F)c1]

The title compound was prepared in analogy to the procedure described in step 184.2 but using the product of step 191.3 and 3-amino-5-chloro-1-methyl-1H-pyridin-2-one (intermediate BJ). After the extraction, the crude product was purified by column chromatography (Silicagel, Hexane/EtOAc, 80% to 95% EtOAc) to yield the title compound as yellow solid. LCMS: (M+H)=623/624; $t_R$=1.26 min (LC-MS 4). TLC: Rf=0.49 (EtOAc). 1H-NMR (DMSO-d6, 400 MHz) δ ppm 8.34–8.23 (m, 1H) 7.89 (m, 1H) 7.20–7.12 (m, 3H) 6.75–6.63 (m, 2H) 6.13 (t, 1H) 4.09 (m, 2H) 3.88–3.82 (m, 3H) 3.44 (s, 3H) 3.19 (m, 3H) 3.18 (s, 6H) 1.18–1.01 (m, 9H).

Step 191.3: Ethyl 44(4-cyano-3-fluorophenyl)(hydroxy)methyl)-1-(2-(dimethylamino)-4-methoxypyrimidin-5-yl)-5-isopropyl-1H-pyrazole-3-carboxylate

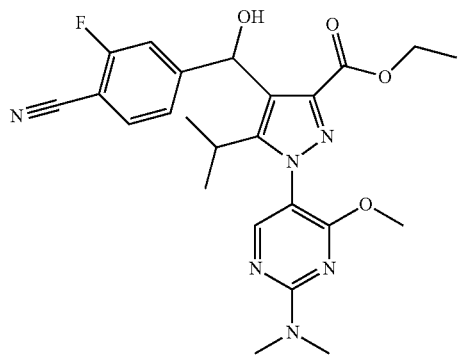 [SMILES: CCOC(=O)c1nn(-c2cnc(N(C)C)nc2OC)c(C(C)C)c1C(O)c1ccc(C#N)c(F)c1]

To a stirred solution of intermediate from step 147.5 (3 g, 8.30 mmol) in 40 ml THF under argon, (4-cyano-3-fluorophenyl)magnesium chloride (19.92 ml, 9.96 mmol, intermediate from step 191.4) was added at 0° C. Then, the reaction mixture was stirred 10 min at 0° C. The reaction mixture was quenched with saturated NH$_4$Cl solution and extracted twice with of EtOAc. The organic layers were combined and washed once with saturated NH$_4$Cl solution, dried (Na$_2$SO$_4$) and evaporated. The crude product was purified by column chromatography (Silicagel, Hexane/EtOAc, 10 to 50% EtOAc) to afford 3.26 g (6.76 mmol, 81% yield) of the title compound as a yellow solid. LCMS: (M+H)=483; $t_R$=1.19 min (LC-MS 4). TLC: Rf=0.32 (Hexane/EtOAc 1:1). 1H-NMR (DMSO-d6, 400.43 MHz) δ ppm 8.19-8.15 (m, 1H) 7.85 (t, 1H) 7.42 (m, 1H) 7.26 (t, 1H) 6.52-6.20 (m, 2H) 4.22 (m, 2H) 3.85 (s, 3H) 3.17 (s, 6H) 3.04 (m, 1H) 1.25-0.76 (m, 9H).

Step 191.4: (4-Cyano-3-fluorophenyl)magnesium chloride

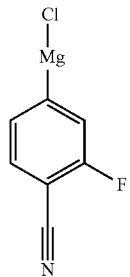

To a stirred solution of 4-iodo-2-fluorobenzonitrile (2.5 g, 10.12 mmol) in 10.12 ml THF under argon, a solution of isopropylmagnesium chloride. LiCl in THF (10.12 ml, 13.16 mmol) was added at 0° C. The reaction mixture was stirred at this temperature for 5 min to afford the title compound, which was used immediately in the next step as a stock solution (~0.5M in THF).

Example 192

4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile

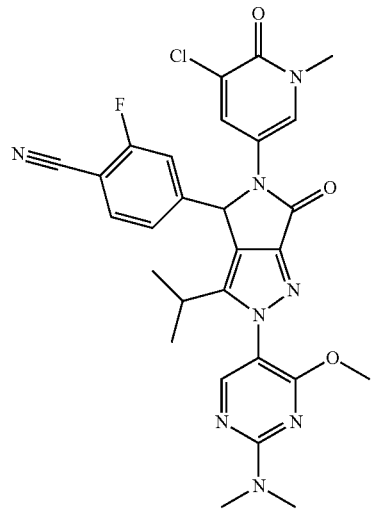 [SMILES: COc1nc(N(C)C)ncc1-n1nc2c(c1C(C)C)C(c1ccc(C#N)c(F)c1)N(c1cc(Cl)c(=O)n(C)c1)C2=O]

The title compound was prepared in analogy to the procedure described in example 184 but using the product of step 192.1. LCMS: (M+H)=577/579; $t_R$=1.05 min (LC-MS 4). TLC: Rf=0.15 (EtOAc). 1H-NMR (DMSO-d6, 600 MHz) δ ppm 8.27 (bs, 1H) 7.98-7.93 (m, 3H) 7.56 (m, 1H) 7.44 (d, 1H) 6.39 (s, 1H) 3.87 (s, 3H) 3.44 (s, 3H) 3.18 (s, 6H) 2.62 (m, 1H) 1.09 (d, 3H) 0.47 (d, 3H).

Step 192.1: 4-((5-Chloro-1-methyl-6-oxo-1,6-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylic acid

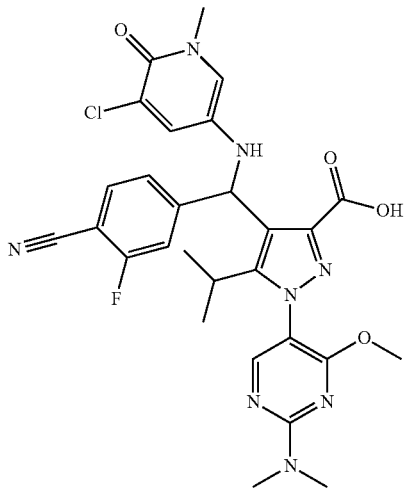 [SMILES: COc1nc(N(C)C)ncc1-n1nc(C(=O)O)c(C(Nc2cc(Cl)c(=O)n(C)c2)c2ccc(C#N)c(F)c2)c1C(C)C]

The title compound was prepared in analogy to the procedure described in step 186.1 but using the product of step 192.2. The reaction mixture was quenched with 0.5N HCl and then extracted twice with EtOAc. The organic layers were combined and washed with 0.5N HCl, dried on Na$_2$SO$_4$ and evaporated to dryness to afford a brown solid, which was used in the next step without purification. LCMS: (M+H)=595/596; $t_R$=0.97 min (LC-MS 4). 1H-NMR (DMSO-d6, 400 MHz) δ ppm 12.90 (bs, 1H) 8.26, 8.14 (m, 1H) 7.97–7.83 (m, 1H) 7.71 (m, 1H) 7.39 (m, 1H) 7.24 (m, 1H) 6.99–6.89 (m, 1H) 5.94–5.60 (m, 2H) 3.86–3.80 (m, 3H) 3.36 (s, 3H) 3.17 (s, 6H) 3.10 (m, 1H) 1.09–0.89 (m, 6H).

Step 192.2: Ethyl 4-((5-chloro-1-methyl-6-oxo-1,6-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylate

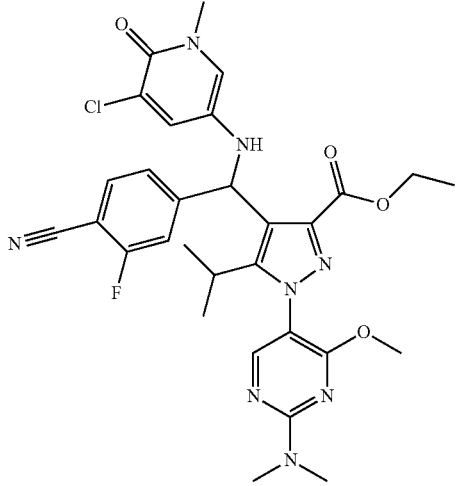 [SMILES: CCOC(=O)c1nn(-c2cnc(N(C)C)nc2OC)c(C(C)C)c1C(Nc1cc(Cl)c(=O)n(C)c1)c1ccc(C#N)c(F)c1]

The title compound was prepared in analogy to the procedure described for step 184.2 but using intermediate 191.3 and 5-amino-3-chloro-1-methyl-1H-pyridin-2-one (intermediate W1). After the extraction, the crude product was purified by column chromatography (Silicagel, EtOAc) to afford a brown solid. LCMS: (M+H)=623/625; $t_R$=1.12 min (LC-MS 4). TLC: Rf=0.24 (EtOAc). 1H-NMR (DMSO-d6, 400 MHz) δ ppm 8.26–8.13 (m, 1H) 7.86 (m, 1H) 7.71 (s, 1H) 7.37 (m, 1H) 7.26 (m, 1H) 6.97–6.86 (m, 1H) 5.92–5.79 (m, 1H) 5.58–5.48 (m, 1H) 4.15–4.09 (m, 2H) 3.86–3.80 (m, 3H) 3.36 (s, 3H) 3.17 (s, 6H) 3.03 (m, 1H) 1.17–1.02 (m, 6H) 0.91 (m, 3H).

Example 193

4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile

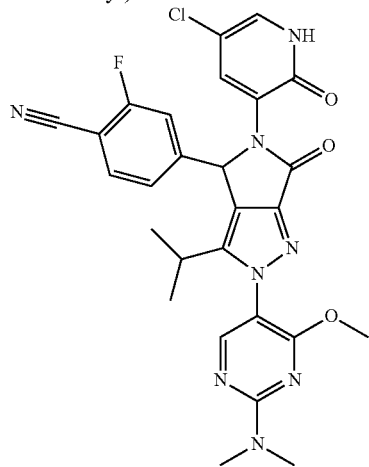

A mixture of 4-(5-(5-chloro-1-(4-methoxybenzyl)-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile (388 mg, 0.568 mmol, product from step 193.1) and TFA (2.188 ml, 28.4 mmol) was stirred at 100° C. for 1 hour. Then the reaction mixture was quenched with a saturated NaHCO₃ solution and extracted twice with CH₂Cl₂. The organic layers were combined and washed with saturated NaHCO₃ solution, dried (Na₂SO₄) and evaporated. The reaction mixture was purified by chromatography (Silicagel, EtOAc). After evaporation of the fractions, the residue was triturated in diisopropylether to afford 121 mg (0.215 mmol, 37.8% yield) of the title compound as a white solid. LCMS: (M+H)=563/565; $t_R$=1.04 min (LC-MS 4). TLC: Rf=0.34 (EtOAc). 1H-NMR (DMSO-d6, 600 MHz) δ ppm 12.36 (s, 1H) 8.28 (s, 1H) 7.91 (t, 1H) 7.65–7.53 (m, 3H) 7.40 (d, 1H) 6.84 (bs, 1H) 3.87 (s, 3H) 3.18 (s, 6H) 2.60 (m, 1H) 1.08 (d, 3H) 0.47 (d, 3H).

Step 193.1: 4-(5-(5-Chloro-1-(4-methoxybenzyl)-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile

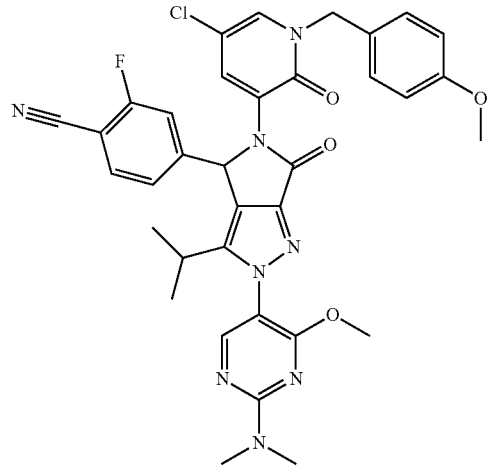 [SMILES: COc1ccc(Cn2cc(Cl)cc(N3C(=O)c4nn(-c5cnc(N(C)C)nc5OC)c(C(C)C)c4C3c3ccc(C#N)c(F)c3)c2=O)cc1]

The title compound was prepared in analogy to the procedure described in example 184 but using the product of step 193.2. LCMS: (M+H)=683/685; $t_R$=1.27 min (LC-MS 4). TLC: Rf=0.14 (Hexane/EtOAc 1:1). 1H-NMR (DMSO-d6, 400 MHz) δ ppm 8.27 (s, 1H) 8.09 (d, 1H) 7.84 (t, 1H) 7.70 (bs, 1H) 7.48 (d, 1H) 7.34 (d, 1H) 7.20 (d, 2H) 6.87 (d, 2H) 6.68 (bs, 1H) 5.03 (m, 2H) 3.86 (s, 3H) 3.73 (s, 3H) 3.17 (s, 6H) 2.60 (m, 1H) 1.07 (d, 3H) 0.47 (d, 3H).

Step 193.2: 4-((5-Chloro-1-(4-methoxybenzyl)-2-oxo-1,2-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylic acid

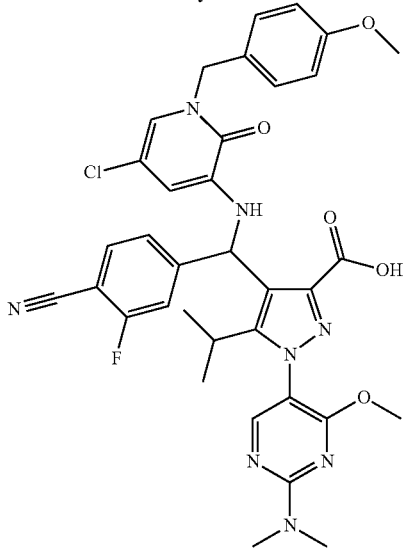 [SMILES: COc1ccc(Cn2cc(Cl)cc(NC(c3ccc(C#N)c(F)c3)c3c(C(=O)O)nn(-c4cnc(N(C)C)nc4OC)c3C(C)C)c2=O)cc1]

The title compound was prepared in analogy to the procedure described in step 186.1 but using the product from step 193.3. The reaction mixture was quenched with 0.5N HCl and then extracted twice with EtOAc. The organic layers were combined and washed with 0.5N HCl, dried on $Na_2SO_4$ and evaporated to dryness to afford a brown solid, which was used in the next step without purification. LCMS: (M+H)=701/702; $t_R$=1.29 min (LC-MS 4). 1H-NMR (DMSO-d6, 400 MHz) δ ppm 13.02 (bs, 1H) 8.32–8.23 (m, 1H) 7.87 (m, 1H) 7.33–7.27 (m, 3H) 7.21–7.12 (m, 2H) 7.08–6.99 (m, 1H) 6.90 (m, 1H) 6.64 (m, 1H) 6.10 (t, 1H) 5.01 (m, 2H) 3.88–3.82 (m, 3H) 3.71 (s, 3H) 3.24–3.10 (m, 7H) 1.18–1.10 (m, 6H).

Step 193.3: Ethyl 4-((5-chloro-1-(4-methoxybenzyl)-2-oxo-1,2-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylate

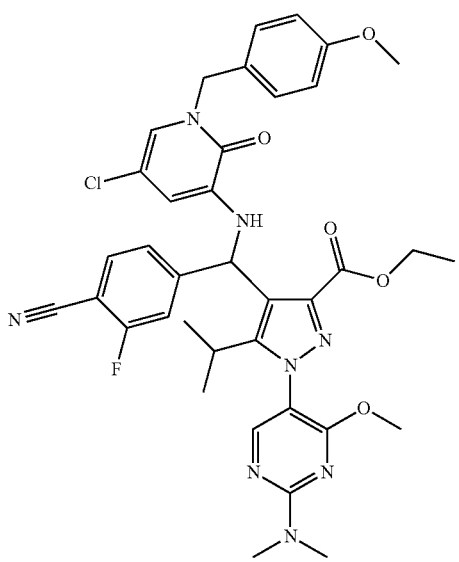 [SMILES: CCOC(=O)c1nn(-c2cnc(N(C)C)nc2OC)c(C(C)C)c1C(Nc1cc(Cl)cn(Cc2ccc(OC)cc2)c1=O)c1ccc(C#N)c(F)c1]

The title compound was prepared in analogy to the procedure described in step 184.2 but using the intermediate 191.3 and 3-amino-5-chloro-1-(4-methoxybenzyl)pyridin-2(1H)-one (intermediate 152.4). After the extraction, the crude product was purified by chromatography (Silicagel, Hexane/EtOAc, 25 to 70% EtOAc) to afford a yellow solid. LCMS: (M+H)=729/730; $t_R$=1.39 min (LC-MS 4). TLC: Rf=0.30 (Hexane/EtOAc 1:1). 1H-NMR (DMSO-d6, 400 MHz) δ ppm 8.33–8.23 (m, 1H) 7.89 (m, 1H) 7.31 (m, 3H) 7.17 (m, 2H) 6.90 (m, 2H) 6.82–6.73 (m, 1H) 6.63 (m, 1H) 6.13 (t, 1H) 5.02 (m, 2H) 4.11 (m, 2H) 3.88–3.82 (m, 3H) 3.71 (s, 3H) 3.20–3.14 (m, 7H) 1.17–1.02 (m, 9H).

Example 194

4-(5-(5-Chloro-6-oxo-1,6-dihydropyridin-3-A-2-(2-(dimethylamino)-4-methoxypyrimidin-5-A-3-isopropyl-6-oxo-2,4,5,6-tetrahydropyrrolo[3,4-c]pyrazol-4-A-2-fluorobenzonitrile

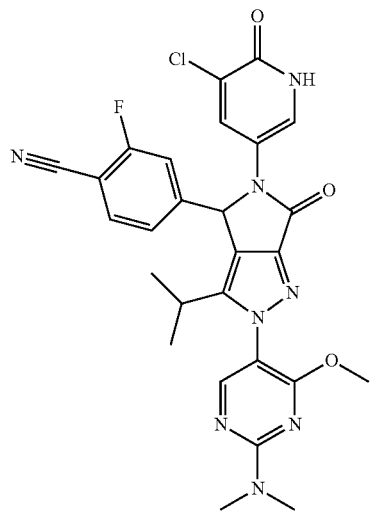

The title compound was prepared in analogy to the procedure described for example 193 but using the product of step 194.1. The reaction was performed under microwave irradiation for 30 min. LCMS: (M+H)=563; $t_R$=1.00 min (LC-MS 4). TLC: Rf=0.22 (EtOAc). 1H-NMR (DMSO-d6, 600 MHz) δ ppm 12.32 (s, 1H) 8.26 (bs, 1H) 7.97 (s, 1H) 7.92 (t, 1H)

7.59 (m, 2H) 7.47 (bs, 1H) 6.43 (s, 1H) 3.86 (s, 3H) 3.18 (s, 6H) 2.60 (m, 1H) 1.09 (d, 3H) 0.46 (d, 3H).

Step 194.1: 4-(5-(5-Chloro-1-(4-methoxybenzyl)-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile

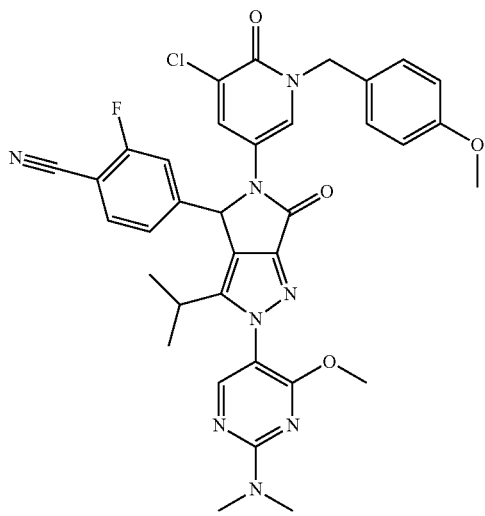 [SMILES: COc1ccc(Cn2cc(N3C(=O)c4nn(-c5cnc(N(C)C)nc5OC)c(C(C)C)c4C3c3ccc(C#N)c(F)c3)cc(Cl)c2=O)cc1]

The title compound was prepared in analogy to the procedure described in example 184 but using the product of step 194.2. LCMS: (M+H)=683/684; $t_R$=1.20 min (LC-MS 4). TLC: Rf=0.62 (EtOAc). 1H-NMR (DMSO-d6, 400 MHz) δ ppm 8.25 (s, 1H) 8.01 (m, 1H) 7.95-7.89 (m, 2H) 7.53 (d, 1H) 7.41 (d, 1H) 7.11 (d, 2H) 6.86 (d, 2H) 6.35 (s, 1H) 4.95 (m, 2H) 3.86 (s, 3H) 3.73 (s, 3H) 3.17 (s, 6H) 2.61 (m, 1H) 1.08 (d, 3H) 0.48 (d, 3H).

Step 194.2: 4-((5-chloro-1-(4-methoxybenzyl)-6-oxo-1,6-dihydropyridin-3-ylamino)(4-cyano-3-fluorophenylmethyl)-1-(2-(dimethylamino)-4-methoxypyrimidin-5-yl)-5-isopropyl-1H-pyrazole-3-carboxylic acid

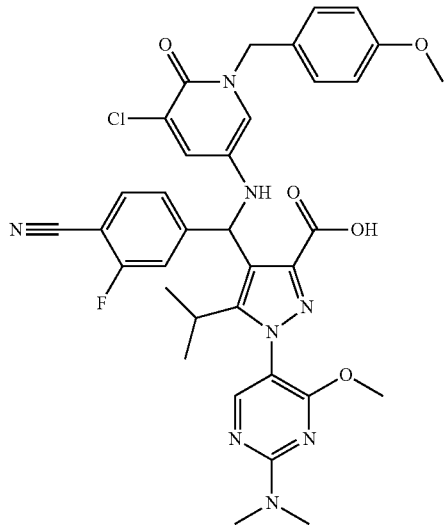 [SMILES: COc1ccc(Cn2cc(NC(c3ccc(C#N)c(F)c3)c3c(C(=O)O)nn(-c4cnc(N(C)C)nc4OC)c3C(C)C)cc(Cl)c2=O)cc1]

The title compound was prepared in analogy to the procedure described for step 186.2 but using the product of step 194.3. The reaction mixture was quenched with 0.5N HCl and then extracted twice with EtOAc. The organic layers were combined and washed with 0.5N HCl, dried on Na₂SO₄ and evaporated to afford a brown solid, which was used in the next step without purification. LCMS: (M+H)=701/703; $t_R$=1.13 min (LC-MS 4).

Step 194.3: Ethyl 4-((5-chloro-1-(4-methoxybenzyl)-6-oxo-1,6-dihydropyridin-3-ylamino)(4-cyano-3-fluorophenyl)methyl)-1-(2-(dimethylamino)-4-methoxypyrimidin-5-yl)-5-isopropyl-1H-pyrazole-3-carboxylate

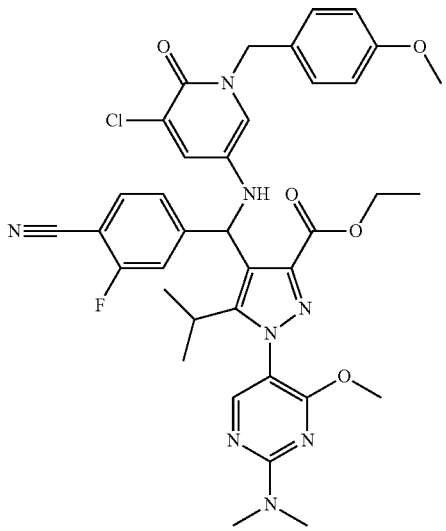 [SMILES: CCOC(=O)c1nn(-c2cnc(N(C)C)nc2OC)c(C(C)C)c1C(Nc1cc(Cl)c(=O)n(Cc2ccc(OC)cc2)c1)c1ccc(C#N)c(F)c1]

The title compound was prepared in analogy to the procedure described in step 184.2 but using ethyl 4-((4-cyano-3-fluorophenyl)(hydroxy)methyl)-1-(2-(dimethylamino)-4-methoxypyrimidin-5-yl)-5-isopropyl-1H-pyrazole-3-carboxylate (intermediate 191.3) and 5-amino-3-chloro-1-(4-methoxy-benzyl)-1H-pyridin-2-one (product from step 155.4). After the extraction, the crude product was purified by chromatography (Silicagel, Hexane/EtOAc 50:50 to 20:80). Pure fractions were collected and evaporated to dryness to afford a brown solid.
LCMS: (M+H)=729/731; $t_R$=1.25 min (LC-MS 4). TLC: Rf=0.67 (Hexane/EtOAc 1:1). 1H-NMR (DMSO-d6, 400 MHz) δ ppm 8.21-8.07 (m, 1H) 7.85 (t, 1H) 7.68 (m, 1H) 7.33–6.78 (m, 7H) 5.91–5.80 (m, 1H) 5.66 (m, 1H) 5.05–4.77

(m, 2H) 4.16–4.05 (m, 2H) 3.85–3.78 (m, 3H) 3.70 (m, 3H) 3.17 (s, 6H) 3.02 (m, 1H) 1.15–0.85 (m, 9H).

Example 195

5-(5-Chloro-1-methyl-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one

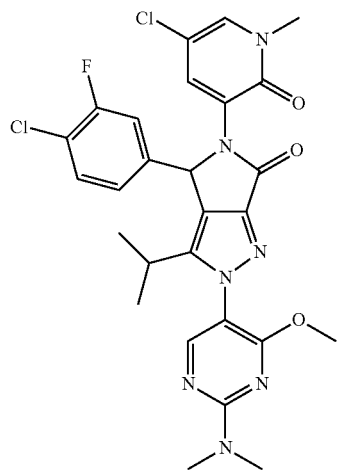 [SMILES: COc1nc(N(C)C)ncc1-n1nc2c(c1C(C)C)C(c1ccc(Cl)c(F)c1)N(c1cc(Cl)cn(C)c1=O)C2=O]

The title compound was prepared in analogy to the procedure described in example 184 but using the product of step 195.1. LCMS: (M+H)=586/588; t$_R$=1.23 min (LC-MS 4). TLC: Rf=0.50 (EtOAc). 1H-NMR (DMSO-d6, 600 MHz) δ ppm 8.29 (bs, 1H) 7.99 (s, 1H) 7.61 (bs, 1H) 7.55 (t, 1H) 7.35 (d, 1H) 7.18 (d, 1H) 6.54 (bs, 1H) 3.87 (s, 3H) 3.44 (s, 3H) 3.18 (s, 6H) 2.61 (m, 1H) 1.09 (d, 3H) 0.48 (d, 3H).

Step 195.1: 4-((5-chloro-1-methyl-2-oxo-1,2-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylic acid

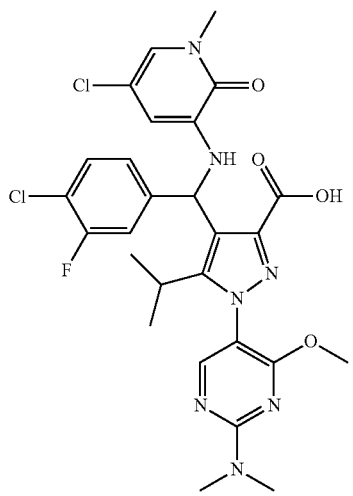 [SMILES: COc1nc(N(C)C)ncc1-n1nc(C(=O)O)c(C(Nc2cc(Cl)cn(C)c2=O)c2ccc(Cl)c(F)c2)c1C(C)C]

The title compound was prepared in analogy to the procedure described in step 186.1 but using the product of step 195.2. The reaction mixture was quenched with 0.5N HCl and then extracted twice with EtOAc. The organic layers were combined and washed with 0.5N HCl, dried on Na$_2$SO$_4$ and evaporated to dryness to afford a brown solid, which was used in the next step without purification. LCMS: (M+H)=604/606; t$_R$=1.26 min (LC-MS 4). 1H-NMR (DMSO-d6, 400 MHz) δ ppm 12.95 (bs, 1H) 8.31, 8.22 (m, 1H) 7.51 (m, 1H) 7.16–6.92 (m, 4H) 6.55 (s, 1H) 6.01 (t, 1H) 3.88–3.82 (m, 3H) 3.43 (s, 3H) 3.21 (m, 1H) 3.17 (s, 6H) 1.18–1.03 (m, 6H).

Step 195.2: Ethyl 4-((5-chloro-1-methyl-2-oxo-1,2-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylate

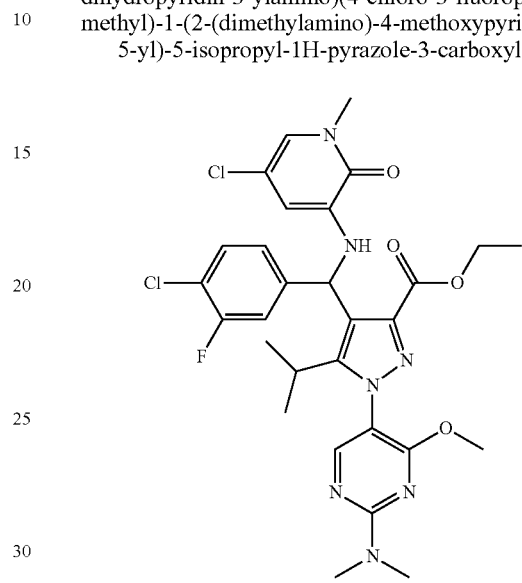

The title compound was prepared in analogy to the procedure described for step 184.2 but using the product of step 195.3 and 3-amino-5-chloro-1-methyl-1H-pyridin-2-one (intermediate BJ). After the extraction, the crude product was purified by column chromatography (Silicagel, Hexane/EtOAc 50:50 to 25:75). Product fractions were collected and evaporated to dryness to afford a white solid. LCMS: (M+H)=632/634; t$_R$=1.39 min (LC-MS 4). TLC: Rf=0.67 (EtOAc). 1H-NMR (DMSO-d6, 400 MHz) δ ppm 8.33–8.23 (m, 1H) 7.57–7.50 (m, 1H) 7.18 (m, 1H) 7.11–6.98 (m, 2H) 6.75–6.66 (m, 1H) 6.56 (m, 1H) 6.04 (t, 1H) 4.11 (m, 2H) 3.88–3.82 (m, 3H) 3.44 (s, 3H) 3.21–3.14 (m, 7H) 1.17–1.03 (m, 9H).

Step 195.3: Ethyl 44(4-chloro-3-fluorophenyl)(hydroxy)methyl)-1-(2-(dimethylamino)-4-methoxypyrimidin-5-yl)-5-isopropyl-1H-pyrazole-3-carboxylate

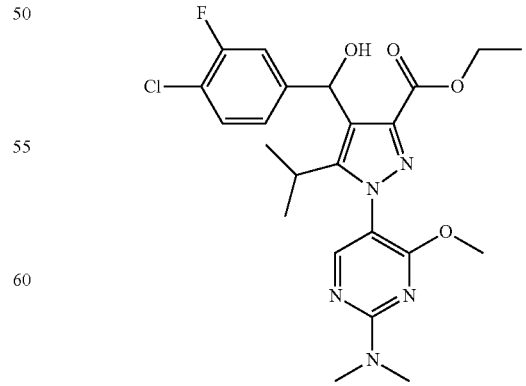

The title compound was prepared in analogy to the procedure described for step 191.3 but using intermediate from step 147.5 and (4-chloro-3-fluorophenyl)magnesium chloride. After the extraction, the crude product was purified by chromatography (Silicagel, Hexane/EtOAc, 20 to 40% EtOAc) to afford a yellow solid. LCMS: (M+H)=492; $t_R$=1.31 min (LC-MS 4). TLC: Rf=0.47 (Hexane/EtOAc 1:1). 1H-NMR (DMSO-d6, 400.43 MHz) δ ppm 8.18-8.15 (m, 1H) 7.50 (m, 1H) 7.27 (m, 1H) 7.09 (t, 1H) 6.45–6.35 (m, 1H) 6.13–6.03 (m, 1H) 4.22 (m, 2H) 3.85–3.82 (m, 3H) 3.17 (s, 6H) 3.09 (m, 1H) 1.22 (t, 3H) 1.01–0.77 (m, 6H).

Example 196

5-(5-Chloro-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one

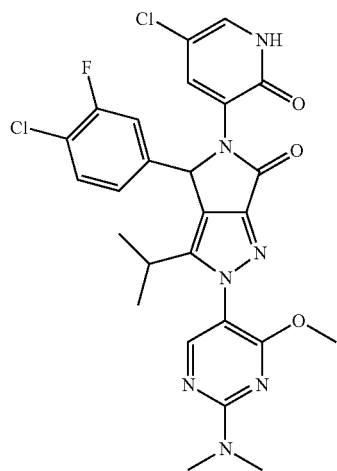 [SMILES: COc1nc(N(C)C)ncc1-n1nc2c(c1C(C)C)C(c1ccc(Cl)c(F)c1)N(c1cc(Cl)c[nH]c1=O)C2=O]

The title compound was prepared in analogy to the procedure described for example 194 but using the product of step 196.1. After the extraction, the crude product was purified by chromatography (Silicagel, CH$_2$Cl$_2$/MeOH, 0.5 to 4% MeOH). After evaporation the residue was triturated in diisopropylether to afford a white solid. LCMS: (M+H)=572/574; $t_R$=1.15 min (LC-MS 4). TLC: Rf=0.42 (CH$_2$Cl$_2$/MeOH 9:1). 1H-NMR (DMSO-d6, 600 MHz) δ ppm 12.35 (s, 1H) 8.29 (s, 1H) 7.61–7.54 (m, 3H) 7.35 (d, 1H) 7.18 (d, 1H) 6.56 (s, 1H) 3.87 (s, 3H) 3.18 (s, 6H) 2.61 (m, 1H) 1.08 (d, 3H) 0.49 (d, 3H).

Step 196.1: 5-(5-Chloro-1-(4-methoxybenzyl)-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one

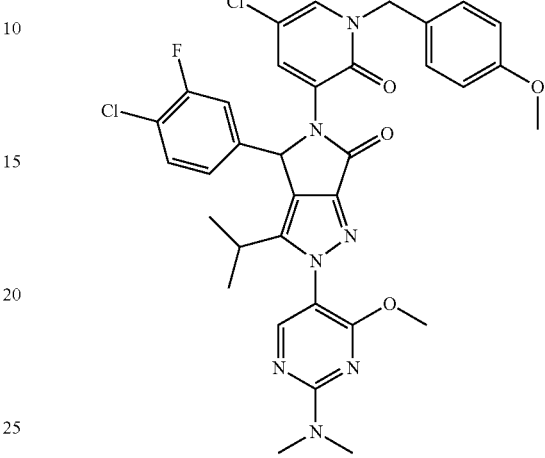

The title compound was prepared in analogy to the procedure described in example 184 but using the product of step 196.2. LCMS: (M+H)=692/694; $t_R$=1.37 min (LC-MS 4). TLC: Rf=0.79 (EtOAc). 1H-NMR (DMSO-d6, 400 MHz) δ ppm 8.27 (s, 1H) 8.08 (d, 1H) 7.65 (bs, 1H) 7.48 (t, 1H) 7.30 (d, 1H) 7.21 (d, 2H) 7.12 (d, 1H) 6.87 (d, 2H) 6.61 (s, 1H) 5.10-4.94 (m, 2H) 3.86 (s, 3H) 3.72 (s, 3H) 3.17 (s, 6H) 2.60 (m, 1H) 1.07 (d, 3H) 0.49 (d, 3H).

Step 196.2: 4-((5-Chloro-1-(4-methoxybenzyl)-2-oxo-1,2-dihydropyridin-3-ylamino)(4-chloro-3-fluorophenylmethyl)-1-(2-(dimethylamino)-4-methoxypyrimidin-5-yl)-5-isopropyl-1H-pyrazole-3-carboxylic acid

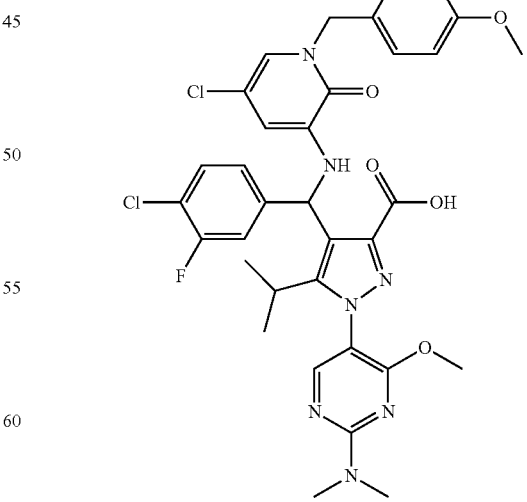

The title compound was prepared in analogy to the procedure described in step 186.2 but using the product of step 196.3. The reaction mixture was quenched with 0.5N HCl and then extracted twice with EtOAc. The organic layers were combined and washed with 0.5N HCl, dried on $Na_2SO_4$ and evaporated to dryness to afford a brown solid, which was used in the next step without purification. LCMS: (M+H)=710/712; $t_R$=1.37 min (LC-MS 4). 1H-NMR (DMSO-d6, 400 MHz) δ ppm 12.97 (bs, 1H) 8.31–8.22 (m, 1H) 7.50 (m, 1H) 7.33–7.25 (m, 3H) 7.12–6.98 (m, 3H) 6.90 (m, 2H) 6.56 (m, 1H) 6.02 (t, 1H) 5.01 (m, 2H) 3.87–3.82 (m, 3H) 3.71 (s, 3H) 3.24–3.12 (m, 7H) 1.16–1.02 (m, 6H).

Step 196.3: Ethyl 4-((5-chloro-1-(4-methoxybenzyl)-2-oxo-1,2-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylate

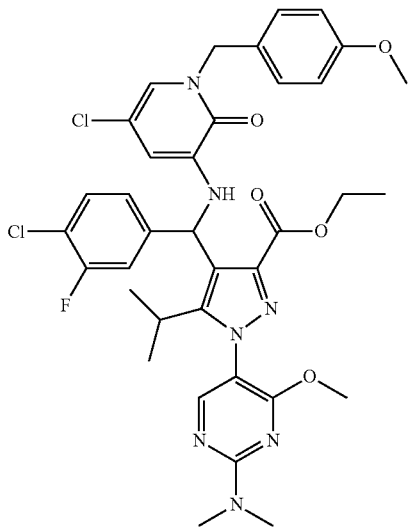 [SMILES: CCOC(=O)c1nn(-c2cnc(N(C)C)nc2OC)c(C(C)C)c1C(Nc1cc(Cl)cn(Cc2ccc(OC)cc2)c1=O)c1ccc(Cl)c(F)c1]

The title compound was prepared in analogy to the procedure described in step 184.2 but using the intermediate of step 195.3 and 3-amino-5-chloro-1-(4-methoxybenzyl)pyridin-2(1H)-one (product of step 152.4). After extraction, the crude product was purified by chromatography (Silicagel, Hexane/EtOAc 70:30 to 50:50) to afford a greenish solid. LCMS: (M+H)=738/740; $t_R$=1.48 min (LC-MS 4). TLC: Rf=0.37 (Hexane/EtOAc 1:1). 1H-NMR (DMSO-d6, 400 MHz) δ ppm 8.32–8.23 (m, 1H) 7.52 (m, 1H) 7.33–7.27 (m, 3H) 7.11–6.98 (m, 2H) 6.90 (m, 2H) 6.81–6.73 (m, 1H) 6.54 (m, 1H) 6.05 (t, 1H) 5.02 (m, 2H) 4.11 (m, 2H) 3.87–3.82 (m, 3H) 3.71 (s, 3H) 3.21–3.14 (m, 7H) 1.17–1.02 (m, 9H).

Example 197

5-(5-Chloro-1-methyl-6-oxo-1,6-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one

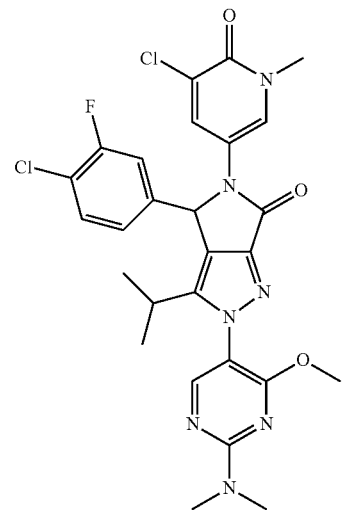 [SMILES: COc1nc(N(C)C)ncc1-n1nc2c(c1C(C)C)C(c1ccc(Cl)c(F)c1)N(c1cc(Cl)c(=O)n(C)c1)C2=O]

The title compound was prepared in analogy to the procedure described in example 184 but using the product of step 197.1. After the workup, the crude product was purified by chromatography (Silicagel, $CH_2Cl_2$/MeOH 0.5 to 4% MeOH). The residue was triturated in diisopropylether to afford a white solid. LCMS: (M+H)=586/588; $t_R$=1.15 min (LC-MS 4). TLC: Rf=0.33 ($CH_2Cl_2$/MeOH 9:1). 1H-NMR (DMSO-d6, 600 MHz) δ ppm 8.28 (bs, 1H) 7.96 (m, 2H) 7.59 (t, 1H) 7.40 (d, 1H) 7.24 (d, 1H) 6.31 (s, 1H) 3.87 (s, 3H) 3.44 (s, 3H) 3.18 (s, 6H) 2.60 (m, 1H) 1.10 (d, 3H) 0.49 (d, 3H).

Step 197.1: 4-((5-Chloro-1-methyl-6-oxo-1,6-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylic acid

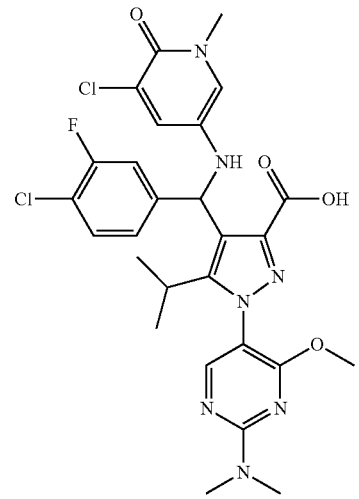 [SMILES: COc1nc(N(C)C)ncc1-n1nc(C(=O)O)c(C(Nc2cc(Cl)c(=O)n(C)c2)c2ccc(Cl)c(F)c2)c1C(C)C]

The title compound was prepared in analogy to the procedure described in step 186.2 but using the product of step 197.2. The reaction mixture was quenched with 0.5N HCl and then extracted twice with EtOAc. The organic layers were combined and washed with 0.5N HCl, dried on $Na_2SO_4$ and evaporated to dryness to afford a brown solid, which was used in the next step without purification. LCMS: (M+H)=604/606; $t_R$=1.07 min (LC-MS 4). 1H-NMR (DMSO-d6, 400 MHz) δ ppm 12.93 (bs, 1H) 8.24–8.15 (m, 1H) 7.68 (m, 1H) 7.53 (m, 1H) 7.29 (m, 1H) 7.08 (t, 1H) 6.95–6.87 (m, 1H) 5.89–5.62 (m, 2H) 3.85–3.79 (m, 3H) 3.36 (s, 3H) 3.17 (s, 6H) 3.10 (m, 1H) 1.03–0.47 (m, 6H).

Step 197.2: Ethyl 4-((5-chloro-1-methyl-6-oxo-1,6-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylate

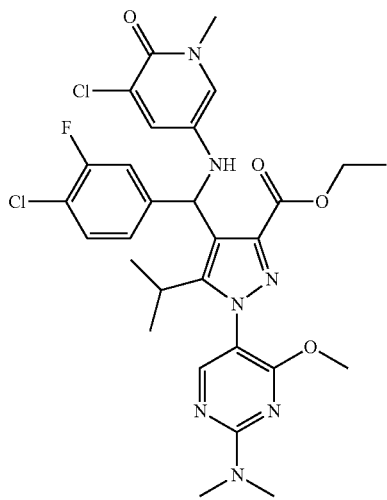 [SMILES: CCOC(=O)c1nn(-c2cnc(N(C)C)nc2OC)c(C(C)C)c1C(Nc1cc(Cl)c(=O)n(C)c1)c1ccc(Cl)c(F)c1]

The title compound was prepared in analogy to the procedure described in step 184.2 but using the intermediate of step 195.3 and 5-amino-3-chloro-1-methylpyridin-2(1H)-one (intermediate W1). After the extraction, the crude product was purified by chromatography (Silicagel, EtOAc). LCMS: (M+H)=632/634; $t_R$=1.23 min (LC-MS 4). TLC: Rf=0.26 (EtOAc). 1H-NMR (DMSO-d6, 400 MHz) δ ppm 8.25–8.15 (m, 1H) 7.68 (m, 1H) 7.53 (m, 1H) 7.27 (m, 1H) 7.08 (t, 1H) 6.92–6.83 (m, 1H) 5.88–5.76 (m, 1H) 5.56–5.47 (m, 1H) 4.13 (m, 2H) 3.85–3.80 (m, 3H) 3.36 (s, 3H) 3.17 (s, 6H) 3.10 (m, 1H) 1.17–0.87 (m, 9H).

Example 198

4-(4-Chloro-3-fluorophenyl)-5-(5-chloro-6-oxo-1,6-dihydropyridin-3-yl)-2-(2-(dimethylamino)-4-methoxypyrimidin-5-A-3-isopropyl-4,5-dihydropyrrolo[3,4-c]pyrazol-6(2H)-one

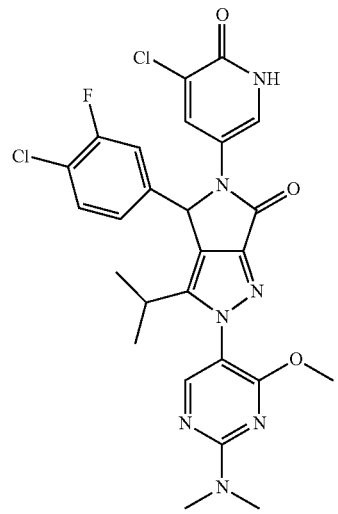 [SMILES: COc1nc(N(C)C)ncc1-n1nc2c(c1C(C)C)C(c1ccc(Cl)c(F)c1)N(c1c[nH]c(=O)c(Cl)c1)C2=O]

The title compound was prepared in analogy to the procedure described in example 193 but using the product of step 198.1. The reaction was performed under microwave irradiation for 30 min. LCMS: (M+H)=572/574; $t_R$=1.10 min (LC-MS 4). TLC: Rf=0.19 (EtOAc). 1H-NMR (DMSO-d6, 600 MHz) δ ppm 12.31 (s, 1H) 8.27 (bs, 1H) 7.95 (s, 1H) 7.58 (t, 1H) 7.54 (bs, 1H) 7.44 (bs, 1H) 7.25 (m, 1H) 6.33 (s, 1H) 3.86 (s, 3H) 3.18 (s, 6H) 2.60 (m, 1H) 1.09 (d, 3H) 0.48 (d, 3H).

Step 198.1: 5-(5-Chloro-1-(4-methoxybenzyl)-6-oxo-1,6-dihydropyridin-3-yl)-4-(4-chloro-3-fluorophenyl)-2-(2-(dimethylamino)-4-methoxypyrimidin-5-yl-3-isopropyl-4,5-dihydropyrrolo[3,4-c]pyrazol-6(2H)-one

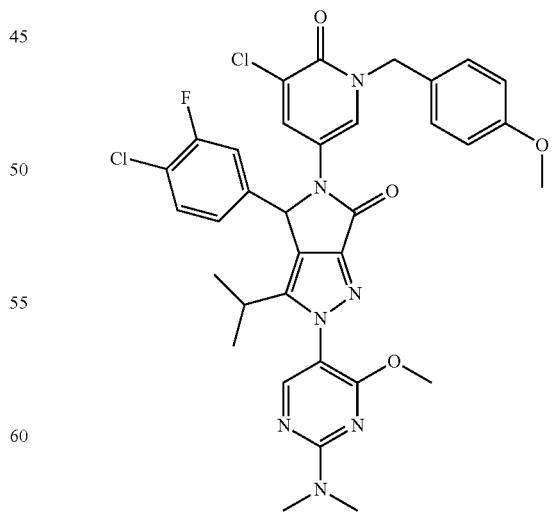

The title compound was prepared in analogy to the procedure described in example 184 but using the product of step 198.2. LCMS: (M+H)=692/694; $t_R$=1.28 min (LC-MS 4).

TLC: Rf=0.61 (EtOAc). 1H-NMR (DMSO-d6, 400 MHz) δ ppm 8.26 (bs, 1H) 8.00 (m, 2H) 7.56 (t, 1H) 7.38 (d, 1H) 7.21 (d, 1H) 7.11 (d, 2H) 6.85 (d, 2H) 6.27 (s, 1H) 4.95 (s, 2H) 3.86 (s, 3H) 3.72 (s, 3H) 3.17 (s, 6H) 2.61 (m, 1H) 1.09 (d, 3H) 0.49 (d, 3H).

Step 198.2: 4-((5-Chloro-1-(4-methoxybenzyl)-6-oxo-1,6-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylic acid

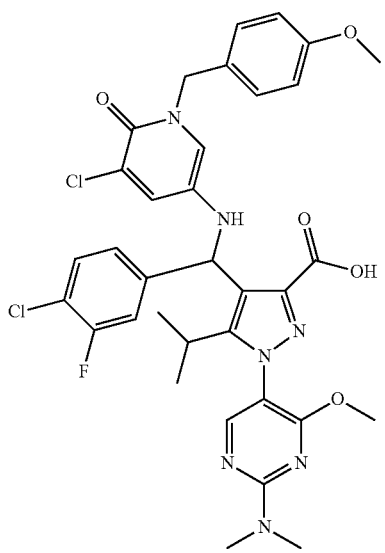 [SMILES: COc1ccc(Cn2cc(NC(c3ccc(Cl)c(F)c3)c3c(C(=O)O)nn(-c4cnc(N(C)C)nc4OC)c3C(C)C)cc(Cl)c2=O)cc1]

The title compound was prepared in analogy to the procedure described in step 186.2 but using the product of step 198.3. The reaction mixture was quenched with 0.5N HCl and then extracted twice with EtOAc. The organic layers were combined and washed with 0.5N HCl, dried on Na$_2$SO$_4$ and evaporated to dryness to afford a brown solid, which was used in the next step without purification. LCMS: (M+H)=710/712; $t_R$=1.20 min (LC-MS 4). 1H-NMR (DMSO-d6, 400 MHz) δ ppm 12.88 (bs, 1H) 8.17–8.08 (m, 1H) 7.67 (m, 1H) 7.50 (t, 1H) 7.26 (d, 1H) 7.10–7.04 (m, 3H) 6.93–6.85 (m, 1H) 6.80 (d, 2H) 5.89–5.73 (m, 2H) 5.05–4.77 (m, 2H) 3.83–3.78 (m, 3H) 3.70 (s, 3H) 3.16 (s, 6H) 3.10 (m, 1H) 0.98 (d, 3H) 0.86 (m, 3H).

Step 198.3: Ethyl 4-((5-chloro-1-(4-methoxybenzyl)-6-oxo-1,6-dihydropyridin-3-ylamino)(4-chloro-3-fluorophenyl)methyl)-1-(2-(dimethylamino)-4-methoxypyrimidin-5-yl)-5-isopropyl-1H-pyrazole-3-carboxylate

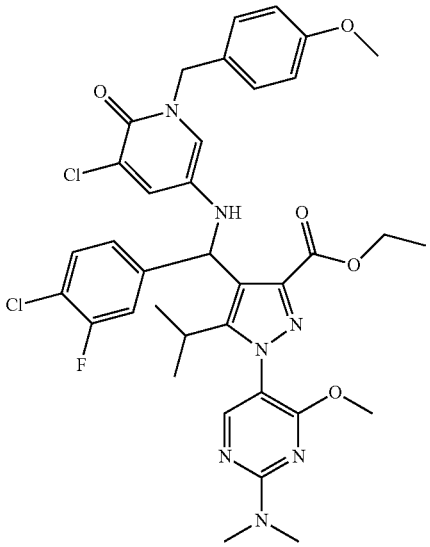 [SMILES: CCOC(=O)c1nn(-c2cnc(N(C)C)nc2OC)c(C(C)C)c1C(Nc1cc(Cl)c(=O)n(Cc2ccc(OC)cc2)c1)c1ccc(Cl)c(F)c1]

The title compound was prepared in analogy to the procedure described in step 184.2 but using intermediate 195.3 and 5-amino-3-chloro-1-(4-methoxy-benzyl)-1H-pyridin-2-one (step 155.4). After the extraction, the crude product was purified by chromatography (Silicagel, Hexane/EtOAc, 70 to 80% EtOAc). LCMS: (M+H)=738/740; $t_R$=1.35 min (LC-MS 4). TLC: Rf=0.67 (Hexane/EtOAc 1:1). 1H-NMR (DMSO-d6, 400 MHz) δ ppm 8.18–8.07 (m, 1H) 7.66 (m, 1H) 7.51 (t, 1H) 7.24 (d, 1H) 7.09–7.04 (m, 3H) 6.88 (m, 1H) 6.79 (d, 2H) 5.87–5.78 (m, 1H) 5.63 (t, 1H) 5.05–4.78 (m, 2H) 4.14 (m, 2H) 3.84–3.78 (m, 3H) 3.70 (m, 3H) 3.17 (s, 6H) 3.08 (m, 1H) 1.17–0.85 (m, 9H).

Example 199

4-(4-Chlorophenyl)-2-(2,4-dimethoxypyrimidin-5-yl)-5-(1,5-dimethyl-2-oxo-1,2-dihydropyridin-3-yl)-3-isopropyl-4,5-dihydropyrrolo[3,4-c]pyrazol-6(2H)-one

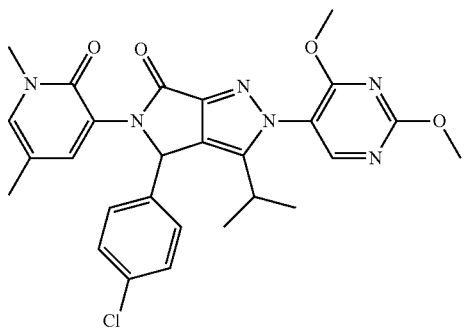 [SMILES: COc1ncc(-n2nc3c(c2C(C)C)C(c2ccc(Cl)cc2)N(c2cc(C)cn(C)c2=O)C3=O)c(OC)n1]

The title compound was prepared in analogy to the procedure described in example 184 but using the product of step 199.1. LCMS: (M+H)=535/537; $t_R$=1.07 min (LC-MS 6). HPLC: $t_R$=3.17 min (HPLC 8). 1H-NMR (DMSO-d6, 600 MHz) δ ppm 8.63 (s, 1H) 7.50 (s, 1H) 7.38 (d, 2H) 7.26 (m, 3H) 6.53 (s, 1H) 4.00 (s, 3H) 3.95 (s, 3H) 3.43 (s, 3H) 2.61 (m, 1H) 1.95 (s, 3H) 1.09 (d, 3H) 0.47 (d, 3H).

Step 199.1: 44(4-chlorophenyl)(1,5-dimethyl-2-oxo-1,2-dihydropyridin-3-ylamino)methyl)-1-(2,4-dimethoxypyrimidin-5-yl)-5-isopropyl-1H-pyrazole-3-carboxylic acid

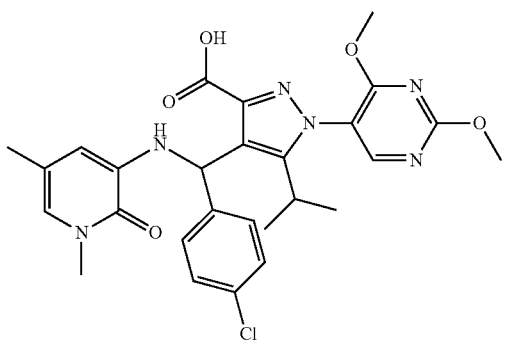

The title compound was prepared in analogy to the procedure described in step 184.1 but using the product of step 199.2. LCMS: (M+H)=553; $t_R$=1.10 min (LC-MS 6). HPLC: $t_R$=3.23 min (HPLC 8).

Step 199.2: Ethyl 4-((4-chlorophenyl)(1,5-dimethyl-2-oxo-1,2-dihydropyridin-3-ylamino)methyl)-1-(2,4-dimethoxypyrimidin-5-yl)-5-isopropyl-1H-pyrazole-3-carboxylate

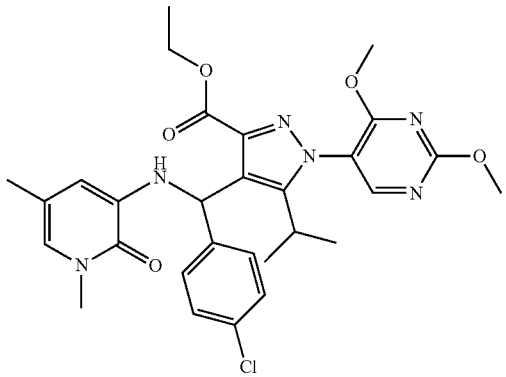

The title compound was prepared in analogy to the procedure described in step 184.2 but using the intermediate from step 199.3 (ethyl 4-((4-chlorophenyl)(hydroxy)methyl)-1-(2,4-dimethoxypyrimidin-5-yl)-5-isopropyl-1H-pyrazole-3-carboxylate) and intermediate from step 199.4 (3-amino-1,5-dimethylpyridin-2(1H)-one). LCMS: (M+H)=581/583; $t_R$=1.24 min (LC-MS 6). HPLC: $t_R$=5.58 min (HPLC 8). 1H-NMR (DMSO-d6, 400 MHz) δ ppm 8.68–8.61 (m, 1H) 7.39 (m, 2H) 7.21 (m, 2H) 6.74 (s, 1H) 6.44–6.29 (m, 2H) 6.04 (t, 1H) 4.17–4.06 (m, 2H) 3.98–3.92 (m, 6H) 3.43 (m, 3H) 3.15 (m, 1H) 1.95 (s, 3H) 1.18–1.04 (m, 9H).

Step 199.3: Ethyl 4-((4-chlorophenyl)(hydroxy)methyl)-1-(2,4-dimethoxypyrimidin-5-yl)-5-isopropyl-1H-pyrazole-3-carboxylate

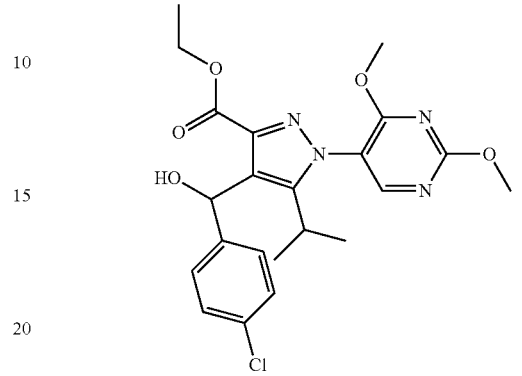

The title compound was prepared in analogy to the procedure described in step 184.4 but using intermediate from step 184.4 and 4-chlorobenzaldehyde. LCMS: (M+H)=461; $t_R$=1.19 min (LC-MS 6). HPLC: $t_R$=3.49 min (HPLC 8). 1H-NMR (DMSO-d6, 400 MHz) δ ppm 8.57 (m, 1H) 7.40–7.32 (m, 4H) 6.49–6.40 (m, 1H) 6.06–5.97 (m, 1H) 4.25 (m, 2H) 4.00 (m, 3H) 3.94–3.91 (m, 3H) 2.56 (m, 1H) 1.26–0.78 (m, 9H).

Step 199.4: 3-amino-1,5-dimethylpyridin-2(1H)-one

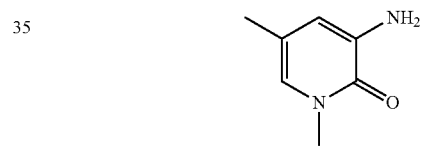

A solution of 9.74 g (57.9 mmol) 1,5-dimethyl-3-nitropyridin-2(1H)-one (product from step 199.5), 2 g (57.9 mmol) Raney-Ni in 230 ml methanol was shaken in a duck glass under $H_2$ atmosphere for 16 hours. After that, the mixture was filtered over celite, washed with MeOH, concentrated in vacuum and dried at high vacuum over night to obtain 7.9 g (57.2 mmol, 99% yield) of the title compound as a brownish solid. LCMS: (M+H)=139; $t_R$=0.43 min (LC-MS 6). HPLC: $t_R$=1.22 min (HPLC 8). 1H-NMR (DMSO-d6, 400 MHz) δ ppm 6.67 (m, 1H) 6.30 (m, 1H) 5.05 (bs, 2H) 3.38 (s, 3H) 1.93 (s, 3H).

Step 199.5: 1,5-dimethyl-3-nitropyridin-2(1H)-one

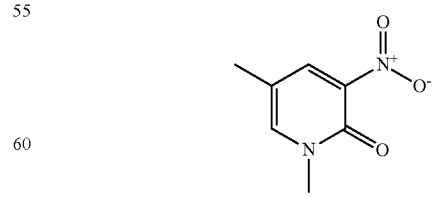

To a suspension of 10 g (63.6 mmol) 2-hydroxy-5-methyl-3-nitropyridine and 17.58 g (127 mmol) $K_2CO_3$ in 100 ml DMF, 5.96 ml (95 mmol) MeI was added at 0° C. Afterwards the reaction mixture was stirred at room temperature for 2 hours. The reaction mixture was concentrated, diluted with water and extracted three times with CH$_2$Cl$_2$. The organic layers were combined, dried over Na$_2$SO$_4$, filtered and concentrated to obtain an orange slurry. The residue was treated with ether and the precipitate was filtered off and dried under high vacuum to obtain 9.74 g (57.9 mmol, 91% yield) of the title compound as an orange solid. LCMS: (M+H)=169; t$_R$=0.47 min (LC-MS 6). HPLC: t$_R$=1.70 min (HPLC 8). 1H-NMR (DMSO-d6, 400 MHz) δ ppm 8.30 (d, 1H) 8.08 (m, 1H) 3.50 (s, 3H) 2.09 (s, 3H).

Example 200

4-(4-chlorophenyl)-5-(1,5-dimethyl-2-oxo-1,2-dihydropyridin-3-yl)-2-(2-(dimethylamino)-4-methoxypyrimidin-5-yl)-3-isopropyl-4,5-dihydropyrrolo[3,4-c]pyrazol-6(2H)-one

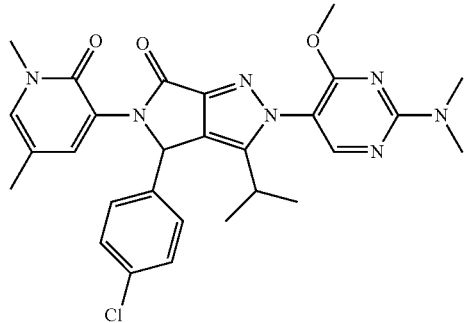 [SMILES: COc1nc(N(C)C)ncc1-n1nc2c(c1C(C)C)C(c1ccc(Cl)cc1)N(c1cc(C)cn(C)c1=O)C2=O]

The title compound was prepared in analogy to the procedure described in example 184 but using the product of step 200.1 After a first purification by column chromatography (Silicagel, CH$_2$Cl$_2$, CH$_2$Cl$_2$/MeOH 95:5), the residue was purified by preparative HPLC (Column: Sunfire 30×100 mm. Flow: 30 ml/min. Gradient: 20% to 70% B in 40 min; A=water+0.1% TFA, B=acetonitrile). The pure fractions were combined and worked up (addition of NaHCO$_3$, removal of acetonitrile followed by extraction with EtOAc). The residue was dissolved in 1,4-dioxane and freeze dried over night to obtain an yellowish solid. LCMS: (M+H)=548/550; t$_R$=1.19 min (LC-MS 6). HPLC: t$_R$=2.97 min (HPLC 8). 1H-NMR (DMSO-d6, 600 MHz) δ ppm 8.29 (bs, 1H) 7.49 (s, 1H) 7.37 (d, 2H) 7.24 (m, 3H) 6.50 (bs, 1H) 3.88 (s, 3H) 3.43 (s, 3H) 3.19 (s, 6H) 2.60 (m, 1H) 1.95 (s, 3H) 1.08 (d, 3H) 0.47 (d, 3H).

Step 200.1: 44(4-Chlorophenyl)(1,5-dimethyl-2-oxo-1,2-dihydropyridin-3-ylamino)methyl)-1-(2-(dimethylamino)-4-methoxypyrimidin-5-yl)-5-isopropyl-1H-pyrazole-3-carboxylic acid

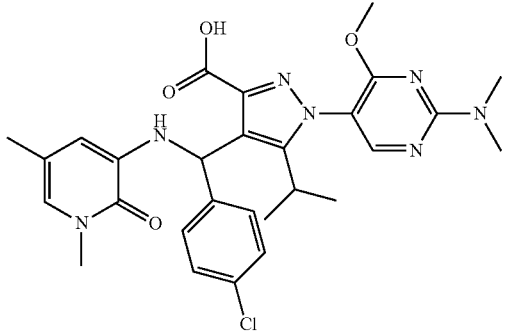

The title compound was prepared in analogy to the procedure described in step 198.2 but using the product of step 200.2. LCMS: (M+H)=566/568; t$_R$=1.21 min (LC-MS 6). HPLC: t$_R$=3.04 min (HPLC 8).

Step 200.2: Ethyl 44(4-chlorophenyl)(1,5-dimethyl-2-oxo-1,2-dihydropyridin-3-ylamino)methyl)-1-(2-(dimethylamino)-4-methoxypyrimidin-5-yl)-5-isopropyl-1H-pyrazole-3-carboxylate

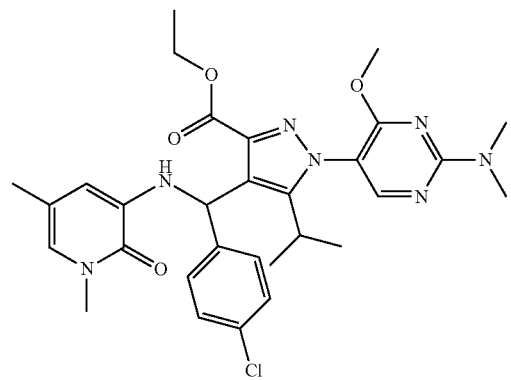

The title compound was prepared in analogy to the procedure described in step 184.2 but using the product of step 200.3 and 3-amino-1,5-dimethylpyridin-2(1H)-one (product of step 199.4). After the extraction, the crude product was purified by chromatography (Silicagel, EtOAc) to give an yellow solid. LCMS: (M+H)=594/596; t$_R$=1.34 min (LC-MS 6). HPLC: t$_R$=3.78 min (HPLC 8).

Step 200.3: Ethyl 44(4-chlorophenyl)(hydroxy)methyl)-1-(2-(dimethylamino)-4-methoxypyrimidin-5-yl)-5-isopropyl-1H-pyrazole-3-carboxylate

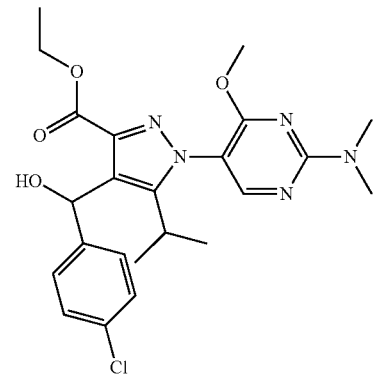 [SMILES: CCOC(=O)c1nn(-c2cnc(N(C)C)nc2OC)c(C(C)C)c1C(O)c1ccc(Cl)cc1]

The title compound was prepared in analogy to the procedure described in step 184.3 but using the product of step 200.4 and 4-chlorobenzaldehyde. LCMS: (M+H)=474; t$_R$=1.30 min (LC-MS 6). HPLC: t$_R$=3.27 min (HPLC 8). 1H-NMR (DMSO-d6, 400 MHz) δ ppm 8.19–8.16 (m, 1H)

7.39–7.31 (m, 4H) 6.48–6.39 (m, 1H) 6.01–5.93 (m, 1H) 4.24 (m, 2H) 3.87–3.84 (m, 3H) 3.21–3.09 (m, 7H) 1.26–0.87 (m, 6H) 0.79 (d, 3H).

Step 200.4: Ethyl 1-(2-(dimethylamino)-4-methoxy-pyrimidin-5-yl)-4-iodo-5-isopropyl-1H-Pyrazole-3-carboxylate

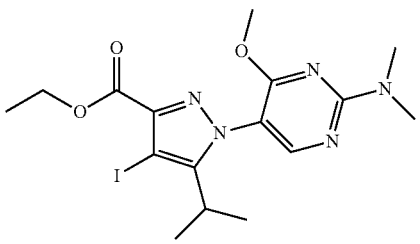 [SMILES: CCOC(=O)c1nn(-c2cnc(N(C)C)nc2OC)c(C(C)C)c1I]

A mixture of 0.5 g (1.00 mmol) (product of step 200.5) and 0.95 ml (2.00 mmol) dimethylamine (2.1 M in THF) was heated at 80° C. for 15 hours. After that the solution was evaporated and the residue was purified by chromatography (Silicagel, Heptane/EtOAc 70:30 to 65:35) to afford 424 mg (0.923 mmol, 92% yield) of the title compound as white foam. LCMS: (M+H)=460; $t_R$=1.27 min (LC-MS 4). HPLC: $t_R$=4.94 min (HPLC 7). TLC: Rf=0.32 (EtOAc/Heptane 1:1). 1H-NMR (DMSO-d6, 600 MHz) δ ppm 8.22 (s, 1H) 4.25 (q, 2H) 3.86 (s, 3H) 3.18 (s, 6H) 2.88 (m, 1H) 1.27 (t, 3H) 1.23 (d, 3H) 1.17 (d, 3H).

Step 200.5: Ethyl 4-iodo-5-isopropyl-1-(4-methoxy-2-(methylsulfonyl)pyrimidin-5-yl)-1H-Pyrazole-3-carboxylate

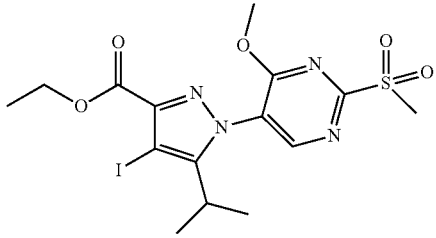 [SMILES: CCOC(=O)c1nn(-c2cnc(S(C)(=O)=O)nc2OC)c(C(C)C)c1I]

The title compound was prepared in analogy to the procedure described in step 184.4 but using the product of step 147.9 (5-isopropyl-1-(2-methanesulfonyl-4-methoxy-pyrimidin-5-yl)-1H-pyrazole-3-carboxylic acid ethyl ester). After the extraction, the crude product was purified by chromatography (Silicagel, Heptane, EtOAc, 80:20 to 50:50). LCMS: (M+H)=494.9; $t_R$=1.05 min (LC-MS 4). HPLC: $t_R$=4.94 min (HPLC 7). TLC: Rf=0.40 (EtOAc/Heptane 1:1). 1H-NMR (DMSO-d6, 600 MHz) δ ppm 9.07 (s, 1H) 4.28 (q, 2H) 4.08 (s, 3H) 3.47 (s, 3H) 2.92 (quin, 1H) 1.32–1.22 (m, 9H).

The following additional compounds of formula (I) can be prepared using procedures described herein and common general knowledge. In particular, synthetic methods disclosed in the Journal of the Chemical Society, Chemical Communications, (3), 91-2; 1977, may be useful in the preparation of starting materials for use in a method such as scheme 3, disclosed herein.

5-(3-Chloro-2-fluoro-phenyl)-4-(4-chloro-phenyl)-2-(2,4-dimethoxy-pyrimidin-5-yl)-3-(2-methoxy-1-methyl-ethyl)-4,5-dihydro-2H-pyrrolo[3,4-c]pyrazol-6-one

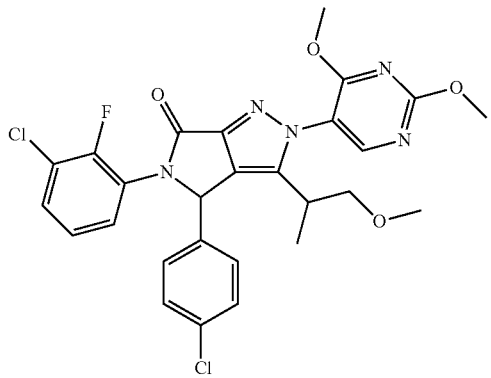 [SMILES: COCC(C)c1c2c(nn1-c1cnc(OC)nc1OC)C(=O)N(c1cccc(Cl)c1F)C2c1ccc(Cl)cc1]

5-(3-Chloro-2-fluoro-phenyl)-4-(4-chloro-phenyl)-2-(2,4-dimethoxy-pyrimidin-5-yl)-3-(2-hydroxy-1-methyl-ethyl)-4,5-dihydro-2H-pyrrolo[3,4-c]pyrazol-6-one

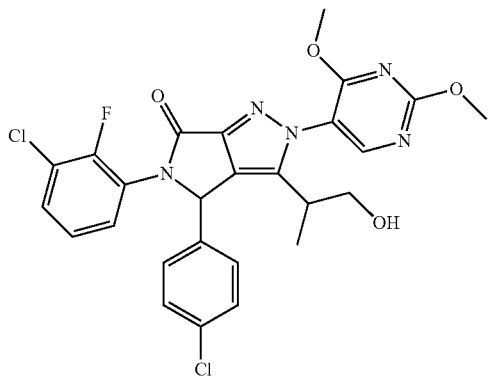 [SMILES: COc1ncc(-n2nc3c(c2C(C)CO)C(c2ccc(Cl)cc2)N(c2cccc(Cl)c2F)C3=O)c(OC)n1]

3-(2-Amino-1-methyl-ethyl)-5-(3-chloro-2-fluoro-phenyl)-4-(4-chloro-phenyl)-2-(2,4-dimethoxy-pyrimidin-5-yl)-4,5-dihydro-2H-pyrrolo[3,4-c]pyrazol-6-one

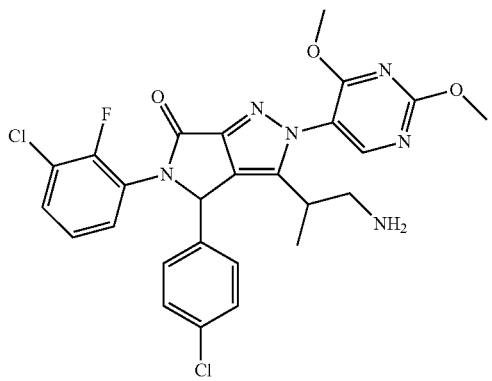 [SMILES: COc1ncc(-n2nc3c(c2C(C)CN)C(c2ccc(Cl)cc2)N(c2cccc(Cl)c2F)C3=O)c(OC)n1]

5-(3-Chloro-2-fluoro-phenyl)-4-(4-chloro-phenyl)-2-(2,4-dimethoxy-pyrimidin-5-yl)-3-(2-dimethy-lamino-1-methyl-ethyl)-4,5-dihydro-2H-pyrrolo[3,4-c]pyrazol-6-one

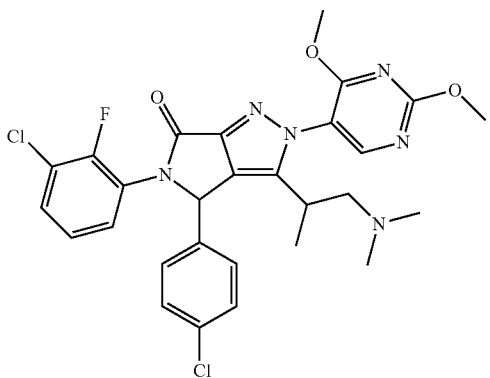 [SMILES: COc1ncc(-n2nc3c(c2C(C)CN(C)C)C(c2ccc(Cl)cc2)N(c2cccc(Cl)c2F)C3=O)c(OC)n1]

N-{2-[5-(3-Chloro-2-fluoro-phenyl)-4-(4-chloro-phenyl)-2-(2,4-dimethoxy-pyrimidin-5-yl)-6-oxo-2,4,5,6-tetrahydro-pyrrolo[3,4-c]pyrazol-3-yl]-propyl}-acetamide

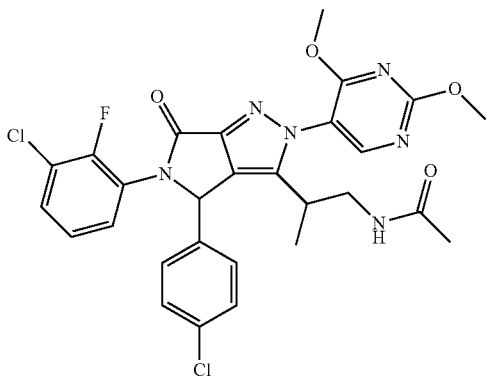 [SMILES: COc1ncc(-n2nc3c(c2C(C)CNC(C)=O)C(c2ccc(Cl)cc2)N(c2cccc(Cl)c2F)C3=O)c(OC)n1]

N-{2-[5-(3-Chloro-2-fluoro-phenyl)-4-(4-chloro-phenyl)-2-(2,4-dimethoxy-pyrimidin-5-yl)-6-oxo-2,4,5,6-tetrahydro-pyrrolo[3,4-c]pyrazol-3-yl]-propyl}-formamide

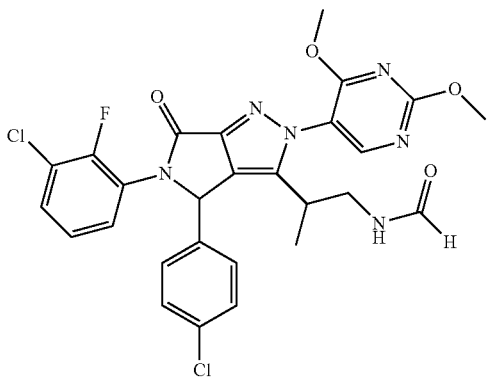 [SMILES: COc1ncc(-n2nc3c(c2C(C)CNC=O)C(c2ccc(Cl)cc2)N(c2cccc(Cl)c2F)C3=O)c(OC)n1]

Selected compounds have been crystallized and further characterized. The experimental procedures and the instrument and method description are outlined below:
Instrument name: X-ray Diffractometer
Model: D8 Advance Manufacturer: Bruker AXS GMBH
Wavelength: 1.5406 A (Cu)
Generator setting: 30 Kv; 40 mA
Monochromator
Detector: PSD-Lynx Eye
Experiment Method:
2-Theta start: 2.0 degree
2-Theta end: 40.0 degree
Integration stepsize: 0.0157 degree
Scan Time: 13.02 min
Temperature: room temperature Example 153 [(S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one] (123 mg, 0.216 mmol) was dissolved in EtOH (615 µl). Then, water (615 µl) was added. The resulting suspension was stirred for 30 min at rt. Stirring was stopped and the mixture was allowed to stand for 40 h at rt. EtOH (100 µl) was added and the suspension was heated until it became a clear solution, which was allowed to cool to rt. After 24 h, the colorless solid material (93 mg) was collected.

| Angle 2-Theta | d value °Angstrom | Intensity % |
|---|---|---|
| 6.320 | 13.97363 | 21.5 |
| 7.436 | 11.87972 | 100.0 |
| 12.645 | 6.99464 | 63.1 |
| 14.134 | 6.26125 | 34.3 |
| 14.979 | 5.90979 | 34.5 |
| 19.185 | 4.62250 | 44.7 |
| 22.477 | 3.95250 | 51.3 |
| 27.315 | 3.26239 | 50.9 |

100 mg of example 168 [(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one] were triturated for 16 hrs in Et$_2$O to afford 80 mg of white solid which are dissolved in 1.5 ml of hot 50% H$_2$O/EtOH, filtered hot and the filtrate was left at RT for 24 hrs. 22 mg of white needles were collected.

| Angle 2-Theta | d value °Angstrom | Intensity % |
|---|---|---|
| 8.829 | 10.00746 | 40.7 |
| 9.960 | 8.87369 | 58.8 |
| 11.595 | 7.62565 | 70.7 |
| 21.927 | 4.05038 | 73.4 |

50 mg of example 176 [(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one] were dissolved in 1.2 ml of hot 50% H$_2$O/EtOH, filtered hot and the filtrate was left at RT for 24 hrs. 38 mg of white needles were collected.

| Angle 2-Theta | d value °Angstrom | Intensity % |
|---|---|---|
| 8.555 | 10.32763 | 18.7 |
| 9.531 | 9.27206 | 56.8 |
| 11.095 | 7.96802 | 58.2 |
| 11.776 | 7.50910 | 100.0 |
| 13.191 | 6.70664 | 36.8 |
| 17.172 | 5.15959 | 34.0 |

-continued

| Angle 2-Theta | d value °Angstrom | Intensity % % |
|---|---|---|
| 20.589 | 4.31049 | 47.7 |
| 23.907 | 3.71921 | 45.8 |
| 25.316 | 3.51528 | 37.9 |
| 30.185 | 2.95837 | 54.4 |
| 36.291 | 2.47341 | 35.3 |
| 38.143 | 2.35747 | 13.3 |

697 mg of example 178 [(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile] were taken up in ethanol (total volume: 19 mL, started with 5 ml at reflux. Additional 14 ml were necessary to get a clear solution) and stirred. Afterwards the solution was allowed to cool to ambient temperature under stirring in 4 hrs. The precipitate was filtered off and dried in vacuum overnight at 40° C. to obtain 0.60 g white solid (1H-NMR: compound contains approx. 1 eq EtOH, purity 100%)

| Angle 2-Theta | d value °Angstrom | Intensity % % |
|---|---|---|
| 7.750 | 11.39783 | 10.6 |
| 9.957 | 8.87631 | 100.0 |
| 12.224 | 7.23462 | 41.3 |
| 14.192 | 6.23556 | 72.8 |
| 16.171 | 5.47685 | 70.3 |
| 17.442 | 5.08027 | 42.3 |
| 18.468 | 4.80039 | 20.6 |
| 22.281 | 3.98667 | 50.4 |
| 24.564 | 3.62119 | 61.5 |
| 25.465 | 3.49505 | 39.0 |
| 28.068 | 3.17650 | 26.0 |

It will be appreciated by the skilled crystallographer that the relative intensities of the various peaks reported in the Tables and Figures may vary due to a number of factors such as the orientation effects of the crystals in the X-ray beam, and the purity of the material being analyzed. The peak positions may also shift for variations in sample weight but will remain substantially the same.

Figure 1:
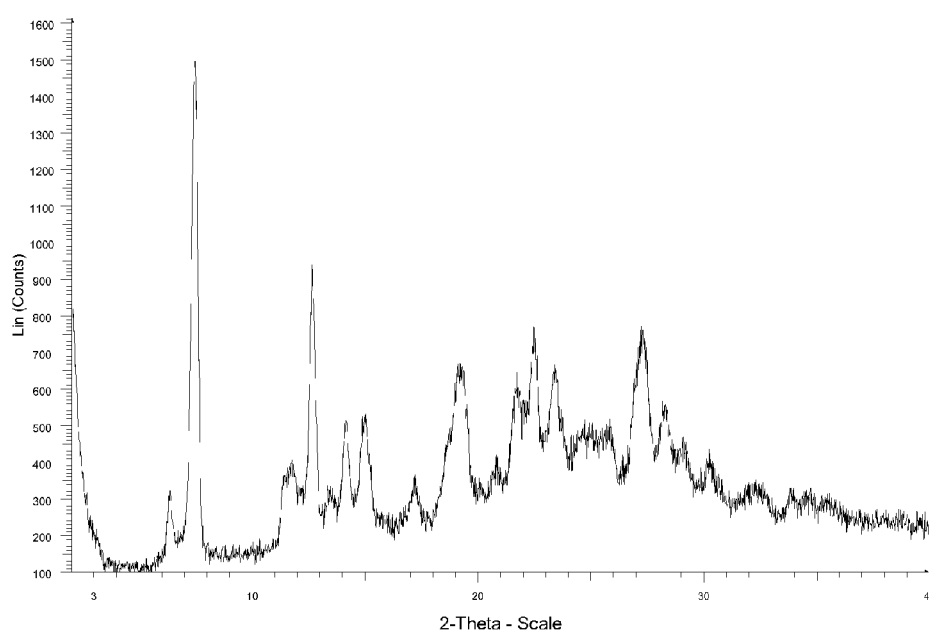
FIG. 1 discloses the X-ray powder diffraction data for example 153 [(S)-5-(5-Chloro-1-methyl-6-oxo-1,6-dihydropyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one]crystalline form as obtained using the procedure described above.
Figure 2:
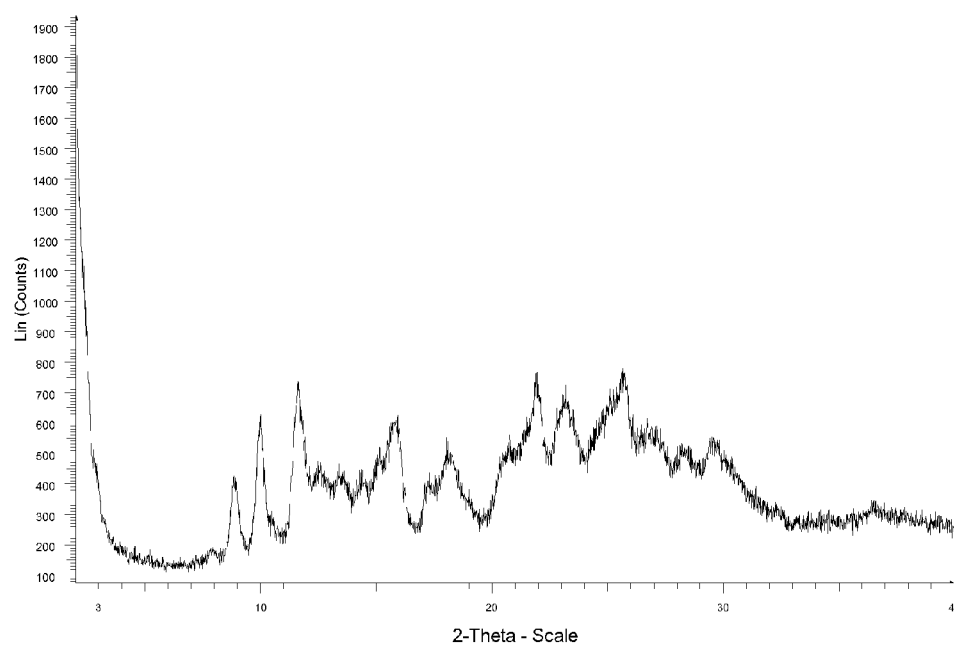
FIG. 2 discloses the X-ray powder diffraction data for example 168 [(S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one] crystalline form as obtained using the procedure described above.
Figure 3:
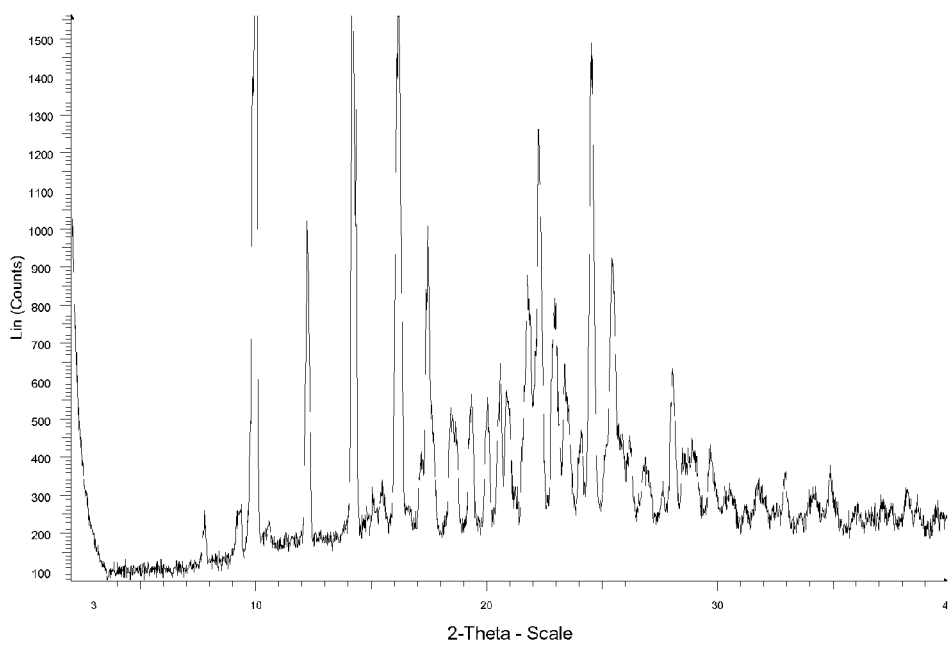
FIG. 3 discloses the X-ray powder diffraction data for example 176 [(S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one]crystalline form as obtained using the procedure described above.
Figure 4:
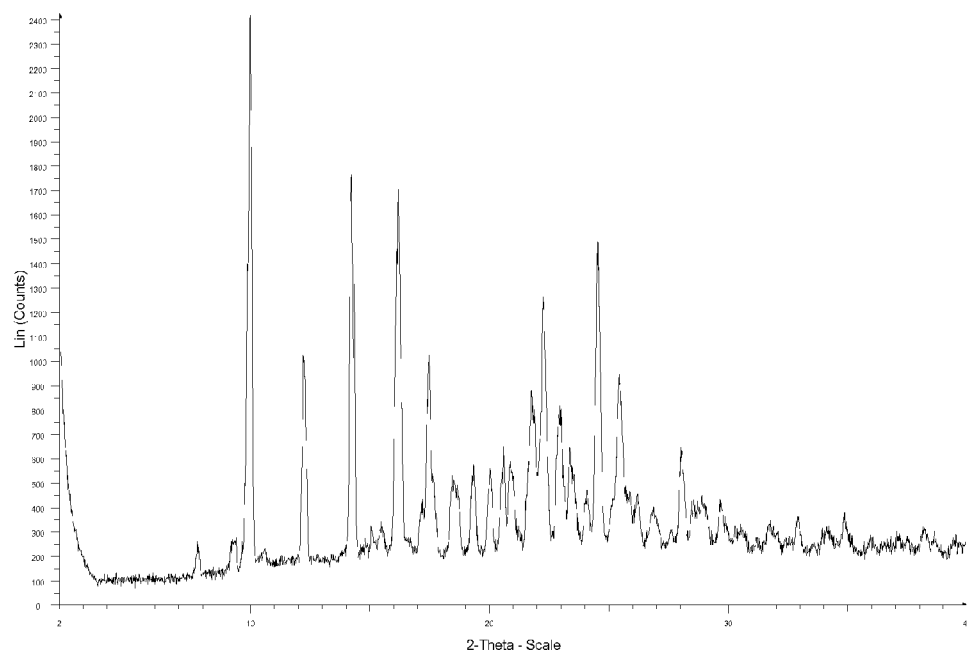
FIG. 4 discloses the X-ray powder diffraction data for example 178 [(S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile]crystalline form as obtained using the procedure described above.

In another embodiment, the invention provides a compound as described herein.

Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 µL by adding 1 µL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 1.25 nM MDM2-biotinylated or 2.5 nM MDM4-biotinylated (internal preparations), and 0.625 nM Europium labeled streptavidin (Perkin Elmer), the solution is pre-incubated for 15 minutes at room temperature, then 10 nM Cy5-p53 peptide (internal preparation) is added before an incubation at room temperature for 15 minutes prior to reading the plate. For measurement of samples, a Victor II microplate reader (Perkin Elmer) is used with the following settings: Excitation 340 nm, Emission Donor 620 nm and Emission Acceptor 665 nm. $IC_{50}$ values are calculated by curve fitting using XLfit. If not specified, reagents are purchased from Sigma-Aldrich Chemie GmBH, Buchs, Switzerland. This assay was used to evaluate compounds displaying inhibition of p53-MDM2 interaction and p53-MDM4 interaction at $IC_{50}$s of 0.005 to 50 µM (p53-MDM2 Assay 1 and p53-MDM4 Assay 1, respectively). For selected compounds displaying $IC_{50}$s between 0.05 and 5 nM on MDM2, a slightly modified assay is used with the following adaptations: 0.1 nM MDM2, 0.1 nM Europium labeled streptavidin and Tecan genios Pro is used as a microplate reader for the fluorescence measurements (p53-MDM2 Assay 2).

TABLE

| Example | IC$_{50}$ (μM) p53-MDM2 Assay 1 | IC$_{50}$ (μM) p53-MDM4 Assay 1 | IC$_{50}$ (nM) p53-MDM2 Assay 2 |
|---|---|---|---|
| 1 | 0.0078 | 4.1557 | 6.507 |
| 2 | 0.0113 | 15.3645 | n.d. |
| 3 | 0.004 | 10.8898 | n.d. |
| 4 | 0.0088 | 35.1448 | n.d. |
| 5 | 0.0053 | 14.2755 | n.d. |
| 6 | 0.0186 | 9.8352 | n.d. |
| 7 | 0.0048 | n.d. | n.d. |
| 8 | 0.0099 | 19.7395 | n.d. |
| 9 | 0.0228 | 51.1685 | n.d. |
| 10 | 0.0089 | n.d. | n.d. |
| 11 | 0.0314 | 12.4703 | n.d. |
| 12 | 0.0166 | 6.5678 | n.d. |
| 13 | 0.0089 | 32.3629 | n.d. |
| 14 | n.d. | n.d. | n.d. |
| 15 | 0.0417 | n.d. | n.d. |
| 16 | 0.0079 | 15.8674 | n.d. |
| 17 | 0.0339 | 20.954 | n.d. |
| 18 | 0.0162 | 7.6137 | n.d. |
| 19 | 0.0061 | 36.7265 | n.d. |
| 20 | 0.0042 | 18.888 | n.d. |
| 21 | 0.0028 | 16.3012 | n.d. |
| 22 | 0.0029 | 16.0691 | n.d. |
| 23 | 0.0044 | 23.5855 | n.d. |
| 24 | 0.003 | 19.2863 | n.d. |
| 25 | 0.0024 | 6.6522 | n.d. |
| 26 | 0.0021 | 12.3366 | n.d. |
| 27 | 0.0014 | 14.9475 | 1.099 |
| 28 | 0.0022 | 14.8854 | n.d. |
| 29 | 0.0031 | 11.8995 | n.d. |
| 30 | 0.0022 | 11.017 | n.d. |
| 31 | 0.0292 | 29.7227 | n.d. |
| 32 | 0.0081 | 15.1101 | n.d. |
| 33 | 0.0193 | n.d. | n.d. |
| 34 | 0.0062 | 13.4852 | n.d. |
| 35 | 0.0042 | 16.43 | n.d. |
| 36 | 0.0062 | 8.4352 | n.d. |
| 37 | 0.0088 | 20.9978 | n.d. |
| 38 | 0.0044 | 14.1625 | n.d. |
| 39 | 0.0026 | 4.1709 | n.d. |
| 40 | 0.0114 | 17.0351 | n.d. |
| 41 | 0.012 | 46.8667 | n.d. |
| 42 | 0.006 | 20.2464 | n.d. |
| 43 | 0.002 | 9.4577 | n.d. |
| 44 | 0.0025 | 16.2272 | n.d. |
| 45 | 0.0007 | 4.8683 | n.d. |
| 46 | 0.004 | 7.5193 | n.d. |
| 47 | 0.0041 | 20.9033 | n.d. |
| 48 | 0.0017 | 9.0429 | n.d. |
| 49 | 0.0034 | 16.4746 | n.d. |
| 50 | 0.0027 | 13.2614 | n.d. |
| 51 | 0.0211 | 40.6894 | n.d. |
| 52 | 0.0011 | 5.628 | n.d. |
| 53 | 0.0016 | 4.8575 | n.d. |
| 54 | 0.0015 | 5.1046 | n.d. |
| 55 | 0.0242 | n.d. | n.d. |
| 56 | 0.0205 | n.d. | n.d. |
| 57 | 0.0059 | 13.0467 | n.d. |
| 58 | 0.0069 | 46.9345 | n.d. |
| 59 | 0.0073 | 27.1826 | n.d. |
| 60 | 0.0132 | 20.2545 | n.d. |
| 61 | 0.0068 | 12.5677 | n.d. |
| 62 | 0.0207 | 23.1629 | n.d. |
| 63 | 0.0147 | 47.9186 | n.d. |
| 64 | 0.0115 | 17.8284 | n.d. |
| 65 | 0.0078 | 15.8067 | n.d. |
| 66 | 0.0067 | 2.2744 | n.d. |
| 67 | 0.0033 | 0.5853 | n.d. |
| 68 | 0.1079 | 11.3629 | n.d. |
| 69 | 0.0018 | 20.8831 | n.d. |
| 70 | 0.002 | 12.4394 | n.d. |
| 71 | 0.0244 | 61.2823 | n.d. |
| 72 | 0.003 | 10.4008 | n.d. |
| 73 | 0.018 | 20.5327 | n.d. |
| 74 | 0.0071 | 80.9824 | n.d. |
| 75 | 0.0104 | 16.2819 | n.d. |
| 76 | 0.0032 | 4.4555 | n.d. |
| 77 | 0.0143 | 25.8447 | n.d. |
| 78 | 0.0156 | 27.8091 | n.d. |
| 79 | 0.0041 | 20.4418 | n.d. |
| 80 | 0.0032 | 2.1159 | n.d. |
| 81 | 0.0056 | 20.6699 | n.d. |
| 82 | 0.0084 | 53.6061 | n.d. |
| 83 | 0.0026 | 17.6042 | n.d. |
| 84 | 0.0011 | 1.6588 | n.d. |
| 85 | 0.0232 | 23.647 | n.d. |
| 86 | 0.0085 | 14.444 | n.d. |
| 87 | 0.0019 | 10.6077 | n.d. |
| 88 | 0.0023 | 15.8476 | n.d. |
| 89 | 0.0011 | 24.2146 | 0.499 |
| 90 | 0.0052 | n.d. | n.d. |
| 91 | 0.0833 | n.d. | n.d. |
| 92 | 0.0017 | 1.3198 | n.d. |
| 93 | 0.0016 | 9.2552 | n.d. |
| 94 | 0.0052 | 5.2781 | n.d. |
| 95 | 0.0034 | 3.1998 | n.d. |
| 96 | 0.0057 | 12.8939 | n.d. |
| 97 | 0.0062 | 35.2964 | n.d. |
| 98 | 0.0019 | 32.5519 | n.d. |
| 99 | 0.0015 | 1.5248 | n.d. |
| 100 | 0.0013 | 3.0565 | n.d. |
| 101 | 0.002 | 0.6498 | n.d. |
| 102 | 0.0018 | 0.1927 | 0.238 |
| 103 | 0.0038 | 43.0144 | n.d. |
| 104 | 0.0021 | 1.1635 | n.d. |
| 105 | 0.0029 | 3.011 | n.d. |
| 106 | 0.0021 | 0.5006 | 0.195 |
| 107 | 0.0017 | 5.8062 | 0.701 |
| 108 | 0.0013 | 2.0614 | 0.425 |
| 109 | 0.0022 | 1.9054 | 0.377 |
| 110 | 0.0012 | 1.1261 | 0.393 |
| 111 | 0.0107 | 15.9977 | n.d. |
| 112 | 0.0011 | 0.8381 | 0.267 |
| 113 | 0.0011 | 0.6254 | 0.42 |
| 114 | 0.0011 | 0.5051 | 0.259 |
| 115 | 0.0038 | 5.7775 | 1.773 |
| 116 | 0.0083 | 19.2135 | 8.671 |
| 117a | 0.0129 | 15.0525 | n.d. |
| 117b | 0.0225 | 17.6925 | n.d. |
| 118 | 0.0072 | 4.4216 | n.d. |
| 119 | 0.0021 | 1.4957 | 0.926 |
| 120 | 0.0225 | n.d. | n.d. |
| 121 | 0.0069 | n.d. | n.d. |
| 122 | 0.0025 | 17.0352 | 1.99 |
| 123 | 0.1101 | 88.4021 | n.d. |
| 124 | 0.0018 | 1.2025 | 0.18 |
| 125 | 0.0017 | 0.452 | 0.187 |
| 126 | 0.0012 | 0.1502 | 0.146 |
| 127 | n.d. | n.d. | 0.196 |
| 128 | n.d. | n.d. | 0.169 |
| 129 | n.d. | n.d. | 0.382 |
| 130 | n.d. | n.d. | 0.551 |
| 131 | n.d. | n.d. | 0.396 |
| 132 | n.d. | n.d. | 0.45 |
| 133 | n.d. | n.d. | 0.22 |
| 134 | n.d. | n.d. | 0.267 |
| 135 | n.d. | n.d. | 0.75 |
| 136 | n.d. | n.d. | 0.242 |
| 137 | n.d. | n.d. | 1.026 |
| 138 | n.d. | n.d. | 0.176 |
| 139 | 0.0026 | 14.1123 | n.d. |
| 140 | 2.0859 | 16.7039 | n.d. |
| 141 | 0.0006 | 0.6999 | 0.161 |
| 142 | 0.5058 | 26.0179 | n.d. |
| 143 | 0.0005 | 0.4891 | 0.101 |
| 144 | 0.0039 | 2.1245 | n.d. |
| 145 | n.d. | n.d. | 0.53 |
| 146 | n.d. | n.d. | 0.348 |
| 147 | n.d. | n.d. | 0.13 |
| 148 | n.d. | n.d. | 0.12 |
| 149 | n.d. | n.d. | 0.103 |

TABLE-continued

| Example | IC$_{50}$ (μM) p53-MDM2 Assay 1 | IC$_{50}$ (μM) p53-MDM4 Assay 1 | IC$_{50}$ (nM) p53-MDM2 Assay 2 |
|---|---|---|---|
| 150 | n.d. | n.d. | 0.25 |
| 151 | n.d. | n.d. | 0.37 |
| 152 | n.d. | n.d. | 0.232 |
| 153 | n.d. | n.d. | 0.241 |
| 154 | n.d. | n.d. | 111.313 |
| 155 | n.d. | n.d. | 0.176 |
| 156 | n.d. | n.d. | 0.13 |
| 157 | n.d. | n.d. | 0.166 |
| 158 | n.d. | n.d. | 0.222 |
| 159 | n.d. | n.d. | 0.772 |
| 160 | n.d. | n.d. | 1.242 |
| 161 | n.d. | n.d. | 1.302 |
| 161 | n.d. | n.d. | 1.447 |
| 163 | n.d. | n.d. | 0.317 |
| 164 | n.d. | n.d. | 0.453 |
| 165 | n.d. | n.d. | 0.408 |
| 166 | n.d. | n.d. | 0.357 |
| 167 | n.d. | n.d. | 14.827 |
| 168 | n.d. | n.d. | 0.161 |
| 169 | n.d. | n.d. | 1.247 |
| 170 | n.d. | n.d. | 86.64 |
| 171 | n.d. | n.d. | 0.129 |
| 172 | n.d. | n.d. | 0.371 |
| 173 | n.d. | n.d. | 0.661 |
| 174 | n.d. | n.d. | 0.663 |
| 175 | n.d. | n.d. | 0.367 |
| 176 | 0.0007 | n.d. | 0.157 |
| 177 | n.d. | n.d. | 266.774 |
| 178 | n.d. | n.d. | 0.120 |
| 179 | n.d. | n.d. | 22.7 |
| 180 | 0.0006 | n.d. | 0.068 |
| 181 | n.d. | n.d. | 24.425 |
| 182 | n.d. | n.d. | 86.074 |
| 183 | n.d. | n.d. | 0.097 |
| 184 | n.d. | n.d. | 1.089 |
| 185 | n.d. | n.d. | 1.437 |
| 186 | n.d. | n.d. | 0.384 |
| 187 | n.d. | n.d. | 0.553 |
| 188 | n.d. | n.d. | 4.058 |
| 189 | n.d. | n.d. | 1.292 |
| 190 | n.d. | n.d. | 10.3 |
| 191 | n.d. | n.d. | 0.376 |
| 192 | n.d. | n.d. | 0.213 |
| 193 | n.d. | n.d. | 0.215 |
| 194 | n.d. | n.d. | 0.197 |
| 195 | n.d. | n.d. | 0.128 |
| 196 | n.d. | n.d. | 0.165 |
| 197 | n.d. | n.d. | 0.155 |
| 198 | n.d. | n.d. | 0.164 |
| 199 | n.d. | n.d. | 2.13 |
| 200 | n.d. | n.d. | 0.528 | n.d.: not determined

Cellular Proliferation Assay in SJSA-1 and SAOS-2 Cells Based on YO-PRO®-1 Iodide Staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated. To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 μM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

In Vivo Experiments

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, 3×10$^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example, the HCT116 colon carcinoma cell line (ATCC No. CCL-247);

the LNCaP clone FGC prostate carcinoma cell line (ATCC No. CRL-1740);

the RKO colon carcinoma cell line (ATCC No. CRL-2577);

the HT1080 fibrosarcoma cell line (ATCC No. CCL-121);

the A375 malignant melanoma cell line (ATCC No. CRL-1619), the NCI-H460 large cell lung carcinoma cell line (ATCC No. HTB-177);

the JEG-3 choriocarcinoma (ATCC No. HTB-36)

the ZR-75-1 breast ductal carcinoma (ATCC No. CRL-1500)

The invention claimed is:

1. A compound of formula (I) or a salt thereof,

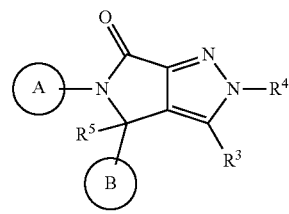

wherein

A is selected from

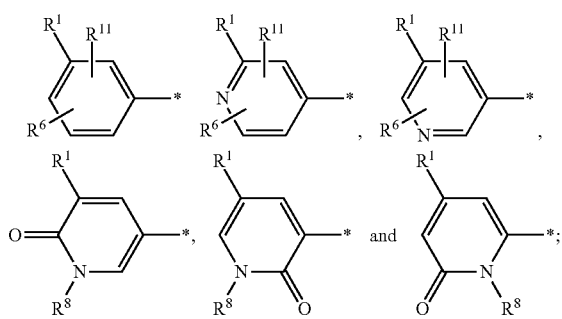

B is selected from

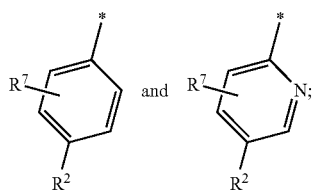

R¹ is selected from chloro, fluoro and methyl;
R² is selected from chloro, fluoro, trifluoromethyl, methyl and cyano;
R³ is selected from isopropyl, cyclopropyl, isobutyl, tert-butyl, cyclobutyl, cyclopentyl, or R³ is:

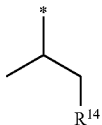

wherein $R^{14}$ is selected from OH, methoxy, $NH_2$, $NMe_2$, NHMe, NHCOMe and NHCOH;
$R^4$ is selected from
  H,
  —$(C_0-C_4)$alkyl-phenyl, said phenyl being optionally substituted with 1, 2 or 3 substituents independently selected from:
    $(C_1-C_4)$alkyl, optionally substituted by $NR^9(R^{10})$ or —O—$(C_1-C_4)$alkyl or by 1, 2 or 3 halo substituents,
    —O—$(C_1-C_4)$alkyl, optionally substituted by $NR^9(R^{10})$, phenyl or —O—$(C_1-C_4)$alkyl, or by 1, 2 or 3 halo substituents,
    —$C(O)NR^9(R^{12})$,
    cyano,
    halo,
    —$(CH_2)_m$—$S(O)_x NR^9(R^{10})$,
    —$C(O)OH$,
    —$C(O)O$—$(C_1-C_4)$alkyl,
    —$(CH_2)_p$—$NR^9(R^{12})$,
    heterocyclyl¹, and
    phenyl
  and wherein —$(C_0-C_4)$alkyl of said —$(C_0-C_4)$alkyl-phenyl, when present, is optionally substituted by 1 or 2 OH,
  —$(C_0-C_4)$alkyl-C(O)-phenyl, said phenyl being optionally substituted with 1, 2 or 3 substituents independently selected from:
    $(C_1-C_4)$alkyl, optionally substituted with from 1 to 3 halo,
    —O—$(C_1-C_4)$alkyl,
    cyano, and
    halo,
  naphthyl,
  —$(C_0-C_4)$alkyl-$(C_3-C_6)$cycloalkyl, said $(C_3-C_6)$cycloalkyl being optionally substituted with 1, 2 or 3 substituents independently selected from OH, —$C(O)NR^9(R^{10})$, —O—$C(O)$—$(C_1-C_4)$alkyl, halo, —$(CH_2)_m$—$NR^9(R^{10})$ and —$C(O)$—$O(C_1-C_4)$alkyl,
  —$(C_0-C_4)$alkyl-heteroaryl¹, the heteroaryl¹ of said —$(C_0-C_4)$alkyl-heteroaryl¹ being optionally substituted by 1, 2, 3 or 4 substituents independently selected from —O—$(C_1-C_4)$alkyl, =O, OH, cyano, $(C_1-C_4)$alkyl, halo and —$NR^9(R^{10})$,
  —$(C_0-C_4)$alkyl-$C(O)NR^9(R^{13})$,
  —$(C_0-C_4)$alkyl-$NR^9(R^{12})$, wherein —$(C_0-C_4)$alkyl of said —$(C_0-C_4)$alkyl-$NR^9(R^{12})$, when present, is optionally substituted with 1 or 2 OH,
  —$(C_0-C_4)$alkyl-heterocyclyl⁴, said heterocyclyl⁴ being optionally substituted by 1, 2, 3 or 4 substituents independently selected from
    —O—$C(O)NR^9(R^{12})$,
    OH,
    —$C(O)(C_1-C_4)$alkyl, optionally substituted by $(C_1-C_4)$alkoxy,
    —$C(O)$—$O(C_1-C_4)$alkyl, optionally substituted by $(C_1-C_4)$alkoxy,
    =O,
    halo,
    —C(O)— heteroaryl², and
    $(C_1-C_4)$alkyl, optionally substituted by phenyl,
  and wherein the —$(C_0-C_4)$alkyl of —$(C_0-C_4)$alkyl-heterocyclyl⁴, when present, is optionally substituted with 1 or 2 OH,
  $(C_1-C_8)$alkyl, said $(C_1-C_8)$alkyl being optionally substituted by 1, 2 or 3 substituents independently selected from OH, halo, —O—$(C_1-C_4)$alkyl, —$C(O)(C_1-C_4)$alkyl, —$C(O)O$—$(C_1-C_4)$alkyl, —$C(O)OH$, cyano and $NR^9(R^{10})$,
  $(C_1-C_8)$alkenyl, said $(C_1-C_8)$alkenyl being optionally substituted by 1, 2 or 3 substituents independently selected from OH, halo and —O—$(C_1-C_4)$alkyl;
$R^5$ is selected from:
  H,
  heterocyclyl¹-C(O)—$(CH_2)_n$—,
  $(C_1-C_4)$alkyl-, said $(C_1-C_4)$alkyl- being optionally substituted with 1 or 2 substituents independently selected from OH, =O,
  heterocyclyl¹-$(C_1-C_4)$alkyl-, wherein said alkyl of heterocyclyl¹-$(C_1-C_4)$alkyl- is optionally substituted by 1 or 2 OH, and said heterocyclyl¹ can be optionally substituted by methyl or ethyl,
  $(C_1-C_4)$alkyl-O—C(O)—$(CH_2)_m$— and
  cyano;
$R^6$ is selected from
  H,
  $(C_1-C_4)$alkyl-, optionally substituted with $(C_1-C_4)$alkoxy,
  $(C_1-C_4)$alkoxy, optionally substituted with $(C_1-C_4)$alkoxy,
  $(C_1-C_4)$alkoxy$(C_1-C_4)$alkoxy$(C_1-C_4)$alkyl-,
  halo,
  $R^9(R^{10})N$—C(O)—$(CH_2)_m$—,
  cyano
  $R^9(R^{10})N$—$(CH_2)_m$—,
  $R^9(R^{10})N$—$(CH_2)_n$—O—$(CH_2)_m$—,
  $(C_1-C_4)$alkyl-$C(O)$—$(R^{10})N$—$(CH_2)_m$—, and
  —O—$(CH_2)_p$-heteroaryl²;

R$^7$ is selected from
H,
halo,
(C$_1$-C$_4$)alkyl-, optionally substituted with (C$_1$-C$_4$)alkoxy,
(C$_1$-C$_4$)alkoxy, optionally substituted with (C$_1$-C$_4$)alkoxy,
(C$_1$-C$_4$)alkoxy(C$_1$-C$_4$)alkoxy(C$_1$-C$_4$)alkyl-,
R$^9$(R$^{10}$)N—(CH$_2$)$_n$—O—(CH$_2$)$_m$—, and
(C$_1$-C$_4$)alkyl-C(O)O—(CH$_2$)$_n$—(R$^{10}$)N—;
R$^8$ is selected from
H,
(C$_1$-C$_4$)alkoxy(C$_1$-C$_4$)alkyl-,
(C$_1$-C$_4$)alkyl-, said (C$_1$-C$_4$)alkyl- being optionally substituted by 1, 2 or 3 substituents independently selected from OH, halo, —O—(C$_1$-C$_4$)alkyl, NR$^9$(R$^{10}$), and (C$_1$-C$_4$)alkyl-C(O)NR$^9$(R$^{10}$);
R$^9$ is H, methyl or ethyl;
R$^{10}$ is H, methyl or ethyl, wherein said methyl and ethyl can each independently be substituted by 1 or 2 substituents independently selected from methoxy, ethoxy and halo;
R$^{11}$ is H, methyl, methoxy or halo;
R$^{12}$ is selected from
H,
(C$_1$-C$_4$)alkyl-, optionally substituted with heterocyclyl$^3$,
—C(O)(C$_1$-C$_4$)alkyl,
—C(O)O(C$_1$-C$_4$)alkyl,
—C(O)H, and
—C(O)-phenyl, optionally substituted with 1 or 2 substituents independently selected from (C$_1$-C$_4$)alkyl, —O—(C$_1$-C$_4$)alkyl, cyano, halo, —C(O)OH, —C(O)O—(C$_1$-C$_4$)alkyl and —C(O)—(C$_1$-C$_4$)alkyl;
R$^{13}$ is selected from
—(C$_0$-C$_3$)alkyl-phenyl, said phenyl being optionally substituted with 1 or 2 substituents independently selected from (C$_1$-C$_4$)alkyl, —O—(C$_1$-C$_4$)alkyl, cyano, halo, —C(O)OH, —C(O)O—(C$_1$-C$_4$)alkyl and —C(O)—(C$_1$-C$_4$)alkyl,
—(C$_0$-C$_3$)alkyl-heterocyclyl$^4$, said heterocyclyl$^4$ being optionally substituted by 1, 2 or 3 substituents independently selected from —O—(C$_1$-C$_4$)alkyl, C(O)(C$_1$-C$_4$)alkyl and C(O)O—(C$_1$-C$_4$)alkyl,
(C$_1$-C$_4$)alkyl, said (C$_1$-C$_4$)alkyl being optionally substituted with a substituent independently selected from —O—(C$_1$-C$_4$)alkyl, C(O)(C$_1$-C$_4$)alkyl and C(O)O—(C$_1$-C$_4$)alkyl,
—(C$_0$-C$_3$)alkyl-(C$_3$-C$_6$)cycloalkyl;
or R$^9$ and R$^{13}$, together with the nitrogen to which they are attached form heterocyclyl$^3$, said heterocyclyl$^3$ being optionally substituted with 1, 2 or 3 substitutents selected independently from
=O,
(C$_1$-C$_4$)alkyl, said (C$_1$-C$_4$)alkyl being optionally substituted with 1, 2 or 3 substitutents selected independently from halo and OH,
OH,
C(O)(C$_1$-C$_4$)alkyl,
C(O)O—(C$_1$-C$_4$)alkyl and
C(O)NR$^9$R$^{10}$;
m is 0, 1 or 2;
n is 1, 2 or 3;
p is 0, 1, 2 or 3;
v is 0, 1 or 2;
heterocyclyl$^1$ is a 3, 4, 5 or 6 membered fully saturated or partially unsaturated monocyclic group comprising ring carbon atoms and 1 or 2 ring heteroatoms independently selected from N, O and S;
heterocyclyl$^3$ is a 4, 5 or 6 membered fully saturated or partially unsaturated monocyclic group comprising ring carbon atoms and 1 or 2 ring heteroatoms independently selected from N, O and S;
heterocyclyl$^4$ is a 3, 4, 5, 6 or 7 membered fully saturated or partially unsaturated monocyclic group comprising carbon ring atoms and 1 or 2 ring atoms selected independently from N, O and S;
heteroaryl$^1$ is a 5, 6, 7, 8, 9 or 10 membered, mono or bicyclic, fully unsaturated or partially unsaturated group, comprising carbon ring atoms and 1, 2, 3 or 4 ring heteratoms independently selected from N, O and S, wherein the total number of S atoms does not exceed 1, and the total number of O atoms does not exceed 1;
heteroaryl$^2$ is 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;
and * indicates the point of attachment to the remainder of the molecule.

2. The compound of formula (I) or a salt thereof, as claimed in claim 1, wherein A is selected from:

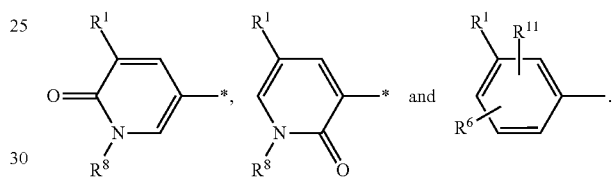

3. The compound of formula (I) or a salt thereof, as claimed in claim 1, wherein B is:

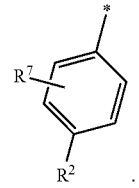

4. The compound of formula (I) or a salt thereof, as claimed in claim 1, wherein R$^4$ is selected from
phenyl, said phenyl being optionally substituted with 1, 2 or 3 substituents independently selected from:
(C$_1$-C$_4$)alkyl, optionally substituted by NR$^9$(R$^{10}$) or —O—(C$_1$-C$_4$)alkyl or by 1, 2 or 3 halo substituents,
—O—(C$_1$-C$_4$)alkyl, optionally substituted by NR$^9$(R$^{10}$), phenyl or —O—(C$_1$-C$_4$)alkyl, or by 1, 2 or 3 halo substituents,
—C(O)NR$^9$(R$^{12}$),
cyano,
halo,
—(CH$_2$)$_m$—S(O)$_v$NR$^9$(R$^{10}$),
—C(O)OH,
—C(O)O—(C$_1$-C$_4$)alkyl,
—(CH$_2$)$_p$—NR$^9$(R$^{12}$),
heterocyclyl$^1$,
phenyl
and
heteroaryl$^1$, said heteroaryl$^1$ being optionally substituted by 1, 2, 3 or 4 substituents independently selected from —O—(C$_1$-C$_4$)alkyl, =O, OH, cyano, (C$_1$-C$_4$)alkyl, halo and —NR$^9$(R$^{10}$).

5. The compound of formula (I) or a salt thereof, as claimed in claim 4, wherein R⁴ is selected from

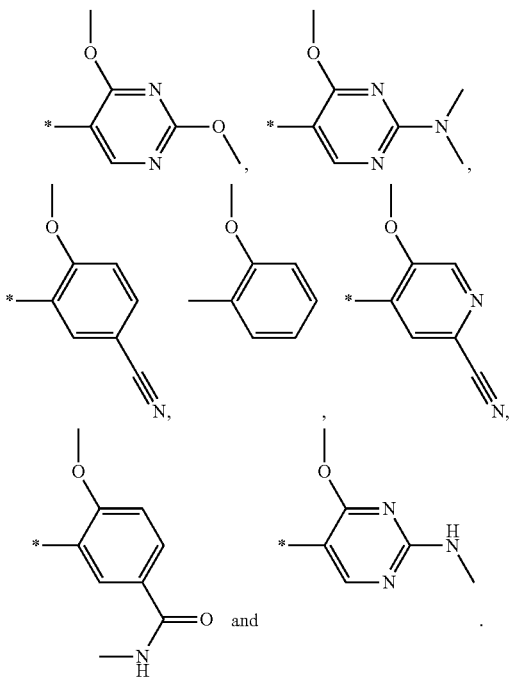

6. The compound of formula (I) or a salt thereof, as claimed in claim 1, wherein R⁵ is H.

7. The compound of formula (I) or a salt thereof, as claimed in claim 1, wherein the compound of formula (I) has the stereochemistry shown in formula (Ia):

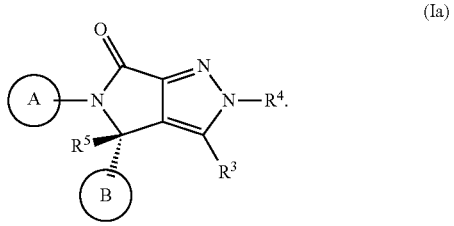

(Ia)

8. A compound of formula (I) or a salt thereof, as claimed in claim 1, selected from:
Example 1: 5-(3-Chloro-2-fluoro-phenyl)-4-(4-chloro-2-methyl-phenyl)-3-isopropyl-2-pyridin-2-ylmethyl-4,5-dihydro-2H-pyrrolo[3,4-c]pyrazol-6-one;
Example 2: 5-(3-Chloro-2-fluoro-phenyl)-4-(4-chloro-2-methyl-phenyl)-3-isopropyl-2-pyridin-3-ylmethyl-4,5-dihydro-2H-pyrrolo[3,4-c]pyrazol-6-one;
Example 3: 5-(3-Chloro-2-fluoro-phenyl)-4-(4-chloro-2-methyl-phenyl)-2-[2-(1H-imidazol-4-yl)-ethyl]-3-isopropyl-4,5-dihydro-2H-pyrrolo[3,4-c]pyrazol-6-one;
Example 4: 5-(3-Chloro-2-fluoro-phenyl)-4-(4-chloro-2-methyl-phenyl)-3-isopropyl-2-(3-methyl-butyl)-4,5-dihydro-2H-pyrrolo[3,4-c]pyrazol-6-one;
Example 5: 4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-1H-quinolin-2-one;
Example 6: 7-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-ylmethyl]-5-oxo-4,5-dihydro-pyrazolo[1,5-a]pyrimidine-3-carbonitrile;
Example 7: 5-(3-Chloro-2-fluoro-phenyl)-4-(4-chloro-2-methyl-phenyl)-3-isopropyl-2-(3-methyl-but-2-enyl)-4,5-dihydro-2H-pyrrolo[3,4-c]pyrazol-6-one;
Example 8: 5-(3-Chloro-2-fluoro-phenyl)-4-(4-chloro-2-methyl-phenyl)-3-isopropyl-2-(2-pyridin-2-yl-ethyl)-4,5-dihydro-2H-pyrrolo[3,4-c]pyrazol-6-one;
Example 9: 5-(3-Chloro-2-fluoro-phenyl)-4-(4-chloro-2-methyl-phenyl)-2-[2-(1H-indol-3-yl)-ethyl]-3-isopropyl-4,5-dihydro-2H-pyrrolo[3,4-c]pyrazol-6-one;
Example 10: 2-{2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-ethyl}-isoindole-1,3-dione;
Example 11: 5-(3-Chloro-2-fluoro-phenyl)-4-(4-fluoro-phenyl)-3-isopropyl-2-(3-methyl-butyl)-4,5-dihydro-2H-pyrrolo[3,4-c]pyrazol-6-one;
Example 12: 5-(3-Chloro-2-fluoro-phenyl)-4-(3,4-difluoro-phenyl)-3-isopropyl-2-(3-methyl-butyl)-4,5-dihydro-2H-pyrrolo[3,4-c]pyrazol-6-one;
Example 13: 5-(3-Chloro-2-fluoro-phenyl)-4-(4-chloro-phenyl)-2-[2-(3-ethyl-2-oxo-imidazolidin-1-yl)-ethyl]-3-isopropyl-4,5-dihydro-2H-pyrrolo[3,4-c]pyrazol-6-one;
Example 14: 4-(4-Chloro-2-methyl-phenyl)-5-(5-chloro-2-methyl-phenyl)-3-isopropyl-2-oxiranylmethyl-4,5-dihydro-2H-pyrrolo[3,4-c]pyrazol-6-one;
Example 15: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-pyrrolidine-1-carboxylic acid tert-butyl ester;
Example 16: 5-(3-Chloro-2-fluoro-phenyl)-4-(4-chloro-phenyl)-2-(2,5-dimethyl-2H-pyrazol-3-ylmethyl)-3-isopropyl-4,5-dihydro-2H-pyrrolo[3,4-c]pyrazol-6-one;
Example 17: 5-(3-Chloro-2-fluoro-phenyl)-4-(4-chloro-phenyl)-2-(1H-imidazol-2-ylmethyl)-3-isopropyl-4,5-dihydro-2H-pyrrolo[3,4-c]pyrazol-6-one;
Example 18: 5-(3-Chloro-2-fluoro-phenyl)-4-(4-chloro-phenyl)-3-isopropyl-2-(1H-tetrazol-5-ylmethyl)-4,5-dihydro-2H-pyrrolo[3,4-c]pyrazol-6-one;
Example 19: 4-(4-Chloro-2-methyl-phenyl)-5-(5-chloro-2-methyl-phenyl)-2-[2-(4-hydroxy-piperidin-1-yl)-2-oxo-ethyl]-3-isopropyl-4,5-dihydro-2H-pyrrolo[3,4-c]pyrazol-6-one;
Example 20: 4-(4-Chloro-2-methyl-phenyl)-5-(5-chloro-2-methyl-phenyl)-2-{2-[4-(2-hydroxy-ethyl)-piperidin-1-yl]-2-oxo-ethyl}-3-isopropyl-4,5-dihydro-2H-pyrrolo[3,4-c]pyrazol-6-one;
Example 21: N-(1-Acetyl-piperidin-4-yl)-2-[4-(4-chloro-2-methyl-phenyl)-5-(5-chloro-2-methyl-phenyl)-3-isopropyl-6-oxo-5,6,-dihydro-4H-pyrrolo[3,4-c]pyrazol-2-yl]-acetamide;
Example 22: 2-[2-(4-Acetyl-piperazin-1-yl)-2-oxo-ethyl]-4-(4-chloro-2-methyl-phenyl)-5-(5-chloro-2-methyl-phenyl)-3-isopropyl-4,5-dihydro-2H-pyrrolo[3,4-c]pyrazol-6-one;
Example 23: 4-(4-Chloro-2-methyl-phenyl)-5-(5-chloro-2-methyl-phenyl)-3-isopropyl-2-[2-oxo-2-(3-oxo-piperazin-1-yl)-ethyl]-4,5-dihydro-2H-pyrrolo[3,4-c]pyrazol-6-one;
Example 24: 4-(4-Chloro-2-methyl-phenyl)-5-(5-chloro-2-methyl-phenyl)-3-isopropyl-2-[2-(4-methyl-3-oxo-piperazin-1-yl)-2-oxo-ethyl]-4,5-dihydro-2H-pyrrolo[3,4-c]pyrazol-6-one;

Example 25: 2-(1-Acetyl-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 26: 4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-piperidine-1-carboxylic acid isopropylamide;

Example 27: 2-Allyl-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 28: 4-(4-Chloro-2-methyl-phenyl)-5-(5-chloro-2-methyl-phenyl)-2-(2,3-dihydroxy-propyl)-3-isopropyl-4,5-dihydro-2H-pyrrolo[3,4-c]pyrazol-6-one;

Example 29: 2-(1-Acetyl-4-hydroxy-piperidin-4-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 30: 4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-4-hydroxy-piperidine-1-carboxylic acid isopropylamide;

Example 31: 5-(3-Chloro-2-fluoro-phenyl)-4-(4-chloro-2-methyl-phenyl)-3-isopropyl-2-phenethyl-4,5-dihydro-2H-pyrrolo[3,4-c]pyrazol-6-one;

Example 32: 5-(3-Chloro-2-fluoro-phenyl)-4-(4-chloro-2-methyl-phenyl)-2-(2-dimethylamino-ethyl)-3-isopropyl-4,5-dihydro-2H-pyrrolo[3,4-c]pyrazol-6-one;

Example 33: 2-[4-(4-Chloro-phenyl)-5-(3,4-difluoro-phenyl)-3-isopropyl-6-oxo-5,6-dihydro-4H-pyrrolo[3,4-c]pyrazol-2-ylmethyl]-benzonitrile;

Example 34: 5-(3-Chloro-2-fluoro-phenyl)-4-(4-chloro-2-methyl-phenyl)-3-isopropyl-2-(2-methyl-thiazol-4-ylmethyl)-4,5-dihydro-2H-pyrrolo[3,4-c]pyrazol-6-one;

Example 35: 5-(3-Chloro-2-fluoro-phenyl)-4-(4-chloro-2-methyl-phenyl)-3-isopropyl-2-(2-methoxy-ethyl)-4,5-dihydro-2H-pyrrolo[3,4-c]pyrazol-6-one;

Example 36: 5-(3-Chloro-2-fluoro-phenyl)-4-(4-chloro-2-methyl-phenyl)-3-isopropyl-2-pyridin-4-ylmethyl-4,5-dihydro-2H-pyrrolo[3,4-c]pyrazol-6-one;

Example 37: 5-(3-Chloro-2-fluoro-phenyl)-4-(4-chloro-2-methyl-phenyl)-3-isopropyl-2-thiazol-4-ylmethyl-4,5-dihydro-2H-pyrrolo[3,4-c]pyrazol-6-one;

Example 38: 4-(4-Chloro-2-methyl-phenyl)-5-(5-chloro-2-methyl-phenyl)-3-isopropyl-2-(2-methoxy-ethyl)-4,5-dihydro-2H-pyrrolo[3,4-c]pyrazol-6-one;

Example 39: 4-(4-Chloro-2-methyl-phenyl)-5-(5-chloro-2-methyl-phenyl)-3-isopropyl-2-pyridin-2-ylmethyl-4,5-dihydro-2H-pyrrolo[3,4-c]pyrazol-6-one;

Example 40: 2-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-N-methyl-acetamide;

Example 41: 5-(3-Chloro-2-fluoro-phenyl)-4-(4-chloro-2-methyl-phenyl)-3-cyclopropyl-2-(3-methyl-butyl)-4,5-dihydro-2H-pyrrolo[3,4-c]pyrazol-6-one;

Example 42: 5-(3-Chloro-2-fluoro-phenyl)-4-(4-chloro-2-methyl-phenyl)-2-(3-hydroxy-propyl)-3-isopropyl-4,5-dihydro-2H-pyrrolo[3,4-c]pyrazol-6-one;

Example 43: 4-(4-Chloro-2-methyl-phenyl)-5-(5-chloro-2-methyl-phenyl)-3-isopropyl-2-(2-oxo-2-pyrrolidin-1-yl-ethyl)-4,5-dihydro-2H-pyrrolo[3,4-c]pyrazol-6-one;

Example 44: 4-(4-Chloro-2-methyl-phenyl)-5-(5-chloro-2-methyl-phenyl)-3-isopropyl-2-(tetrahydro-furan-2-ylmethyl)-4,5-dihydro-2H-pyrrolo[3,4-c]pyrazol-6-one;

Example 45: 4-(4-Chloro-2-methyl-phenyl)-5-(5-chloro-2-methyl-phenyl)-3-isopropyl-2-[2-(4-methyl-piperazin-1-yl)-ethyl]-4,5-dihydro-2H-pyrrolo[3,4-c]pyrazol-6-one;

Example 46: 5-(3-Chloro-2-fluoro-phenyl)-4-(4-chloro-2-methyl-phenyl)-2-(2-hydroxy-2-methyl-propyl)-3-isopropyl-4,5-dihydro-2H-pyrrolo[3,4-c]pyrazol-6-one;

Example 47: 5-[5-Chloro-2-(2-dimethylamino-ethoxy)-phenyl]-4-(4-chloro-2-methyl-phenyl)-2-ethyl-3-isopropyl-4,5-dihydro-2H-pyrrolo[3,4-c]pyrazol-6-one;

Example 48: 4-(4-Chloro-2-methyl-phenyl)-5-(5-chloro-2-methyl-phenyl)-3-isopropyl-2-[2-(2-oxo-pyrrolidin-1-yl)-ethyl]-4,5-dihydro-2H-pyrrolo[3,4-c]pyrazol-6-one;

Example 49: 2-Benzyl-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 50: 4-(4-Chloro-2-methyl-phenyl)-5-(5-chloro-2-methyl-phenyl)-3-isopropyl-2-(4-methyl-piperazine-1-carbonyl)-4,5-dihydro-2H-pyrrolo[3,4-c]pyrazol-6-one;

Example 51: 4-(4-Chloro-2-methyl-phenyl)-5-(5-chloro-2-methyl-phenyl)-3-isopropyl-6-oxo-5,6-dihydro-4H-pyrrolo[3,4-c]pyrazole-2-carboxylic acid methyl-phenyl-amide;

Example 52: (2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid methyl ester;

Example 53: (2S)-2-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-ylmethyl]-pyrrolidine-1-carboxylic acid dimethylamide;

Example 54: 2-((2S)-1-Acetyl-pyrrolidin-2-ylmethyl)-4-(4-chloro-2-methyl-phenyl)-5-(5-chloro-2-methyl-phenyl)-3-isopropyl-4,5-dihydro-2H-pyrrolo[3,4-c]pyrazol-6-one;

Example 55: 2-Benzyl-5-(3-chloro-2-fluoro-phenyl)-4-(4-chloro-2-methyl-phenyl)-3-isopropyl-4,5-dihydro-2H-pyrrolo[3,4-c]pyrazol-6-one;

Example 56: 5-(3-Chloro-2-fluoro-phenyl)-4-(4-chloro-2-methyl-phenyl)-2-cyclohexylmethyl-3-isopropyl-4,5-dihydro-2H-pyrrolo[3,4-c]pyrazol-6-one;

Example 57: 5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 58: 4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile;

Example 59: 5-(3-Chloro-2-fluoro-phenyl)-4-(4-chloro-2-methyl-phenyl)-2-(2-fluoro-phenyl)-3-isopropyl-4,5-dihydro-2H-pyrrolo[3,4-c]pyrazol-6-one;

Example 60: 5-(3-Chloro-2-fluoro-phenyl)-4-(2,4-dichloro-phenyl)-2-(2-hydroxy-ethyl)-3-isopropyl-4,5-dihydro-2H-pyrrolo[3,4-c]pyrazol-6-one;

Example 61: C-{4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-phenyl}-N-methyl-methanesulfonamide;

Example 62: 5-(3-Chloro-2-fluoro-phenyl)-4-(4-chloro-2-methyl-phenyl)-3-isopropyl-2-(1-methyl-piperidin-4-yl)-4,5-dihydro-2H-pyrrolo[3,4-c]pyrazol-6-one;

Example 63: 5-(3-Chloro-2-fluoro-phenyl)-4-(4-chloro-2-methyl-phenyl)-2-(4-chloro-phenyl)-3-isopropyl-4,5-dihydro-2H-pyrrolo[3,4-c]pyrazol-6-one;

Example 64: 4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzamide;

Example 65: 4-(4-Chloro-3-fluoro-phenyl)-5-(3-chloro-2-fluoro-phenyl)-2-(2-hydroxy-ethyl)-3-isopropyl-4,5-dihydro-2H-pyrrolo[3,4-c]pyrazol-6-one;

Example 66: 5-(3-Chloro-2-fluoro-phenyl)-4-(4-fluoro-phenyl)-3-isopropyl-2-(2-methoxy-phenyl)-4,5-dihydro-2H-pyrrolo[3,4-c]pyrazol-6-one;

Example 67: 5-(3-Chloro-2-fluoro-phenyl)-4-(3,4-difluoro-phenyl)-3-isopropyl-2-(2-methoxy-phenyl)-4,5-dihydro-2H-pyrrolo[3,4-c]pyrazol-6-one;

Example 68: 5-(3-Chloro-2-fluoro-phenyl)-4-(4-chloro-phenyl)-3-isopropyl-2-pyridin-4-yl-4,5-dihydro-2H-pyrrolo[3,4-c]pyrazol-6-one;

Example 69: 5-(3-Chloro-2-fluoro-phenyl)-3-isopropyl-2-(2-methoxy-phenyl)-4-p-tolyl-4,5-dihydro-2H-pyrrolo[3,4-c]pyrazol-6-one;

Example 70: 5-(3-Chloro-2-fluoro-phenyl)-4-(4-chloro-phenyl)-3-isopropyl-2-(2-methoxy-phenyl)-4,5-dihydro-2H-pyrrolo[3,4-c]pyrazol-6-one;

Example 71: 6-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-1,3-dimethyl-1H-pyrimidine-2,4-dione;

Example 72: 4-(4-Chloro-2-methyl-phenyl)-5-(5-chloro-2-methyl-phenyl)-3-isopropyl-2-(1-methyl-piperidin-4-yl)-4,5-dihydro-2H-pyrrolo[3,4-c]pyrazol-6-one;

Example 73: 5-(3-Chloro-2-fluoro-phenyl)-4-(4-chloro-2-methyl-phenyl)-3-isopropyl-2-(tetrahydro-pyran-4-yl)-4,5-dihydro-2H-pyrrolo[3,4-c]pyrazol-6-one;

Example 74: 5-(3-Chloro-2-fluoro-phenyl)-4-(4-chloro-phenyl)-3-isopropyl-2-(2-methoxy-phenyl)-4-(2-morpholin-4-yl-2-oxo-ethyl)-4,5-dihydro-2H-pyrrolo[3,4-c]pyrazol-6-one;

Example 75: 5-(3-Chloro-2-fluoro-phenyl)-4-(4-chloro-2-methyl-phenyl)-2-(2-chloro-phenyl)-3-isopropyl-4,5-dihydro-2H-pyrrolo[3,4-c]pyrazol-6-one;

Example 76: 5-(3-Chloro-2-fluoro-phenyl)-4-(4-chloro-2-methyl-phenyl)-3-isopropyl-2-(2-methoxy-phenyl)-4,5-dihydro-2H-pyrrolo[3,4-c]pyrazol-6-one;

Example 77: 5-(3-Chloro-2-fluoro-phenyl)-4-(4-chloro-2-methyl-phenyl)-2-(2,4-difluoro-phenyl)-3-isopropyl-4,5-dihydro-2H-pyrrolo[3,4-c]pyrazol-6-one;

Example 78: 3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-propionitrile;

Example 79: 5-(3-Chloro-4-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 80: 4-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-3-methyl-benzonitrile;

Example 81: 5-(3-Chloro-2-fluoro-phenyl)-4-(4-chloro-2-methyl-phenyl)-3-cyclobutyl-2-(2-hydroxy-ethyl)-4,5-dihydro-2H-pyrrolo[3,4-c]pyrazol-6-one;

Example 82: 3-[5-(3-Chloro-2-fluoro-phenyl)-4-(4-chloro-2-methyl-phenyl)-3-isopropyl-6-oxo-5,6-dihydro-4H-pyrrolo[3,4-c]pyrazol-2-yl]-benzonitrile;

Example 83: 4-(4-Chloro-2-methyl-phenyl)-5-(5-chloro-2-methyl-phenyl)-2-(2-hydroxy-ethyl)-3-isopropyl-4,5-dihydro-2H-pyrrolo[3,4-c]pyrazol-6-one;

Example 84: 4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 85: 5-(3-Chloro-2-fluoro-phenyl)-4-(4-chloro-2-methyl-phenyl)-3-cyclopropyl-2-(2-hydroxy-ethyl)-4,5-dihydro-2H-pyrrolo[3,4-c]pyrazol-6-one;

Example 86: 5-(3-Chloro-2-fluoro-phenyl)-4-(4-chloro-2-methyl-phenyl)-3-cyclopropyl-2-(2-methoxy-phenyl)-4,5-dihydro-2H-pyrrolo[3,4-c]pyrazol-6-one;

Example 87: 5-(5-Chloro-2,4-difluoro-phenyl)-4-(4-chloro-2-methyl-phenyl)-3-isopropyl-2-(2-methoxy-phenyl)-4,5-dihydro-2H-pyrrolo[3,4-c]pyrazol-6-one;

Example 88: 5-(3-Chloro-4-fluoro-phenyl)-4-(4-chloro-phenyl)-3-isopropyl-2-(2-methoxy-phenyl)-4,5-dihydro-2H-pyrrolo[3,4-c]pyrazol-6-one;

Example 89: 3-[5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazol-4-yl]-propionic acid methyl ester;

Example 90: 5-(3-Chloro-4-fluoro-phenyl)-4-(4-chloro-phenyl)-3-isopropyl-2-(2-methoxy-phenyl)-6-oxo-2,4,5,6-tetrahydro-pyrrolo[3,4-c]pyrazole-4-carboxylic acid ethyl ester;

Example 91: 4-(4-Chloro-2-methyl-phenyl)-5-(5-chloro-pyridin-3-yl)-3-isopropyl-2-(2-methoxy-phenyl)-4,5-dihydro-2H-pyrrolo[3,4-c]pyrazol-6-one;

Example 92: 5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 93: 5-(3-Chloro-4-fluoro-phenyl)-4-(4-chloro-phenyl)-3-isopropyl-2-(2-methoxy-phenyl)-4-methyl-4,5-dihydro-2H-pyrrolo[3,4-c]pyrazol-6-one;

Example 94: 5-(3-Chloro-2-fluoro-phenyl)-4-[4-chloro-2-(2-methoxy-ethoxymethyl)-phenyl]-3-isopropyl-2-(2-methoxy-phenyl)-4,5-dihydro-2H-pyrrolo[3,4-c]pyrazol-6-one;

Example 95: 5-(3-Chloro-4-fluoro-phenyl)-4-(4-chloro-phenyl)-4-(2-hydroxy-3-pyrrolidin-1-yl-propyl)-3-isopropyl-2-(2-methoxy-phenyl)-4,5-dihydro-2H-pyrrolo[3,4-c]pyrazol-6-one;

Example 96: 3-[5-(5-Chloro-2-methyl-phenyl)-3-isopropyl-6-oxo-4-(4-trifluoromethyl-phenyl)-5,6-dihydro-4H-pyrrolo[3,4-c]pyrazol-2-yl]-4,N-dimethyl-benzamide;

Example 97: 5-(3-Chloro-4-fluoro-phenyl)-4-(5-chloro-pyridin-2-yl)-3-isopropyl-2-(2-methoxy-phenyl)-4,5-dihydro-2H-pyrrolo[3,4-c]pyrazol-6-one;

Example 98: 5-(5-Chloro-2-methyl-phenyl)-4-(5-chloro-pyridin-2-yl)-3-isopropyl-2-(2-methoxy-phenyl)-4,5-dihydro-2H-pyrrolo[3,4-c]pyrazol-6-one;

Example 99: 5-(3-Chloro-4-fluoro-phenyl)-4-(4-chloro-phenyl)-4-(2,3-dihydroxy-propyl)-3-isopropyl-2-(2-methoxy-phenyl)-4,5-dihydro-2H-pyrrolo[3,4-c]pyrazol-6-one;

Example 100: 5-(3-Chloro-4-fluoro-phenyl)-4-(4-chloro-phenyl)-4-(2-hydroxy-ethyl)-3-isopropyl-2-(2-methoxy-phenyl)-4,5-dihydro-2H-pyrrolo[3,4-c]pyrazol-6-one;

Example 101: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-methyl-benzamide;

Example 102: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N-(2-pyrrolidin-1-yl-ethyl)-benzamide;

Example 103: 3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzonitrile;

Example 104: 3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-benzamide;
Example 105: N-{3-Chloro-5-[4-(4-chloro-2-methyl-phenyl)-3-isopropyl-2-(2-methoxy-phenyl)-6-oxo-2,6-dihydro-4H-pyrrolo[3,4-c]pyrazol-5-yl]-phenyl}-acetamide;
Example 106: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-N,N-dimethyl-benzamide;
Example 107: 4-(4-Chloro-phenyl)-5-(3,4-difluoro-phenyl)-3-isopropyl-2-(2-methoxy-phenyl)-4,5-dihydro-2H-pyrrolo[3,4-c]pyrazol-6-one;
Example 108: 5-(5-Chloro-1-methyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one;
Example 109: 5-(5-Chloro-1-ethyl-6-oxo-1,6-dihydro-pyridin-3-yl)-4-(4-chloro-phenyl)-3-isopropyl-2-(2-methoxy-phenyl)-4,5-dihydro-2H-pyrrolo[3,4-c]pyrazol-6-one;
Example 110: 5-(5-Chloro-1-methyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one;
Example 111: 5-[5-Chloro-1-(2-hydroxy-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one;
Example 112: 5-[5-Chloro-1-(2-methoxy-ethyl)-6-oxo-1,6-dihydro-pyridin-3-yl]-4-(4-chloro-2-methyl-phenyl)-3-isopropyl-2-(2-methoxy-phenyl)-4,5-dihydro-2H-pyrrolo[3,4-c]pyrazol-6-one;
Example 113: 5-(5-Chloro-1-ethyl-6-oxo-1,6-dihydro-pyridin-3-yl)-4-(4-chloro-2-methyl-phenyl)-3-isopropyl-2-(2-methoxy-phenyl)-4,5-dihydro-2H-pyrrolo[3,4-c]pyrazol-6-one;
Example 114: 3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-N-methyl-benzamide;
Example 115: 5-[5-Chloro-1-(2-dimethylamino-ethyl)-6-oxo-1,6-dihydro-pyridin-3-yl]-4-(4-chloro-phenyl)-3-isopropyl-2-(2-methoxy-phenyl)-4,5-dihydro-2H-pyrrolo[3,4-c]pyrazol-6-one;
Example 116: 5-(3-Chloro-2-fluoro-phenyl)-4-(4-chloro-2-methyl-phenyl)-2-cyclopropyl-3-isopropyl-4,5-dihydro-2H-pyrrolo[3,4-c]pyrazol-6-one;
Example 117: 5-(3-Chloro-2-fluoro-phenyl)-4-(4-chloro-2-methyl-phenyl)-2-(4-hydroxy-cyclohexyl)-3-isopropyl-4,5-dihydro-2H-pyrrolo[3,4-c]pyrazol-6-one;
Example 118: 4-(4-Chloro-2-methyl-phenyl)-5-(2-chloro-pyridin-4-yl)-3-isopropyl-2-(2-methoxy-phenyl)-4,5-dihydro-2H-pyrrolo[3,4-c]pyrazol-6-one;
Example 119: 5-(2-Chloro-5-methoxy-pyridin-4-yl)-4-(4-chloro-2-methyl-phenyl)-3-isopropyl-2-(2-methoxy-phenyl)-4,5-dihydro-2H-pyrrolo[3,4-c]pyrazol-6-one;
Example 120: 5-(3-Chloro-2-fluoro-phenyl)-4-(4-chloro-phenyl)-3-isopropyl-2-(1H-pyrazol-4-yl)-4,5-dihydro-2H-pyrrolo[3,4-c]pyrazol-6-one;
Example 121: 5-(3-Chloro-2-fluoro-phenyl)-4-(4-chloro-phenyl)-3-isopropyl-2-(4-methoxy-pyridin-3-yl)-4,5-dihydro-2H-pyrrolo[3,4-c]pyrazol-6-one;
Example 122: 4-(4-Chloro-2-methyl-phenyl)-5-(5-chloro-2-methyl-phenyl)-3-isopropyl-2-(4-methoxy-pyridin-3-yl)-4,5-dihydro-2H-pyrrolo[3,4-c]pyrazol-6-one;
Example 123: 3-tert-Butyl-5-(3-chloro-2-fluoro-phenyl)-4-(4-chloro-phenyl)-4,5-dihydro-2H-pyrrolo[3,4-c]pyrazol-6-one;
Example 124: 4-(4-Chloro-phenyl)-5-[5-chloro-2-(2H-tetrazol-5-ylmethoxy)-phenyl]-3-isopropyl-2-(2-methoxy-phenyl)-4,5-dihydro-2H-pyrrolo[3,4-c]pyrazol-6-one;
Example 125: 3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzonitrile;
Example 126: 2-(5-Aminomethyl-2-methoxy-phenyl)-4-(4-chloro-2-methyl-phenyl)-5-(5-chloro-2-methyl-phenyl)-3-isopropyl-4,5-dihydro-2H-pyrrolo[3,4-c]pyrazol-6-one;
Example 127: N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-acetamide;
Example 128: N-{3-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-4-methoxy-benzyl}-formamide;
Example 129: 3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzonitrile;
Example 130: 2-(5-Aminomethyl-2-methoxy-phenyl)-5-(5-chloro-1-methyl-6-oxo-1,6-dihydro-pyridin-3-yl)-4-(4-chloro-2-methyl-phenyl)-3-isopropyl-4,5-dihydro-2H-pyrrolo[3,4-c]pyrazol-6-one;
Example 131: N-{3-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-4-methoxy-benzyl}-acetamide;
Example 132: 5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;
Example 133: 4-(4-Chloro-2-methyl-phenyl)-5-(5-chloro-2-methyl-phenyl)-2-(2,4-dimethoxy-pyrimidin-5-yl)-3-isopropyl-4,5-dihydro-2H-pyrrolo[3,4-c]pyrazol-6-one;
Example 134: 4-[4-(4-Chloro-2-methyl-phenyl)-5-(5-chloro-2-methyl-phenyl)-3-isopropyl-6-oxo-5,6-dihydro-4H-pyrrolo[3,4-c]pyrazol-2-yl]-5-methoxy-pyridine-2-carbonitrile;
Example 135: 4-[5-(5-Chloro-1-methyl-6-oxo-1,6-dihydro-pyridin-3-yl)-4-(4-chloro-2-methyl-phenyl)-3-isopropyl-6-oxo-5,6-dihydro-4H-pyrrolo[3,4-c]pyrazol-2-yl]-5-methoxy-pyridine-2-carbonitrile;
Example 136: 3-[5-(5-Chloro-2-methyl-phenyl)-4-(4-cyano-phenyl)-3-isopropyl-6-oxo-5,6-dihydro-4H-pyrrolo[3,4-c]pyrazol-2-yl]-4-methoxy-benzonitrile;
Example 137: 3-[5-(5-Chloro-1-methyl-6-oxo-1,6-dihydro-pyridin-3-yl)-4-(4-cyano-2-methyl-phenyl)-3-isopropyl-6-oxo-5,6-dihydro-4H-pyrrolo[3,4-c]pyrazol-2-yl]-4-methoxy-benzonitrile;
Example 138: 3-[5-(5-Chloro-2-methyl-phenyl)-4-(4-cyano-2-methyl-phenyl)-3-isopropyl-6-oxo-5,6-dihydro-4H-pyrrolo[3,4-c]pyrazol-2-yl]-4-methoxy-benzonitrile;
Example 139: (S)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 140: (R)-5-(3-Chloro-2-fluoro-phenyl)-4-(4-chloro-2-methyl-phenyl)-2-(2-hydroxy-ethyl)-3-isopropyl-4,5-dihydro-2H-pyrrolo[3,4-c]pyrazol-6-one;

Example 141: (S)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 142: (R)-4-(4-Chloro-2-methyl-phenyl)-5-(5-chloro-2-methyl-phenyl)-3-isopropyl-2-(2-methoxy-phenyl)-4,5-dihydro-2H-pyrrolo[3,4-c]pyrazol-6-one;

Example 143: (S)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 144: (R)-5-[5-Chloro-2-(2-dimethylamino-ethoxy)-phenyl]-4-(4-chloro-2-methyl-phenyl)-3-isopropyl-2-(2-methoxy-phenyl)-4,5-dihydro-2H-pyrrolo[3,4-c]pyrazol-6-one;

Example 145: 5-(5-Chloro-1-methyl-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 146: 5-(5-Chloro-1-methyl-2-oxo-1,2-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 147: 5-(5-Chloro-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 148: 5-(5-Chloro-1-methyl-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 149: 5-(5-Chloro-1-methyl-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 150: 4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 151: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 152: 5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 153: (S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 154: (R)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;

Example 155: 5-(5-Chloro-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 156: 5-(5-Chloro-6-oxo-1,6-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;

Example 157: 4-[5-(5-Chloro-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 158: 4-[5-(5-Chloro-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 159: 4-[5-(5-Chloro-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 160: 4-[5-(5-Chloro-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 161: 4-[5-(5-Chloro-1-methyl-6-oxo-1,6-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 162: 4-[5-(5-Chloro-1-methyl-2-oxo-1,2-dihydro-pyridin-3-yl)-2-(2,4-dimethoxy-pyrimidin-5-yl)-3-isopropyl-6-oxo-2,4,5,6-tetrahydro-pyrrolo[3,4-c]pyrazol-4-yl]-benzonitrile;

Example 163: 5-(5-Chloro-1-methyl-2-oxo-1,2-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 164: 5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 165: 5-(5-Chloro-2-oxo-1,2-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 166: 5-(5-Chloro-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 167: (R)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 168: (S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;

Example 169: 4-[5-(5-Chloro-1-methyl-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-ylF benzonitrile;

Example 170: 4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;

Example 171: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-ylFbenzonitrile;

Example 172: 5-(5-Chloro-1-methyl-6-oxo-1,6-dihydro-pyridin-3-yl)-4-(4-chloro-phenyl)-3-isopropyl-2-(4-methoxy-2-methylamino-pyrimidin-5-yl)-4,5-dihydro-2H-pyrrolo[3,4-c]pyrazol-6-one;

Example 173: 4-[5-(5-Chloro-2-oxo-1,2-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]-benzonitrile;

Example 174: 4-[5-(5-Chloro-1-methyl-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]benzonitrile;

Example 175: 4-[5-(5-Chloro-6-oxo-1,6-dihydro-pyridin-3-yl)-3-isopropyl-2-(4-methoxy-2-methylamino-pyrimidin-5-yl)-6-oxo-2,4,5,6-tetrahydro-pyrrolo[3,4-c]pyrazol-4-yl]benzonitrile;

Example 176: (S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 177: (R)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;

Example 178: (S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 179: (R)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 180: ((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;

Example 181: ((R)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one;

Example 182: (R)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 183: (S)-4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile;

Example 184: 5-(5-Chloro-1-methyl-6-oxo-1,6-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one;

Example 185: 5-(5-chloro-1-methyl-2-oxo-1,2-dihydropyridin-3-yl)-4-(4-chloro-2-fluorophenyl)-2-(2,4-dimethoxypyrimidin-5-yl)-3-isopropyl-4,5-dihydropyrrolo[3,4-c]pyrazol-6(2H)-one;

Example 186: 5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one;

Example 187: 5-(5-chloro-1-methyl-6-oxo-1,6-dihydropyridin-3-yl)-4-(4-chloro-3-fluorophenyl)-2-(2,4-dimethoxypyrimidin-5-yl)-3-isopropyl-4,5-dihydropyrrolo[3,4-c]pyrazol-6(2H)-one;

Example 188: 4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile;

Example 189: 4-(5-(5-chloro-1-methyl-2-oxo-1,2-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-2-fluorobenzonitrile;

Example 190: 4-(5-(5-chloro-1-methyl-6-oxo-1,6-dihydropyridin-3-yl)-2-(2,4-dimethoxypyrimidin-5-yl)-3-isopropyl-6-oxo-2,4,5,6-tetrahydropyrrolo[3,4-c]pyrazol-4-yl)-3-fluorobenzonitrile;

Example 191: 4-(5-(5-chloro-1-methyl-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 192: 4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 193: 4-(5-(5-Chloro-2-oxo-1,2-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 194: 4-(5-(5-Chloro-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)-2-fluorobenzonitrile;

Example 195: 5-(5-Chloro-1-methyl-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 196: 5-(5-Chloro-2-oxo-1,2-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 197: 5-(5-Chloro-1-methyl-6-oxo-1,6-dihydropyridin-3-yl)-4-(4-chloro-3-fluorophenyl)-2-(2-(dimethylamino)-4-methoxypyrimidin-5-yl)-3-isopropyl-4,5-dihydropyrrolo[3,4-c]pyrazol-6(2H)-one;

Example 198: 4-(4-Chloro-3-fluorophenyl)-5-(5-chloro-6-oxo-1,6-dihydropyridin-3-yl)-2-(2-(dimethylamino)-4-methoxypyrimidin-5-yl)-3-isopropyl-4,5-dihydropyrrolo[3,4-c]pyrazol-6(2H)-one;

Example 199: 4-(4-Chlorophenyl)-2-(2,4-dimethoxypyrimidin-5-yl)-5-(1,5-dimethyl-2-oxo-1,2-dihydropyridin-3-yl)-3-isopropyl-4,5-dihydropyrrolo[3,4-c]pyrazol-6(2H)-one;

Example 200: 4-(4-chlorophenyl)-5-(1,5-dimethyl-2-oxo-1,2-dihydropyridin-3-yl)-2-(2-(dimethylamino)-4-methoxypyrimidin-5-yl)-3-isopropyl-4,5-dihydropyrrolo[3,4-c]pyrazol-6(2H)-one;

5-(3-Chloro-2-fluoro-phenyl)-4-(4-chloro-phenyl)-2-(2,4-dimethoxy-pyrimidin-5-yl)-3-(2-methoxy-1-methyl-ethyl)-4,5-dihydro-2H-pyrrolo[3,4-c]pyrazol-6-one;

5-(3-Chloro-2-fluoro-phenyl)-4-(4-chloro-phenyl)-2-(2,4-dimethoxy-pyrimidin-5-yl)-3-(2-hydroxy-1-methyl-ethyl)-4,5-dihydro-2H-pyrrolo[3,4-c]pyrazol-6-one;

3-(2-Amino-1-methyl-ethyl)-5-(3-chloro-2-fluoro-phenyl)-4-(4-chloro-phenyl)-2-(2,4-dimethoxy-pyrimidin-5-yl)-4,5-dihydro-2H-pyrrolo[3,4-c]pyrazol-6-one;

5-(3-Chloro-2-fluoro-phenyl)-4-(4-chloro-phenyl)-2-(2,4-dimethoxy-pyrimidin-5-yl)-3-(2-dimethylamino-1-methyl-ethyl)-4,5-dihydro-2H-pyrrolo[3,4-c]pyrazol-6-one;

N-{2-[5-(3-Chloro-2-fluoro-phenyl)-4-(4-chloro-phenyl)-2-(2,4-dimethoxy-pyrimidin-5-yl)-6-oxo-2,4,5,6-tetrahydro-pyrrolo[3,4-c]pyrazol-3-yl]-propyl}-acetamide; and N-{2-[5-(3-Chloro-2-fluoro-phenyl)-4-(4-chloro-phenyl)-2-(2,4-dimethoxy-pyrimidin-5-yl)-6-oxo-2,4,5,6-tetrahydro-pyrrolo[3,4-c]pyrazol-3-yl]-propyl}-formamide;

or a salt thereof.

9. The compound of formula (I) or a salt thereof, as claimed in claim 1, selected from:
- Example 132: 5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one;
- Example 147: 5-(5-Chloro-2-oxo-1,2-dihydro-pyridin-3-yl)-4-(4-chloro-phenyl)-2-(2-dimethylamino-4-methoxy-pyrimidin-5-yl)-3-isopropyl-4,5-dihydro-2H-pyrrolo[3,4-c]pyrazol-6-one;
- Example 150: 4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-2,4,5,6-tetrahydro-pyrrolo[3,4-c]pyrazol-4-yl]-benzonitrile;
- Example 152: 5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;
- Example 153: (S)-5-(5-Chloro-1-methyl-6-oxo-1,6-dihydro-pyridin-3-yl)-4-(4-chloro-2-methyl-phenyl)-2-(2,4-dimethoxy-pyrimidin-5-yl)-3-isopropyl-4,5-dihydro-2H-pyrrolo[3,4-c]pyrazol-6-one
- Example 164: 5-(5-Chloro-1-methyl-6-oxo-1,6-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;
- Example 168: (S)-5-(5-Chloro-2-oxo-1,2-dihydro-pyridin-3-yl)-4-(4-chloro-phenyl)-2-(2,4-dimethoxy-pyrimidin-5-yl)-3-isopropyl-4,5-dihydro-2H-pyrrolo[3,4-c]pyrazol-6-one;
- Example 176: (S)-5-(5-Chloro-1-methyl-6-oxo-1,6-dihydropyridin-3-yl)-4-(4-chlorophenyl)-2-(2,4-dimethoxypyrimidin-5-yl)-3-isopropyl-4,5-dihydropyrrolo[3,4-c]pyrazol-6(2H)-one;
- Example 178: (S)-4-(5-(5-Chloro-1-methyl-6-oxo-1,6-dihydropyridin-3-yl)-2-(2-(dimethylamino)-4-methoxypyrimidin-5-yl)-3-isopropyl-6-oxo-2,4,5,6-tetrahydropyrrolo[3,4-c]pyrazol-4-yl)benzonitrile; and
- Example 180: ((S)-5-(5-Chloro-2-oxo-1,2-dihydropyridin-3-yl)-4-(4-chlorophenyl)-2-(2-(dimethylamino)-4-methoxypyrimidin-5-yl)-3-isopropyl-4,5-dihydropyrrolo[3,4-c]pyrazol-6(2H)-one.

10. A pharmaceutical composition comprising a therapeutically effective amount of a compound of formula (I) or salt thereof as defined in claim 1, and one or more pharmaceutically acceptable carriers.

11. A method of modulating MDM2 and/or MDM4 activity in a subject, comprising the step of administering to a subject a therapeutically effective amount of a compound of formula (I) or salt thereof as defined in claim 1.

12. A method for the alleviation or amelioration of a disorder or a disease mediated by the activity of MDM2 and/or MDM4 comprising the step of administering to a subject a therapeutically effective amount of a compound of formula (I) or salt thereof as defined in claim 1.

13. A compound of the formula (I) or salt thereof as claimed in claim 1, in combination with one or more therapeutically active agents.

* * * * *